US007977080B2

(12) United States Patent
Gramatikova et al.

(10) Patent No.: US 7,977,080 B2
(45) **Date of Patent: *Jul. 12, 2011**

(54) PHOSPHOLIPASES, NUCLEIC ACIDS ENCODING THEM AND METHODS FOR MAKING AND USING THEM

(75) Inventors: Svetlana Gramatikova, San Diego, CA (US); Geoff Hazlewood, San Diego, CA (US); David Lam, San Elijo Hills, CA (US); Nelson R. Barton, San Diego, CA (US); Blake G. Sturgis, Carlsbad, CA (US); Dan E. Robertson, Belmont, MA (US); Jincai Li, San Diego, CA (US); Joel A. Kreps, Encinitas, CA (US); Roderick James Fielding, San Diego, CA (US); Robert C. Brown, San Diego, CA (US); Amit Vasavada, Poway, CA (US); Xuqiu Tan, San Diego, CA (US); Adrian Badillo, Poway, CA (US); Wilhelmus P. Van Hoek, Camarillo, CA (US); Giselle Janssen, Dixon, CA (US); Charles Isaac, Carlsbad, CA (US); Mark J. Burk, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 318 days.

This patent is subject to a terminal disclaimer.

(21) Appl. No.: 10/592,450

(22) PCT Filed: Mar. 8, 2005

(86) PCT No.: PCT/US2005/007908

§ 371 (c)(1), (2), (4) Date: Jul. 29, 2008

(87) PCT Pub. No.: WO2005/086900

PCT Pub. Date: Sep. 22, 2005

(65) Prior Publication Data

US 2008/0317731 A1 Dec. 25, 2008

Related U.S. Application Data

(63) Continuation-in-part of application No. 10/796,907, filed on Mar. 8, 2004, now Pat. No. 7,226,771, which is a continuation-in-part of application No. 10/421,654, filed on Apr. 21, 2003, now abandoned, which is a continuation-in-part of application No. PCT/US03/12556, filed on Apr. 21, 2003.

(60) Provisional application No. 60/374,313, filed on Apr. 19, 2002.

(51) Int. Cl.

| | |
|---|---|
| *C12N 9/20* | (2006.01) |
| *C12N 1/20* | (2006.01) |
| *C12N 15/00* | (2006.01) |
| *C12Q 1/50* | (2006.01) |
| *C07H 21/04* | (2006.01) |

(52) U.S. Cl. ....... 435/198; 435/18; 435/197; 435/252.3; 435/320.1; 536/23.2

(58) Field of Classification Search .................. 435/197, 435/252.3, 320.1, 18, 198; 536/23.2
See application file for complete search history.

(56) References Cited

U.S. PATENT DOCUMENTS

| | | | | |
|---|---|---|---|---|
| 4,707,364 | A | 11/1987 | Barach | |
| 4,752,483 | A | 6/1988 | Hagberg | |
| 5,264,367 | A | 11/1993 | Aalrust et al. | |
| 5,288,619 | A | 2/1994 | Brown et al. | |
| 5,532,163 | A | 7/1996 | Yagi et al. | |
| 6,001,640 | A | 12/1999 | Loeffler et al. | |
| 6,172,247 | B1 | 1/2001 | Copeland | |
| 6,172,248 | B1 | 1/2001 | Copeland | |
| 6,660,491 | B2 | 12/2003 | Norinobu et al. | |
| 7,226,771 | B2 * | 6/2007 | Gramatikova et al. ........ | 435/197 |
| 2007/0202566 | A1 | 8/2007 | Bornscheuer | |

FOREIGN PATENT DOCUMENTS

| | | | |
|---|---|---|---|
| EP | 0 070 269 | | 6/1982 |
| EP | 0268456 | | 5/1998 |
| EP | 0 513 709 | | 10/1999 |
| JP | 06306386 | A | 11/1994 |
| WO | WO 96/40844 | | 12/1996 |
| WO | WO-98/18912 | | 5/1998 |
| WO | WO-98/26057 | | 6/1998 |
| WO | WO-99/66805 | | 12/1999 |
| WO | WO-00/54601 | | 9/2000 |
| WO | WO-03/70013 | | 8/2003 |
| WO | WO 03/089620 | | 10/2003 |
| WO | WO 2005/032496 | | 4/2005 |
| WO | WO 2005/086900 | | 9/2005 |

(Continued)

OTHER PUBLICATIONS

International Search Report for PCT/US05/32351, mailed on Jun. 3, 2008, 5 pages.
Written Opinion of the International Searching Authority for PCT/US05/32351, mailed on Jun. 3, 2008, 8 pages.
Johansen et al., Nucleic Acids Research (1988) 16(21):10370.
Office Action for Japanese Patent Application No. 2003-586333, notified in letter to Morrison & Foerster LLP on Oct. 1, 2008 (English translation only).
International Search Report for PCT/US05/07908, mailed on Jul. 9, 2008, 7 pages.
Written Opinion of the International Searching Authority for PCT/US05/07908, mailed on Jul. 9, 2008, 16 pages.
EP05762779—Supplemental EP Search Report—Sep. 16, 2009.
Khamessan—Journal of Food Biochemistry (1994)—20—311-328.
Bitar—Journal of the American Oil Chemists' Society (2004)—81—927-932.

(Continued)

*Primary Examiner* — Tekchand Saidha
(74) *Attorney, Agent, or Firm* — Lynn M. Linkowski

(57) ABSTRACT

The invention provides novel polypeptides having phospholipase activity, including, e.g., phospholipase A, B, C and D activity, patatin activity, phosphatidic acid phosphatases (PAP)) and/or lipid acyl hydrolase (LAH) activity, nucleic acids encoding them and antibodies that bind to them. Industrial methods, e.g., oil degumming, and products comprising use of these phospholipases are also provided.

48 Claims, 43 Drawing Sheets

FOREIGN PATENT DOCUMENTS

WO WO 2006/096834 9/2006

OTHER PUBLICATIONS

GENESEQ Accession No. AEH46911, Environmental isolate DNA encoding a hydrolase—Jul. 27, 2006.
GENESEQ Accession No. AEH46912, Environmental isolate hydrolase—Jul. 27, 2006.
NCBI Accession No. YP001643484—Phospholipase C—Sep. 24, 2004.
EP07853585—Supplementary EP Search Report—Dec. 3, 2009.
GENESEQ Accession No. AED28321—(2005) Gramatikova.
GENESEQ Accession No. AED28443 (2005)—Gramatikova.
GENESEQ Accession No. AEH47258 (2006)—Bornscheuer.
Tan—Biochemistry (1998)—37—4275-4279.
EP05727242—Supp. EP Search Report—Sep. 28, 2009.
Horstman—Archives of Biochemistry and Biophysics (1999)—361—149-155.
AUIP—Sep. 23, 2009—Examiner's First Report—AU 2005221136.
Titball—Microbiological Reviews (1993)—57—347-366.
Dennis—Journal of Biological Chemistry (1994)—269—13057-13060.
Roberts—FASEB Journal (1996)—10—1159-1172.
Rebecchi—Physiological Reviews (2000)—4—1291-1335.
GENBANK Accession No. AY195600 (2003)—Pomerantsev.
GENBANK Accession No. Y16268 (1998)—Lovgren.
GENBANK Accession No. M24149 (1989)—Gilmore.
GENBANK Accession No. X64140 (1992)—Gavrilenko.
GENBANK Accession No. X64141 (1992)—Gavrilenko.
GENBANK Accession No. X12854 (1988)—Johansen.
Brindisi et al., Journal of Food Science (2001) 66(8):1100-1107.
Buenrostro and Lopez-Munguia, Biotechnology Letters (1986) 8(7):505-506.
Carter et al., Int'l Journal of Oncology (1998) 13:819-825.
Davidsen et al., Int'l Journal of Pharmaceutics (2001) 215:67-69.
Dawson et al., Br. J. Nutr. (1977) 38:225.
De Felice et al., Lait (1991) 71:637-643.
Dominguez et al., Food Chemistry (1995) 54:223-231.
Fernandes et al., Marschall Italian & Specialty Cheese Seminars (1987) 1-6.
Fullbrook, JAOCS (1983) 60(2):428A.
Gilmore et al., Database on Genbank, Feb. 1, 1994, Accession No. P33376.
Gilmore et al., Database on Genbank, Mar. 11, 1996, Accession No. M24149.
Gilmore et al., Journal of Bacteriology (1989) 744-753.
Henke et al., Angew. Chem. Int. Ed. (2002) 41(17):3211-3213.
Henke et al., Angew. Chem. Int. Ed. (2002) supp. info. For Z18885:1-9.
Hergenrother et al., Analytical Biochemistry (1995) 229:313-316.
Hough et al., Nature (1989) 338:357-360.
International Search Report for PCT/US03/12556, mailed on Aug. 27, 2004, 8 pages.
Johansen et al., Gene (1998) 65:293-304.
Kasai et al., J. Agric. Food Chem. (2003) 51:6217-6222.
Little, Methods in Enzymology (1981) 71:725-730.
Little et al., FEBS Letters (1975) 52(2):175-179.
Lovgren et al., Current Microbiology (1998) 37:245-250.
Lovgren et al., Database on Genbank, Jun. 1, 1998, Accession No. Q52864.
Lovgren et al., Database on Genbank, Oct. 2, 1998, Accession No. BTY16268.
Marsman et al., J. Agric. Food Chem. (1997) 45:4088-4095.
McGlone et al., Journal of Food Science (1986) 51(3):695.
Montedoro et al., Acta Vitamin. Enzymol. (Milano) (1976) 30:13.
Nakamura et al., Biosci. Biotechnol. Biochem (2001) 65(10):2249-2258.
Ouhida et al., J. Agric. Food Chem. (2002) 50:1933-1938.
Rosenthal et al., Enzyme and Microbiol Technology (2001) 28:499-509.
Shahani, Marschall Italian & Specialty Cheese Seminars (1971) 1-13.
Shinitzky et all, The Journal of Biological Chemistry (1993) 268(19):14109-14115.
Smith et al., JAOCS (1993) 70(9):885.
Sosulski et al., JAOCS (1988) 65(3):357-361.
Taguchi et al., J. Biochem (1977) 82:1225-1230.
Tan et al., Protein Expression and Purification (1997) 10:365-372.
Titball, Microbiological Reviews (1993) 57(2):347-366.
Zyla et al., Poultry Science (1996) 75:381-387.
Birschbach—Bulletin of the IDF (1992)—269—36-39.
Harboe—Bulletin of the IDF (1994)—294—11-16.
Kanfer—Lipids—(1975)—10—391-394.
Kotting—Lipases and phospholipases in organic synthesis. In: P. Woolley and S.B. Petersen, Editors, Lipases, Their Structure, Biochemistry and Application, Cambridge University Press, Cambridge (1994), pp. 289-314.
Zwaal—Phospholipase C from *Bicillus cereus* —Methods in Enzymology (1974)—32—154-161.
Jun. 3, 2010—Office Action—U.S. Appl. No. 11/625,765.
UniProt Accession No. Q81A32 (2003) *Bacillus cereus* —Ivanova .
UniProt Accession No. P08954 (1988) phosphatidylinositol phosphodiesterase—Henner.
JPO—Oct. 12, 2010—Office Action—2007-502990.
AUIP—Oct. 11, 2010—First Examination Report—2005264938.
USPTO—Dec. 9, 2010—Office Action—11570169.
SIPO—Nov. 18, 2010—First Chinese Office Action—200780042983.3 (including English translation attached).

* cited by examiner

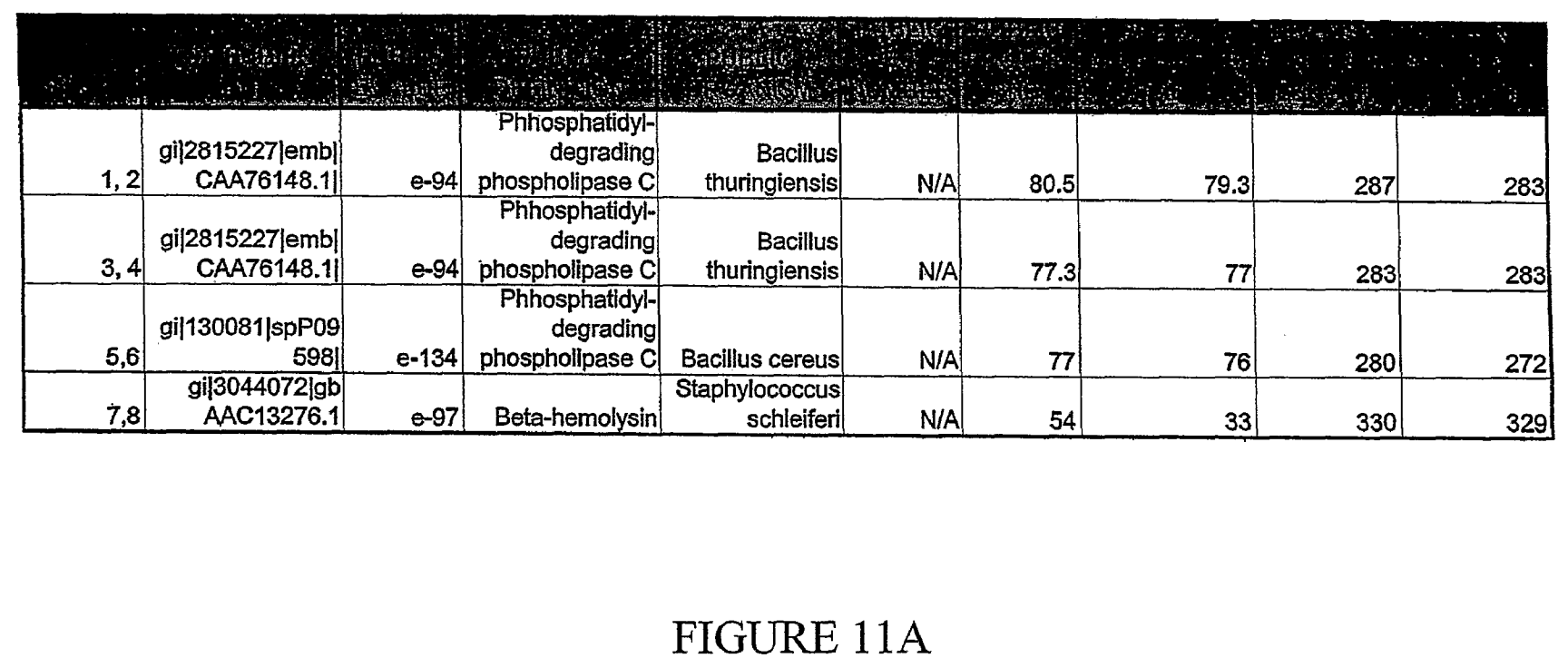

| | | | | | | | | | |
|---|---|---|---|---|---|---|---|---|---|
| 1, 2 | gi\|2815227\|emb\|CAA76148.1\| | e-94 | Phhosphatidyl-degrading phospholipase C | Bacillus thuringiensis | N/A | 80.5 | 79.3 | 287 | 283 |
| 3, 4 | gi\|2815227\|emb\|CAA76148.1\| | e-94 | Phhosphatidyl-degrading phospholipase C | Bacillus thuringiensis | N/A | 77.3 | 77 | 283 | 283 |
| 5,6 | gi\|130081\|spP09598\| | e-134 | Phhosphatidyl-degrading phospholipase C | Bacillus cereus | N/A | 77 | 76 | 280 | 272 |
| 7,8 | gi\|3044072\|gbAAC13276.1 | e-97 | Beta-hemolysin | Staphylococcus schleiferi | N/A | 54 | 33 | 330 | 329 |

FIGURE 11A

| | | | | | | | | | | | |
|---|---|---|---|---|---|---|---|---|---|---|---|
| 9, 10 | beta-hemolysin - Staphylococcus aureus | Staphylococcus aureus | 3.1.4.3 | 97786 | 9E-34 | 14647263 | 999 | 332 | 993 | 331 | 32 |
| 11, 12 | | | 3.4.21.- | 23474722 | 3E-62 | 14278066 | 1041 | 346 | N/A | 339 | 38 |
| 13, 14 | | | 3.4.21.- | 23474722 | 7E-65 | 14530226 | 1038 | 345 | N/A | 339 | 38 |
| 15, 16 | hypothetical protein [Pseudomonas aeruginosa PA01] | Pseudomonas aeruginosa PA01 | | 15598123 | 1E-102 | 9949021 | 1344 | 447 | 1329 | 443 | 46 |
| 17, 18 | | | 3.1.1.4 | 23127917 | 4E-24 | 14670061 | 1137 | 378 | N/A | 391 | 29 |
| 19, 20 | | | | 27367835 | 0 | 3746408 | 1248 | 415 | N/A | 417 | 72 |
| 21, 22 | phospholipase C [Aeromonas hydrophila] | Aeromonas hydrophila | | 3746953 | 1E-169 | 3746952 | 1716 | 571 | 1716 | 572 | 53 |
| 23, 24 | conserved hypothetical protein [Xanthomonas campestris pv. campestris str. ATCC 33913] | | | 21232725 | 2E-51 | 4753846 | 1473 | 490 | 1344 | 448 | 31 |
| 25, 26 | | | 3.4.21.- | 23474722 | 4E-50 | 13938818 | 1098 | 365 | N/A | 339 | 36 |
| 27, 28 | | | | 23474722 | 4E-26 | 13173617 | 1287 | 428 | N/A | 339 | 27 |
| 29, 30 | conserved hypothetical protein [Xanthomonas campestris pv. campestris str. ATCC 33913] | | | 21233052 | 0.00007 | 14589793 | 753 | 250 | 1311 | 437 | 20 |
| 31, 32 | phospholipase C (EC 3.1.4.3) precursor - Bacillus cereus | Bacillus cereus | 3.1.4.3 | 2126777 | 2E-48 | 11558558 | 1422 | 473 | 1776 | 592 | 32 |
| 33, 34 | hypothetical protein [Xanthomonas campestris] | Xanthomonas campestris | | 6689533 | 1E-18 | 1160468 | 792 | 263 | 855 | 285 | 30 |
| 35, 36 | Sequence 2 from patent US 5824864 | | | 5972806 | 5E-14 | 2723462 | 1389 | 462 | 1230 | 410 | 20 |
| 37, 38 | phospholipase C [Aeromonas hydrophila] | Aeromonas hydrophila | | 3746953 | 1E-149 | 3746952 | 1329 | 443 | 1716 | 572 | 59 |
| 39, 40 | hypothetical protein [Pseudomonas aeruginosa PA01] | Pseudomonas aeruginosa PA01 | | 15598123 | 1E-106 | 9949021 | 1335 | 444 | 1329 | 443 | 49 |
| 41, 42 | conserved hypothetical protein [Xanthomonas axonopodis pv. citri str. 306] | Xanthomonas axonopodis pv. citri str. 306 | | 21241345 | 2E-63 | 3885908 | 1419 | 472 | 1320 | 440 | 35 |
| 43, 44 | | | | 23474722 | 4E-26 | 13529454 | 1287 | 428 | N/A | 339 | 27 |
| 45, 46 | | | 3.4.21.- | 23474722 | 4E-55 | 14530226 | 1038 | 345 | N/A | 339 | 38 |
| 47, 48 | hypothetical protein [Nostoc sp. PCC 7120] | Nostoc sp. PCC 7120 | | 17230632 | 6E-25 | 6322016 | 1476 | 491 | 1365 | 455 | 23 |
| 49, 50 | | | | 27367835 | 1E-166 | 10998526 | 1257 | 418 | N/A | 417 | 65 |
| 51, 52 | conserved hypothetical protein [Xanthomonas campestris pv. campestris str. ATCC 33913] | | | 21232725 | 2E-50 | 13122711 | 1482 | 493 | 1344 | 448 | 30 |
| 53, 54 | hypothetical protein [Pseudomonas aeruginosa PA01] | Pseudomonas aeruginosa PA01 | | 15598123 | 1E-16 | 13928640 | 1491 | 496 | 1329 | 443 | 22 |
| 55, 56 | | | 3.4.21.- | 23474722 | 2E-53 | 8896126 | 1041 | 346 | N/A | 339 | 39 |
| 57, 58 | hypothetical protein [Pseudomonas aeruginosa PA01] | Pseudomonas aeruginosa PA01 | | 15598123 | 1E-18 | 3337392 | 1413 | 470 | 1329 | 443 | 22 |
| 59, 60 | | | 3.4.21.- | 23474722 | 9E-56 | 14280415 | 1038 | 345 | N/A | 339 | 39 |
| 61, 62 | lecithinase [Vibrio mimicus] | | | 3746409 | 0 | 3746408 | 1257 | 418 | 1410 | 470 | 77 |
| 63, 64 | | | | 27367835 | 1E-173 | 3746408 | 1242 | 413 | N/A | 417 | 67 |
| 65, 66 | | | 3.1.1.4 | 23041851 | 3E-19 | 14993667 | 1164 | 387 | N/A | 337 | 32 |
| 67, 68 | hypothetical protein [Pseudomonas aeruginosa PA01] | Pseudomonas aeruginosa PA01 | | 15598123 | 9E-25 | 13880526 | 1419 | 472 | 1329 | 443 | 26 |
| 69, 70 | | | 3.4.21.- | 23474722 | 9E-56 | 14530226 | 1038 | 345 | N/A | 339 | 38 |

FIGURE 11B

| | | | | | | | | | | | |
|---|---|---|---|---|---|---|---|---|---|---|---|
| 71, 72 | chitinase (EC 3.2.1.14) A - Pseudoalteromonas sp. (strain S9) | Pseudoalteromonas sp. | 3.2.1.14 | 7521919 | 2E-28 | 7340814 | 3264 | 1088 | 3162 | 1054 | 11 |
| 73, 74 | conserved hypothetical protein [Xanthomonas campestris pv. campestris str. ATCC 33913] | | | 21233052 | 0.00007 | 14589793 | 753 | 250 | 1311 | 437 | 20 |
| 75, 76 | hypothetical protein [Pseudomonas aeruginosa PA01] | Pseudomonas aeruginosa PA01 | | 15598123 | 1E-22 | 13157620 | 1335 | 444 | 1329 | 443 | 21 |
| 77, 78 | | | 3.4.21.- | 23474722 | 4E-52 | 14550312 | 1026 | 341 | N/A | 339 | 36 |
| 79, 80 | phospholipase C [Aeromonas hydrophila] | Aeromonas hydrophila | | 3746953 | 1E-168 | 15022386 | 1701 | 566 | 1716 | 572 | 52 |
| 81, 82 | PHOSPHOLIPASE C PRECURSOR (PLC) (PHOSPHATIDYLCHOLINE CHOLINEPHOSPHOHYDROLASE) (CEREOLYSIN A) | Bacillus cereus | 3.1.4.3 | 130081 | 1E-49 | 8570206 | 1422 | 473 | 849 | 283 | 26 |
| 83, 84 | hemolysin [Vibrio harveyi] | Vibrio harveyi | | 10998525 | 5E-61 | 10716598 | 1290 | 429 | 1254 | 418 | 33 |
| 85, 86 | | | 3.4.21.- | 23474722 | 1E-65 | 14530226 | 1038 | 345 | N/A | 339 | 38 |
| 87, 88 | | | 3.4.21.- | 23041851 | 3E-12 | 11121040 | 870 | 289 | N/A | 337 | 28 |
| 89, 90 | PHOSPHOLIPASE C PRECURSOR (PLC) (PHOSPHATIDYLCHOLINE CHOLINEPHOSPHOHYDROLASE) (CEREOLYSIN A) | Bacillus cereus | 3.1.4.3 | 130081 | 1E-49 | 8570206 | 1422 | 473 | 849 | 283 | 26 |
| 91, 92 | | | 3.4.21.- | 23474722 | 4E-54 | 3947685 | 1035 | 344 | N/A | 339 | 38 |
| 93, 94 | beta-hemolysin - Staphylococcus aureus | Staphylococcus aureus | 3.1.4.3 | 97786 | 6E-95 | 3044071 | 963 | 320 | 993 | 331 | 54 |
| 95, 96 | | | 3.4.21.- | 23474722 | 2E-52 | 13518253 | 1038 | 345 | N/A | 339 | 38 |
| 97, 98 | phospholipase C (EC 3.1.4.3) precursor - Bacillus cereus | Bacillus cereus | 3.1.4.3 | 2126777 | 2E-49 | 3766134 | 1422 | 473 | 1776 | 592 | 32 |
| 99, 100 | | | 3.1.1.4 | 23129073 | 4E-43 | 7544033 | 1053 | 350 | N/A | 698 | 34 |
| 101, 102 | | | 3.1.4.3 | 27466926 | 3E-73 | 5802872 | 996 | 331 | N/A | 334 | 45 |
| 103, 104 | Y4ll [Rhizobium sp. NGR234] | Rhizobium sp. NGR234 | | 16519782 | 3E-07 | 6755291 | 2205 | 734 | 2109 | 703 | 15 |
| 105, 106 | Phospholipase C related protein [Clostridium acetobutylicum] | Clostridium acetobutylicum | | 15894306 | 0.005 | 2182412 | 756 | 251 | 735 | 245 | 18 |

FIGURE 11C

| SEQ ID No. | NR Description | NR Accession Code | NR E-value | NR Organism | Geneseq Protein Description | Geneseq Protein Accession Code | Geneseq Protein Evalue | Geneseq DNA Description | Geneseq DNA Accession Code | Geneseq DNA E value | Predicted EC No. | Query DNA Length | Query Protein Length | Subject seq or NR DNA Length | Subject seq or NR Protein Length | Geneseq or NR % ID Protein | Geneseq or NR % ID DNA |
|---|---|---|---|---|---|---|---|---|---|---|---|---|---|---|---|---|---|
| 107, 108 | 1-phosphatidylinositol phosphodiesterase precursor [Bacillus cereus ATCC 14579] | 30021854 | 0 | Bacillus cereus ATCC 14579 | Listeria monocytogenes protein #849. | ABB47680 | 3E-18 | Arabidopsis yellow stripe1-like 4 SEQ ID NO 10. | ABN85766 | 0.25 | 3.1.4.10 | 990 | 329 | 990 | 329 | 92 | 91 |
| 109, 110 | 1-phosphatidylinositol phosphodiesterase precursor [Bacillus cereus ATCC 14579] | 30021854 | 0 | Bacillus cereus ATCC 14579 | Listeria monocytogenes protein #849. | ABB47680 | 6E-18 | Arabidopsis yellow stripe1-like 4 SEQ ID NO 10. | ABN85766 | 0.25 | 3.1.4.10 | 990 | 329 | 990 | 329 | 92 | 92 |

FIGURE 11D

| | | | | | | | | | | | | | | | |
|---|---|---|---|---|---|---|---|---|---|---|---|---|---|---|---|
| 111, 112 | phosphatidyl inositol-specific phospholipase C [Listeria seeligeri]. | 2231002 | 8E-25 | Listeria seeligeri | Listeria monocytogenes protein #849. | ABB47680 | 2E-24 | Human cDNA sequence #13 upregulated in non-aggressive CC-RCC. | ABX74467 | 3.2 | 3.1.4.10 | 828 | 275 | 963 | 320 | 31 | 42 |
| 113, 114 | 1-phosphatidylinositol phosphodiesterase precursor [Bacillus cereus ATCC 14579] | 30021854 | 1E-180 | Bacillus cereus ATCC 14579 | Listeria monocytogenes protein #849. | ABB47680 | 8E-18 | Arabidopsis yellow stripe1-like 4 SEQ ID NO 10. | ABN85766 | 0.24 | 3.1.4.10 | 981 | 326 | 990 | 329 | 92 | 92 |
| 115, 116 | 1-phosphatidylinositol phosphodiesterase precursor [Bacillus cereus ATCC 14579] | 30021854 | 1E-178 | Bacillus cereus ATCC 14579 | Listeria monocytogenes protein #849. | ABB47680 | 2E-16 | Murine apoptosis related DNA sequence #201. | ABL01358 | 0.97 | 3.1.4.10 | 987 | 328 | 990 | 329 | 89 | 90 |

FIGURE 11E

| | | | | | | | | | | | | | | | | | |
|---|---|---|---|---|---|---|---|---|---|---|---|---|---|---|---|---|---|
| 117, 118 | 1-phosphatidylinositol phosphodiesterase precursor [Bacillus cereus ATCC 14579] | 30021854 | 1E-179 | Bacillus cereus ATCC 14579 | Listeria monocytogenes protein #849. | ABB47680 | 8E-16 | Human central cannabinoid receptor 47.08 probe, SEQ ID NO:9. | ABZ57017 | 0.97 | 3.1.4.10 | 987 | 328 | 990 | 329 | 90 | 91 |
| 119, 120 | 1-phosphatidylinositol phosphodiesterase precursor [Bacillus cereus ATCC 14579] | 30021854 | 1E-178 | Bacillus cereus ATCC 14579 | Listeria monocytogenes protein #849. | ABB47680 | 8E-16 | Murine apoptosis related DNA sequence #201. | ABL01358 | 0.97 | 3.1.4.10 | 987 | 328 | 990 | 329 | 89 | 90 |

FIGURE 11F

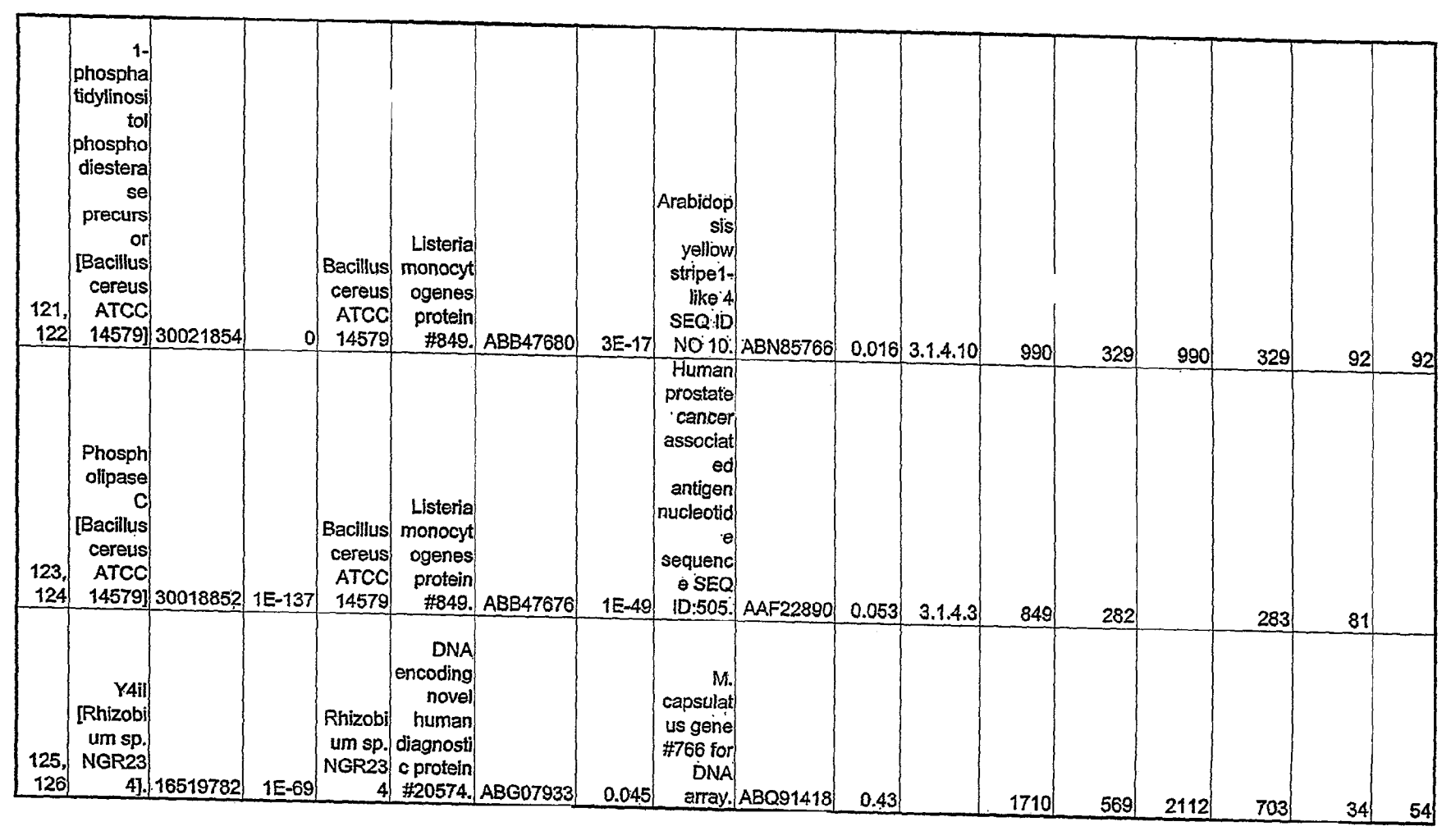

| | | | | | | | | | | | | | | | | | |
|---|---|---|---|---|---|---|---|---|---|---|---|---|---|---|---|---|---|
| 121, 122 | 1-phosphatidylinositol phosphodiesterase precursor [Bacillus cereus ATCC 14579] | 30021854 | 0 | Bacillus cereus ATCC 14579 | Listeria monocytogenes protein #849. | ABB47680 | 3E-17 | Arabidopsis yellow stripe1-like 4 SEQ ID NO 10. | ABN85766 | 0.016 | 3.1.4.10 | 990 | 329 | 990 | 329 | 92 | 92 |
| 123, 124 | Phospholipase C [Bacillus cereus ATCC 14579] | 30018852 | 1E-137 | Bacillus cereus ATCC 14579 | Listeria monocytogenes protein #849. | ABB47676 | 1E-49 | Human prostate cancer associated antigen nucleotide sequence SEQ ID:505. | AAF22890 | 0.053 | 3.1.4.3 | 849 | 282 | | 283 | 81 | |
| 125, 126 | Y4il [Rhizobium sp. NGR234]. | 16519782 | 1E-69 | Rhizobium sp. NGR234 | DNA encoding novel human diagnostic protein #20574. | ABG07933 | 0.045 | M. capsulatus gene #766 for DNA array. | ABQ91418 | 0.43 | | 1710 | 569 | 2112 | 703 | 34 | 54 |

FIGURE 11G

| | | | | | | | | | | | | | | | | | |
|---|---|---|---|---|---|---|---|---|---|---|---|---|---|---|---|---|---|
| 127, 128 | conserved hypothetical protein [Porphyromonas gingivalis W83] | 34541487 | 2E-96 | Porphyromonas gingivalis W83 | Mycobacterium tuberculosis protein 10. | ABJ04710 | 2E-14 | Human NS cDNA sequence SEQ ID NO:76. | ABL39805 | 1 | 3.4.21. | 1038 | 345 | | 339 | 52 | |
| 129, 130 | phospholipase C (EC 3.1.4.3) precursor - Bacillus cereus. | 2126777 | 2E-50 | Bacillus cereus | Listeria monocytogenes protein #849. | ABB47676 | 2E-34 | Human secretory polynucleotide SPTM SEQ ID NO 534. | ABZ35958 | 0.36 | 3.1.4.3 | 1434 | 477 | | 592 | 31 | |
| 131, 132 | latex allergen from Hevea brasiliensis [Chromobacterium violaceum ATCC 12472] | 34495896 | 4E-51 | Chromobacterium violaceum ATCC 12472 | Arabidopsis thaliana protein fragment SEQ ID NO: 76191. | AAG42787 | 4E-22 | Arabidopsis thaliana protein fragment SEQ ID NO: 76191. | AAC42405 | 0.058 | 3.1.1.4 | 927 | 308 | | 322 | 37 | |

FIGURE 11H

| | | | | | | | | | | | | | | | | | |
|---|---|---|---|---|---|---|---|---|---|---|---|---|---|---|---|---|---|
| 133, 134 | conserved hypothetical protein [Porphyromonas gingivalis W83] | 34541487 | 1E-90 | Porphyromonas gingivalis W83 | *Mycobacterium tuberculosis* protein 10. | ABJ04710 | 2E-20 | | | | 3.4.21. | 1053 | 350 | | 339 | 50 | |
| 135, 136 | Y4il [Rhizobium sp. NGR234]. | 16519782 | 1E-69 | Rhizobium sp. NGR234 | DNA encoding novel human diagnostic protein #20574. | ABG07933 | 1.5 | Staphylococcus aureus DNA for cellular proliferation protein #1219: | AAS51470 | 1.7 | | 1710 | 569 | 2112 | 703 | 33 | 54 |
| 137, 138 | conserved hypothetical protein [Porphyromonas gingivalis W83] | 34541487 | 7E-97 | Porphyromonas gingivalis W83 | Mycobacterium tuberculosis protein 10. | ABJ04710 | 2E-13 | Human NS cDNA sequence SEQ ID NO:76: | ABL39805 | 1 | 3.4.21. | 1038 | 345 | | 339 | 53 | |

FIGURE 11I

| | | | | | | | | | | | | | | | | | |
|---|---|---|---|---|---|---|---|---|---|---|---|---|---|---|---|---|---|
| 139, 140 | phospholipase C [Aeromonas hydrophila]. | 3746953 | 1E-180 | Aeromonas hydrophila | PCR primer for Topoisomerase II binding protein coding sequence. | AAY03183 | 3.2 | Angiotensin gene methylation analysing oligonucleotide #2. | AAD28391 | 6.6 | | 1692 | 563 | 1719 | 572 | 53 | 58 |

FIGURE 11J

Figure 13 – PLC Biodegumming (Crude soy): 2 centrifugation step process (Crude soy): 3 centrifugation step process (Crude soy oil) centrifugation step process
with acid treatment Figure 17
PLC Challenge: *Pichia* SN; 37 °C; pH 5.2, 6 Hr
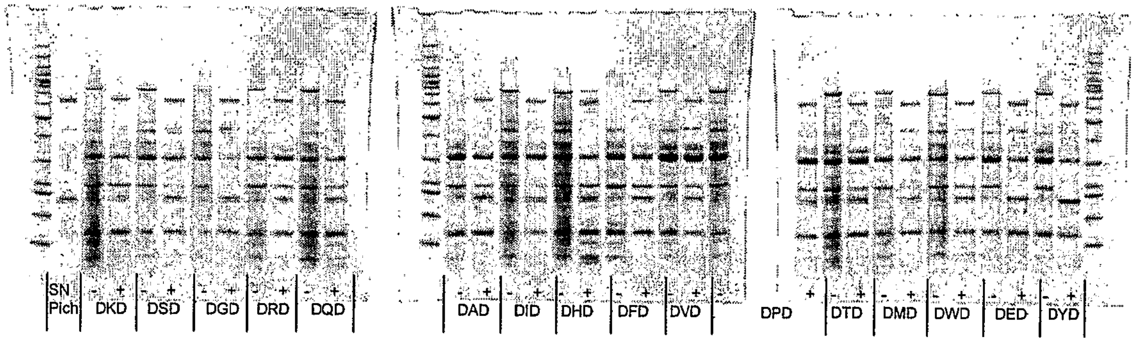
PLC Challenge: *Pichia* SN; 37 °C; pH 6.2 and 5.2, 22 Hr
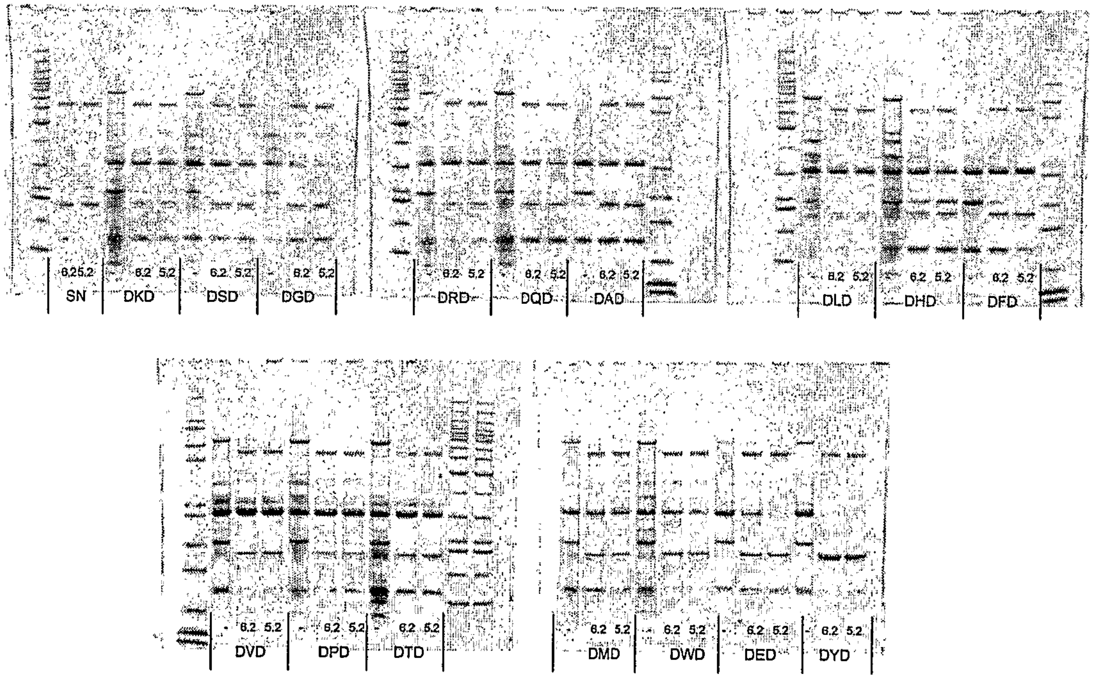

Figure 23

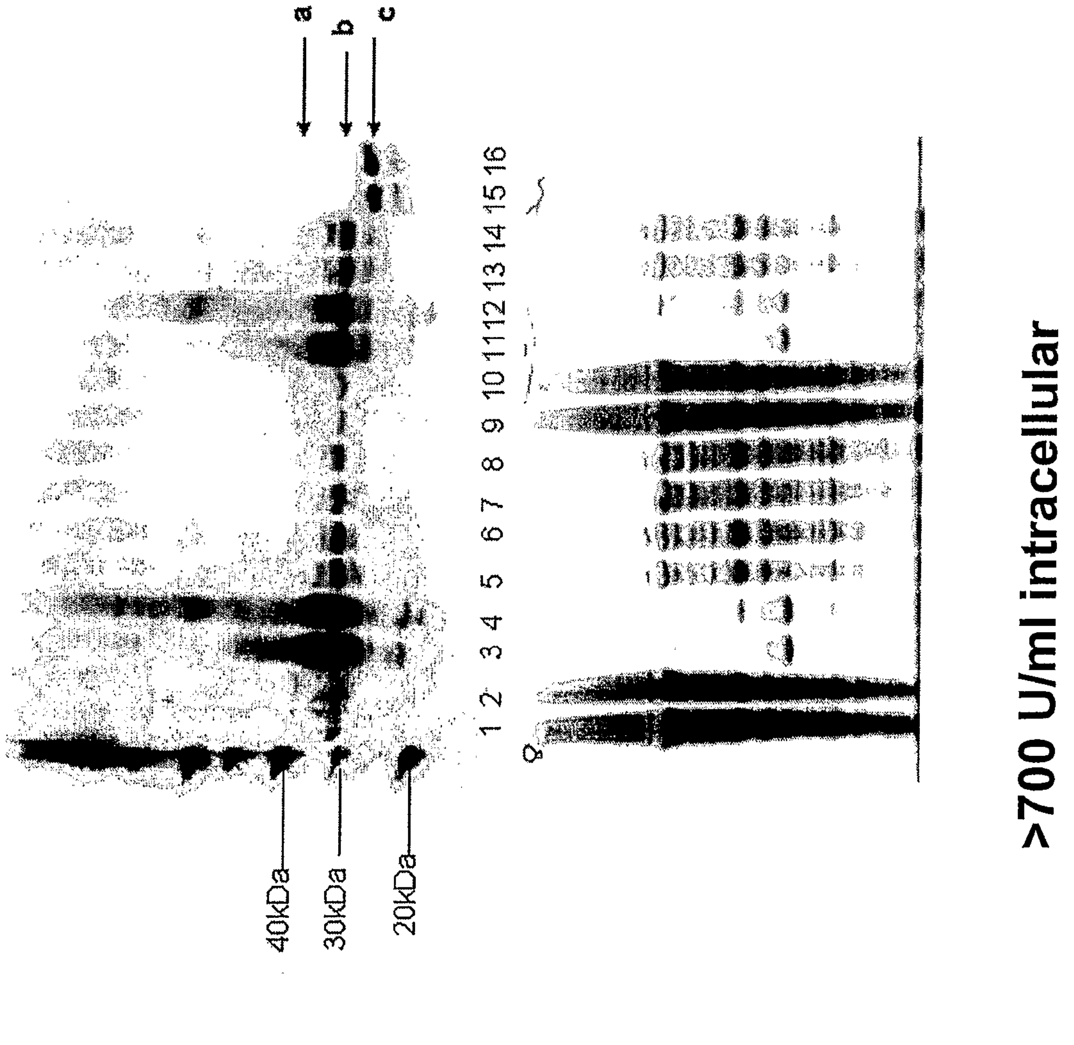

a: Plc + α + glycos
b: Plc + glycos
c: Plc

1. B washed cell
2. H washed cell
3. B Sup
4. H Sup
5. BCell lysate sonicate Sup
6. H Cell lysate sonicate Sup
7. B Cell lysate beads & Zymolyase Sup
8. H Cell lysate beads & Zymolyase Sup
9. B washed cell
10. H washed cell
11. B Sup
12. H Sup
13. B Cell lysate sonicate Sup
14. H Cell lysate sonicate Sup
15. Plc (ex *E. coli*) 0.3μg
16. Plc (ex *E. coli*) 0.6μg 1-8 1μl original culture volume
9-14 0.5μl original culture volume

Figure 26

| tank | Condition | MeOH feed rate | Total MeOH fed | Glucose feed rate | Total glucose fed | Total Base feed | OD600 (88 hr) | **pH stat U/ml (from 5x broth)** |
|---|---|---|---|---|---|---|---|---|
| 1 | Colony #1 from zeo200 culture, 6x DSD | 0.6-1.2 ml/hr | 59 ml | 1.8 ml/hr | 135.3 ml | 55.5 ml | 436 | **3119 @ 75 hr<br>3987 @ 88 hr<br>4138 @ 92 hr** |
| 2 | Colony #2 from zeo200 culture, 6x DSD | 0.6-1.2 ml/hr | 61 ml | 1.8 ml/hr | 135.6 ml | 56.1 ml | 461 | **3511 @ 92 hr** |
| 4 | Colony #4 from zeo200 culture, 6x DSD | 0.6-1.2 ml/hr | 58 ml | 1.8 ml/hr | 135.6 ml | 56.1 ml | 444 | **3354 @ 75 hr<br>3998 @ 88 hr<br>4133 @ 92 hr** |
| 6 | Colony #6 from zeo200 culture, 6x DSD | 0.6-1.2 ml/hr | 48 ml | 1.8 ml/hr | 112.1 ml | 40.2 ml | 445 | **2117 @ 92 hr** |
| 7 | 6x DSD control | 0.6-1.2 ml/hr | 56 ml | 1.8 ml/hr | 135.1 ml | 55.1 ml | 436 | **2369 @ 92 hr** |
| 8 | Duplicate of tank 7 | 0.6-1.2 ml/hr | 53 ml | 1.8 ml/hr | 132.7 ml | 51.9 ml | 428 | **1932 @ 92 hr** |

| ta nk | Condition |
|---|---|
| 1 | Colony #1 from zeo200 culture, 6x DSD |
| 2 | Colony #2 from zeo200 culture, 6x DSD |
| 4 | Colony #4 from zeo200 culture, 6x DSD |
| 6 | Colony #6 from zeo200 culture, 6x DSD |
| 7 | 6x DSD control |
| 8 | Duplicate of tank 7 |

Run 101804, zeocin-adapted 6x DSD

Figure 29
85°C Heating Experiment
- •10U SEQ ID NO:2
- •30min @ 60°C
- •15 min @ 85°C
- •30 min @ 60°C with fresh 10U enzyme dose
Data set 1.27.04
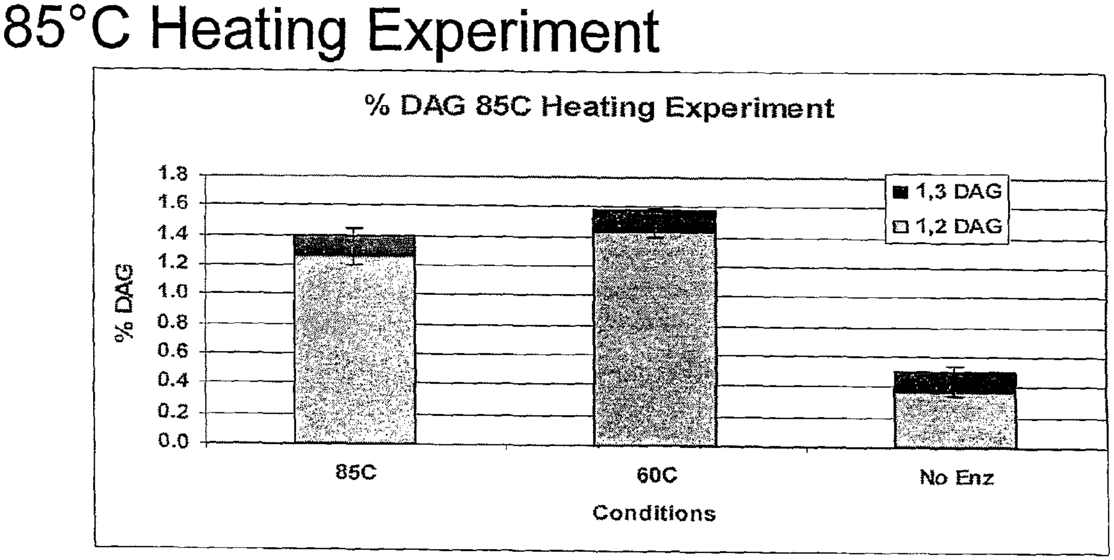
Data set 1.29.04
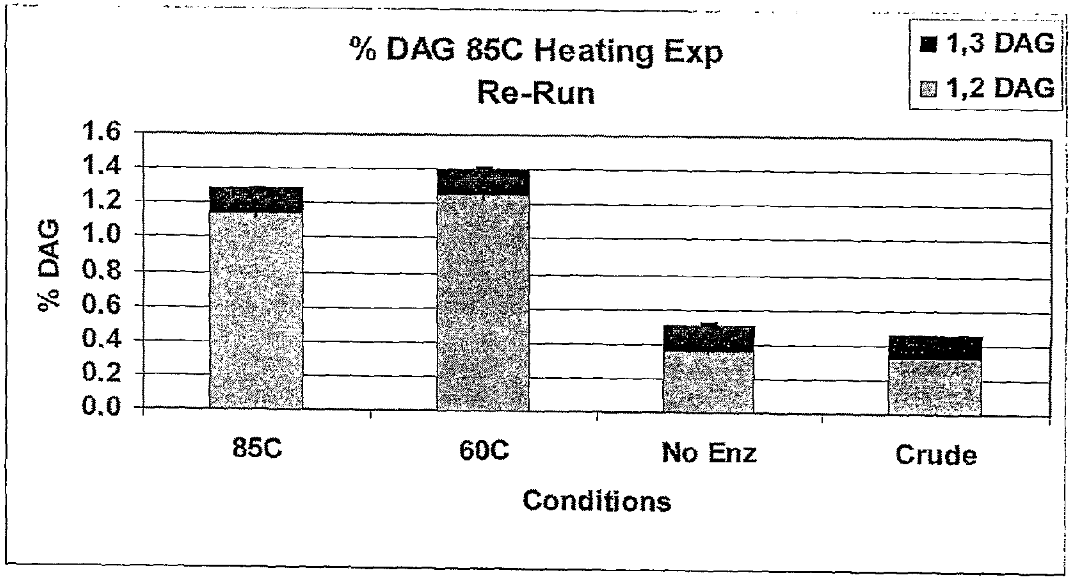

85°C Heating Experiment
NMR Data

Thermal Stability of 3D PLC (SEQ ID NO:2) Using p-NPPC

- 50 °C, 50 min
- 25 µL enzyme in 1 mL 20mM p-NPPC
- Enzyme [ ] = 0.048 mU/mL

Thermal Stability of 3D PLC (SEQ ID NO:2) Using p-NPPC, 80°C

- 80 °C, 50 min
- 25 μL enzyme in 1 mL 20mM p-NPPC
- Enzyme [ ] = 0.024 mU/mL

PHOSPHOLIPASES, NUCLEIC ACIDS ENCODING THEM AND METHODS FOR MAKING AND USING THEM

CROSS-REFERENCE TO RELATED APPLICATIONS

This application is a United States national phase application claiming benefit of priority under 35 U.S.C. §371 to Patent Convention Treaty (PCT) International Application Serial No: PCT/US05/007908, filed Mar. 8, 2005, which is a continuation-in-part (CIP) of and claims the benefit of U.S. patent application Ser. No. ("USSN") 10/796,907, filed Mar. 8, 2004, now U.S. Pat. No. 7,226,771 issued Jun. 5, 2007, which is a CIP of application of U.S. Ser. No. 10/421,654, filed Apr. 21, 2003, now abandoned, which claims the benefit of priority under 35 U.S.C. §119(e) of U.S. Provisional Application No. 60/374,313, filed Apr. 19, 2002; and U.S. Ser. No. 10/796,907, filed Mar. 8, 2004, now U.S. Pat. No. 7,226,771, issued Jun. 5, 2007, is also a CIP of and claims the benefit of priority to Patent Convention Treaty (PCT) International Application Serial No. PCT/US03/12556, filed Apr. 21, 2003, which claims the benefit of priority under 35 U.S.C. §119(e) of U.S. Ser. No. 60/374,313, filed Apr. 19, 2002. The aforementioned applications are explicitly incorporated herein by reference in their entirety and for all purposes.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 564462004202seqlist.txt | Jun. 27, 2007 | 419,443 bytes |

FIELD OF THE INVENTION

This invention relates generally to phospholipase enzymes, polynucleotides encoding the enzymes, methods of making and using these polynucleotides and polypeptides. In particular, the invention provides novel polypeptides having phospholipase activity, nucleic acids encoding them and antibodies that bind to them. Industrial methods and products comprising use of these phospholipases are also provided.

BACKGROUND

Phospholipases are enzymes that hydrolyze the ester bonds of phospholipids. Corresponding to their importance in the metabolism of phospholipids, these enzymes are widespread among prokaryotes and eukaryotes. The phospholipases affect the metabolism, construction and reorganization of biological membranes and are involved in signal cascades. Several types of phospholipases are known which differ in their specificity according to the position of the bond attacked in the phospholipid molecule. Phospholipase A1 (PLA1) removes the 1-position fatty acid to produce free fatty acid and 1-lyso-2-acylphospholipid. Phospholipase A2 (PLA2) removes the 2-position fatty acid to produce free fatty acid and 1-acyl-2-lysophospholipid. PLA1 and PLA2 enzymes can be intra- or extra-cellular, membrane-bound or soluble. Intracellular PLA2 is found in almost every mammalian cell. Phospholipase C (PLC) removes the phosphate moiety to produce 1,2 diacylglycerol and phosphate ester. Phospholipase D (PLD) produces 1,2-diacylglycerophosphate and base group. PLC and PLD are important in cell function and signaling. PLD had been the dominant phospholipase in biocatalysis (see, e.g., Godfrey, T. and West S. (1996) Industrial enzymology, 299-300, Stockton Press, New York). Patatins are another type of phospholipase, thought to work as a PLA (see for example, Hirschberg H J, et al., (2001), Eur J Biochem 268(19):5037-44).

Common oilseeds, such as soybeans, rapeseed, sunflower seeds, rice bran oil, sesame and peanuts are used as sources of oils and feedstock. In the oil extraction process, the seeds are mechanically and thermally treated. The oil is separated and divided from the meal by a solvent. Using distillation, the solvent is then separated from the oil and recovered. The oil is "degummed" and refined. The solvent content in the meal can be evaporated by thermal treatment in a "desolventizer toaster," followed by meal drying and cooling. After a solvent had been separated by distillation, the produced raw oil is processed into edible oil, using special degumming procedures and physical refining. It can also be utilized as feedstock for the production of fatty acids and methyl ester. The meal can be used for animal rations.

Degumming is the first step in vegetable oil refining and it is designed to remove contaminating phosphatides that are extracted with the oil but interfere with the subsequent oil processing. These phosphatides are soluble in the vegetable oil only in an anhydrous form and can be precipitated and removed if they are simply hydrated. Hydration is usually accomplished by mixing a small proportion of water continuously with substantially dry oil. Typically, the amount of water is 75% of the phosphatides content, which is typically 1 to 1.5%. The temperature is not highly critical, although separation of the hydrated gums is better when the viscosity of the oil is reduced at 50° C. to 80° C.

Many methods for oil degumming are currently used. The process of oil degumming can be enzymatically assisted by using phospholipase enzymes. Phospholipases A1 and A2 have been used for oil degumming in various commercial processes, e.g., "ENZYMAX™ degumming" (Lurgi Life Science Technologies GmbH, Germany). Phospholipase C (PLC) also has been considered for oil degumming because the phosphate moiety generated by its action on phospholipids is very water soluble and easy to remove and the diglyceride would stay with the oil and reduce losses; see e.g., Godfrey, T. and West S. (1996) Industrial Enzymology, pp. 299-300, Stockton Press, New York; Dahlke (1998) "An enzymatic process for the physical refining of seed oils," Chem. Eng. Technol. 21:278-281; Clausen (2001) "Enzymatic oil degumming by a novel microbial phospholipase," Eur. J. Lipid Sci. Technol. 103:333-340.

High phosphatide oils such as soy, canola and sunflower are processed differently than other oils such as palm. Unlike the steam or "physical refining" process for low phosphatide oils, these high phosphorus oils require special chemical and mechanical treatments to remove the phosphorus-containing phospholipids. These oils are typically refined chemically in a process that entails neutralizing the free fatty acids to form soap and an insoluble gum fraction. The neutralization process is highly effective in removing free fatty acids and phospholipids but this process also results in significant yield losses and sacrifices in quality. In some cases, the high phosphatide crude oil is degummed in a step preceding caustic neutralization. This is the case for soy oil utilized for lecithin wherein the oil is first water or acid degummed.

Phytosterols (plant sterols) are members of the "triterpene" family of natural products, which includes more than 100 different phytosterols and more than 4000 other types of triterpenes. In general, phytosterols are thought to stabilize plant membranes, with an increase in the sterol/phospholipid ration leading to membrane rigidification. Chemically, phytosterols closely resemble cholesterol in structure and are thought to regulate membrane fluidity in plant membranes, as does cholesterol in animal membranes. The major phytosterols are β-sitosterol, campesterol and stigmasterol. Others include stigmastanol (β-sitostanol), sitostanol, desmosterol, dihydrobrassicasterol, chalinasterol, poriferasterol, clionasterol and brassicasterol.

Plant sterols are important agricultural products for health and nutritional industries. They are useful emulsifiers for cosmetic manufacturers and supply the majority of steroidal intermediates and precursors for the production of hormone pharmaceuticals. The saturated analogs of phytosterols and their esters have been suggested as effective cholesterol-lowering agents with cardiologic health benefits. Plant sterols reduce serum cholesterol levels by inhibiting cholesterol absorption in the intestinal lumen and have immunomodulating properties at extremely low concentrations, including enhanced cellular response of T lymphocytes and cytotoxic ability of natural killer cells against a cancer cell line. In addition, their therapeutic effect has been demonstrated in clinical studies for treatment of pulmonary tuberculosis, rheumatoid arthritis, management of HIV-infested patients and inhibition of immune stress in marathon runners.

Plant sterol esters, also referred to as phytosterol esters, were approved as GRAS (Generally Recognized As Safe) by the US Food and Drug Administration (FDA) for use in margarines and spreads in 1999. In September 2000, the FDA also issued an interim rule that allows health-claims labeling of foods containing phytosterol ester. Consequently enrichment of foods with phytosterol esters is highly desired for consumer acceptance.

Soybean oil is widely used and is an important foodstuff, accounting for ~30% of the oil production from seeds and fruits. Soybeans contain only 20% oil, and the extraction is usually done by using a solvent such as hexane on a commercial scale. The recognized quality of its oil and the nutritive value of the meal protein make soya bean a primary oilseed. Before extraction, soybeans must be cleaned, cracked and flaked as efficient solvent extraction of oil requires that every oil cell is broken to improve the mass transfer. Cell walls mostly composed of cellulose, associated with hemicelluloses, pectic substances and lignin), could also be broken by means of enzymes, to achieve a significant improvement in extraction yields and rates.

Diacylglycerol (DAG) oil is an edible oil containing 80% or greater amount of DAG than natural fatty acids. It has been shown in humans that postprandial elevation of triglyceride in chylomicrons is markedly smaller after ingestion of a DAG oil emulsion compared to a TAG oil with a similar fatty acid composition. In studies using Japanese men and American men and women, long-term DAG oil consumption promoted weight loss and body fat reduction. One study showed that substitution of DAG oil for ordinary cooking oil reduces the incidence of obesity and other risk factors.

SUMMARY OF THE INVENTION

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:199, SEQ ID NO:161, SEQ ID NO:163, SEQ ID NO:165, SEQ ID NO:167, SEQ ID NO:169, SEQ ID NO:171 or SEQ ID NO:173, over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues, and in one aspect the nucleic acid encodes at least one polypeptide having a phospholipase (PL) activity, e.g., a phospholipase A, C or D activity, or any combination of phospholipase activity, for example, a PL A, PL C and/or PL D activity—as a multifunctional activity. In one aspect, the sequence identities are determined by analysis with a sequence comparison algorithm or by a visual inspection.

The invention provides isolated or recombinant nucleic acids comprising a nucleic acid sequence having at least 81%, 82%, 83%, 84%, 85%, 86%, 87%, 88%, 89%, 90%, 91%, 92%, 93%, 94%, 95%, 96%, 97%, 98%, or 99%, or more, or complete (100%) sequence identity to SEQ ID NO:1 over a region of at least about 10, 15, 20, 25, 30, 35, 40, 45, 50, 75, 100, 150, 200, 250, 300, 350, 400, 450, 500, 550, 600, 650, 700, 750, 800, 850 more consecutive residues, and in one aspect the nucleic acid encodes at least one polypeptide having a phospholipase (PL) activity, e.g., a phospholipase A, C or D activity, or any combination of phospholipase activity, for example, a PLA, PL C and/or PL D activity—as a multifunctional activity. In one aspect, the sequence identities are determined by analysis with a sequence comparison algorithm or by a visual inspection.

The invention provides isolated or recombinant nucleic acids comprising a nucleic acid sequence having at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:3 over a region of at least about 10, 15, 20, 25, 30, 35, 40, 45, 50, 75, 100, 150, 200, 250, 300, 350, 400, 450, 500, 550, 600, 650, 700, 750, 800, 850 or more residues, and in one aspect the nucleic acid encodes at least one polypeptide having a phospholipase (PL) activity, e.g., a phospholipase A, C or D activity, or any combination of phospholipase activity, for example, a PL A, PL C and/or PL D activity—as a multifunctional activity. In one aspect, the sequence identities are determined by analysis with a sequence comparison algorithm or by a visual inspection.

The invention provides isolated or recombinant nucleic acids comprising a nucleic acid sequence having at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:5 over a region of at least about 10, 15, 20, 25, 30, 35, 40, 45, 50, 75, 100, 150, 200, 250, 300, 350, 400, 450, 500, 550, 600, 650, 700, 750, 800, 850 or more residues, and in one aspect the nucleic acid encodes at least one polypeptide having a phospholipase (PL) activity, e.g., a phospholipase A, C or D activity, or any combination of phospholipase activity, for example, a PLA, PL C and/or PL D activity—as a multifunctional activity. In one aspect, the sequence identities are determined by analysis with a sequence comparison algorithm or by a visual inspection.

The invention provides isolated or recombinant nucleic acids comprising a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:7 over a region of at least about 10, 15, 20, 25, 30, 35, 40, 45, 50, 75, 100, 150, 200, 250, 300, 350, 400, 450, 500, 550, 600, 650, 700, 750, 800, 850 or more residues, and in one aspect the nucleic acid encodes at least one polypeptide having a phospholipase (PL) activity, e.g., a phospholipase A, C or D activity, or any combination of phospholipase activity, for example, a PL A, PL C and/or PL D activity—as a multifunctional activity. In one aspect, the sequence identities are determined by analysis with a sequence comparison algorithm or by a visual inspection.

In alternative aspects, the isolated or recombinant nucleic acid encodes a polypeptide comprising a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO: 82, SEQ ID NO:84, SEQ ID NO: 86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174. In one aspect these polypeptides have a phospholipase, e.g., a phospholipase A, B, C or D activity, or any combination of phospholipase activity, for example, a PLA, PL C and/or PL D activity—as a multifunctional activity.

In one aspect, the sequence comparison algorithm is a BLAST algorithm, such as a BLAST version 2.2.2 algorithm. In one aspect, the filtering setting is set to blastall-p blastp-d "nr pataa"-F F and all other options are set to default.

In one aspect, the phospholipase activity comprises catalyzing hydrolysis of a glycerolphosphate ester linkage (i.e., cleavage of glycerolphosphate ester linkages). The phospholipase activity can comprise catalyzing hydrolysis of an ester linkage in a phospholipid in a vegetable oil. The vegetable oil phospholipid can comprise an oilseed phospholipid. The phospholipase activity can comprise a phospholipase C (PLC) activity; a phospholipase A (PLA) activity, such as a phospholipase A1 or phospholipase A2 activity; a phospholipase D (PLD) activity, such as a phospholipase D1 or a phospholipase D2 activity; a phospholipase B (PLB) activity, e.g., a phospholipase and a lysophospholipase (LPL) activity or a phospholipase and a lysophospholipase-transacylase (LPTA) activity or a phospholipase and a lysophospholipase (LPL) activity and lysophospholipase-transacylase (LPTA) activity; or patatin activity, or a combination thereof. The phospholipase activity can comprise hydrolysis of a glycoprotein, e.g., as a glycoprotein found in a potato tuber. The phospholipase activity can comprise a patatin enzymatic activity. The phospholipase activity can comprise a lipid acyl hydrolase (LAH) activity. In one aspect, a phospholipase of the invention can have multifunctional activity, e.g., a combination of one or more of the enzyme activities described herein, for example, a phospholipase of the invention can have PLC and PLA activity; PLB and PLA activity; PLC and PLD activity; PLC and PLB activity; PLB and patatin activity; PLC and patatin activity; PLD and PLA; PLD, PLA, PLB and PLC activity; or PLD, PLA, PLB, PLC and patatin activity; or, a phospholipase and a lysophospholipase (LPL) activity or a phospholipase and a lysophospholipase-transacylase (LPTA) activity or a phospholipase and a lysophospholipase (LPL) activity and lysophospholipase-transacylase (LPTA) activity, or any combination thereof.

For example, in one aspect, a polypeptide of the invention is enzymatically active, but lacks a lipase activity, e.g., lacks any enzymatic activity that affects a neutral oil (triglyceride) fraction. It may be desirable to use such a polypeptide in a particular process, e.g., in a degumming process where it is important that the neutral oil fraction not be harmed (diminished, e.g., hydrolyzed). Thus, in one aspect, the invention provides a degumming process comprising use of a polypeptide of the invention having a phospholipase activity, but not a lipase activity.

In one aspect, the isolated or recombinant nucleic acid encodes a polypeptide having a phospholipase activity which is thermostable. The polypeptide can retain a phospholipase activity under conditions comprising a temperature range of between about 20° C. to about 30° C., between about 25° C. to about 40° C., between about 37° C. to about 95° C.; between about 55° C. to about 85° C., between about 70° C. to about 95° C., or, between about 90° C. to about 95° C. In another aspect, the isolated or recombinant nucleic acid encodes a polypeptide having a phospholipase activity which is thermotolerant. The polypeptide can retain a phospholipase activity after exposure to a temperature in the range from greater than 37° C. to about 95° C. or anywhere in the range from greater than 55° C. to about 85° C. In one aspect, the polypeptide retains a phospholipase activity after exposure to a temperature in the range from greater than 90° C. to about 95° C. at pH 4.5.

The polypeptide can retain a phospholipase activity under conditions comprising about pH 8, pH 7.5, pH 7, pH 6.5, pH 6.0, pH 5.5, pH 5, or pH 4.5. The polypeptide can retain a phospholipase activity under conditions comprising a temperature range of between about 40° C. to about 70° C.

In one aspect, the isolated or recombinant nucleic acid comprises a sequence that hybridizes under stringent conditions to a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 or SEQ ID NO:173, wherein the nucleic acid encodes a polypeptide having a phospholipase activity. The nucleic acid can at least about 10, 20, 30, 40, 50, 60, 70, 80, 90, 100, 150, 200, 250, 300, 350, 400, 450, 500, 550, 600, 650, 700, 750, 800, 850 or residues in length or the full length of the gene or transcript, with or without a signal sequence, as described herein. The stringent conditions can be highly stringent, moderately stringent or of low stringency, as described herein. The stringent conditions can include a wash step, e.g., a wash step comprising a wash in 0.2×SSC at a temperature of about 65° C. for about 15 minutes.

The invention provides a nucleic acid probe for identifying a nucleic acid encoding a polypeptide with a phospholipase, e.g., a phospholipase, activity, wherein the probe comprises at least 10, 20, 30, 40, 50, 60, 70, 80, 90, 100, 150, 200, 250, 300, 350, 400, 450, 500, 550, 600, 650, 700, 750, 800, 850, or more, consecutive bases of a sequence of the invention, e.g., a sequence as set forth in SEQ ID NO:1, SEQ ID NO:3, SEQ ID NO:5, or SEQ ID NO:7, and the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence as set forth in SEQ ID NO:1, SEQ ID NO:3, SEQ ID NO:5 and/or SEQ ID NO:7.

The invention provides a nucleic acid probe for identifying a nucleic acid encoding a polypeptide with a phospholipase, e.g., a phospholipase activity, wherein the probe comprises a nucleic acid of the invention, e.g., a nucleic acid having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:1, SEQ ID NO:3, SEQ ID NO:5 and/or SEQ ID NO:7, or a subsequence thereof, over a region of at least about 10, 20, 30, 40, 50, 60, 70, 80, 90, 100, 150, 200, 250, 300, 350, 400, 450, 500, 550, 600, 650, 700, 750, 800, 850 or more consecutive residues; and, in one aspect, the sequence identities are determined by analysis with a sequence comparison algorithm or by visual inspection.

The invention provides an amplification primer sequence pair for amplifying a nucleic acid encoding a polypeptide having a phospholipase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 10, 11, 12, 13, 14, 15, 16, 17, 18, 19, 20, 21, 22, 23, 24, or 25 or more consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, or 25 or more residues of a nucleic acid of the invention, and a second member having a sequence as set forth by about the first (the 5') 12, 13, 14, 15, 16, 17, 18, 19, 20, 21, 22, 23, 24, or 25 or more residues of the complementary strand of the first member.

The invention provides phospholipases generated by amplification, e.g., polymerase chain reaction (PCR), using an amplification primer pair of the invention. The invention provides methods of making a phospholipase by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having a phospholipase activity comprising amplification of a template nucleic acid with an amplification primer sequence pair capable of amplifying a nucleic acid sequence of the invention, or fragments or subsequences thereof. The amplification primer pair can be an amplification primer pair of the invention.

The invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell.

The invention provides transgenic non-human animals comprising a nucleic acid of the invention or an expression cassette (e.g., a vector) of the invention. In one aspect, the animal is a mouse, a rat, a cow, a sheep or another mammal.

The invention provides transgenic plants comprising a nucleic acid of the invention or an expression cassette (e.g., a vector) of the invention. The transgenic plant can be a corn plant, a potato plant, a tomato plant, a wheat plant, an oilseed plant, a rapeseed plant, a soybean plant, a rice plant, a barley plant or a tobacco plant. The invention provides transgenic seeds comprising a nucleic acid of the invention or an expression cassette (e.g., a vector) of the invention. The transgenic seed can be a corn seed, a wheat kernel, an oilseed, a rapeseed (a canola plant), a soybean seed, a palm kernel, a sunflower seed, a sesame seed, a peanut, rice or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of a phospholipase message in a cell comprising administering to the cell or expressing in the cell an antisense oligonucleotide comprising a nucleic acid sequence complementary to or capable of hybridizing under stringent conditions to a nucleic acid of the invention.

The invention provides an antisense oligonucleotide comprising a nucleic acid sequence complementary to or capable of hybridizing under stringent conditions to a nucleic acid of the invention. The invention provides methods of inhibiting the translation of a phospholipase message in a cell comprising administering to the cell or expressing in the cell an antisense oligonucleotide comprising a nucleic acid sequence complementary to or capable of hybridizing under stringent conditions to a nucleic acid of the invention. The antisense oligonucleotide can be between about 10 to 50, about 20 to 60, about 30 to 70, about 40 to 80, about 60 to 100, about 70 to 110, or about 80 to 120 bases in length.

The invention provides methods of inhibiting the translation of a phospholipase, e.g., a phospholipase, message in a cell comprising administering to the cell or expressing in the cell an antisense oligonucleotide comprising a nucleic acid sequence complementary to or capable of hybridizing under stringent conditions to a nucleic acid of the invention. The invention provides double-stranded inhibitory RNA (RNAi) molecules comprising a subsequence of a sequence of the invention. In one aspect, the RNAi is about 15, 16, 17, 18, 19, 20, 21, 22, 23, 24, 25 or more duplex nucleotides in length. The invention provides methods of inhibiting the expression of a phospholipase, e.g., a phospholipase, in a cell comprising administering to the cell or expressing in the cell a double-stranded inhibitory RNA (iRNA), wherein the RNA comprises a subsequence of a sequence of the invention.

The invention provides an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or more, or complete (100%) sequence identity to an exemplary polypeptide or peptide of the invention (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120 or SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174) over a region of at least about 10, 15, 20, 25, 30, 35, 40, 45, 50, 55, 60, 65, 70, 75, 80, 90, 100, 125, 150, 175, 200, 225, 250, 275, 300, 325, 350, 400, 450, 500, 550 or 600 or more residues, or over the full length of the polypeptide; and, in one aspect, the sequence identities are determined by analysis with a sequence comparison algorithm or by a visual inspection.

In one aspect, the invention provides an isolated or recombinant polypeptide comprising an amino acid sequence having at least about 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2. In one aspect, the invention provides an isolated or recombinant polypeptide comprising an amino acid sequence having at least about 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:4. In one aspect, the invention provides an isolated or recombinant polypeptide comprising an amino acid sequence having at least about 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:6. In one aspect, the invention provides an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:8.

The invention provides isolated or recombinant polypeptides encoded by a nucleic acid of the invention. In alternative aspects, the polypeptide can have a sequence as set forth in SEQ ID NO:2, SEQ ID NO:4, SEQ ID NO:6, SEQ ID NO: 8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174. The polypeptide can have a phospholipase activity, e.g., a phospholipase A, B, C or D activity, or any combination of phospholipase activity, for example, a PL A, PL C and/or PL D activity—as a multifunctional activity. For example, in one aspect, a polypeptide of the invention is enzymatically active, but lacks a lipase activity, e.g., lacks any enzymatic activity that affects a neutral oil (triglyceride) fraction. In one aspect, the invention provides a degumming process comprising use of a polypeptide of the invention having a phospholipase activity, but not a lipase activity, such that in the degumming process any neutral oil fraction is not harmed (diminished, altered, degraded, e.g., hydrolyzed).

The invention provides isolated or recombinant polypeptides comprising a polypeptide of the invention lacking a signal sequence. In one aspect, the polypeptide lacking a signal sequence has at least 81%, 82%, 83%, 84%, 85%, 86%, 87%, 88%, 89%, 90%, 91%, 92%, 93%, 94%, 95%, 96%, 97%, 98%, 99% or more sequence identity to residues 30 to 287 of SEQ ID NO:2, an amino acid sequence having at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to residues 25 to 283 of SEQ ID NO:4, an amino acid sequence having at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to residues 26 to 280 of SEQ ID NO:6, or, an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to residues 40 to 330 of SEQ ID NO:8. The sequence identities can be determined by analysis with a sequence comparison algorithm or by visual inspection.

Another aspect of the invention provides an isolated or recombinant polypeptide or peptide including at least 10, 15, 20, 25, 30, 35, 40, 45, 50, 55, 60, 65, 70, 75, 80, 85, 90, 95 or 100 or more consecutive bases of a polypeptide or peptide sequence of the invention, sequences substantially identical thereto, and the sequences complementary thereto. The peptide can be, e.g., an immunogenic fragment, a motif (e.g., a binding site) or an active site.

In one aspect, the isolated or recombinant polypeptide of the invention (with or without a signal sequence) has a phospholipase activity. In one aspect, the phospholipase activity comprises catalyzing hydrolysis of a glycerolphosphate ester linkage (i.e., cleavage of glycerolphosphate ester linkages). The phospholipase activity can comprise catalyzing hydrolysis of an ester linkage in a phospholipid in a vegetable oil. The vegetable oil phospholipid can comprise an oilseed phospholipid. The phospholipase activity can comprise a phospholipase C (PLC) activity; a phospholipase A (PLA) activity, such as a phospholipase A1 or phospholipase A2 activity; a phospholipase D (PLD) activity, such as a phospholipase D1 or a phospholipase D2 activity; a phospholipase B (PLB) activity, e.g., a phospholipase and a lysophospholipase (LPL) activity or a phospholipase and a lysophospholipase-transacylase (LPTA) activity or a phospholipase and a lysophospholipase (LPL) activity and lysophospholipase-transacylase (LPTA) activity; or patatin activity, or a combination thereof. For example, in one aspect a phospholipase comprises a combination of one or more of the enzyme activities described herein, for example, an phospholipase can have PLC and PLA activity; PLB and PLA activity; PLC and PLD activity; PLC and PLB activity; PLB and patatin activity; PLC and patatin activity; PLD and PLA; PLD, PLA, PLB and PLC activity; or PLD, PLA, PLB, PLC and patatin activity; or, a phospholipase and a lysophospholipase (LPL) activity or a phospholipase and a lysophospholipase-transacylase (LPTA) activity or a phospholipase and a lysophospholipase (LPL) activity and lysophospholipase-transacylase (LPTA) activity, or any combination thereof.

The phospholipase activity can comprise hydrolysis of a glycoprotein, e.g., as a glycoprotein found in a potato tuber. The phospholipase activity can comprise a patatin enzymatic activity. The phospholipase activity can comprise a lipid acyl hydrolase (LAH) activity.

In one aspect, the phospholipase activity is thermostable. The polypeptide can retain a phospholipase activity under conditions comprising a temperature range of between about 20 to about 30° C., between about 25° C. to about 40° C., between about 37° C. to about 95° C., between about 55° C. to about 85° C., between about 70° C. to about 95° C., or between about 90° C. to about 95° C. In another aspect, the phospholipase activity can be thermotolerant. The polypeptide can retain a phospholipase activity after exposure to a temperature in the range from greater than 37° C. to about 95° C., or in the range from greater than 55° C. to about 85° C. In one aspect, the polypeptide can retain a phospholipase activity after exposure to a temperature in the range from greater than 90° C. to about 95° C. at pH 4.5.

In one aspect, the polypeptide can retain a phospholipase activity under conditions comprising about pH 6.5, pH 6, pH 5.5, pH 5, pH 4.5 or pH 4 or less (more acidic). In one aspect, the polypeptide can retain a phospholipase activity under conditions comprising about pH 7, pH 7.5 pH 8.0, pH 8.5, pH 9, pH 9.5, pH 10, pH 10.5 or pH 11 or more (more basic).

In one aspect, the isolated or recombinant polypeptide can comprise the polypeptide of the invention that lacks a signal sequence. In one aspect, the isolated or recombinant polypeptide can comprise the polypeptide of the invention comprising a heterologous signal sequence, such as a heterologous phospholipase or non-phospholipase signal sequence.

The invention provides isolated or recombinant peptides comprising an amino acid sequence having at least 95%, 96%, 97%, 98%, 99%, or more sequence identity to residues 1 to 29 of SEQ ID NO:2, at least 95%, 96%, 97%, 98%, 99%, or more sequence identity to residues 1 to 24 of SEQ ID NO:4, at least 95%, 96%, 97%, 98%, 99%, or more sequence identity to residues 1 to 25 of SEQ ID NO:6, or at least 95%, 96%, 97%, 98%, 99%, or more sequence identity to residues 1 to 39 of SEQ ID NO:8, and to other signal sequences as set forth in the SEQ ID listing, wherein the sequence identities are determined by analysis with a sequence comparison algorithm or by visual inspection. These peptides can act as signal sequences on its endogenous phospholipase, on another phospholipase, or a heterologous protein (a non-phospholipase enzyme or other protein). In one aspect, the invention provides chimeric proteins comprising a first domain comprising a signal sequence of the invention and at least a second domain. The protein can be a fusion protein. The second domain can comprise an enzyme. The enzyme can be a phospholipase.

The invention provides chimeric polypeptides comprising at least a first domain comprising signal peptide (SP) of the invention or a catalytic domain (CD), or active site, of a phospholipase of the invention and at least a second domain comprising a heterologous polypeptide or peptide, wherein the heterologous polypeptide or peptide is not naturally associated with the signal peptide (SP) or catalytic domain (CD). In one aspect, the heterologous polypeptide or peptide is not a phospholipase. The heterologous polypeptide or peptide can be amino terminal to, carboxy terminal to or on both ends of the signal peptide (SP) or catalytic domain (CD).

The invention provides isolated or recombinant nucleic acids encoding a chimeric polypeptide, wherein the chimeric polypeptide comprises at least a first domain comprising signal peptide (SP) or a catalytic domain (CD), or active site, of a polypeptide of the invention, and at least a second domain comprising a heterologous polypeptide or peptide, wherein the heterologous polypeptide or peptide is not naturally associated with the signal peptide (SP) or catalytic domain (CD).

In one aspect, the phospholipase activity comprises a specific activity at about 37° C. in the range from about 10 units per milligram to about 100 units per milligram of protein. In another aspect, the phospholipase activity comprises a specific activity from about 100 units per milligram to about 1000 units per milligram, from about 500 units per milligram to about 750 units per milligram of protein. Alternatively, the phospholipase activity comprises a specific activity at 37° C. in the range from about 100 to about 500 units per milligram of protein. In one aspect, the phospholipase activity comprises a specific activity at 37° C. in the range from about 500 to about 1200 units per milligram of protein. In another aspect, the phospholipase activity comprises a specific activity at 37° C. in the range from about 750 to about 1000 units per milligram of protein. In another aspect, the thermotolerance comprises retention of at least half of the specific activity of the phospholipase at 37° C. after being heated to the elevated temperature. Alternatively, the thermotolerance can comprise retention of specific activity at 37° C. in the range from about 500 to about 1200 units per milligram of protein after being heated to the elevated temperature.

The invention provides an isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a *P. pastoris* or a *S. pombe.*

The invention provides phospholipase enzymes, and the nucleic acids that encode them, having a sequence of any of the exemplary phospholipases of the invention with one or more or all of the glycosylation sites altered, as described above. Thus, the invention provides methods of making variant phospholipase coding sequences having increased expression in a host cell, where the method comprises modifying a phospholipase coding sequence of the invention such that one, several or all N-linked glycosylation site coding motifs are modified to a non-glycosylated motif. The invention also provides phospholipase coding sequence made by this process, and the enzymes they encode.

The invention provides methods for making a variant phospholipase coding sequence encoding a phospholipase having increased resistance to a protease comprising modifying an amino acid equivalent to position 131 of SEQ ID NO:2 to one, several or all of the following residues: Lysine (K); Serine (S); Glycine (G); Arginine (R); Glutamine (Q); Alanine (A); Isoleucine (I); Histidine (H); Phenylalanine (F); Threonine (T); Methionine (M) Leucine (L), including variants to SEQ ID NO:2 (and the nucleic acid that encode them) having these exemplary modifications. The invention also provides isolated, synthetic or recombinant phospholipases encoded by a sequence made by this method.

The invention provides methods for making a variant phospholipase coding sequence encoding a phospholipase having decreased resistance to a protease comprising modifying an amino acid equivalent to position 131 of SEQ ID NO:2 to one, several or all of the following residues: Tryptophan (W); Glutamate (E); Tyrosine (Y), including variants to SEQ ID NO:2 (and the nucleic acid that encode them) having these exemplary modifications. The invention also provides isolated, synthetic or recombinant phospholipases encoded by a sequence made by this method.

The invention provides protein preparations comprising a polypeptide of the invention, wherein the protein preparation comprises a liquid, a solid or a gel.

The invention provides heterodimers comprising a polypeptide of the invention and a second protein or domain. The second member of the heterodimer can be a different phospholipase, a different enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having a phospholipase activity, wherein the polypeptide comprises a polypeptide of the invention, a polypeptide encoded by a nucleic acid of the invention, or a polypeptide comprising a polypeptide of the invention and a second domain (e.g., a fusion protein). In one aspect, a polypeptide of the invention is immobilized on a cell, a vesicle, a liposome, a film, a membrane, a metal, a resin, a polymer, a ceramic, a glass, a microelectrode, a graphitic particle, a bead, a gel, a plate, crystals, a tablet, a pill, a capsule, a powder, an agglomerate, a surface, a porous structure, an array or a capillary tube. In one aspect, a polypeptide of the invention is immobilized on materials such as grains, husks, bark, skin, hair, enamel, bone, shell and materials deriving from them, or animal feed materials, or a combination thereof.

Polypeptides of the invention (e.g., phospholipases) can be also present alone or as mixture of phospholipases or phospholipases and other hydrolytic enzymes such as cellulases, xylanases, proteases, lipases, amylases, or redox enzymes such as laccases, peroxidases, catalases, oxidases, or reductases. They can be formulated in a solid form such as a powder, lyophilized preparations, granules, tablets, bars, crystals, capsules, pills, pellets, or in a liquid form such as an aqueous solution, an aerosol, a gel, a paste, a slurry, an aqueous/oil emulsion, a cream, a capsule, vesicular, or micellar suspension. In one aspect, these formulations of the invention can comprise any or a combination of the following ingredients: polyols such as polyethylene glycols, polyvinylalcohols, glycerol, sugars such as sucrose, sorbitol, trehalose, glucose, fructose, maltose, gelling agents such as guar gums, carageenans, alginates, dextrans, cellulosic derivatives, pectins, salts such as sodium chloride, sodium sulfate, ammonium sulfate, calcium chloride, magnesium chloride, zinc chloride, zinc sulfate, salts of fatty acids and their derivatives, metal chelators such as EDTA, EGTA, sodium citrate, antimicrobial agents such as fatty acids, derivatives thereof, parabens, sorbates, benzoates, additionally compounds to block the impact of proteases such as bulk proteins such as BSA, wheat hydrolysates, borate compounds, emulsifiers such as non-ionic and ionic detergents may used alone or in combination, phytosterols, vitamins, amino acids, reducing agents, such as cysteine or antioxidant compounds such as ascorbic acid may be included as well dispersants.

In one aspect, cross-linking and protein modification such as pegylation, fatty acid modification and glycosylation are used to improve the stability of a polypeptide of the invention (e.g., enzyme stability). In one aspect, the polyols and/or sugars comprise from about 5% to about 60%, or more, of the formulation, from about 10% to about 50% of the formulation, from about 20% to about 40% of the formulation, or from about 5% to about 20% of the formulation. In another aspect, the gelling agents comprise from about 0.5% to about 10% of the formulation, from about 1% to about 8% of the formulation, from about 2% to about 5% of the formulation, or from about 0.5% to about 3% of the formulation. In another aspect, the salts such as sodium chloride, sodium sulfate, ammonium sulfate, calcium chloride and/or magnesium chloride comprise from about 1% to about 30% of the formulation, from about 2% to about 20% of the formulation, from about 5% to about 15% of the formulation, or from about 1% to about 10% of the formulation. In another aspect, zinc chloride is present in the formulation at concentrations comprising from about 0.1 mM to about 20 mM, from about 0.5 mM to about 10 mM, from about 1 mM to about 5 mM, or from about 0.1 mM to about 5 mM). In yet another aspect, zinc sulfate is present in the formulation at concentrations comprising from about 0.1 mM to about 20 mM, from about 0.5 mM to about 10 mM, from about 1 mM to about 5 mM, or from about 0.1 mM to about 5 mM). In another aspect, salts of fatty acids and/or their derivatives comprise from about 5% to about 40% of the formulation, from about 10% to about 30% of the formulation, from about 15% to about 25% of the formulation, or from about 5% to about 20% of the formulation. In another aspect, metal chelators such as EDTA, EGTA, and/or sodium citrate are present in the formulation at concentrations comprising from 0.1 mM to about 10 mM), from about 0.5 mM to about 8 mM, from about 1 mM to about 5 mM, or from about 0.1 mM to about 1 mM. In another aspect, antimicrobials such as parabens, sorbates, and/or benzoates comprise from about 0.01% to about 10% of the formulation, from about 0.05% to about 5% of the formulation, from about 0.1% to about 1% of the formulation, or from about 0.05% to about 0.5% of the formulation. In yet another aspect, bulk proteins such as BSA and/or wheat hydrolysates comprise from about 1% to about 20% of the formulation, from about 5% to about 15% of the formulation, from about 2.5% to about 7.5% of the formulation, or from about 1% to about 5% of the formulation. In another aspect, emulsifiers such as non-ionic and/or ionic detergents are present in the formulation at concentrations comprising from about 1× critical micelle concentration (CMC) to about 10×CMC, from about 2.5×CMC to about 7.5×CMC, from about 1× CMC to about 5×CMC, or from about 3×CMC to about 6×CMC. In another aspect, vitamins, amino acids, reducing agents and/or antioxidant compounds comprise from about 0.1% to about 5% of the formulation, from about 0.5% to about 4% of the formulation, from about 1% to about 2.5% of the formulation, or from about 0.1% to about 1% of the formulation.

The invention provides arrays comprising an immobilized polypeptide, wherein the polypeptide is a phospholipase of the invention or is a polypeptide encoded by a nucleic acid of the invention. The invention provides arrays comprising an immobilized nucleic acid of the invention. The invention provides an array comprising an immobilized antibody of the invention.

The invention provides isolated or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention.

The invention provides methods of isolating or identifying a polypeptide with a phospholipase activity comprising the steps of: (a) providing an antibody of the invention; (b) providing a sample comprising polypeptides; and, (c) contacting the sample of step (b) with the antibody of step (a) under conditions wherein the antibody can specifically bind to the polypeptide, thereby isolating or identifying a phospholipase. The invention provides methods of making an anti-phospholipase antibody comprising administering to a non-human animal a nucleic acid of the invention, or a polypeptide of the invention, in an amount sufficient to generate a humoral immune response, thereby making an anti-phospholipase antibody.

The invention provides methods of producing a recombinant polypeptide comprising the steps of: (a) providing a nucleic acid of the invention operably linked to a promoter; and, (b) expressing the nucleic acid of step (a) under conditions that allow expression of the polypeptide, thereby producing a recombinant polypeptide. The nucleic acid can comprise a sequence having at least 85% sequence identity to SEQ ID NO:1 over a region of at least about 100 residues, having at least 80% sequence identity to SEQ ID NO:3 over a region of at least about 100 residues, having at least 80% sequence identity to SEQ ID NO:5 over a region of at least about 100 residues, or having at least 70% sequence identity to SEQ ID NO:7 over a region of at least about 100 residues, wherein the sequence identities are determined by analysis with a sequence comparison algorithm or by visual inspection. The nucleic acid can comprise a nucleic acid that hybridizes under stringent conditions to a nucleic acid as set forth in SEQ ID NO:1, or a subsequence thereof; a sequence as set forth in SEQ ID NO:3, or a subsequence thereof; a sequence as set forth in SEQ ID NO:5, or a subsequence thereof; or, a sequence as set forth in SEQ ID NO:7, or a subsequence thereof. The method can further comprise transforming a host cell with the nucleic acid of step (a) followed by expressing the nucleic acid of step (a), thereby producing a recombinant polypeptide in a transformed cell. The method can further comprise inserting into a host non-human animal the nucleic acid of step (a) followed by expressing the nucleic acid of step (a), thereby producing a recombinant polypeptide in the host non-human animal.

The invention provides methods for identifying a polypeptide having a phospholipase activity comprising the following steps: (a) providing a polypeptide of the invention or a polypeptide encoded by a nucleic acid of the invention, or a fragment or variant thereof, (b) providing a phospholipase substrate; and, (c) contacting the polypeptide or a fragment or variant thereof of step (a) with the substrate of step (b) and detecting an increase in the amount of substrate or a decrease in the amount of reaction product, wherein a decrease in the amount of the substrate or an increase in the amount of the reaction product detects a polypeptide having a phospholipase activity. In alternative aspects, the nucleic acid comprises a sequence having at least 85% sequence identity to SEQ ID NO:1 over a region of at least about 100 residues, having at least 80% sequence identity to SEQ ID NO:3 over a region of at least about 100 residues, having at least 80% sequence identity to SEQ ID NO:5 over a region of at least about 100 residues, or having at least 70% sequence identity to SEQ ID NO: 7 over a region of at least about 100 residues, wherein the sequence identities are determined by analysis with a sequence comparison algorithm or by visual inspection. In alternative aspects the nucleic acid hybridizes under stringent conditions a sequence as set forth in SEQ ID NO:1, or a subsequence thereof; a sequence as set forth in SEQ ID NO:3, or a subsequence thereof; a sequence as set forth in SEQ ID NO:5, or a subsequence thereof; or, a sequence as set forth in SEQ ID NO:7, or a subsequence thereof.

The invention provides methods for identifying a phospholipase substrate comprising the following steps: (a) providing a polypeptide of the invention or a polypeptide encoded by a nucleic acid of the invention; (b) providing a test substrate; and, (c) contacting the polypeptide of step (a) with the test substrate of step (b) and detecting an increase in the amount of substrate or a decrease in the amount of reaction product, wherein a decrease in the amount of the substrate or an increase in the amount of the reaction product identifies the test substrate as a phospholipase substrate. In alternative aspects, the nucleic acid can have at least 85% sequence identity to SEQ ID NO:1 over a region of at least about 100 residues, at least 80% sequence identity to SEQ ID NO:3 over a region of at least about 100 residues, at least 80% sequence identity to SEQ ID NO: 5 over a region of at least about 100 residues, or, at least 70% sequence identity to SEQ ID NO:7 over a region of at least about 100 residues, wherein the sequence identities are determined by analysis with a sequence comparison algorithm or by visual inspection. In alternative aspects, the nucleic acid hybridizes under stringent conditions to a sequence as set forth in SEQ ID NO:1, or a subsequence thereof; a sequence as set forth in SEQ ID NO:3, or a subsequence thereof; a sequence as set forth in SEQ ID NO:5, or a subsequence thereof; or, a sequence as set forth in SEQ ID NO:7, or a subsequence thereof.

The invention provides methods of determining whether a compound specifically binds to a phospholipase comprising the following steps: (a) expressing a nucleic acid or a vector comprising the nucleic acid under conditions permissive for translation of the nucleic acid to a polypeptide, wherein the nucleic acid and vector comprise a nucleic acid or vector of the invention; or, providing a polypeptide of the invention (b) contacting the polypeptide with the test compound; and, (c) determining whether the test compound specifically binds to the polypeptide, thereby determining that the compound specifically binds to the phospholipase. In alternative aspects, the nucleic acid sequence has at least 85% sequence identity to SEQ ID NO:1 over a region of at least about 100 residues, at least 80% sequence identity to SEQ ID NO:3 over a region of at least about 100 residues, least 80% sequence identity to SEQ ID NO:5 over a region of at least about 100 residues, or, at least 70% sequence identity to SEQ ID NO:7 over a region of at least about 100 residues, wherein the sequence identities are determined by analysis with a sequence comparison algorithm or by visual inspection. In alternative aspects, the nucleic acid hybridizes under stringent conditions to a sequence as set forth in SEQ ID NO:1, or a subsequence thereof; a sequence as set forth in SEQ ID NO:3, or a subsequence thereof; a sequence as set forth in SEQ ID NO:5, or a subsequence thereof; or, a sequence as set forth in SEQ ID NO:7, or a subsequence thereof.

The invention provides methods for identifying a modulator of a phospholipase activity comprising the following steps: (a) providing a polypeptide of the invention or a polypeptide encoded by a nucleic acid of the invention; (b) providing a test compound; (c) contacting the polypeptide of step (a) with the test compound of step (b); and, measuring an activity of the phospholipase, wherein a change in the phospholipase activity measured in the presence of the test compound compared to the activity in the absence of the test compound provides a determination that the test compound modulates the phospholipase activity. In alternative aspects, the nucleic acid can have at least 85% sequence identity to SEQ ID NO:1 over a region of at least about 100 residues, at least 80% sequence identity to SEQ ID NO:3 over a region of at least about 100 residues, at least 80% sequence identity to SEQ ID NO:5 over a region of at least about 100 residues, or, at least 70% sequence identity to SEQ ID NO:7 over a region of at least about 100 residues, wherein the sequence identities are determined by analysis with a sequence comparison algorithm or by visual inspection. In alternative aspects, the nucleic acid can hybridize under stringent conditions to a nucleic acid sequence selected from the group consisting of a sequence as set forth in SEQ ID NO:1, or a subsequence thereof; a sequence as set forth in SEQ ID NO:3, or a subsequence thereof; a sequence as set forth in SEQ ID NO:5, or a subsequence thereof; and, a sequence as set forth in SEQ ID NO:7, or a subsequence thereof.

In one aspect, the phospholipase activity is measured by providing a phospholipase substrate and detecting an increase in the amount of the substrate or a decrease in the amount of a reaction product. The decrease in the amount of the substrate or the increase in the amount of the reaction product with the test compound as compared to the amount of substrate or reaction product without the test compound identifies the test compound as an activator of phospholipase activity. The increase in the amount of the substrate or the decrease in the amount of the reaction product with the test compound as compared to the amount of substrate or reaction product without the test compound identifies the test compound as an inhibitor of phospholipase activity.

The invention provides computer systems comprising a processor and a data storage device wherein said data storage device has stored thereon a polypeptide sequence of the invention or a nucleic acid sequence of the invention.

In one aspect, the computer system can further comprise a sequence comparison algorithm and a data storage device having at least one reference sequence stored thereon. The sequence comparison algorithm can comprise a computer program that indicates polymorphisms. The computer system can further comprising an identifier that identifies one or more features in said sequence.

The invention provides computer readable mediums having stored thereon a sequence comprising a polypeptide sequence of the invention or a nucleic acid sequence of the invention.

The invention provides methods for identifying a feature in a sequence comprising the steps of: (a) reading the sequence using a computer program which identifies one or more features in a sequence, wherein the sequence comprises a polypeptide sequence of the invention or a nucleic acid sequence of the invention; and, (b) identifying one or more features in the sequence with the computer program.

The invention provides methods for comparing a first sequence to a second sequence comprising the steps of: (a) reading the first sequence and the second sequence through use of a computer program which compares sequences, wherein the first sequence comprises a polypeptide sequence of the invention or a nucleic acid sequence of the invention; and, (b) determining differences between the first sequence and the second sequence with the computer program. In one aspect, the step of determining differences between the first sequence and the second sequence further comprises the step of identifying polymorphisms. In one aspect, the method further comprises an identifier (and use of the identifier) that identifies one or more features in a sequence. In one aspect, the method comprises reading the first sequence using a computer program and identifying one or more features in the sequence.

The invention provides methods for isolating or recovering a nucleic acid encoding a polypeptide with a phospholipase activity from an environmental sample comprising the steps of: (a) providing an amplification primer sequence pair for amplifying a nucleic acid encoding a polypeptide with a phospholipase activity, wherein the primer pair is capable of amplifying a nucleic acid of the invention (e.g., SEQ ID NO:1, or a subsequence thereof; SEQ ID NO:3, or a subsequence thereof; SEQ ID NO:5, or a subsequence thereof; or SEQ ID NO:7, or a subsequence thereof, etc.); (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide with a phospholipase activity from an environmental sample. In one aspect, each member of the amplification primer sequence pair comprises an oligonucleotide comprising at least about 10 to 50 consecutive bases of a nucleic acid sequence of the invention. In one aspect, the amplification primer sequence pair is an amplification pair of the invention.

The invention provides methods for isolating or recovering a nucleic acid encoding a polypeptide with a phospholipase activity from an environmental sample comprising the steps of: (a) providing a polynucleotide probe comprising a nucleic acid sequence of the invention, or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and, (d) isolating a nucleic acid that specifically hybridizes with the polynucleotide probe of step (a), thereby isolating or recovering a nucleic acid encoding a polypeptide with a phospholipase activity from the environmental sample. In alternative aspects, the environmental sample comprises a water sample, a liquid sample, a soil sample, an air sample or a biological sample. In alternative aspects, the biological sample is derived from a bacterial cell, a protozoan cell, an insect cell, a yeast cell, a plant cell, a fungal cell, an algal (algae) cell, a lichen, or a mammalian cell.

The invention provides methods of generating a variant of a nucleic acid encoding a phospholipase comprising the steps of: (a) providing a template nucleic acid comprising a nucleic acid of the invention; (b) modifying, deleting or adding one or more nucleotides in the template sequence, or a combination thereof, to generate a variant of the template nucleic acid.

In one aspect, the method further comprises expressing the variant nucleic acid to generate a variant phospholipase polypeptide. In alternative aspects, the modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and/or a combination thereof. In alternative aspects, the modifications, additions or deletions are introduced by a method selected from the group consisting of recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and/or a combination thereof.

In one aspect, the method is iteratively repeated until a phospholipase having an altered or different activity or an altered or different stability from that of a phospholipase encoded by the template nucleic acid is produced. In one aspect, the altered or different activity is a phospholipase activity under an acidic condition, wherein the phospholipase encoded by the template nucleic acid is not active under the acidic condition. In one aspect, the altered or different activity is a phospholipase activity under a high temperature, wherein the phospholipase encoded by the template nucleic acid is not active under the high temperature. In one aspect, the method is iteratively repeated until a phospholipase coding sequence having an altered codon usage from that of the template nucleic acid is produced. The method can be iteratively repeated until a phospholipase gene having higher or lower level of message expression or stability from that of the template nucleic acid is produced.

The invention provides methods for modifying codons in a nucleic acid encoding a phospholipase to increase its expression in a host cell, the method comprising (a) providing a nucleic acid of the invention encoding a phospholipase; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a phospholipase, the method comprising (a) providing a nucleic acid of the invention encoding a phospholipase; and, (b) identifying a codon in the nucleic acid of step (a) and replacing it with a different codon encoding the same amino acid as the replaced codon, thereby modifying codons in a nucleic acid encoding a phospholipase.

The invention provides methods for modifying codons in a nucleic acid encoding a phospholipase to increase its expression in a host cell, the method comprising (a) providing a nucleic acid of the invention encoding a phospholipase; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a phospholipase to decrease its expression in a host cell, the method comprising (a) providing a nucleic acid of the invention encoding a phospholipase; and, (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In alternative aspects, the host cell is a bacterial cell, a fungal cell, an insect cell, a yeast cell, a plant cell, an algal (algae) cell, a lichen, or a mammalian cell.

The invention provides methods for producing a library of nucleic acids encoding a plurality of modified phospholipase active sites or substrate binding sites, wherein the modified active sites or substrate binding sites are derived from a first nucleic acid comprising a sequence encoding a first active site or a first substrate binding site the method comprising: (a) providing a first nucleic acid encoding a first active site or first substrate binding site, wherein the first nucleic acid sequence comprises a nucleic acid of the invention; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified phospholipase active sites or substrate binding sites. In alternative aspects, the method comprises mutagenizing the first nucleic acid of step (a) by a method comprising an optimized directed evolution system, Gene Site Saturation Mutagenesis™ (GSSM™), and synthetic ligation reassembly (SLR). The method can further comprise mutagenizing the first nucleic acid of step (a) or variants by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and a combination thereof. The method can further comprise mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the steps of: (a) providing a plurality of biosynthetic enzymes capable of synthesizing or modifying a small molecule, wherein one of the enzymes comprises a phospholipase enzyme encoded by a nucleic acid of the invention; (b) providing a substrate for at least one of the enzymes of step (a); and, (c) reacting the substrate of step (b) with the enzymes under conditions that facilitate a plurality of biocatalytic reactions to generate a small molecule by a series of biocatalytic reactions.

The invention provides methods for modifying a small molecule comprising the steps: (a) providing a phospholipase enzyme encoded by a nucleic acid of the invention; (b) providing a small molecule; and, (c) reacting the enzyme of step (a) with the small molecule of step (b) under conditions that facilitate an enzymatic reaction catalyzed by the phospholipase enzyme, thereby modifying a small molecule by a phospholipase enzymatic reaction. In one aspect, the method comprises providing a plurality of small molecule substrates for the enzyme of step (a), thereby generating a library of modified small molecules produced by at least one enzymatic reaction catalyzed by the phospholipase enzyme. In one aspect, the method further comprises a plurality of additional enzymes under conditions that facilitate a plurality of biocatalytic reactions by the enzymes to form a library of modified small molecules produced by the plurality of enzymatic reactions. In one aspect, the method further comprises the step of testing the library to determine if a particular modified small molecule that exhibits a desired activity is present within the library. The step of testing the library can further comprises the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a phospholipase enzyme comprising the steps of: (a) providing a phospholipase enzyme comprising an amino acid sequence of the invention; and, (b) deleting a plurality of amino acid residues from the sequence of step (a) and testing the remaining subsequence for a phospholipase activity, thereby determining a functional fragment of a phospholipase enzyme. In one aspect, the phospholipase activity is measured by providing a phospholipase substrate and detecting an increase in the amount of the substrate or a decrease in the amount of a reaction product. In one aspect, a decrease in the amount of an enzyme substrate or an increase in the amount of the reaction product with the test compound as compared to the amount of substrate or reaction product without the test compound identifies the test compound as an activator of phospholipase activity.

The invention provides methods for cleaving a glycerolphosphate ester linkage comprising the following steps: (a) providing a polypeptide having a phospholipase activity, wherein the polypeptide comprises an amino acid sequence of the invention, or the polypeptide is encoded by a nucleic acid of the invention; (b) providing a composition comprising a glycerolphosphate ester linkage; and, (c) contacting the polypeptide of step (a) with the composition of step (b) under conditions wherein the polypeptide cleaves the glycerolphosphate ester linkage. In one aspect, the conditions comprise between about pH 5 to about 8.5, or, between about pH 4.5 (or more acidic, i.e., pH<4.5) to about 9.0 (or more alkaline (i.e., pH>9). In one aspect, the conditions comprise a temperature of between about 40° C. and about 70° C. In one aspect, the composition comprises a vegetable oil. In one aspect, the composition comprises an oilseed phospholipid. In one aspect, the cleavage reaction can generate a water extractable phosphorylated base and a diglyceride.

The invention provides methods hydrolyzing, breaking up or disrupting a phospholipid-comprising composition comprising providing at least one polypeptide of the invention having a phospholipase activity, or a polypeptide having a phospholipase activity encoded by at least one nucleic acid of the invention; providing a composition comprising a phospholipid; and contacting the polypeptide with the composition under conditions wherein the phospholipase hydrolyzes, breaks up or disrupts the phospholipid-comprising composition. In one aspect, the method comprises use of high shear mixing of the composition, followed by no or low shear mixing with the at least one polypeptide of the invention having a phospholipase activity to allow adequate "contacting" of the phospholipid substrate with the phospholipase. The at least one polypeptide having a phospholipase activity can also be present in the high shear mixing step. The process can be practiced at any scale, e.g., at a scale comprising about 1 gram (g) to about 500, 1000, 2000, 2500, 5000 g, or more, or any amount in this range.

The invention provides methods for oil degumming comprising the following steps: (a) providing at least one polypeptide having a phospholipase activity, wherein the polypeptide comprises an amino acid sequence of the invention, or the polypeptide is encoded by a nucleic acid of the invention; (b) providing a composition comprising a vegetable oil; and, (c) contacting the polypeptide of step (a) and the vegetable oil of step (b) under conditions wherein the polypeptide can cleave ester linkages in the vegetable oil, thereby degumming the oil. In one aspect, the vegetable oil comprises oilseed. The vegetable oil can comprise rice bran oils, palm oil, rapeseed oil, corn oil, soybean oil, canola oil, sesame oil, peanut oil or sunflower oil. In one aspect, the method further comprises addition of a phospholipase of the invention, another phospholipase or a combination thereof. In one aspect, more than one polypeptide having a phospholipase activity is added to the process, wherein at least one polypeptide is an enzyme of the invention. In one aspect, the enzymes are added in a specific order, e.g., PLCs with differing specificities in are added in a specific order, for example, an enzyme with PC and PE activity is added first (or two enzymes are added together, one with PC and the other with PE activity), then an enzyme with PI PLC activity is added, or any combination thereof.

In one aspect of the oil degumming process, the oil-comprising composition comprises a plant, an animal, an algae or a fish oil or fat. The plant oil can comprise a rice bran oil, a soybean oil, a rapeseed oil, a corn oil, an oil from a palm kernel, a canola oil, a sunflower oil, a sesame oil or a peanut oil. The polypeptide can hydrolyze a phosphatide from a hydratable and/or a non-hydratable phospholipid in the oil-comprising composition. In one aspect, the polypeptide hydrolyzes a phosphatide at a glyceryl phosphoester bond to generate a diglyceride and water-soluble phosphate compound. In one aspect, the polypeptide has a phospholipase C activity. In one aspect, the polypeptide is a phospholipase D and a phosphatase enzyme is also added.

In one aspect of the oil degumming process, the contacting comprises hydrolysis of a hydrated phospholipid in an oil. The hydrolysis conditions can comprise alkaline conditions, e.g., in one aspect, the conditions comprise a temperature of about 20° C. to 40° C. at the alkaline pH. The alkaline conditions can comprise a pH of about pH 8 to pH 10, or more. The hydrolysis conditions can be made alkaline at any time in the process, e.g., in one aspect, a phospholipase, such as a PLC, is added before the conditions are made alkaline (e.g., a "caustic neutralization" of an acid-comprising oil, such as phosphatidic acid).

In one aspect of the oil degumming process, the base causes the isomerization of 1,2-DAG, produced by PLC, into 1,3-DAG which provides a nutritional health benefit over 1,2-DAG, e.g., the 1,3-DAG is burned as energy instead of being stored as fat (as is 1,2-DAG). Thus, the invention provides a caustic oil refining process wherein a phospholipase, e.g., an enzyme of the invention, including a PLC, is added "at the front end", i.e., before adding any acid and caustic, e.g., as illustrated in the exemplary process of FIG. 13. One of the consequences of adding the PLC at the front end of a caustic refining process of the invention (see further discussion, below), and adding the acid and caustic subsequently, is the generation of an elevated level of 1,3-DAG (not 1,2-DAG). This may be a consequence of acid or base-catalyzed acyl migration. Nutritionally, 1,3-DAG is better than 1,2-DAG. Thus, the invention comprises an oil degumming process using a PLC of the invention, whereby the final degummed oil product contains not less than about 0.5%, 1.0%, 2.0%, 3.0%, 4.0% or 5.0% 1,3-DAG.

In one aspect of the oil degumming process, the hydrolysis conditions can comprise a reaction time of about 3 to 10 or more minutes. The hydrolysis conditions can comprise hydrolysis of hydratable and non-hydratable phospholipids in oil at a temperature of between about 50° C. to 60° C., at a pH of between about pH 5 to pH 6.5, or between about pH 5 to pH 7.5, or between about pH 5 to pH 8.0, using a reaction time of about 30 to 60 minutes.

In one aspect of the oil degumming process, the polypeptide is bound to a filter and the phospholipid-containing fat or oil is passed through the filter. The polypeptide can be added to a solution comprising the phospholipid-containing fat or oil and then the solution is passed through a filter.

In one aspect the oil degumming method further comprises physical removal of gum produced by the degumming process by addition of a hardening substance, e.g., a talc or equivalent. In one aspect, this increases oil gain.

The invention also provides methods for converting a non-hydratable phospholipid to a hydratable form comprising the following steps: (a) providing a polypeptide having a phospholipase activity, wherein the polypeptide comprises an amino acid sequence of the invention, or the polypeptide is encoded by a nucleic acid of the invention; (b) providing a composition comprising a non-hydratable phospholipid; and, (c) contacting the polypeptide of step (a) and the non-hydratable phospholipid of step (b) under conditions wherein the polypeptide can cleave ester linkages in the non-hydratable phospholipid, thereby converting a non-hydratable phospholipid to a hydratable form.

The invention provides methods for degumming an oil comprising the following steps: (a) providing a composition comprising a polypeptide of the invention having a phospholipase activity or a polypeptide encoded by a nucleic acid of the invention; (b) providing an composition comprising a fat or an oil comprising a phospholipid; and (c) contacting the polypeptide of step (a) and the composition of step (b) under conditions wherein the polypeptide can degum the phospholipid-comprising composition (under conditions wherein the polypeptide of the invention can catalyze the hydrolysis of a phospholipid). In one aspect the oil-comprising composition comprises a plant, an animal, an algae or a fish oil. The plant oil can comprise a rice bran oil, a soybean oil, a rapeseed oil, a corn oil, an oil from a palm kernel, a canola oil, a sunflower oil, a sesame oil or a peanut oil. The polypeptide can hydrolyze a phosphatide from a hydratable and/or a non-hydratable phospholipid in the oil-comprising composition. The polypeptide can hydrolyze a phosphatide at a glyceryl phosphoester bond to generate a diglyceride and water-soluble phosphate compound. The polypeptide can have a phospholipase C, B, A or D activity. In one aspect, a phospholipase D activity and a phosphatase enzyme are added. The contacting can comprise hydrolysis of a hydrated phospholipid in an oil. The hydrolysis conditions of can comprise a temperature of about 20° C. to 40° C. at an alkaline pH. The alkaline conditions can comprise a pH of about pH 8 to pH 10. The hydrolysis conditions can comprise a reaction time of about 3 to 10 minutes. The hydrolysis conditions can comprise hydrolysis of hydratable and non-hydratable phospholipids in oil at a temperature of about 50° C. to 60° C., at a pH of about pH 5 to pH 6.5 using a reaction time of about 30 to 60 minutes. The polypeptide can be bound to a filter and the phospholipid-containing fat or oil is passed through the filter. The polypeptide can be added to a solution comprising the phospholipid-containing fat or oil and then the solution is passed through a filter.

The invention provides methods for converting a non-hydratable phospholipid to a hydratable form comprising the following steps: (a) providing a composition comprising a polypeptide having a phospholipase activity of the invention, or a polypeptide encoded by a nucleic acid of the invention; (b) providing an composition comprising a non-hydratable phospholipid; and (c) contacting the polypeptide of step (a) and the composition of step (b) under conditions wherein the polypeptide converts the non-hydratable phospholipid to a hydratable form. The polypeptide can have a phospholipase C activity. The polypeptide can have a phospholipase D activity and a phosphatase enzyme is also added.

The invention provides methods for caustic refining of a phospholipid-containing composition comprising the following steps: (a) providing a composition comprising a phospholipase, which can be a polypeptide of the invention having a phospholipase activity, or a polypeptide encoded by a nucleic acid of the invention; (b) providing an composition comprising a phospholipid; and (c) contacting the polypeptide of step (a) with the composition of step (b) before, during or after the caustic refining. The polypeptide can have a phospholipase activity, e.g., PLC, PLB, PLD and/or PLA activity. The polypeptide can be added before caustic refining, i.e., at the "front end" of the process, before adding acid or caustic, as illustrated in FIG. 13.

The polypeptide (which can be an enzyme, e.g., a PLC, of the invention) can be added during caustic refining and varying levels of acid and caustic can be added depending on levels of phosphorus and levels of free fatty acids. The polypeptide (which can be an enzyme of the invention) can be added before caustic refining, or, after caustic refining: in an intense mixer or retention mixer prior to separation; following a heating step; in a centrifuge; in a soapstock; in a washwater; and/or, during bleaching or deodorizing steps. The method can comprise use of concentrated solutions of caustic, e.g., more concentrated than the industrial standard of 11%, to decrease mass of gum. In alternative aspects, the concentrated solution of caustic is between about 12% and 50% concentrated, e.g., about 20%, 30%, 40%, 50% or 60%, or more, concentrated.

The composition comprising the phospholipid can comprise a plant. The polypeptide can be expressed transgenically in the plant. The polypeptide having a phospholipase activity can be added during crushing of a seed or other plant part, or, the polypeptide having a phospholipase activity is added following crushing or prior to refining.

Also provided is a caustic refining process for hydrolyzing phospholipids in oil (e.g., plant oil) using a polypeptide of the invention to generate diacylglycerol (DAG) and water-soluble phosphate ester. In one aspect, the enzyme of the invention must operate in a caustic refining process, including, optionally low water and/or in a temperature range of about 55° C. to about 70° C. Use of a caustic refining process with low water in this temperature range will maximize yield by increasing DAG and reducing entrained oil. In one aspect, the enzyme used in this caustic refining process of the invention has both very good activity on phosphatidylcholine (PC) and phosphatidylethanolamine (PE), is active between a pH of about pH 6 to pH 9, is active up to 75° C., and is active in low water in oil, e.g., about 2% to 5% water, e.g., the enzyme encoded by the sequence of SEQ ID NO:2, encoded e.g., by SEQ ID NO: 1.

In another aspect of the invention's caustic refining process for hydrolyzing phospholipids in oils, two enzymes are used: a PI-specific PLC (hydrolyzes PI), and a PC-PLC that hydrolyzes PC, PE and PA. This embodiment generates oil suitable for chemical or physical refining and maximizes yield increase from DAG and less entrained oil.

The invention provides methods for purification of a phytosterol or a triterpene comprising the following steps: (a) providing a composition comprising a polypeptide of the invention having a phospholipase activity, or a polypeptide encoded by a nucleic acid of the invention; (b) providing an composition comprising a phytosterol or a triterpene; and (c) contacting the polypeptide of step (a) with the composition of step (b) under conditions wherein the polypeptide can catalyze the hydrolysis of a phospholipid in the composition. The polypeptide can have a phospholipase C activity. The phytosterol or a triterpene can comprise a plant sterol. The plant sterol can be derived from a vegetable oil. The vegetable oil can comprise a rice bran oil, a coconut oil, canola oil, cocoa butter oil, corn oil, cottonseed oil, linseed oil, olive oil, palm oil, peanut oil, oil derived from a rice bran, safflower oil, sesame oil, soybean oil or a sunflower oil. The method can comprise use of nonpolar solvents to quantitatively extract free phytosterols and phytosteryl fatty-acid esters. The phytosterol or a triterpene can comprise a β-sitosterol, a campesterol, a stigmasterol, a stigmastanol, a β-sitostanol, a sitostanol, a desmosterol, a chalinasterol, a poriferasterol, a clionasterol or a brassicasterol.

The invention provides methods for refining a crude oil comprising the following steps: (a) providing a composition comprising a polypeptide of the invention having a phospholipase activity, or a polypeptide encoded by a nucleic acid of the invention; (b) providing a composition comprising an oil comprising a phospholipid; and (c) contacting the polypeptide of step (a) with the composition of step (b) under conditions wherein the polypeptide can catalyze the hydrolysis of a phospholipid in the composition. The polypeptide can have a phospholipase C activity. The polypeptide can have a phospholipase activity is in a water solution that is added to the composition. The water level can be between about 0.5 to 5%. The process time can be less than about 2 hours, less than about 60 minutes, less than about 30 minutes, less than 15 minutes, or less than 5 minutes. The hydrolysis conditions can comprise a temperature of between about 25° C.-70° C. The hydrolysis conditions can comprise use of caustics. Concentrated solutions of caustic, e.g., more concentrated than the industrial standard of 11%, to decrease mass of gum can be used. In alternative aspects, the concentrated solution of caustic is between about 12% and 50% concentrated, e.g., about 20%, 30%, 40%, 50%, or 60% or more concentrated.

The hydrolysis conditions can comprise a pH of between about pH 3 and pH 10, between about pH 4 and pH 9, or between about pH 5 and pH 8. The hydrolysis conditions can comprise addition of emulsifiers and/or mixing after the contacting of step (c). The methods can comprise addition of an emulsion-breaker and/or heat or cooling (e.g. to between about 4° C. to about −20° C., or less) to promote separation of an aqueous phase. The methods can comprise degumming before the contacting step to collect lecithin by centrifugation and then adding a PLC, a PLC and/or a PLA to remove non-hydratable phospholipids. The methods can comprise water degumming of crude oil to less than 10 ppm phosphorus for edible oils and subsequent physical refining to less than about 50 ppm phosphorus for biodiesel oils. The methods can comprise addition of acid to promote hydration of non-hydratable phospholipids. In one aspect, addition of acid promotes lowering of the calcium and magnesium metal content.

The invention provides a method for ameliorating or preventing lipopolysaccharide (LPS)-mediated toxicity comprising administering to a patient a pharmaceutical composition comprising a polypeptide of the invention. The invention provides a method for detoxifying an endotoxin comprising contacting the endotoxin with a polypeptide of the invention. The invention provides a method for deacylating a 2' or a 3' fatty acid chain from a lipid A comprising contacting the lipid A with a polypeptide of the invention.

The invention provides a method for refining a lubricant comprising the following steps: (a) providing a composition comprising an enzyme of the invention; (b) providing a lubricant; and (c) treating the lubricant with an enzyme under conditions wherein the enzyme can selective hydrolyze oils in the lubricant, thereby refining it. The lubricant can be a hydraulic oil.

The invention provides a method of treating a fabric comprising the following steps: (a) providing a composition comprising an enzyme of the invention, (b) providing a fabric; and (c) treating the fabric with the enzyme. The treatment of the fabric can comprise improvement of the hand and drape of the final fabric, dyeing, obtaining flame retardancy, obtaining water repellency, obtaining optical brightness, or obtaining resin finishing. The fabric can comprise cotton, viscose, rayon, lyocell, flax, linen, ramie, all blends thereof, or blends thereof with polyesters, wool, polyamides acrylics or polyacrylics. The invention provides a fabric, yarn or fiber comprising an enzyme of the invention. The enzyme can be adsorbed, absorbed or immobilized on the surface of the fabric, yarn or fiber.

The invention provides methods for expressing phospholipase C comprising providing a *Pichia* strain with a $Mut^+$ phenotype; inserting a heterologous phospholipase C-encoding nucleic acid in the *Pichia* strain; and, culturing the *Pichia* strain under conditions whereby the phospholipase C is expressed. The method can further comprise supplementing the culture conditions with zinc. The invention also provides cell systems, isolated cells and cell lines for expressing phospholipase C comprising a $Mut^+$ phenotype *Pichia* strain comprising a heterologous phospholipase C-encoding nucleic acid operably linked to a promoter operable in the *Pichia* strain.

The invention provides zeocin-resistant yeast cell systems (e.g., yeast cells, cell lines, individual cells) for expressing a heterologous protein comprising the steps of providing a *Pichia* sp. (e.g., *P. pastoris*) cell comprising a heterologous nucleic acid capable of expressing a heterologous protein; culturing the cell under conditions comprising zeocin at an initial concentration; selecting cells resistant to the initial concentration of zeocin, and reculturing under conditions comprising a higher concentration of zeocin; and selecting the cells cultured in step (c) resistant to the higher concentration of zeocin. In one aspect, the heterologous protein is an enzyme, or optionally, a phospholipase, or optionally a phospholipase C (PLC), e.g., any enzyme of the invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims.

FIG. 11 is a chart describing selected characteristics of exemplary nucleic acids and polypeptides of the invention, as described in further detail, below.

FIG. 17 illustrates the results of the in vitro digestion experiments wherein the phospholipase C variants of the invention, as discussed in detail in Example 4, below.

FIG. 23 illustrates results from an SDS-PAGE showing the quantity of active PLC located intracellularly in a culture of a recombinant form of the exemplary PLC enzyme of the invention SEQ ID NO:2, as discussed in detail in Example 5, below.

FIG. 26 is a table summary of data from expression screening of exemplary zeocin-adapted cell colonies of the invention, as discussed in detail in Example 5, below.

FIG. 29 illustrates the results of a heating experiment demonstrating the thermostability of the exemplary enzyme of the invention SEQ ID NO:2, with the conditions indicated in the figure, as discussed in detail in Example 6, below.

Like reference symbols in the various drawings indicate like elements.

DETAILED DESCRIPTION OF THE INVENTION

Figure 1:
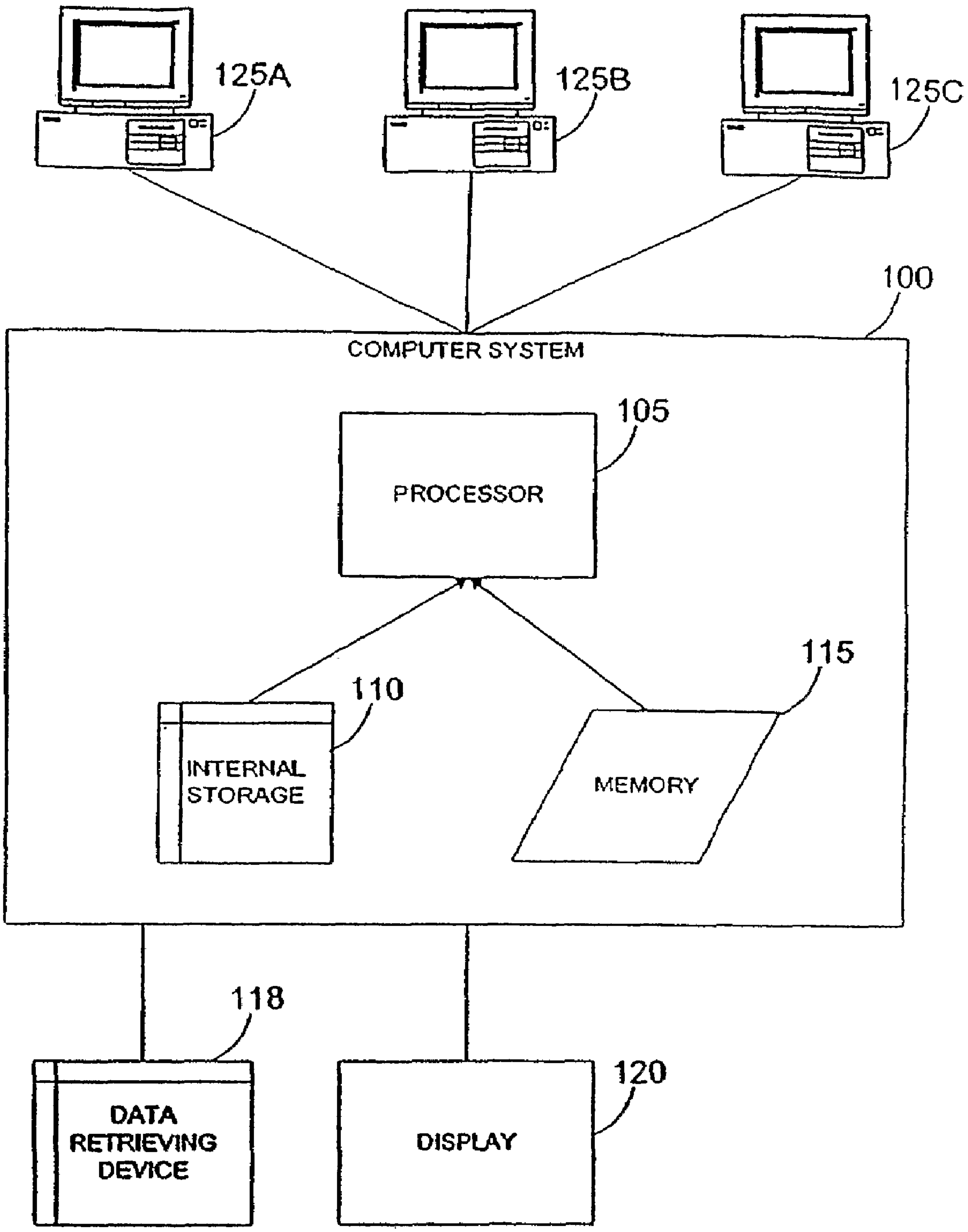
FIG. 1 is a block diagram of a computer system, as described in detail, below.

The present invention provides phospholipases, e.g., polypeptides having phospholipase A, B, C, D, patatin, phosphatidic acid phosphatases (PAP) and/or lipid acyl hydrolase (LAH) or equivalent activity, polynucleotides encoding them and methods for making and using them. The invention provides enzymes that efficiently cleave glycerolphosphate ester linkage in oils, such as vegetable oils, e.g., oilseed phospholipids, to generate a water extractable phosphorylated base and a diglyceride. In one aspect, the phospholipases of the invention have a lipid acyl hydrolase (LAH) activity. In alternative aspects, the phospholipases of the invention can cleave glycerolphosphate ester linkages in phosphatidylcholine (PC), phosphatidylethanolamine (PE), phosphatidylserine (PS), phosphatidylinositol (PI), phosphatidic acid, and/or sphingomyelin, or a combination thereof. For example, in one aspect a phospholipase of the invention is specific for one or more specific substrates, e.g., an enzyme of the invention can have a specificity of action for PE and PC; PE an PI; PE and PS; PS and PE; PS and PI; PI and PE; PS, PI and PC; PE, PI and PC; or, PE, PS, PI and PC.

A phospholipase of the invention (e.g., polypeptides having phospholipase A, B, C, D, patatin, phosphatidic acid phosphatases (PAP) and/or lipid acyl hydrolase (LAH) or equivalent activity) can be used for enzymatic degumming of vegetable oils because the phosphate moiety is soluble in water and easy to remove. The diglyceride product will remain in the oil and therefore will reduce losses. The PLCs of the invention can be used in addition to or in place of PLA1s and PLA2s in commercial oil degumming, such as in the ENZYMAX® process, where phospholipids are hydrolyzed by PLA1 and PLA2.

In one aspect, the phospholipases of the invention are active at a high and/or at a low temperature, or, over a wide range of temperature, e.g., they can be active in the temperatures ranging between 20° C. to 90° C., between 30° C. to 80° C., or between 40° C. to 70° C. The invention also provides phospholipases of the invention have activity at alkaline pHs or at acidic pHs, e.g., low water acidity. In alternative aspects, the phospholipases of the invention can have activity in acidic pHs as low as pH 6.5, pH 6.0, pH 5.5, pH 5.0, pH 4.5, pH 4.0 and pH 3.5 or more acidic (i.e., <pH 3.5). In alternative aspects, the phospholipases of the invention can have activity in alkaline pHs as high as pH 7.5, pH 8.0, pH 8.5, pH 9.0, pH 9.5, pH 10 or more alkaline (i.e., >pH 10). In one aspect, the phospholipases of the invention are active in the temperature range of between about 40° C. to about 70° C., 75° C., or 80° C., or more, under conditions of low water activity (low water content).

The invention also provides methods for further modifying the exemplary phospholipases of the invention to generate enzymes with desirable properties. For example, phospholipases generated by the methods of the invention can have altered substrate specificities, substrate binding specificities, substrate cleavage patterns, thermal stability, pH/activity profile, pH/stability profile (such as increased stability at low, e.g. pH<6 or pH<5, or high, e.g. pH>9, pH values), stability towards oxidation, $Ca^{2+}$ dependency, specific activity and the like. The invention provides for altering any property of interest. For instance, the alteration may result in a variant which, as compared to a parent phospholipase, has altered pH and temperature activity profile.

In one aspect, the phospholipases of the invention are used in various vegetable oil processing steps, such as in vegetable oil extraction, particularly, in the removal of "phospholipid gums" in a process called "oil degumming," as described herein. The invention provides compositions (e.g., comprising enzymes of the invention) and processes for the production of vegetable oils from various sources, such as oil from rice bran, soybeans, rapeseed, peanut, sesame, sunflower and corn. The phospholipase enzymes of the invention can be used in place of PLA, e.g., phospholipase A2, in any vegetable oil processing step.

Definitions

The term "phospholipase" encompasses enzymes having any phospholipase activity, for example, cleaving a glycerolphosphate ester linkage (catalyzing hydrolysis of a glycerolphosphate ester linkage), e.g., in an oil, such as a vegetable oil. The phospholipase activity of the invention can generate a water extractable phosphorylated base and a diglyceride. The phospholipase activity of the invention also includes hydrolysis of glycerolphosphate ester linkages at high temperatures, low temperatures, alkaline pHs and at acidic pHs. The term "a phospholipase activity" also includes cleaving a glycerolphosphate ester to generate a water extractable phosphorylated base and a diglyceride. The term "a phospholipase activity" also includes cutting ester bonds of glycerin and phosphoric acid in phospholipids. The term "a phospholipase activity" also includes other activities, such as the ability to bind to and hydrolyze a substrate, such as an oil, e.g. a vegetable oil, substrate also including plant and animal phosphatidylcholines, phosphatidyl-ethanolamines, phosphatidylserines and sphingomyelins. The phospholipase activity can comprise a phospholipase C (PLC) activity; a phospholipase A (PLA) activity, such as a phospholipase A1 or phospholipase A2 activity; a phospholipase B (PLB) activity, such as a phospholipase B1 or phospholipase B2 activity, including lysophospholipase (LPL) activity and/or lysophospholipase-transacylase (LPTA) activity; a phospholipase D (PLD) activity, such as a phospholipase D1 or a phospholipase D2 activity; and/or a patatin activity or any combination thereof. The phospholipase activity can comprise hydrolysis of a glycoprotein, e.g., as a glycoprotein found in a potato tuber or any plant of the genus *Solanum*, e.g., *Solanum tuberosum*. The phospholipase activity can comprise a patatin enzymatic activity, such as a patatin esterase activity (see, e.g., Jimenez (2002) Biotechnol. Prog. 18:635-640). The phospholipase activity can comprise a lipid acyl hydrolase (LAH) activity. The phospholipase activity can comprise being specific for one or more specific substrates, e.g., an enzyme of the invention can have a specificity of action for PE and PC; PE an PI; PE and PS; PS and PE; PS and PI; PI and PE; PS, PI and PC; PE, PI and PC; or, PE, PS, PI and PC, or any combination thereof.

In one aspect, a phospholipase of the invention can have multifunctional activity, e.g., a combination of one or more of the enzyme activities described herein. For example, in one aspect, a polypeptide of the invention is enzymatically active, but lacks a lipase activity or lacks any enzymatic activity that affects a neutral oil (triglyceride) fraction. It may be desirable to use such a polypeptide in a particular process, e.g., in a degumming process where it is important that the neutral oil fraction not be harmed (diminished, degraded, e.g., hydrolyzed). Thus, in one aspect, the invention provides a degumming process comprising use of a polypeptide of the invention having a phospholipase activity, but not a lipase activity.

In one aspect, PLC phospholipases of the invention utilize (e.g., catalyze hydrolysis of) a variety of phospholipid substrates including phosphatidylcholine (PC), phosphatidylethanolamine (PE), phosphatidylserine (PS), phosphatidylinositol (PI), and/or phosphatidic acid or a combination thereof. In addition, these enzymes can have varying degrees of activity on the lysophospholipid forms of these phospholipids. In various aspects, PLC enzymes of the invention may show a preference for phosphatidylcholine and phosphatidylethanolamine as substrates.

In one aspect, phosphatidylinositol PLC phospholipases of the invention utilize a variety of phospholipid substrates including phosphatidylcholine, phosphatidylethanolamine, phosphatidylserine, phosphatidylinositol, and phosphatidic acid, or a combination thereof. In addition, these enzymes can have varying degrees of activity on the lysophospholipid forms of these phospholipids. In various aspects, phosphatidylinositol PLC enzymes of the invention may show a preference for phosphatidylinositol as a substrate.

In one aspect, patatin enzymes of the invention utilize a variety of phospholipid substrates including phosphatidylcholine, phosphatidylethanolamine, phosphatidylserine, phosphatidylinositol, and phosphatidic acid, or a combination thereof. In addition, these enzymes can have varying degrees of activity on the lysophospholipid forms of these phospholipids. In various aspects, patatins of the invention are based on a conservation of amino acid sequence similarity. In various aspects, these enzymes display a diverse set of biochemical properties and may perform reactions characteristic of PLA1, PLA2, PLC, or PLD enzyme classes.

In one aspect, PLD phospholipases of the invention utilize a variety of phospholipid substrates including phosphatidylcholine, phosphatidylethanolamine, phosphatidylserine, phosphatidylinositol, and phosphatidic acid, or a combination thereof. In addition, these enzymes can have varying degrees of activity on the lysophospholipid forms of these phospholipids. In one aspect, these enzymes are useful for carrying out transesterification reactions to produce structured phospholipids.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below.

A "coding sequence of" or a "sequence encodes" a particular polypeptide or protein, is a nucleic acid sequence which is transcribed and translated into a polypeptide or protein when placed under the control of appropriate regulatory sequences.

The term "expression cassette" as used herein refers to a nucleotide sequence which is capable of affecting expression of a structural gene (i.e., a protein coding sequence, such as a phospholipase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers.

"Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

The term "gene" means the segment of DNA involved in producing a polypeptide chain, including, inter alia, regions preceding and following the coding region, such as leader and trailer, promoters and enhancers, as well as, where applicable, intervening sequences (introns) between individual coding segments (exons).

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Amino acid" or "amino acid sequence" as used herein refer to an oligopeptide, peptide, polypeptide, or protein sequence, or to a fragment, portion, or subunit of any of these, and to naturally occurring or synthetic molecules.

The terms "polypeptide" and "protein" as used herein, refer to amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" means that the nucleic acid is adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 15%, 20%, 30%, 40%, 50%, 60%, 70%, 80%, 90% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence is "operably linked to" a coding sequence when RNA polymerase which initiates transcription at the promoter will transcribe the coding sequence into mRNA, as discussed further, below.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 75%, 80%, 85%, 90%, 95%, 98% or 99% nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO: 8, etc., over a region of at least about 100 residues, 150 residues, 200 residues, 300 residues, 400 residues, or a region ranging from between about 50 residues to the full length of the nucleic acid or polypeptide. Nucleic acid sequences of the invention can be substantially identical over the entire length of a polypeptide coding region.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a phospholipase polypeptide, resulting in modification of the structure of the polypeptide, without significantly altering its biological activity. For example, amino- or carboxyl-terminal amino acids that are not required for phospholipase biological activity can be removed. Modified polypeptide sequences of the invention can be assayed for phospholipase biological activity by any number of methods, including contacting the modified polypeptide sequence with a phospholipase substrate and determining whether the modified polypeptide decreases the amount of specific substrate in the assay or increases the bioproducts of the enzymatic reaction of a functional phospholipase with the substrate, as discussed further, below.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

The term "variant" refers to polynucleotides or polypeptides of the invention modified at one or more base pairs, codons, introns, exons, or amino acid residues (respectively) yet still retain the biological activity of a phospholipase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM™ and any combination thereof. Techniques for producing variant phospholipases having activity at a pH or temperature, for example, that is different from a wild-type phospholipase, are included herein.

The term "saturation mutagenesis", Gene Site Saturation Mutagenesis™ (GSSM™) or "GSSM™" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides isolated and recombinant nucleic acids (e.g., the exemplary SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 or SEQ ID NO:173), including expression cassettes such as expression vectors, encoding the polypeptides and phospholipases of the invention. The invention also includes methods for discovering new phospholipase sequences using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression vectors and cloning vehicles comprising nucleic acids of the invention, e.g., sequences encoding the phospholipases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *Bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector may comprise a promoter, a ribosome-binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding a phospholipase of the invention, a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Enzymes of the invention can be expressed in any host cell, e.g., any bacterial cell, any yeast cell, e.g., *Pichia pastoris, Saccharomyces cerevisiae* or *Schizosaccharomyces pombe*. Exemplary bacterial cells include *E. coli, Lactococcus lactis, Streptomyces, Bacillus subtilis, Bacillus cereus, Salmonella typhimurium* or any species within the genera *Bacillus, Streptomyces* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

An exemplary phospholipase C enzyme (having a sequence as set forth in SEQ ID NO:2) has been over-expressed in active form in a variety of host systems including gram negative bacteria, such as *E. coli*, gram positive bacteria, such as any *Bacillus* sp. (e.g., *Bacillus subtilis, Bacillis cereus*), yeast host cells (including, e.g., *Pichia pastoris, Saccharomyces* sp., such as *S. cerevisiae* and *S. pombe*) and *Lactococcus* lactis, or mammalian, fingi, plant or insect cells. The active enzyme is expressed from a variety of constructs in each host system. These nucleic acid expression constructs can comprise nucleotides encoding the full-length open reading frame (composed of the signal sequence, the pro-sequence, and the mature protein coding sequence) or they can comprise a subset of these genetic elements either alone or in combination with heterologous genetic elements that serve as the signal sequence and/or the pro-sequence for the mature open reading frame. Each of these systems can serve as a commercial production host for the expression of PLC for use in the previously described enzymatic oil degumming processes.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with a phospholipase activity. In one aspect, the primer pairs are capable of amplifying nucleic acid sequences of the invention, e.g., including the exemplary SEQ ID NO:1, or a subsequence thereof; a sequence as set forth in SEQ ID NO:3, or a subsequence thereof; a sequence as set forth in SEQ ID NO:5, or a subsequence thereof; and, a sequence as set forth in SEQ ID NO:7, or a subsequence thereof, etc. One of skill in the art can design amplification primer sequence pairs for any part of or the full length of these sequences.

The invention provides an amplification primer sequence pair for amplifying a nucleic acid encoding a polypeptide having a phospholipase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, or 25 consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, or 25 residues of a nucleic acid of the invention, and a second member having a sequence as set forth by about the first (the 5') 12, 13, 14, 15, 16, 17, 18, 19, 20, 21, 22, 23, 24, or 25 residues of the complementary strand of the first member. The invention provides phospholipases generated by amplification, e.g., polymerase chain reaction (PCR), using an amplification primer pair of the invention. The invention provides methods of making a phospholipase by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides isolated and recombinant nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 or SEQ ID NO:173, and nucleic acids encoding SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters. In alternative embodiments, the sequence identify can be over a region of at least about 5, 10, 20, 30, 40, 50, 100, 150, 200, 250, 300, 350, 400 consecutive residues, or the full length of the nucleic acid or polypeptide. The extent of sequence identity (homology) may be determined using any computer program and associated parameters, including those described herein, such as BLAST 2.2.2. or FASTA version 3.0t78, with the default parameters.

FIG. 11 is a chart describing selected characteristics of exemplary nucleic acids and polypeptides of the invention, including sequence identity comparison of the exemplary sequences to public databases. All sequences described in FIG. 11 have been subject to a BLAST search (as described in detail, below) against two sets of databases. The first database set is available through NCBI (National Center for Biotechnology Information). All results from searches against these databases are found in the columns entitled “NR Description”, “NR Accession Code”, “NR Evalue” or “NR Organism”. “NR” refers to the Non-Redundant nucleotide database maintained by NCBI. This database is a composite of GenBank, GenBank updates, and EMBL updates. The entries in the column “NR Description” refer to the definition line in any given NCBI record, which includes a description of the sequence, such as the source organism, gene name/protein name, or some description of the function of the sequence. The entries in the column “NR Accession Code” refer to the unique identifier given to a sequence record. The entries in the column “NR Evalue” refer to the Expect value (Evalue), which represents the probability that an alignment score as good as the one found between the query sequence (the sequences of the invention) and a database sequence would be found in the same number of comparisons between random sequences as was done in the present BLAST search. The entries in the column “NR Organism” refer to the source organism of the sequence identified as the closest BLAST hit. The second set of databases is collectively known as the Geneseq™ database, which is available through Thomson Derwent (Philadelphia, Pa.). All results from searches against this database are found in the columns entitled “Geneseq Protein Description”, “Geneseq Protein Accession Code”, “Geneseq Protein Evalue”, “Geneseq DNA Description”, “Geneseq DNA Accession Code” or “Geneseq DNA Evalue”. The information found in these columns is comparable to the information found in the NR columns described above, except that it was derived from BLAST searches against the Geneseq database instead of the NCBI databases. In addition, this table includes the column “Predicted EC No.”. An EC number is the number assigned to a type of enzyme according to a scheme of standardized enzyme nomenclature developed by the Enzyme Commission of the Nomenclature Committee of the International Union of Biochemistry and Molecular Biology (IUBMB). The results in the “Predicted EC No.” column are determined by a BLAST search against the Kegg (Kyoto Encyclopedia of Genes and Genomes) database. If the top BLAST match has an Evalue equal to or less than $e^{-6}$, the EC number assigned to the top match is entered into the table. The EC number of the top hit is used as a guide to what the EC number of the sequence of the invention might be. The columns “Query DNA Length” and “Query Protein Length” refer to the number of nucleotides or the number amino acids, respectively, in the sequence of the invention that was searched or queried against either the NCBI or Geneseq databases. The columns “Geneseq or NR DNA Length” and “Geneseq or NR Protein Length” refer to the number of nucleotides or the number amino acids, respectively, in the sequence of the top match from the BLAST search. The results provided in these columns are from the search that returned the lower Evalue, either from the NCBI databases or the Geneseq database. The columns “Geneseq or NR % ID Protein” and “Geneseq or NR % ID DNA” refer to the percent sequence identity between the sequence of the invention and the sequence of the top BLAST match. The results provided in these columns are from the search that returned the lower Evalue, either from the NCBI databases or the Geneseq database.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms “homology” and “identity” in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, etc.) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous residues. For example, in alternative aspects of the invention, contiguous residues ranging anywhere from 20 to the full length of an exemplary sequence of the invention, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, etc., are compared to a reference sequence of the same number of contiguous positions after the two sequences are optimally aligned. If the reference sequence has the requisite sequence identity to an exemplary sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO: 8, etc., that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used. default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention, and to determine the values in FIG. 11, as discussed above, include:

"Filter for low complexity: ON

>Word Size: 3

>Matrix: Blosum62

>Gap Costs: Existence: 11

>Extension: 1"

Other default settings are: filter for low complexity OFF, word size of 3 for protein, BLOSUM62 matrix, gap existence penalty of −11 and a gap extension penalty of −1.

An exemplary NCBI BLAST 2.2.2 program setting is set forth in Example 1, below. Note that the "−W" option defaults to 0. This means that, if not set, the word size defaults to 3 for proteins and 11 for nucleotides.

Computer Systems and Computer Program Products

To determine and identify sequence identities, structural homologies, motifs and the like in silico, a polypeptide or nucleic acid sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention, e.g., an exemplary sequence of the invention, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, etc. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media, magnetic/optical media, flash memories. For example, the computer readable media may be a hard disk, a floppy disk, a magnetic tape, a flash memory, CD-ROM, Digital Versatile Disk (DVD), Random Access Memory (RAM), or Read Only Memory (ROM), or any type of media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100. Software for accessing and processing the nucleotide or amino acid sequences of the invention can reside in main memory 115 during execution.

In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of an exemplary sequence, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, etc. stored on a computer readable medium to reference sequences stored on a computer readable medium to identify homologies or structural motifs.

Figure 2:
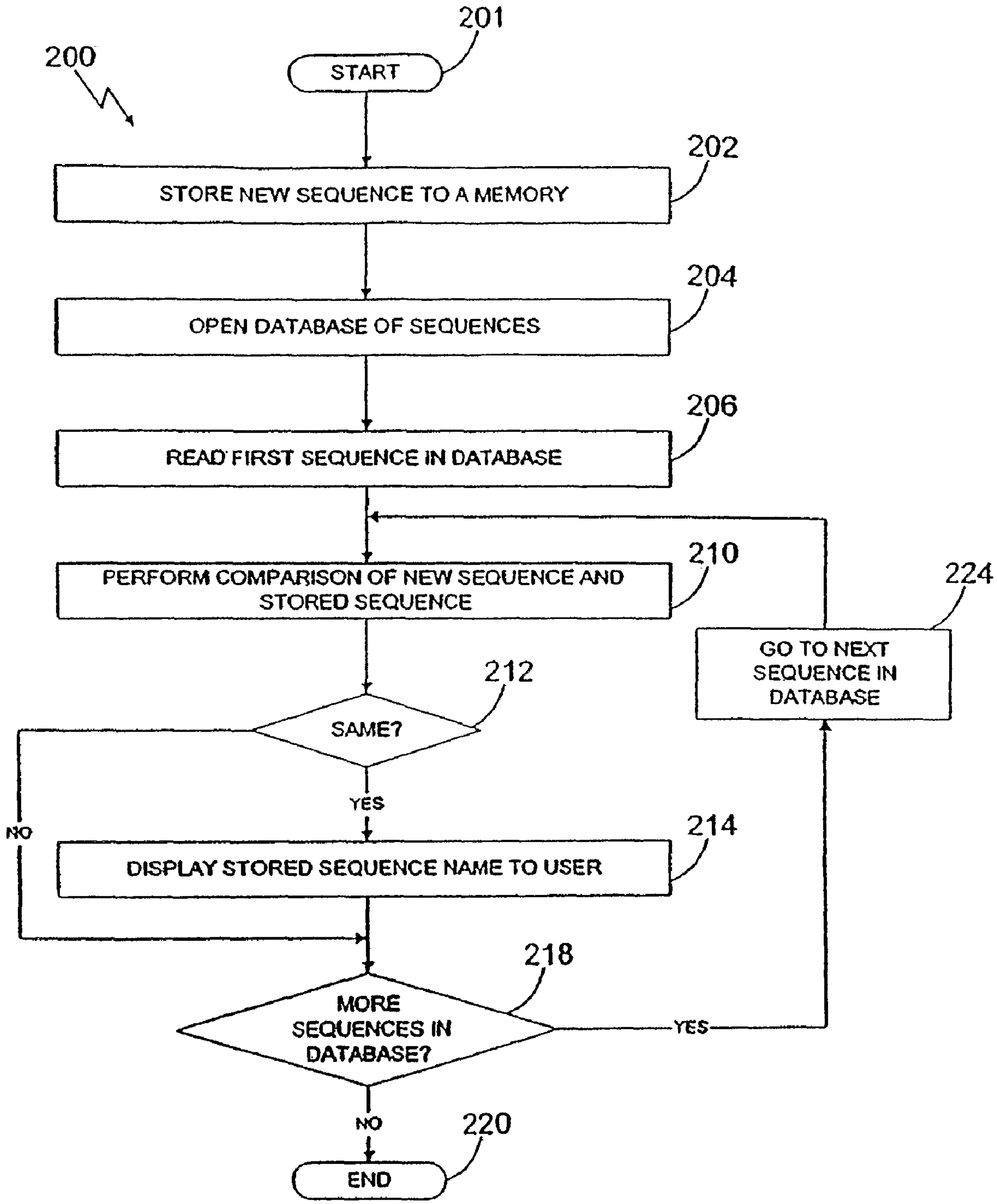
FIG. 2 is a flow diagram illustrating one aspect of a process 200 for comparing a new nucleotide or protein sequence with a database of sequences in order to determine the homology levels between the new sequence and the sequences in the database, as described in detail, below.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes.

Figure 3:
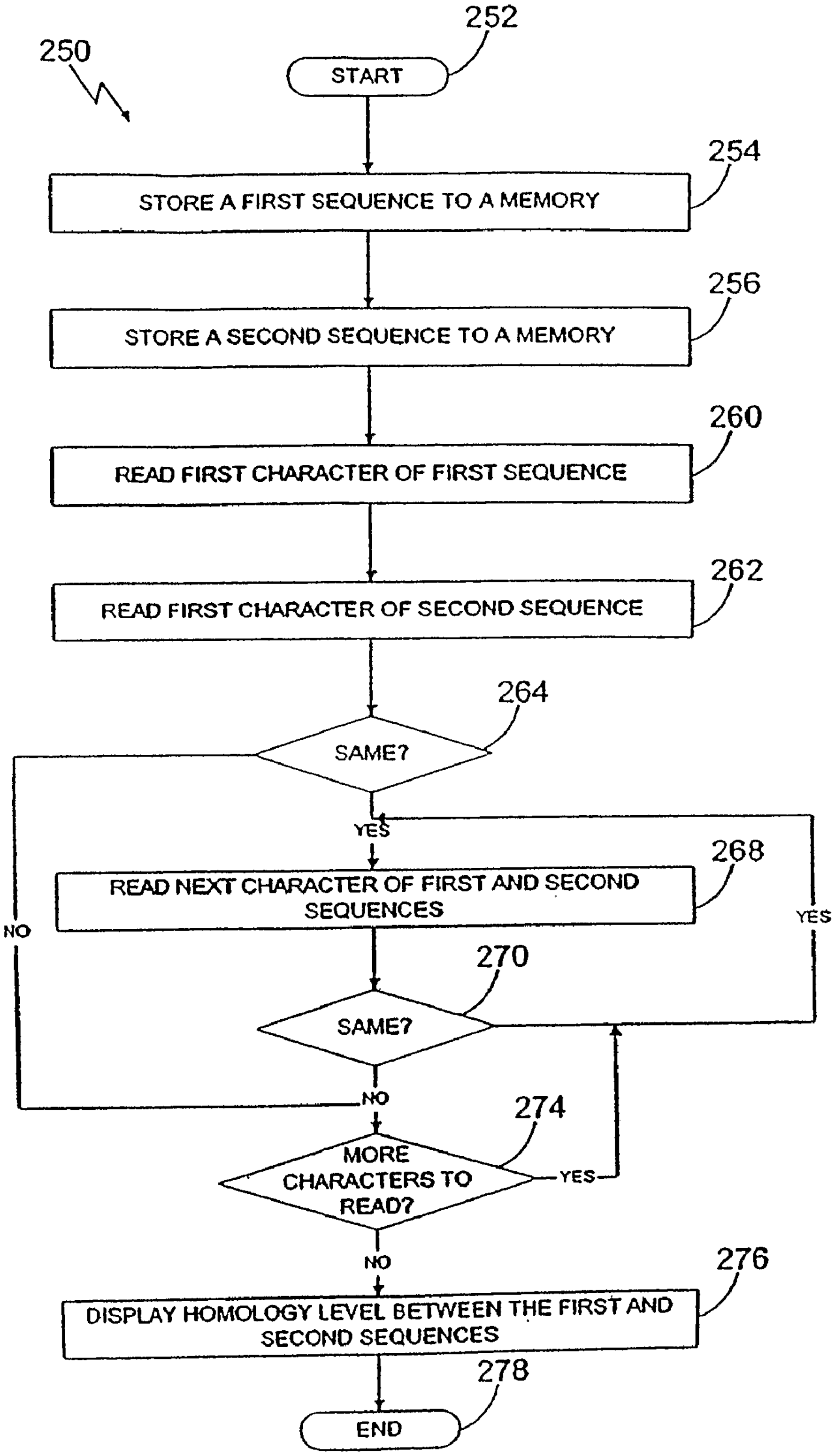
FIG. 3 is a flow diagram illustrating one embodiment of a process in a computer for determining whether two sequences are homologous, as described in detail, below.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
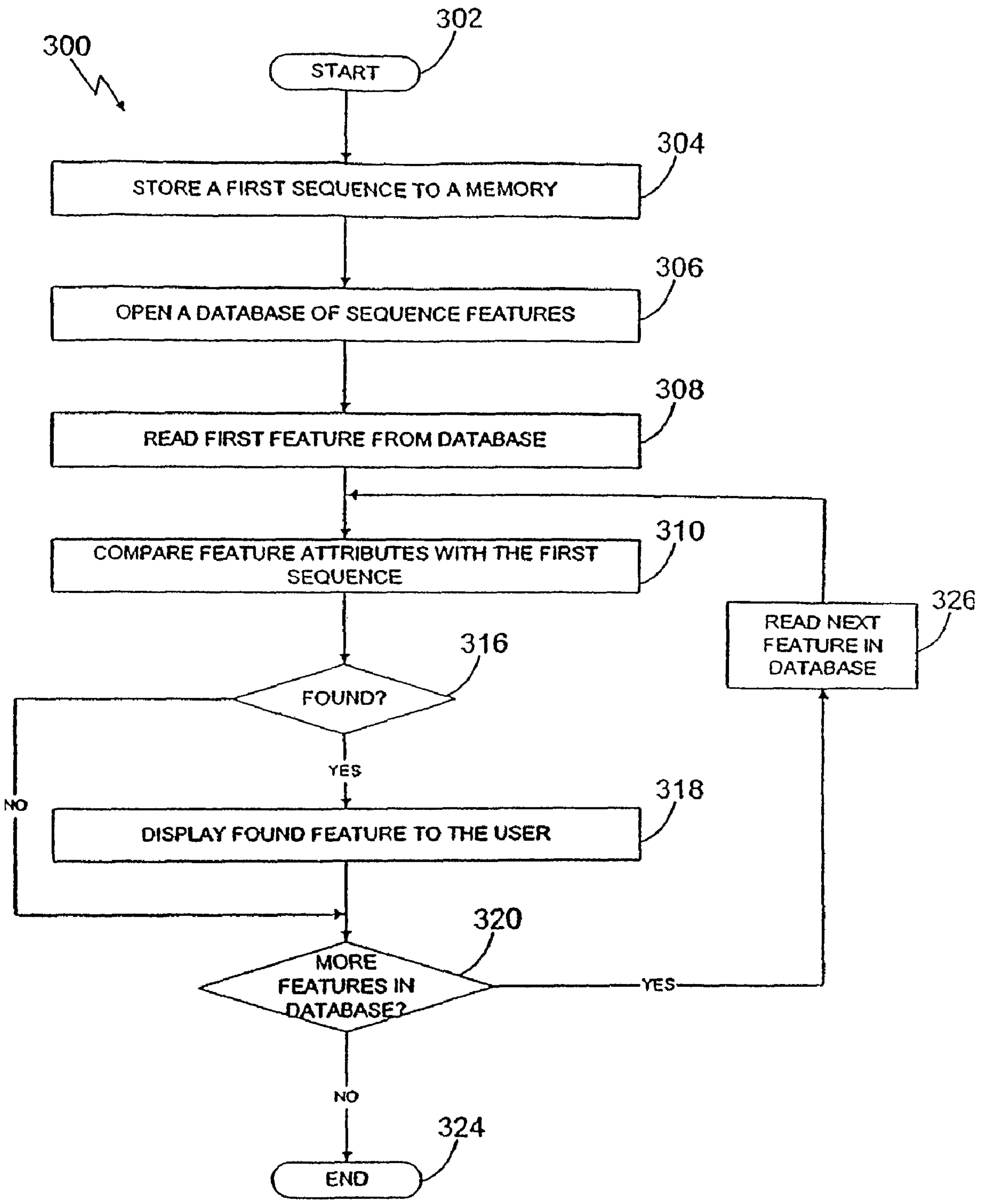
FIG. 4 is a flow diagram illustrating one aspect of an identifier process for detecting the presence of a feature in a sequence, as described in detail, below.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention may be stored and manipulated in a variety of data processor programs in a variety of formats. For example, a sequence can be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 or SEQ ID NO:173, or a nucleic acid that encodes a polypeptide comprising a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174. The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of the molecule, e.g., an exemplary nucleic acid of the invention. For example, they can be at least 5, 10, 15, 20, 25, 30, 35, 40, 50, 55, 60, 65, 70, 75, 80, 90, 100, 150, 200, 250, 300, 350, 400 or more residues in length. Nucleic acids shorter than full length are also included. These nucleic acids are useful as, e.g., hybridization probes, labeling probes, PCR oligonucleotide probes, iRNA (single or double stranded), antisense or sequences encoding antibody binding peptides (epitopes), motifs, active sites, binding domains, regulatory domains and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions can be used to practice the invention and are well known in the art. Hybridization conditions are discussed further, below.

Oligonucleotides Probes and Methods for Using them

The invention also provides nucleic acid probes for identifying nucleic acids encoding a polypeptide having a phospholipase activity. In one aspect, the probe comprises at least 10 consecutive bases of a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 or SEQ ID NO:173. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 50, 55, 60, 65, 70, 75, 80, 90, 100, or 150, or more, or about 10 to 50, about 20 to 60 about 30 to 70, consecutive bases of a sequence as set forth in a sequence of the invention. The probes identify a nucleic acid by binding or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10×Denhardt's, and 0.5 mg/ml polyriboadenylic acid. Approximately 2×107 cpm (specific activity 4–9×108 cpm/ug) of $^{32}$P end-labeled oligonucleotide probe are then added to the solution. After 12-16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)–(600/N) where N is the length of the probe. If the hybridization is carried out in a solution containing formamide, the melting temperature may be calculated using the equation: Tm=81.5+16.6(log [Na+])+0.41 (fraction G+C)–(0.63% formamide)–(600/N) where N is the length of the probe. Prehybridization may be carried out in 6×SSC, 5×Denhardt's reagent, 0.5% SDS, 100 μg denatured fragmented salmon sperm DNA or 6×SSC, 5×Denhardt's reagent, 0.5% SDS, 100 μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to practice the invention, e.g., to wash filters. One of skill in the art would know that there are numerous recipes for different stringency washes, all of which can be used to practice the invention.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, at least 98%, at least 97%, at least 96%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, or 500 consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to nucleic acids of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of Phospholipases

The invention further provides for nucleic acids complementary to (e.g., antisense sequences to) the nucleic acids of the invention, e.g., phospholipase-encoding nucleic acids. Antisense sequences are capable of inhibiting the transport, splicing or transcription of phospholipase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind phospholipase gene or message, in either case preventing or inhibiting the production or function of phospholipase enzyme. The association can be though sequence specific hybridization. Another useful class of inhibitors includes oligonucleotides which cause inactivation or cleavage of phospholipase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Inhibition of phospholipase expression can have a variety of industrial applications. For example, inhibition of phospholipase expression can slow or prevent spoilage. Spoilage can occur when lipids or polypeptides, e.g., structural lipids or polypeptides, are enzymatically degraded. This can lead to the deterioration, or rot, of fruits and vegetables. In one aspect, use of compositions of the invention that inhibit the expression and/or activity of phospholipase, e.g., antibodies, antisense oligonucleotides, ribozymes and RNAi, are used to slow or prevent spoilage. Thus, in one aspect, the invention provides methods and compositions comprising application onto a plant or plant product (e.g., a fruit, seed, root, leaf, etc.) antibodies, antisense oligonucleotides, ribozymes and RNAi of the invention to slow or prevent spoilage. These compositions also can be expressed by the plant (e.g., a transgenic plant) or another organism (e.g., a bacterium or other microorganism transformed with a phospholipase gene of the invention).

The compositions of the invention for the inhibition of phospholipase expression (e.g., antisense, iRNA, ribozymes, antibodies) can be used as pharmaceutical compositions.

Antisense Oligonucleotides

The invention provides antisense oligonucleotides capable of binding phospholipase message which can inhibit phospholipase activity by targeting mRNA. Strategies for designing antisense oligonucleotides are well described in the scientific and patent literature, and the skilled artisan can design such phospholipase oligonucleotides using the novel reagents of the invention. For example, gene waking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense phospholipase sequences of the invention (see, e.g., Gold (1995) J. of Biol. Chem. 270:13581-13584).

Inhibitory Ribozymes

The invention provides for with ribozymes capable of binding phospholipase message which can inhibit phospholipase enzyme activity by targeting mRNA. Strategies for designing ribozymes and selecting the phospholipase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a phospholipase sequence of the invention. The RNAi molecule comprises a double-stranded RNA (dsRNA) molecule. The RNAi can inhibit expression of a phospholipase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. No. 6,506,559; U.S. Pat. No. 6,511,824; U.S. Pat. No. 6,515,109; U.S. Pat. No. 6,489,127.

Modification of Nucleic Acids

The invention provides methods of generating variants of the nucleic acids of the invention, e.g., those encoding a phospholipase enzyme. In alternative embodiment, the invention provides methods for modifying an enzyme of the invention, e.g., by mutation of its coding sequence by random or stochastic methods, or, non-stochastic, or "directed evolution," such as Gene Site Saturation Mutagenesis™ (GSSM™), to alter the enzymes pH range of activity or range of optimal activity, temperature range of activity or range of optimal activity, specificity, activity (kinetics); the enzyme's use of glycosylation, phosphorylation or metals (e.g., Ca, Mg, Zn, Fe, Na), e.g., to impact pH/temperature stability. The invention provides methods for modifying an enzyme of the invention, e.g., by mutation of its coding sequence, e.g., by GSSM™, to increase its resistance to protease activity. The invention provides methods for modifying an enzyme of the invention, e.g., by mutation of its coding sequence, e.g., by GSSM™, to modify the enzyme's use of metal chelators specific for Ca, Mg, Na that would not chelate Zn. The invention provides methods for modifying an enzyme of the invention, e.g., by mutation of its coding sequence, e.g., by GSSM™, that would have a desired combination of activities, e.g., PI, PA and PC/PE specific PLCs.

These methods can be repeated or used in various combinations to generate phospholipase enzymes having an altered or different activity or an altered or different stability from that of a phospholipase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods.

Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wild-type cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367;

Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols used in the methods of the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

See also U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (e.g., GSSM™), synthetic ligation reassembly (SLR), or a combination thereof are used to modify the nucleic acids of the invention to generate phospholipases with new or altered properties (e.g., activity under highly acidic or alkaline conditions, high temperatures, and the like). Polypeptides encoded by the modified nucleic acids can be screened for an activity before testing for a phospholipase or other activity. Any testing modality or protocol can be used, e.g., using a capillary array platform. See, e.g., U.S. Pat. Nos. 6,280,926; 5,939,250.

Saturation Mutagenesis, or, GSSM™

In one aspect of the invention, non-stochastic gene modification, a "directed evolution process," is used to generate phospholipases with new or altered properties. Variations of this method have been termed "gene site mutagenesis," "site-saturation mutagenesis," "Gene Site Saturation Mutagenesis™" or simply "GSSM™." It can be used in combination with other mutagenization processes. See, e.g., U.S. Pat. Nos. 6,171,820; 6,238,884. In one aspect, GSSM™ comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N,N,G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., phospholipase) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased phospholipase activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process(es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate phospholipases with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled.

In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another embodiment, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate phospholipases with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found in U.S. Ser. No. 09/332,835. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a $1/3$ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding an polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that a oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Embodiments of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB® (The Mathworks, Natick, Mass.) a programming language and development environment for technical computing.

Iterative Processes

In practicing the invention, these processes can be iteratively repeated. For example a nucleic acid (or, the nucleic acid) responsible for an altered phospholipase phenotype is identified, re-isolated, again modified, re-tested for activity. This process can be iteratively repeated until a desired phenotype is engineered. For example, an entire biochemical anabolic or catabolic pathway can be engineered into a cell, including phospholipase activity.

Similarly, if it is determined that a particular oligonucleotide has no affect at all on the desired trait (e.g., a new phospholipase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In vivo Shuffling

In vivo shuffling of molecules is use in methods of the invention that provide variants of polypeptides of the invention, e.g., antibodies, phospholipase enzymes, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides methods of making sequence variants of the nucleic acid and phospholipase sequences of the invention or isolating phospholipase enzyme, e.g., phospholipase, sequence variants using the nucleic acids and polypeptides of the invention. In one aspect, the invention provides for variants of a phospholipase gene of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/μl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some embodiments, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250.

The invention also provides variants of polypeptides of the invention comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., a phospholipase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying phospholipase-encoding nucleic acids to modify codon usage. In one aspect, the invention provides methods for modifying codons in a nucleic acid encoding a phospholipase to increase or decrease its expression in a host cell. The invention also provides nucleic acids encoding a phospholipase modified to increase its expression in a host cell, phospholipase enzymes so modified, and methods of making the modified phospholipase enzymes. The method comprises identifying a "non-preferred" or a "less preferred" codon in phospholipase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as any *Bacillus* (e.g., *B. cereus*) or *Streptomyces, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding a phospholipase isolated from a bacterial cell are modified such that the nucleic acid is optimally expressed in a bacterial cell different from the bacteria from which the phospholipase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study phospholipase activity, or, as models to screen for modulators of phospholipase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express a phospholipase.

Transgenic Plants and Seeds

The invention provides transgenic plants and seeds comprising a nucleic acid, a polypeptide (e.g., a phospholipase), an expression cassette or vector or a transfected or transformed cell of the invention. The invention also provides plant products, e.g., oils, seeds, leaves, extracts and the like, comprising a nucleic acid and/or a polypeptide (e.g., a phospholipase) of the invention. The transgenic plant can be dicotyledonous (a dicot) or monocotyledonous (a monocot). The invention also provides methods of making and using these transgenic plants and seeds. The transgenic plant or plant cell expressing a polypeptide of the invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's phospholipase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on oil-seed containing plants, such as rice, soybeans, rapeseed, sunflower seeds, sesame and peanuts. Nucleic acids of the invention can be used to manipulate metabolic pathways of a plant in order to optimize or alter host's expression of phospholipase. The can change phospholipase activity in a plant. Alternatively, a phospholipase of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a phospholipase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants (e.g., as transgenic plants), such as oil-seed containing plants, e.g., rice, soybeans, rapeseed, sunflower seeds, sesame and peanuts. The nucleic acids of the invention can be expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum.*

The invention also provides for transgenic plants to be used for producing large amounts of the polypeptides (e.g., a phospholipase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agiobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

The invention provides isolated or recombinant polypeptides having a sequence identity (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174. As discussed above, the identity can be over the full length of the polypeptide, or, the identity can be over a subsequence thereof, e.g., a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides (e.g., SEQ ID NO:2; SEQ ID NO:4; SEQ ID NO:6; SEQ ID NO:8, etc.). In alternative embodiment, the invention provides polypeptides (peptides, fragments) ranging in size between about 5 and the full length of a polypeptide, e.g., an enzyme, such as a phospholipase, e.g., phospholipase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400 or more residues, e.g., contiguous residues of the exemplary phospholipases of SEQ ID NO:2; SEQ ID NO:4; SEQ ID NO:6; SEQ ID NO:8, etc. Peptides of the invention can be useful as, e.g., labeling probes, antigens, toleragens, motifs, phospholipase active sites, binding domains, regulatory domains, and the like.

In one aspect, the polypeptide has a phospholipase activity, e.g., cleavage of a glycerolphosphate ester linkage, the ability to hydrolyze phosphate ester bonds, including patatin, lipid acyl hydrolase (LAH), phospholipase A, B, C and/or phospholipase D activity, or any combination thereof.

In alternative aspects, exemplary polypeptides of the invention have a phospholipase activity, Signal Sequence Location, and an initial source, as set forth in the following Table 1, below. To aid in reading the table, for example, in the first row, where SEQ ID NO:143, 144, means the polypeptide having a sequence as set forth in SEQ ID NO:144, and encoded by, e.g., SEQ ID NO:143, having a PLA-specific PLA activity, initially isolated from an unknown source; another example in the SEQ ID NO:167, 168 row where 167, 168 means the polypeptide having a sequence as set forth in SEQ ID NO:168, and encoded by, e.g., SEQ ID NO:167, having a phosphatidic acid phosphatase activity, a signal sequence at residues 1 to 30 ("AA1-30" means amino acid residues 1 to 30, etc.), i.e., MARSWKWRPLLSSFLLVSLAPFSTSVPCFK, and initially isolated from an unknown source. The invention also provides peptides comprising signal sequences, and chimeric polypeptides, where the peptides or chimerics comprise signal sequences as set forth in Table 1, and as described below.

TABLE 1

| SEQ ID NO: | Enzyme type | Signal Seq. Location (AA = Amino Acid) | Signal (AA) | Source |
|---|---|---|---|---|
| 143, 144 | PA-specific PLA | | | Unknown |
| 25, 26 | Patatin | | | Unknown |
| 77, 78 | Patatin | | | Unknown |
| 35, 36 | Patatin | | | Unknown |
| 125, 126 | Patatin | | | Unknown |
| 135, 136 | Patatin | | | Unknown |
| 99, 100 | Patatin | | | Unknown |
| 65, 66 | Patatin | | | Unknown |
| 87, 88 | Patatin | | | Unknown |
| 86, 87 | Patatin | | | Unknown |
| 45, 46 | Patatin | | | Unknown |
| 59, 60 | Patatin | | | Unknown |
| 13, 14 | Patatin | | | Unknown |
| 71, 72 | Patatin | | | Unknown |
| 55, 56 | Patatin | | | Unknown |
| 33, 34 | Patatin | | | Unknown |
| 91, 92 | Patatin | | | Unknown |
| 103, 104 | Patatin | | | Unknown |
| 11, 12 | Patatin | | | Unknown |
| 17, 18 | Patatin | | | Unknown |
| 95, 96 | Patatin | | | Unknown |
| 43, 44 | Patatin | | | Unknown |
| 27, 28 | Patatin | | | Unknown |
| 131, 132 | Patatin | | | Unknown |
| 127, 128 | Patatin | | | Unknown |
| 133, 134 | Patatin | | | Unknown |
| 137, 138 | Patatin | | | Unknown |
| 165, 166 | Patatin | | | Unknown |
| 167, 168 | Phosphatidic acid phosphatases | AA1-30 | MARSWKWRPLLSSFL LVSLAPFSTSVPCFK | Unknown |

TABLE 1-continued

| SEQ ID NO: | Enzyme type | Signal Seq. Location (AA = Amino Acid) | Signal (AA) | Source |
|---|---|---|---|---|
| 169, 170 | Phosphatidic acid phosphatases | | | Unknown |
| 171, 172 | Phosphatidic acid phosphatases | | | Unknown |
| 173, 174 | Phosphatidic acid phosphatases | | | Unknown |
| 111, 112 | Phosphatidy linositol PLC | AA1-16 | MGAGAILLTGAPTASA | Bacteria |
| 107, 108 | Phosphatidy-linositol PLC | AA1-23 | MSNKKFILKLFICSTI LSTFVFA | Unknown |
| 109, 110 | Phosphatidy linositol PLC | AA1-23 | MSNKKFILKLFICSTI LSTFVFA | Unknown |
| 113, 114 | phosphatidylin ositol PLC | AA1-23 | MSNKKFILKLFICSTI LSTFVFA | Unknown |
| 117, 118 | Phosphatidy-linositol PLC | AA1-23 | MNNKKFILKLFICSMV LSAFVFA | Unknown |
| 119, 120 | phosphatidylin ositol PLC | AA1-23 | MNNKKFILKLFICSMV LSAFVFA | Unknown |
| 115, 116 | Phosphatidy-linositol PLC | AA1-23 | MNNKKFILKLFICSMV LSAFVFA | Unknown |
| 121, 122 | Phosphatidy-linositol PLC | AA1-23 | MRNKKFILKLLICSTV LSTFVFA | Unknown |
| 141, 142 | Phospholipase | | | Unknown |
| 155, 156 | Phospholipase | AA1-36 | MRTTTTNWRQIVKSLK LFLMGLCLFISASSAY A | Unknown |
| 159, 160 | Pbospholipase | | | Unknown |
| 145, 146 | PLA | | | Unknown |
| 147, 148 | PLA | | | Unknown |
| 149, 150 | PLA | | | Unknown |
| 151, 152 | PLA | | | Unknown |
| 153, 154 | PLA | | | Unknown |
| 157, 158 | PLA | | | Unknown |
| 163, 164 | PLA | | | Unknown |
| 101, 102 | PLC | AA1-39 | LSLVASLRRAPGAALA LALAAATLAVTAQGAT AAPAAAAA | Bacteria |
| 1, 2 | PLC | AA1-24 | MKKKVLALAAMVALAA PVQSWFAQ | Unknown |
| 3, 4 | PLC | AA1-24 | MKRKILAIASVIALTA PIQSVAFAH | Unknown |
| 5, 6 | PLC | AA1-24 | MKRKILAIASVIALTA PIQSVAFAH | Unknown |
| 97, 98 | PLC | AA1-25 | MKRKLCTWALVTAIAS STAVIPTAAE | Unknown |
| 7, 8 | PLC | AA1-29 | MITLIKKCLLVLTMTL LLGVFVPLQPSHAT | Unknown |
| 31, 32 | PLC | AA1-20 | MKKKLCTWALVTAISS GVVAI | Unknown |
| 81, 82 | PLC | AA1-25 | MKKKLCTMALVTAISS GVVTIPTEAQ | Unknown |
| 93, 94 | PLC | AA1-29 | MITLIKKCLLVLTMTL LSGVFVPLQPSYAT | Unknown |
| 89, 90 | PLC | AA1-25 | MKKKLCTLAFVTAISS IAITIPTEAQ | Unknown |
| 123, 124 | PLC | AA1-24 | MKKKVLALAAMVALAA PVQSWFA | Unknown |
| 129, 130 | PLC | AA1-27 | MKKKICTLALVSAITS GVVTIPTVASA | Unknown |
| 139, 140 | PLC | AA1-20 | MKIKPLTFSFGLAVTS SVQA | Unknown |
| 105, 106 | PLC | AA1-30 | MNRCRNSLNLQLRAVT VAALVVVASSAALAW | Unknown |
| 9, 10 | PLC | AA1-20 | MKLLRVFVCVFALLSA HSKAD | Unknown |
| 47, 48 | PLD | | | Unknown |
| 15, 16 | PLD | | | Unknown |
| 41, 42 | PLD | | | Unknown |
| 23, 24 | PLD | | | Unknown |
| 51, 52 | PLD | | | Unknown |
| 53, 54 | PLD | | | Unknown |

TABLE 1-continued

| SEQ ID NO: | Enzyme type | Signal Seq. Location (AA = Amino Acid) | Signal (AA) | Source |
|---|---|---|---|---|
| 19, 20 | PLD | AA1-19 | MKKTTLVLALLMPFGA ASAQ | Unknown |
| 75, 76 | PLD | | | Unknown |
| 57, 58 | PLD | | | Unknown |
| 63, 64 | PLD | AA1-18 | MKNTLILAGCILAAPA VAD | Unknown |
| 79, 80 | PLD | AA1-23 | MRNFSKGLTSILLSIA TSTSAMAF | Unknown |
| 37, 38 | PLD | AA1-23 | MRNFSKGLTSILLSIA TSTSAMAF | Unknown |
| 61, 62 | PLD | AA1-21 | MTLKLSLLIASLSAVS PAVLAN | Unknown |
| 67, 68 | PLD | | No | Unknown |
| 83, 84 | PLD | AA1-21 | MKKIVIYSFVAGVMTS GGVFAA | Unknown |
| 49, 50 | PLD | AA1-23 | MNFWSFLLSITLPMGV GVAHAQPD | Unknown |
| 39, 40 | PLD | | | Unknown |
| 73, 74 | PLD | | | Unknown |
| 29, 30 | PLD | | | Unknown |
| 21, 22 | PLD | AA1-28 | MQQHKLRNFNKGLTGV VLSVLTSTSAMAF | Unknown |
| 71, 72 | PLD | | | Unknown |
| 161, 162 | PLD | AA1-24 | MNRKLLSLCLGATSCI ALSLPVHA | Unknown |

In one aspect, the invention provides polypeptides having sequences as set forth in SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171 and/or SEQ ID NO:173, and subsequences thereof, e.g., their active sites ("catalytic domains") having a phospholipase activity, e.g., a phospholipase C (PLC) activity. In one aspect, the polypeptide has a phospholipase activity but lacks neutral oil (triglyceride) hydrolysis activity. For example, in one aspect, the polypeptide has a phospholipase activity but lacks any activity that affects a neutral oil (triglyceride) fraction. In one aspect, the invention provides a degumming process comprising use of a polypeptide of the invention having a phospholipase activity, but not a lipase activity.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a phospholipase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-di-isopropylcarbodiimide (DIC). Linking groups that can be an alternative to the traditional amide bond ("peptide bond") linkages include, e.g., ketomethylene (e.g., —C(=O)—CH2 for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N.Y.).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenyl-phenylalanine; K- or L-p-methoxy-biphenylphenylalanine; D- or L-2-indole-(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4, 4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where allyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

Phospholipase Enzymes

The invention provides novel phospholipases, nucleic acids encoding them, antibodies that bind them, peptides representing the enzyme's antigenic sites (epitopes) and active sites, regulatory and binding domains, and methods for making and using them. In one aspect, polypeptides of the invention have a phospholipase activity, or any combination of phospholipase activities, as described herein (e.g., cleavage of a glycerolphosphate ester linkage, lacking lipase activity, etc.). In alternative aspects, the phospholipases of the invention have activities that have been modified from those of the exemplary phospholipases described herein.

The invention includes phospholipases with and without signal sequences and the signal sequences themselves. The invention includes fragments or subsequences of enzymes of the invention, e.g., peptides or polypeptides comprising or consisting of catalytic domains ("active sites"), binding sites, regulatory domains, epitopes, signal sequences, prepro domains, and the like. The invention also includes immobilized phospholipases, anti-phospholipase antibodies and fragments thereof. The invention includes heterocomplexes, e.g., fusion proteins, heterodimers, etc., comprising the phospholipases of the invention. Determining peptides representing the enzyme's antigenic sites (epitopes), active sites, binding sites, signal sequences, and the like can be done by routine screening protocols.

These enzymes and processes of the invention can be used to achieve a more complete degumming of high phosphorus oils, in particular, rice, soybean, corn, canola, and sunflower oils. For example, in one aspect, upon cleavage by PI-PLC, phosphatidylinositol is converted to diacylglycerol and phosphoinositol. The diacylglycerol partitions to the aqueous phase (improving oil yield) and the phosphoinositol partitions to the aqueous phase where it is removed as a component of the heavy phase during centrifugation. An enzyme of the invention, e.g., a PI-PLC of the invention, can be incorporated into either a chemical or physical oil refining process.

In alternative aspects, enzymes of the invention have phosphatidylinositol-specific phospholipase C (PI-PLC) activity, phosphatidylcholine-specific phospholipase C activity, phosphatidic acid phosphatase activity, phospholipase A activity and/or patatin-related phospholipase activity. These enzymes can be used alone or in combination each other or with other enzymes of the invention, or other enzymes. In one aspect, the invention provides methods wherein these enzymes (including phosphatidylinositol-specific phospholipase C (PIPLC), phosphatidylcholine-specific phospholipase C, and/or phospholipase D (in conjunction with a phosphatase), phosphatidic acid phosphatase, phospholipase A, patatin-related phospholipases of the invention) are used alone or in combination in the degumming of oils, e.g., vegetable oils, e.g., high phosphorus oils, such as soybean, corn, canola, rice bran and sunflower oils. These enzymes and processes of the invention can be used to achieve a more complete degumming of high phosphorus oils, in particular, soybean, corn, canola, rice bran and sunflower oils. Upon cleavage by PI-PLC, phosphatidylinositol is converted to diacylglycerol and phosphoinositol. The diacylglycerol partitions to the aqueous phase (improving oil yield) and the phosphoinositol partitions to the aqueous phase where it is removed as a component of the heavy phase during centrifugation. An enzyme of the invention, e.g., a PI-PLC of the invention, can be incorporated into either a chemical or physical oil refining process.

In one aspect, the invention provides compositions, e.g., solutions, comprising sodium citrate at neutral pH to hydrate non-hydratables. For example, the invention provides sodium citrate solutions in a pH range of between about 4 to 9, or, 5 to 8, or, 6 to 7, that can be used to hydrate non-hydratable phospholipids (including enzymes of the invention) in high phosphorus oils. In one aspect, the hydration of non-hydratable phospholipids is by chelating the calcium and magnesium associated with the phospholipids, thereby allowing the formerly insoluble phospholipid salts to more readily partition in the aqueous phase. In one aspect, once phospholipids move to the water/oil interface or into the aqueous phase, a phospholipase of the invention (e.g., a phospholipase-specific phosphohydrolase of the invention), or another phospholipase, will convert the phospholipid to diacylglycerol and a phosphate-ester. In one aspect, calcium and magnesium metal content are lowered upon addition of acid and caustic (see discussion on caustic processes).

The enzymes of the invention are highly selective catalysts. As with other enzymes, they catalyze reactions with exquisite stereo-, region-, and chemo-selectivities that are unparalleled in conventional synthetic chemistry. Moreover, the enzymes of the invention are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates. Enzymes of the invention can be designed to be reactive toward a wide range of natural and unnatural substrates, thus enabling the modification of virtually any organic lead compound. Enzymes of the invention can also be designed to be highly enantio- and regio-selective. The high degree of functional group specificity exhibited by these enzymes enables one to keep track of each reaction in a synthetic sequence leading to a new active compound. Enzymes of the invention can also be designed to catalyze many diverse reactions unrelated to their native physiological function in nature.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound. The present invention uses selected biocatalysts, i.e., the enzymes of the invention, and reaction conditions that are specific for functional groups that are present in many starting compounds. Each biocatalyst is specific for one functional group, or several related functional groups, and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process that is very difficult to achieve using traditional chemical methods. This high degree of biocatalytic specificity provides the means to identify a single active enzyme within a library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

The invention also provides methods of discovering new phospholipases using the nucleic acids, polypeptides and antibodies of the invention. In one aspect, lambda phage libraries are screened for expression-based discovery of phospholipases. Use of lambda phage libraries in screening allows detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. Screening in liquid phase gives greater flexibility in assay conditions; additional substrate flexibility; higher sensitivity for weak clones; and ease of automation over solid phase screening.

Many of the procedural steps are performed using robotic automation enabling the execution of many thousands of biocatalytic reactions and screening assays per day as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Phospholipase Signal Sequences

The invention provides phospholipase signal sequences (e.g., signal peptides (SPs)), e.g., peptides comprising signal sequences and/or chimeric polypeptides, where the peptides or chimerics have a signal sequence as set forth in Table 1, or as set forth, below. The invention provides nucleic acids encoding these signal sequences (SPs, e.g., a peptide having a sequence comprising/consisting of amino terminal residues of a polypeptide of the invention). In one aspect, the invention provides a signal sequence comprising a peptide comprising/consisting of a sequence as set forth in residues 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32 or 1 to 33 of a polypeptide of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138; SEQ ID NO:140; SEQ ID NO:142; SEQ ID NO:144; NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, or SEQ ID NO:174. Any of these peptides can be part of a chimeric protein, e.g., a recombinant protein. A signal sequence peptide can be matched with another enzyme of the invention (e.g., a phospholipase of the invention from which is was not derived), or, with another phospholipase, or with any polypeptide, as discussed further, below.

Exemplary signal sequences are set forth in Table 1 and the SEQ ID listing, e.g., residues 1 to 24 of SEQ ID NO:2, SEQ ID NO:4, SEQ ID NO:6; residues 1 to 29 of SEQ ID NO:8; residues 1 to 20 of SEQ ID NO:10; residues 1 to 19 of SEQ ID NO:20; residues 1 to 28 of SEQ ID NO:22; residues 1 to 20 of SEQ ID NO:32; residues 1 to 23 of SEQ ID NO: 38; see Table 1 and the SEQ ID listing for other exemplary signal sequences of the invention.

In some aspects phospholipases of the invention do not have signal sequences. In one aspect, the invention provides the phospholipases of the invention lacking all or part of a signal sequence. In one aspect, the invention provides a nucleic acid sequence encoding a signal sequence from one phospholipase operably linked to a nucleic acid sequence of a different phospholipase or, optionally, a signal sequence from a non-phospholipase protein may be desired.

Phospholipase Prepro Domains, Binding Domains and Catalytic Domains

In addition to signal sequences (e.g., signal peptides (SPs)), as discussed above, the invention provides prepro domains, binding domains (e.g., substrate binding domain) and catalytic domains (CDs). The SP domains, binding domains, prepro domains and/or CDs of the invention can be isolated or recombinant peptides or can be part of a fusion protein, e.g., as a heterologous domain in a chimeric protein. The invention provides nucleic acids encoding these catalytic domains (CDs) (e.g., "active sites"), prepro domains, binding domains and signal sequences (SPs, e.g., a peptide having a sequence comprising/consisting of amino terminal residues of a polypeptide of the invention).

The phospholipase signal sequences (SPs), binding domains, catalytic domains (CDs) and/or prepro sequences of the invention can be isolated peptides, or, sequences joined to another phospholipase or a non-phospholipase polypeptide, e.g., as a fusion (chimeric) protein. In one aspect, polypeptides comprising phospholipase signal sequences SPs and/or prepro of the invention comprise sequences heterologous to phospholipases of the invention (e.g., a fusion protein comprising an SP and/or prepro of the invention and sequences from another phospholipase or a non-phospholipase protein). In one aspect, the invention provides phospholipases of the invention with heterologous CDs, SPs and/or prepro sequences, e.g., sequences with a yeast signal sequence. A phospholipase of the invention can comprise a heterologous CD, SP and/or prepro in a vector, e.g., a pPIC series vector (Invitrogen, Carlsbad, Calif.).

In one aspect, SPs, CDs, and/or prepro sequences of the invention are identified following identification of novel phospholipase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from 13 to 45 or more amino acid residues. Various methods of recognition of signal sequences are known to those of skill in the art. For example, in one aspect, novel hydrolase signal peptides are identified by a method referred to as SignalP. SignalP uses a combined neural network which recognizes both signal peptides and their cleavage sites. (Nielsen, et al., "Identification of prokaryotic and eulcaryotic signal peptides and prediction of their cleavage sites." Protein Engineering, vol. 10, no. 1, p. 1-6 (1997).

In some aspects, a phospholipase of the invention may not have SPs and/or prepro sequences, and/or catalytic domains (CDs). In one aspect, the invention provides phospholipases lacking all or part of an SP, a CD and/or a prepro domain. In one aspect, the invention provides a nucleic acid sequence encoding a signal sequence (SP), a CD and/or prepro from one phospholipase operably linked to a nucleic acid sequence of a different phospholipase or, optionally, a signal sequence (SPs), a CD and/or prepro domain from a non-phospholipase protein may be desired.

The invention also provides isolated or recombinant polypeptides comprising signal sequences (SPs), prepro domain and/or catalytic domains (CDs) of the invention and heterologous sequences. The heterologous sequences are sequences not naturally associated (e.g., to a phospholipase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., phospholipase sequence). Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

The polypeptides of the invention include phospholipases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include phospholipases inactive for other reasons, e.g., before "activation" by a post-translational processing event, e.g., an endo- or exo-peptidase or proteinase action, a phosphorylation event, an amidation, a glycosylation, a de-glycosylation, a sulfation, a dimerization event, and/or the like. Methods for identifying "prepro" domain sequences, CDs, binding domains and signal sequences are routine and well known in the art, see, e.g., Van de Ven (1993) Crit. Rev. Oncog. 4(2): 115-136; yeast two-hybrid screenings for identifying protein-protein interactions, described e.g., by Miller (2004) Methods Mol. Biol. 261:247-62; Heyninck (2004) Methods Mol. Biol. 282:223-41, U.S. Pat. Nos. 6,617,122; 6,190,874. For example, to identify a prepro sequence, the protein is purified from the extracellular space and the N-terminal protein sequence is determined and compared to the unprocessed form.

The polypeptides of the invention can be formulated as a protein preparation into any liquid, solid, semi-solid or gel form. For example, a protein preparation of the invention can comprise a formulation comprising a non-aqueous liquid composition, a cast solid, a powder, a lyophilized powder, a granular form, a particulate form, a compressed tablet, a pellet, a pill, a gel form, a hydrogel, a paste, an aerosol, a spray, a lotion or a slurry formulation.

The polypeptides of the invention include all active forms, including active subsequences, e.g., catalytic domains (CDs) or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (which is a large collection of multiple sequence alignments and hidden Markov models covering many common protein families, The Pfam protein families database, A. Bateman, E. Birney, L. Ceruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent.

The invention provides fusion of N-terminal or C-terminal subsequences of enzymes of the invention (e.g., signal sequences, prepro sequences) with other polypeptides, active proteins or protein fragments. The production of an enzyme of the invention (e.g., a phospholipase C enzyme) may also be accomplished by expressing the enzyme as an inactive fusion protein that is later activated by a proteolytic cleavage event (using either an endogenous or exogenous protease activity, e.g. trypsin) that results in the separation of the fusion protein partner and the mature enzyme, e.g., phospholipase C enzyme. In one aspect, the fusion protein of the invention is expressed from a hybrid nucleotide construct that encodes a single open reading frame containing the following elements: the nucleotide sequence for the fusion protein, a linker sequence (defined as a nucleotide sequence that encodes a flexible amino acid sequence that joins two less flexible protein domains), protease cleavage recognition site, and the mature enzyme (e.g., any enzyme of the invention, e.g., a phospholipase) sequence. In alternative aspects, the fusion protein can comprise a pectate lyase sequence, a xylanase sequence, a phosphatidic acid phosphatase sequence, or another sequence, e.g., a sequence that has previously been shown to be over-expressed in a host system of interest.

Any host system can be used (see discussion, above), for example, any bacteria, e.g., a gram positive bacteria, such as *Bacillus*, or a gram negative bacteria, such as *E. coli*, or any yeast, e.g., *Pichia pastoris*. The arrangement of the nucleotide sequences in the chimeric nucleotide construction can be determined based on the protein expression levels achieved with each fusion construct. Proceeding from the 5' end of the nucleotide construct to the 3' prime end of the construct, in one aspect, the nucleotide sequences is assembled as follows: Signal sequence/fusion protein/linker sequence/protease cleavage recognition site/mature enzyme (e.g., any enzyme of the invention, e.g., a phospholipase) or Signal sequence/pro sequence/mature enzyme/linker sequence/fusion protein. The expression of enzyme (e.g., any enzyme of the invention, e.g., a phospholipase) as an inactive fusion protein may improve the overall expression of the enzyme's sequence, may reduce any potential toxicity associated with the overproduction of active enzyme and/or may increase the shelf life of enzyme prior to use because enzyme would be inactive until the fusion protein e.g. pectate lyase is separated from the enzyme, e.g., phospholipase protein.

In various aspects, the invention provides specific formulations for the activation of phospholipase of the invention expressed as a fusion protein. In one aspect, the activation of the phospholipase activity initially expressed as an inactive fusion protein is accomplished using a proteolytic activity or potentially a proteolytic activity in combination with an amino-terminal or carboxyl-terminal peptidase. This activation event may be accomplished in a variety of ways and at variety of points in the manufacturing/storage process prior to application in oil degumming. Exemplary processes of the invention include: Cleavage by an endogenous activity expressed by the manufacturing host upon secretion of the fusion construct into the fermentation media; Cleavage by an endogenous protease activity that is activated or comes in contact with intracellularly expressed fusion construct upon rupture of the host cells; Passage of the crude or purified fusion construct over a column of immobilized protease activity to accomplish cleavage and enzyme (e.g., phospholipase of the invention, e.g., a phospholipase C) activation prior to enzyme formulation; Treatment of the crude or purified fusion construct with a soluble source of proteolytic activity; Activation of a phospholipase (e.g., a phospholipase of the invention, e.g., a phospholipase C) at the oil refinery using either a soluble or insoluble source of proteolytic activity immediately prior to use in the process; and/or, Activation of the phospholipase (e.g., a phospholipase of the invention, e.g., a phospholipase C) activity by continuously circulating the fusion construct formulation through a column of immobilized protease activity at reduced temperature (for example, any between about 4° C. and 20° C.). This activation event may be accomplished prior to delivery to the site of use or it may occur on-site at the oil refinery.

Glycosylation

The peptides and polypeptides of the invention (e.g., hydrolases, antibodies) can also be glycosylated, for example, in one aspect, comprising at least one glycosylation site, e.g., an N-linked or O-linked glycosylation. In one aspect, the polypeptide can be glycosylated after being expressed in a *P. pastoris* or a *S. pombe*. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence.

In one aspect, the invention provides a polypeptide comprising an N-linked glycosylated SEQ ID NO:2, as described, e.g., in the following table:

| Site number | Glycosylation site | Length | Amino acid position of glycosylation site | |
|---|---|---|---|---|
| 1 | Match: NNS | Length: 3 | Start: 27 | Stop: 29 |
| 2 | Match: NTT | Length: 3 | Start: 65 | Stop: 67 |
| 3 | Match: NET | Length: 3 | Start: 72 | Stop: 74 |
| 4 | Match: NST | Length: 3 | Start: 100 | Stop: 102 |
| 5 | Match: NFT | Length: 3 | Start: 168 | Stop: 170 |
| 6 | Match: NLS | Length: 3 | Start: 171 | Stop: 173 |
| 7 | Match: NDT | Length: 3 | Start: 229 | Stop: 231 |

The full-length SEQ ID NO:2 (which in one aspect is encoded by SEQ ID NO:1) open reading frame encodes seven (7) potential asparagine-linked (N-linked) glycosylation sites. The expression of the wild-type SEQ ID NO:2 open reading frame in a glycosylating host (e.g. *Pichia pastoris, Saccharomyces cerevisiae, Schizosaccharomyces pombe*, or a mammalian cell) results in the production of a glycosylated SEQ ID NO:2 phospholipase enzyme that is essentially inactive due to the presence of N-linked glycosylation. Enzymatic deglycosylation of the wild-type, glycosylated SEQ ID NO:2 with PNGase F or Endoglycosidase H results in the activation of the SEQ ID NO:2 activity. In addition, modification of one or more of the N-linked glycosylation sites through mutagenesis (so that the site is no longer recognized as an N-linked glycosylation site and glycosylation no longer occurs at that site) results in the production of SEQ ID NO:2 with varying degrees of increased activity.

Mutagenesis of the nucleotide codon encoding the asparagine in SEQ ID NO:2 glycosylation sites 4,5, and/or 6 (e.g. converting the asparagine to an aspartic acid) results in the production of an enzyme with increased PLC activity compared to the wild-type open reading frame expressed in the same host (the triple mutant expressed in *Pichia pastoris* possesses a specific activity and a functional activity that is essentially identical to that of the wild-type sequence expressed in a non-glycosylating host like *E. coli*. It is also possible to abolish the N-linked glycosylation site by mutagenesis of the serine or threonine residue in the N-linked glycosylation consensus sequence (NXS/T), for example by converting these nucleotide codons to produce valine or isoleucine at these positions instead of serine or threonine. The use of this strategy to remove N-linked glycosylation sites also results in the production of active SEQ ID NO:2 phospholipase in glycosylating host expression systems.

Assays for Phospholiase Activity

The invention provides isolated, synthetic or recombinant polypeptides (e.g., enzymes, antibodies) having a phospholipase activity, or any combination of phospholipase activities, and nucleic acids encoding them. Any of the many phospholipase activity assays known in the art can be used to determine if a polypeptide has a phospholipase activity and is within the scope of the invention. Routine protocols for determining phospholipase A, B, D and C, patatin and lipid acyl hydrolase activities, or lipase activity, are well known in the art.

Exemplary activity assays include turbidity assays, methylumbelliferyl phosphocholine (fluorescent) assays, Amplex red (fluorescent) phospholipase assays, thin layer chromatography assays (TLC), cytolytic assays and p-nitrophenylphosphorylcholine assays. Using these assays polypeptides, peptides or antibodies can be quickly screened for a phospholipase activity.

The phospholipase activity can comprise a lipid acyl hydrolase (LAH) activity. See, e.g., Jimenez (2001) Lipids 36:1169-1174, describing an octaethylene glycol monododecyl ether-based mixed micellar assay for determining the lipid acyl hydrolase activity of a patatin. Pinsirodom (2000) J. Agric. Food Chem. 48:155-160, describes an exemplary lipid acyl hydrolase (LAH) patatin activity.

Turbidity assays to determine phospholipase activity are described, e.g., in Kauffmann (2001) "Conversion of *Bacillus thermocatenulatus* lipase into an efficient phospholipase with increased activity towards long-chain fatty acyl substrates by directed evolution and rational design," Protein Engineering 14:919-928; Ibrahim (1995) "Evidence implicating phospholipase as a virulence factor of *Candida albicans*," Infect. Immun. 63:1993-1998.

Methylumbelliferyl (fluorescent) phosphocholine assays to determine phospholipase activity are described, e.g., in Goode (1997) "Evidence for cell surface and internal phospholipase activity in ascidian eggs," Develop. Growth Differ. 39:655-660; Diaz (1999) "Direct fluorescence-based lipase activity assay," BioTechniques 27:696-700.

Amplex Red (fluorescent) Phospholipase Assays to determine phospholipase activity are available as kits, e.g., the detection of phosphatidylcholine-specific phospholipase using an Amplex Red phosphatidylcholine-specific phospholipase assay kit from Molecular Probes Inc. (Eugene, Oreg.), according to manufacturer's instructions. Fluorescence is measured in a fluorescence microplate reader using excitation at 560±10 nm and fluorescence detection at 590±10 nm. The assay is sensitive at very low enzyme concentrations.

Thin layer chromatography assays (TLC) to determine phospholipase activity are described, e.g., in Reynolds (1991) Methods in Enzymol. 197:3-13; Taguchi (1975) "Phospholipase from *Clostridium novyi* type A.I," Biochim. Biophys. Acta 409:75-85. Thin layer chromatography (TLC) is a widely used technique for detection of phospholipase activity. Various modifications of this method have been used to extract the phospholipids from the aqueous assay mixtures. In some PLC assays the hydrolysis is stopped by addition of chloroform/methanol (2:1) to the reaction mixture. The unreacted starting material and the diacylglycerol are extracted into the organic phase and may be fractionated by TLC, while the head group product remains in the aqueous phase. For more precise measurement of the phospholipid digestion, radiolabeled substrates can be used (see, e.g., Reynolds (1991) Methods in Enzymol. 197:3-13). The ratios of products and reactants can be used to calculate the actual number of moles of substrate hydrolyzed per unit time. If all the components are extracted equally, any losses in the extraction will affect all components equally. Separation of phospholipid digestion products can be achieved by silica gel TLC with chloroform/methanol/water (65:25:4) used as a solvent system (see, e.g., Taguchi (1975) Biochim. Biophys. Acta 409:75-85).

p-Nitrophenylphosphorylcholine assays to determine phospholipase activity are described, e.g., in Korbsrisate (1999) J. Clin. Microbiol. 37:3742-3745; Berka (1981) Infect. Immun. 34:1071-1074. This assay is based on enzymatic hydrolysis of the substrate analog p-nitrophenylphosphorylcholine to liberate a yellow chromogenic compound p-nitrophenol, detectable at 405 nm. This substrate is convenient for high-throughput screening.

A cytolytic assay can detect phospholipases with cytolytic activity based on lysis of erythrocytes. Toxic phospholipases can interact with eukaryotic cell membranes and hydrolyze phosphatidylcholine and sphingomyelin, leading to cell lysis. See, e.g., Titball (1993) Microbiol. Rev. 57:347-366.

Hybrid (Chimeric) Phospholipases and Peptide Libraries

In one aspect, the invention provides hybrid phospholipases and fusion proteins, including peptide libraries, comprising sequences of the invention. The peptide libraries of the invention can be used to isolate peptide modulators (e.g., activators or inhibitors) of targets, such as phospholipase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP) and/or catalytic domain (CD) of the invention and a heterologous sequence (see above).

The invention also provides methods for generating "improved" and hybrid phospholipases using the nucleic acids and polypeptides of the invention. For example, the invention provides methods for generating enzymes that have activity, e.g., phospholipase activity (such as, e.g., phospholipase A, B, C or D activity, patatin esterase activity, cleavage of a glycerolphosphate ester linkage, cleavage of an ester linkage in a phospholipid in a vegetable oil) at extreme alkaline pHs and/or acidic pHs, high and low temperatures, osmotic conditions and the like. The invention provides methods for generating hybrid enzymes (e.g., hybrid phospholipases).

In one aspect, the methods of the invention produce new hybrid polypeptides by utilizing cellular processes that integrate the sequence of a first polynucleotide such that resulting hybrid polynucleotides encode polypeptides demonstrating activities derived from the first biologically active polypeptides. For example, the first polynucleotides can be an exemplary nucleic acid sequence (e.g., SEQ ID NO:1, SEQ ID NO:3, SEQ ID NO:5, SEQ ID NO:7, etc.) encoding an exemplary phospholipase of the invention (e.g., SEQ ID NO:2, SEQ ID NO:4, SEQ ID NO:6, SEQ ID NO: 8, etc.). The first nucleic acid can encode an enzyme from one organism that functions effectively under a particular environmental condition, e.g. high salinity. It can be "integrated" with an enzyme encoded by a second polynucleotide from a different organism that functions effectively under a different environmental condition, such as extremely high temperatures. For example, when the two nucleic acids can produce a hybrid molecule by e.g., recombination and/or reductive reassortment. A hybrid polynucleotide containing sequences from the first and second original polynucleotides may encode an enzyme that exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Alternatively, a hybrid polypeptide resulting from this method of the invention may exhibit specialized enzyme activity not displayed in the original enzymes. For example, following recombination and/or reductive reassortment of polynucleotides encoding phospholipase activities, the resulting hybrid polypeptide encoded by a hybrid polynucleotide can be screened for specialized activities obtained from each of the original enzymes, i.e. the type of bond on which the phospholipase acts and the temperature at which the phospholipase functions. Thus, for example, the phospholipase may be screened to ascertain those chemical functionalities which distinguish the hybrid phospholipase from the original phospholipases, such as: (a) amide (peptide bonds), i.e., phospholipases; (b) ester bonds, i.e., phospholipases and lipases;

(c) acetals, i.e., glycosidases and, for example, the temperature, pH or salt concentration at which the hybrid polypeptide functions.

Sources of the polynucleotides to be "integrated" with nucleic acids of the invention may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity. "Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample that may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions that promote recombination and/or reductive reassortment creating potentially active biomolecules with novel or enhanced activities.

The microorganisms from which hybrid polynucleotides may be prepared include prokaryotic microorganisms, such as *Eubacteria* and *Archaebacteria*, and lower eukaryotic microorganisms such as fungi, some algae and protozoa. Polynucleotides may be isolated from environmental samples. Nucleic acid may be recovered without culturing of an organism or recovered from one or more cultured organisms. In one aspect, such microorganisms may be extremophiles, such as hyperthermophiles, psychrophiles, psychrotrophs, halopliles, barophiles and acidophiles. In one aspect, polynucleotides encoding phospholipase enzymes isolated from extremophilic microorganisms are used to make hybrid enzymes. Such enzymes may function at temperatures above 100° C. in, e.g., terrestrial hot springs and deep sea thermal vents, at temperatures below 0° C. in, e.g., arctic waters, in the saturated salt environment of, e.g., the Dead Sea, at pH values around 0 in, e.g., coal deposits and geothermal sulfur-rich springs, or at pH values greater than 11 in, e.g., sewage sludge. For example, phospholipases cloned and expressed from extremophilic organisms can show high activity throughout a wide range of temperatures and pHs.

Polynucleotides selected and isolated as described herein, including at least one nucleic acid of the invention, are introduced into a suitable host cell. A suitable host cell is any cell that is capable of promoting recombination and/or reductive reassortment. The selected polynucleotides can be in a vector that includes appropriate control sequences. The host cell can be a higher eukaryotic cell, such as a mammalian cell, or a lower eulcaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

Exemplary appropriate hosts include bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells (see also, discussion above). The selection of an appropriate host for recombination and/or reductive reassortment or just for expression of recombinant protein is deemed to be within the scope of those skilled in the art from the teachings herein. Mammalian cell culture systems that can be employed for recombination and/or reductive reassortment or just for expression of recombinant protein include, e.g., the COS-7 lines of monkey kidney fibroblasts, described in "SV40-transformed simian cells support the replication of early SV40 mutants" (Gluzman, 1981), the C127, 3T3, CHO, HeLa and BHK cell lines. Mammalian expression vectors can comprise an origin of replication, a suitable promoter and enhancer, and necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

Host cells containing the polynucleotides of interest (for recombination and/or reductive reassortment or just for expression of recombinant protein) can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, the nucleic acids and methods of the present invention can be used to generate novel polynucleotides for biochemical pathways, e.g., pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. "Fosmids," cosmids or bacterial artificial chromosome (BAC) vectors can be used as cloning vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Thus, in one aspect, the invention relates to a method for producing a biologically active hybrid polypeptide using a nucleic acid of the invention and screening the polypeptide for an activity (e.g., enhanced activity) by:

(1) introducing at least a first polynucleotide (e.g., a nucleic acid of the invention) in operable linkage and a second polynucleotide in operable linkage, said at least first polynucleotide and second polynucleotide sharing at least one region of partial sequence homology, into a suitable host cell;

(2) growing the host cell under conditions which promote sequence reorganization resulting in a hybrid polynucleotide in operable linkage;

(3) expressing a hybrid polypeptide encoded by the hybrid polynucleotide;

(4) screening the hybrid polypeptide under conditions which promote identification of the desired biological activity (e.g., enhanced phospholipase activity); and (5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

In vivo reassortment can be focused on "inter-molecular" processes collectively referred to as "recombination." In bacteria it is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. Thus, in one aspect of the invention, using the nucleic acids of the invention novel polynucleotides are generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species.

Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. "Quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units. When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, in one aspect of the invention, the sequences to be reasserted are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following: a) Primers that include a poly-A head and poly-T tail which when made single-stranded would provide orientation can be utilized. This is accomplished by having the first few bases of the primers made from RNA and hence easily removed RNase H. b) Primers that include unique restriction cleavage sites can be utilized. Multiple sites, a battery of unique sequences, and repeated synthesis and ligation steps would be required. c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by: 1) The use of vectors only stably maintained when the construct is reduced in complexity. 2) The physical recovery of shortened vectors by physical procedures. In this case, the cloning vector would be recovered using standard plasmid isolation procedures and size fractionated on either an agarose gel, or column with a low molecular weight cut off utilizing standard procedures. 3) The recovery of vectors containing interrupted genes which can be selected when insert size decreases. 4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, this process is not limited to such nearly identical repeats.

The following is an exemplary method of the invention. Encoding nucleic acid sequences (quasi-repeats) are derived from three (3) species, including a nucleic acid of the invention. Each sequence encodes a protein with a distinct set of properties, including an enzyme of the invention. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI). Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations. In one aspect, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure. The polypeptides, e.g., phospholipases, that are identified from such libraries can be used for various purposes, e.g., the industrial processes described herein and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for phospholipase activity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The phospholipase enzymes, fragments thereof and nucleic acids that encode the enzymes and fragments can be affixed to a solid support. This is often economical and efficient in the use of the phospholipases in industrial processes. For example, a consortium or cocktail of phospholipase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof.

Another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support.

Other exemplary solid supports used to practice the invention comprise diatomaceous earth products and silicates. Some examples include CELITE®KENITE®, DIACTIV®, PRIMISIL®, DIAFIL® diatomites and MICRO-CEL®, CALFLO®, SILASORB™, and CELKATE® synthetic calcium and magnesium silicates. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

Arrays, or "BioChips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a phospholipase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. "Polypeptide arrays" can also be used to simultaneously quantify a plurality of proteins.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to a phospholipase of the invention. These antibodies can be used to isolate, identify or quantify the phospholipases of the invention or related polypeptides. These antibodies can be used to inhibit the activity of an enzyme of the invention. These antibodies can be used to isolated polypeptides related to those of the invention, e.g., related phospholipase enzymes.

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention.

Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., a kit having at least one phospholipase of the invention) and/or antibodies (e.g., a kit having at least one antibody of the invention. The kits also can contain instructional material teaching the methodologies and industrial uses of the invention, as described herein.

Industrial and Medical Uses of the Enzymes of the Invention

The invention provides many industrial uses and medical applications using polypeptides of the invention, e.g., a phospholipase and other enzymes of the invention, e.g., phospholipases A, B, C and D, patatins, including converting a non-hydratable phospholipid to a hydratable form, oil degumming, processing of oils from plants, fish, algae and the like, to name just a few applications. In any of these alternative industrial uses and medical applications, an enzymes can be added in a specific order, e.g., phospholipases with differing specificities are added in a specific order, for example, an enzyme with PC- and PE-hydrolyzing activity is added first (or two enzymes are added, one with PC-hydrolyzing activity and the other with PE-hydrolyzing activity), then an enzyme with PI-hydrolyzing activity (e.g., PLC activity) is added, or any combination thereof.

Any or all of the methods of the invention can be used on a "process scale", e.g., an oil processes or refining on a scale from about 15,000; 25,000; 50,000; 75,000; or 100,000 lbs of refined oil/day up to about 1, 2, 3, 4, 5 or 6 or more million lbs refined oil/day.

Methods of using phospholipase enzymes in industrial applications are well known in the art. For example, the phospholipases and methods of the invention can be used for the processing of fats and oils as described, e.g., in JP Patent Application Publication H6-306386, describing converting phospholipids present in the oils and fats into water-soluble substances containing phosphoric acid groups.

Phospholipases of the invention can be used to process plant oils and phospholipids such as those derived from or isolated from rice bran, soy, canola, palm, cottonseed, corn, palm kernel, coconut, peanut, sesame, sunflower. Phospholipases of the invention can be used to process essential oils, e.g., those from fruit seed oils, e.g., grapeseed, apricot, borage, etc. Phospholipases of the invention can be used to process oils and phospholipids in different forms, including crude forms, degummed, gums, wash water, clay, silica, soapstock, and the like. The phospholipids of the invention can be used to process high phosphorus oils, fish oils, animal oils, plant oils, algae oils and the like. In any aspect of the invention, any time a phospholipase C can be used, an alternative comprises use of a phospholipase D of the invention and a phosphatase (e.g., using a PLD/phosphatase combination to improve yield in a high phosphorus oil, such as a soy bean oil).

Phospholipases of the invention can be used to process and make edible oils, biodiesel oils, liposomes for pharmaceuticals and cosmetics, structured phospholipids and structured lipids. Phospholipases of the invention can be used in oil extraction. Phospholipases of the invention can be used to process and make various soaps.

Processing Edible Oils: Generation of 1,3-diacylglycerol (1,3 DAG)

The invention provides processes using enzyme(s) of the invention to make 1,3-diacylglycerol (1,3 DAG). In one aspect, a phospholipase C or phospholipase D plus a phosphatase generates 1,2-diacylglycerol; this improves oil yield during edible oil refining. When used in a process that includes a caustic neutralization step, for example as a caustic refining aid, as much as 70% of the 1,2-diacylglyceride (1,2-DAG) undergoes acyl migration and is converted to 1,3-DAG. 1,3-DAG possesses increased health benefits and therefore the use of PLC as a caustic refining aid produces an oil with increased nutritional value.

The invention provides processes using enzyme(s) of the invention to make and process edible oils, including generation of edible oils with increased amounts of 1,3-DAG. Diacylglycerols are naturally occurring compounds found in many edible oils. In one aspect of a method of the invention, e.g., the oil degumming process, a base (caustic) causes the isomerization of 1,2-DAG, produced by PLC, into 1,3-DAG which provides a nutritional health benefit over 1,2-DAG, e.g., the 1,3-DAG is burned as energy instead of being stored as fat (as is 1,2-DAG). By adding the PLC at the front end of caustic refining process (and the acid and caustic subsequently), the methods of the invention generate an elevated level of 1,3-DAG (decreasing 1,2-DAG). Nutritionally, 1,3-DAG is better for you than 1,2-DAG. In alternative aspects, the invention comprises an oil degumming process using a PLC of the invention, whereby the final degummed oil product contains not less than 0.5%, 1.0%, 2.0% or 3.0% or more 1,3-DAG.

Thus, the invention provides a process for making (through interesterification) a refined oil (e.g., a diacylglycerol oil), including edible oils, containing increased levels of 1,3-diacylglycerol (1,3-DAG), e.g., as illustrated in Example 13, where a phospholipase, such as an enzyme of the invention, is "front-loaded" or added before addition of acid or caustic. The generation by enzymatic hydrolysis of a DAG from a triglyceride generates by interesterification 1,3 DAG from 1,2 DAG. The 1,3 DAG-comprising edible oil shows different metabolic effects compared to conventional edible oils. Differences in metabolic pathways between 1,3 DAG and either 1,2 DAG or triglycerides allow a greater portion of fatty acids from 1,3 diacylglycerol to be burned as energy rather than being stored as fat. Clinical studies have shown that regular consumption of DAG oil as part of a sensible diet can help individuals to manage their body weight and body fat. In addition, metabolism of 1,3 DAG reduces circulating post-meal triglycerides in the bloodstream. Since obesity and elevated blood lipids are associated as risk factors for chronic diseases including cardiovascular disease and Type II diabetes, these lifestyle-related health conditions may be impacted in a beneficial manner with regular consumption of DAG oils.

Consumption of DAG-comprising oil can take place through a variety of means. Thus, in one aspect, the invention provides a process using an enzyme of the invention for making a food, e.g., a baked good, having increased levels of 1,3-DAG diacylglycerol and baked goods comprising diacylglycerol oils. In one aspect, the baked goods are cookies, cakes and similar baked goods.

In alternative embodiments, combination of enzymes that can be used in the methods of the invention, including the processing of edible oils, include (where one, several or all of the enzymes in the combination comprise an enzyme of the instant invention):

PLC+PI-PLC+PLA (PLA added after completion of PLC reactions);

PLD+phosphatase+PI-PLC followed by PLA; or,

PLC or (PLC+PI-PLC)+PLA specific for phosphatidic acid (all enzymes added together or sequentially).

Oil Degumming and Vegetable Oil Processing

The enzymes of the invention (e.g., polypeptides of the invention having lipase, phospholipase, esterase and/or glycosidase or equivalent activity) can be used in various vegetable oil processing steps, such as in vegetable oil extraction, particularly, in the removal of "phospholipid gums" in a process called "oil degumming".

These processes of the invention can be used on a "process scale", e.g., on a scale from about 15,000; 25,000; 50,000; 75,000; or 100,000 lbs of refined oil/day up to about 1, 2, 3, 4, 5 or 6 or more million lbs refined oil/day.

In one aspect, the invention provides oil degumming processes comprising use of a phospholipase of the invention, e.g., a PLC of the invention. In one aspect, the process further comprises addition of another phospholipase (which can also be a phospholipase of the invention), e.g., another PLC, a PLA, a PLB, a PLB or a patatin of the invention, or an enzyme (which can also be an enzyme of the invention) having a lysophospholipase-transacylase (LPTA) activity or lysophospholipase (LPL) activity and lysophospholipase-transacylase (LPTA), or a combination thereof, and/or a patatin-like phospholipase (which can also be an enzyme of the invention). In one aspect, all enzymes are added together, or, alternatively, the enzymes are added in a specific order, e.g., PLC addition is followed by PLA and/or patatin addition; or, an enzyme or enzymes of the invention having PC and PE activity added first, then PI PLC added second.

In one aspect, this process provides a yield improvement as a result of the phospholipase (e.g., PLC of the invention) treatment. In one aspect, this process provides an additional decrease of the phosphorus content of the oil as a result of the phospholipase (e.g., PLA of the invention) treatment.

In one aspect, the invention provides processes comprising use of a phospholipase of the invention, e.g., a PLC of the invention, to reduce gum mass and increase neutral oil (triglyceride) gain through reduced oil entrapment. In one aspect, the invention provides processes comprising use of a phospholipase of the invention, e.g., a PLC of the invention, for increasing neutral oils and diacylglycerol (DAG) production to contribute to the oil phase. In alternative aspects, processes of the invention (e.g., degumming processes) may comprise one or more other enzymes such as a protease, an amylase, a lipase, a cutinase, another phospholipase (including, e.g., an enzyme of the invention), a carbohydrase, a cellulase, a pectinase, a mannanase, an arabinase, a galactanase, a xylanase, an oxidase, e.g., a lactase, and/or a peroxidase, or polypeptides with equivalent activity, or a combination thereof.

The phospholipases of the invention can be used in various vegetable oil processing steps, such as in vegetable oil extraction, particularly, in the removal of "phospholipid gums" in a process called "oil degumming," as described above. The invention provides methods for processing vegetable oils from various sources, such as rice bran, soybeans, rapeseed, peanuts and other nuts, sesame, sunflower, palm and corn. The methods can used in conjunction with processes based on extraction with as hexane, with subsequent refining of the crude extracts to edible oils, including use of the methods and enzymes of the invention. The first step in the refining sequence is the so-called "degumming" process, which serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, mainly phospholipids, and oil, mainly triglycerides.

The phospholipases of the invention can be used in any "degumming" procedure, including water degumming, ALCON oil degumming (e.g., for soybeans), safinco degumming, "super degumming," UF degumming, TOP degumming, uni-degumming, dry degumming and ENZYMAX™ degumming. See, e.g., U.S. Pat. Nos. 6,355,693; 6,162,623; 6,103,505; 6,001,640; 5,558,781; 5,264,367. Various "degumming" procedures incorporated by the methods of the invention are described in Bockisch, M. (1998) In Fats and Oils Handbook, The extraction of Vegetable Oils (Chapter 5), 345-445, AOCS Press, Champaign, Ill. The phospholipases of the invention can be used in the industrial application of enzymatic degumming of triglyceride oils as described, e.g., in EP 513 709.

In one aspect, phospholipases of the invention are used to treat vegetable oils, e.g., crude oils, such as rice bran, soy, canola, flower and the like. In one aspect, this improves the efficiency of the degumming process. In one aspect, the invention provides methods for enzymatic degumming under conditions of low water, e.g., in the range of between about 0.1% to 20% water, or, 0.5% to 10% water. In one aspect, this results in the improved separation of a heavy phase from the oil phase during centrifugation. The improved separation of these phases can result in more efficient removal of phospholipids from the oil, including both hydratable and nonhydratable oils. In one aspect, this can produce a gum fraction that contains less entrained neutral oil (triglycerides), thereby improving the overall yield of oil during the degumming process.

In one aspect, phospholipases of the invention, e.g., a polypeptide having PLC activity, are used to treat oils (e.g., vegetable oils, including crude oils, such as rice bran, soy, canola, flower and the like), e.g., in degumming processes, to reduce gum mass and increase neutral oil gain through reduced oil entrapment. In one aspect, phospholipases of the invention e.g., a polypeptide having PLC activity, are used for diacylglycerol (DAG) production and to contribute to the oil phase.

The phospholipases of the invention can be used in the industrial application of enzymatic degumming as described, e.g., in CA 1102795, which describes a method of isolating polar lipids from cereal lipids by the addition of at least 50% by weight of water. This method is a modified degumming in the sense that it utilizes the principle of adding water to a crude oil mixture.

In one aspect, the invention provides enzymatic processes comprising use of phospholipases of the invention (e.g., a PLC) comprising hydrolysis of hydrated phospholipids in oil at a temperature of about 20° C. to 40° C., at an alkaline pH, e.g., a pH of about pH 8 to pH 10, using a reaction time of about 3 to 10 minutes. This can result in less than 10 ppm final oil phosphorus levels. The invention also provides enzymatic processes comprising use of phospholipases of the invention (e.g., a PLC) comprising hydrolysis of hydratable and non-hydratable phospholipids in oil at a temperature of about 50° C. to 60° C., at a pH slightly below neutral, e.g., of about pH 5 to pH 6.5, using a reaction time of about 30 to 60 minutes. This can result in less than 10 ppm final oil phosphorus levels.

In one aspect, the invention provides enzymatic processes that utilize a phospholipase C enzyme to hydrolyze a glyceryl phosphoester bond and thereby enable the return of the diacylglyceride portion of phospholipids back to the oil, e.g., a vegetable, fish or algae oil (a "phospholipase C (PLC) caustic refining aid"); and, reduce the phospholipid content in a degumming step to levels low enough for high phosphorus oils to be physically refined (a "phospholipase C (PLC) degumming aid"). The two approaches can generate different values and have different target applications.

Figure 6:
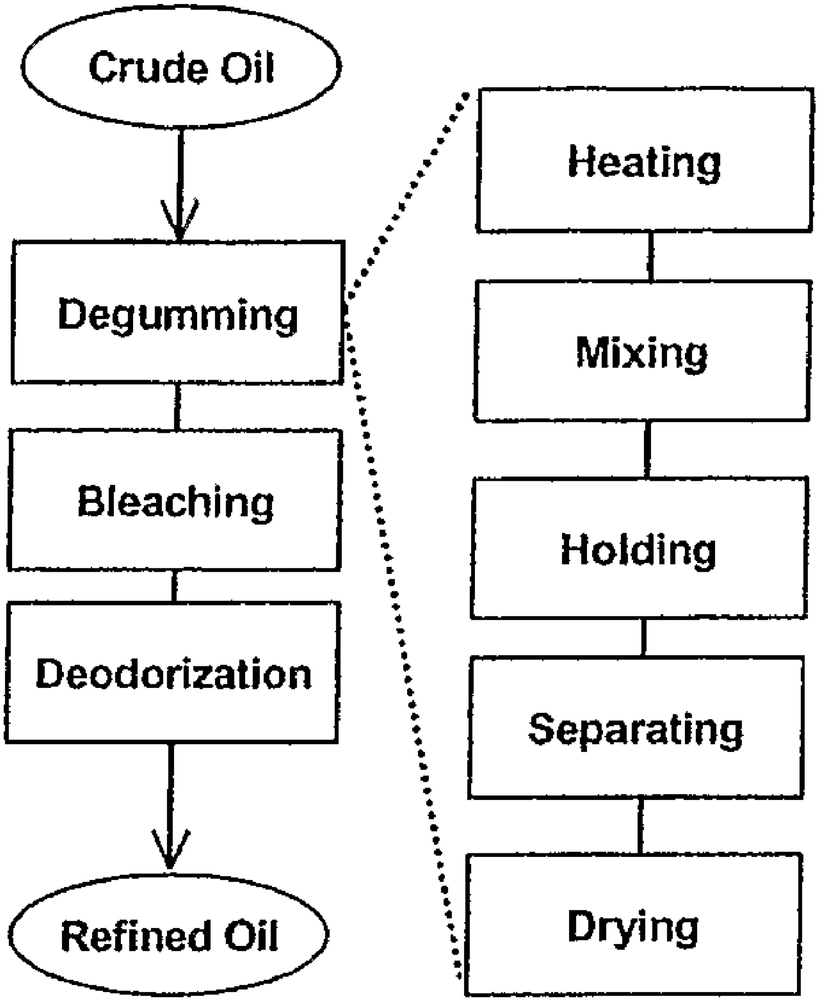
FIG. 6 schematically illustrates an exemplary vegetable oil refining process using the phospholipases of the invention.

In various exemplary processes of the invention, a number of distinct steps compose the degumming process preceding the core bleaching and deodorization refining processes. These steps include heating, mixing, holding, separating and drying. Following the heating step, water and often acid are added and mixed to allow the insoluble phospholipid "gum" to agglomerate into particles which may be separated. While water separates many of the phosphatides in degumming, portions of the phospholipids are non-hydratable phosphatides (NHPs) present as calcium or magnesium salts. Degumming processes address these NHPs by the addition of acid. Following the hydration of phospholipids, the oil is mixed, held and separated by centrifugation. Finally, the oil is dried and stored, shipped or refined, as illustrated, e.g., in FIG. 6. The resulting gums are either processed further for lecithin products or added back into the meal.

Figure 7:
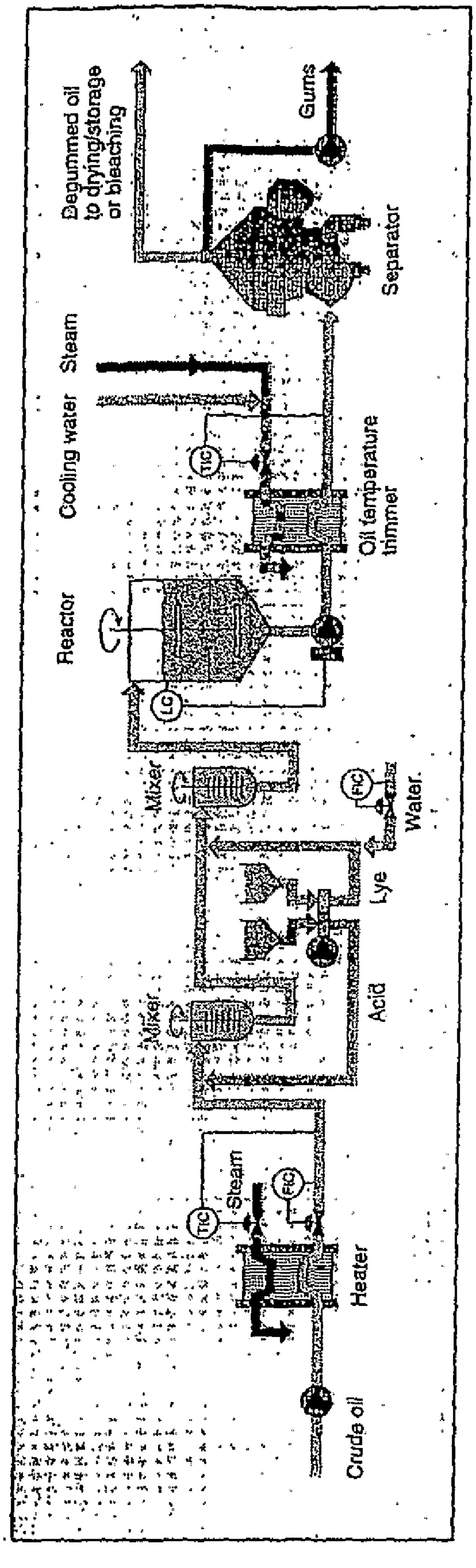
FIG. 7 schematically illustrates an exemplary degumming process of the invention for physically refined oils, as discussed in detail, below.

In various exemplary processes of the invention phosphorus levels are reduced low enough for physical refining. The separation process can result in potentially higher yield losses than caustic refining. Additionally, degumming processes may generate waste products that may not be sold as commercial lecithin, see, e.g., FIG. 7 for an exemplary degumming process for physically refined oils. Therefore, these processes have not achieved a significant share of the market and caustic refining processes continue to dominate the industry for rice bran, soy, canola and sunflower. Note however, that a phospholipase C enzyme employed in a special degumming process would decrease gum formation and return the diglyceride portion of the phospholipid back to the oil.

In one aspect, the invention provides methods using a PLC of the invention in the gum fraction. In one aspect of this method, oil is added to the crude oil to create an emulsion that results in the movement of the phosphatidylcholine, phosphatidyl-ethanolamine and phosphatidylinositol into the aqueous phase (water degumming). Following centrifugation, these phospholipids are major components of the aqueous gum fraction. The phospholipids in the gum fraction can be treated with phospholipase C or phospholipase D plus phosphatase (or other combinations, noted below) to generate diacylglycerol (DAG) and a phosphate ester. At this point, the DAG can be extracted from the other gum components and treated with a lipase under conditions suitable for the transesterification of the DAG to produce a desired triacylglycerol (structured lipid).

In another aspect, the majority of the 1,2-DAG can be converted to 1,3-DAG by increasing the pH of the gum following the PLC reaction, for example, by adding caustic. The 1,3-DAG can then be extracted from the gum and reacted with a lipase under the appropriate conditions to transesterify the 1,3-DAG at the sn2 position to create the desired structured triacylglycerol.

In alternative aspects, the fatty acids used in the transesterification reaction could come from a variety of sources including the free fatty acids found in the crude oil.

In one aspect, the phospholipids from water degumming are used in combination with a PLC of the invention to create structured lipids. The water-degummed oil can be exposed to a PLC and/or PLD (either or both can be enzymes of the invention) plus phosphatase or one of these combinations followed by PLA (can be an enzyme of the invention) to reduce the phosphorus to levels suitable for caustic or physical refining.

In alternative embodiments, combination of enzymes that can be used in the methods of the invention, including these degumming processes, include (where one, several or all of the enzymes in the combination comprise an enzyme of the instant invention):

PLC+PI-PLC+PLA (PLA added after completion of PLC reactions);

PLD+phosphatase+PI-PLC followed by PLA; or,

PLC or (PLC+PI-PLC)+PLA specific for phosphatidic acid (all enzymes added together or sequentially).

Caustic Refining

The invention provides processes using phospholipases (including enzymes of the invention) in caustic refining, where the enzymes are used as caustic refining aids. In alternative aspects, a PLC or PLD and/or a phosphatase are used in the processes as a drop-in, either before, during, or after a caustic neutralization refining process (either continuous or batch refining). The amount of enzyme added may vary according to the process. The water level used in the process can be low, e.g., about 0.5 to 5%. Alternatively, caustic is be added to the process multiple times. In addition, the process may be performed at different temperatures (25° C. to 70° C.), with different acids orcaustics, and at varying pH (4-12). Concentrated solutions of caustic, e.g., more concentrated than the industrial standard of 11%, to decrease mass of gum can be used. In alternative aspects, the concentrated solution of caustic is between about 12% and 50% concentrated, e.g., about 20%, 30%, 40%, 50%, or 60% or more concentrated.

Figure 8:
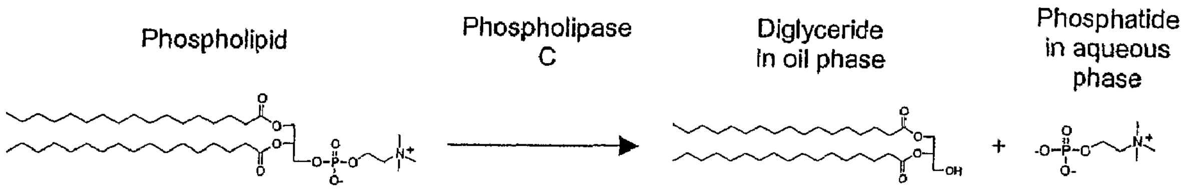
FIG. 8 schematically illustrates phosphatide hydrolysis with a phospholipase C of the invention, as discussed in detail, below.

In one aspect, a phospholipase C enzyme of the invention hydrolyzes a phosphatide at a glyceryl phosphoester bond to generate a diglyceride and water-soluble phosphate compound. The hydrolyzed phosphatide moves to the aqueous phase, leaving the diglyceride in the oil phase, as illustrated in FIG. 8. One objective of the PLC "Caustic Refining Aid" is to convert the phospholipid gums formed during neutralization into a diacylglyceride that will migrate back into the oil phase. In contrast, one objective of the "PLC Degumming Aid" is to reduce the phospholipids in crude oil to a phosphorus equivalent of less than 10 parts per million (ppm).

Acids that may be used in a caustic refining process include, but are not limited to, phosphoric, citric, ascorbic, sulfuric, fumaric, maleic, hydrochloric and/or acetic acids. Acids are used to hydrate non-hydratable phospholipids. Caustics that may be used include, but are not limited to, KOH— and NaOH. Caustics are used to neutralize free fatty acids. Alternatively, phospholipases, or more particularly a PLC or a PLD and a phosphatase, are used for purification of phytosterols from the gum/soapstock.

An alternate embodiment of the invention to add the phospholipase before caustic refining is to express the phospholipase in a plant. In another embodiment, the phospholipase is added during crushing of the plant, seeds or other plant part. Alternatively, the phospholipase is added following crushing, but prior to refining (i.e. in holding vessels). In addition, phospholipase is added as a refining pre-treatment, either with or without acid.

Another embodiment of the invention, already described, is to add the phospholipase during a caustic refining process. In this process, the levels of acid and caustic are varied depending on the level of phosphorus and the level of free fatty acids. In addition, broad temperature and pH ranges are used in the process, dependent upon the type of enzyme used.

Figure 9:
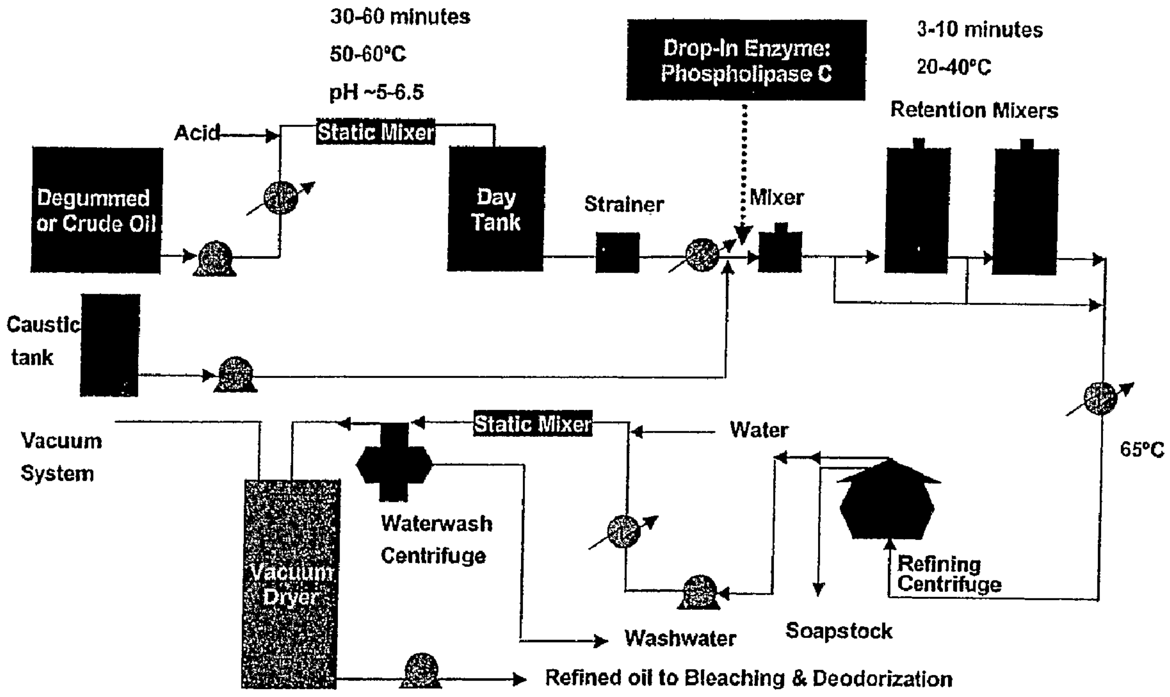
FIG. 9 schematically illustrates an exemplary caustic refining process of the invention, and illustrates an alternative embodiment comprising application of a phospholipase C of the invention as a "Caustic Refining Aid" (Long Mix Caustic Refining), as discussed in detail, below.

In another embodiment of the invention, the phospholipase is added after caustic refining (FIG. 9). In one instance, the phospholipase is added in an intense mixer or in a retention mixer, prior to separation. Alternatively, the phospholipase is added following the heat step. In another embodiment, the phospholipase is added in the centrifugation step. In an additional embodiment, the phospholipase is added to the soapstock. Alternatively, the phospholipase is added to the wash-water. In another instance, the phospholipase is added during the bleaching and/or deodorizing steps.

Figure 13:
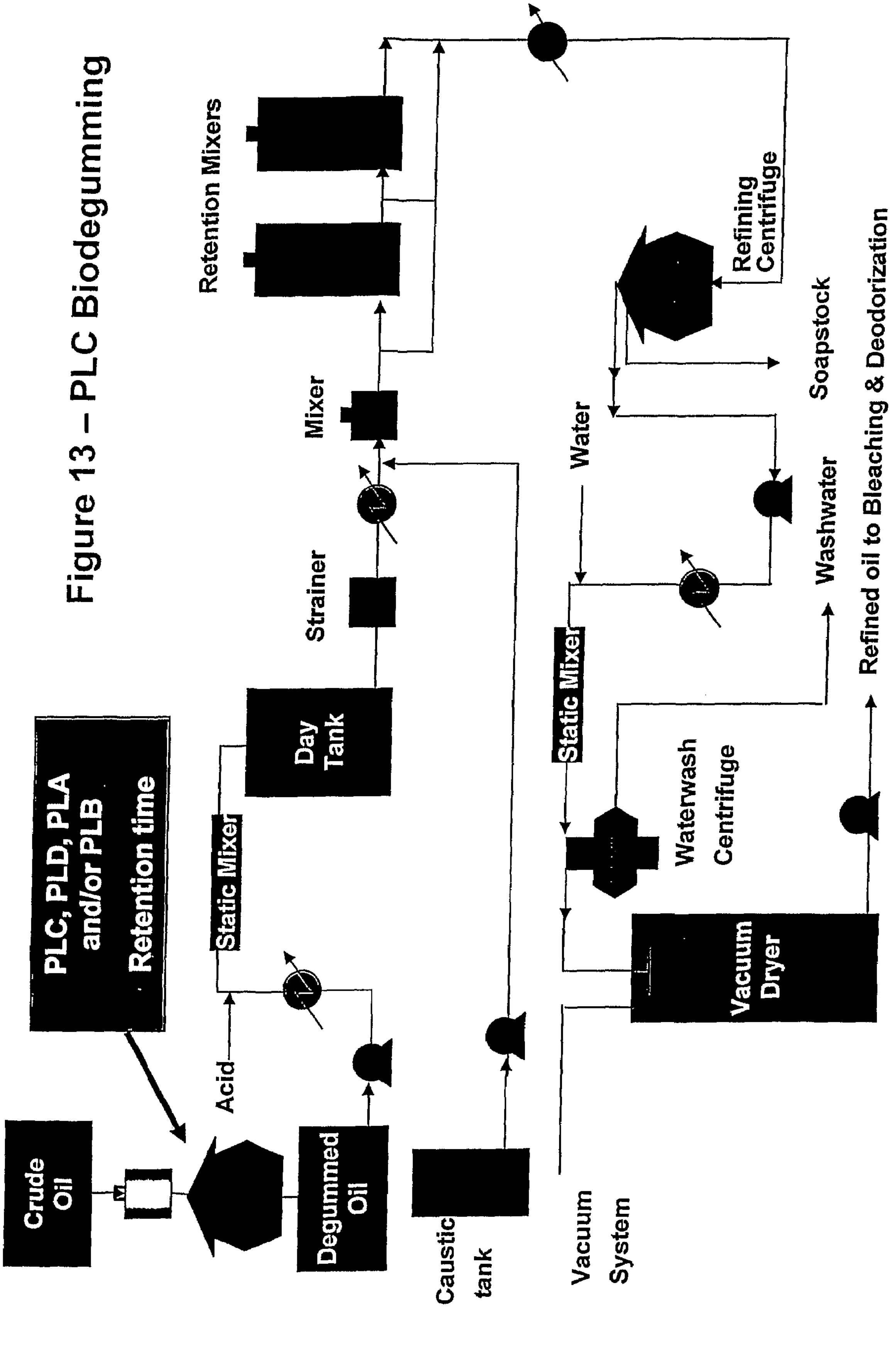
FIG. 13 schematically illustrates an exemplary caustic refining process of the invention, and illustrates an alternative embodiment comprising application of a phospholipase C of the invention as a "Caustic Refining Aid" (Long Mix Caustic Refining), as discussed in detail, below.
Figure 14:
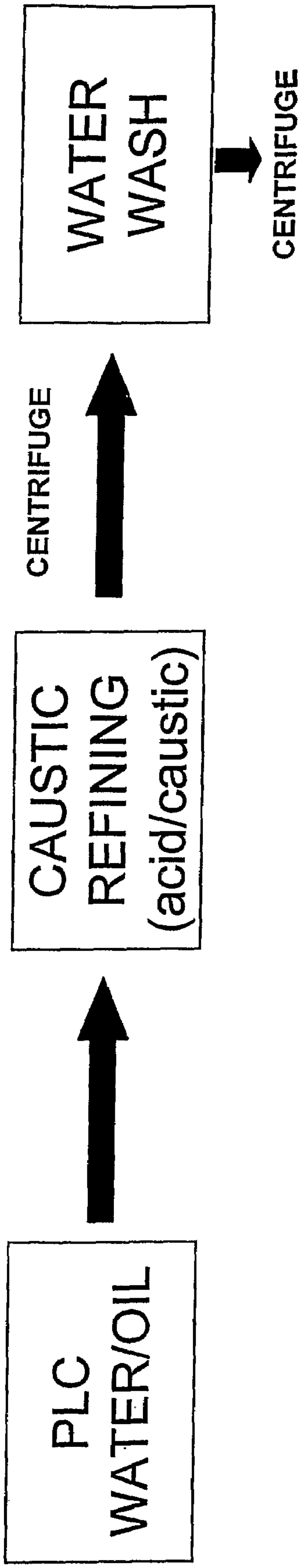
FIG. 14 illustrates another variation of methods of the invention where two centrifugation steps are used in the process, as discussed in detail, below.
Figure 15:
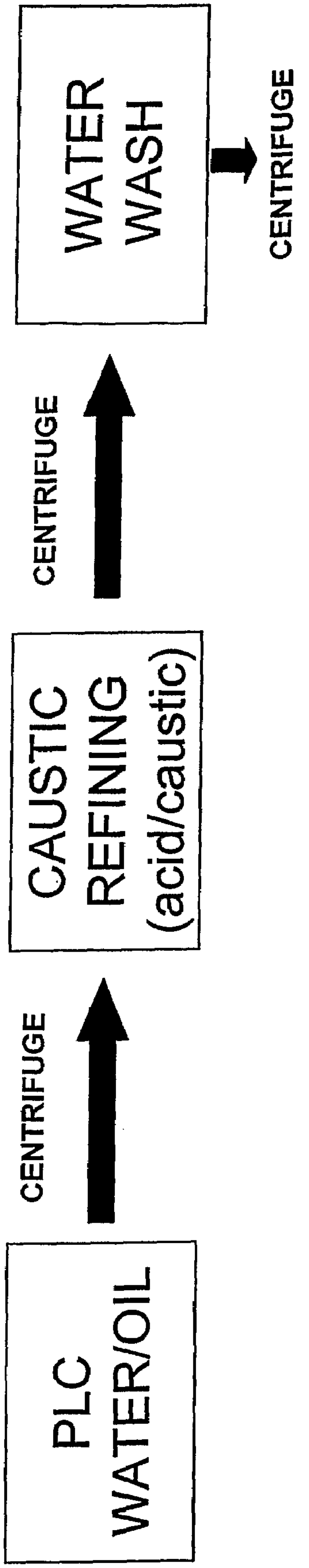
FIG. 15 illustrates another variation of methods of the invention where three centrifugation steps are used in the process, as discussed in detail, below.
Figure 16:
FIG. 16 illustrates another exemplary variation of this process using acid treatment and having a centrifugation step before a degumming step, as discussed in detail, below.

In one aspect, a phospholipase, e.g., a phospholipase C, enzyme of the invention will hydrolyze the phosphatide from both hydratable and non-hydratable phospholipids in neutralized crude and degummed oils before bleaching and deodorizing. Exemplary "caustic refining" processes of the invention are illustrated in FIG. 9 and FIG. 13. FIG. 9 includes exemplary times, temperature and pHs for static mixer (30 to 60 min, 50 to 60° C., pH 5 to 6.5) and retention mixer (3 to 10 min, 20 to 40° C.). The target enzyme can be applied as a drop-in product in the existing caustic neutralization process, as illustrated in FIG. 9. In this aspect, the enzyme will not be required to withstand extreme pH levels if it is added after the addition of caustic. As illustrated in FIG. 13 (an enzyme "front loading" exemplary process), any phospholipase, including, e.g., a phospholipase of the invention, such as a PLC, PLB, PLA and/or PLC, can be used in a crude oil degumming process, as described, e.g., in Bailey's Industrial Oil & Fat Products v.4 (ed. Y. H. Hui). FIG. 14 and FIG. 15 illustrate variations of methods of the invention where two or three centrifugation steps, respectively, are used in the process, which can be used to process any oil, e.g., a vegetable oil such as crude soy oil, as shown in the figure. The exemplary method of FIG. 15 has a centrifugation step before caustic refining (in addition to a centrifugation step after caustic refining and before the water wash, and, after the water wash), while the exemplary method of FIG. 14 does not have a centrifugation step before caustic refining. FIG. 16 illustrates another exemplary variation of this process using acid treatment and having a centrifugation step before a degumming step; this exemplary process can be used to process any oil, e.g., a vegetable oil such as crude soy oil, as shown in the figure.

Figure 10:
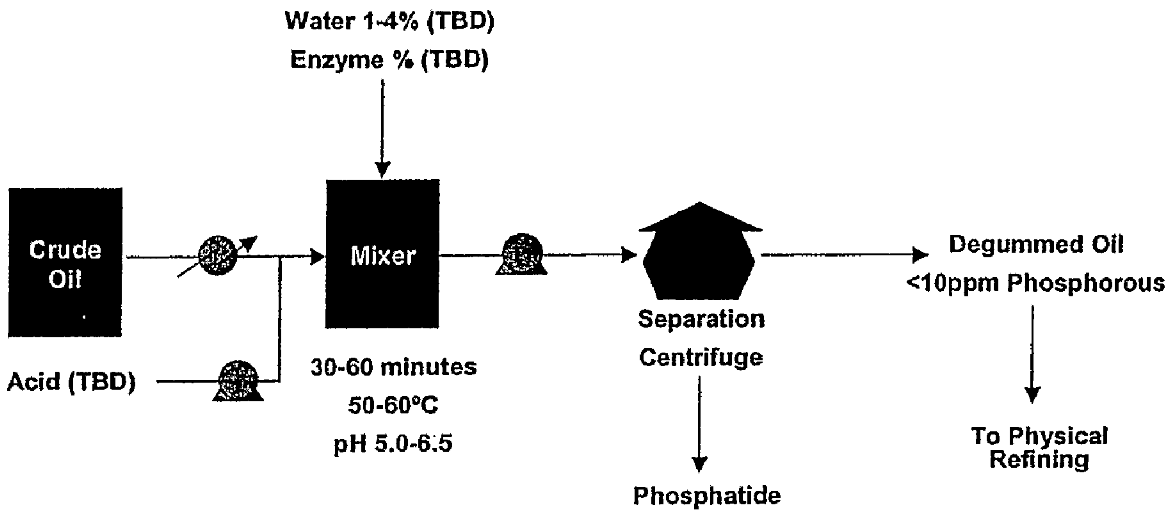
FIG. 10 schematically illustrates application of a phospholipase C of the invention as a degumming aid, as discussed in detail, below.

In one aspect, a phospholipase of the invention enables phosphorus to be removed to the low levels acceptable in physical refining. In one aspect, a PLC of the invention will hydrolyze the phosphatide from both hydratable and non-hydratable phospholipids in crude oils before bleaching and deodorizing. The target enzyme can be applied as a drop-in product in an existing degumming operation, see, e.g., FIG. 10. Given sub-optimal mixing in commercial equipment, it is likely that acid will be required to bring the non-hydratable phospholipids in contact with the enzyme at the oil/water interface. Therefore, in one aspect, an acid-stable PLC of the invention is used.

In one aspect, a PLC Degumming Aid process of the invention can eliminate losses in one, or all three, areas noted in Table 2. Losses associated in a PLC process can be estimated to be about 0.8% versus 5.2% on a mass basis due to removal of the phosphatide.

TABLE 2

Losses Addressed by PLC Products

| | | Caustic Refining Aid | Degumming Aid |
|---|---|---|---|
| 1) Oil lost in gum formation & separation | 2.1% | X | X |
| 2) Saponified oil in caustic addition | 3.1% | | X |
| 3) Oil trapped in clay in bleaching* | <1.0% | X | X |
| Total Yield Loss | ~5.2% | ~2.1% | ~5.2% |

Additional potential benefits of this process of the invention include the following:

Reduced adsorbents—less adsorbents required with lower (<5 ppm) phosphorus

Lower chemical usage—less chemical and processing costs associated with hydration of non-hydratable phospholipids Lower waste generation—less water required to remove phosphorus from oil Oils processed (e.g., "degummed") by the methods of the invention include plant oilseeds, e.g., soybean oil, rapeseed oil, rice bran oil and sunflower oil. In one aspect, the "PLC Caustic Refining Aid" of the invention can save 1.2% over existing caustic refining processes. The refining aid application addresses soy oil that has been degummed for lecithin and these are also excluded from the value/load calculations.

Performance targets of the processes of the invention can vary according to the applications and more specifically to the point of enzyme addition, see Table 3.

TABLE 3

Performance Targets by Application

| | Caustic Refining Aid | Degumming Aid |
|---|---|---|
| Incoming Oil Phosphorus Levels | <200 ppm* | 600-1,400 ppm |
| Final Oil Phosphorus Levels | <10 ppm† | <10 ppm |
| Hydratable & Non-hydratable gums | Yes | Yes |
| Residence Time | 3-10 minutes | 30 minutes‡ |
| Liquid Formulation | Yes | Yes |
| Target pH | 8-10‡‡‡ | 5.0-5.5‡‡ |
| Target Temperature | 20-40° C. | ~50-60° C. |
| Water Content | <5% | 1-1.25% |
| Enzyme Formulation Purity | No lipase/protease[1] | No lipase/protease |
| Other Key Requirements | Removal of Fe | Removal of Fe |

*Water degummed oil

†Target levels achieved in upstream caustic neutralization step but must be maintained ‡1-2 hours existing ‡‡Acid degumming will require an enzyme that is stable in much more acidic conditions: pH at 2.3 for citric acid at 5%. (~Roehm USPN 6,001,640).

‡‡‡The pH of neutralized oil is NOT neutral. Testing at POS indicates that the pH will be in the alkaline range from 6.5-10 (Dec. 9, 2002). Typical pH range needs to be determined.

Other processes that can be used with a phospholipase of the invention, e.g., a phospholipase $A_1$ can convert non-hydratable native phospholipids to a hydratable form. In one aspect, the enzyme is sensitive to heat. This may be desirable, since heating the oil can destroy the enzyme. However, the degumming reaction must be adjusted to pH 4-5 and 60° C. to accommodate this enzyme. At 300 Units/kg oil saturation dosage, this exemplary process is successful at taking previously water-degummed oil phosphorus content down to ≦10 ppm P. Advantages can be decreased $H_2O$ content and resultant savings in usage, handling and waste. Table 4 lists exemplary applications for industrial uses for enzymes of the invention:

TABLE 4

Exemplary Application

| | Caustic Refining Aid | Degumming Aid |
|---|---|---|
| Soy oil w/lecithin production | X | |
| Chemical refined soy oil, Sunflower oil, Canola oil | X | X |
| Low phosphatide oils (e.g. palm) | | X |

In addition to these various "degumming" processes, the phospholipases of the invention can be used in any vegetable oil processing step. For example, phospholipase enzymes of the invention can be used in place of PLA, e.g., phospholipase A2, in any vegetable oil processing step. Oils that are "processed" or "degummed" in the methods of the invention include soybean oils, rapeseed oils, corn oils, oil from palm kernels, canola oils, sunflower oils, sesame oils, peanut oils, rice bran oil and the like. The main products from this process include triglycerides.

In one exemplary process, when the enzyme is added to and reacted with a crude oil, the amount of phospholipase employed is about 10-10,000 units, or, alternatively, about, 100-2,000 units, per 1 kg of crude oil. The enzyme treatment is conducted for 5 min to 10 hours at a temperature of 30° C. to 90° C., or, alternatively, about, 40° C. to 70° C. The conditions may vary depending on the optimum temperature of the enzyme. The amount of water added to dissolve the enzyme is 5-1,000 wt. parts per 100 wt. parts of crude oil, or, alternatively, about, 10 to 200 wt. parts per 100 wt. parts of crude oil.

Upon completion of such enzyme treatment, the enzyme liquid is separated with an appropriate means such as a centrifugal separator and the processed oil is obtained. Phosphorus-containing compounds produced by enzyme decomposition of gummy substances in such a process are practically all transferred into the aqueous phase and removed from the oil phase. Upon completion of the enzyme treatment, if necessary, the processed oil can be additionally washed with water or organic or inorganic acid such as, e.g., acetic acid, citric acid, phosphoric acid, succinic acid, and equivalent acids, or with salt solutions.

In one exemplary process for ultra-filtration degumming, the enzyme is bound to a filter or the enzyme is added to an oil prior to filtration or the enzyme is used to periodically clean filters.

In one exemplary process for a phospholipase-mediated physical refining aid, water and enzyme are added to crude oil (e.g., crude vegetable oil). In one aspect, a PLC or a PLD of the invention and a phosphatase are used in the process. In phospholipase-mediated physical refining, the water level can be low, i.e. 0.5-5% and the process time should be short (less than 2 hours, or, less than 60 minutes, or, less than 30 minutes, or, less than 15 minutes, or, less than 5 minutes). The process can be run at different temperatures (25° C. to 70° C.), using different acids and/or caustics, at different pHs (e.g., 3-10).

In alternate aspects, water degumming is performed first to collect lecithin by centrifugation and then PLC or PLC and PLA of the invention is added to remove non-hydratable phospholipids (the process should be performed under low water concentration). In another aspect, water degumming of crude oil to less than 10 ppm (edible oils) and subsequent physical refining (less than 50 ppm for biodiesel) is performed. In one aspect, an emulsifier is added and/or the crude oil is subjected to an intense mixer to promote mixing. Alternatively, an emulsion-breaker is added and/or the crude oil is heated to promote separation of the aqueous phase. In another aspect, an acid is added to promote hydration of non-hydratable phospholipids. Additionally, phospholipases can be used to mediate purification of phytosterols from the gum/soapstock.

In one aspect, the invention provides compositions and methods (which can comprise use of phospholipases of the invention) for oil degumming comprising using varying amounts of acid and base without making soapstock. Using this aspect of the invention for oil degumming, acid (including phosphoric and/or citric) can be used to hydrate non-hydratable phospholipids in high phosphorus oils (including soybean, canola, and sunflower). Once the phospholipids are hydrated, the pH of the aqueous phase can be raised using caustic addition: the amount of caustic added can create a favorable pH for enzyme activity but will not result in the formation of a significant soapstock fraction in the oil. Because a soapstock is not formed, the free fatty acids in the oil can be removed downstream, following the degumming step, during bleaching and deodorization.

Enzymes of the invention are used to improve oil extraction and oil degumming (e.g., vegetable oils). In one aspect, a PLC of the invention and at least one plant cell wall degrader (e.g., a cellulase, a hemicellulase or the like, to soften walls and increase yield at extraction) is used in a process of the invention. In this exemplary approach to using enzymes of the invention to improve oil extraction and oil degumming, a phospholipase C of the invention as well as other hydrolases (e.g., a cellulase, a hemicellulase, an esterase, a protease and/or a phosphatase) are used during the crushing steps associated with oil production (including but not limited to soybean, canola, sunflower, rice bran oil). By using enzymes prior to or in place of solvent extraction, it is possible to increase oil yield and reduce the amount of hydratable and non-hydratable phospholipids in the crude oil. The reduction in non-hydratable phospholipids may result from conversion of potentially non-hydratable phospholipids to diacylglycerol and corresponding phosphate-ester prior to complexation with calcium or magnesium. The overall reduction of phospholipids in the crude oil will result in improved yields during refining with the potential for eliminating the requirement for a separate degumming step prior to bleaching and deodorization.

In one aspect, the invention provides processes using a phospholipase of the invention (e.g., a phospholipase-specific phosphohydrolase of the invention), or another phospholipase, in a modified "organic refining process," which can comprise addition of the enzyme (e.g., a PLC) in a citric acid holding tank.

The enzymes of the invention can be used in any oil processing method, e.g., degumming or equivalent processes. For example, the enzymes of the invention can be used in processes as described in U.S. Pat. Nos. 5,558,781; 5,264,367; 6,001,640. The process described in U.S. Pat. No. 5,558,781 uses either phospholipase A1, A2 or B, essentially breaking down lecithin in the oil that behaves as an emulsifier.

The enzymes and methods of the invention can be used in processes for the reduction of phosphorus-containing components in edible oils comprising a high amount of non-hydratable phosphorus by using of a phospholipase of the invention, e.g., a polypeptide having a phospholipase A and/or B activity, as described, e.g., in EP Patent Number: EP 0869167. In one aspect, the edible oil is a crude oil, a so-called "non-degummed oil." In one aspect, the method treat a non-degummed oil, including pressed oils or extracted oils, or a mixture thereof, from, e.g., rapeseed, soybean, sesame, peanut, corn, rice bran or sunflower. The phosphatide content in a crude oil can vary from 0.5 to 3% w/w corresponding to a phosphorus content in the range of 200 to 1200 ppm, or, in the range of 250 to 1200 ppm. Apart from the phosphatides, the crude oil can also contains small concentrations of carbohydrates, sugar compounds and metal/phosphatide acid complexes of Ca, Mg and Fe. In one aspect, the process comprises treatment of a phospholipid or lysophospholipid with the phospholipase of the invention so as to hydrolyze fatty acyl groups. In one aspect, the phospholipid or lysophospholipid comprises lecithin or lysolecithin. In one aspect of the process the edible oil has a phosphorus content from between about 50 to 250 ppm, and the process comprises treating the oil with a phospholipase of the invention so as to hydrolyze a major part of the phospholipid and separating an aqueous phase containing the hydrolyzed phospholipid from the oil. In one aspect, prior to the enzymatic degumming process the oil is water-degummed. In one aspect, the methods provide for the production of an animal feed comprising mixing the phospholipase of the invention with feed substances and at least one phospholipid.

The enzymes and methods of the invention can be used in processes of oil degumming as described, e.g., in WO 98/18912. The phospholipases of the invention can be used to reduce the content of phospholipid in an edible oil. The process can comprise treating the oil with a phospholipase of the invention to hydrolyze a major part of the phospholipid and separating an aqueous phase containing the hydrolyzed phospholipid from the oil. This process is applicable to the purification of any edible oil, which contains a phospholipid, e.g. vegetable oils, such as soybean oil, rice bran oil, rapeseed oil and sunflower oil, fish oils, algae and animal oils and the like. Prior to the enzymatic treatment, the vegetable oil is preferably pretreated to remove slime (mucilage), e.g. by wet refining. The oil can contain between about 50 to 250 ppm, or between 50 to about 1500 ppm, or more, of phosphorus, as phospholipid at the start of the treatment with phospholipase, and the process of the invention can reduce this value to below between about 5 to 10 ppm.

The enzymes of the invention can be used in processes as described in JP Application No.: H5-132283, filed Apr. 25, 1993, which comprises a process for the purification of oils and fats comprising a step of converting phospholipids present in the oils and fats into water-soluble substances containing phosphoric acid groups and removing them as water-soluble substances. An enzyme action is used for the conversion into water-soluble substances. An enzyme having a phospholipase C activity is preferably used as the enzyme.

The enzymes of the invention can be used in processes as described as the "Organic Refining Process," (ORP) (IPH, Omaha, Nebr.) which is a method of refining seed oils. ORP may have advantages over traditional chemical refining, including improved refined oil yield, value added co-products, reduced capital costs and lower environmental costs.

The enzymes of the invention can be used in processes for the treatment of an oil or fat, animal or vegetal, raw, semi-processed or refined, comprising adding to such oil or fat at least one enzyme of the invention that allows hydrolyzing and/or depolymerizing the non-glyceridic compounds contained in the oil, as described, e.g., in EP Application number: 82870032.8. Exemplary methods of the invention for hydrolysis and/or depolymerization of non-glyceridic compounds in oils are:

1) The addition and mixture in oils and fats of an enzyme of the invention or enzyme complexes previously dissolved in a small quantity of appropriate solvent (for example water). A certain number of solvents are possible, but a non-toxic and suitable solvent for the enzyme is chosen. This addition may be done in processes with successive loads, as well as in continuous processes. The quantity of enzyme(s) necessary to be added to oils and fats, according to this process, may range, depending on the enzymes and the products to be processed, from between about 5 to 400 ppm, or between about 20 to 400 ppm; e.g., 0.005 kg to 0.4 kg of enzyme for 1000 kg of oil or fat, and preferably from 5 to 100 ppm, i.e., from 0.005 to 0.1 kg of enzyme for 1000 kg of oil, these values being understood to be for concentrated enzymes, i.e., without diluent or solvent.
2) Passage of the oil or fat through a fixed or insoluble filtering bed of enzyme(s) of the invention on solid or semi-solid supports, preferably presenting a porous or fibrous structure. In this technique, the enzymes are trapped in the micro-cavities of the porous or fibrous structure of the supports. These consist, for example, of resins or synthetic polymers, cellulose carbonates, gels such as agarose, filaments of polymers or copolymers with porous structure, trapping small droplets of enzyme in solution in their cavities. Concerning the enzyme concentration, it is possible to go up to the saturation of the supports.

3) Dispersion of the oils and fats in the form of fine droplets, in a diluted enzymatic solution, in alternative aspects containing between about 0.05 to 4%, or containing between about 0.2 to 4%, in volume of an enzyme of the invention. This technique is described, e.g., in Belgian patent No. 595,219. A cylindrical column with a height of several meters, with conical lid, is filled with a diluted enzymatic solution. For this purpose, a solvent that is non-toxic and non-miscible in the oil or fat to be processed, preferably water, is chosen. The bottom of the column is equipped with a distribution system in which the oil or fat is continuously injected in an extremely divided form (approximately 10,000 flux per $m^2$). Thus an infinite number of droplets of oil or fat are formed, which slowly rise in the solution of enzymes and meet at the surface, to be evacuated continuously at the top of the conical lid of the reactor.

Palm oil can be pre-treated before treatment with an enzyme of the invention. For example, about 30 kg of raw palm oil is heated to +50° C. 1% solutions were prepared in distilled water with cellulases and pectinases. 600 g of each of these was added to aqueous solutions of the oil under strong agitation for a few minutes. The oil is then kept at +50° C. under moderate agitation, for a total reaction time of two hours. Then, temperature is raised to +90° C. to deactivate the enzymes and prepare the mixture for filtration and further processing. The oil is dried under vacuum and filtered with a filtering aid.

The enzymes of the invention can be used in processes as described in EP patent EP 0 513 709 B2. For example, the invention provides a process for the reduction of the content process for the reduction of the content of phosphorus-containing components in animal and vegetable oils by enzymatic decomposition using a phospholipase of the invention. In alternative aspects, predemucilaginated animal and vegetable oil with a phosphorus content of between about of 50 to 1500 ppm, or, between about 50 to 250 ppm, is agitated with an organic carboxylic acid and the pH value of the resulting mixture set to between about pH 4 to pH 6, an enzyme solution which contains phospholipase $A_1$, $A_2$, or B of the invention is added to the mixture in a mixing vessel under turbulent stirring and with the formation of fine droplets, where an emulsion with 0.5 to 5% by weight relative to the oil is formed, said emulsion being conducted through at least one subsequent reaction vessel under turbulent motion during a reaction time of 0.1 to 10 hours at temperatures in the range of 20 to 80° C. and where the treated oil, after separation of the aqueous solution, has a phosphorus content under 5 ppm.

The organic refining process is applicable to both crude and degummed oil. The process uses inline addition of an organic acid under controlled process conditions, in conjunction with conventional centrifugal separation. The water separated naturally from the vegetable oil phospholipids ("VOP") is recycled and reused. The total water usage can be substantially reduced as a result of the Organic Refining Process.

The phospholipases and methods of the invention can also be used in the enzymatic treatment of edible oils, as described, e.g., in U.S. Pat. No. 6,162,623. In this exemplary methods, the invention provides an amphiphilic enzyme. It can be immobilized, e.g., by preparing an emulsion containing a continuous hydrophobic phase and a dispersed aqueous phase containing the enzyme and a carrier for the enzyme and removing water from the dispersed phase until this phase turns into solid enzyme coated particles. The enzyme can be a lipase. The immobilized lipase can be used for reactions catalyzed by lipase such as interesterification of mono-, di- or triglycerides, de-acidification of a triglyceride oil, or removal of phospholipids from a triglyceride oil when the lipase is a phospholipase. The aqueous phase may contain a fermentation liquid, an edible triglyceride oil may be the hydrophobic phase, and carriers include sugars, starch, dextran, water soluble cellulose derivatives and fermentation residues. This exemplary method can be used to process triglycerides, diglycerides, monoglycerides, glycerol, phospholipids, glycolipids or fatty acids, which may be in the hydrophobic phase. In one aspect, the process for the removal of phospholipids from triglyceride oil comprising mixing a triglyceride oil containing phospholipids with a preparation containing a phospholipase of the invention; hydrolyzing the phospholipids to lysophospholipid; separating the hydrolyzed phospholipids from the oil, wherein the phospholipase is an immobilized phospholipase.

The phospholipases and methods of the invention can also be used in the enzymatic treatment of edible oils, as described, e.g., in U.S. Pat. No. 6,127,137. This exemplary method hydrolyzes both fatty acyl groups in intact phospholipid. The phospholipase of the invention used in this exemplary method has no lipase activity and is active at very low pH. These properties make it very suitable for use in oil degumming, as enzymatic and alkaline hydrolysis (saponification) of the oil can both be suppressed. In one aspect, the invention provides a process for hydrolyzing fatty acyl groups in a phospholipid or lysophospholipid comprising treating the phospholipid or lysophospholipid with the phospholipase that hydrolyzes both fatty acyl groups in a phospholipid and is essentially free of lipase activity. In one aspect, the phospholipase of the invention has a temperature optimum at about 50° C., measured at pH 3 to pH 4 for 10 minutes, and a pH optimum of about pH 3, measured at 40° C. for about 10 minutes. In one aspect, the phospholipid or lysophospholipid comprises lecithin or lysolecithin. In one aspect, after hydrolyzing a major part of the phospholipid, an aqueous phase containing the hydrolyzed phospholipid is separated from the oil. In one aspect, the invention provides a process for removing phospholipid from an edible oil, comprising treating the oil at pH 1.5 to 3 with a dispersion of an aqueous solution of the phospholipase of the invention, and separating an aqueous phase containing the hydrolyzed phospholipid from the oil. In one aspect, the oil is treated to remove mucilage prior to the treatment with the phospholipase. In one aspect, the oil prior to the treatment with the phospholipase contains the phospholipid in an amount corresponding to 50 to 250 ppm of phosphorus. In one aspect, the treatment with phospholipase is done at 30° C. to 45° C. for 1 to 12 hours at a phospholipase dosage of 0.1 to 10 mg/l in the presence of 0.5 to 5% of water.

The phospholipases and methods of the invention can also be used in the enzymatic treatment of edible oils, as described, e.g., in U.S. Pat. No. 6,025,171. In this exemplary methods, enzymes of the invention are immobilized by preparing an emulsion containing a continuous hydrophobic phase, such as a triglyceride oil, and a dispersed aqueous phase containing an amphiphilic enzyme, such as lipase or a phospholipase of the invention, and carrier material that is partly dissolved and partly undissolved in the aqueous phase, and removing water from the aqueous phase until the phase turns into solid enzyme coated carrier particles. The undissolved part of the carrier material may be a material that is insoluble in water and oil, or a water soluble material in undissolved form because the aqueous phase is already saturated with the water soluble material. The aqueous phase may be formed with a crude lipase fermentation liquid containing fermentation residues and biomass that can serve as carrier materials. Immobilized lipase is useful for ester re-arrangement and de-acidification in oils. After a reaction, the immobilized enzyme can be regenerated for a subsequent reaction by adding water to obtain partial dissolution of the carrier, and with the resultant enzyme and carrier-containing aqueous phase dispersed in a hydrophobic phase evaporating water to again form enzyme coated carrier particles.

The phospholipases and methods of the invention can also be used in the enzymatic treatment of edible oils, as described, e.g., in U.S. Pat. No. 6,143,545. This exemplary method is used for reducing the content of phosphorus containing components in an edible oil comprising a high amount of non-hydratable phosphorus content using a phospholipase of the invention. In one aspect, the method is used to reduce the content of phosphorus containing components in an edible oil having a non-hydratable phosphorus content of at least 50 ppm measured by pre-treating the edible oil, at 60° C., by addition of a solution comprising citric acid monohydrate in water (added water vs. oil equals 4.8% w/w; (citric acid) in water phase=106 mM, in water/oil emulsion=4.6 mM) for 30 minutes; transferring 10 ml of the pre-treated water in oil emulsion to a tube; heating the emulsion in a boiling water bath for 30 minutes; centrifuging at 5000 rpm for 10 minutes, transferring about 8 ml of the upper (oil) phase to a new tube and leaving it to settle for 24 hours; and drawing 2 g from the upper clear phase for measurement of the non-hydratable phosphorus content (ppm) in the edible oil. The method also can comprise contacting an oil at a pH from about pH 5 to 8 with an aqueous solution of a phospholipase A or B of the invention (e.g., PLA1, PLA2, or a PLB), which solution is emulsified in the oil until the phosphorus content of the oil is reduced to less than 11 ppm, and then separating the aqueous phase from the treated oil.

The phospholipases and methods of the invention can also be used in the enzymatic treatment of edible oils, as described, e.g., in U.S. Pat. No. 5,532,163. The invention provides processes for the refining of oil and fat by which phospholipids in the oil and fat to be treated can be decomposed and removed efficiently. In one aspect, the invention provides a process for the refining of oil and fat which comprises reacting, in an emulsion, the oil and fat with an enzyme of the invention, e.g., an enzyme having an activity to decompose glycerol-fatty acid ester bonds in glycerophospholipids (e.g., a PLA2 of the invention); and another process in which the enzyme-treated oil and fat is washed with water or an acidic aqueous solution. In one aspect, the acidic aqueous solution to be used in the washing step is a solution of at least one acid, e.g., citric acid, acetic acid, phosphoric acid and salts thereof. In one aspect, the emulsified condition is formed using 30 weight parts or more of water per 100 weight parts of the oil and fat. Since oil and fat can be purified without employing the conventional alkali refining step, generation of washing waste water and industrial waste can be reduced. In addition, the recovery yield of oil is improved because loss of neutral oil and fat due to their inclusion in these wastes does not occur in the inventive process. In one aspect, the invention provides a process for refining oil and fat containing about 100 to 10,000 ppm of phospholipids which comprises: reacting, in an emulsified condition, said oil and fat with an enzyme of the invention having activity to decompose glycerol-fatty acid ester bonds in glycerophospholipids. In one aspect, the invention provides processes for refining oil and fat containing about 100 to 10,000 ppm of phospholipids which comprises reacting, in an emulsified condition, oil and fat with an enzyme of the invention having activity to decompose glycerol-fatty acid ester bonds in glycerophospholipids; and subsequently washing the treated oil and fat with a washing water.

The phospholipases and methods of the invention can also be used in the enzymatic treatment of edible oils, as described, e.g., in U.S. Pat. No. 5,264,367. The content of phosphorus-containing components and the iron content of an edible vegetable or animal oil, such as an oil, e.g., soybean oil, which has been wet-refined to remove mucilage, are reduced by enzymatic decomposition by contacting the oil with an aqueous solution of an enzyme of the invention, e.g., a phospholipase A1, A2, or B, and then separating the aqueous phase from the treated oil. In one aspect, the invention provides an enzymatic method for decreasing the content of phosphorus- and iron-containing components in oils, which have been refined to remove mucilage. An oil, which has been refined to remove mucilage, can be treated with an enzyme of the invention, e.g., phospholipase C, A1, A2, or B. Phosphorus contents below 5 ppm and iron contents below 1 ppm can be achieved. The low iron content can be advantageous for the stability of the oil.

The phospholipases and methods of the invention can also be used for preparing transesterified oils, as described, e.g., in U.S. Pat. No. 5,288,619. The invention provides methods for enzymatic transesterification for preparing a margarine oil having both low trans-acid and low intermediate chain fatty acid content. The method includes the steps of providing a transesterification reaction mixture containing a stearic acid source material and an edible liquid vegetable oil, transesterifying the stearic acid source material and the vegetable oil using a 1-, 3-positionally specific lipase, and then finally hydrogenating the fatty acid mixture to provide a recycle stearic acid source material for a recyclic reaction with the vegetable oil. The invention also provides a counter-current method for preparing a transesterified oil. The method includes the steps of providing a transesterification reaction zone containing a 1-, 3-positionally specific lipase, introducing a vegetable oil into the transesterification zone, introducing a stearic acid source material, conducting a supercritical gas or subcritical liquefied gas counter-current fluid, carrying out a transesterification reaction of the triglyceride stream with the stearic acid or stearic acid monoester stream in the reaction zone, withdrawing a transesterified triglyceride margarine oil stream, withdrawing a counter-current fluid phase, hydrogenating the transesterified stearic acid or stearic acid monoester to provide a hydrogenated recycle stearic acid source material, and introducing the hydrogenated recycle stearic acid source material into the reaction zone.

In one aspect, the highly unsaturated phospholipid compound may be converted into a triglyceride by appropriate use of a phospholipase C of the invention to remove the phosphate group in the sn-3 position, followed by 1,3 lipase acyl ester synthesis. The 2-substituted phospholipid may be used as a functional food ingredient directly, or may be subsequently selectively hydrolyzed in reactor 160 using an immobilized phospholipase C of the invention to produce a 1-diglyceride, followed by enzymatic esterification as described herein to produce a triglyceride product having a 2-substituted polyunsaturated fatty acid component.

The phospholipases and methods of the invention can also be used in a vegetable oil enzymatic degumming process as described, e.g., in U.S. Pat. No. 6,001,640. This method of the invention comprises a degumming step in the production of edible oils. Vegetable oils from which hydratable phosphatides have been eliminated by a previous aqueous degumming process are freed from non-hydratable phosphatides by enzymatic treatment using a phospholipase of the invention. The process can be gentle, economical and environment-friendly. Phospholipases that only hydrolyze lysolecithin, but not lecithin, are used in this degumming process.

In one aspect, to allow the enzyme of the invention to act, both phases, the oil phase and the aqueous phase that contain the enzyme, must be intimately mixed. It may not be sufficient to merely stir them. Good dispersion of the enzyme in the oil is aided if it is dissolved in a small amount of water, e.g., 0.5-5 weight-% (relative to the oil), and emulsified in the oil in this form, to form droplets of less than 10 micrometers in diameter (weight average). The droplets can be smaller than 1 micrometer. Turbulent stirring can be done with radial velocities above 100 cm/sec. The oil also can be circulated in the reactor using an external rotary pump. The aqueous phase containing the enzyme can also be finely dispersed by means of ultrasound action. A dispersion apparatus can be used.

The enzymatic reaction probably takes place at the border surface between the oil phase and the aqueous phase. It is the goal of all these measures for mixing to create the greatest possible surface for the aqueous phase which contains the enzyme. The addition of surfactants increases the microdispersion of the aqueous phase. In some cases, therefore, surfactants with HLB values above 9, such as Na-dodecyl sulfate, are added to the enzyme solution, as described, e.g., in EP-A 0 513 709. A similar effective method for improving emulsification is the addition of lysolecithin. The amounts added can lie in the range of 0.001% to 1%, with reference to the oil. The temperature during enzyme treatment is not critical. Temperatures between 20° C. and 80° C. can be used, but the latter can only be applied for a short time. In this aspect, a phospholipase of the invention having a good temperature and/or low pH tolerance is used. Application temperatures of between 30° C. and 50° C. are optimal. The treatment period depends on the temperature and can be kept shorter with an increasing temperature. Times of 0.1 to 10 hours, or, 1 to 5 hours are generally sufficient. The reaction takes place in a degumming reactor, which can be divided into stages, as described, e.g., in DE-A 43 39 556. Therefore continuous operation is possible, along with batch operation. The reaction can be carried out in different temperature stages. For example, incubation can take place for 3 hours at 40° C., then for 1 hour at 60° C. If the reaction proceeds in stages, this also opens up the possibility of adjusting different pH values in the individual stages. For example, in the first stage the pH of the solution can be adjusted to 7, for example, and in a second stage to 2.5, by adding citric acid. In at least one stage, however, the pH of the enzyme solution must be below 4, or, below 3. If the pH was subsequently adjusted below this level, a deterioration of effect may be found. Therefore the citric acid can be added to the enzyme solution before the latter is mixed into the oil.

After completion of the enzyme treatment, the enzyme solution, together with the decomposition products of the NHP contained in it, can be separated from the oil phase, in batches or continuously, e.g., by means of centrifugation. Since the enzymes are characterized by a high level of stability and the amount of the decomposition products contained in the solution is slight (they may precipitate as sludge) the same aqueous enzyme phase can be used several times. There is also the possibility of freeing the enzyme of the sludge, see, e.g., DE-A 43 39 556, so that an enzyme solution which is essentially free of sludge can be used again. In one aspect of this degumming process, oils which contain less than 15 ppm phosphorus are obtained. One goal is phosphorus contents of less than 10 ppm; or, less than 5 ppm. With phosphorus contents below 10 ppm, further processing of the oil according to the process of distillative de-acidification is easily possible. A number of other ions, such as magnesium, calcium, zinc, as well as iron, can be removed from the oil, e.g., below 0.1 ppm. Thus, this product possesses ideal prerequisites for good oxidation resistance during further processing and storage.

The phospholipases and methods of the invention also can also be used for reducing the amount of phosphorus-containing components in vegetable and animal oils as described, e.g., in EP patent EP 0513709. In this method, the content of phosphorus-containing components, especially phosphatides, such as lecithin, and the iron content in vegetable and animal oils, which have previously been deslimed, e.g. soya oil, are reduced by enzymatic breakdown using a phospholipase A1, A2 or B of the invention.

The phospholipases and methods of the invention can also be used for refining fat or oils as described, e.g., in JP 06306386. The invention provides processes for refining a fat or oil comprising a step of converting a phospholipid in a fat or an oil into a water-soluble phosphoric-group-containing substance and removing this substance. The action of an enzyme of the invention (e.g., a PLC) is utilized to convert the phospholipid into the substance. Thus, it is possible to refine a fat or oil without carrying out an alkali refining step from which industrial wastes containing alkaline waste water and a large amount of oil are produced. Improvement of yields can be accomplished because the loss of neutral fat or oil from escape with the wastes can be reduced to zero. In one aspect, gummy substances are converted into water-soluble substances and removed as water-soluble substances by adding an enzyme of the invention having a phospholipase C activity in the stage of degumming the crude oil and conducting enzymatic treatment. In one aspect, the phospholipase C of the invention has an activity that cuts ester bonds of glycerin and phosphoric acid in phospholipids. If necessary, the method can comprise washing the enzyme-treated oil with water or an acidic aqueous solution. In one aspect, the enzyme of the invention is added to and reacted with the crude oil. The amount of phospholipase C employed can be 10 to 10,000 units, or, about 100 to 2,000 units, per 1 kg of crude oil.

The phospholipases and methods of the invention can also be used for water-degumming processes as described, e.g., in Dijkstra, Albert J., et al., Oleagineux, Corps Gras, Lipides (1998), 5(5), 367-370. In this exemplary method, the water-degumming process is used for the production of lecithin and for dry degumming processes using a degumming acid and bleaching earth. This method may be economically feasible only for oils with a low phosphatide content, e.g., palm oil, lauric oils, etc. For seed oils having a high NHP-content, the acid refining process is used, whereby this process is carried out at the oil mill to allow gum disposal via the meal. In one aspect, this acid refined oil is a possible "polishing" operation to be carried out prior to physical refining.

The phospholipases and methods of the invention can also be used for degumming processes as described, e.g., in Dijkstra, et al., Res. Dev. Dep., N.V. Vandemoortele Coord. Cent., Izegem, Belg. JAOCS, J. Am. Oil Chem. Soc. (1989), 66:1002-1009. In this exemplary method, the total degumming process involves dispersing an acid such as $H_3PO_4$ or citric acid into soybean oil, allowing a contact time, and then mixing a base such as caustic soda or Na silicate into the acid-in-oil emulsion. This keeps the degree of neutralization low enough to avoid forming soaps, because that would lead to increased oil loss. Subsequently, the oil passed to a centrifugal separator where most of the gums are removed from the oil stream to yield a gum phase with minimal oil content. The oil stream is then passed to a second centrifugal separator to remove all remaining gums to yield a dilute gum phase, which is recycled. Washing and drying or in-line alkali refining complete the process. After the adoption of the total degumming process, in comparison with the classical alkali refining process, an overall yield improvement of about 0.5% is realized. The totally degummed oil can be subsequently alkali refined, bleached and deodorized, or bleached and physically refined.

The phospholipases and methods of the invention can also be used for the removal of nonhydratable phospholipids from a plant oil, e.g., soybean oil, as described, e.g., in Hvolby, et al., Sojakagefabr., Copenhagen, Den., J. Amer. Oil Chem. Soc. (1971) 48:503-509. In this exemplary method, water-degummed oil is mixed at different fixed pH values with buffer solutions with and without $Ca^{++}$, Mg/Ca-binding reagents, and surfactants. The nonhydratable phospholipids can be removed in a nonconverted state as a component of micelles or of mixed emulsifiers. Furthermore, the nonhydratable phospholipids are removable by conversion into dissociated forms, e.g., by removal of Mg and Ca from the phosphatidates, which can be accomplished by acidulation or by treatment with Mg/Ca-complexing or Mg/Ca-precipitating reagents. Removal or chemical conversion of the nonhydratable phospholipids can result in reduced emulsion formation and in improved separation of the deacidified oil from the emulsion layer and the soapstock.

The phospholipases and methods of the invention can also be used for the degumming of vegetable oils as described, e.g., Buchold, et al., Frankfurt/Main, Germany. Fett Wissenschaft Technologie (1993), 95(8), 300-304. In this exemplary process of the invention for the degumming of edible vegetable oils, aqueous suspensions of an enzyme of the invention, e.g., phospholipase A2, is used to hydrolyze the fatty acid bound at the sn2 position of the phospholipid, resulting in 1-acyl-lysophospholipids which are insoluble in oil and thus more amenable to physical separation. Even the addition of small amounts corresponding to about 700 lecitase units/kg oil results in a residual P concentration of less than 10 ppm, so that chemical refining is replaceable by physical refining, eliminating the necessity for neutralization, soapstock splitting, and wastewater treatment.

The phospholipases and methods of the invention can also be used for the degumming of vegetable oils as described, e.g., by EnzyMax, Dahlke, Klaus, Dept. G-PDO, Lurgi Ol-Gas, Chemie, GmbH, Frankfurt, Germany. Oleagineux, Corps Gras, Lipides (1997), 4 (1), 55-57. This exemplary process is a degumming process for the physical refining of almost any kind of oil. By an enzymatic-catalyzed hydrolysis, phosphatides are converted to water-soluble lysophosphatides which are separated from the oil by centrifugation. The residual phosphorus content in the enzymatically degummed oil can be as low as 2 ppm P.

The phospholipases and methods of the invention can also be used for the degumming of vegetable oils as described, e.g., by Cleenewerck, et al., N.V. Vamo Mills, Izegem, Belg. Fett Wissenschaft Technologie (1992), 94:317-22; and, Clausen, Kim; Nielsen, Munk. Novozymes A/S, Den. Dansk Kemi (2002) 83(2):24-27. The phospholipases and methods of the invention can incorporate the pre-refining of vegetable oils with acids as described, e.g., by Nilsson-Johansson, et al., Fats Oils Div., Alfa-Laval Food Eng. AB, Tumba, Swed. Fett Wissenschaft Technologie (1988), 90 (11), 447-51; and, Munch, Ernst W. Cereol Deutschland GmbH, Mannheim, Germany. Editor(s): Wilson, Richard F. Proceedings of the World Conference on Oilseed Processing Utilization, Cancun, MX, Nov. 12-17, (2001), Meeting Date 2000, 17-20.

The phospholipases and methods of the invention can also be used for the degumming of vegetable oils as described, e.g., by Jerzewska, et al., Inst. Przemyslu Miesnego i Tluszczowego, Warsaw, Pol., Tluszcze Jadalne (2001), 36 (3/4), 97-110. In this process of the invention, enzymatic degumming of hydrated low-erucic acid rapeseed oil is by use of a phospholipase A2 of the invention. The enzyme can catalyze the hydrolysis of fatty acid ester linkages to the central carbon atom of the glycerol moiety in phospholipids. It can hydrolyze non-hydratable phospholipids to their corresponding hydratable lyso-compounds. With a nonpurified enzyme preparation, better results can be achieved with the addition of 2% preparation for 4 hours (87% P removal).

In another exemplary process of the invention for oil degumming (or an oil degumming process using an enzyme of the invention), an acidic polymer, e.g., an alginate or pectin, is added. In this oil degumming process of the invention, an acidic polymer (e.g. alginic acid or pectin or a more soluble salt form) is added to the crude oil with a low amount of water (e.g., in a range of between about 0.5 to 5%). In this aspect, the acidic polymers can reduce and/or disrupt phospholipid-metal complexes by binding calcium and/or magnesium in the crude oil, thereby improving the solubility of nonhydratable phospholipids. In alternative aspects, these phospholipids will move to the oil/water interface or enter the aqueous phase and either be converted to diacylglycerol and the corresponding side chain or the intact phospholipid will be removed by subsequent centrifugation as a component of the heavy phase. The presence of the acidic polymer in the aqueous phase can also increase the density of the aqueous phase and result in an improved separation of the heavy phase from the oil (light) phase.

One exemplary process of the invention for oil degumming (or an oil degumming process using an enzyme of the invention) alters the deodorization procedure to get a diacylglycerol (DAG) fraction. In alternative aspect, if necessary or desired, following enzyme-assisted degumming, the deodorization conditions (temperature, pressure, configuration of the distillation apparatus) can be modified with the goal of improving the separation of the free fatty acids (FFA) from the diacylglycerol/triacylglycerol fraction or further modified to separate the diacylglycerol from the triacylglycerol fraction. As a result of these modifications, using this method of the invention, it is possible to obtain food grade FFA and diacylglycerol if an enzyme of the invention (e.g., a phosphatase, or, a PLC or a combination of PLC and phosphatases) are used to degum edible oil in a physical refining process.

In various aspects, practicing the methods of the invention as described herein (or using the enzymes of the invention), have advantages such as: decrease or eliminate solvent and solvent recovery; lower capital costs; decrease downstream refining costs, decrease chemical usage, equipment, process time, energy (heat) and water usage/wastewater generation; produce higher quality oil; expeller pressed oil may be used without refining in some cooking and sautéing applications (this pressed oil may have superior stability, color and odor characteristics and high tocopherol content); produce higher quality meal; produce a lower fat content in meal (currently, meal coming out of mechanical press causes digestion problems in ruminants); produce improved nutritional attributes—reduced levels of glucosinolates, tannins, sinapine, phytic acid (as described, e.g., in Technology and Solvents for Extracting Oilseeds and Nonpetroleum Oils, AOCS 1997).

In one aspect, the invention provides methods for refining vegetable oils (e.g., soybean oil, corn oil, cottonseed oil, palm oil, peanut oil, rapeseed oil, safflower oil, sunflower seed oil, sesame seed oil, rice bran oil, coconut oil or canola oil) and their byproducts, and processes for deodorizing lecithin, for example, as described in U.S. Pat. No. 6,172,248, or 6,172,247, wherein the methods comprise use of at least one enzyme of the invention, e.g., a phospholipase C of the invention. Thus, the invention provides lecithin and vegetable oils comprising at least one enzyme of the invention. In an exemplary organic acid refining process, vegetable oil is combined with a dilute aqueous organic acid solution and subjected to high shear to finely disperse the acid solution in the oil. The resulting acid-and-oil mixture is mixed at low shear for a time sufficient to sequester contaminants into a hydrated impurities phase, producing a purified vegetable oil phase. In this exemplary process, a mixer or recycle system (e.g., recycle water tank) and/or a phosphatide or lecithin storage tank can be used, e.g., as described in U.S. Pat. No. 4,240,972, 4,049,686, 6,172,247 or 6,172,248. These processes can be conducted as a batch or continuous process. Crude or degummed vegetable oil can be supplied from a storage tank (e.g., through a pump) and can be heated. The vegetable oil to be purified can be either crude or "degummed" oil.

In one aspect, phosphatidylinositol-PLC (PI-PLC) enzymes of the invention are used for vegetable oil degumming. PI-PLC enzymes of the invention can be used alone or in combination with other enzymes (for instance PLC, PLD, phosphatase enzymes of the invention) to improve oil yield during the degumming of vegetable oils (including soybean, canola, and sunflower). The PI-PLC may preferentially convert phosphatidylinositol to 1,2-diacylglycerol (DAG) and phosphoinositol but it may also demonstrate activity on other phospholipids including phosphatidylcholine, phosphatidylethanolamine, phosphatidylserine, or phosphatidic acid, or a combination thereof. The improvement in yield will be realized as an increase in the amount of DAG in the enzyme-treated vegetable oil and an increase in neutral oil, due to a decrease in the amount of oil entrained in the smaller gum fraction that results from enzyme treatment of the vegetable oil.

Enzymatic Processing of Oilseeds

The invention provides compositions (e.g., enzymes) and methods for enzymatic processing of oilseeds, including soybean, canola, coconut, avocado and olive paste. In one aspect, these processes of the invention can increase the oil yield and to improve the nutritional quality of the obtained meals. In some aspects, enzymatic processing of oilseeds using the enzymes and methods of the invention will provide economical and environmental benefits, as well as alternative technologies for oil extraction and processing food for human and animal consumption. In alternative aspects, the processes of the invention comprise use of phospholipases of the invention, other phospholipases, proteases, phosphatases, phytases, xylanases, amylases (e.g., α-amylases), glucanases (e.g., β-glucanases), polygalacturonases, galactolipases, cellulases, hemicellulases, pectinases and other plant cell wall degrading enzymes, as well as mixed enzyme preparations and cell lysates.

In alternative aspects, the processes of the invention can be practiced in conjunction with other processes, e.g., enzymatic treatments, e.g., with carbohydrases, including cellulase, hemicellulase and other side degrading activities, or, chemical processes, e.g., hexane extraction of soybean oil. The enzymatic treatment can increase the oil extractability by 8-10% when the enzymatic treatment is carried out prior to the solvent extraction.

In alternative aspects, the processes of the invention can be practiced with aqueous extraction processes. The aqueous extraction methods can be environmentally cleaner alternative technologies for oil extraction. Low extraction yields of aqueous process can be overcome by using enzymes that hydrolyze the structural polysaccharides forming the cell wall of oilseeds, or that hydrolyze the proteins which form the cell and lipid body membranes, e.g., utilizing digestions comprising cellulase, hemicellulase, and/or protopectinase for extraction of oil from soybean cells. In one aspect, methods are practiced with an enzyme of the invention as described by Kasai (2003) J. Agric. Food Chem. 51:6217-6222, who reported that the most effective enzyme to digest the cell wall was cellulase.

In one aspect, proteases are used in combination with the methods of the invention. The combined effect of operational variables and enzyme activity of protease and cellulase on oil and protein extraction yields combined with other process parameters, such as enzyme concentration, time of hydrolysis, particle size and solid-to-liquid ratio has been evaluated. In one aspect, methods are practiced with an enzyme of the invention as described by Rosenthal (2001) Enzyme and Microb. Tech. 28:499-509, who reported that use of protease can result in significantly higher yields of oil and protein over the control when heat treated flour is used.

In one aspect, complete protein, pectin, and hemicellulose extraction are used in combination with the methods of the invention. The plant cell consists of a series of polysaccharides often associated with or replaced by proteins or phenolic compounds. Most of these carbohydrates are only partially digested or poorly utilized by the digestive enzymes. The disruption of these structures through processing or degrading enzymes can improve their nutrient availability. In one aspect, methods are practiced with an enzyme of the invention as described by Ouhida (2002) J. Agric. Food Chem. 50:1933-1938, who reported that a significant degradation of the soybean cell wall cellulose (up to 20%) has been achieved after complete protein, pectin, and hemicellulose extraction.

In one aspect, the methods of the invention further comprise incorporation of various enzymatic treatments in the treatment of seeds, e.g., canola seeds, these treatments comprising use of proteases, cellulases, and hemicellulases (in various combinations with each other and with one or more enzymes of the invention). For example, the methods can comprise enzymatic treatments of canola seeds at 20 to 40 moisture during the incubation with enzymes prior to a conventional process; as described, e.g., by Sosulski (1990) Proc. Can. Inst. Food Sci. Technol. 3:656. The methods of the invention can further comprise incorporation of proteases, α-amylases, polygalacturonases (in various combinations with each other and with one or more enzymes of the invention) to hydrolyze cellular material in coconut meal and release the coconut oil, which can be recovered by centrifugation, as described, e.g., by McGlone (1986) J. of Food Sci. 51:695-697. The methods of the invention can further comprise incorporation of pectinases, α-amylases, proteases, cellulases in different combinations (with each other and with one or more enzymes of the invention) to result in significant yield improvement (~70% in the best case) during enzymatic extraction of avocado oil, as described, e.g., by Buenrostro (1986) Biotech. Letters 8 (7):505-506. In processes of the invention for olive oil extraction, olive paste is treated with cellulase, hemicellulase, poligalacturonase, pectin-methyltransferase, protease and their combinations (with each other and with one or more enzymes of the invention), as described, e.g., by Montedoro (1976) Acta Vitamin. Enzymol. (Milano) 30:13.

Purification of Phytosterols from Vegetable Oils

The invention provides methods for purification of phytosterols and triterpenes, or plant sterols, from vegetable oils. Phytosterols that can be purified using phospholipases and methods of the invention include β-sitosterol, campesterol, stigmasterol, stigmastanol, β-sitostanol, sitostanol, desmosterol, chalinasterol, poriferasterol, clionasterol and brassicasterol. Plant sterols are important agricultural products for health and nutritional industries. Thus, phospholipases and methods of the invention are used to make emulsifiers for cosmetic manufacturers and steroidal intermediates and precursors for the production of hormone pharmaceuticals. Phospholipases and methods of the invention are used to make (e.g., purify) analogs of phytosterols and their esters for use as cholesterol-lowering agents with cardiologic health benefits. Phospholipases and methods of the invention are used to purify plant sterols to reduce serum cholesterol levels by inhibiting cholesterol absorption in the intestinal lumen. Phospholipases and methods of the invention are used to purify plant sterols that have immunomodulating properties at extremely low concentrations, including enhanced cellular response of T lymphocytes and cytotoxic ability of natural killer cells against a cancer cell line. Phospholipases and methods of the invention are used to purify plant sterols for the treatment of pulmonary tuberculosis, rheumatoid arthritis, management of HIV-infested patients and inhibition of immune stress, e.g., in marathon runners.

Phospholipases and methods of the invention are used to purify sterol components present in the sterol fractions of commodity vegetable oils (e.g., coconut, canola, cocoa butter, corn, cottonseed, linseed, olive, palm, peanut, rice bran, safflower, sesame, soybean, sunflower oils), such as sitosterol (40.2-92.3%), campesterol (2.6-38.6%), stigmasterol (0-31%) and 5-avenasterol (1.5-29%).

Methods of the invention can incorporate isolation of plant-derived sterols in oil seeds by solvent extraction with chloroform-methanol, hexane, methylene chloride, or acetone, followed by saponification and chromatographic purification for obtaining enriched total sterols. Alternatively, the plant samples can be extracted by supercritical fluid extraction with supercritical carbon dioxide to obtain total lipid extracts from which sterols can be enriched and isolated. For subsequent characterization and quantification of sterol compounds, the crude isolate can be purified and separated by a wide variety of chromatographic techniques including column chromatography (CC), gas chromatography, thin-layer chromatography (TLC), normal phase high-performance liquid chromatography (HPLC), reversed-phase HPLC and capillary electrochromatography. Of all chromatographic isolation and separation techniques, CC and TLC procedures employ the most accessible, affordable and suitable for sample clean up, purification, qualitative assays and preliminary estimates of the sterols in test samples.

Phytosterols are lost in the vegetable oils lost as byproducts during edible oil refining processes. Phospholipases and methods of the invention use phytosterols isolated from such byproducts to make phytosterol-enriched products isolated from such byproducts. Phytosterol isolation and purification methods of the invention can incorporate oil processing industry byproducts and can comprise operations such as molecular distillation, liquid-liquid extraction and crystallization.

Methods of the invention can incorporate processes for the extraction of lipids to extract phytosterols. For example, methods of the invention can use nonpolar solvents as hexane (commonly used to extract most types of vegetable oils) quantitatively to extract free phytosterols and phytosteryl fatty-acid esters. Steryl glycosides and fatty-acylated steryl glycosides are only partially extracted with hexane, and increasing polarity of the solvent gave higher percentage of extraction. One procedure that can be used is the Bligh and Dyer chloroform-methanol method for extraction of all sterol lipid classes, including phospholipids. One exemplary method to both qualitatively separate and quantitatively analyze phytosterol lipid classes comprises injection of the lipid extract into HPLC system.

Phospholipases and methods of the invention can be used to remove sterols from fats and oils, as described, e.g., in U.S. Pat. No. 6,303,803. This is a method for reducing sterol content of sterol-containing fats and oils. It is an efficient and cost effective process based on the affinity of cholesterol and other sterols for amphipathic molecules that form hydrophobic, fluid bilayers, such as phospholipid bilayers. Aggregates of phospholipids are contacted with, for example, a sterol-containing fat or oil in an aqueous environment and then mixed. The molecular structure of this aggregated phospholipid mixture has a high affinity for cholesterol and other sterols, and can selectively remove such molecules from fats and oils. The aqueous separation mixture is mixed for a time sufficient to selectively reduce the sterol content of the fat/oil product through partitioning of the sterol into the portion of phospholipid aggregates. The sterol-reduced fat or oil is separated from the aqueous separation mixture. Alternatively, the correspondingly sterol-enriched fraction also may be isolated from the aqueous separation mixture. These steps can be performed at ambient temperatures, costs involved in heating are minimized, as is the possibility of thermal degradation of the product. Additionally, a minimal amount of equipment is required, and since all required materials are food grade, the methods require no special precautions regarding handling, waste disposal, or contamination of the final product(s).

Phospholipases and methods of the invention can be used to remove sterols from fats and oils, as described, e.g., in U.S. Pat. No. 5,880,300. Phospholipid aggregates are contacted with, for example, a sterol-containing fat or oil in an aqueous environment and then mixed. Following adequate mixing, the sterol-reduced fat or oil is separated from the aqueous separation mixture. Alternatively, the correspondingly sterol-enriched phospholipid also may be isolated from the aqueous separation mixture. Plant (e.g., vegetable) oils contain plant sterols (phytosterols) that also may be removed using the methods of the present invention. This method is applicable to a fat/oil product at any stage of a commercial processing cycle. For example, the process of the invention may be applied to refined, bleached and deodorized oils ("RBD oils"), or to any stage of processing prior to attainment of RBD status. Although RBD oil may have an altered density compared to pre-RBD oil, the processes of the are readily adapted to either RBD or pre-RBD oils, or to various other fat/oil products, by variation of phospholipid content, phospholipid composition, phospholipid:water ratios, temperature, pressure, mixing conditions, and separation conditions as described below.

Alternatively, the enzymes and methods of the invention can be used to isolate phytosterols or other sterols at intermediate steps in oil processing. For example, it is known that phytosterols are lost during deodorization of plant oils. A sterol-containing distillate fraction from, for example, an intermediate stage of processing can be subjected to the sterol-extraction procedures described above. This provides a sterol-enriched lecithin or other phospholipid material that can be further processed in order to recover the extracted sterols.

Detergent Compositions

The invention provides detergent compositions comprising one or more phospholipase of the invention, and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Phospholipases of the invention can facilitate the removal of stains by means of catalytic hydrolysis of phospholipids. Phospholipases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of phospholipase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Phospholipases of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of phospholipases of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning or disinfecting compositions including detergent and/or disinfecting compositions for cleaning and/or disinfecting hard surfaces, detergent compositions for cleaning and/or disinfecting fabrics, dishwashing compositions, oral cleaning compositions, denture cleaning compositions, and/or contact lens cleaning solutions.

In one aspect, the invention provides a method for washing an object comprising contacting the object with a phospholipase of the invention under conditions sufficient for washing. A phospholipase of the invention may be included as a detergent additive. The detergent composition of the invention may, for example, be formulated as a hand or machine laundry detergent composition comprising a phospholipase of the invention. A laundry additive suitable for pre-treatment of stained fabrics can comprise a phospholipase of the invention. A fabric softener composition can comprise a phospholipase of the invention. Alternatively, a phospholipase of the invention can be formulated as a detergent composition for use in general household hard surface cleaning operations. In alternative aspects, detergent additives and detergent compositions of the invention may comprise one or more other enzymes such as a protease, a lipase, a cutinase, another phospholipase, a carbohydrase, a cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, phospholipase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

Waste Treatment

The phospholipases of the invention can be used in waste treatment. In one aspect, the invention provides a solid waste digestion process using phospholipases of the invention. The methods can comprise reducing the mass and volume of substantially untreated solid waste. Solid waste can be treated with an enzymatic digestive process in the presence of an enzymatic solution (including phospholipases of the invention) at a controlled temperature. The solid waste can be converted into a liquefied waste and any residual solid waste. The resulting liquefied waste can be separated from said any residual solidified waste. See e.g., U.S. Pat. No. 5,709,796.

Detoxification

The phospholipases (e.g., PLCs, patatins of the invention) can be used in detoxification processes, e.g., for the detoxification of endotoxins, e.g., compositions comprising lipopolysaccharides (LPS), and, the invention provides detoxification processes using at least one enzyme of the invention, e.g., a patatin having a sequence as set forth in SEQ ID NO:12 (encoded by SEQ ID NO:11), SEQ ID NO:14 (encoded by SEQ ID NO: 13), SEQ ID NO:18 (encoded by SEQ ID NO:17), SEQ ID NO:26 (encoded by SEQ ID NO:25), SEQ ID NO:28 (encoded by SEQ ID NO:27), SEQ ID NO:34 (encoded by SEQ ID NO:33), SEQ ID NO:36 (encoded by SEQ ID NO:35), SEQ ID NO:44 (encoded by SEQ ID NO:43), SEQ ID NO:46 (encoded by SEQ ID NO:45), SEQ ID NO:56 (encoded by SEQ ID NO:55), SEQ ID NO:60 (encoded by SEQ ID NO:59), SEQ ID NO:66 (encoded by SEQ ID NO:65), SEQ ID NO:72 (encoded by SEQ ID NO:71), SEQ ID NO:78 (encoded by SEQ ID NO:77), SEQ ID NO:87 (encoded by SEQ ID NO:86), SEQ ID NO:88 (encoded by SEQ ID NO:87), SEQ ID NO:92 (encoded by SEQ ID NO:91), SEQ ID NO:96 (encoded by SEQ ID NO:95), SEQ ID NO:100 (encoded by SEQ ID NO:99), SEQ ID NO:104 (encoded by SEQ ID NO:103), SEQ ID NO:126 (encoded by SEQ ID NO:125), SEQ ID NO:128 (encoded by SEQ ID NO:127), SEQ ID NO:132 (encoded by SEQ ID NO:131), SEQ ID NO:134 (encoded by SEQ ID NO:133), SEQ ID NO:136 (encoded by SEQ ID NO:135), or SEQ ID NO:138 (encoded by SEQ ID NO:137). In one aspect, a phospholipase of the invention is used to detoxify a lipopolysaccharide (LPS). In one aspect, this detoxification is by deacylation of 2' and/or 3' fatty acid chains from lipid A. In one aspect, a phospholipase (e.g., a PLC, a patatin) of the invention is used to hydrolyze a 2'-lauroyl and/or a 3'-myristoyl chain from a lipid, e.g., a lipid A (e.g., from a bacterial endotoxin). In one aspect, the process of the invention is used to destroy an endotoxin, e.g., a toxin from a gram negative bacteria, as from *E. coli*. In one aspect, a phospholipase (e.g., a PLC, a patatin) of the invention is used to ameliorate the effects of toxin poisoning (e.g., from an on-going gram negative infection), or, to prophylactically to prevent the effects of endotoxin during an infection (e.g., an infection in an animal or a human). Accordingly, the invention provides a pharmaceutical composition comprising a phospholipase (e.g., a PLC, a patatin) of the invention, and method using a hydrolase of the invention, for the amelioration or prevention of lipopolysaccharide (LPS) toxic effects, e.g., during sepsis.

Processing Foods

The phospholipases of the invention can be used to process foods, e.g., to change their stability, shelf-life, flavor, texture, improve on their nutritional status, and the like. For example, in one aspect, phospholipases of the invention are used to generate acidic phospholipids for controlling bitter taste in foods.

In one aspect, the invention provides cheese-making processes using phospholipases of the invention (and, thus, the invention also provides cheeses comprising phospholipases of the invention). In one aspect, the enzymes of the invention (e.g., phospholipase A, lysophospholipase or a combination thereof) are used to process cheeses for flavor enhancement, to increase yield and/or for "stabilizing" cheeses, e.g., by reducing the tendency for "oil-off," or, in one aspect, the enzymes of the invention are used to produce cheese from cheese milk. These processes of the invention can incorporate any method or protocol, e.g., as described, e.g., in U.S. Pat. Nos. 6,551,635, and 6,399,121, WO 03/070013, WO 00/054601. For example, in one aspect, the phospholipases of the invention are used to stabilize fat emulsion in milk or milk-comprising compositions, e.g. cream, and are used to stabilize milk compositions, e.g. for the manufacturing of creams or cream liquors. In one aspect, the invention provides a process for enhancing the favor of a cheese using at least one enzyme of the invention, the process comprising incubating a protein, a fat and a protease and a lipase in an aqueous medium under conditions that produce an enhanced cheese flavor (e.g., reduced bitterness), e.g., as described in WO 99/66805. In one aspect, phospholipases of the invention are used to enhance flavor in a cheese (e.g., a curd) by mixing with water, a protease, and a lipase (of the invention) at an elevated temperature, e.g., between about 75° C. to 95° C., as described, e.g., in U.S. Pat. No. 4,752,483. In one aspect, phospholipases of the invention are used to accelerate cheese aging by adding an enzyme of the invention (e.g., a lipase or a phospholipase) to a cheese (e.g., a cheese milk) before adding a coagulant to the milk, or, adding an enzyme of the invention to a curd with salt before pressing, e.g., as described, e.g., in U.S. Pat. No. 4,707,364. In one aspect, a lipase of the invention is used degrade a triglyceride in milk fat to liberate free fatty acids, resulting in flavor enhancement. A protease also can be used in any of these processes of the invention, see, e.g., Brindisi (2001) J. of Food Sci. 66:1100-1107. In another aspect, a combination of esterases, lipases, phospholipases and/or proteases can be used in these or any process of the invention.

In one aspect, a phospholipase of the invention is used to reduce the content of phosphorus components in a food, e.g., an oil, such as a vegetable oil having a high non-hydratable phosphorus content, e.g., as described in WO 98/26057.

Other Uses for the Phospholipases of the Invention

The phospholipases of the invention can also be used to study the phosphoinositide (PI) signaling system; in the diagnosis, prognosis and development of treatments for bipolar disorders (see, e.g., Pandey (2002) Neuropsychopharmacology 26:216-228); as antioxidants; as modified phospholipids; as foaming and gelation agents; to generate angiogenic lipids for vascularizing tissues; to identify phospholipase, e.g., PLA, PLB, PLC, PLD and/or patatin modulators (agonists or antagonists), e.g., inhibitors for use as anti-neoplastics, anti-inflammatory and as analgesic agents. They can be used to generate acidic phospholipids for controlling the bitter taste in food and pharmaceuticals. They can be used in fat purification. They can be used to identify peptides inhibitors for the treatment of viral, inflammatory, allergic and cardiovascular diseases. They can be used to make vaccines. They can be used to make polyunsaturated fatty acid glycerides and phosphatidylglycerols.

The phospholipases of the invention, for example PLA and PLC enzymes, are used to generate immunotoxins and various therapeutics for anti-cancer treatments.

The phospholipases of the invention can be used in conjunction with other enzymes for decoloring (i.e. chlorophyll removal) and in detergents (see above), e.g., in conjunction with other enzymes (e.g., lipases, proteases, esterases, phosphatases). For example, in any instance where a PLC is used, a PLD and a phosphatase may be used in combination, to produce the same result as a PLC alone.

The following table summaries several exemplary processes and formulations of the invention:

| Exemplary Process of the invention | Purpose |
| --- | --- |
| Chemical usage in PLC oil degumming | |
| No use of acid | Chemical elimination |
| No use of caustic | Chemical elimination |
| Range of acid and caustic use (no excess to excess) | Chemical reduction/degumming process alternative embodiment |
| Other types of acid and caustic | Degumming process alternative embodiments |
| Impact of water in PLC oil degumming | |
| Use of silica gel | Replacement of water wash step |
| Use of water drying agent | Elimination of water in final product |
| Impact of lower water during caustic treatment | Elimination of water in final product |
| Minimal water content (<5%) | Elimination of water in final product |
| Maximal water content (>5%) | Process alternative |
| Humidity profiles on PLC degumming | Degumming process alternative embodiment |
| Oil dependence on water content for PLC degumming | Degumming process alternative embodiment |

-continued

| Exemplary Process of the invention | Purpose |
|---|---|
| In situ removal of free fatty acids, FFAs | |
| Addition of FFA chelating agent- | Degumming process alternative embodiment; improves conditions in oil from spoilt beans |
| Impact of mixing regimen on PLC oil degumming | |
| PLC degumming with minimal mixing | Protection of enzyme from mixing induced denaturation, energy savings |
| PLC degumming with initial shear mixing, followed by paddle mixing | Degumming process alternative embodiment |
| Order of addition of chemicals | |
| Order of addition: enzyme-water followed by acid then caustic | Allow the PLC to work before exposure to acid and or caustic, causing potential pH or metal chelation PLC inactivation |
| PLC oil degumming process alternative embodiments for temperature and time | |
| Enzyme treatment step (time): <60 min, preferably <30 min | Degumming process alternative embodiment |
| Enzyme treatment step (temperature): 50-70° C., possibly <50° C. (e.g. RT) | Degumming process alternative embodiment |
| Benefits from PLC oil degumming | |
| Producing soapstock with minimized PL content and enriched in water soluble phosphate esters | Degumming process alternative embodiment |
| Reduced neutral oil in gum through use of PLC | Degumming process alternative embodiment |
| Process of generating increase of DAG in vegetable oils (for ex, 1,3-DAG) | Degumming process alternative embodiment |
| Benefits of using increased DAG vegetable oils with other oils for health benefits | Exemplary Product benefit |
| Investigate degumming process that leaves no PLC activity in oil | Degumming process alternative embodiment/regulatory improvement |
| Investigate degumming process that leaves no detectable PLC protein in oil | Degumming process alternative embodiment/regulatory improvement |
| Use of an enzyme to produce DAG from lecithin gum mass | Exemplary Product benefit |
| Use of PLC with specialty oils (PA, PI enriched) | Exemplary Product benefit |
| Use of PA/PI specific enzymes (e.g. 596ES2/PI specific) | Degumming process alternative embodiment |
| Use of PA/PI specific enzymes (e.g. 596ES2/PI specific) + PC/PE specific enzymes; impact of order of addition | Degumming process alternative embodiment |
| Batch or continuous process | Degumming process alternative embodiment |
| Use of resuspended PLC treated gum for further oil degumming operations | Degumming process alternative embodiment |
| Mass balance for DAG, FFA, P, metals, neutral oil in gum | Degumming process alternative embodiment |
| Miscellaneous | |
| Addition of PLC to flaked oil seed kernels before extrusion | Process alternative embodiment |
| Small scale degumming assay | Degumming process alternative embodiment |
| Use of other enzymes to reduce gum mass (e.g., PYROLASE ™ enzyme, chlorophyllase, peroxidase, lipase, laccase, mannanase, protease, lactase, amylase, etc. or combinations thereof) | Degumming process alternative embodiment |
| Use of compound to better facilitate oil/gum separation | Degumming process alternative embodiment |
| Harden gum from PLC treated oil | Degumming process alternative embodiment |
| Glycosylated/deglycosylated variants of phospholipase | Degumming process alternative embodiment |
| Exemplary Liquid formulation for stability | |
| Use of compounds to increase the stability of PLC at different pH and temp, ranges (polyols, salts, metals . . . ) | Stabilization of enzyme for maximum DAG production, possibly for altering substrate specificity or directing product formation towards the 1,3-DAG type |

-continued

| Exemplary Process of the invention | Purpose |
|---|---|
| Use of a hydrophobic delivery system for PLC (liposomes, hydrated enzyme in refined oil droplets) | Stabilization of enzyme for maximum DAG production, possibly for altering substrate specificity or directing product formation towards the 1,3-DAG type |
| Solid formulation for stability | |
| Use of different PLC, phospholipase carrier systems (immobilization resins, porous matrices, gels, granules, powders, tablets, vesicles/micelles, encapsulates, structured liquids, etc) to stabilize phospholipase and co-enzymes | Stabilization of the enzyme(s) and ease of separation of the enzyme from the oil or gum phase after degumming; recyclability of the enzyme preparation; physical separation of the enzyme phase during oil processing; attack of PI/PA by PLC |
| Use of degumming waste materials (gum components, seed hulls) for PLC formulation | Cost reduction of formulation ingredient, better miscibility of enzyme with oil, thermostabilization of enzyme |
| Exemplary Formulation and processes for activity boost | |
| Use of chemical or enzyme to help disperse the enzyme better in oil (e.g. effervescent matrix, etc) | Faster reaction time/degumming process/reduction of chemical usage |
| Re-use of gums/enzyme for further degumming reactions | Recyclability of enzyme |
| Use of formulations that enhance the segregation or enzyme capture of PLs for hydrolysis | Faster reaction time/degumming process/reduction of chemical usage |
| Use of multiple formulations to accommodate PLCs with different PL specificities | Versatility of process; different enzymes may require different formulations or may be added at different stages in the process |
| Use of multiple formulations to prevent inactivation of one PLC by a component in the prep of another PLC with a different substrate specificity | Protection of PLC activities in a multi-enzyme format embodiment |
| Use of multiple formulations to prevent inactivation of one PLC by a component in the prep of another enzyme (hydrolase, oxidase) | Protection of PLC activity in a multi-enzyme format embodiment |
| Use of intermittent caustic additions as in time released caustic addition formulation | Protection of enzyme from mixing induced denaturation, energy savings |

Inactivating and Modulating Activity of Enzymes by Glycosylation

This invention provides methods comprising use of recombinant technology to make and expressing enzymes or other proteins with biological activity, e.g., noxious or toxic enzymes, (wherein the enzymes or other proteins are not normally glycosylated) in an inactive or less active, but re-activatable, form. The method comprises adding one or more glycosylation sites (e.g., N-linked or O-linked glycosylation) into the enzymes or other proteins with biological activity (e.g., an enzyme of the present invention) by engineering a coding sequence incorporating the new glycosylation site(s); expressing the variant coding sequences in eukaryotic cells or an equivalent engineered or in vitro system capable of post-translational glycosylation. For example, the 3 amino acid sequence NXS/T is the site for glycosylation in eukaryotic cells, prokaryotic cells do not do this. Thus, the invention comprises adding at least one 3 amino acid sequence NXS/T to the protein such that its activity is decreased or inactivated because of post-translational glycosylation.

The glycosylation can result in 2 molecules of N-acetyl glucosamine (NGlucNac) being added to the N residue. Subsequent additions can be organism specific. In most species mannose (Mann) sugars are then added onto the NGlucNac, with the number Mann residues ranging from 10 to 100. Sialic acid can also be added in some species. In *Pichia* after the NGlucNac is added, 10 to 25 Mann residues can be added.

These methods comprise using any deglycosylating enzyme or set of enzymes, many of which can have been identified and/or are commercially available. For example, the endoglycosidase H enzyme cleaves at the last NGlucNac leaving one NClucNac still attached to the N residue. The PNGaseF enzyme cleaves off all of the sugars and converts the amino side chain of the N residue into a hydroxyl group resulting in the N amino acid becoming an aspartate (D) amino acid in the enzyme. Thus, the methods comprise using endoglycosidase H and/or PNGaseF or equivalent enzymes in vivo or in vitro to re-activate partially or completely the engineered "temporarily inactivated" proteins.

The method comprises targeting the enzymes or other polypeptides to the host secretory pathway so that the enzymes will be glycosylated. The new glycosylation sites are designed such that glycosylation inactivates the enzyme or modifies its activity, e.g., decreases it activity or other otherwise modifies activity, such as blocks a substrate binding site. Because the enzyme is inactive or less active, noxious or toxic enzymes could be expressed at higher levels since the negative effects of their activity are no longer a limitation to how much of the protein can accumulate in the host cells. The inactive, glycosylated enzyme can be re-activated (partially or completely) by removing the sugars, e.g., using commercially available deglycosylating enzymes, for example, by removing the sugars in vitro, or removing the sugars in vivo using whole cell engineering approaches.

In one aspect, a eukaryotic glycosylation target site such as NXS/T is added to any protein, for example, an enzyme of the invention. This enables one skilled in the art to add glycosylation sites to a protein of interest with the expectation of converting that protein into one that is temporarily inactive when that protein is glycosylated by expressing that protein in a eukaryotic host cell and targeting the protein to the host cell's secretory pathway.

Thus, the invention provides methods for the production of enzymes that normally are too noxious or toxic to be tolerated in large amounts by a host cell. The effect can temporary as it is possible to regenerate the active enzyme (by deglycosylation, e.g., by post-translational modification/deglycosylation) for future work requiring an active enzyme.

In one aspect, the invention provides methods for making and expressing a protein having a biological activity whose activity is temporarily inactivated by glycosylation comprising: (a) providing a nucleic acid encoding a protein having a biological activity, wherein the protein is not naturally glycosylated; (b) inserting at least one glycosylation motif coding sequence into the protein-encoding nucleic acid, wherein the glycosylated form of the protein is inactive; (c) inserting a targeting sequence into the protein such that it is directed to a host cell's secretory pathway, wherein the host cell is capable of recognizing the glycosylation motif and glycosylating the protein; and (d) expressing the modified nucleic acid in the host cell. In one aspect, the method further comprises deglycosylating the expressed the protein, thereby re-activating the activity of the protein, e.g., an enzyme, such as an enzyme of the invention. In one aspect, the host cell is a eukaryotic cell. In one aspect, the inactivated expressed recombinant protein is re-activated in vitro by deglycosylation, either chemical or enzymatic.

Determining the placement of one or more glycosylation motifs to temporarily inactivate a protein involves only routine methods of making variant protein-encoding nucleic acids, e.g., by GSSM™, and routine screening protocols, e.g., activity or binding assays.

An enzyme whose activity was detrimental to the host cell was rendered inactive because of glycosylation. Because it was inactive it could accumulate in much higher levels in the eukaryotic host cells. Because it was no longer active it could no longer able to exert its negative effects. The inactivation of the toxic enzyme was temporary because deglycosylating the enzyme using EndoH or PNGase F resulted in a complete restoration of normal activity to the enzyme. A large amount of the glycosylated, inactive enzyme accumulated in the medium suggesting that it was tolerated well by the host as the inactive form.

The invention will be further described with reference to the following examples; however, it is to be understood that the invention is not limited to such examples.

EXAMPLES

Example 1

Blast Program Used for Sequence Identify Profiling

This example describes an exemplary sequence identity program to determine if a nucleic acid is within the scope of the invention. An NCBI BLAST 2.2.2 program is used, default options to blastp. All default values were used except for the default filtering setting (i.e., all parameters set to default except filtering which is set to OFF); in its place a "–F F" setting is used, which disables filtering. Use of default filtering often results in Karlin-Altschul violations due to short length of sequence. The default values used in this example:

"Filter for low complexity: ON
>Word Size: 3
>Matrix: Blosum62
>Gap Costs: Existence:11
>Extension: 1

Other default settings were: filter for low complexity OFF, word size of 3 for protein, BLOSUM62 matrix, gap existence penalty of −11 and a gap extension penalty of −1. The "–W" option was set to default to 0. This means that, if not set, the word size defaults to 3 for proteins and 11 for nucleotides. The settings read:

```
<<README.bls.txt>>
> ---------------------------------------------------------------------------
> blastall arguments:
>
>   -p Program Name [String]
>   -d Database [String]
>       default = nr
>   -i Query File [File In]
>       default = stdin
>   -e Expectation value (E) [Real]
>       default =10.0
>   -m alignment view options:
> 0 = pairwise,
> 1 = query-anchored showing identities,
> 2 = query-anchored no identities,
> 3 = flat query-anchored, show identities,
> 4 = flat query-anchored, no identities,
> 5 = query-anchored no identities and blunt ends,
> 6 = flat query-anchored, no identities and blunt ends,
> 7 = XML Blast output,
> 8 = tabular,
> 9 tabular with comment lines [Integer]
>       default = 0
>   -o BLAST report Output File [File Out] Optional
>       default = stdout
>   -F Filter query sequence (DUST with blastn, SEG with others) [String]
>       default = T
>   -G Cost to open a gap (zero invokes default behavior) [Integer]
>       default = 0
>   -E Cost to extend a gap (zero invokes default behavior) [Integer]
>       default = 0
>   -X X dropoff value for gapped alignment (in bits) (zero invokes
> default behavior) [Integer]
>       default = 0
>   -I Show GI's in deflines [T/F]
>       default = F
>   -q Penalty for a nucleotide mismatch (blastn only) [Integer]
>       default = −3
>   -r Reward for a nucleotide match (blastn only) [Integer]
>       default = 1
>   -v Number of database sequences to show one-line descriptions for (V)
> [Integer]
>       default = 500
>   -b Number of database sequence to show alignments for (B) [Integer]
>       default = 250
>   -f Threshold for extending hits, default if zero [Integer]
>       default = 0
>   -g Perform gapped alignment (not available with tblastx) [T/F]
>       default = T
>   -Q Query Genetic code to use [Integer]
>       default = 1
>   -D DB Genetic code (for tblast[nx] only) [Integer]
>       default = 1
>   -a Number of processors to use [Integer]
>       default = 1
>   -O SeqAlign file [File Out] Optional
>   -J Believe the query defline [T/F]
>       default = F
>   -M Matrix [String]
>       default = BLOSUM62
>   -W Word size, default if zero [Integer]
>       default = 0
>   -z Effective length of the database (use zero for the real size)
> [String]
>       default = 0
>   -K Number of best hits from a region to keep (off by default, if used a
> value of 100 is recommended) [Integer]
>       default = 0
>   -P 0 for multiple hits 1-pass, 1 for single hit 1-pass, 2 for 2-pass
```

-continued

```
> [Integer]
>       default = 0
>   -Y Effective length of the search space (use zero for the real size)
> [Real]
>       default = 0
>   -S Query strands to search against database (for blast[nx], and
> tblastx). 3 is both, 1 is top, 2 is bottom [Integer]
>       default = 3
>   -T Produce HTML output [T/F]
>       default = F
>   -l Restrict search of database to list of GI's [String] Optional
>   -U Use lower case filtering of FASTA sequence [T/F] Optional
>       default = F
>   -y Dropoff (X) for blast extensions in bits (0.0 invokes default
> behavior) [Real]
>       default = 0.0
>   -Z X dropoff value for final gapped alignment (in bits) [Integer]
>       default = 0
>   -R PSI-TBLASTN checkpoint file [File In] Optional
>   -n MegaBlast search [T/F]
>               default = F
>   -L Location on query sequence [String] Optional
>   -A Multiple Hits window size (zero for single hit algorithm) [Integer]
>       default = 40
```

Example 2

Simulation of PLC Mediated Degumming

This example describes the simulation of phospholipase C (PLC)-mediated degumming.

Due to its poor solubility in water phosphatidylcholine (PC) was originally dissolved in ethanol (100 mg/ml). For initial testing, a stock solution of PC in 50 mM 3-morpholinopropanesulpholic acid or 60 mM citric acid/NaOH at pH 6 was prepared. The PC stock solution (10 μl, 1 μg/μl) was added to 500 μl of refined soybean oil (2% water) in an Eppendorf tube. To generate an emulsion the content of the tube was mixed for 3 min by vortexing (see FIG. 5A). The oil and the water phase were separated by centrifugation for 1 min at 13,000 rpm (FIG. 5B). The reaction tubes were pre-incubated at the desired temperature (37° C., 50° C., or 60° C.) and 3 μl of PLC from *Bacillus cereus* (0.9 U/μl) were added to the water phase (FIG. 5C). The disappearance of PC was analyzed by TLC using chloroform/methanol/water (65:25:4) as a solvent system (see, e.g., Taguchi (1975) supra) and was visualized after exposure to 12 vapor.

Figure 5:
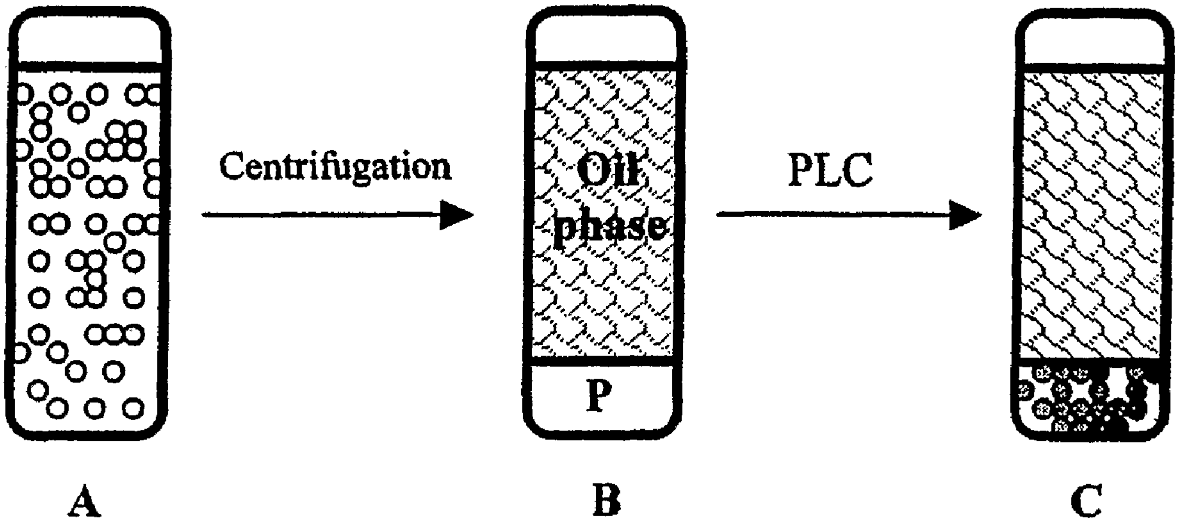
FIGS. 5A, 5B and 5C schematically illustrate a model two-phase system for simulation of PLC-mediated degumming, as described in detail in Example 2, below.

FIG. 5 schematically illustrates a model two-phase system for simulation of PLC-mediated degumming. FIG. 5A: Generation of emulsion by mixing crude oil with 2% water to hydrate the contaminating phosphatides (P). FIG. 5B: The oil and water phases are separated after centrifugation and PLC is added to the water phase, which contains the precipitated phosphatides ("gums"). The PLC hydrolysis takes place in the water phase. FIG. 5C: The time course of the reaction is monitored by withdrawing aliquots from the water phase and analyzing them by TLC.

Example 3

Expression of Phospholipases

This example describes the construction of a commercial production strain of the invention that can express multiple phospholipases (including enzymes of the invention). In order to produce a multi-enzyme formulation suitable for use in the degumming of food-grade vegetable oils (including soybean, canola, and sunflower), a recombinant expression strain can be generated that expresses two different phospholipase sequences in the same expression host. For example, this strain may be constructed to contain one or more copies of a PLC gene and one or more copies of a phosphatidylinositol-PLC gene. These genes may exist on one plasmid, multiple plasmids, or the genes may be inserted into the genome of the expression host by homologous recombination. When the genes are introduced by homologous recombination, the genes may be introduced into a single site in the host genome as a DNA expression cassette that contains one or more copies of both genes. Alternatively, one or more copies of each gene may be introduced into distinct sites in the host chromosome. The expression of these two gene sequences could be driven by one type of promoter or each gene sequence may be driven by an independent promoter. Depending on the number of copies of each gene and the type of promoter, the final strain will express varying ratios of each active enzyme type. The expression strains can be constructed using any *Bacillus* (e.g., *B. cereus*) or *Streptomyces, E. coli, S. pombe, P. pastoris*, or other gram-negative, gram-positive, or yeast expression systems.

Figure 12:
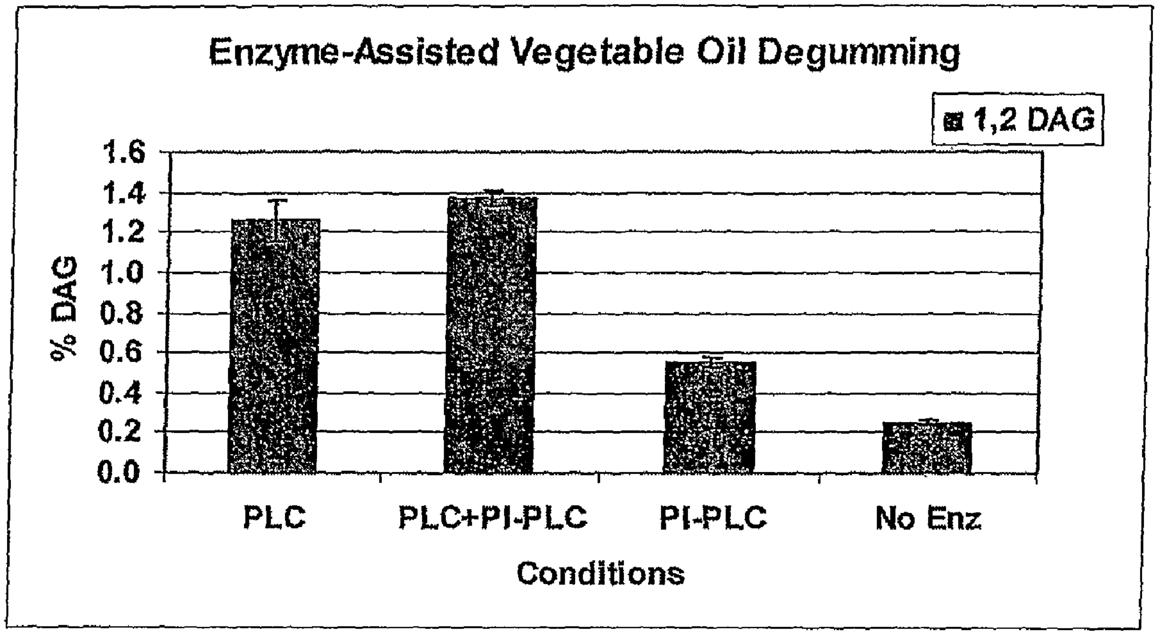
FIG. 12 schematically illustrates data from a two enzyme system of the invention, as described in Example 3, below.

In one aspect, the invention provides a two-enzyme system for degumming of soybean oil, wherein at least one enzyme is an enzyme of the invention. PLC plus PI-PLC produces more DAG than either enzyme alone. However both enzymes produce more DAG than a no enzyme control sample. In one aspect, reaction conditions comprise 1 milliliter soybean oil, ~0.4% initial moisture in the oil before any additions, 50° C., 0.2% Citric acid neutralized with 2.75M NaOH, 10 U PLC, 15 μL PI-PLC (0.45 mg total protein), 1 hour total reaction time. FIG. 12 illustrates a table summarizing data from this two-enzyme degumming system of the invention.

In another aspect, a PI-PLC enzyme of the invention can be used under the same conditions described for PLC. These include chemical refining of vegetable oils and water degumming of vegetable oils.

Example 4

Phospholipases with Improved Expression and Altered Protease Resistance

The invention provides method for selectioning Phospholipase C variants (mutants) having improved expression in a glycosylating host and altered resistance to secreted proteases.

Improved Expression in a Glycosylating Host.

Potential asparagines-linked glycosylation sites with the amino acid consensus sequence, asparagine-any amino acid-serine or threonine (NXS/T in the one letter amino acid code), were knocked out using mutagenesis methods to change the asparagines or the serine or the threonine in the glycosylation recognition motif to a different amino acid so the sequence no longer encodes a potential glycosylation site. The elimination of the glycosylation sites was effected as indicated below: amino acid positions amino acid 63, amino acid 131, and amino acid 134, of the phospholipase C enzyme of the invention having an amino acid sequence as set forth in SEQ ID NO:2, encoded, e.g., by SEQ ID NO:1. This elimination of the glycosylation sites improved expression of this variant, active phospholipase C enzyme (PLC, SEQ ID NO:2) when the protein was heterologously expressed in the yeast *Pichia pastoris*. This strategy of reducing or eliminating potential glycosylation sites in the PLC enzyme can improve the expression of active PLC in any glycosylating host. Thus, the invention provides phospholipase enzymes (and the nucleic acids that encode them) having a sequence of any of the exemplary phospholipases of the invention with one or more or all of the glycosylation sites altered, as described above. Thus, the invention provides methods of making variant phospholipase coding sequences having increased expression in a host cell, where the method comprises modifying a phospholipase coding sequence of the invention such that one, several or all N-linked glycosylation site coding motifs are modified to a non-glycosylated motif. The invention also provides phospholipase coding sequence made by this process, and the enzymes they encode.

Altered Resistance to Protease

The invention provides methods for making a variant phospholipase coding sequence encoding a phospholipase having increased resistance to a protease comprising modifying an amino acid equivalent to position 131 of SEQ ID NO:2 to one, several or all of the following residues: Lysine (K); Serine (S); Glycine (G); Arginine (R); Glutamine (Q); Alanine (A); Isoleucine (I); Histidine (H); Phenylalanine (F); Threonine (T); Methionine (M) Leucine (L), including variants to SEQ ID NO:2 (and the nucleic acid that encode them) having these exemplary modifications. The invention also provides isolated, synthetic or recombinant phospholipases encoded by a sequence made by this method. The invention also provides methods for making a variant phospholipase coding sequence encoding a phospholipase having decreased resistance to a protease comprising modifying an amino acid equivalent to position 131 of SEQ ID NO:2 to one, several or all of the following residues: Tryptophan (W); Glutamate (E); Tyrosine (Y), including variants to SEQ ID NO:2 (and the nucleic acid that encode them) having these exemplary modifications. The invention also provides isolated, synthetic or recombinant phospholipases encoded by a sequence made by this method.

Supernatant containing a mixture of native secreted *Pichia pastoris* proteases is mixed and incubated with wild type and mutant PLC enzyme preparations. Reactions are quenched and degradation visualized by SDS-PAGE versus the no protease negative control. Degradation may also determined by measurement of residual PLC activity. Novelty was derived from the observation that certain mutations to knock-out glycosylation significantly change the susceptibility of the expressed phospholipase to degradation during fermentation. An advantage to the method is direct selection of mutants with increased or decreased resistance to the proteases secreted by the host organism during production.

This process of the invention can employ site directed mutagenesis (e.g., GSSM™) to change the amino acid sequence of a phospholipase C enzyme of the invention, e.g., as shown below—a subsequence of SEQ ID NO:2 encoded by SEQ ID NO:1. Each of the amino acids highlighted in red (below) were changed from asparagine (N in single letter code) to Aspartate (D), serine (S), or another amino acid as described below. These amino acids are designated as amino acid 63, amino acid 131, and amino acid 134 of the sequence below where tryptophan (W) is designated amino acid 1. These mutations were made to increase the expression of active phospholipase C protein (SEQ ID NO:176) by reducing glycosylation of the expressed protein in the *Pichia pastoris* expression system. These same mutations can increase expression of any active phospholipase C of the invention in any other expression system that glycosylates asparagines (N-linked glycosylation) according to the NXS/T system where N is asparagine, X is any amino acid, and S/T is serine or threonine. Thus, the invention also provides a process for changing the susceptibility of the expressed phospholipase C by changing the amino acid in position 131.

Amino acids 38-286 of SEQ ID NO:2; with these three modifications the full length phospholipase C protein amino acid sequence is SEQ ID NO:175:

NOTE: To count the positions changed, count the first amino acid (W) as position 1.

```
WSAEDKHNEGINSHLWIVNRAIDIMSRNTTIVNPNETALLNEWRADLENG
IYSADYENPYYDDSTYASHFYDPDTGTTYIPFAKHAKETGAKYFNLAGQA
YQNQDMQQAFFYLGLSLHYLGDVNQPMHAASFTDLSYPMGFHSKYENFVD
TIKNNYIVSDSNGYWNWKGANPEDWIEGAAVAAKQDYPGVVNDTTKDWFV
KAAVSQEYADKWRAEVTPVTGKRLMEAQRVTAGYIHLWFDTYVNR-
```

The expressed phospholipase C variants were incubated in the presence of *P. pastoris* proteases as described below and the following results were obtained:

The following amino acids at amino acid position 131 of SEQ ID NO:2 increased the resistance of the expressed phospholipase C to degradation by *P. pastoris* proteases: Lysine (K); Serine (S); Glycine (G); Arginine (R); Glutamine (Q); Alanine (A); Isoleucine (I); Histidine (H); Phenylalanine (F); Threonine (T); Methionine (M) Leucine (L). The following amino acids at amino acid position 131 of SEQ ID NO:2 decreased the resistance of the expressed phospholipase C to degradation by *P. pastoris* proteases: Tryptophan (W); Glutamate (E); Tyro sine (Y). Thus, the invention provides variant phospholipases having any one of, or several or all of these modifications, depending on whether it was desired to increase or decrease the resistance of the expressed phospholipase C to degradation by protease. The invention provides variant phospholipases having any one of, or several or all of these modifications in positions equivalent to position 131 of SEQ ID NO:2. Which residue is equivalent to position 131 of SEQ ID NO:2, and whether any particular amino acid residue modification can increase or decrease the resistance of the enzyme to degradation by a protease, can be routinely and predictably ascertained by protocols well known in the art, e.g., the exemplary assay used to evaluate protease susceptibility of the (SEQ ID NO:2, encoded by SEQ ID NO:1) phospholipase C described below:

Buffers:

1.0 M MES, pH 6.2

0.7 M sodium acetate ("NaAc"), pH 5.2

Challenge:

Use separate 1.5 mL microfuge tubes

To 25 μL PLC enzyme sample add 5 μL NaAc or 7 μL MES buffer and mix

Add 25 μL protease-containing *Pichia pastoris* supernatant and mix

Add 2 μL 5% sodium azide and mix

Place tubes in floating rack in prewarmed beaker of water in a humidified incubator Controls include PLC+buffer+d$H_2$O and *Pichia* SN+buffer+d$H_2$O Incubate from 0-24 hours, sampling multiple timepoints if desired Detection:

Visualize on SDS-PAGE by mixing samples 1:2 with sample buffer containing 5 mM EDTA, heat 100° C., 4 minutes, cool, centrifuge, mix, load 5 μL sample per lane, Coomassie stain.

Samples and timepoints may also be taken directly to standard PLC activity assay.

Results: SDS-PAGE gels were run and the results are illustrated in FIG. 17; which shows the results of the in vitro digestion experiments wherein the phospholipase C variants were incubated in crude protease extracts for up to 22 hr at 37° C. Each PLC mutant is named according to the amino acid found in the "X" position of the sequence "DXD" (Aspartate at amino acid position 63-any amino acid at amino acid position 131-Aspartate at amino acid position 134). The gels show the stability or sensitivity of the expressed PLC mutant protein following incubation with crude protease. A stable mutant shows a PLC band of similar staining intensity in the "–" (control no protease reaction) and the "+" (reaction contains protease). A mutant more sensitive to protease will show a reduction in PLC protein band staining intensity in the "=" lane compared to the "–" lane.

Example 5

Process for Stable High Level Expression PLC

The invention provides a fermentation process for stable, high level expression and high specific activity of phospholipase enzymes, e.g., PLC, in yeast cultures, e.g., *Pichia pastoris* cultures. The enzymes produced by this method can be used, e.g., in vegetable oil refinement, such as soybean, canola, sunflower or other oils.

The invention provides a production process comprising characteristics that enable production of active phospholipase, e.g., PLC, in a yeast cell culture, e.g., *Pichia pastoris*, as fed-batch cultures at a g/l scale. Heterologous expression of active PLC protein in microbial cultures had occasionally been described in the literature only at the mg/l scale. The process of the present invention is based, inter alia, on the finding that expression of PLC protein in *Pichia* cultures impairs the MeOH uptake capacity, but no other studied physiological growth characteristics. In contrast to conventional heterologous protein expression in *Pichia* cultures, high co-feed rates (glucose/or glycerol) are required. In addition to improving enzyme production characteristics, higher co-feeding also eliminates the expression of general protease activity which is correlated with PLC degradation. In addition, the poor MeOH utilization characteristics can be overcome, thereby improving the production characteristics further, by producing PLC in *Pichia* strains with a $Mut^+$ phenotype without compromising scalability challenges normally associated with a $Mut^+$ phenotype (and are therefore, not used on industrial scale). Thus, this process of the invention improves the production of active PLC by >50-fold (from 100 U/ml using conventional methods to >5000 U/ml whole broth; >5 g/l protein) compared to conditions that are normally applied in industrial scale *Pichia* systems. In addition, because PLC is a metallo-enzyme requiring binding of zinc for proper folding and activity, in one aspect the invention comprises a zinc supplementation. This zinc supplementation strategy for the cultures of the invention renders the PLC activity nearly completely stable (<5% loss in activity) as a whole broth, e.g., at 4° C. for >5 days. This significantly aides the recovery process since 1) production of unstable protein activity continues to worsen during the recovery process, and 2) it allows for more processing flexibility, especially at large-scale.

Tryptophanyl Aminopeptidase Microplate Assay

The invention provides a Tryptophanyl Aminopeptidase Microplate Assay, which was developed for determination of relative tryptophanyl aminopeptidase activities in *Pichia* fermentation timepoint samples. The throughput capacity of this assay is sufficient for sampling of multiple timepoints from numerous fermentations.

Materials and Methods

Buffer:

15 mM $NaPO_4$, 2 mM $MnCl_2$, pH 7.5, aq.

Substrate:

HTrp-AMC (Bachem, 11670)

Substrate solution:

Dissolve substrate to 10 mM in methanol

Add 100 μL 10 mM substrate to 6 mL of buffer

Samples:

*Pichia* fermentation timepoints

Centrifuge to remove cells.

Microplate preparation:

Aliquot 90 μl substrate solution per well of black 96-well for each sample replicate, blanks and references Place microplate on fluorescent microplate reader stage (e.g. SpectraMax, Molecular Dynamics)

Sample Addition and Reaction Kinetics:

Set-up fluorescent microplate reader:

Ex. 350 nm/Em. 460 nm; auto cutoff (455 nm); PMT medium; 3 reads per well; autocalibrate "on"

RT 0-30 minute timecourse; read every 30 seconds

Initialize the instrument plate mix function to mix for 5 seconds before first read Aliquot samples in a 96-well format and use a multichannel pipet to transfer samples at 10 μL per well With lid removed, replace microplate in microplate reader Begin reading Depending on the inherent activity of unknown samples, it may be desirable to vary sample dilution, assay duration and kinetic sampling, all variables that can be determined by routine screening.

The substrate has been shown to be very stable under these conditions and a negative control blank should show no increase in absorbance over time.

Bodipy BSA Protease Microplate Assay

The invention provides a Bodipy BSA Protease Microplate Assay to aid in the determination of general protease activity in *Pichia* fermentation timepoint samples. The throughput capacity of this assay is sufficient for sampling of multiple timepoints from numerous fermentations.

Materials and Methods

Substrate:

DQ BSA green (Molecular Probes, D12050)

Substrate solution:

Dissolve contents of one vial of substrate (1 mg) in 1 mL water containing 0.1% sodium azide Samples:

*Pichia* fermentation timepoints

Centrifuge to remove cells.

Positive Control:

0.2 mg/mL subtilisin (Sigma, P5380) in 50 mM $NaPO_4$, pH 7.5

Serially dilute in water

Microplate Preparation:

Aliquot 90 μl substrate solution per well of black 96-well for each sample replicate, blanks and references Sample Addition and Reaction:

Aliquot samples in a 96-well format and use a multichannel pipet to transfer samples at 10 μL per well Replace microplate cover, wrap with foil and place in humidified incubator at 37° C. and allow to incubate 3-4 hours or overnight Fluorescence Measurement:

Set-up fluorescent microplate reader (SpectraMax):

Ex. 495 nm/Em. 525 nm; auto cutoff (515 nm); PMT low; 3 reads per well; autocalibrate "on"

RT

Bodipy BSA was selected as a general protease substrate. Lack of hydrolysis of bodipy BSA does not indicate the absence of protease(s) but it has been shown to correlate to hydrolysis of PLC enzyme and loss of PLC activity. It has been demonstrated that BSA may be substituted with bodipy ovalbumin or casein.

In one aspect, it is useful to characterize protease activity across a fermentation timecourse since the activity may be temporal and transient.

The substrate has been shown to be very stable under these conditions and a negative control blank should show no increase in absorbance over time Plc Activity Measurement in Whole Culture Broth or Supernatant:

The invention provides a PLC activity measurement assay in whole culture broth or supernatant; this is a modification of a method described, e.g., by Edward A. Dennis (1973) Kinetic dependence of phospholipase A2 activity on the detergent Triton X-100. *J. Lipid Res.* 14:152-159, USP 24/NF 19, Pancrealipase-Assay for lipase activity. Page 1256-1257. The PLC activity measurement assay of the invention comprises:

Solutions:

100 mM Zinc Sulfate Solution 100 mM Calcium Chloride Solution

Substrate Solution (20 mM Phosphatidyl Choline, 40 mM Triton X-100, 5 mM Calcium Chloride)

Dilution Buffer (0.1% Triton X-100, 1 mM Zinc Sulfate, 1% Gum Arabic)

Assay Procedure:

Prepare dilutions of the samples to be assayed using the dilution buffer (1.0% Gum Arabic, 1.0% Triton X-100, 1 mM zinc sulfate). Prepare dilutions immediately before assay, using ice-cold buffer, and store in an ice bath until used.

Transfer 20 mL of the substrate solution into a jacketed glass vessel of about 50 mL capacity, the outer chamber of which is connected to a thermostatically controlled water bath. Cover the mixture, and stir continuously with a mechanical stirring device. With mixture maintained at a temperature of 37±0.1° C. pre-titrate the substrate with 0.01 N KOH VS, from a microburet inserted through an opening in the cover, to adjust the pH to 7.3. Add 50 μL of enzyme dilution, and then continue automatically to add the 0.01 N KOH VS for 6 minutes to maintain the pH at 7.

In addition, standard PAGE gel electrophoresis, Western and Northern blot analysis on fermenter cultures as well as standard analysis techniques for on-line/off-line fermentation parameters (biomass levels, gas analysis etc.)

Generating the $Mut^+$ Phenotype *Pichia* Strains

The invention provides cells, cell systems and methods for expressing phospholipase C comprising using a *Pichia* strain with a $Mut^+$ phenotype. The method comprises inserting a heterologous PLC-encoding nucleic acid in the *Pichia* strain. The cell is then cultured under conditions whereby the PLC is expressed. The method can further comprise supplementing the culture conditions with zinc.

In one aspect, these methods, cells and cell systems use SEQ ID NO:2, which is a zinc-requiring metalloenzyme. In one aspect, it is used at 3 moles/mole. It has a MW of approximately 28 kDa and a pI of approximately 5.2, and has a broad substrate tolerance: PC>PE>PS>>PI. The unprocessed enzyme has a signal sequence of 24 amino acids, a prosequence of 13 amino acids, and a "mature" enzyme of 245 amino acid residues.

In one aspect, the $Mut^+$ *Pichia* strains of the invention have two copies of alcohol oxidase (AOX) genes, AOX1 and AOX2, affected during transformation ("Mut" stands for "Methanol Utilization"), as follows:

$Mut^+$

Single crossover event, AOX1 and AOX2 genes intact

Growth and expression on methanol alone. Co-feeding possible $Mut^S$

Double crossover event disrupts the AOX1 gene

Growth and expression improved with co-feeding $Mut^-$

Recombination event disrupts AOX1 and 2 genes

Cannot metabolize methanol, requires co-feeding

In summary: $Mut^- < Mut^s_{plc} < Mut^s/Mut^+_{plc} < Mut^+$

There are fermentation differences between $Mut^+$ and $Mut^s$, including:

Optimal Induction Concentration of Methanol

Oxygen Consumption Rate $Mut^+$ grows faster than $Mut^s$ on Methanol due to faster uptake capacity Ease of Transition Period after Induction $Mut^+$ not used for expression at large scale Aeration/cooling capacity, MeOH sensitivity The methanol utilization pathway in *Pichia pastoris* is well known in the art. Alcohol oxidase (AOX) catalyzes the conversion of methanol to formaldehyde; thus, if the AOX is overexpressed, results in a "pickled" yeast cell.

An exemplary fermentation protocol for *Pichia pastoris* used in one aspect of the invention comprises:

Seed Culture (flask or tank)

Batch fermentation in rich medium to enhance biomass

Fed-Batch Fermentor Culture

Batch Phase (Glycerol)

Biomass growth as initial carbon source is consumed.

Glucose or Glycerol Feeding Phase

Addition of feed triggered by D.O. content or linear/exponential feeding

Growth to sufficient biomass for induction and expression (absence of Ethanol, C-limited)

Methanol Induction

Addition of feed regulated (D.O. %, MeOH sensor, RQ) or preset feeding profiles

Figure 18:
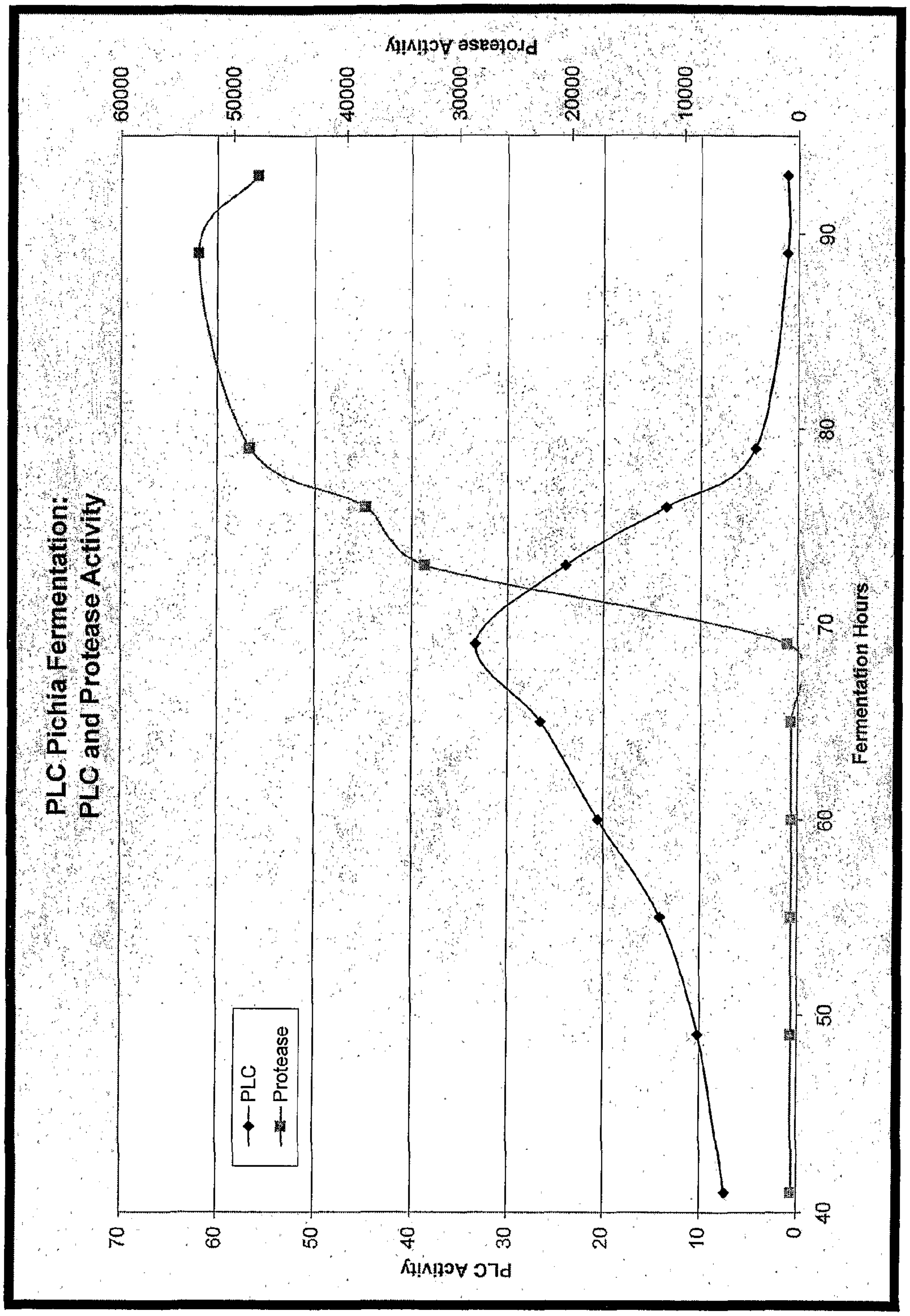
FIG. 18 illustrates the results of a batch fermentor culture using an exemplary enzyme of the invention, as discussed in detail in Example 5, below.

Co-feeding with glucose or glycerol dependent on phenotype and expression parameters $Mut^+$ Induction at 1-3 g/L MeOH $Mut^s$ Induction at 4-7 g/L MeOH FIG. 18 illustrates the results of a batch fermentor culture, as discussed above, using only glycerol. Protease activity is from an endogenous protease in *Pichia*. The batch fermentation can be rich medium to enhance biomass. As noted in FIG. 18, the progressive increase in protease activity beginning at about 69 hours corresponds to a progressive decrease in PLC activity. A higher co-feed rate of glycerol (glyc) improves active PLC expression and decreases (eliminates) protease production, as the following data summary table illustrates:

| Co-feed rate (ml/min) | C-source before/ after induction | Induction OD | PLC activity (U/ml sup) | MeOH consumed (L) | Bodipy protease | Final OD |
|---|---|---|---|---|---|---|
| 0.5 | Glyc/Glyc | 250-300 | 100 | 1 | Yes | 450 |
| 1.5 | Glyc/Glyc | | 1100 | 1.7 | No | 680 |
| 2 | Glyc/Glyc | | 1550 | 1.3 | No | 860 |
| 2.5 | Glyc/Glyc | | 1550 | 1.4 | No | 900 |
| 3 | Glyc/Glyc | | 1715 | 1.4 | No | 820 |

Figure 19:
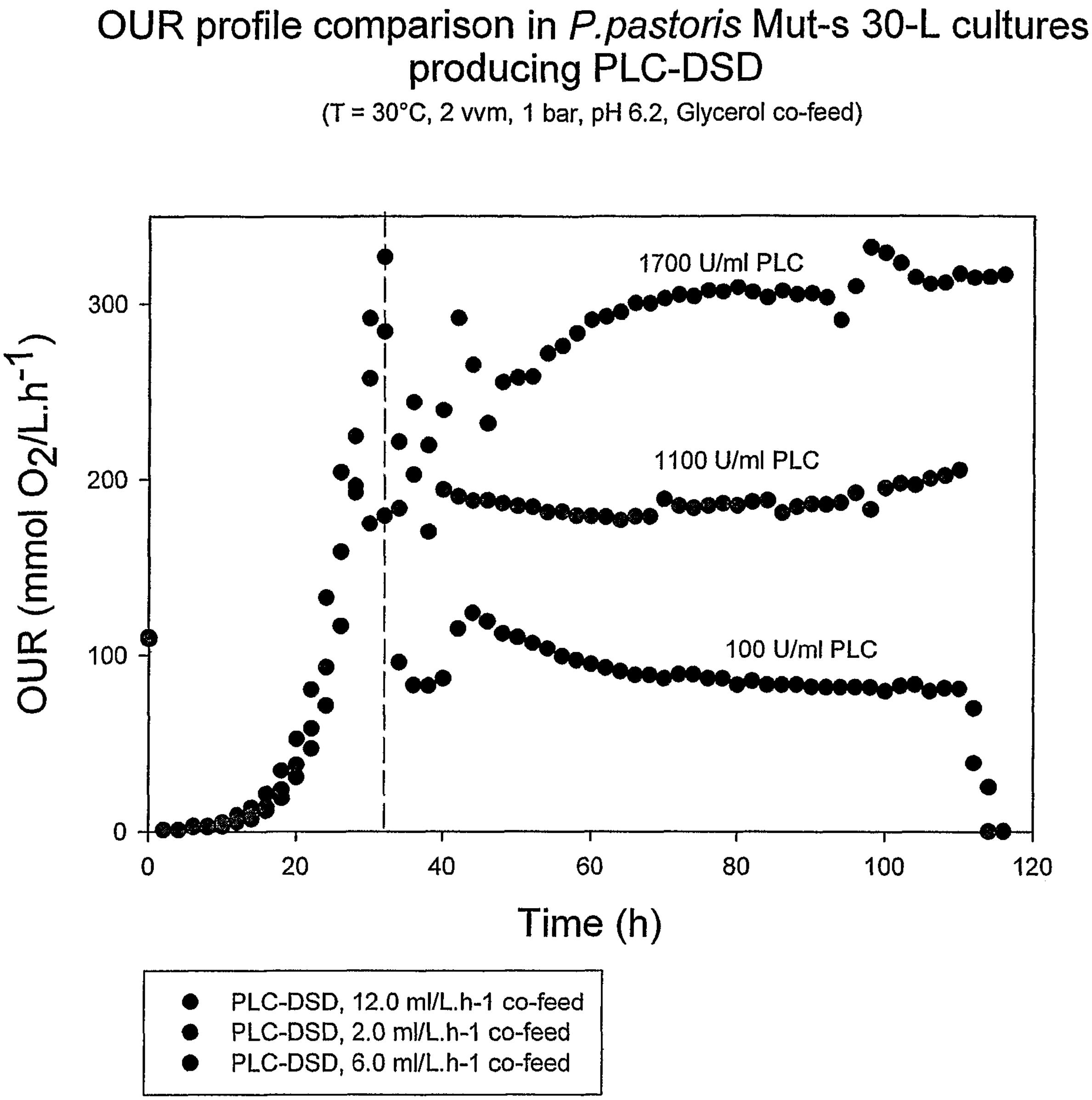
FIG. 19 illustrates the results of Oxygen Uptake Rate ("OUR") comparisons of cultures of *P. pastoris* MutS strains of the invention, as discussed in detail in Example 5, below.

These studies were done in 30-L BB fermenters with DSD-PLC. The OUR, or Vol. Oxygen Uptake Rate ("OUR"), as an 'overall culture health' indicator or 'Biomarker' for good expression, was measured. FIG. 19 illustrates the results of such a study, an OUR profile comparison of cultures of *P. pastoris* MutS 30 L cultures producing DSD-PLC, using 1700 U/ml, 1100 U/ml and 100 U/ml PLC, 30° C., glycerol co-feed, as discussed above.

Figure 20:
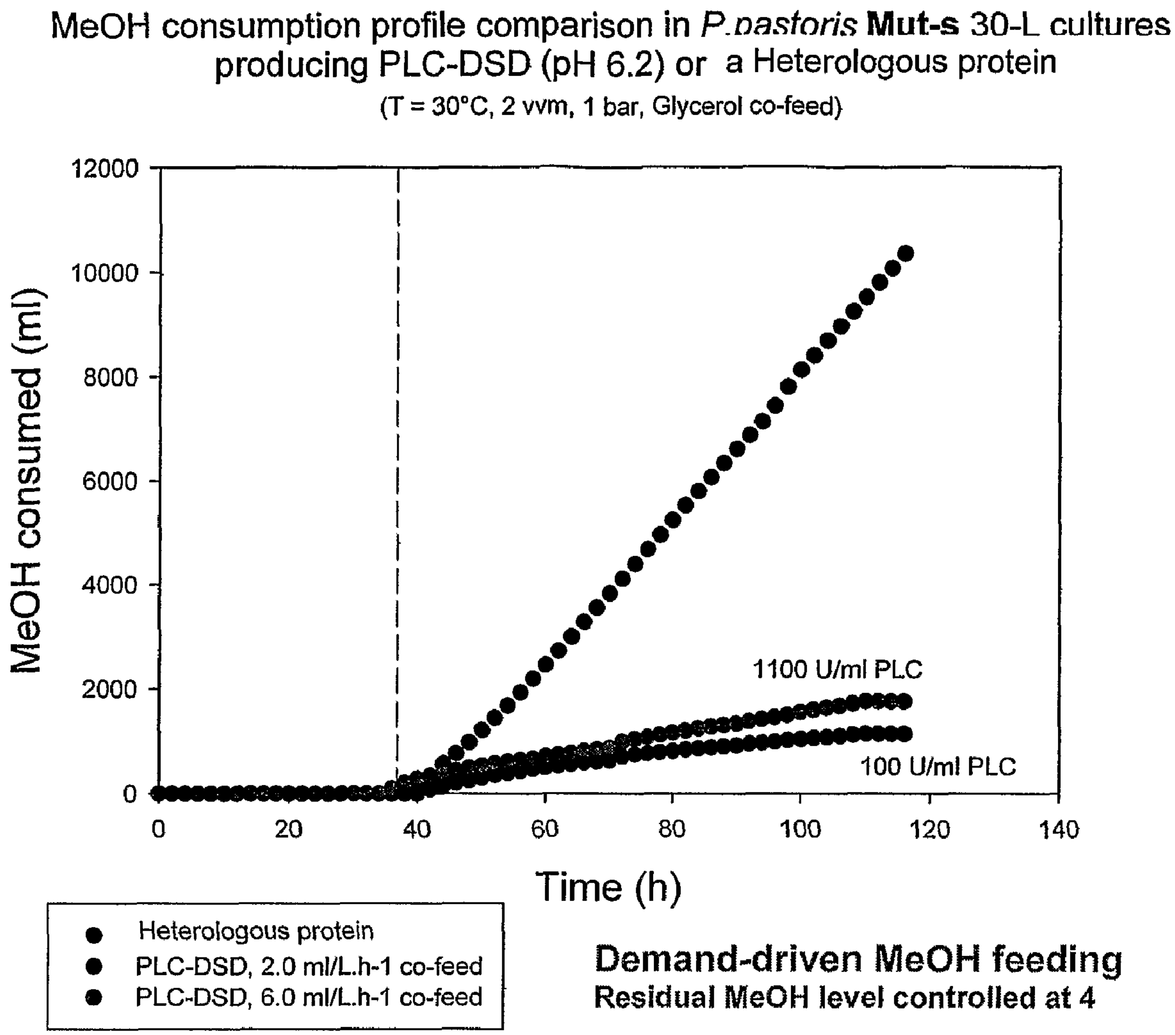
FIG. 20 illustrates a methanol consumption profile comparison in *P. pastoris* MutS strains of the invention, as discussed in detail in Example 5, below.

FIG. 20 illustrates a methanol consumption profile comparison in *P. pastoris* MutS 30 L cultures producing DSD-PLC, pH 6.2 (1100 U/ml and 100 U/ml PLC), or a heterologous protein, with a glycerol co-feed, as discussed above. This was a demand-driven MeOH feeding, and the residual MeOH level was controlled at 4 g/l.

In addition, $Mut^+$ phenotype improves active PLC expression and enhances MeOH uptake, as this data table summarizes:

| Mut | Co-feed rate (ml/min) | Induction OD | PLC activity (U/ml sup) | MeOH consumed (L) | Bodipy protease | Final OD |
|---|---|---|---|---|---|---|
| S | 0.5 | 250-300 | 100 | 1 | Yes | 450 |
| | 1.5 | | 1100 | 1.7 | No | 680 |
| | 2 | | 1550 | 1.3 | No | 860 |
| | 2.5 | | 1550 | 1.4 | No | 900 |
| | 3 | | 1715 | 1.4 | No | 820 |
| + | 0.5 | 250-300 | 1001 | 5.6 | yes | 871 |
| | 0.5 | | 1200 | 7 | No | 908 |
| | 1 | | 1786 | 5.9 | No | 988 |
| | 1 | | 2010 | 6.8 | No | 930 |
| | 1 | | 1768 | 7.9 | No | 700 |
| | 1.5 | | 2669 | 10 | No | 701 |
| | 1.5 | | 2693 | 7.1 | No | 818 |
| | 1.5 | | 2597 | 8.1 | No | 804 |
| | 2 | | 2154 | 8.3 | No | 752 |

Figure 21:
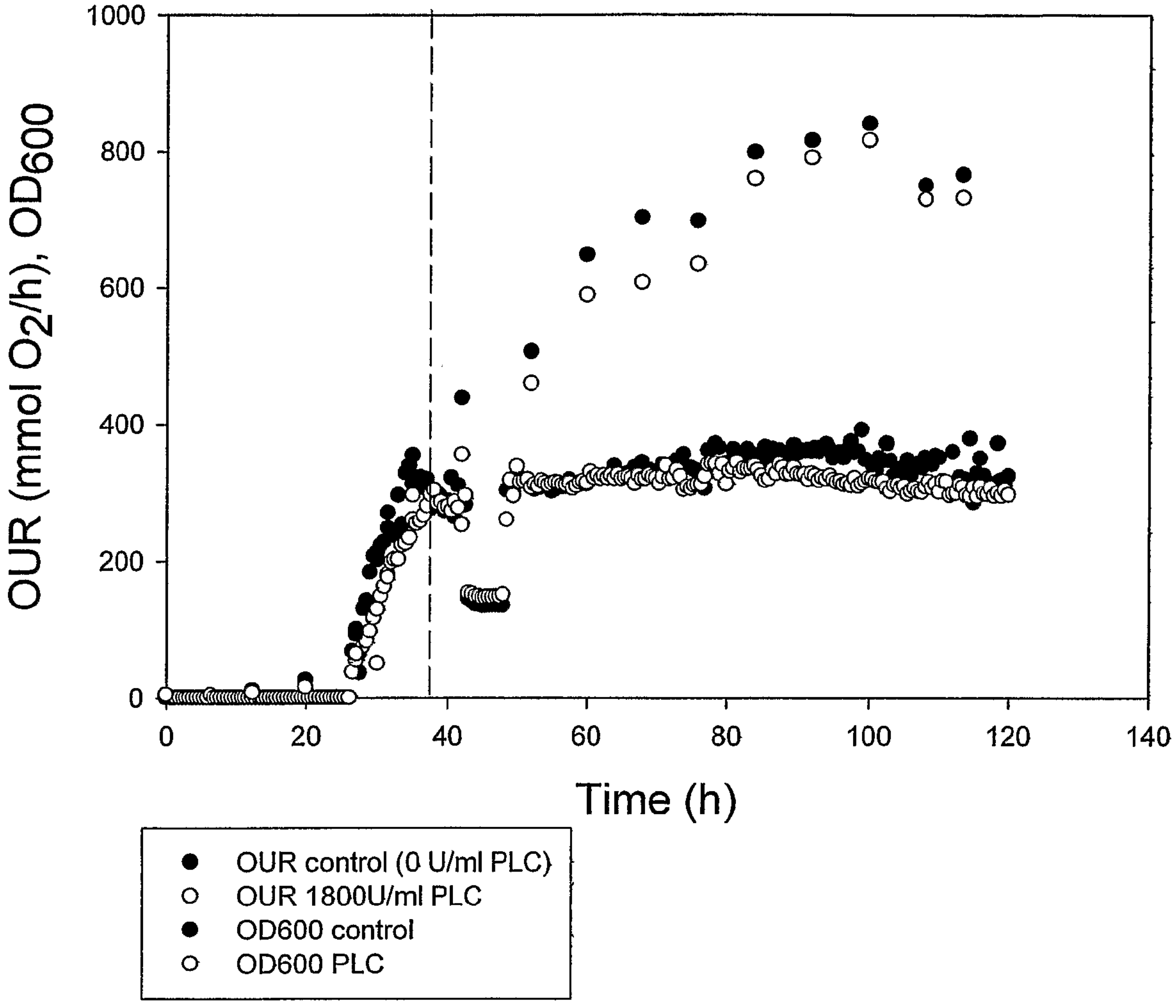
FIG. 21 illustrates an "OUR" profile of a culture of a recombinant form of the exemplary PLC enzyme of the invention SEQ ID NO:2, as discussed in detail in Example 5, below.

PLC does not seem to affect physiological growth characteristics of this $Mut^+$ phenotype strain—which expresses recombinant PLC SEQ ID NO:2, in a 6× copy number, the data illustrated in FIG. 21, an OUR profile as set forth in the figure description. This is a supply-driven MeOH feeding with no residual glucose or MeOH in $Mut^+$ cultures.

Figure 22:
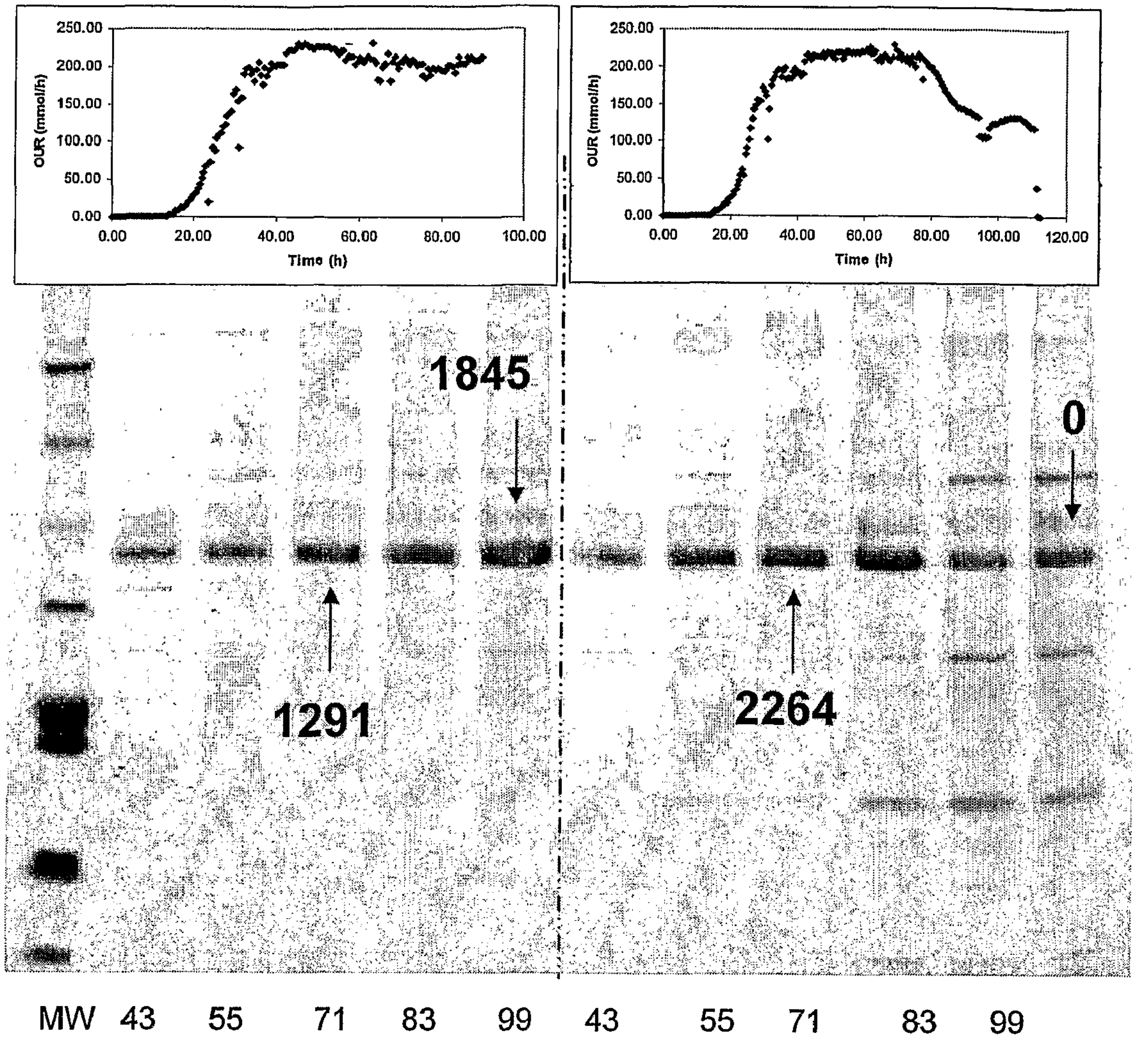
FIG. 22 illustrates results from an SDS-PAGE showing the quality of PLC protein produced in a culture, and a corresponding OUR profile, of a culture of a recombinant form of the exemplary PLC enzyme of the invention SEQ ID NO:2, as discussed in detail in Example 5, below.
Figure 24:
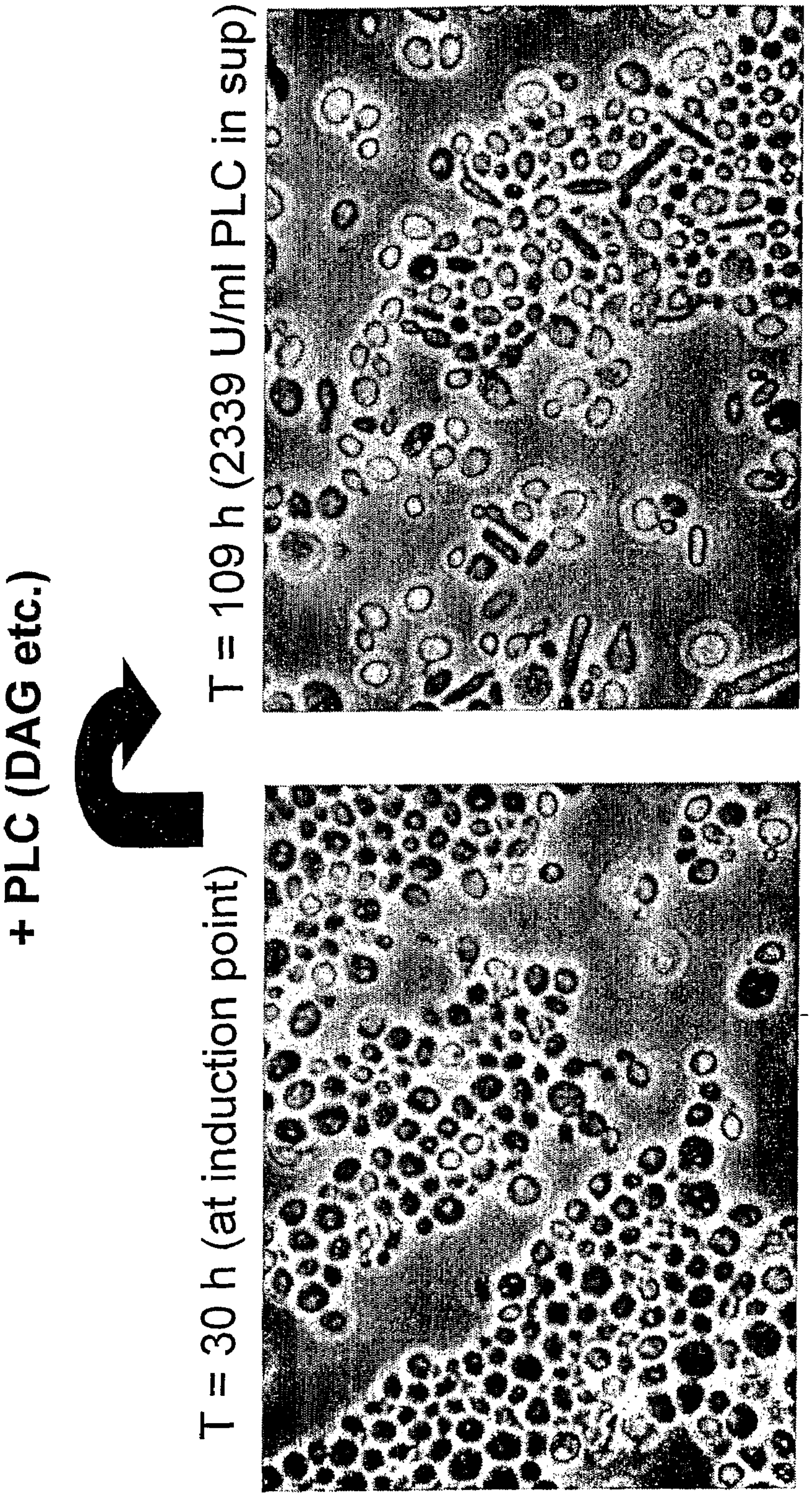
FIG. 24 illustrates a visualization of the morphological changes in yeast cells associated with active PLC—a recombinant form of the exemplary PLC enzyme of the invention SEQ ID NO:2, as discussed in detail in Example 5, below.

Additionally, the quality of PLC protein produced is unpredictably variable, e.g., <<or >> 50% of total PLC protein is active, as illustrated by the representation of the results from SDS-PAGE, in FIG. 22. The OUR profile (discussed above) graphic summary of data is inserted into the upper section of the SDS-PAGE illustration. The control is designated JG=0.5 μl 1.6 mg ml−1. There was no correlation with protease or aminopeptidase activity. A significant quantity of active PLC was located intracellularly, as illustrated in FIG. 23 (also showing the study's protocol), where >700 U/ml PLC was detected intracellularly (in FIG. 23, PLC (SEQ ID NO:2)+ an alpha signal peptide (from *Saccharomyces*)+glycosylation). Morphological changes were correlated with active PLC concentration, as illustrated in FIG. 24. Magnitude of the morphological change was strain and C-source dependent.

Increased Zn did not boost expression in a *Pichia* strain having 2× copy number Mut+ SEQ ID NO:2 with DSD mutation, as summarizes in the data chart, below (excess over 1× supplied via co-feed) (first, upper row is empty vector control). Increased Zn did improve storage stability as whole broth (similar activity level after >100 h at 4° C.) and overall robustness of process.

| Zn | MeOH (L) | Base (L) | 70% (v/v) Glycerol (L) | OD600 | PLC (U/ml) |
|---|---|---|---|---|---|
| 1X (2.2 mM) | 7.1 | 2.3 | 9.6 | 765 | 0 |
| 0.2X | 7.4 | 2.1 | 8.6 | 731 | 392 |
| 1X | 7.1 | 2.8 | 9.0 | 776 | 2700 |
| 4X | 6.1 | 2.2 | 10 | 780 | 2448 |
| 12X | 6.4 | 2.3 | 9.8 | 776 | 2498 |

Figure 25:
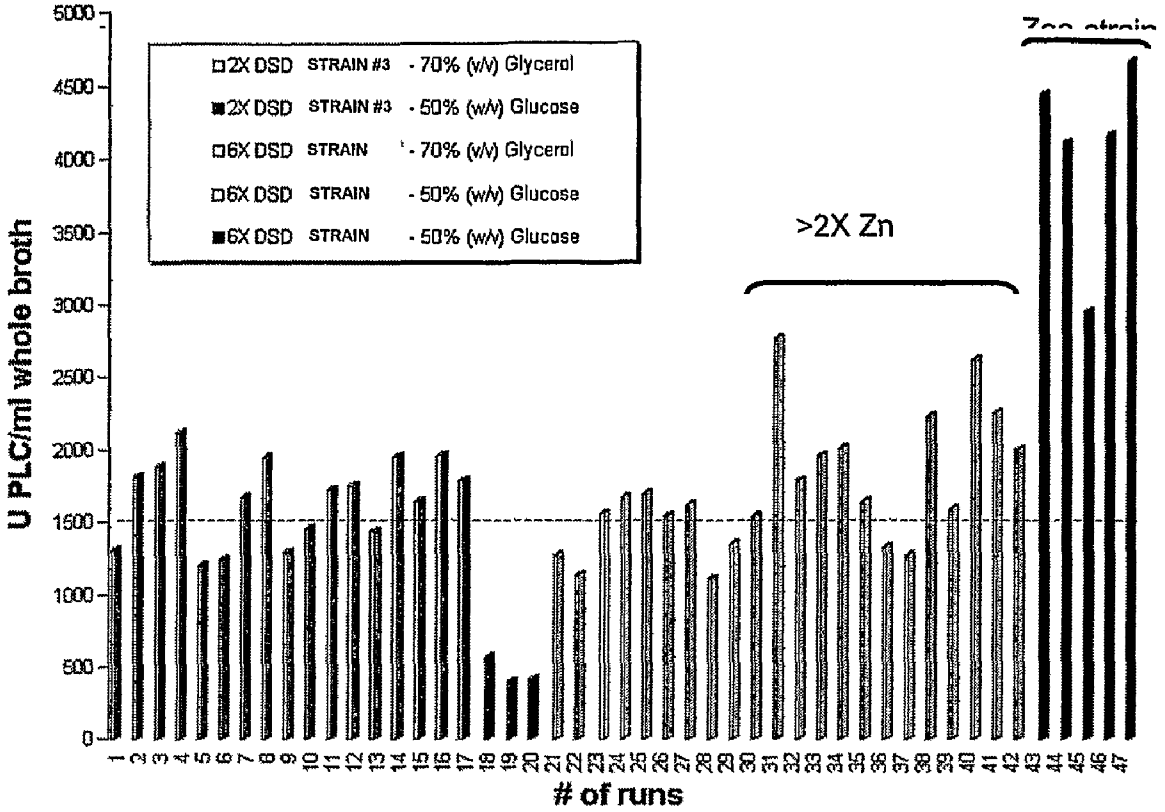
FIG. 25 graphically summarizes data showing the status of a PLC production performance at 95 h TFT (total fermentation time) in *Pichia* using an exemplary PLC enzyme of the invention SEQ ID NO:2, as discussed in detail in Example 5, below.

FIG. 25 graphically summarizes data showing the status of a PLC production performance at 95 h TFT (total fermentation time) in *Pichia*. The five bars on the right side of the graph show results from the "Zeo strain", or Zeocin adaptation of the PLC producing *Pichia pastoris* strain. This strain is an antibiotic-resistant markerless strain expressing as a heterologous gene a PLC of the invention (SEQ ID NO:2) in a *Pichia pastoris* strain. It has been demonstrated that by adapting the strain with zeocin, an antibiotic, one can obtain a new stable strain with greatly improved expression level for the protein of interest.

The original antibiotic-resistant markerless strain, strain #1 (containing SEQ ID NO:2), was grown in a series of dilution steps, each time with an increasing concentration of zeocin, which is an antibiotic. On each step, a portion of the culture from previous step was diluted to an optical density at 600 nm (OD600) of 1.0 with fresh medium and an increasing amount of zeocin was added to the new culture for another 24 hours of growth. At the final stage, a zeocin concentration of 200 ug/ml was used and the final culture was streaked to a MD/YPD plate to allow individual colonies to grow. It was found that the colonies from the final stage culture show high tolerance to zeocin, while the parent strain exhibits very little tolerance. One of the colonies, strain #2 (containing SEQ ID NO:2), showed dramatic improvement (about 70% higher) in PLC expression compared to the original PLC strain, strain #1. It was also demonstrated that strain #2 is stable both in zeocin tolerance and PLC expression after a 40-generation passage, indicating that the new strain acquired the "permanent" trait of high PLC expression and zeocin tolerance.

A high level of PLC activity was achieved using the "Zeo strain" (Zeocin *Pichia* adaptation) of the invention: 4100 u/ml achieved in mini-tanks. This result comes from the *Pichia* strain comprising 6×DSD SEQ ID NO:2. Briefly, this SEQ ID NO:2-expressing strain was "adapted" by growing it in a series of steps, each with increasing concentration of zeocin. Apparently, this adaptation process forced some changes (in molecular or genetic level) to the strain/construct and resulted in significant improvement of PLC activity level. Exemplary results are:

Tank 1, 2, and 4 (each representing different colonies) all out-performed the original pre-adapted SEQ ID NO:2-expressing strain, with tank 1 & 4 both got to 4100 u/ml and tank 2 got to 3500 u/ml.

Tank 1 & 4 got to over 3000 u/ml as early as in 75 hrs, representing a much faster activity accumulation comparing to the original pre-adapted SEQ ID NO:2-expressing strain (which is normally well below 2000 u/ml at the time).

Details of the Experimental Design and Result are:

Rationale of Zeocin Adaptation:

Earlier stage of work on PLC expression was done in the *Pichia* pPICZa vector, which contains the zeocin-resistance marker. Zeocin was thus used for transformation selection. Later on, we switched to the AMR-less version construct to develop commercial product candidates. While doing mini-tank fermentations, we observed a significant drop of PLC activity level obtained using the AMR-less constructs: supernatant activity reached 4000 u/ml in pPICZa-DSD constructs, whereas only ca. 2000 u/ml was obtained in the 2×DSD. Significant physiological differences, e.g., lower methanol consumption rates and a lot more cell lysis, were also observed with the AMR-less constructs, especially when testing higher copy number (5×, 6×) constructs using the same fermentation protocols.

With one of the apparent differences between the pPIZa construct and the AMR-less construct being the use of zeocin in transformation, the question was raised on what the cells might have gone through with zeocin selection. The invention provides growing the AMR-less construct in the presence of zeocin—the cells then go through some changes beneficial to PLC expression.

Zeocin Adaptation Experiment on 2×DSD:

The experiment was first used with the 2×DSD (as it was the transfer molecule at the time). The study started with a zeocin concentration of 1 ug/ml ("zeo 1") and grew the culture for ~24 hrs. From there, step increase of zeocin concentration to zeo 5, zeo 10, zeo 15, zeo 20, zeo 40, zeo 60, zeo 80, zeo 100 and finally to zeo 200 were carried out (zeo 100 is normally used for transformation selection). Each step fresh medium was used and previous stage culture was used to inoculate the next stage culture with OD of 1.0 and grown for 24 hrs. Cultures of each stage were also streaked to YPD plates for preservation and to obtain individual colonies.

Mini-Tank Fermentation Results of Zeo-Adapted Colonies:

To test the effects of zeocin adaptation, a dozen of colonies from zeo 200 and zeo 100 cultures (that were streaked to YPD plates) was picked and screened with mini-tanks. The results are summarized in slide 6. We were able to find several colonies that significantly outperformed the original construct (Pichia strain comprising SEQ ID NO:2). Among them, colony #5 from zeo 200 culture showed about 50% improvement on PLC activity level. Observations on the screening:

There were no apparent differences on growth profiles between the zeo-adapted cultures and the original SEQ ID NO:2-expressing strain.

Although stability of the adapted cultures was not extensively tested, they were re-streaked several times on YPD and/or MD plates without the presence of zeocin. All fermentation was also done without the presence of zeocin.

There were apparent colony to colony variations, both on growth and on PLC expression.

Some technical problems with the fermentation might be partly responsible for the variations.

Zeocin Adaptation Experiment on 6×DSD:

Encouraged by the results from the zeo-adapted 2×DSD, we then carried the same experiment on the 6×DSD (which at the time was determined as being superior to the 2×DSD). We started with zeocin concentration of 5 ug/ml ("zeo 5") and grew the culture for ~24 hrs. From there, step increase of zeocin concentration to zeo 15, zeo 30, zeo 50, zeo 100 and finally to zeo 200 were carried out. Same as with the 2×DSD, each step fresh medium was used and previous stage culture was used to inoculate the next stage culture with OD of 1.0 and grown for ~24 hrs. Cultures of each stage were also streaked to YPD plates for preservation and to obtain individual colonies.

Mini-Tank Results of Zeo-Adapted 6×DSD Colonies:

Six colonies from the zeo 200 culture (that was streaked to MD plate) were picked and tested together with the original SEQ ID NO:2-expressing strain in the mini-tanks. Key observations are as below:

All three colonies (tank 1, 2, and 4) out-performed the original SEQ ID NO:2-expressing strain, with tank 1 & 4 both got to 4100 u/ml and tank 2 got to 3500 u/ml.

Tank 1 & 4 got to over 3000 u/ml as early as in 75 hrs, representing a much faster activity accumulation comparing to the SEQ ID NO:2-expressing strain (which is normally well below 2000 u/ml at the time).

PLC protein level also seems to be higher in tanks 1, 2, & 4 comparing to the 3000 u/ml run in 10-L tank (see slide 4). It is thus not clear whether apparent specific activity is higher in tanks 1, 2, & 4, i.e., whether the PLC being produced is different than from the original SEQ ID NO:2-expressing strain. The control, tank 7 & 8, did not get to 3000 u/ml this time. It's not clear whether tank 1, 2, & 4 might be able to reach even higher level. Note that the percent increase (35%, 4100 u/ml vs 3000 u/ml) is smaller than the 2× adapted culture.

Figure 27:
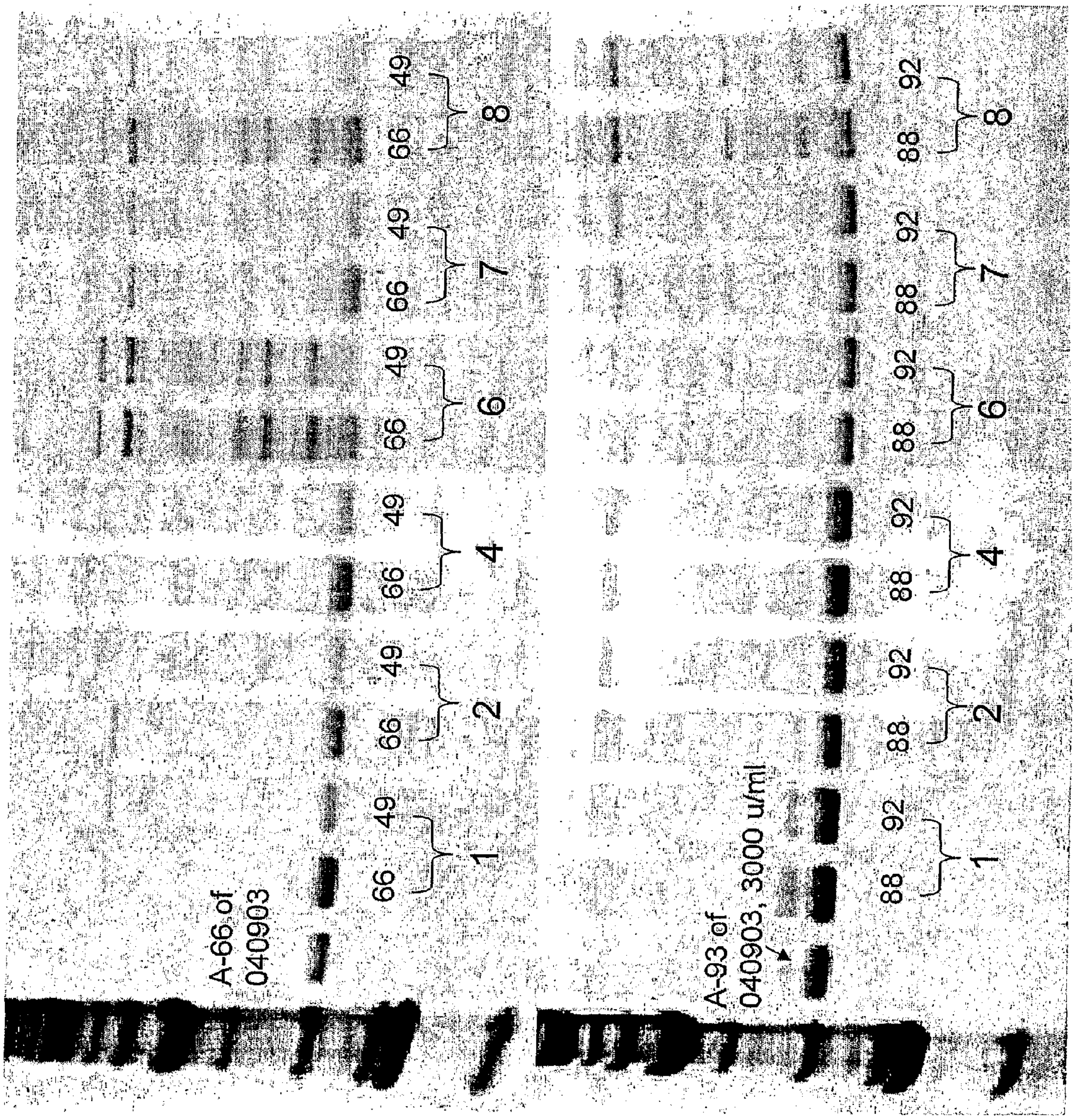
FIG. 27 illustrates data showing that PLC protein levels were higher in cultures comprising exemplary zeocin-adapted cell colonies of the invention, as discussed in detail in Example 5, below.
Figure 28:
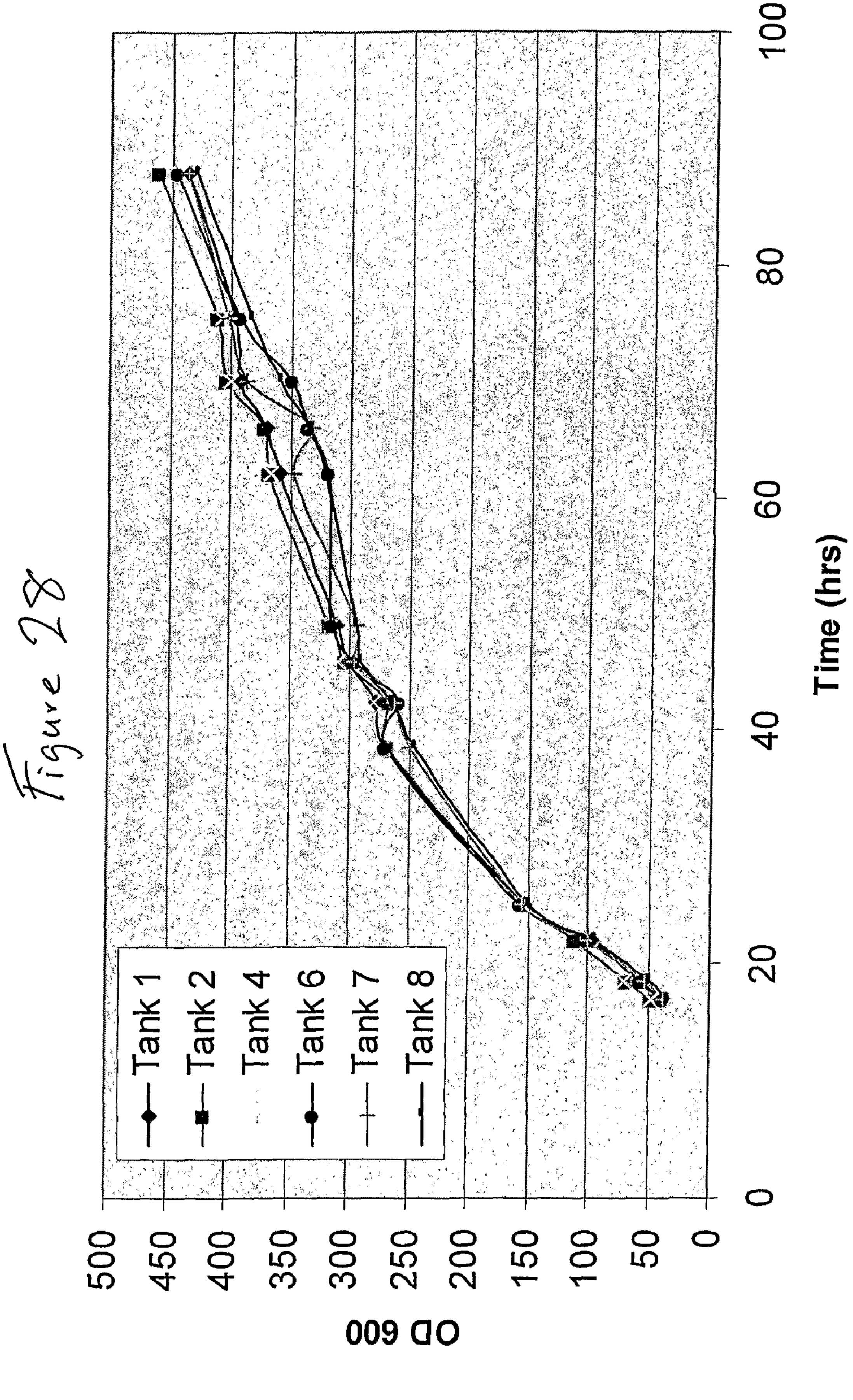
FIG. 28 illustrates data showing a growth comparison of zeo-adapted colonies of the invention vs control, as discussed in detail in Example 5, below.

A summary of expression screening from the 6×DSD zeocin-adapted colonies is found in FIG. 26. The highest activity level seen with the original strain was ~3000 u/ml (mini-tank & 10-L); the level achieved with zeocin-adapted 6×DSD was 4100 u/ml (~35% increase). FIG. 27 illustrates data showing that PLC protein level was higher in tanks 1, 2, & 4 comparing to the 3000 u/ml run in 10-L tank (and tank conditions), as discussed above (the gel loading was at 1.0 ul of 5× diluted broth, 0.2 ul of whole broth). FIG. 28 shows the growth comparison of zeo-adapted colonies vs control. The Zeocin-adapted 6×DSD colonies have similar growth profile compared to the original SEQ ID NO:2-expressing strain (6×DSD).

The Qp of secreted protein in C-limited aerobic yeast cultures is generally 0.5-2.5 mg/g·h−1 at μ=0.10 h−1. Based on protein content of 400 mg/g DW, 'metabolic burden' is <10% of overall protein production rate. PLC mRNA level remains high throughout fermentation and does not correlate with expression. Based on 5 g/l (150 g) PLC protein, less than 0.1 mol C/h of total 5 mol C/h (2% of total C consumed) goes to PLC carbon and ~25% goes to biomass. PLC activity does not seem to impact general growth physiological characteristics under these production conditions (except MeOH utilization capacity is affected).

In summary, the invention provides zeocin-resistant yeast cell systems, such as yeast cells, cell lines and/or individual cells, for expressing a heterologous protein (e.g., an enzyme, such as a PLC) made by a process comprising the steps of providing a *Pichia* sp. (e.g., *P. pastoris*) cell comprising a heterologous nucleic acid (e.g., a vector comprising an enzyme coding sequence; an ORF operably linked to a promoter) capable of expressing a heterologous protein; culturing the cell(s) under conditions comprising zeocin at an initial concentration (a concentration low enough that some cells survive, but, high enough to select for antibiotic resistant cells); selecting cells resistant to the initial concentration of zeocin, and reculturing under conditions comprising a higher concentration of zeocin; and selecting the cells resistant to the higher concentration of zeocin. The invention also provides yeast cells, cell lines and/or individual cells made by this process. Routine screening can determine which initial concentration of antibiotic to use, how many rounds of selection are needed, or desired, and how quickly to increase concentrations of antibiotic between selection rounds.

Example 6

Thermostable PLC

The invention provide thermostable phospholipase enzymes. The thermostability for the exemplary enzyme having a sequence as set forth in SEQ ID NO:2 was demonstrated. Thermostability of comparable phospholipids of the invention was demonstrated using SEQ ID NO:2. The activity of SEQ ID NO:2 was tested in two different systems: aqueous and in oil. In the aqueous system, a surrogate substrate (p-nppc) was used to measure activity; the enzyme began to loose activity at 86 C. However in the oil assays, the enzyme showed good activity in hydrolyzing PC and PE substrates present in soy oil at 85 C. Tm of the same enzyme was checked and found that it was 86 C @15 mg/mL, and not reversible.

Figure 30:
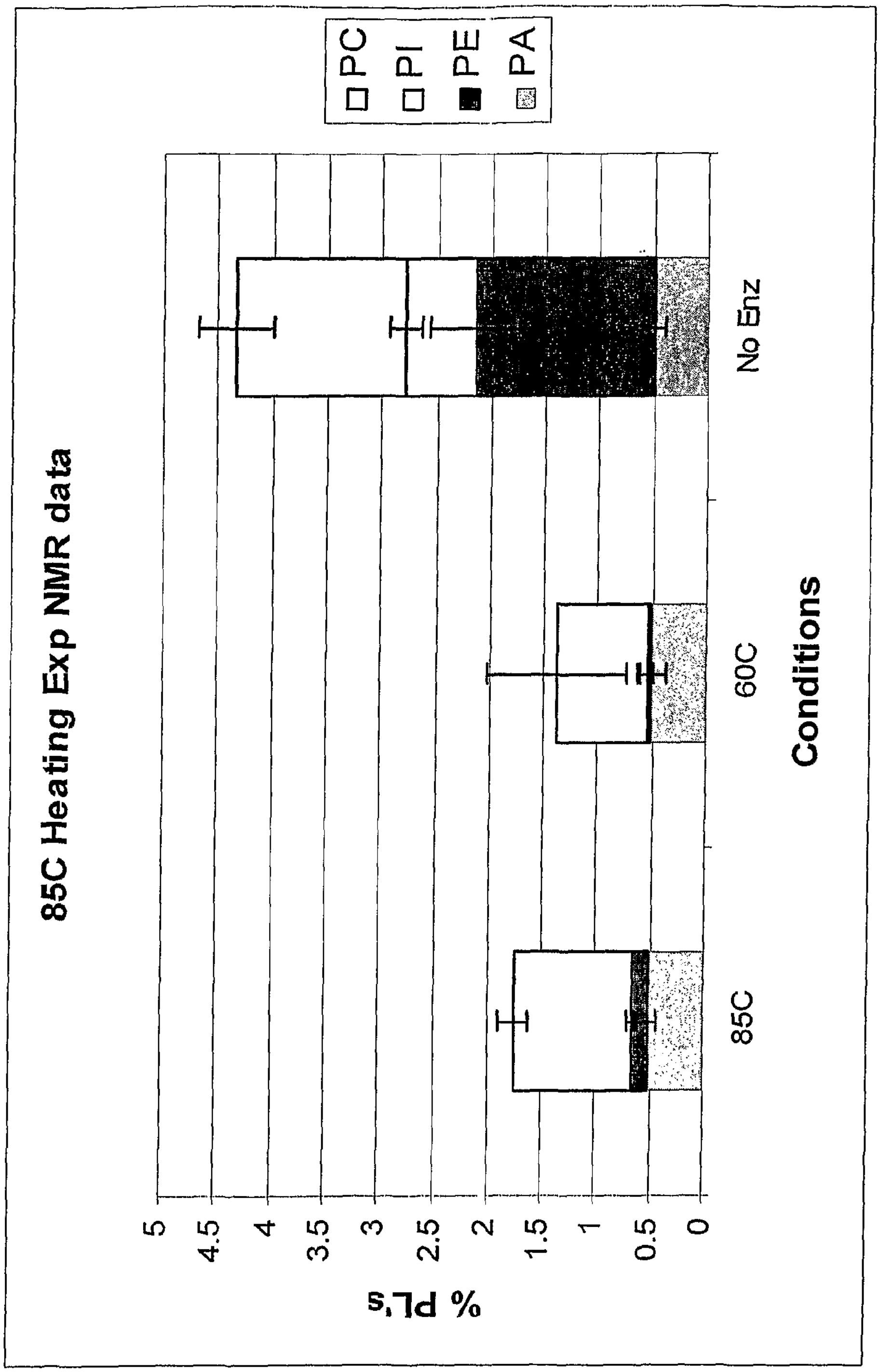
FIG. 30 illustrates NMR data summarizing the heating experiment demonstrating the thermostability of the exemplary enzyme of the invention SEQ ID NO:2, as discussed in detail in Example 6, below.
Figure 31:
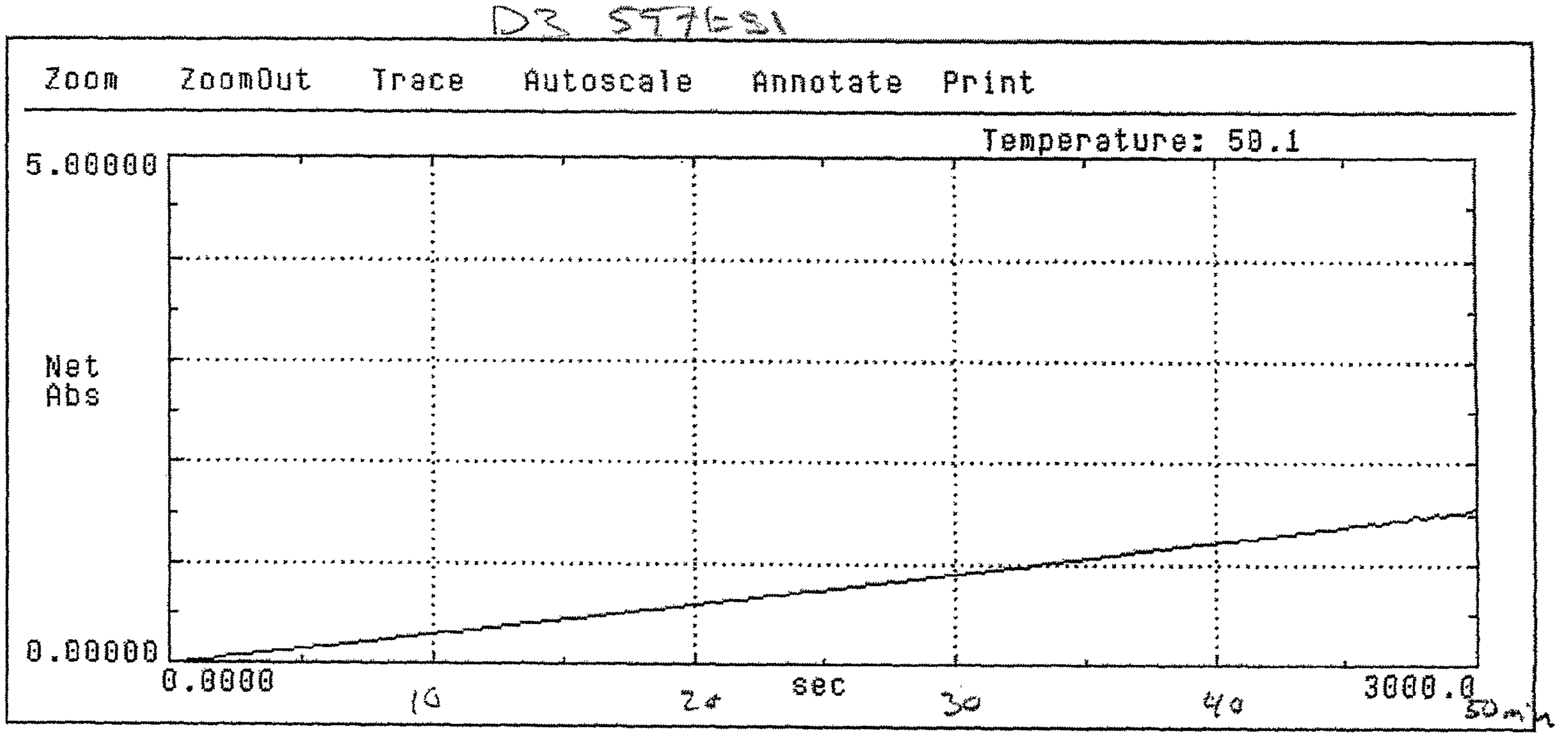
FIGS. 31, 32 and 33 illustrate data demonstrating the thermal stability of SEQ ID NO:2 using p-NPPC, at the conditions shown in the figure, as discussed in detail in Example 6, below.
Figure 32:
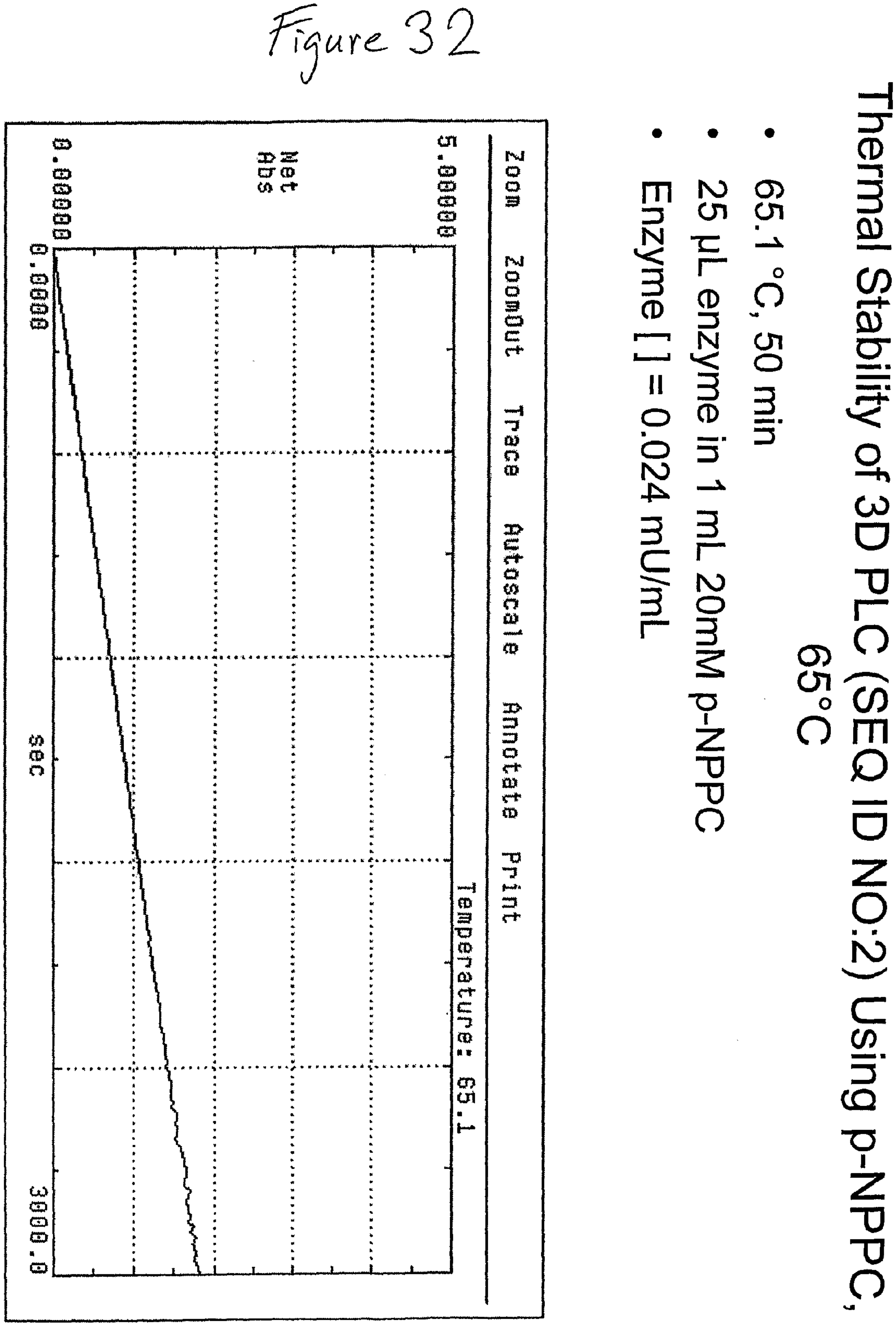
Figure 33:
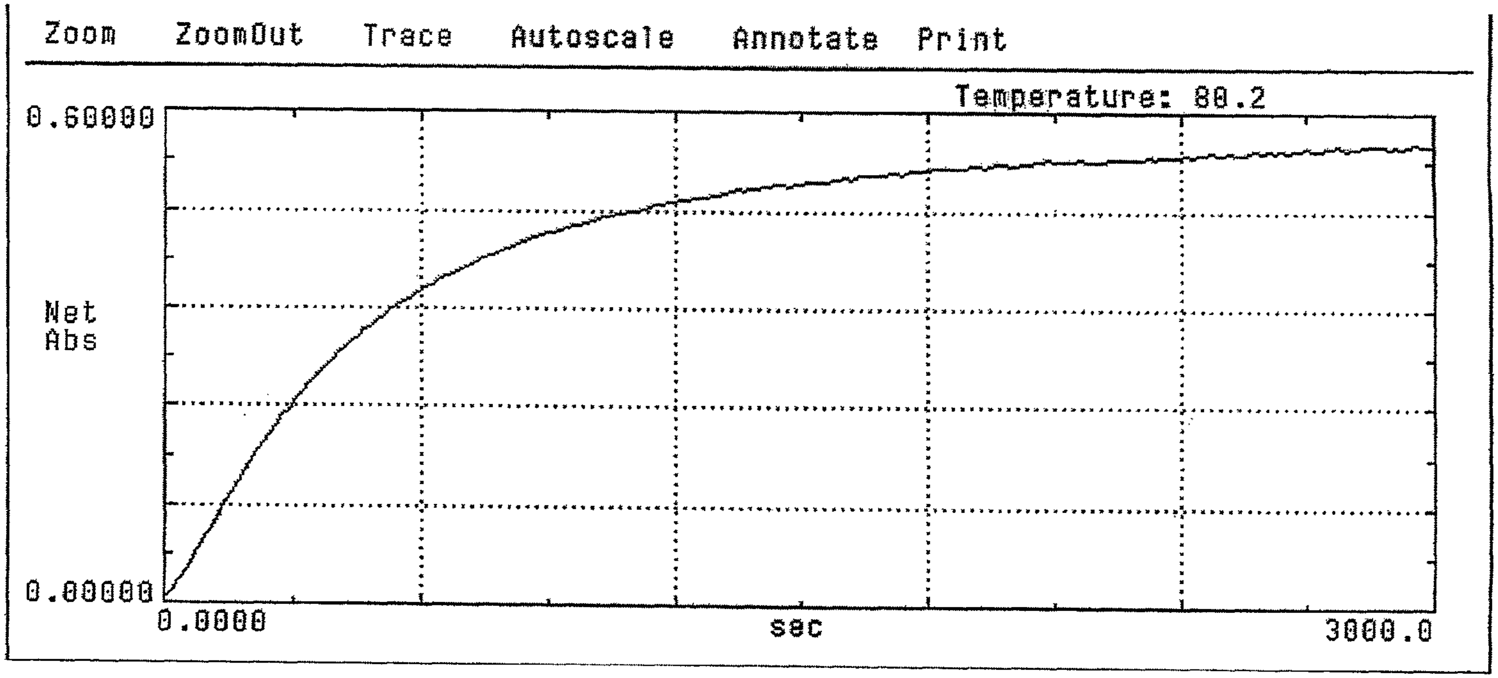
Figure 34:
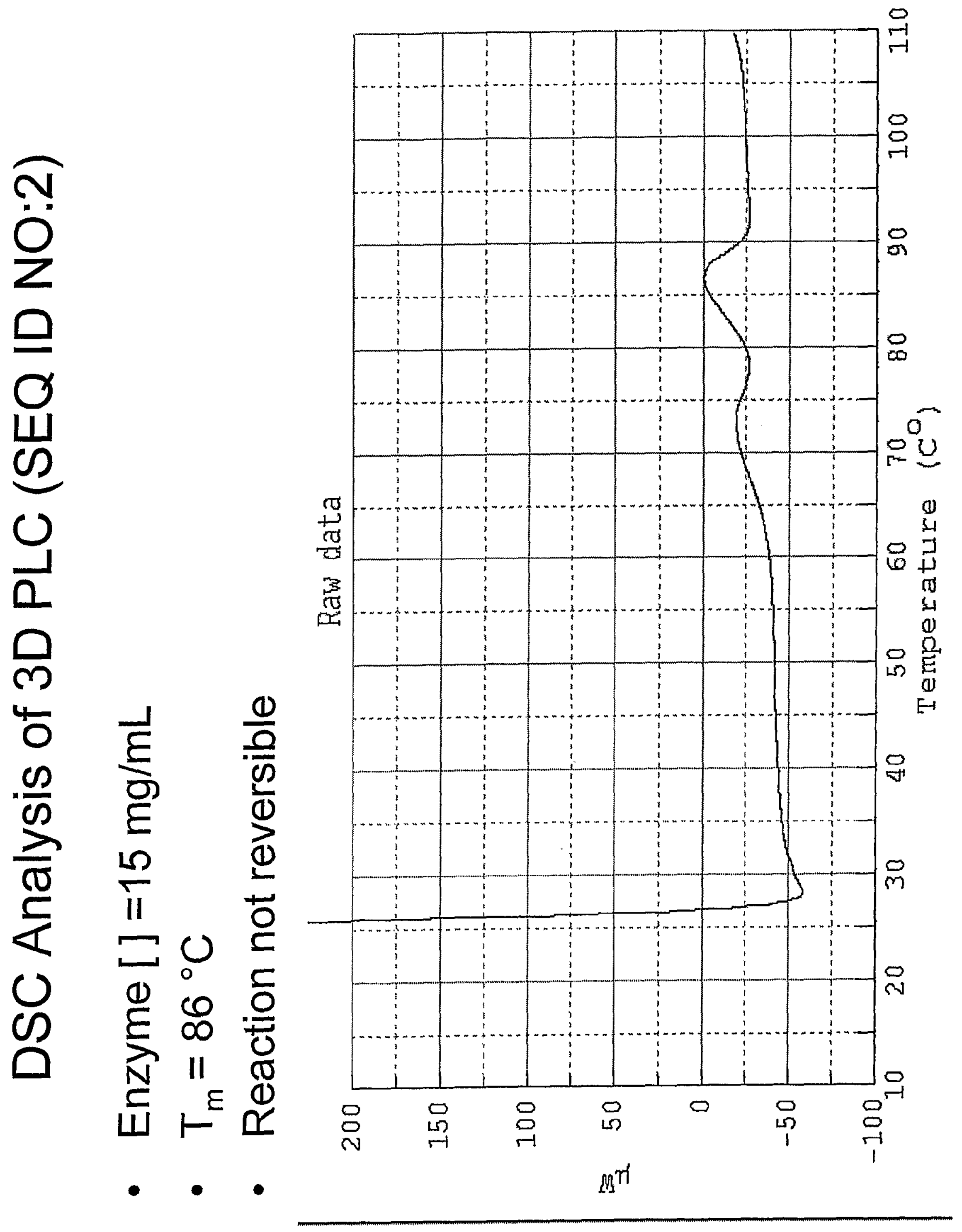
FIG. 34 illustrates data demonstrating the thermal stability of SEQ ID NO:2 using DSC analysis, as discussed in detail in Example 6, below.

FIG. 29 illustrates the results of an 85° C. heating experiment with 10 U of SEQ ID NO:2, with the conditions indicated in the figure. FIG. 30 illustrates NMR data summarizing this heating experiment. FIGS. 31, 32 and 33 illustrate data summarizing the thermal stability of SEQ ID NO:2 using p-NPPC, at the conditions shown in the figure. FIG. 34 illustrates data from DSC analysis showing the thermostability of SEQ ID NO:2, with the enzyme at a concentration of 15 mg/mL and the Tm at 86° C.

What is claimed is:

1. An isolated, synthetic or recombinant nucleic acid comprising (i) a nucleic acid having at least 95%, 96%, 97%, 98%, 99%, or more or complete sequence identity to (a) a nucleic acid that encodes a polypeptide having the sequence as set forth in SEQ ID NO:2; or (b) SEQ ID NO:1, wherein the nucleic acid encodes at least one polypeptide having a phospholipase C activity;

(ii) the nucleic acid of (i), wherein the nucleic acid encodes: SEQ ID NO:2, minus amino acids 1-37, and having at least one amino acid modification selected from the group consisting of N63D, N131S and N134D, or having at least two of the amino acid modifications selected from the group consisting of N63D, N131S and N134D;

(iii) a fragment of the nucleic acid of (i) or (ii), wherein the fragment encodes a polypeptide having a phospholipase C activity;

(iv) the nucleic acid of any of (i) to (iii), wherein the phospholipase C activity comprises catalyzing hydrolysis of a glycerolphosphate ester linkage in phosphatidylcholine (PC), phosphatidylethanolamine (PE), phosphatidylserine (PS), phosphatidylinositol (PI), and/or phosphatidic acid or a combination thereof;

(v) the nucleic acid of any of (i) to (iv), wherein the nucleic acid further comprises a heterologous nucleic acid sequence;

(vi) the nucleic acid of (v), wherein the heterologous nucleic acid sequence encodes a heterologous polypeptide;

(vii) the nucleic acid of (vi), wherein the heterologous polypeptide comprises or consists of a signal sequence (a signal peptide), a catalytic domain, a linker sequence, a protease cleavage recognition site, a non-phospholipase enzyme sequence, a phospholipase enzyme sequence; or (viii) a nucleic acid comprising a sequence completely (fully) complementary to the nucleic acid sequence of any of (i) to (vii).

2. An expression cassette comprising a nucleic acid comprising the sequence of claim 1.

3. A vector or a cloning vehicle comprising (a) a nucleic acid comprising the sequence of claim 1, or (b) the vector or cloning vehicle of (a), wherein the cloning vehicle comprises a viral vector, a plasmid, a phage, a phagemid, a cosmid, a fosmid, a bacteriophage or an artificial chromosome, or the viral vector comprises an adenovirus vector, a retroviral vector or an adeno-associated viral vector, or the vector or a cloning vehicle comprises or is contained within a bacterial artificial chromosome (BAC), a plasmid, a bacteriophage P1-derived vector (PAC), a yeast artificial chromosome (YAC), or a mammalian artificial chromosome (MAC).

4. A transformed cell comprising (a) a nucleic acid comprising the sequence of claim 1, or the expression cassette of claim 2, or the vector or cloning vehicle of claim 3, or (b) the transformed cell of (a), wherein the cell is a bacterial cell, a mammalian cell, a fungal cell, a yeast cell, an insect cell or a plant cell.

5. A transgenic plant or seed comprising (a) the sequence of claim 1, or (b) the transgenic plant or seed of (a), wherein the plant is a corn plant, a sorghum plant, a potato plant, a tomato plant, a wheat plant, an oilseed plant, a rapeseed plant, a soybean plant, a rice plant, a barley plant, a grass, a cottonseed, a palm, a sesame plant, a peanut plant, a sunflower plant or a tobacco plant, or (c) the transgenic plant or seed of (a), wherein the seed is a corn seed, a wheat kernel, an oilseed, a rapeseed, a soybean seed, a palm kernel, a sunflower seed, a sesame seed, a rice, a barley, a peanut, a cottonseed, a palm, a peanut, a sesame seed, a sunflower seed or a tobacco plant seed.

6. An isolated, synthetic or recombinant polypeptide having a phospholipase C activity, wherein the polypeptide comprises:

(i) an amino acid sequence having at least 95%, 96%, 97%, 98%, 99%, or more or complete sequence identity to the amino acid sequence of SEQ ID NO:2;

(ii) the amino acid sequence of SEQ ID NO:2, minus amino acids 1-37, and having at least one amino acid modification selected from the group consisting of N63D, N131S and N134D, or having at least two of the amino acid modifications selected from the group consisting of N63D, N131S and N134D;

(iii) a fragment of the amino acid sequence of (i) or (ii), wherein the fragment has a phospholipase C activity;

(iv) the amino acid sequence of (i), (ii) or (iii) and further comprising a heterologous amino acid sequence;

(v) the sequence of (iv), wherein the heterologous amino acid sequence comprises or consists of a signal sequence (a signal peptide), a catalytic domain, a linker sequence, a protease cleavage recognition site, a non-phospholipase enzyme sequence, a phospholipase enzyme sequence;

(vi) comprising the amino acid sequence of (v), wherein the heterologous amino acid sequence comprises an N-terminal identification peptide or a peptide or protein that increases stability or simplifies purification of the polypeptide;

(vii) the amino acid sequence of any of (i) to (vi), wherein the phospholipase C activity comprises catalyzing hydrolysis of a glycerolphosphate ester linkage in phosphatidylcholine (PC), phosphatidylethanolamine (PE), phosphatidylserine (PS), phosphatidylinositol (PI), and/or phosphatidic acid or a combination thereof; or (viii) the amino acid sequence of any of (i) to (vii), wherein the polypeptide comprises at least one glycosylation site or is glycosylated, and optionally the glycosylation is an N-linked glycosylation, or the polypeptide is glycosylated after being expressed in a *P. pastoris* or a *S. pombe*.

7. A protein preparation comprising the polypeptide of claim 6, wherein the protein preparation comprises a buffer, a liquid, a solid or a gel.

8. A heterodimer comprising (a) the polypeptide of claim 6 and a second domain, or (b) the heterodimer of (a), wherein the second domain is a polypeptide and the heterodimer is a fusion protein, or the second domain comprises an epitope or a tag.

9. A homodimer comprising the polypeptide of claim 6.

10. An immobilized polypeptide, wherein the polypeptide comprises (a) the polypeptide of claim 6; or, (b) the immobilized polypeptide of (a), wherein the polypeptide is immobilized on a cell, a metal, a resin, a polymer, a ceramic, a glass, a microelectrode, a graphitic particle, a bead, a gel, a plate, an array or a capillary tube.

11. A method of producing a recombinant polypeptide comprising:

(A) (a) providing the nucleic acid of claim 1; and (b) expressing the nucleic acid of (a) under conditions that allow expression of the polypeptide, thereby producing a recombinant polypeptide, or (B) (a) transforming a host cell with the nucleic acid of claim 1, and (b) expressing the nucleic acid of (a), thereby producing a recombinant polypeptide in a transformed cell.

12. A method for identifying a polypeptide having a phospholipase activity comprising:

(a) providing the polypeptide of claim 6;

(b) providing a phospholipase substrate; and (c) contacting the polypeptide with the substrate of step (b) and detecting a decrease in the amount of substrate or an increase in the amount of a reaction product, wherein a decrease in the amount of the substrate or an increase in the amount of the reaction product detects a polypeptide having a phospholipase activity.

13. A method for identifying a phospholipase substrate comprising:

(a) providing the polypeptide of claim 6;

(b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a phospholipase substrate.

14. A method of determining whether a test compound specifically binds to a polypeptide comprising:

(i) (a) expressing a nucleic acid or a vector comprising the nucleic acid under conditions permissive for translation of the nucleic acid to a polypeptide, wherein the nucleic acid has the sequence of claim 1;

(b) providing a test compound;

(c) contacting the polypeptide with the test compound; and (d) determining whether the test compound of step (b) specifically binds to the polypeptide; or, (ii) (a) providing the polypeptide of claim 6;

(b) providing a test compound;

(c) contacting the polypeptide with the test compound; and (d) determining whether the test compound of step (b) specifically binds to the polypeptide.

15. A method for identifying a modulator of a phospholipase activity comprising:

(A) (a) providing the polypeptide of claim 6;

(b) providing a test compound;

(c) contacting the polypeptide of step (a) with the test compound of step (b) and measuring an activity of the phospholipase, wherein a change in the phospholipase activity measured in the presence of the test compound compared to the activity in the absence of the test compound provides a determination that the test compound modulates the phospholipase activity, or (B) the method of (A), wherein the phospholipase activity is measured by providing a phospholipase substrate and detecting a decrease in the amount of the substrate or an increase in the amount of a reaction product, or, an increase in the amount of the substrate or a decrease in the amount of a reaction product, or (C) the method of (B), wherein a decrease in the amount of the substrate or an increase in the amount of the reaction product with the test compound as compared to the amount of substrate or reaction product without the test compound identifies the test compound as an activator of phospholipase activity, or (D) the method of (B), wherein an increase in the amount of the substrate or a decrease in the amount of the reaction product with the test compound as compared to the amount of substrate or reaction product without the test compound identifies the test compound as an inhibitor of phospholipase activity.

16. A chimeric polypeptide comprising at least a first domain comprising a polypeptide of claim 6, and at least a second domain comprising a heterologous polypeptide or peptide.

17. An isolated, synthetic or recombinant nucleic acid encoding a chimeric polypeptide, wherein the chimeric polypeptide comprises at least a first domain comprising a polypeptide encoded by the nucleic acid of claim 1 and at least a second domain comprising a heterologous polypeptide or peptide, wherein the heterologous polypeptide or peptide is not naturally associated with the signal peptide (SP).

18. A method for overexpressing a recombinant phospholipase in a cell comprising expressing a vector comprising the nucleic acid of claim 1, wherein overexpression is effected by use of a high activity promoter, a dicistronic vector or by gene amplification of the vector.

19. A method for hydrolyzing, breaking up or disrupting a phospholipid-comprising composition comprising:

(A) (a) providing the polypeptide having a phospholipase activity of claim 6, or a polypeptide encoded by the nucleic acid of claim 1;

(b) providing a composition comprising a phospholipid; and (c) contacting the polypeptide of step (a) with the composition of step (b) under conditions wherein the phospholipase hydrolyzes, breaks up or disrupts the phospholipid-comprising composition, or (B) the method of (A), wherein the composition comprises a phospholipid-comprising lipid bilayer or membrane, and optionally the composition comprises a plant cell, a bacterial cell, a yeast cell, an insect cell, or an animal cell, or (C) the method of (A), wherein the method comprises use of high shear mixing of the composition, followed by no or low shear mixing with the at least one polypeptide of the invention having a phospholipase activity to allow adequate contacting of the phospholipid substrate with the phospholipase.

20. A method for liquefying or removing a phospholipid-comprising composition comprising:

(a) providing the polypeptide having a phospholipase activity of claim 6, or a polypeptide encoded by the nucleic acid of claim 1;

(b) providing a composition comprising a phospholipid; and (c) contacting the polypeptide of step (a) with the composition of step (b) under conditions wherein the phospholipase removes or liquefies the phospholipid-comprising composition.

21. A method for washing an object comprising:

(a) providing a composition comprising the polypeptide having a phospholipase activity of claim 6, or a polypeptide encoded by the nucleic acid of claim 1;

(b) providing an object; and (c) contacting the polypeptide of step (a) and the object of step (b) under conditions wherein the composition can wash the object.

22. A method for degumming an oil or a fat comprising:

(A) (a) providing a composition comprising the polypeptide having a phospholipase activity of claim 6, or a polypeptide encoded by the nucleic acid of claim 1;

(b) providing a composition comprising an phospholipid-containing fat or oil; and (c) contacting the polypeptide of step (a) and the composition of step (b) under conditions wherein the polypeptide can catalyze the hydrolysis of a phospholipid in the composition, or (B) the method of (A), wherein the oil-comprising composition comprises a plant, an animal, an algae or a fish oil or fat, and optionally the plant oil comprises a rice bran oil, a soybean oil, a rapeseed oil, a corn oil, an oil from a palm kernel, a canola oil, a sunflower oil, a sesame oil or a peanut oil, or (C) the method of (A) or (B), wherein the polypeptide hydrolyzes a phosphatide from a hydratable and/or a non-hydratable phospholipid in the oil-comprising composition, or optionally the polypeptide hydrolyzes a phosphatide at a glyceryl phosphoester bond to generate a diglyceride and water-soluble phosphate compound, or (D) the method of any of (A) to (C), wherein optionally the polypeptide has a phospholipase D activity and a phosphatase enzyme is also added or optionally the method increases neutral oils or increases diacylglycerol (DAG) production to contribute to an oil phase, or (E) the method of any of (A) to (D), wherein the contacting comprises hydrolysis of a hydrated phospholipid in an oil, or (F) the method of any of (A) to (E), wherein the hydrolysis conditions of step (c) comprise a temperature of about 20° C. to 40° C. at an alkaline pH, or optionally the alkaline conditions comprise a pH of about pH 8 to pH 10, or (G) the method of any of (A) to (F), wherein the hydrolysis conditions comprise an alkaline pH, or the hydrolysis conditions of step (c) comprise a reaction time of about 3 to 10 minutes, or the hydrolysis conditions of step (c) comprise hydrolysis of hydratable and non-hydratable phospholipids in oil at a temperature of about 50° C. to 60° C., at a pH of about pH 5 to pH 6.5, at a pH of about pH 6.0 to pH 7.5, or at a pH of about pH 5 to pH 8.0, using a reaction time of about 30 to 60 minutes, or the alkaline conditions are sufficient to cause isomerization of a 1,2-DAG produced by a PLC into a 1,3-DAG, or (H) the method of any of (A) to (G), wherein the polypeptide is bound to a filter and the phospholipid-containing fat or oil is passed through the filter, or optionally the polypeptide is added to a solution comprising the phospholipid-containing fat or oil and then the solution is passed through a filter, or (I) the method of (A) or (H), wherein the method further comprises addition of one or more polypeptides having a protease, an amylase, a lipase, a cutinase, another phospholipase, a carbohydrase, a cellulase, a pectinase, a mannanase, an arabinase, a galactanase, a xylanase, an oxidase, e.g., a lactase, and/or a peroxidase, or polypeptides with equivalent activity, or a combination thereof, to further break down gum mass and enhance oil yields, or (J) the method of any of (A) to (I), wherein the method further comprises physical removal of gum produced by the degumming method by addition of a hardening substance, or (K) the method of (J), wherein the final degummed oil or fat product is enriched in 1,3-DAG, or (L) the method of any of (K), wherein the final degummed oil or fat product comprises not less than 1.0% 1,3-DAG.

23. A method for converting a non-hydratable phospholipid to a hydratable form comprising:

(A) (a) providing a composition comprising the polypeptide having a phospholipase activity of claim 6, or a polypeptide encoded by the nucleic acid of claim 1;

(b) providing a composition comprising a non-hydratable phospholipid; and (c) contacting the polypeptide of step (a) and the composition of step (b) under conditions wherein the polypeptide converts the non-hydratable phospholipid to a hydratable form, or (B) the method of (A), wherein the polypeptide has a phospholipase D activity and a phosphatase enzyme is also added.

24. A method for caustic refining of a phospholipid-containing composition comprising:

(A) (a) providing a composition comprising a polypeptide having a phospholipase activity, wherein the polypeptide has the sequence of claim 6, or comprises a polypeptide encoded by the nucleic acid of claim 1;

(b) providing a composition comprising a phospholipid; and (c) contacting the polypeptide of step (a) with the composition of step (b) before, during or after the caustic refining, or (B) the method of (A), wherein the polypeptide having a phospholipase activity is added before addition of acid or caustic, or the polypeptide having a phospholipase activity is added during caustic refining and varying levels of acid and caustic are added depending on levels of phosphorus and levels of free fatty acids, or the polypeptide having a phospholipase activity is added after caustic refining: in an intense mixer or retention mixer prior to separation; following a heating step; in a centrifuge; in a soapstock; in a washwater; or, during bleaching or deodorizing steps, or (C) the method of (B), wherein the caustic refining conditions are generated by addition of a concentrated solution of caustic, and optionally the concentrated solution of caustic is more concentrated than the industrial standard of 11%, and optionally the concentrated solution of caustic is between about 12% and 50% concentrated, or (D) the method of any of (A) to (C), wherein the composition comprising the phospholipid comprises a plant, and optionally the polypeptide is expressed transgenically in the plant, and optionally the polypeptide having a phospholipase activity added during crushing of a seed or other plant part, or, the polypeptide having a phospholipase activity added following crushing or prior to refining, or (E) the method of any of (A) to (D), wherein the method comprises a process as set forth in FIG. 13.

25. A method for purification of a phytosterol or a triterpene comprising:

(A) (a) providing a composition comprising the polypeptide having a phospholipase activity of claim 6, or a polypeptide encoded by the nucleic acid of claim 1;

(b) providing a composition comprising a phytosterol or a triterpene; and (c) contacting the polypeptide of step (a) with the composition of step (b) under conditions wherein the polypeptide can catalyze the hydrolysis of a phospholipid in the composition, or (B) the method of (A), wherein the phytosterol or a triterpene comprises a plant sterol, or (C) the method of any of (A) to (B), wherein the plant sterol is derived from a vegetable oil, or (D) the method of (C), wherein the vegetable oil comprises a coconut oil, canola oil, cocoa butter oil, corn oil, cottonseed oil, linseed oil, olive oil, palm oil, peanut oil, oil derived from a rice bran, safflower oil, sesame oil, soybean oil or a sunflower oil, or (E) the method of any of (A) to (D), wherein the method further comprises use of nonpolar solvents to quantitatively extract free phytosterols and phytosteryl fatty-acid esters, or (F) the method of any of (A) to (E), wherein the phytosterol or a triterpene comprises a β-sitosterol, a campesterol, a stigmasterol, a stigmastanol, a β-sitostanol, a sitostanol, a desmosterol, a chalinasterol, a poriferasterol, a clionasterol or a brassicasterol.

26. A method for refining a crude oil comprising:

(A) (a) providing a composition comprising the polypeptide having a phospholipase activity of claim 6, or a polypeptide encoded by the nucleic acid of claim 1;

(b) providing a composition comprising an oil comprising a phospholipid; and (c) contacting the polypeptide of step (a) with the composition of step (b) under conditions wherein the polypeptide can catalyze the hydrolysis of a phospholipid in the composition, or (B) the method of (A), wherein the polypeptide having a phospholipase activity is in a water solution that is added to the composition, or the water level is between about 0.5 to 5%, or the process time is less than about 2 hours, or the process time is less than about 60 minutes, or the process time is less than about 30 minutes, less than about 15 minutes, or less than about 5 minutes, or (C) the method of any of (A) to (B), wherein the hydrolysis conditions comprise a temperature of between about 25° C.-70° C., or the hydrolysis conditions comprise use of caustics, or the hydrolysis conditions comprise a pH of between about pH 3 and pH 10, or the hydrolysis conditions comprise addition of emulsifiers and/or mixing after the contacting of step (c), or (D) the method of any of (A) to (C), wherein the method further comprises addition of an emulsion-breaker and/or heat or cooling to promote separation of an aqueous phase, or (E) the method of any of (A) to (D), wherein the method further comprises degumming before the contacting step to collect lecithin by centrifugation and then adding a PLC, a PLC and/or a PLA to remove non-hydratable phospholipids, or (F) the method of any of (A) to (E), wherein the method further comprises water degumming of crude oil to less than 10 ppm phosphorus for edible oils and subsequent physical refining to less than about 50 ppm phosphorus for biodiesel oils, or (G) the method of any of (A) to (F), wherein the method further comprises addition of acid to promote hydration of non-hydratable phospholipids, or (H) the method of any of (A) to (G), wherein sufficient acid is added to promote lowering of the calcium and magnesium metal content.

27. A method for degumming an oil or a fat comprising:

(a) providing a composition comprising the polypeptide having a phospholipase activity of claim 6, or a polypeptide encoded by the nucleic acid of claim 1, wherein the phospholipase activity comprises a phospholipase D activity, and a phosphatase enzyme;

(b) providing a composition comprising an phospholipid-containing fat or oil; and (c) contacting the polypeptide of step (a) and the composition of step (b) under conditions wherein the polypeptide can catalyze the hydrolysis of a phospholipid in the composition.

28. A composition comprising the polypeptide of claim 6.

29. The composition of claim 28, wherein the composition is a detergent composition, wherein optionally the polypeptide is formulated in a non-aqueous liquid composition, a cast solid, a lyophilized powder, a granular form, a particulate form, a compressed tablet, a pellet, a gel form, a paste, an aerosol, or a slurry form.

30. A method for detoxifying an endotoxin comprising contacting the endotoxin with the polypeptide of claim 6, or a polypeptide encoded by the nucleic acid of claim 1.

31. A method for deacylating a 2' or a 3' fatty acid chain from a lipid A comprising contacting the lipid A with the polypeptide of claim 6, or a polypeptide encoded by the nucleic acid of claim 1.

32. A process for reducing gum mass and increasing neutral oil (triglyceride) gain through reduced oil entrapment comprising:

(A) (a) providing a composition comprising the polypeptide having a phospholipase activity of claim 6, or a polypeptide encoded by the nucleic acid of claim 1;

(b) providing a composition comprising an phospholipid-containing fat or oil; and (c) contacting the polypeptide of step (a) and the composition of step (b) under conditions wherein the polypeptide can catalyze the hydrolysis of a phospholipid in the composition for a time sufficient to reduce gum mass and increase neutral oils, or (B) the method of (A), wherein the protein preparation comprises a formulation comprising a non-aqueous liquid composition, a cast solid, a powder, a lyophilized powder, a granular form, a particulate form, a compressed tablet, a pellet, a pill, a gel form, a hydrogel, a paste, an aerosol, a spray, a lotion, a slurry formulation, an aqueous/oil emulsion, a cream, a capsule, a vesicle, or a micellar suspension.

33. A method for making a variant phospholipase coding sequence having increased expression in a host cell comprising modifying the nucleic acid sequence of claim 1 such that one, several or all N-linked glycosylation site motifs in the phospholipase are modified to a non-glycosylated motif in the variant phospholipase.

34. The polypeptide of claim 6, wherein the polypeptide has increased resistance to a protease and wherein in the polypeptide comprises modification of the amino acid at position 131 of SEQ ID NO:2, or an amino acid equivalent to position 131 in the amino acid sequence of claim 6, to one, several or all of the following residues: Lysine (K); Serine (S); Glycine (G); Arginine (R); Glutamine (Q); Alanine (A); Isoleucine (I); Histidine (H); Phenylalanine (F); Threonine (T); Methionine (M) Leucine (L).

35. The polypeptide of claim 6, wherein the polypeptide has decreased resistance to a protease and wherein in the polypeptide comprises modification of the amino acid at position 131 of SEQ ID NO:2, or an amino acid equivalent to position 131 in the amino acid sequence of claim 6, to one, several or all of the following residues: Tryptophan (W); Glutamate (E); Tyrosine (Y).

36. A method for making and expressing a protein having a biological activity whose activity is temporarily inactivated by glycosylation comprising:

(A) (a) providing a nucleic acid encoding a protein having a biological activity, wherein the protein is not naturally glycosylated, and the polypeptide comprises the polypeptide of claim 6, or comprises a polypeptide encoded by the nucleic acid of claim 1;

(b) inserting at least one glycosylation motif coding sequence into the protein-encoding nucleic acid, wherein the glycosylated form of the protein is inactive;

(c) inserting a targeting sequence into the protein such that it is directed to a host cell's secretory pathway, wherein the host cell is capable of recognizing the glycosylation motif and glycosylating the protein; and (d) expressing the modified nucleic acid in the host cell, or (B) the method of (A), wherein the method further comprises deglycosylating the expressed the protein, thereby re-activating the activity of the protein, or (C) the method of (A) or (B), wherein the host cell is a eukaryotic cell.

37. A method for expressing a phospholipase C comprising (A) (a) providing a *Pichia* strain with a $Mut^+$ phenotype;

(b) inserting a heterologous phospholipase C-encoding nucleic acid in the *Pichia* strain, wherein the phospholipase C-encoding nucleic acid comprises the nucleic acid of claim 1; and, (c) culturing the *Pichia* strain under conditions whereby the phospholipase C is expressed, or (B) the method of (A), wherein the method further comprises supplementing the culture conditions with zinc.

38. A cell system for expressing phospholipase C comprising a $Mut^+$ phenotype *Pichia* strain comprising a heterologous phospholipase C-encoding nucleic acid operably linked to a promoter operable in the *Pichia* strain, wherein the phospholipase C-encoding nucleic acid comprises the nucleic acid of claim 1.

39. A cell system for expressing a heterologous protein comprising a *Pichia* strain cell resistant to zeocin, wherein the heterologous protein is encoded by a nucleic acid comprising the nucleic acid of claim 1.

40. A zeocin-resistant yeast cell system for expressing a heterologous protein having phospholipase C activity made by the method comprising the steps of (a) providing a *Pichia* sp, cell comprising a heterologous nucleic acid capable of expressing a heterologous protein, wherein the heterologous protein-encoding nucleic acid comprises the nucleic acid of claim 1;

(b) culturing the cell under conditions comprising zeocin at an initial concentration;

(c) selecting cells resistant to the initial concentration of zeocin, and reculturing under conditions comprising a higher concentration of zeocin; and (d) selecting the cells cultured in step (c) resistant to the higher concentration of zeocin.

41. A treated oil made by the process of (a) providing a polypeptide of claim 6 or a polypeptide encoded by the nucleic acid of claim 1, (b) providing an oil, and (c) contacting the oil of (b) with the polypeptide of (a), thereby producing a treated oil.

42. An isolated, synthetic or recombinant polypeptide having a phospholipase C activity, wherein the polypeptide comprises an amino acid sequence encoded by (i) a nucleic acid having at least 95%, 96%, 97%, 98%, 99%, or more or complete sequence identity to SEQ ID NO:1;

(ii) a nucleic acid encoding SEQ ID NO:2, minus amino acids 1-37, and having at least one amino acid modification selected from the group consisting of N63D, N131S and N134D, or having at least two of the amino acid modifications selected from the group consisting of N63D, N131S and N134D;

(iii) a fragment of the nucleic acid of (i) or (ii), wherein the fragment encodes a polypeptide having a phospholipase C activity;

(iv) the nucleic acid of any of (i) to (iii), wherein the phospholipase C activity comprises catalyzing hydrolysis of a glycerolphosphate ester linkage in phosphatidylcholine (PC), phosphatidylethanolamine (PE), phosphatidylserine (PS), phosphatidylinositol (PI), and/or phosphatidic acid or a combination thereof;

(v) the nucleic acid of any of (i) to (iv), wherein the nucleic acid further comprises a heterologous nucleic acid sequence;

(vi) the nucleic acid of (v), wherein the heterologous nucleic acid sequence encodes a heterologous polypeptide; or (vii) the nucleic acid of (vi), wherein the heterologous polypeptide comprises or consists of a signal sequence (a signal peptide), a catalytic domain, a linker sequence, a protease cleavage recognition site, a non-phospholipase enzyme sequence, a phospholipase enzyme sequence.

43. An isolated, synthetic or recombinant nucleic acid comprising (a) a nucleic acid that encodes a polypeptide having the sequence as set forth in SEQ ID NO:2; or (b) SEQ ID NO:1, wherein the nucleic acid encodes a polypeptide having a phospholipase C activity.

44. An isolated, synthetic or recombinant nucleic acid comprising a nucleic acid that encodes a polypeptide having a phospholipase C activity, wherein the nucleic acid encodes SEQ ID NO:2, minus amino acids 1-37, and having at least one amino acid modification selected from the group consisting of N63D, N131S and N134D, or having at least two of the amino acid modifications selected from the group consisting of N63D, N131S and N134D.

45. An isolated, synthetic or recombinant nucleic acid comprising a nucleic acid that encodes a polypeptide having a phospholipase C activity, wherein the nucleic acid encodes SEQ ID NO:2, minus amino acids 1-37, and having the amino acid modifications N63D, N131S and N134D.

46. An isolated, synthetic or recombinant polypeptide having a phospholipase C activity, wherein the polypeptide comprises the amino acid sequence of SEQ ID NO:2.

47. An isolated, synthetic or recombinant polypeptide having a phospholipase C activity, wherein the polypeptide comprises the amino acid sequence of SEQ ID NO:2, minus amino acids 1-37, and having at least one amino acid modification selected from the group consisting of N63D, N131S and N134D, or having at least two of the amino acid modifications selected from the group consisting of N63D, N131S and N134D.

48. An isolated, synthetic or recombinant polypeptide having a phospholipase C activity, wherein the polypeptide comprises the amino acid sequence of SEQ ID NO:2, minus amino acids 1-37, and having the amino acid modifications N63D, N131S and N134D.

* * * * *

SEQUENCE LISTING

```
<160> NUMBER OF SEQ ID NOS: 176

<210> SEQ ID NO 1
<211> LENGTH: 849
<212> TYPE: DNA
<213> ORGANISM: Unknown
<220> FEATURE:
<223> OTHER INFORMATION: Obtained from an environmental sample.

<400> SEQUENCE: 1

atgaaaaaga aagtattagc actagcagct atggttgctt tagctgcgcc agttcaaagt      60

gtagtatttg cacaaacaaa taatagtgaa agtcctgcac cgattttaag atggtcagct     120

gaggataagc ataatgaggg gattaactct catttgtgga ttgtaaatcg tgcaattgac     180

atcatgtctc gtaatacaac gattgtgaat ccgaatgaaa ctgcattatt aaatgagtgg     240

cgtgctgatt tagaaaatgg tatttattct gctgattacg agaatcctta ttatgataat     300

agtacatatg cttctcactt ttatgatccg gatactggaa caacatatat tccttttgcg     360

aaacatgcaa aagaaacagg cgcaaaatat tttaaccttg ctggtcaagc ataccaaaat     420

caagatatgc agcaagcatt cttctactta ggattatcgc ttcattattt aggagatgtg     480

aatcagccaa tgcatgcagc aaactttacg aatctttctt atccaatggg tttccattct     540

aaatacgaaa attttgttga tacaataaaa aataactata ttgtttcaga tagcaatgga     600

tattggaatt ggaaaggagc aaacccagaa gattggattg aaggagcagc ggtagcagct     660

aaacaagatt atcctggcgt tgtgaacgat acgacaaaag attggtttgt aaaagcagcc     720

gtatctcaag aatatgcaga taaatggcgt gcggaagtaa caccggtgac aggaaagcgt     780

ttaatggaag cgcagcgcgt tacagctggt tatattcatt tgtggtttga tacgtatgta     840

aatcgctaa                                                             849

<210> SEQ ID NO 2
<211> LENGTH: 282
<212> TYPE: PRT
<213> ORGANISM: Unknown
<220> FEATURE:
<221> NAME/KEY: SIGNAL
<222> LOCATION: (1)...(24)
<223> OTHER INFORMATION: Obtained from an environmental sample.

<400> SEQUENCE: 2

Met Lys Lys Lys Val Leu Ala Leu Ala Ala Met Val Ala Leu Ala Ala
```

-continued

```
1               5                   10                  15

Pro Val Gln Ser Val Val Phe Ala Gln Thr Asn Asn Ser Glu Ser Pro
            20                  25                  30

Ala Pro Ile Leu Arg Trp Ser Ala Glu Asp Lys His Asn Glu Gly Ile
        35                  40                  45

Asn Ser His Leu Trp Ile Val Asn Arg Ala Ile Asp Ile Met Ser Arg
    50                  55                  60

Asn Thr Thr Ile Val Asn Pro Asn Glu Thr Ala Leu Leu Asn Glu Trp
65                  70                  75                  80

Arg Ala Asp Leu Glu Asn Gly Ile Tyr Ser Ala Asp Tyr Glu Asn Pro
                85                  90                  95

Tyr Tyr Asp Asn Ser Thr Tyr Ala Ser His Phe Tyr Asp Pro Asp Thr
            100                 105                 110

Gly Thr Thr Tyr Ile Pro Phe Ala Lys His Ala Lys Glu Thr Gly Ala
        115                 120                 125

Lys Tyr Phe Asn Leu Ala Gly Gln Ala Tyr Gln Asn Gln Asp Met Gln
    130                 135                 140

Gln Ala Phe Phe Tyr Leu Gly Leu Ser Leu His Tyr Leu Gly Asp Val
145                 150                 155                 160

Asn Gln Pro Met His Ala Ala Asn Phe Thr Asn Leu Ser Tyr Pro Met
                165                 170                 175

Gly Phe His Ser Lys Tyr Glu Asn Phe Val Asp Thr Ile Lys Asn Asn
            180                 185                 190

Tyr Ile Val Ser Asp Ser Asn Gly Tyr Trp Asn Trp Lys Gly Ala Asn
        195                 200                 205

Pro Glu Asp Trp Ile Glu Gly Ala Ala Val Ala Ala Lys Gln Asp Tyr
    210                 215                 220

Pro Gly Val Val Asn Asp Thr Thr Lys Asp Trp Phe Val Lys Ala Ala
225                 230                 235                 240

Val Ser Gln Glu Tyr Ala Asp Lys Trp Arg Ala Glu Val Thr Pro Val
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn Arg
        275                 280
```

<210> SEQ ID NO 3
<211> LENGTH: 852
<212> TYPE: DNA
<213> ORGANISM: Unknown
<220> FEATURE:
<223> OTHER INFORMATION: Obtained from an environmental sample.

<400> SEQUENCE: 3

```
atgaaaagaa aaattttagc tatagcttcc gtaattgctt taacagctcc tatccaaagt     60

gtggcgtttg cgcatgaaaa tggtcaccaa gatccaccaa ttgctctaaa gtggtcagca    120

gaatctatac ataatgaagg agtaagttct catttatgga ttgtaaacag agccattgat    180

attatgtccc aaaatacgac tgttgtgaag caaaatgaga cagctctatt aaatgaatgg    240

cgtacggatc tagagaaagg catttactct gcggattatg aaaacccata ctatgataat    300

tccacattcg cttcacactt ctatgatcct gattcaggaa aaacgtatat tccatttgct    360

aaacaagcaa agcaaacagg agcgaaatat tttaaattag ctggtgaagc ttatcaaaat    420

aaagatctga aaaacgcatt cttttattta ggattatcac ttcactattt aggggatgtc    480

aaccaaccaa tgcatgcagc aaactttact aatatttcgc atccatttgg cttccactca    540
```

```
aaatatgaaa atttcgttga tacagtgaaa gacaattata gagtaacgga tggaaatggc    600

tattggaatt ggcaaagtgc aaatccagaa gagtgggttc atgcatcagc atcagcagca    660

aaagctgatt ttccatcaat tgttaatgat aagacgaaaa attggttcct aaaagcagct    720

gtatcacaag actctgctga taaatggcgt gcagaagtaa caccgataac aggaaaacgt    780

ttaatggaag cgcagcgtgt tacagctgga tatatccatt tatggtttga tacgtacgtg    840

aataacaaat aa                                                        852
```

<210> SEQ ID NO 4
<211> LENGTH: 283
<212> TYPE: PRT
<213> ORGANISM: Unknown
<220> FEATURE:
<221> NAME/KEY: SIGNAL
<222> LOCATION: (1)...(24)
<223> OTHER INFORMATION: Obtained from an environmental sample.

<400> SEQUENCE: 4

```
Met Lys Arg Lys Ile Leu Ala Ile Ala Ser Val Ile Ala Leu Thr Ala
 1               5                  10                  15

Pro Ile Gln Ser Val Ala Phe Ala His Glu Asn Gly His Gln Asp Pro
            20                  25                  30

Pro Ile Ala Leu Lys Trp Ser Ala Glu Ser Ile His Asn Glu Gly Val
        35                  40                  45

Ser Ser His Leu Trp Ile Val Asn Arg Ala Ile Asp Ile Met Ser Gln
    50                  55                  60

Asn Thr Thr Val Val Lys Gln Asn Glu Thr Ala Leu Leu Asn Glu Trp
65                  70                  75                  80

Arg Thr Asp Leu Glu Lys Gly Ile Tyr Ser Ala Asp Tyr Glu Asn Pro
                85                  90                  95

Tyr Tyr Asp Asn Ser Thr Phe Ala Ser His Phe Tyr Asp Pro Asp Ser
            100                 105                 110

Gly Lys Thr Tyr Ile Pro Phe Ala Lys Gln Ala Lys Gln Thr Gly Ala
        115                 120                 125

Lys Tyr Phe Lys Leu Ala Gly Glu Ala Tyr Gln Asn Lys Asp Leu Lys
    130                 135                 140

Asn Ala Phe Phe Tyr Leu Gly Leu Ser Leu His Tyr Leu Gly Asp Val
145                 150                 155                 160

Asn Gln Pro Met His Ala Ala Asn Phe Thr Asn Ile Ser His Pro Phe
                165                 170                 175

Gly Phe His Ser Lys Tyr Glu Asn Phe Val Asp Thr Val Lys Asp Asn
            180                 185                 190

Tyr Arg Val Thr Asp Gly Asn Gly Tyr Trp Asn Trp Gln Ser Ala Asn
        195                 200                 205

Pro Glu Glu Trp Val His Ala Ser Ala Ser Ala Ala Lys Ala Asp Phe
    210                 215                 220

Pro Ser Ile Val Asn Asp Lys Thr Lys Asn Trp Phe Leu Lys Ala Ala
225                 230                 235                 240

Val Ser Gln Asp Ser Ala Asp Lys Trp Arg Ala Glu Val Thr Pro Ile
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn Asn Lys
        275                 280
```

<210> SEQ ID NO 5
<211> LENGTH: 843
<212> TYPE: DNA
<213> ORGANISM: Unknown
<220> FEATURE:
<223> OTHER INFORMATION: Obtained from an environmental sample.

<400> SEQUENCE: 5

```
atgaaaagaa aaattttagc tatagcttct gtaattgctt taacagctcc tattcaaagt      60

gtggcgtttg cgcatgaatc tgatgggcct attgctttaa gatggtcagc ggaatctgta     120

cataatgaag gagtaagttc tcatttatgg attgtaaaca gagcaattga tattatgtcc     180

caaaatacga ctgtggtgaa gcaaaatgag acagctctat taaatgaatg gcgtacgaat     240

ttggaggaag gtatttattc tgcagattat aaaaacccat actatgataa ttccacattc     300

gcttcacact tctatgatcc tgattcagaa aaaacgtata ttccatttgc taaacaagca     360

aagcaaacgg gagcaaagta ttttaaatta gctggtgaag cttatcaaaa taaagatctg     420

aaaaatgcat tcttttattt aggattatca cttcattatt taggggatgt caatcaacca     480

atgcatgcag caaactttac taacatttcg catccatttg gcttccactc aaaatatgaa     540

aacttcgttg atacagtgaa agacaattat agagtaacag atggagatgg ctattggaat     600

tggaaaagtg caaatccaga agagtgggtt catgcatcag catcagcagc aaaagctgat     660

ttcccatcaa ttgttaatga taatacgaaa agttggttcc taaaagcagc ggtatcacaa     720

gactctgctg acaaatggcg tgctgaagta acaccggtaa caggaaaacg tttaatggaa     780

gcacagcgta ttacagctgg atatattcat ttatggtttg atacgtacgt gaataacaaa     840

taa                                                                   843
```

<210> SEQ ID NO 6
<211> LENGTH: 280
<212> TYPE: PRT
<213> ORGANISM: Unknown
<220> FEATURE:
<221> NAME/KEY: SIGNAL
<222> LOCATION: (1)...(24)
<223> OTHER INFORMATION: Obtained from an environmental sample.

<400> SEQUENCE: 6

```
Met Lys Arg Lys Ile Leu Ala Ile Ala Ser Val Ile Ala Leu Thr Ala
 1               5                  10                  15

Pro Ile Gln Ser Val Ala Phe Ala His Glu Ser Asp Gly Pro Ile Ala
            20                  25                  30

Leu Arg Trp Ser Ala Glu Ser Val His Asn Glu Gly Val Ser Ser His
        35                  40                  45

Leu Trp Ile Val Asn Arg Ala Ile Asp Ile Met Ser Gln Asn Thr Thr
    50                  55                  60

Val Val Lys Gln Asn Glu Thr Ala Leu Leu Asn Glu Trp Arg Thr Asn
65                  70                  75                  80

Leu Glu Glu Gly Ile Tyr Ser Ala Asp Tyr Lys Asn Pro Tyr Tyr Asp
                85                  90                  95

Asn Ser Thr Phe Ala Ser His Phe Tyr Asp Pro Asp Ser Glu Lys Thr
            100                 105                 110

Tyr Ile Pro Phe Ala Lys Gln Ala Lys Gln Thr Gly Ala Lys Tyr Phe
        115                 120                 125

Lys Leu Ala Gly Glu Ala Tyr Gln Asn Lys Asp Leu Lys Asn Ala Phe
    130                 135                 140

Phe Tyr Leu Gly Leu Ser Leu His Tyr Leu Gly Asp Val Asn Gln Pro
145                 150                 155                 160
```

```
Met His Ala Ala Asn Phe Thr Asn Ile Ser His Pro Phe Gly Phe His
                165                 170                 175

Ser Lys Tyr Glu Asn Phe Val Asp Thr Val Lys Asp Asn Tyr Arg Val
            180                 185                 190

Thr Asp Gly Asp Gly Tyr Trp Asn Trp Lys Ser Ala Asn Pro Glu Glu
        195                 200                 205

Trp Val His Ala Ser Ala Ser Ala Ala Lys Ala Asp Phe Pro Ser Ile
    210                 215                 220

Val Asn Asp Asn Thr Lys Ser Trp Phe Leu Lys Ala Ala Val Ser Gln
225                 230                 235                 240

Asp Ser Ala Asp Lys Trp Arg Ala Glu Val Thr Pro Val Thr Gly Lys
                245                 250                 255

Arg Leu Met Glu Ala Gln Arg Ile Thr Ala Gly Tyr Ile His Leu Trp
            260                 265                 270

Phe Asp Thr Tyr Val Asn Asn Lys
        275                 280
```

<210> SEQ ID NO 7
<211> LENGTH: 963
<212> TYPE: DNA
<213> ORGANISM: Unknown
<220> FEATURE:
<223> OTHER INFORMATION: Obtained from an environmental sample.

<400> SEQUENCE: 7

```
gtgattactt tgataaaaaa atgtttatta gtattgacga tgactctatt gttaggggtt     60

ttcgtaccgc tgcagccatc acatgctact gaaaattatc caaatgattt taaactgttg    120

caacataatg tatttttatt gcctgaatca gtttcttatt ggggtcagga cgaacgtgca    180

gattatatga gtaatgcaga ttacttcaag ggacatgatg ctctgctctt aaatgagctt    240

tttgacaatg gaaattcgaa catgctgcta atgaacttat ccacggaata tccatatcaa    300

acgccagtgc ttggccgttc gatgagtgga tgggatgaaa ctagaggaag ctattctaat    360

tttgtacccg aagatggcgg tgtagcaatt atcagtaaat ggccaatcgt ggagaaaata    420

cagcatgttt acgcgaatgg ttgcggtgca gactattatg caaataaagg atttgtttat    480

gcaaaagtac aaaaagggga taaattctat catcttatca gcactcatgc tcaagccgaa    540

gatactgggt gtgatcaggg tgaaggagca gaaattcgtc attcacagtt tcaagaaatc    600

aacgacttta ttaaaaataa aaacattccg aaagatgaag tggtatttat tggtggtgac    660

tttaatgtga tgaagagtga cacaacagag tacaatagca tgttatcaac attaaatgtc    720

aatgcgccta ccgaatattt agggcatagc tctacttggg acccagaaac gaacagcatt    780

acaggttaca attaccctga ttatgcgcca cagcatttag attatatttt tgtggaaaaa    840

gatcataaac aaccaagttc atgggtaaat gaaacgatta ctccgaagtc tccaacttgg    900

aaggcaatct atgagtataa tgattattcc gatcactatc ctgttaaagc atacgtaaaa    960

taa                                                                  963
```

<210> SEQ ID NO 8
<211> LENGTH: 320
<212> TYPE: PRT
<213> ORGANISM: Unknown
<220> FEATURE:
<221> NAME/KEY: SIGNAL
<222> LOCATION: (1)...(29)
<223> OTHER INFORMATION: Obtained from an environmental sample.

<400> SEQUENCE: 8

```
Met Ile Thr Leu Ile Lys Lys Cys Leu Leu Val Leu Thr Met Thr Leu
 1               5                  10                  15

Leu Leu Gly Val Phe Val Pro Leu Gln Pro Ser His Ala Thr Glu Asn
            20                  25                  30

Tyr Pro Asn Asp Phe Lys Leu Leu Gln His Asn Val Phe Leu Leu Pro
        35                  40                  45

Glu Ser Val Ser Tyr Trp Gly Gln Asp Glu Arg Ala Asp Tyr Met Ser
    50                  55                  60

Asn Ala Asp Tyr Phe Lys Gly His Asp Ala Leu Leu Leu Asn Glu Leu
65                  70                  75                  80

Phe Asp Asn Gly Asn Ser Asn Met Leu Leu Met Asn Leu Ser Thr Glu
                85                  90                  95

Tyr Pro Tyr Gln Thr Pro Val Leu Gly Arg Ser Met Ser Gly Trp Asp
            100                 105                 110

Glu Thr Arg Gly Ser Tyr Ser Asn Phe Val Pro Glu Asp Gly Gly Val
        115                 120                 125

Ala Ile Ile Ser Lys Trp Pro Ile Val Glu Lys Ile Gln His Val Tyr
    130                 135                 140

Ala Asn Gly Cys Gly Ala Asp Tyr Tyr Ala Asn Lys Gly Phe Val Tyr
145                 150                 155                 160

Ala Lys Val Gln Lys Gly Asp Lys Phe Tyr His Leu Ile Ser Thr His
                165                 170                 175

Ala Gln Ala Glu Asp Thr Gly Cys Asp Gln Gly Glu Gly Ala Glu Ile
            180                 185                 190

Arg His Ser Gln Phe Gln Glu Ile Asn Asp Phe Ile Lys Asn Lys Asn
        195                 200                 205

Ile Pro Lys Asp Glu Val Val Phe Ile Gly Gly Asp Phe Asn Val Met
    210                 215                 220

Lys Ser Asp Thr Thr Glu Tyr Asn Ser Met Leu Ser Thr Leu Asn Val
225                 230                 235                 240

Asn Ala Pro Thr Glu Tyr Leu Gly His Ser Ser Thr Trp Asp Pro Glu
                245                 250                 255

Thr Asn Ser Ile Thr Gly Tyr Asn Tyr Pro Asp Tyr Ala Pro Gln His
            260                 265                 270

Leu Asp Tyr Ile Phe Val Glu Lys Asp His Lys Gln Pro Ser Ser Trp
        275                 280                 285

Val Asn Glu Thr Ile Thr Pro Lys Ser Pro Thr Trp Lys Ala Ile Tyr
    290                 295                 300

Glu Tyr Asn Asp Tyr Ser Asp His Tyr Pro Val Lys Ala Tyr Val Lys
305                 310                 315                 320
```

<210> SEQ ID NO 9
<211> LENGTH: 999
<212> TYPE: DNA
<213> ORGANISM: Unknown
<220> FEATURE:
<223> OTHER INFORMATION: Obtained from an environmental sample.

<400> SEQUENCE: 9

```
atgaaattac tgcgtgtctt tgtgtgcgtt tttgctttac tcagcgcaca cagcaaagcc      60

gatacactta aagtaatggc ttataatatt atgcaactaa acgtacaaga ttgggatcaa     120

gcaaatcgtg cacagcgctt gccaaacgtc atatctcaat taagtgacag tcctgatgtc     180

attcttatca gcgaagcgtt tagcagccaa tcagaatctg cgttagcgca acttgctcaa     240

ctttaccctt atcaaactcc caatgttggc gaagactgta gtggcgctgg ctggcaaagc     300
```

```
ttaacgggta actgctcgaa tagccccttt gtgatccgcg gtggagtggt gattttatct    360

aagtacccca tcattacgca aaaagcccat gtgtttaata acagcctgac tgatagttgg    420

gattatttag caaacaaagg tttcgcttat gttgaaatag aaaaacatgg caaacgttac    480

caccttattg gcacgcattt acaagcaacg catgatggcg acacagaagc tgagcatatt    540

gtgagaatgg gtcaattaca agagatacaa gatttcattc aaagcgagca aattcacact    600

tctgagccgg tcattatcgg cggtgatatg aacgtagagt ggagcaagca atctgaaatt    660

acagatatgc tcgaagtggt tcgcagccgt ctaattttca acacacctga agttggctct    720

ttctctgcaa aacacaactg gtttaccaaa gctaacgcct actatttcga ctacagctta    780

gagtataacg acacgctcga ttatgtactt tggcatgcag accataagca acccaccaat    840

accccagaaa tgttagtacg ttacccaaaa gcagagcgtg acttttactg gcgttactta    900

cgcggaaatt ggaacttacc ttctggccgt tattatcatg atggatacta taacgaactg    960

tctgatcact acccagtgca agttaacttt gaattttaa                           999
```

<210> SEQ ID NO 10
<211> LENGTH: 332
<212> TYPE: PRT
<213> ORGANISM: Unknown
<220> FEATURE:
<221> NAME/KEY: SIGNAL
<222> LOCATION: (1)...(20)
<223> OTHER INFORMATION: Obtained from an environmental sample.

<400> SEQUENCE: 10

```
Met Lys Leu Leu Arg Val Phe Val Cys Val Phe Ala Leu Leu Ser Ala
 1               5                  10                  15

His Ser Lys Ala Asp Thr Leu Lys Val Met Ala Tyr Asn Ile Met Gln
            20                  25                  30

Leu Asn Val Gln Asp Trp Asp Gln Ala Asn Arg Ala Gln Arg Leu Pro
        35                  40                  45

Asn Val Ile Ser Gln Leu Ser Asp Ser Pro Asp Val Ile Leu Ile Ser
    50                  55                  60

Glu Ala Phe Ser Ser Gln Ser Glu Ser Ala Leu Ala Gln Leu Ala Gln
65                  70                  75                  80

Leu Tyr Pro Tyr Gln Thr Pro Asn Val Gly Glu Asp Cys Ser Gly Ala
                85                  90                  95

Gly Trp Gln Ser Leu Thr Gly Asn Cys Ser Asn Ser Pro Phe Val Ile
            100                 105                 110

Arg Gly Gly Val Val Ile Leu Ser Lys Tyr Pro Ile Ile Thr Gln Lys
        115                 120                 125

Ala His Val Phe Asn Asn Ser Leu Thr Asp Ser Trp Asp Tyr Leu Ala
    130                 135                 140

Asn Lys Gly Phe Ala Tyr Val Glu Ile Glu Lys His Gly Lys Arg Tyr
145                 150                 155                 160

His Leu Ile Gly Thr His Leu Gln Ala Thr His Asp Gly Asp Thr Glu
                165                 170                 175

Ala Glu His Ile Val Arg Met Gly Gln Leu Gln Glu Ile Gln Asp Phe
            180                 185                 190

Ile Gln Ser Glu Gln Ile His Thr Ser Glu Pro Val Ile Ile Gly Gly
        195                 200                 205

Asp Met Asn Val Glu Trp Ser Lys Gln Ser Glu Ile Thr Asp Met Leu
    210                 215                 220

Glu Val Val Arg Ser Arg Leu Ile Phe Asn Thr Pro Glu Val Gly Ser
```

-continued

```
225                 230                 235                 240

Phe Ser Ala Lys His Asn Trp Phe Thr Lys Ala Asn Ala Tyr Tyr Phe
                245                 250                 255

Asp Tyr Ser Leu Glu Tyr Asn Asp Thr Leu Asp Tyr Val Leu Trp His
            260                 265                 270

Ala Asp His Lys Gln Pro Thr Asn Thr Pro Glu Met Leu Val Arg Tyr
        275                 280                 285

Pro Lys Ala Glu Arg Asp Phe Tyr Trp Arg Tyr Leu Arg Gly Asn Trp
    290                 295                 300

Asn Leu Pro Ser Gly Arg Tyr Tyr His Asp Gly Tyr Tyr Asn Glu Leu
305                 310                 315                 320

Ser Asp His Tyr Pro Val Gln Val Asn Phe Glu Phe
                325                 330
```

<210> SEQ ID NO 11
<211> LENGTH: 1041
<212> TYPE: DNA
<213> ORGANISM: Unknown
<220> FEATURE:
<223> OTHER INFORMATION: Obtained from an environmental sample.

<400> SEQUENCE: 11

```
atggcttcac aattcaggaa tctggttttt gaaggaggcg gtgtaaaggg aatcgcctat      60

atcggcgcca tgcaggtgct ggagcagcgc ggacatttgg agcacgttgt gagggtggga     120

ggaacaagtg caggggctat taacgctctc atttttcgc tgggctttac cattaaagag     180

cagcaggata ttctcaattc caccaacttc agggagttta tggacagctc tttcggattt     240

gtgcgaaact tcagaaggct ctggagtgaa ttcgggtgga accgcggtga tgtgttttcg     300

gagtgggcag gagagctggt gaaagagaaa ctcggcaaga agaacgccac cttcggcgat     360

ctgaaaaaag cgaagcgccc cgatctctac gttatcggaa ccaacctctc caccgggttt     420

tccgagactt tttcgcatga acgccacgcc aacatgccgc tggtggatgc ggtgcggatc     480

agcatgtcga tcccgctctt ttttgcggca cgcagacttg gcaaacgaag cgatgtgtat     540

gtggatggag gtgttatgct caactacccg gtaaagctgt tcgacaggga gaaatacatc     600

gatttggaga aggagaaaga ggcagcccgc tacgtggagt actacaatca agagaatgcc     660

cggtttctgc ttgagcggcc cggccgaagc ccgtacgttt acaaccggca gaccctaggc     720

ctgcggctcg actcgcagga agagatcggc ctgttccgtt acgatgagcc gctgaagggc     780

aaacagatca accgcttccc cgaatatgcc aaagccctga tcggtgcact gatgcaggtg     840

caggagaaca tccacctgaa aagcgacgac tggcagcgaa cgctctacat caacacgctg     900

gatgtgggta ccacagattt cgacattaat gacgagaaga aaaaagtgct ggtgaatgag     960

ggaatcaagg gagcggaaac ctacttccgc tggtttgagg atcccgaagc taaaccggtg    1020

aacaaggtgg atttggtctg a                                              1041
```

<210> SEQ ID NO 12
<211> LENGTH: 346
<212> TYPE: PRT
<213> ORGANISM: Unknown
<220> FEATURE:
<223> OTHER INFORMATION: Obtained from an environmental sample.

<400> SEQUENCE: 12

```
Met Ala Ser Gln Phe Arg Asn Leu Val Phe Glu Gly Gly Gly Val Lys
 1               5                  10                  15

Gly Ile Ala Tyr Ile Gly Ala Met Gln Val Leu Glu Gln Arg Gly His
```

-continued

```
            20                  25                  30

Leu Glu His Val Val Arg Val Gly Gly Thr Ser Ala Gly Ala Ile Asn
        35                  40                  45

Ala Leu Ile Phe Ser Leu Gly Phe Thr Ile Lys Glu Gln Gln Asp Ile
    50                  55                  60

Leu Asn Ser Thr Asn Phe Arg Glu Phe Met Asp Ser Ser Phe Gly Phe
65                  70                  75                  80

Val Arg Asn Phe Arg Arg Leu Trp Ser Glu Phe Gly Trp Asn Arg Gly
                85                  90                  95

Asp Val Phe Ser Glu Trp Ala Gly Glu Leu Val Lys Glu Lys Leu Gly
            100                 105                 110

Lys Lys Asn Ala Thr Phe Gly Asp Leu Lys Lys Ala Lys Arg Pro Asp
        115                 120                 125

Leu Tyr Val Ile Gly Thr Asn Leu Ser Thr Gly Phe Ser Glu Thr Phe
    130                 135                 140

Ser His Glu Arg His Ala Asn Met Pro Leu Val Asp Ala Val Arg Ile
145                 150                 155                 160

Ser Met Ser Ile Pro Leu Phe Phe Ala Ala Arg Arg Leu Gly Lys Arg
                165                 170                 175

Ser Asp Val Tyr Val Asp Gly Gly Val Met Leu Asn Tyr Pro Val Lys
            180                 185                 190

Leu Phe Asp Arg Glu Lys Tyr Ile Asp Leu Glu Lys Glu Lys Glu Ala
        195                 200                 205

Ala Arg Tyr Val Glu Tyr Tyr Asn Gln Glu Asn Ala Arg Phe Leu Leu
    210                 215                 220

Glu Arg Pro Gly Arg Ser Pro Tyr Val Tyr Asn Arg Gln Thr Leu Gly
225                 230                 235                 240

Leu Arg Leu Asp Ser Gln Glu Glu Ile Gly Leu Phe Arg Tyr Asp Glu
                245                 250                 255

Pro Leu Lys Gly Lys Gln Ile Asn Arg Phe Pro Glu Tyr Ala Lys Ala
            260                 265                 270

Leu Ile Gly Ala Leu Met Gln Val Gln Glu Asn Ile His Leu Lys Ser
        275                 280                 285

Asp Asp Trp Gln Arg Thr Leu Tyr Ile Asn Thr Leu Asp Val Gly Thr
    290                 295                 300

Thr Asp Phe Asp Ile Asn Asp Glu Lys Lys Lys Val Leu Val Asn Glu
305                 310                 315                 320

Gly Ile Lys Gly Ala Glu Thr Tyr Phe Arg Trp Phe Glu Asp Pro Glu
                325                 330                 335

Ala Lys Pro Val Asn Lys Val Asp Leu Val
            340                 345
```

<210> SEQ ID NO 13
<211> LENGTH: 1038
<212> TYPE: DNA
<213> ORGANISM: Unknown
<220> FEATURE:
<223> OTHER INFORMATION: Obtained from an environmental sample.

<400> SEQUENCE: 13

```
atgacaacac aatttagaaa cttgatattt gaaggcggcg gtgtaaaagg tgttgcttac      60

attggcgcca tgcagattct cgaaaatcgt ggcgtgttgc aagatattca cagagtcgga     120

gggtgcagtg cgggtgcgat caacgcgctg atttttgcgc tgggttacac ggtccgtgag     180

caaaaagaga tcttacaagc cacggatttt aaccagttta tggataactc ttggggtgtt     240
```

-continued

```
attcgtgata ttcgcaggct tgctcgagac tttggctggc acaagggtga cttctttaat    300

agctggatag gtgatttgat tcatcgtcgt ttggggaatc gccgagcgac gttcaaagat    360

ctgcaaaagg ccaagcttcc tgatctttat gtcatcggta ctaatctgtc tacagggtat    420

gcagaggttt tttcagccga aagacacccc gatatggagc tagcgacagc ggtgcgtatc    480

tccatgtcga taccgctgtt ctttgcggcc gtgcgtcacg gtgaacgaca agatgtgtat    540

gtcgatgggg gtgttcaact taactatccg attaaactgt ttgatcggga gcgttacatt    600

gatctggtca aagatcccgg tgccgttcgg cgaacgggtt attacaacaa agaaaacgct    660

cgctttcagc ttgagcggcc gggccatagc ccctatgttt acaatcgcca gaccttgggt    720

ttgcgactgg atagtcgaga ggagataggg ctctttcgtt atgacgaacc cctcaagggc    780

aaacccatta agtccttcac tgactacgct cgacaacttt tcggtgcgtt gatgaatgca    840

caggaaaaca ttcatctaca tggcgatgat tgggcgcgca cggtctatat cgatacattg    900

gatgtgggta cgacggattt caatctttct gatgcaacca agcaagcact gattgagcaa    960

ggaattaacg gcaccgaaaa ttatttcgac tggtttgata atccgttaga gaagcctgtg   1020

aatagagtgg agtcatag                                                 1038


<210> SEQ ID NO 14
<211> LENGTH: 345
<212> TYPE: PRT
<213> ORGANISM: Unknown
<220> FEATURE:
<223> OTHER INFORMATION: Obtained from an environmental sample.

<400> SEQUENCE: 14

Met Thr Thr Gln Phe Arg Asn Leu Ile Phe Glu Gly Gly Gly Val Lys
 1               5                  10                  15

Gly Val Ala Tyr Ile Gly Ala Met Gln Ile Leu Glu Asn Arg Gly Val
            20                  25                  30

Leu Gln Asp Ile His Arg Val Gly Gly Cys Ser Ala Gly Ala Ile Asn
        35                  40                  45

Ala Leu Ile Phe Ala Leu Gly Tyr Thr Val Arg Glu Gln Lys Glu Ile
    50                  55                  60

Leu Gln Ala Thr Asp Phe Asn Gln Phe Met Asp Asn Ser Trp Gly Val
65                  70                  75                  80

Ile Arg Asp Ile Arg Arg Leu Ala Arg Asp Phe Gly Trp His Lys Gly
                85                  90                  95

Asp Phe Phe Asn Ser Trp Ile Gly Asp Leu Ile His Arg Arg Leu Gly
            100                 105                 110

Asn Arg Arg Ala Thr Phe Lys Asp Leu Gln Lys Ala Lys Leu Pro Asp
        115                 120                 125

Leu Tyr Val Ile Gly Thr Asn Leu Ser Thr Gly Tyr Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Glu Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Val Lys Asp Pro Gly Ala
        195                 200                 205

Val Arg Arg Thr Gly Tyr Tyr Asn Lys Glu Asn Ala Arg Phe Gln Leu
    210                 215                 220
```

-continued

```
Glu Arg Pro Gly His Ser Pro Tyr Val Tyr Asn Arg Gln Thr Leu Gly
225                 230                 235                 240

Leu Arg Leu Asp Ser Arg Glu Glu Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Asn Ile His Leu His Gly
        275                 280                 285

Asp Asp Trp Ala Arg Thr Val Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Asp Trp Phe Asp Asn Pro Leu
                325                 330                 335

Glu Lys Pro Val Asn Arg Val Glu Ser
            340                 345
```

<210> SEQ ID NO 15
<211> LENGTH: 1344
<212> TYPE: DNA
<213> ORGANISM: Unknown
<220> FEATURE:
<223> OTHER INFORMATION: Obtained from an environmental sample.

<400> SEQUENCE: 15

```
atgctggtca tcattcatgg ctggagcgat gaggcgggct cgttcaagac cctggccaga     60

cgtttggcca aggcgccacc cgagggcctc gggacgcagg tcacggaaat ccatctgggt    120

gattatgtgt ccctggatga ccaggtgacg ttcaatgatc tggtcgatgc catggccaga    180

gcctggagcg atcgtggtct gcccacggcc ccgcgcagcg tcgatgccgt cgtgcacagc    240

accggcggcc tggtgatccg cgactggctc acgcagctgt acacgccgga aacagccccc    300

attcgtcgcc tgctgatgct cgctccggcc aatttcggct cgccgctggc acacaccgga    360

cgcagcatga tcggccgggt caccaagggc tggaagggca cgcggctctt tgaaacgggc    420

aagcacattc tcaaagggct cgaactggcc agcccctacg cctgggcgct ggccgaacgc    480

gatctgttca gcgatcagaa ctattatggc gccgggcgca tcctgtgcac tgtcctggtg    540

ggcaacgccg gttatcgcgg catcagcgcc gtcgccaacc ggcccggcac ggacggcacc    600

gtgcgcgtca gcagcgccaa tctccaagcg gccaggatgc tgctcgattt cagcgccagt    660

ccacaggctg agccggaatt caccctgcac gacagcaccg cggaaattgc cttcggcatc    720

gccgacgagg aagaccacag caccatcgcc gccaaggatc gcggcccgcg caaggcagtc    780

acctgggaac tgattctcaa agccctgcag atcgaggatg caagctttgc tcaatggtgc    840

cggcagatgc aggagcattc cgcggccgtg acggaaacgg cggaaaagcg ccgcaatgtt    900

cactacaaca gcttccagaa taccgtcgtg cgcgtggtgg acaaccacgg tgccgccgtg    960

caggattatc tcatcgagtt ttacatgaat gatgatcgca aactccgcga tcagcgcctc   1020

acccagcgcc tgcaggagca ggtgattacc aacgtgcacg gctacggtga cgacaagtcc   1080

tatcgcagca tgctgatcaa ctgcacggag ctctatgcgc tgatgtccag accgcaggat   1140

cgcctgaaca tcagcatcac cgcctatccg gatctctcca agggactggt ggggtatcgc   1200

acctacacgg acgaggatat cggttccctc tctctggatg cagcgcagat ccgaaagctc   1260

tttaagccgc accgtaccct gttgatgaca ctgtgcctgc aacgctatca gaaagatgat   1320

gtgttccgat tcagggatgt ttga                                          1344
```

<210> SEQ ID NO 16
<211> LENGTH: 447
<212> TYPE: PRT
<213> ORGANISM: Unknown
<220> FEATURE:
<223> OTHER INFORMATION: Obtained from an environmental sample.

<400> SEQUENCE: 16

```
Met Leu Val Ile Ile His Gly Trp Ser Asp Glu Ala Gly Ser Phe Lys
1               5                   10                  15

Thr Leu Ala Arg Arg Leu Ala Lys Ala Pro Pro Glu Gly Leu Gly Thr
            20                  25                  30

Gln Val Thr Glu Ile His Leu Gly Asp Tyr Val Ser Leu Asp Asp Gln
        35                  40                  45

Val Thr Phe Asn Asp Leu Val Asp Ala Met Ala Arg Ala Trp Ser Asp
    50                  55                  60

Arg Gly Leu Pro Thr Ala Pro Arg Ser Val Asp Ala Val Val His Ser
65                  70                  75                  80

Thr Gly Gly Leu Val Ile Arg Asp Trp Leu Thr Gln Leu Tyr Thr Pro
                85                  90                  95

Glu Thr Ala Pro Ile Arg Arg Leu Leu Met Leu Ala Pro Ala Asn Phe
            100                 105                 110

Gly Ser Pro Leu Ala His Thr Gly Arg Ser Met Ile Gly Arg Val Thr
        115                 120                 125

Lys Gly Trp Lys Gly Thr Arg Leu Phe Glu Thr Gly Lys His Ile Leu
    130                 135                 140

Lys Gly Leu Glu Leu Ala Ser Pro Tyr Ala Trp Ala Leu Ala Glu Arg
145                 150                 155                 160

Asp Leu Phe Ser Asp Gln Asn Tyr Tyr Gly Ala Gly Arg Ile Leu Cys
                165                 170                 175

Thr Val Leu Val Gly Asn Ala Gly Tyr Arg Gly Ile Ser Ala Val Ala
            180                 185                 190

Asn Arg Pro Gly Thr Asp Gly Thr Val Arg Val Ser Ser Ala Asn Leu
        195                 200                 205

Gln Ala Ala Arg Met Leu Leu Asp Phe Ser Ala Ser Pro Gln Ala Glu
    210                 215                 220

Pro Glu Phe Thr Leu His Asp Ser Thr Ala Glu Ile Ala Phe Gly Ile
225                 230                 235                 240

Ala Asp Glu Glu Asp His Ser Thr Ile Ala Ala Lys Asp Arg Gly Pro
                245                 250                 255

Arg Lys Ala Val Thr Trp Glu Leu Ile Leu Lys Ala Leu Gln Ile Glu
            260                 265                 270

Asp Ala Ser Phe Ala Gln Trp Cys Arg Gln Met Gln Glu His Ser Ala
        275                 280                 285

Ala Val Thr Glu Thr Ala Glu Lys Arg Arg Asn Val His Tyr Asn Ser
    290                 295                 300

Phe Gln Asn Thr Val Val Arg Val Val Asp Asn His Gly Ala Ala Val
305                 310                 315                 320

Gln Asp Tyr Leu Ile Glu Phe Tyr Met Asn Asp Asp Arg Lys Leu Arg
                325                 330                 335

Asp Gln Arg Leu Thr Gln Arg Leu Gln Glu Gln Val Ile Thr Asn Val
            340                 345                 350

His Gly Tyr Gly Asp Asp Lys Ser Tyr Arg Ser Met Leu Ile Asn Cys
        355                 360                 365

Thr Glu Leu Tyr Ala Leu Met Ser Arg Pro Gln Asp Arg Leu Asn Ile
```

370 375 380

Ser Ile Thr Ala Tyr Pro Asp Leu Ser Lys Gly Leu Val Gly Tyr Arg
385 390 395 400

Thr Tyr Thr Asp Glu Asp Ile Gly Ser Leu Ser Leu Asp Ala Ala Gln
405 410 415

Ile Arg Lys Leu Phe Lys Pro His Arg Thr Leu Leu Met Thr Leu Cys
420 425 430

Leu Gln Arg Tyr Gln Lys Asp Asp Val Phe Arg Phe Arg Asp Val
435 440 445

<210> SEQ ID NO 17
<211> LENGTH: 1137
<212> TYPE: DNA
<213> ORGANISM: Unknown
<220> FEATURE:
<223> OTHER INFORMATION: Obtained from an environmental sample.

<400> SEQUENCE: 17
atgaaaaaaa gccttcaaca acatcttgcc gctgacggca gcccaaagaa tattctttct 60
ctcgacgggg gaggaatcag aggggctttg acccttggtt ttctcaaaaa aatagaaagc 120
atcctgcagg aaaaacatgg gaaggactat ctcctttgcg atcactttga tttgatcggt 180
ggaacttcca caggctccat cattgcagca gcattggcta taggcatgac agtggaggaa 240
atcactaaaa tgtatatgga tctgggcgga aaaattttcg gcaagaaaag gagtttctgg 300
agaccctggg aaactgcgaa atacttgaaa gcaggatatg accacaaagc tcttgaaaag 360
agtctgaaag atgctttcca ggatttttctt ttaggaagtg accaaattag aacaggtctt 420
tgtatagtag ccaaaagagc agataccaat agtatatggc cattgattaa ccaccccaaa 480
ggaaaattct atgattcaga acaaggcaaa aacaaaaata tccccttatg gcaggcagta 540
agggcgagta ccgctgctcc aacctatttc gctccacaat taatagatgt gggtgatggt 600
caaaaggctg cttttgtgga cggaggggta agcatggcca ataaccccgc attaaccctg 660
ttaaaagtgg ctacacttaa aggttttcct tttcattggc caatgggaga agacaaactg 720
accatagttt cagtaggcac cggatatagt gttttccaaa gacaaaaggg tgaaatcacc 780
aaagcttcct tattaacttg ggccaaaaac gtcccggaaa tgttgatgca ggatgcttct 840
tggcagaatc agaccatact tcagtggatt tctaaatccc ccactgcaca ttccatagat 900
atggaaatgg aagaccttag agatgacttt ctaggcggaa gaccactcat caaatacctc 960
aggtacaact tccccttgac agtaaatgat ctcaatggat tgaagcttgg gaaaagcttt 1020
acccaaaaag aggtcgaaga tttggtggaa atgagcaatg cacataaccg agaggagttg 1080
tataggattg ggagaaggc ggctgaaggg tcggtaaaaa aagaacattt tgaataa 1137

<210> SEQ ID NO 18
<211> LENGTH: 378
<212> TYPE: PRT
<213> ORGANISM: Unknown
<220> FEATURE:
<223> OTHER INFORMATION: Obtained from an environmental sample.

<400> SEQUENCE: 18

Met Lys Lys Ser Leu Gln Gln His Leu Ala Ala Asp Gly Ser Pro Lys
1 5 10 15

Asn Ile Leu Ser Leu Asp Gly Gly Gly Ile Arg Gly Ala Leu Thr Leu
20 25 30

Gly Phe Leu Lys Lys Ile Glu Ser Ile Leu Gln Glu Lys His Gly Lys
35 40 45

```
Asp Tyr Leu Leu Cys Asp His Phe Asp Leu Ile Gly Gly Thr Ser Thr
    50                  55                  60

Gly Ser Ile Ile Ala Ala Ala Leu Ala Ile Gly Met Thr Val Glu Glu
65                  70                  75                  80

Ile Thr Lys Met Tyr Met Asp Leu Gly Gly Lys Ile Phe Gly Lys Lys
                85                  90                  95

Arg Ser Phe Trp Arg Pro Trp Glu Thr Ala Lys Tyr Leu Lys Ala Gly
            100                 105                 110

Tyr Asp His Lys Ala Leu Glu Lys Ser Leu Lys Asp Ala Phe Gln Asp
        115                 120                 125

Phe Leu Leu Gly Ser Asp Gln Ile Arg Thr Gly Leu Cys Ile Val Ala
    130                 135                 140

Lys Arg Ala Asp Thr Asn Ser Ile Trp Pro Leu Ile Asn His Pro Lys
145                 150                 155                 160

Gly Lys Phe Tyr Asp Ser Glu Gln Gly Lys Asn Lys Asn Ile Pro Leu
                165                 170                 175

Trp Gln Ala Val Arg Ala Ser Thr Ala Ala Pro Thr Tyr Phe Ala Pro
            180                 185                 190

Gln Leu Ile Asp Val Gly Asp Gly Gln Lys Ala Ala Phe Val Asp Gly
        195                 200                 205

Gly Val Ser Met Ala Asn Asn Pro Ala Leu Thr Leu Leu Lys Val Ala
    210                 215                 220

Thr Leu Lys Gly Phe Pro Phe His Trp Pro Met Gly Glu Asp Lys Leu
225                 230                 235                 240

Thr Ile Val Ser Val Gly Thr Gly Tyr Ser Val Phe Gln Arg Gln Lys
                245                 250                 255

Gly Glu Ile Thr Lys Ala Ser Leu Leu Thr Trp Ala Lys Asn Val Pro
            260                 265                 270

Glu Met Leu Met Gln Asp Ala Ser Trp Gln Asn Gln Thr Ile Leu Gln
        275                 280                 285

Trp Ile Ser Lys Ser Pro Thr Ala His Ser Ile Asp Met Glu Met Glu
    290                 295                 300

Asp Leu Arg Asp Asp Phe Leu Gly Gly Arg Pro Leu Ile Lys Tyr Leu
305                 310                 315                 320

Arg Tyr Asn Phe Pro Leu Thr Val Asn Asp Leu Asn Gly Leu Lys Leu
                325                 330                 335

Gly Lys Ser Phe Thr Gln Lys Glu Val Glu Asp Leu Val Glu Met Ser
            340                 345                 350

Asn Ala His Asn Arg Glu Glu Leu Tyr Arg Ile Gly Glu Lys Ala Ala
        355                 360                 365

Glu Gly Ser Val Lys Lys Glu His Phe Glu
    370                 375
```

<210> SEQ ID NO 19
<211> LENGTH: 1248
<212> TYPE: DNA
<213> ORGANISM: Unknown
<220> FEATURE:
<223> OTHER INFORMATION: Obtained from an environmental sample.

<400> SEQUENCE: 19

```
atgaaaaaga caacgttagt tttggctcta ttgatgccat ttggtgccgc ctccgcacaa      60

gacaatagta tgactccaga agcaatcaca tcagctcaag tcgcacaaac acaatcagcc     120

tccacctata cctacgttag gtgttggtat cgaacagacg caagccatga ttcaccagca     180
```

-continued

```
accgactggg agtgggctag aaaggaaaac ggagactatt acaccattga cggttactgg    240

tggtcatcga tctcctttaa aaatatgttc tatagcgaga ctcctcaaca agagatcaag    300

cagcgttgtg tagacacctt ggatgttcag cacgacaaag ccgacatcac ctactttgcc    360

gctgacaacc gcttctctta caaccattct atctggacta acgatcacgg ctttcaagcg    420

aaccaaatca accgaatagt cgcttttggc gatagtcttt cagacacggg caacctattt    480

aatgggtcac aatggatttt ccctaaccct aattcttggt tcttgggtca cttctctaac    540

ggcttcgttt ggactgaata cttggctaac gctaagggcg ttccactcta taactgggct    600

gtgggtggcg cagcaggaac caaccaatat gtcgctctaa ctggtgtcta tgatcaggtc    660

acttcgtacc tgacttacat gaagatggcg aaaaattatc gcccagagaa cacactattc    720

acattagagt ttggattgaa tgactttatg aattacggac gtgaagtagc tgatgtaaaa    780

gctgacttta gtagcgcact gattcgcctc accgacgctg gcgcaaaaaa cattctgttg    840

ttcaccctac cagatgcgac caaagcccct cagtttaagt actcaacggc ccaagaaatc    900

gagacagttc gtggcaagat tctggcgttc aaccagttca tcaaagaaca agcagagtac    960

tatcaaagca aaggtgacaa cgtgatccta tttgatgcgc acgctctatt ctctagcatc   1020

accagcgacc cacaaaaaca cgggttcaga aacgcaaaag atgcctgcct agatattaat   1080

cgtagtgcat ctcaagacta cctatacagc catagtctga ccaacgactg tgcaacctat   1140

ggttctgata gctatgtatt ttggggcgta acacacccaa ccacagcaac tcataaatac   1200

atcgcaacgc atatactgat gaattcaatg tcgaccttcg acttttaa                1248


<210> SEQ ID NO 20
<211> LENGTH: 415
<212> TYPE: PRT
<213> ORGANISM: Unknown
<220> FEATURE:
<221> NAME/KEY: SIGNAL
<222> LOCATION: (1)...(19)
<223> OTHER INFORMATION: Obtained from an environmental sample.

<400> SEQUENCE: 20

Met Lys Lys Thr Thr Leu Val Leu Ala Leu Leu Met Pro Phe Gly Ala
 1               5                  10                  15

Ala Ser Ala Gln Asp Asn Ser Met Thr Pro Glu Ala Ile Thr Ser Ala
            20                  25                  30

Gln Val Ala Gln Thr Gln Ser Ala Ser Thr Tyr Thr Tyr Val Arg Cys
        35                  40                  45

Trp Tyr Arg Thr Asp Ala Ser His Asp Ser Pro Ala Thr Asp Trp Glu
    50                  55                  60

Trp Ala Arg Lys Glu Asn Gly Asp Tyr Tyr Thr Ile Asp Gly Tyr Trp
65                  70                  75                  80

Trp Ser Ser Ile Ser Phe Lys Asn Met Phe Tyr Ser Glu Thr Pro Gln
                85                  90                  95

Gln Glu Ile Lys Gln Arg Cys Val Asp Thr Leu Asp Val Gln His Asp
            100                 105                 110

Lys Ala Asp Ile Thr Tyr Phe Ala Ala Asp Asn Arg Phe Ser Tyr Asn
        115                 120                 125

His Ser Ile Trp Thr Asn Asp His Gly Phe Gln Ala Asn Gln Ile Asn
    130                 135                 140

Arg Ile Val Ala Phe Gly Asp Ser Leu Ser Asp Thr Gly Asn Leu Phe
145                 150                 155                 160

Asn Gly Ser Gln Trp Ile Phe Pro Asn Pro Asn Ser Trp Phe Leu Gly
                165                 170                 175
```

```
His Phe Ser Asn Gly Phe Val Trp Thr Glu Tyr Leu Ala Asn Ala Lys
            180                 185                 190

Gly Val Pro Leu Tyr Asn Trp Ala Val Gly Gly Ala Ala Gly Thr Asn
        195                 200                 205

Gln Tyr Val Ala Leu Thr Gly Val Tyr Asp Gln Val Thr Ser Tyr Leu
    210                 215                 220

Thr Tyr Met Lys Met Ala Lys Asn Tyr Arg Pro Glu Asn Thr Leu Phe
225                 230                 235                 240

Thr Leu Glu Phe Gly Leu Asn Asp Phe Met Asn Tyr Gly Arg Glu Val
                245                 250                 255

Ala Asp Val Lys Ala Asp Phe Ser Ser Ala Leu Ile Arg Leu Thr Asp
            260                 265                 270

Ala Gly Ala Lys Asn Ile Leu Leu Phe Thr Leu Pro Asp Ala Thr Lys
        275                 280                 285

Ala Pro Gln Phe Lys Tyr Ser Thr Ala Gln Glu Ile Glu Thr Val Arg
    290                 295                 300

Gly Lys Ile Leu Ala Phe Asn Gln Phe Ile Lys Glu Gln Ala Glu Tyr
305                 310                 315                 320

Tyr Gln Ser Lys Gly Asp Asn Val Ile Leu Phe Asp Ala His Ala Leu
                325                 330                 335

Phe Ser Ser Ile Thr Ser Asp Pro Gln Lys His Gly Phe Arg Asn Ala
            340                 345                 350

Lys Asp Ala Cys Leu Asp Ile Asn Arg Ser Ala Ser Gln Asp Tyr Leu
        355                 360                 365

Tyr Ser His Ser Leu Thr Asn Asp Cys Ala Thr Tyr Gly Ser Asp Ser
    370                 375                 380

Tyr Val Phe Trp Gly Val Thr His Pro Thr Thr Ala Thr His Lys Tyr
385                 390                 395                 400

Ile Ala Thr His Ile Leu Met Asn Ser Met Ser Thr Phe Asp Phe
                405                 410                 415
```

<210> SEQ ID NO 21
<211> LENGTH: 1716
<212> TYPE: DNA
<213> ORGANISM: Unknown
<220> FEATURE:
<223> OTHER INFORMATION: Obtained from an environmental sample.

<400> SEQUENCE: 21

```
atgcagcagc ataaattgag gaatttcaac aagggattga ccggcgtcgt attgagcgta      60

ttgacctcta ccagcgccat ggcttttaca caaatcggtg gcggcggcgc gattccgatg     120

ggccatgaat ggctcacgcg cagatccgca ctggaattat taaatgcaga ccatatcgtc     180

tccaacgacc cgctcgaccc acgcttgggc tggagccagg gcttggccaa aaatttggat     240

ctctccaatg cattgaacga agtgcagcgc atccagagcg ttaccaagac caacgcactt     300

tatgaaccac gctatgatga cgtgttttct gcgattgtcg gcgaacgctg ggtggacacg     360

gccggtttca acgttgcgaa ggctaccgtc ggtaaaatcg attgtttcag cgcggtcgcg     420

caagaacctg ccgatgttca gcaagaccat ttcatgcgtc gttacgatga cgtgggcgga     480

caaggtggcg ttaacgccgc acgccgcggg caacaacgtt tcatcaccca tttcatcaac     540

gccgcgatgg ccgaagaaaa aagcataaaa gcgtgggacg gcggtggata ctccacgctg     600

gaaaaagtca gccacaatta tttcttgttt ggtcgcgctg tgcatttgtt ccaggattct     660

ttcagcccgg aacacaccgt gcgtctgccg caagacaact acgaaaaagt acgtcaggta     720
```

```
aaagcctatc tgtgttccga aggcgcagag caacatacgc ataacgcgca ggatgcgatc     780

agcttcacca gcggcgacgt tatctggaag aaaaacaccc gtctggatgc cggctggagc     840

acctacaaac ccagcaatat gaaacccgtt gccttggtgg cgatggaagc ctcgaaggac     900

ttgtgggccg ccttcattcg caccatggcc gcaccgcgca gcgagcgtcg cgccattgct     960

cagcaagagg cacaaacgct ggtaaacaac tggttgtcgt tcgacgaaca ggaaatgctg    1020

agctggtacg acgaagaaac tcatcgcgat cacacttacg tgctcgaacc cggccagaac    1080

ggccccggta tttccatgtt cgattgcatg gtgggtctgg gcgtgacgtc tggcagccag    1140

gctgcgcgtg tggccgaact ggatcaacaa cgtcgccagt gcttgttcaa cgtcaaggcc    1200

accaccggtt acagcgatct gaacgatccg cacatggata tcccgtataa ctggcaatgg    1260

acgtcgacca cgcagtggaa agtgccaagc gcgagctgga cgattccgca gttgccggcc    1320

gacgcaggca agaaagtgac gatcaaaaac gccatcaacg gcaatccgct ggtagcgccg    1380

gctggcgtca aacacaacag cgatatttat tccgcgccgg gtgaagccat cgaattcatt    1440

ttcgtcggtg actacaacaa tgagtcttat ctgcgctcga aaaaagatgc ggatttgttc    1500

ttgagctaca gtgcggtatc cggcaagggc ttgctgtaca acacaccgaa tcaggcaggt    1560

tatcgcgtga aaccggcggg cgtgctgtgg acgatcgaga acacctactg gaatgatttc    1620

ctgtggttca acagttcgaa caaccgcatc tacgtaagcg gcacgggcga tgccaacaag    1680

ttacattcac agtggatcat tgacggtctg aaataa                              1716
```

```
<210> SEQ ID NO 22
<211> LENGTH: 571
<212> TYPE: PRT
<213> ORGANISM: Unknown
<220> FEATURE:
<221> NAME/KEY: SIGNAL
<222> LOCATION: (1)...(28)
<223> OTHER INFORMATION: Obtained from an environmental sample.

<400> SEQUENCE: 22

Met Gln Gln His Lys Leu Arg Asn Phe Asn Lys Gly Leu Thr Gly Val
 1               5                  10                  15

Val Leu Ser Val Leu Thr Ser Thr Ser Ala Met Ala Phe Thr Gln Ile
            20                  25                  30

Gly Gly Gly Gly Ala Ile Pro Met Gly His Glu Trp Leu Thr Arg Arg
        35                  40                  45

Ser Ala Leu Glu Leu Leu Asn Ala Asp His Ile Val Ser Asn Asp Pro
    50                  55                  60

Leu Asp Pro Arg Leu Gly Trp Ser Gln Gly Leu Ala Lys Asn Leu Asp
65                  70                  75                  80

Leu Ser Asn Ala Leu Asn Glu Val Gln Arg Ile Gln Ser Val Thr Lys
                85                  90                  95

Thr Asn Ala Leu Tyr Glu Pro Arg Tyr Asp Asp Val Phe Ser Ala Ile
            100                 105                 110

Val Gly Glu Arg Trp Val Asp Thr Ala Gly Phe Asn Val Ala Lys Ala
        115                 120                 125

Thr Val Gly Lys Ile Asp Cys Phe Ser Ala Val Ala Gln Glu Pro Ala
    130                 135                 140

Asp Val Gln Gln Asp His Phe Met Arg Arg Tyr Asp Asp Val Gly Gly
145                 150                 155                 160

Gln Gly Gly Val Asn Ala Ala Arg Arg Gly Gln Gln Arg Phe Ile Thr
                165                 170                 175

His Phe Ile Asn Ala Ala Met Ala Glu Glu Lys Ser Ile Lys Ala Trp
```

```
            180                 185                 190

Asp Gly Gly Gly Tyr Ser Thr Leu Glu Lys Val Ser His Asn Tyr Phe
        195                 200                 205

Leu Phe Gly Arg Ala Val His Leu Phe Gln Asp Ser Phe Ser Pro Glu
    210                 215                 220

His Thr Val Arg Leu Pro Gln Asp Asn Tyr Glu Lys Val Arg Gln Val
225                 230                 235                 240

Lys Ala Tyr Leu Cys Ser Glu Gly Ala Glu Gln His Thr His Asn Ala
                245                 250                 255

Gln Asp Ala Ile Ser Phe Thr Ser Gly Asp Val Ile Trp Lys Lys Asn
            260                 265                 270

Thr Arg Leu Asp Ala Gly Trp Ser Thr Tyr Lys Pro Ser Asn Met Lys
        275                 280                 285

Pro Val Ala Leu Val Ala Met Glu Ala Ser Lys Asp Leu Trp Ala Ala
    290                 295                 300

Phe Ile Arg Thr Met Ala Ala Pro Arg Ser Glu Arg Arg Ala Ile Ala
305                 310                 315                 320

Gln Gln Glu Ala Gln Thr Leu Val Asn Asn Trp Leu Ser Phe Asp Glu
                325                 330                 335

Gln Glu Met Leu Ser Trp Tyr Asp Glu Glu Thr His Arg Asp His Thr
            340                 345                 350

Tyr Val Leu Glu Pro Gly Gln Asn Gly Pro Gly Ile Ser Met Phe Asp
        355                 360                 365

Cys Met Val Gly Leu Gly Val Thr Ser Gly Ser Gln Ala Ala Arg Val
    370                 375                 380

Ala Glu Leu Asp Gln Gln Arg Arg Gln Cys Leu Phe Asn Val Lys Ala
385                 390                 395                 400

Thr Thr Gly Tyr Ser Asp Leu Asn Asp Pro His Met Asp Ile Pro Tyr
                405                 410                 415

Asn Trp Gln Trp Thr Ser Thr Thr Gln Trp Lys Val Pro Ser Ala Ser
            420                 425                 430

Trp Thr Ile Pro Gln Leu Pro Ala Asp Ala Gly Lys Lys Val Thr Ile
        435                 440                 445

Lys Asn Ala Ile Asn Gly Asn Pro Leu Val Ala Pro Ala Gly Val Lys
    450                 455                 460

His Asn Ser Asp Ile Tyr Ser Ala Pro Gly Glu Ala Ile Glu Phe Ile
465                 470                 475                 480

Phe Val Gly Asp Tyr Asn Asn Glu Ser Tyr Leu Arg Ser Lys Lys Asp
                485                 490                 495

Ala Asp Leu Phe Leu Ser Tyr Ser Ala Val Ser Gly Lys Gly Leu Leu
            500                 505                 510

Tyr Asn Thr Pro Asn Gln Ala Gly Tyr Arg Val Lys Pro Ala Gly Val
        515                 520                 525

Leu Trp Thr Ile Glu Asn Thr Tyr Trp Asn Asp Phe Leu Trp Phe Asn
    530                 535                 540

Ser Ser Asn Asn Arg Ile Tyr Val Ser Gly Thr Gly Asp Ala Asn Lys
545                 550                 555                 560

Leu His Ser Gln Trp Ile Ile Asp Gly Leu Lys
                565                 570
```

<210> SEQ ID NO 23
<211> LENGTH: 1473
<212> TYPE: DNA
<213> ORGANISM: Unknown
<220> FEATURE:

<223> OTHER INFORMATION: Obtained from an environmental sample.

<400> SEQUENCE: 23

```
atgacgatcc gctcgaccga ctacgcgctg ctcgcgcagg agagctacca cgacagccag     60
gtcgatgctg acgtcaagct cgatggcatc tcctacaagg tattcgccac cacggacgac    120
cccctcaccg gcttccaggc caccgcttac cagcgccagg atacgggcga ggtggtcatc    180
gcctaccgcg gcacggaatt cgaccgcgaa cccgtgcgcg atggcggcgt cgacgcaggc    240
atggtgttgc ttggcgtcaa cgcccagtca cctgcatccg aggtattcac ccgcgaagtg    300
atcgaaaagg cgaagcacga agccgagctc aacgatcgcg agccgaagat caccgtcacc    360
gggcattccc tcggcggcac cctcgccgaa atcaatgccg cgaaatacgg cctccacggc    420
gaaaccttca atgcctacgg tgcggccagc ctcaagggca tccccgaggg cggcgacacg    480
gtgatcgacc atgtccgcgc cggcgatctc gtcagcgccg ccagcccgca ctacgggcag    540
gtgcgtgtgt acgcagctca gcaggatatc gataccctgc aacatgccgg ctaccgcgac    600
gacagtggca tcttcagcct gcgcaacccc atcaaggcca cggatttcga cgcccacgcg    660
atcgataact tcgtgcccaa cagcaagctg cttggccaat cgatcatcgc tcctgagaac    720
gaagcccgtt acgaagccca caagggcatg atcgatcgct atcgcgatga cgtggccgat    780
atccggaaag gcatctccgc tccctgggaa atccccaagg ccgtcggcga gctgaaggac    840
aagctcgaac acgaagcctt cgagctggcc ggcaagggca tcctcgccgt cgagcacggt    900
gtagccgagg tcgttcacga ggcgaaggaa gggttcgatc atctcaagga aggcttgcac    960
cacgtcaggg aagagatcag cgagggcatc cacgccgtgg aagagaaggc ttccagcgca   1020
tggcacaccc tcacccaccc gaaggaatgg ttcgagcacg acaaacctca agtgaatctc   1080
gaccatcccc agcatccaga caacgccttg ttcaagcagg cgcagggcgc ggtacacgcc   1140
ctcgatgcca cgcaaggccg cacgccagat aggacgagcg accagatcgc aggttctctg   1200
gtggtcgcgg cgcgacgcga tggtctcgag cgggtggacc gcgccgtgct cagcgatgac   1260
actagccggc tctacggcgt gcagggtgcg acggattcgc ccttgaagca gttcaccgag   1320
gtgaacacga cagtggcggc gcaaacgtca ctgcagcaaa gcagccaggc atggcagcag   1380
caagcagaga tcgcgcgaca gaaccaggca accagccagg ctcagcgcat ggaaccgcag   1440
gtgcccccgc aggcaccggc acatggcatg taa                                1473
```

<210> SEQ ID NO 24
<211> LENGTH: 490
<212> TYPE: PRT
<213> ORGANISM: Unknown
<220> FEATURE:
<223> OTHER INFORMATION: Obtained from an environmental sample.

<400> SEQUENCE: 24

```
Met Thr Ile Arg Ser Thr Asp Tyr Ala Leu Leu Ala Gln Glu Ser Tyr
 1               5                  10                  15

His Asp Ser Gln Val Asp Ala Asp Val Lys Leu Asp Gly Ile Ser Tyr
            20                  25                  30

Lys Val Phe Ala Thr Thr Asp Asp Pro Leu Thr Gly Phe Gln Ala Thr
        35                  40                  45

Ala Tyr Gln Arg Gln Asp Thr Gly Glu Val Val Ile Ala Tyr Arg Gly
    50                  55                  60

Thr Glu Phe Asp Arg Glu Pro Val Arg Asp Gly Gly Val Asp Ala Gly
65                  70                  75                  80

Met Val Leu Leu Gly Val Asn Ala Gln Ser Pro Ala Ser Glu Val Phe
```

```
                85                  90                  95

Thr Arg Glu Val Ile Glu Lys Ala Lys His Glu Ala Glu Leu Asn Asp
            100                 105                 110

Arg Glu Pro Lys Ile Thr Val Thr Gly His Ser Leu Gly Gly Thr Leu
        115                 120                 125

Ala Glu Ile Asn Ala Ala Lys Tyr Gly Leu His Gly Glu Thr Phe Asn
    130                 135                 140

Ala Tyr Gly Ala Ala Ser Leu Lys Gly Ile Pro Glu Gly Gly Asp Thr
145                 150                 155                 160

Val Ile Asp His Val Arg Ala Gly Asp Leu Val Ser Ala Ala Ser Pro
            165                 170                 175

His Tyr Gly Gln Val Arg Val Tyr Ala Ala Gln Gln Asp Ile Asp Thr
            180                 185                 190

Leu Gln His Ala Gly Tyr Arg Asp Asp Ser Gly Ile Phe Ser Leu Arg
        195                 200                 205

Asn Pro Ile Lys Ala Thr Asp Phe Asp Ala His Ala Ile Asp Asn Phe
    210                 215                 220

Val Pro Asn Ser Lys Leu Leu Gly Gln Ser Ile Ile Ala Pro Glu Asn
225                 230                 235                 240

Glu Ala Arg Tyr Glu Ala His Lys Gly Met Ile Asp Arg Tyr Arg Asp
                245                 250                 255

Asp Val Ala Asp Ile Arg Lys Gly Ile Ser Ala Pro Trp Glu Ile Pro
            260                 265                 270

Lys Ala Val Gly Glu Leu Lys Asp Lys Leu Glu His Glu Ala Phe Glu
        275                 280                 285

Leu Ala Gly Lys Gly Ile Leu Ala Val Glu His Gly Val Ala Glu Val
    290                 295                 300

Val His Glu Ala Lys Glu Gly Phe Asp His Leu Lys Glu Gly Leu His
305                 310                 315                 320

His Val Arg Glu Glu Ile Ser Glu Gly Ile His Ala Val Glu Glu Lys
                325                 330                 335

Ala Ser Ser Ala Trp His Thr Leu Thr His Pro Lys Glu Trp Phe Glu
            340                 345                 350

His Asp Lys Pro Gln Val Asn Leu Asp His Pro Gln His Pro Asp Asn
        355                 360                 365

Ala Leu Phe Lys Gln Ala Gln Gly Ala Val His Ala Leu Asp Ala Thr
    370                 375                 380

Gln Gly Arg Thr Pro Asp Arg Thr Ser Asp Gln Ile Ala Gly Ser Leu
385                 390                 395                 400

Val Val Ala Ala Arg Arg Asp Gly Leu Glu Arg Val Asp Arg Ala Val
                405                 410                 415

Leu Ser Asp Asp Thr Ser Arg Leu Tyr Gly Val Gln Gly Ala Thr Asp
            420                 425                 430

Ser Pro Leu Lys Gln Phe Thr Glu Val Asn Thr Thr Val Ala Ala Gln
        435                 440                 445

Thr Ser Leu Gln Gln Ser Ser Gln Ala Trp Gln Gln Gln Ala Glu Ile
    450                 455                 460

Ala Arg Gln Asn Gln Ala Thr Ser Gln Ala Gln Arg Met Glu Pro Gln
465                 470                 475                 480

Val Pro Pro Gln Ala Pro Ala His Gly Met
                485                 490
```

<210> SEQ ID NO 25
<211> LENGTH: 1098

<212> TYPE: DNA
<213> ORGANISM: Unknown
<220> FEATURE:
<223> OTHER INFORMATION: Obtained from an environmental sample.

<400> SEQUENCE: 25

```
atgtgcgcca aagttaaagt agtcaaaata aagacaaaca caggcagccc aaacaaatac     60
cacttcaaga acctcgtctt cgaaggcggc ggcgtgaaag gcattgccta tgtgggagcc    120
cttaccaagc tcgacgagga aggcatcctt caaaacatta agcgcgtggc cggcacctca    180
gcaggagcaa tggtggccgt cctcgtcgga ttgggcttca ccgctaagga gataagcgac    240
atcctgtggg acatcaaatt ccagaacttt ttagacaact catggggcgt gatacgcaac    300
accaatcgtc tgctgacgga atacggctgg tataagggcg agtttttccg cgacctcatg    360
gctgattaca tcaaaagaaa gacagacgat ggcgagatta ctttcgggga gttggaggcc    420
atgagaaaag agggcaagcc cttcttggaa atccatctgg ttggctccga cctcacgaca    480
gggtattcca gagtgttcaa ctccaaaaac accccaaatg tgaaagtcgc cgatgccgcc    540
cgcatctcca tgtcgatacc gctgtttttc tccgctgtga gaggcgtgca aggcgacgac    600
cacctctatg tggacggtgg gcttttggac aactacgcca tcaagatttt cgaccagtcg    660
aaactcgttt cagacaaaaa caacaaaagg aagaccgagt attacaacag gctcaaccag    720
caagtgaacg cgaaagcaac gaaaagcaag acggaatctg tagagtatgt ctacaacaag    780
gagactttgg gcttccgctt ggatgccaaa gaggacatca acctcttcct caaccacgat    840
gatgcccctc aaaaagaaat caagagtttc ttctcttaca ccaaagcttt ggtttccacg    900
ctcatcgatt tccagaacaa tgtacacctg cacagcgacg actggcagcg tacggtctac    960
atcgacacac tcggtgtcag ctccattgac ttcggtctgt caaacacaac gaaacaagct   1020
cttgtcgatt cgggctacaa ctacaccaca gcctacctcg actggtacaa caacgacgag   1080
gataaagcca acaagtaa                                                 1098
```

<210> SEQ ID NO 26
<211> LENGTH: 365
<212> TYPE: PRT
<213> ORGANISM: Unknown
<220> FEATURE:
<223> OTHER INFORMATION: Obtained from an environmental sample.

<400> SEQUENCE: 26

```
Met Cys Ala Lys Val Lys Val Val Lys Ile Lys Thr Asn Thr Gly Ser
 1               5                  10                  15

Pro Asn Lys Tyr His Phe Lys Asn Leu Val Phe Glu Gly Gly Gly Val
            20                  25                  30

Lys Gly Ile Ala Tyr Val Gly Ala Leu Thr Lys Leu Asp Glu Glu Gly
        35                  40                  45

Ile Leu Gln Asn Ile Lys Arg Val Ala Gly Thr Ser Ala Gly Ala Met
    50                  55                  60

Val Ala Val Leu Val Gly Leu Gly Phe Thr Ala Lys Glu Ile Ser Asp
65                  70                  75                  80

Ile Leu Trp Asp Ile Lys Phe Gln Asn Phe Leu Asp Asn Ser Trp Gly
                85                  90                  95

Val Ile Arg Asn Thr Asn Arg Leu Leu Thr Glu Tyr Gly Trp Tyr Lys
            100                 105                 110

Gly Glu Phe Phe Arg Asp Leu Met Ala Asp Tyr Ile Lys Arg Lys Thr
        115                 120                 125

Asp Asp Gly Glu Ile Thr Phe Gly Glu Leu Glu Ala Met Arg Lys Glu
```

```
    130                 135                 140

Gly Lys Pro Phe Leu Glu Ile His Leu Val Gly Ser Asp Leu Thr Thr
145                 150                 155                 160

Gly Tyr Ser Arg Val Phe Asn Ser Lys Asn Thr Pro Asn Val Lys Val
                165                 170                 175

Ala Asp Ala Ala Arg Ile Ser Met Ser Ile Pro Leu Phe Phe Ser Ala
            180                 185                 190

Val Arg Gly Val Gln Gly Asp Asp His Leu Tyr Val Asp Gly Gly Leu
        195                 200                 205

Leu Asp Asn Tyr Ala Ile Lys Ile Phe Asp Gln Ser Lys Leu Val Ser
    210                 215                 220

Asp Lys Asn Asn Lys Arg Lys Thr Glu Tyr Tyr Asn Arg Leu Asn Gln
225                 230                 235                 240

Gln Val Asn Ala Lys Ala Thr Lys Ser Lys Thr Glu Ser Val Glu Tyr
                245                 250                 255

Val Tyr Asn Lys Glu Thr Leu Gly Phe Arg Leu Asp Ala Lys Glu Asp
            260                 265                 270

Ile Asn Leu Phe Leu Asn His Asp Asp Ala Pro Gln Lys Glu Ile Lys
        275                 280                 285

Ser Phe Phe Ser Tyr Thr Lys Ala Leu Val Ser Thr Leu Ile Asp Phe
    290                 295                 300

Gln Asn Asn Val His Leu His Ser Asp Asp Trp Gln Arg Thr Val Tyr
305                 310                 315                 320

Ile Asp Thr Leu Gly Val Ser Ser Ile Asp Phe Gly Leu Ser Asn Thr
                325                 330                 335

Thr Lys Gln Ala Leu Val Asp Ser Gly Tyr Asn Tyr Thr Thr Ala Tyr
            340                 345                 350

Leu Asp Trp Tyr Asn Asn Asp Glu Asp Lys Ala Asn Lys
        355                 360                 365
```

<210> SEQ ID NO 27
<211> LENGTH: 1287
<212> TYPE: DNA
<213> ORGANISM: Unknown
<220> FEATURE:
<223> OTHER INFORMATION: Obtained from an environmental sample.

<400> SEQUENCE: 27

```
gtgtcgatta ccgtttaccg gaagccctcc ggcgggtttg gagcgatagt tcctcaagcg      60

aaaattgaga accttgtttt cgagggcggc ggaccaaagg gcctggtcta tgtcggcgcg     120

gtcgaggttc tcggcgaaag gggactgctg gaagggatcg caaatgtcgg cggcgcttca     180

gcaggcgcca tgaccgctct agccgtcggt ctgggactga gccccaggga aattcgcgcg     240

gtcgtcttta accagaacat tgcggacctc accgatatcg agaagaccgt cgagccgtcc     300

tccgggatta caggcatgtt caagagcgtg ttcaagaagg gttggcaggc ggtgcgcaac     360

gtaaccggca cctctgacga gcgcgggcgc gggctctatc gcggcgagaa gttgcgagcc     420

tggatcagag acctgattgc acagcgagtc gaggcggggc gctccgaggt cctgagccga     480

gccgacgccg atggacggaa cttctatgag aaagccgccg caaagaaggg cgccctgaca     540

tttgccgagc ttgatcgggt ggcgcaaatg gcgccgggcc tgcggcttcg ccgcctggcc     600

ttcaccggaa ccaacttcac gtcgaagaag ctcgaagtgt tcagtctgca cgagaccccg     660

gacatgccga tcgacgtcgc ggtacgcatc tccgcatcgt tgccatggtt tttcaaatcc     720

gtgaaatgga acggctccga atacatagat ggcggctgcc tgtcgaactt cccaatgccg     780
```

```
atattcgacg tcgatcccta tcgtggcgac gcatcgtcga aaatccggct cggcatcttc    840

ggccagaacc tcgcgacgct cggcttcaag gtcgacagcg aggaggagat ccgcgacatt    900

ctctggcgta gccccgagag cacgagcgac ggctttttcc aaggcatcct gtcaagcgtg    960

aaagcttctg cagaacactg ggtcgtcggc atcgacgtcg aaggcgccac ccgcgcgtcg   1020

aacgtggccg ttcacggcaa gtatgctcag cgaacgatcc agataccgga cctcggatat   1080

agcacgttca agttcgatct ttcggacgct gacaaggagc gcatggccga ggccggcgca   1140

aaggccacgc gggaatggct ggcgctgtac ttcgacgacg ccggaataga ggtcgaattt   1200

tctgatccga acgaattgcg cggccagttg tccgacgccg cattcgcaga cctcgaggat   1260

tcgtttcgag ccttgatcgc ggcctag                                       1287


<210> SEQ ID NO 28
<211> LENGTH: 428
<212> TYPE: PRT
<213> ORGANISM: Unknown
<220> FEATURE:
<223> OTHER INFORMATION: Obtained from an environmental sample.

<400> SEQUENCE: 28

Met Ser Ile Thr Val Tyr Arg Lys Pro Ser Gly Gly Phe Gly Ala Ile
1               5                   10                  15

Val Pro Gln Ala Lys Ile Glu Asn Leu Val Phe Glu Gly Gly Gly Pro
            20                  25                  30

Lys Gly Leu Val Tyr Val Gly Ala Val Glu Val Leu Gly Glu Arg Gly
        35                  40                  45

Leu Leu Glu Gly Ile Ala Asn Val Gly Gly Ala Ser Ala Gly Ala Met
    50                  55                  60

Thr Ala Leu Ala Val Gly Leu Gly Leu Ser Pro Arg Glu Ile Arg Ala
65                  70                  75                  80

Val Val Phe Asn Gln Asn Ile Ala Asp Leu Thr Asp Ile Glu Lys Thr
                85                  90                  95

Val Glu Pro Ser Ser Gly Ile Thr Gly Met Phe Lys Ser Val Phe Lys
            100                 105                 110

Lys Gly Trp Gln Ala Val Arg Asn Val Thr Gly Thr Ser Asp Glu Arg
        115                 120                 125

Gly Arg Gly Leu Tyr Arg Gly Glu Lys Leu Arg Ala Trp Ile Arg Asp
    130                 135                 140

Leu Ile Ala Gln Arg Val Glu Ala Gly Arg Ser Glu Val Leu Ser Arg
145                 150                 155                 160

Ala Asp Ala Asp Gly Arg Asn Phe Tyr Glu Lys Ala Ala Ala Lys Lys
                165                 170                 175

Gly Ala Leu Thr Phe Ala Glu Leu Asp Arg Val Ala Gln Met Ala Pro
            180                 185                 190

Gly Leu Arg Leu Arg Arg Leu Ala Phe Thr Gly Thr Asn Phe Thr Ser
        195                 200                 205

Lys Lys Leu Glu Val Phe Ser Leu His Glu Thr Pro Asp Met Pro Ile
    210                 215                 220

Asp Val Ala Val Arg Ile Ser Ala Ser Leu Pro Trp Phe Phe Lys Ser
225                 230                 235                 240

Val Lys Trp Asn Gly Ser Glu Tyr Ile Asp Gly Gly Cys Leu Ser Asn
                245                 250                 255

Phe Pro Met Pro Ile Phe Asp Val Asp Pro Tyr Arg Gly Asp Ala Ser
            260                 265                 270

Ser Lys Ile Arg Leu Gly Ile Phe Gly Gln Asn Leu Ala Thr Leu Gly
```

```
        275                 280                 285

Phe Lys Val Asp Ser Glu Glu Glu Ile Arg Asp Ile Leu Trp Arg Ser
    290                 295                 300

Pro Glu Ser Thr Ser Asp Gly Phe Phe Gln Gly Ile Leu Ser Ser Val
305                 310                 315                 320

Lys Ala Ser Ala Glu His Trp Val Val Gly Ile Asp Val Glu Gly Ala
                325                 330                 335

Thr Arg Ala Ser Asn Val Ala Val His Gly Lys Tyr Ala Gln Arg Thr
            340                 345                 350

Ile Gln Ile Pro Asp Leu Gly Tyr Ser Thr Phe Lys Phe Asp Leu Ser
        355                 360                 365

Asp Ala Asp Lys Glu Arg Met Ala Glu Ala Gly Ala Lys Ala Thr Arg
    370                 375                 380

Glu Trp Leu Ala Leu Tyr Phe Asp Asp Ala Gly Ile Glu Val Glu Phe
385                 390                 395                 400

Ser Asp Pro Asn Glu Leu Arg Gly Gln Leu Ser Asp Ala Ala Phe Ala
                405                 410                 415

Asp Leu Glu Asp Ser Phe Arg Ala Leu Ile Ala Ala
            420                 425
```

<210> SEQ ID NO 29
<211> LENGTH: 753
<212> TYPE: DNA
<213> ORGANISM: Unknown
<220> FEATURE:
<223> OTHER INFORMATION: Obtained from an environmental sample.

<400> SEQUENCE: 29

```
atgggaaacg gtgcagcagt tggttcgaat gataatggta gagaagaaag tgtttacgta      60

ctttctgtga tcgcctgtaa tgtttattat ttacaaaagt gtgaaggtgg ggcatcgcgt     120

gatagcgtga ttagagaaat caatagccaa actcaacctt taggatatga gattgtagca     180

gattctattc gtgatggtca tattggctct tttgcctgta agatggctgt ctttagaaat     240

aatggaaacg gcaattgtgt tttagcaatc aaagggactg atatgaataa tatcaatgac     300

ttggtgaatg acctaaccat gatattagga ggtattggtt ctgttgctgc aatccaacca     360

acgattaaca tggcacaaga actcatcgac caatatggag tgaatttgat tacaggtcac     420

tcccttggag gctacatgac tgagatcatc gccaccaatc gtggacttcc aggtattgca     480

ttttgcgcac caggttcaaa tggtcccatt gtaaaattag gtggacaaga gacacctggc     540

tttcacaatg tgaactttga acatgatcca gcaggtaacg ttatgacggg ggtttatact     600

catgtccaat ggagtattta tgtaggatgt gatggtatga ctcatggtat tgaaaatatg     660

gtgaattatt ttaaagataa aagagattta accaatcgca atattcaagg aagaagtgaa     720

agtcataata cgggttatta ttacccaaaa taa                                  753
```

<210> SEQ ID NO 30
<211> LENGTH: 250
<212> TYPE: PRT
<213> ORGANISM: Unknown
<220> FEATURE:
<223> OTHER INFORMATION: Obtained from an environmental sample.

<400> SEQUENCE: 30

```
Met Gly Asn Gly Ala Ala Val Gly Ser Asn Asp Asn Gly Arg Glu Glu
 1               5                  10                  15

Ser Val Tyr Val Leu Ser Val Ile Ala Cys Asn Val Tyr Tyr Leu Gln
            20                  25                  30
```

```
Lys Cys Glu Gly Gly Ala Ser Arg Asp Ser Val Ile Arg Glu Ile Asn
        35                  40                  45

Ser Gln Thr Gln Pro Leu Gly Tyr Glu Ile Val Ala Asp Ser Ile Arg
    50                  55                  60

Asp Gly His Ile Gly Ser Phe Ala Cys Lys Met Ala Val Phe Arg Asn
65                  70                  75                  80

Asn Gly Asn Gly Asn Cys Val Leu Ala Ile Lys Gly Thr Asp Met Asn
                85                  90                  95

Asn Ile Asn Asp Leu Val Asn Asp Leu Thr Met Ile Leu Gly Gly Ile
            100                 105                 110

Gly Ser Val Ala Ala Ile Gln Pro Thr Ile Asn Met Ala Gln Glu Leu
        115                 120                 125

Ile Asp Gln Tyr Gly Val Asn Leu Ile Thr Gly His Ser Leu Gly Gly
    130                 135                 140

Tyr Met Thr Glu Ile Ile Ala Thr Asn Arg Gly Leu Pro Gly Ile Ala
145                 150                 155                 160

Phe Cys Ala Pro Gly Ser Asn Gly Pro Ile Val Lys Leu Gly Gly Gln
                165                 170                 175

Glu Thr Pro Gly Phe His Asn Val Asn Phe Glu His Asp Pro Ala Gly
            180                 185                 190

Asn Val Met Thr Gly Val Tyr Thr His Val Gln Trp Ser Ile Tyr Val
        195                 200                 205

Gly Cys Asp Gly Met Thr His Gly Ile Glu Asn Met Val Asn Tyr Phe
    210                 215                 220

Lys Asp Lys Arg Asp Leu Thr Asn Arg Asn Ile Gln Gly Arg Ser Glu
225                 230                 235                 240

Ser His Asn Thr Gly Tyr Tyr Tyr Pro Lys
                245                 250
```

<210> SEQ ID NO 31
<211> LENGTH: 1422
<212> TYPE: DNA
<213> ORGANISM: Unknown
<220> FEATURE:
<223> OTHER INFORMATION: Obtained from an environmental sample.

<400> SEQUENCE: 31

```
atgaaaaaga aattatgtac atgggctctc gtaacagcga tatcttctgg agttgttgcg     60

attccaaccg tagcatctgc ttgcggaatg ggtgaagtaa tgaaacagga ggatcaagag    120

cacaaacgtg tgaagagatg gtctgcggag catccgcacc atgctaatga aagcacgcac    180

ttatggattg ctcgaaatgc gattcaaatt atgagtcgta atcaagataa gacggttcaa    240

gaaaatgaat tacaattctt aaaaaatacct gaatataagg agttatttga aagagggctt    300

tatgatgccg attatcttga tgagtttaac gatggaggta caggtacaat cggtattgat    360

gggctaatta aaggaggctg gaaatctcat ttctatgatc ctgatacgaa aaagaactat    420

aaaggagaag aagaaccaac agccctttcg caaggggata aatattttaa attagcagga    480

gattatttta agaaagaaga ttggaaacaa gctttctatt atttaggtgt tgcgacgcat    540

tacttcacag atgctactca gccaatgcat gctgctaatt ttacagctgt cgacatgagt    600

gcaataaagt ttcatagcgc ttttgaaaat tatgtaacga cagttcagac accgtttgaa    660

gtgaaggatg ataagggaac atataatttg gtcaattctg atgatccgaa gcagtggata    720

catgaaacag cgaaactcgc aaaagcagaa attatgaata ttactagtga taatattaaa    780

tctcaatata ataaaggaaa caaagatctt tggcaacaag aagttatgcc agctgtccag    840
```

```
aggagtttag agaaagcgca aagaaacacg gcgggattta ttcatttatg gtttaaaaca    900

tatgttggca aaactgcagc tgaagatatt gaaactacac aggtaaaaga ttctaatgga    960

gaagcaatac aagaacaaaa aaaatactac gttgtgccta gtgagttttt aaatagaggt   1020

ttgacctttg aggtatatgc ttcgaatgac tacgcactat tatctaatca cgtagatgat   1080

aataaagttc atggtacacc tgttcagttt gtttttgata aagagaataa cggaattgtt   1140

catcggggag aaagtgtact gctgaaaatg acgcaatcta actatgatga ttatgtattt   1200

cttaattact ctaatatgac aaattggtta catcttgcga aacgaaaaac aaatactgca   1260

cagtttaaag tgtatccaaa tccggataac tcatctgaat atttcctata tacagatgga   1320

tacccggtaa attatcaaga aaatggtaat gggaagagct ggattgagtt aggaaagaaa   1380

acggataaac cgaaagcgtg gaaatttcaa caggcagaat aa                      1422
```

```
<210> SEQ ID NO 32
<211> LENGTH: 473
<212> TYPE: PRT
<213> ORGANISM: Unknown
<220> FEATURE:
<221> NAME/KEY: SIGNAL
<222> LOCATION: (1)...(20)
<223> OTHER INFORMATION: Obtained from an environmental sample.

<400> SEQUENCE: 32

Met Lys Lys Lys Leu Cys Thr Trp Ala Leu Val Thr Ala Ile Ser Ser
 1               5                  10                  15

Gly Val Val Ala Ile Pro Thr Val Ala Ser Ala Cys Gly Met Gly Glu
            20                  25                  30

Val Met Lys Gln Glu Asp Gln Glu His Lys Arg Val Lys Arg Trp Ser
        35                  40                  45

Ala Glu His Pro His His Ala Asn Glu Ser Thr His Leu Trp Ile Ala
    50                  55                  60

Arg Asn Ala Ile Gln Ile Met Ser Arg Asn Gln Asp Lys Thr Val Gln
65                  70                  75                  80

Glu Asn Glu Leu Gln Phe Leu Lys Ile Pro Glu Tyr Lys Glu Leu Phe
                85                  90                  95

Glu Arg Gly Leu Tyr Asp Ala Asp Tyr Leu Asp Glu Phe Asn Asp Gly
            100                 105                 110

Gly Thr Gly Thr Ile Gly Ile Asp Gly Leu Ile Lys Gly Gly Trp Lys
        115                 120                 125

Ser His Phe Tyr Asp Pro Asp Thr Lys Lys Asn Tyr Lys Gly Glu Glu
    130                 135                 140

Glu Pro Thr Ala Leu Ser Gln Gly Asp Lys Tyr Phe Lys Leu Ala Gly
145                 150                 155                 160

Asp Tyr Phe Lys Lys Glu Asp Trp Lys Gln Ala Phe Tyr Tyr Leu Gly
                165                 170                 175

Val Ala Thr His Tyr Phe Thr Asp Ala Thr Gln Pro Met His Ala Ala
            180                 185                 190

Asn Phe Thr Ala Val Asp Met Ser Ala Ile Lys Phe His Ser Ala Phe
        195                 200                 205

Glu Asn Tyr Val Thr Thr Val Gln Thr Pro Phe Glu Val Lys Asp Asp
    210                 215                 220

Lys Gly Thr Tyr Asn Leu Val Asn Ser Asp Asp Pro Lys Gln Trp Ile
225                 230                 235                 240

His Glu Thr Ala Lys Leu Ala Lys Ala Glu Ile Met Asn Ile Thr Ser
                245                 250                 255
```

```
Asp Asn Ile Lys Ser Gln Tyr Asn Lys Gly Asn Lys Asp Leu Trp Gln
            260                 265                 270

Gln Glu Val Met Pro Ala Val Gln Arg Ser Leu Glu Lys Ala Gln Arg
        275                 280                 285

Asn Thr Ala Gly Phe Ile His Leu Trp Phe Lys Thr Tyr Val Gly Lys
    290                 295                 300

Thr Ala Ala Glu Asp Ile Glu Thr Thr Gln Val Lys Asp Ser Asn Gly
305                 310                 315                 320

Glu Ala Ile Gln Glu Gln Lys Lys Tyr Tyr Val Val Pro Ser Glu Phe
                325                 330                 335

Leu Asn Arg Gly Leu Thr Phe Glu Val Tyr Ala Ser Asn Asp Tyr Ala
            340                 345                 350

Leu Leu Ser Asn His Val Asp Asp Asn Lys Val His Gly Thr Pro Val
        355                 360                 365

Gln Phe Val Phe Asp Lys Glu Asn Asn Gly Ile Val His Arg Gly Glu
    370                 375                 380

Ser Val Leu Leu Lys Met Thr Gln Ser Asn Tyr Asp Asp Tyr Val Phe
385                 390                 395                 400

Leu Asn Tyr Ser Asn Met Thr Asn Trp Leu His Leu Ala Lys Arg Lys
                405                 410                 415

Thr Asn Thr Ala Gln Phe Lys Val Tyr Pro Asn Pro Asp Asn Ser Ser
            420                 425                 430

Glu Tyr Phe Leu Tyr Thr Asp Gly Tyr Pro Val Asn Tyr Gln Glu Asn
        435                 440                 445

Gly Asn Gly Lys Ser Trp Ile Glu Leu Gly Lys Lys Thr Asp Lys Pro
    450                 455                 460

Lys Ala Trp Lys Phe Gln Gln Ala Glu
465                 470
```

<210> SEQ ID NO 33
<211> LENGTH: 792
<212> TYPE: DNA
<213> ORGANISM: Unknown
<220> FEATURE:
<223> OTHER INFORMATION: Obtained from an environmental sample.

<400> SEQUENCE: 33

```
atgagagcac tcgtgctggc aggcggtgga gccaagggct cgtttcaagt gggcgtgctg      60

cagcggttca cccccgcaga cttcggtctc gtggtgggat gctcggtcgg agctttaaac     120

gccgcggggt ttgcccacct gggtagccat ggcatcaaag acctctggca agggatcagg     180

agtcgagatg acatcctgtc ccgtgtctgg tggccgtttg gctcagacgg gatcttctcg     240

cagaagcctc ttgaaaagct cgtctccaaa gcatgcacgg gtcctgctcg ggtgccggtc     300

cacgtggcga cggtctgcct tgaacgcggc cttgtccact acgggatctc cggggactct     360

gactttgaga agaaagtgct ggcatcggct gcgatcccag gcgtggtgaa gccagttaag     420

atccatggcg accactacgt cgacggtggt gtcagagaga tctgtccgct gcgtcgagcc     480

atcgacctgg gcgcccacgga gatcacagtc atcatgtgcg ctccggaata catcccgacc     540

tggtcgcgta gttcctcgct gttcccgttt gtgaacgtga tgatccggtc tctcgacatc     600

ctgaccgatg agatcctggt caacgacatc gccgagtgcg tggcaaagaa caagatgcca     660

ggtaaacgtc acgtaaagct caccatctac cggccgaaga aagagctcat gggcacgctc     720

gactttgacc ccaaagccat cgccgcaggg atcaaggcag gcaccgaagc ccagccaagg     780

ttctgggagt aa                                                         792
```

<210> SEQ ID NO 34
<211> LENGTH: 263
<212> TYPE: PRT
<213> ORGANISM: Unknown
<220> FEATURE:
<223> OTHER INFORMATION: Obtained from an environmental sample.

<400> SEQUENCE: 34

```
Met Arg Ala Leu Val Leu Ala Gly Gly Gly Ala Lys Gly Ser Phe Gln
 1               5                  10                  15

Val Gly Val Leu Gln Arg Phe Thr Pro Ala Asp Phe Gly Leu Val Val
            20                  25                  30

Gly Cys Ser Val Gly Ala Leu Asn Ala Ala Gly Phe Ala His Leu Gly
        35                  40                  45

Ser His Gly Ile Lys Asp Leu Trp Gln Gly Ile Arg Ser Arg Asp Asp
    50                  55                  60

Ile Leu Ser Arg Val Trp Trp Pro Phe Gly Ser Asp Gly Ile Phe Ser
65                  70                  75                  80

Gln Lys Pro Leu Glu Lys Leu Val Ser Lys Ala Cys Thr Gly Pro Ala
                85                  90                  95

Arg Val Pro Val His Val Ala Thr Val Cys Leu Glu Arg Gly Leu Val
            100                 105                 110

His Tyr Gly Ile Ser Gly Asp Ser Asp Phe Glu Lys Lys Val Leu Ala
        115                 120                 125

Ser Ala Ala Ile Pro Gly Val Val Lys Pro Val Lys Ile His Gly Asp
    130                 135                 140

His Tyr Val Asp Gly Gly Val Arg Glu Ile Cys Pro Leu Arg Arg Ala
145                 150                 155                 160

Ile Asp Leu Gly Ala Thr Glu Ile Thr Val Ile Met Cys Ala Pro Glu
                165                 170                 175

Tyr Ile Pro Thr Trp Ser Arg Ser Ser Ser Leu Phe Pro Phe Val Asn
            180                 185                 190

Val Met Ile Arg Ser Leu Asp Ile Leu Thr Asp Glu Ile Leu Val Asn
        195                 200                 205

Asp Ile Ala Glu Cys Val Ala Lys Asn Lys Met Pro Gly Lys Arg His
    210                 215                 220

Val Lys Leu Thr Ile Tyr Arg Pro Lys Lys Glu Leu Met Gly Thr Leu
225                 230                 235                 240

Asp Phe Asp Pro Lys Ala Ile Ala Ala Gly Ile Lys Ala Gly Thr Glu
                245                 250                 255

Ala Gln Pro Arg Phe Trp Glu
            260
```

<210> SEQ ID NO 35
<211> LENGTH: 1389
<212> TYPE: DNA
<213> ORGANISM: Unknown
<220> FEATURE:
<223> OTHER INFORMATION: Obtained from an environmental sample.

<400> SEQUENCE: 35

```
atgcccgagc cgcccgccgc atgccgttgc gattgcgcct gcgagcgcga ccagcacctt      60

ttttgcaagg gacccaagcg tatcctcgcg ctcgacggcg gcggcgtgcg cggcgccgtc     120

agcgtcgcat tcctcgaacg gatcgaggcg gtgctcgagg cccggctcgg acgcaaggtg     180

ctgctcggcc actggttcga cctgatcggc ggcacctcga cgggcgccat catcggcggc     240
```

```
gcgctggcga tgggattcgc ggccgaggac gtccaaagat tctatcacga gctcgcgccg    300

cgggtgttca ggcatccgct cctgcgcatc ggtctcctgc gcccgttccg cgcgaaattc    360

gacgcccgcc tgctgcgcga ggagatccac cgcatcatcg gcgacagcac gctcggcgac    420

aaagcgctga tgaccgggtt cgcgctcgtc gccaagcgga tggacaccgg cagcacctgg    480

atcctcgcca acaacaagcg cagcaaatac tgggaagggc gggacggcgt cgtcggcaac    540

aaggattatc tcctcggcag cctcattcgc gcgagcacgg cggcgccgct gtatttcgac    600

cccgaggagg tcgtgatcgc ggaggcccgc aaggacatcg agggcatcag gggcctgttc    660

gtcgacggcg gcgtcacgcc gcacaacaat ccttcgctcg cgatgctgct gctggcgctg    720

ctcgacgcct accggctgcg ctgggaaacg ggaccggaca agctcacggt cgtctcgatc    780

ggcactggaa cgcatcgcga ccgcgtcgtt cccgacacgc tcggcatggg caagaacgcg    840

aagatcgcgc tgcgcgccat gagctcgctg atgaacgacg tgcacgagct cgcgctcacg    900

cagatgcagt acctcggtga gacgctcacc ccgtggcgca tcaacgacga gctcggcgac    960

atgcggaccg agcggccgcc gcaaggcaag ctcttccgct tcctccgcta cgacgtccgg   1020

ctggagctcg attggatcaa cgaggacgag gagcgccggc gcaagatcaa gaacaaattc   1080

aagcgcgagc tgaccgagac cgacatgatc cgcctgcgca gcctcgacga tccgacgacc   1140

atcccggacc tctacatgct tgcccaggtc gcggccgagg agcaggtcaa ggcggagcac   1200

tggctcggcg acgtgccgga gtggagcgaa ggcgcgcgcc cgtgtgcgcc gcgccggcac   1260

ctgccgccga cgccgccggg ccgctccgag gattcggcgc gcttccgggc cgagaaggcc   1320

gtcggcgagt ggctcagttt tgcgcgcgcg aacatcacgc gcctcatgtc gcggaagccg   1380

ccgggttga                                                           1389
```

<210> SEQ ID NO 36
<211> LENGTH: 462
<212> TYPE: PRT
<213> ORGANISM: Unknown
<220> FEATURE:
<223> OTHER INFORMATION: Obtained from an environmental sample.

<400> SEQUENCE: 36

```
Met Pro Glu Pro Pro Ala Ala Cys Arg Cys Asp Cys Ala Cys Glu Arg
1               5                   10                  15

Asp Gln His Leu Phe Cys Lys Gly Pro Lys Arg Ile Leu Ala Leu Asp
            20                  25                  30

Gly Gly Gly Val Arg Gly Ala Val Ser Val Ala Phe Leu Glu Arg Ile
        35                  40                  45

Glu Ala Val Leu Glu Ala Arg Leu Gly Arg Lys Val Leu Leu Gly His
    50                  55                  60

Trp Phe Asp Leu Ile Gly Gly Thr Ser Thr Gly Ala Ile Ile Gly Gly
65                  70                  75                  80

Ala Leu Ala Met Gly Phe Ala Ala Glu Asp Val Gln Arg Phe Tyr His
                85                  90                  95

Glu Leu Ala Pro Arg Val Phe Arg His Pro Leu Leu Arg Ile Gly Leu
            100                 105                 110

Leu Arg Pro Phe Arg Ala Lys Phe Asp Ala Arg Leu Leu Arg Glu Glu
        115                 120                 125

Ile His Arg Ile Ile Gly Asp Ser Thr Leu Gly Asp Lys Ala Leu Met
    130                 135                 140

Thr Gly Phe Ala Leu Val Ala Lys Arg Met Asp Thr Gly Ser Thr Trp
145                 150                 155                 160
```

```
Ile Leu Ala Asn Asn Lys Arg Ser Lys Tyr Trp Glu Gly Arg Asp Gly
                165                 170                 175

Val Val Gly Asn Lys Asp Tyr Leu Leu Gly Ser Leu Ile Arg Ala Ser
            180                 185                 190

Thr Ala Ala Pro Leu Tyr Phe Asp Pro Glu Glu Val Val Ile Ala Glu
        195                 200                 205

Ala Arg Lys Asp Ile Glu Gly Ile Arg Gly Leu Phe Val Asp Gly Gly
    210                 215                 220

Val Thr Pro His Asn Asn Pro Ser Leu Ala Met Leu Leu Leu Ala Leu
225                 230                 235                 240

Leu Asp Ala Tyr Arg Leu Arg Trp Glu Thr Gly Pro Asp Lys Leu Thr
                245                 250                 255

Val Val Ser Ile Gly Thr Gly Thr His Arg Asp Arg Val Val Pro Asp
            260                 265                 270

Thr Leu Gly Met Gly Lys Asn Ala Lys Ile Ala Leu Arg Ala Met Ser
        275                 280                 285

Ser Leu Met Asn Asp Val His Glu Leu Ala Leu Thr Gln Met Gln Tyr
    290                 295                 300

Leu Gly Glu Thr Leu Thr Pro Trp Arg Ile Asn Asp Glu Leu Gly Asp
305                 310                 315                 320

Met Arg Thr Glu Arg Pro Pro Gln Gly Lys Leu Phe Arg Phe Leu Arg
                325                 330                 335

Tyr Asp Val Arg Leu Glu Leu Asp Trp Ile Asn Glu Asp Glu Glu Arg
            340                 345                 350

Arg Arg Lys Ile Lys Asn Lys Phe Lys Arg Glu Leu Thr Glu Thr Asp
        355                 360                 365

Met Ile Arg Leu Arg Ser Leu Asp Asp Pro Thr Thr Ile Pro Asp Leu
    370                 375                 380

Tyr Met Leu Ala Gln Val Ala Ala Glu Glu Gln Val Lys Ala Glu His
385                 390                 395                 400

Trp Leu Gly Asp Val Pro Glu Trp Ser Glu Gly Ala Arg Pro Cys Ala
                405                 410                 415

Pro Arg Arg His Leu Pro Pro Thr Pro Pro Gly Arg Ser Glu Asp Ser
            420                 425                 430

Ala Arg Phe Arg Ala Glu Lys Ala Val Gly Glu Trp Leu Ser Phe Ala
        435                 440                 445

Arg Ala Asn Ile Thr Arg Leu Met Ser Arg Lys Pro Pro Gly
    450                 455                 460
```

<210> SEQ ID NO 37
<211> LENGTH: 1329
<212> TYPE: DNA
<213> ORGANISM: Unknown
<220> FEATURE:
<223> OTHER INFORMATION: Obtained from an environmental sample.

<400> SEQUENCE: 37

```
atgagaaatt tcagcaaggg attgaccagt attttgctta gcatagcgac atccaccagt      60

gcgatggcct ttacccagat cggggccggc ggagcgattc cgatgggcca tgagtggcta     120

acccgccgct cggcgctgga actgctgaat gccgacaatc tggtcggcaa tgacccggcc     180

gacccacgct tgggctggag cgaaggtctc gccaacaatc tcgatctctc gaatgcccag     240

aacgaagtgc agcgcatcaa gagcattacc aagagccacg ccctgtatga gccgcgttac     300

gatgacgttt tcgccgccat cgtcggcgag cgctgggttg ataccgccgg tttcaacgtg     360

gccaaggcca ccgtcggcaa gatcgattgc ttcagcgccg tcgcgcaaga gcccgccgat     420
```

```
gtgcaacaag accatttcat gcgccgttat gacgacgtgg gtggacaagg gggcgtgaac    480

gctgcccgcc gcgcgcagca gcgctttatc aatcacttcg tcaacgcagc catggccgaa    540

gagaagagca tcaaggcatg ggatggcggc ggttattctt cgctggaaaa agtcagccac    600

aactacttct tgtttggccg cgccgttcat ttgttccagg attctttcag ccccgaacac    660

accgtgcgcc tgcctgaaga caattacgtc aaagtccgtc aggtcaaggc gtatctctgc    720

tctgaaggtg ccgaacagca tacgcacaac acgcaagatg ccatcaactt caccagcggc    780

gatgtcatct ggaaacagaa cacccgtctg gatgcaggct ggagcaccta caaggccagc    840

aacatgaagc cggtggcatt ggttgccctc gaagccagca aagatttgtg ggccgccttt    900

attcgcacca tggccgtttc ccgcgaggag cgtcgcgccg tcgccgaaca ggaagcgcag    960

gctctcgtca atcactggtt gtcgttcgac gaacaggaaa tgctgaactg gtacgaagaa   1020

gaagagcacc gcgatcatac gtacgtcaag gaacccggcc agagcggccc aggttcgtcg   1080

ttattcgatt gcatggttgg tctgggtgtg gcctcgggca gtcaggcgca acgggtggcg   1140

gaactcgatc agcaacgccg ccaatgtttg ttcaacgtca aggccgctac tggctatggc   1200

gatctgaatg atccacacat ggatattccg tacaactggc aatgggtgtc gtcgacgcaa   1260

tggaaaatcc ctgcggccga ctggaaaatc ccgcagctgc ccgccgattc agggaaatca   1320

gtcgtcatc                                                           1329
```

<210> SEQ ID NO 38
<211> LENGTH: 443
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample.

<400> SEQUENCE: 38

```
Met Arg Asn Phe Ser Lys Gly Leu Thr Ser Ile Leu Leu Ser Ile Ala
 1               5                  10                  15

Thr Ser Thr Ser Ala Met Ala Phe Thr Gln Ile Gly Ala Gly Gly Ala
            20                  25                  30

Ile Pro Met Gly His Glu Trp Leu Thr Arg Arg Ser Ala Leu Glu Leu
        35                  40                  45

Leu Asn Ala Asp Asn Leu Val Gly Asn Asp Pro Ala Asp Pro Arg Leu
    50                  55                  60

Gly Trp Ser Glu Gly Leu Ala Asn Asn Leu Asp Leu Ser Asn Ala Gln
65                  70                  75                  80

Asn Glu Val Gln Arg Ile Lys Ser Ile Thr Lys Ser His Ala Leu Tyr
                85                  90                  95

Glu Pro Arg Tyr Asp Asp Val Phe Ala Ala Ile Val Gly Glu Arg Trp
            100                 105                 110

Val Asp Thr Ala Gly Phe Asn Val Ala Lys Ala Thr Val Gly Lys Ile
        115                 120                 125

Asp Cys Phe Ser Ala Val Ala Gln Glu Pro Ala Asp Val Gln Gln Asp
    130                 135                 140

His Phe Met Arg Arg Tyr Asp Asp Val Gly Gly Gln Gly Gly Val Asn
145                 150                 155                 160

Ala Ala Arg Arg Ala Gln Gln Arg Phe Ile Asn His Phe Val Asn Ala
                165                 170                 175

Ala Met Ala Glu Glu Lys Ser Ile Lys Ala Trp Asp Gly Gly Gly Tyr
            180                 185                 190
```

```
Ser Ser Leu Glu Lys Val Ser His Asn Tyr Phe Leu Phe Gly Arg Ala
        195                 200                 205

Val His Leu Phe Gln Asp Ser Phe Ser Pro Glu His Thr Val Arg Leu
    210                 215                 220

Pro Glu Asp Asn Tyr Val Lys Val Arg Gln Val Lys Ala Tyr Leu Cys
225                 230                 235                 240

Ser Glu Gly Ala Glu Gln His Thr His Asn Thr Gln Asp Ala Ile Asn
                245                 250                 255

Phe Thr Ser Gly Asp Val Ile Trp Lys Gln Asn Thr Arg Leu Asp Ala
            260                 265                 270

Gly Trp Ser Thr Tyr Lys Ala Ser Asn Met Lys Pro Val Ala Leu Val
        275                 280                 285

Ala Leu Glu Ala Ser Lys Asp Leu Trp Ala Ala Phe Ile Arg Thr Met
    290                 295                 300

Ala Val Ser Arg Glu Glu Arg Arg Ala Val Ala Glu Gln Glu Ala Gln
305                 310                 315                 320

Ala Leu Val Asn His Trp Leu Ser Phe Asp Glu Gln Glu Met Leu Asn
                325                 330                 335

Trp Tyr Glu Glu Glu Glu His Arg Asp His Thr Tyr Val Lys Glu Pro
            340                 345                 350

Gly Gln Ser Gly Pro Gly Ser Ser Leu Phe Asp Cys Met Val Gly Leu
        355                 360                 365

Gly Val Ala Ser Gly Ser Gln Ala Gln Arg Val Ala Glu Leu Asp Gln
    370                 375                 380

Gln Arg Arg Gln Cys Leu Phe Asn Val Lys Ala Ala Thr Gly Tyr Gly
385                 390                 395                 400

Asp Leu Asn Asp Pro His Met Asp Ile Pro Tyr Asn Trp Gln Trp Val
                405                 410                 415

Ser Ser Thr Gln Trp Lys Ile Pro Ala Ala Asp Trp Lys Ile Pro Gln
            420                 425                 430

Leu Pro Ala Asp Ser Gly Lys Ser Val Val Ile
        435                 440
```

<210> SEQ ID NO 39
<211> LENGTH: 1335
<212> TYPE: DNA
<213> ORGANISM: Unknown
<220> FEATURE:
<223> OTHER INFORMATION: Obtained from an environmental sample.

<400> SEQUENCE: 39

```
atggccaacc ccatcgtcat catccacggc tggagcgacg acttcggctc gttccgcaag      60

ctgcgcgact tcctctccac caacctcggc gttccggcga agatcctcaa gctcggcgac     120

tggatctcgc tcgacgacga cgtcggctac gccgacatcg cgatggcgct ggaacgcgcg     180

tggaaggcgg agaaactgcc gaccgcgccg cgttcggtcg acgtcgtcgt gcacagcacc     240

ggcgcgctgg tggtgcgcga atggatgacg cgctaccacg cgcccgaaac cgtgccgatc     300

cagcgcttcc tgcacctggc gccggccaac ttcggctcgc acctcgcgca caagggccgc     360

tcgttcatcg gccgcgcggt gaagggctgg aagaccggct tcgaaaccgg cacccgcatc     420

ctgcgcgggc tggaactcgc ctcgccctac tcgcgcgcgc tggccgagcg cgacctgttc     480

gtggcgccgt cgaagcgctg gtacggcgcc ggccgcatcc tcgccaccgt gctggtcggc     540

aacagcggct actccggcat ccaggccatc gccaacgagg acggctccga cggcaccgtg     600

cgcatcggca ccgccaacct gcaggcggcg cttgcgaagg tggtgttccc gcccggcccg     660
```

```
gtcgcgccgg tggtgcagtt ccgcaacatc gcgggcgcca ccgcgttcgc catcgtcgac    720

ggcgacaacc attccgacat caccatgaag gacaagccgt cgaagaccgg catccgcgag    780

gaactgatcc tcggcgcgct gaaggtgcgc gacgccgact tccccgagaa cgccgacggc    840

gcgttcccgt ggcaggcgaa gctcgacgcg aaggccggtg cggccaaggt gtcttcgccc    900

gggcgccaga acaccgtggt gcacctcacc gacagcttcg gcgacgacgt cgtcgatttc    960

ttcttcgagt tctggcgcag cgaacgcagc gacaaggtgt tcgagcagcg cttctacaag   1020

gacgtcatcg acgacgtgca cgtgtacgac ggcaacggcg cgtggcgctc gctcaacctc   1080

gacctcgaca agttcgaggc gctgcgcaag gacccgaagc tcggcttcga gaaactgctg   1140

gtcagcgtgt tcgcctcgcc cgcgaagaag ggcgacgcca aggtcggcta cagcaccgcc   1200

accggccgcg acatcggcgc ctggcacgtc gaaggccgtg acttcgccaa ggccttcacg   1260

ccgcaccgca ccctgttcgt cgacatcgag atcccacgca tcgtcgacga cgcggtgttc   1320

cggttccggg aatag                                                    1335


<210> SEQ ID NO 40
<211> LENGTH: 444
<212> TYPE: PRT
<213> ORGANISM: Unknown
<220> FEATURE:
<223> OTHER INFORMATION: Obtained from an environmental sample.

<400> SEQUENCE: 40

Met Ala Asn Pro Ile Val Ile Ile His Gly Trp Ser Asp Asp Phe Gly
 1               5                  10                  15

Ser Phe Arg Lys Leu Arg Asp Phe Leu Ser Thr Asn Leu Gly Val Pro
            20                  25                  30

Ala Lys Ile Leu Lys Leu Gly Asp Trp Ile Ser Leu Asp Asp Asp Val
        35                  40                  45

Gly Tyr Ala Asp Ile Ala Met Ala Leu Glu Arg Ala Trp Lys Ala Glu
    50                  55                  60

Lys Leu Pro Thr Ala Pro Arg Ser Val Asp Val Val Val His Ser Thr
65                  70                  75                  80

Gly Ala Leu Val Val Arg Glu Trp Met Thr Arg Tyr His Ala Pro Glu
                85                  90                  95

Thr Val Pro Ile Gln Arg Phe Leu His Leu Ala Pro Ala Asn Phe Gly
            100                 105                 110

Ser His Leu Ala His Lys Gly Arg Ser Phe Ile Gly Arg Ala Val Lys
        115                 120                 125

Gly Trp Lys Thr Gly Phe Glu Thr Gly Thr Arg Ile Leu Arg Gly Leu
    130                 135                 140

Glu Leu Ala Ser Pro Tyr Ser Arg Ala Leu Ala Glu Arg Asp Leu Phe
145                 150                 155                 160

Val Ala Pro Ser Lys Arg Trp Tyr Gly Ala Gly Arg Ile Leu Ala Thr
                165                 170                 175

Val Leu Val Gly Asn Ser Gly Tyr Ser Gly Ile Gln Ala Ile Ala Asn
            180                 185                 190

Glu Asp Gly Ser Asp Gly Thr Val Arg Ile Gly Thr Ala Asn Leu Gln
        195                 200                 205

Ala Ala Leu Ala Lys Val Val Phe Pro Pro Gly Pro Val Ala Pro Val
    210                 215                 220

Val Gln Phe Arg Asn Ile Ala Gly Ala Thr Ala Phe Ala Ile Val Asp
225                 230                 235                 240
```

```
Gly Asp Asn His Ser Asp Ile Thr Met Lys Asp Lys Pro Ser Lys Thr
                245                 250                 255

Gly Ile Arg Glu Glu Leu Ile Leu Gly Ala Leu Lys Val Arg Asp Ala
            260                 265                 270

Asp Phe Pro Glu Asn Ala Asp Gly Ala Phe Pro Trp Gln Ala Lys Leu
        275                 280                 285

Asp Ala Lys Ala Gly Ala Ala Lys Val Ser Ser Pro Gly Arg Gln Asn
    290                 295                 300

Thr Val Val His Leu Thr Asp Ser Phe Gly Asp Asp Val Val Asp Phe
305                 310                 315                 320

Phe Phe Glu Phe Trp Arg Ser Glu Arg Ser Asp Lys Val Phe Glu Gln
                325                 330                 335

Arg Phe Tyr Lys Asp Val Ile Asp Asp Val His Val Tyr Asp Gly Asn
            340                 345                 350

Gly Ala Trp Arg Ser Leu Asn Leu Asp Leu Asp Lys Phe Glu Ala Leu
        355                 360                 365

Arg Lys Asp Pro Lys Leu Gly Phe Glu Lys Leu Leu Val Ser Val Phe
    370                 375                 380

Ala Ser Pro Ala Lys Lys Gly Asp Ala Lys Val Gly Tyr Ser Thr Ala
385                 390                 395                 400

Thr Gly Arg Asp Ile Gly Ala Trp His Val Glu Gly Arg Asp Phe Ala
                405                 410                 415

Lys Ala Phe Thr Pro His Arg Thr Leu Phe Val Asp Ile Glu Ile Pro
            420                 425                 430

Arg Ile Val Asp Asp Ala Val Phe Arg Phe Arg Glu
        435                 440
```

<210> SEQ ID NO 41
<211> LENGTH: 1419
<212> TYPE: DNA
<213> ORGANISM: Unknown
<220> FEATURE:
<223> OTHER INFORMATION: Obtained from an environmental sample.

<400> SEQUENCE: 41

```
atgacgctcc gatcaacgga ctatgcgctg ctggcgcagg agagctacca cgacagccag     60

gtggacgccg acgtcaagct ggatggcgtg gcgtataaag tcttcgccac caccagcgac    120

gggctcaccg gattccaggc cacggcctac cagcgccagg acaccggcga ggtagtgatt    180

gcgtaccgcg gcacggagtt tgatcgcgag cccgtccgcg acggcggcgt cgatgcgggc    240

atggtgctgc tcggtgtcaa cgcacaggca ccagcgtcgg aagtgttcac ccggcaagtg    300

atcgagaagg cgaaacacga agccgagctc aacgaccgcg aaccgcagat caccgtcacc    360

ggccattccc tcggcggcac cctcgccgag atcaacgccg cgaagtacgg cctccatggc    420

gaaaccttca acgcctacgg cgcagccagc ctcaagggta ttccggaggg cggcgatacc    480

gtcatcgacc acgtccgtgc cggcgatctc gtcagcgcgg ccagccccca ctacgggcag    540

gtacgcgtct acgcggcgca gcaggacatc gatacgctgc aacacgccgg ttaccgcgat    600

gacagcggca tcctcagctt gcgcaacccg atcaaggcca cggatttcga tgcccatgcc    660

atcgataact tcgtgcccaa cagcaagctg ctcggtcagt cgatcatcgc gccggaaaac    720

gtggcgcgtt acgatgccca caaaggcatg gtcgaccgtt accgcgatga cgtggccgat    780

atccgcaagg gcatctcggc gccctgggaa atccccaagg ccatcggcga gctgaaggac    840

accctggagc acgaagcctt cgaactcgcc ggcaagggca ttctcgcggt ggagcacggc    900

ttcgaacatc tcaaggagga gatcggcgaa ggcatccacg ccgtggagga gaaagcttcc    960
```

agcgcgtggc ataccctcac ccatcccaag gaatggttcg agcacgataa acccaaggtg 1020
accctggacc acccggacca ccccgaccat gccctgttca agcaggcgca gggcgcggtg 1080
cacacagtcg atgcctcgca cggccgcacc cctgacaaga ccagcgacca gatcgccggc 1140
tcgctggtgg tatcggcacg ccgtgacggc cttgagcggg tagaccgcgc tgtactcagc 1200
gatgacgcca accgcctgta cggtgtgcag ggtgcggtgg actcgccgct gaagcaggtc 1260
accgaagtga acaccgccac cgccgcgcag acatcgctcc agcagagcag cgtggcctgg 1320
cagcaacagg cagaaatcgc gcgtcagaac caggcggcaa gccaggctca gcgcatggac 1380
cagcaggtgc cgccgcaggc acccgcgcac ggcatgtaa 1419

<210> SEQ ID NO 42
<211> LENGTH: 472
<212> TYPE: PRT
<213> ORGANISM: Unknown
<220> FEATURE:
<223> OTHER INFORMATION: Obtained from an environmental sample.

<400> SEQUENCE: 42

Met Thr Leu Arg Ser Thr Asp Tyr Ala Leu Leu Ala Gln Glu Ser Tyr
1 5 10 15

His Asp Ser Gln Val Asp Ala Asp Val Lys Leu Asp Gly Val Ala Tyr
20 25 30

Lys Val Phe Ala Thr Thr Ser Asp Gly Leu Thr Gly Phe Gln Ala Thr
35 40 45

Ala Tyr Gln Arg Gln Asp Thr Gly Glu Val Val Ile Ala Tyr Arg Gly
50 55 60

Thr Glu Phe Asp Arg Glu Pro Val Arg Asp Gly Gly Val Asp Ala Gly
65 70 75 80

Met Val Leu Leu Gly Val Asn Ala Gln Ala Pro Ala Ser Glu Val Phe
85 90 95

Thr Arg Gln Val Ile Glu Lys Ala Lys His Glu Ala Glu Leu Asn Asp
100 105 110

Arg Glu Pro Gln Ile Thr Val Thr Gly His Ser Leu Gly Gly Thr Leu
115 120 125

Ala Glu Ile Asn Ala Ala Lys Tyr Gly Leu His Gly Glu Thr Phe Asn
130 135 140

Ala Tyr Gly Ala Ala Ser Leu Lys Gly Ile Pro Glu Gly Gly Asp Thr
145 150 155 160

Val Ile Asp His Val Arg Ala Gly Asp Leu Val Ser Ala Ala Ser Pro
165 170 175

His Tyr Gly Gln Val Arg Val Tyr Ala Ala Gln Gln Asp Ile Asp Thr
180 185 190

Leu Gln His Ala Gly Tyr Arg Asp Asp Ser Gly Ile Leu Ser Leu Arg
195 200 205

Asn Pro Ile Lys Ala Thr Asp Phe Asp Ala His Ala Ile Asp Asn Phe
210 215 220

Val Pro Asn Ser Lys Leu Leu Gly Gln Ser Ile Ile Ala Pro Glu Asn
225 230 235 240

Val Ala Arg Tyr Asp Ala His Lys Gly Met Val Asp Arg Tyr Arg Asp
245 250 255

Asp Val Ala Asp Ile Arg Lys Gly Ile Ser Ala Pro Trp Glu Ile Pro
260 265 270

Lys Ala Ile Gly Glu Leu Lys Asp Thr Leu Glu His Glu Ala Phe Glu
275 280 285

```
Leu Ala Gly Lys Gly Ile Leu Ala Val Glu His Gly Phe Glu His Leu
    290                 295                 300

Lys Glu Glu Ile Gly Glu Gly Ile His Ala Val Glu Glu Lys Ala Ser
305                 310                 315                 320

Ser Ala Trp His Thr Leu Thr His Pro Lys Glu Trp Phe Glu His Asp
                325                 330                 335

Lys Pro Lys Val Thr Leu Asp His Pro Asp His Pro Asp His Ala Leu
            340                 345                 350

Phe Lys Gln Ala Gln Gly Ala Val His Thr Val Asp Ala Ser His Gly
        355                 360                 365

Arg Thr Pro Asp Lys Thr Ser Asp Gln Ile Ala Gly Ser Leu Val Val
    370                 375                 380

Ser Ala Arg Arg Asp Gly Leu Glu Arg Val Asp Arg Ala Val Leu Ser
385                 390                 395                 400

Asp Asp Ala Asn Arg Leu Tyr Gly Val Gln Gly Ala Val Asp Ser Pro
                405                 410                 415

Leu Lys Gln Val Thr Glu Val Asn Thr Ala Thr Ala Ala Gln Thr Ser
            420                 425                 430

Leu Gln Gln Ser Ser Val Ala Trp Gln Gln Gln Ala Glu Ile Ala Arg
        435                 440                 445

Gln Asn Gln Ala Ala Ser Gln Ala Gln Arg Met Asp Gln Gln Val Pro
    450                 455                 460

Pro Gln Ala Pro Ala His Gly Met
465                 470
```

<210> SEQ ID NO 43
<211> LENGTH: 1287
<212> TYPE: DNA
<213> ORGANISM: Unknown
<220> FEATURE:
<223> OTHER INFORMATION: Obtained from an environmental sample.

<400> SEQUENCE: 43

```
atgtcgatta ccgtttaccg gaagccctcc ggcgggtttg gagcgatagt tcctcaagcg     60

aaaattgaga accttgtttt cgagggcggc ggaccaaagg gcctggtcta tgtcggcgcg    120

gtcgaggttc tcggtgaaag gggactgctg gaagggatcg caaatgtcgg cggcgcttca    180

gcaggcgcca tgaccgctct agccgtcggt ctgggactga gccccaggga aattcgcgcg    240

gtcgtcttta accagaacat tgcggacctc accgatatcg agaagaccgt cgagccgtcc    300

tccgggatca caggcatgtt caagagcgtg ttcaagaagg gttggcaggc ggtgcgcaac    360

gtaaccggca cctctgacga gcgcgggcgc gggctctatc gcggcgagaa gttgcgagcc    420

tggatcagag acctgattgc acagcgagtc gaggcagggc gctcagaggt gctgagccga    480

gccgacgccg acgggcggaa cttctatgag aaagccgccg caaagaaggg cgccctgaca    540

tttgccgaac ttgatcgggt ggcgcaaatg gcgccgggcc tgcggcttcg ccgcctggcc    600

ttcaccggaa ccaacttcac gtcgaagaag ctcgaagtgt tcagtctgca cgagaccccg    660

gacatgccga tcgacgtcgc ggtacgcatc tcggcatcgt tgccatggtt tttcaaatcc    720

gtgaaatgga acggctccga atacatagat ggcggatgcc tgtcgaactt cccaatgccg    780

atattcgacg tcgatcccta tcgtggcgac gcatcgtcga agatccggct cggcatcttc    840

ggccagaacc tcgcgacgct cggcttcaag gtcgacagcg aggaggagat ccgcgacatc    900

ctctggcgta gccccgagag cacgagcgac ggctttttcc aaggcatcct gtcaagcgtg    960

aaagcctcgg cagaacactg ggtcgtcggc atcgatgtcg agggcgccac ccgcgcgtcg   1020
```

```
aacgtggccg ttcacggcaa gtatgctcag cgaacgatcc agataccgga cctcggatat   1080

agcacgttca agttcgatct ctcagacgcg gacaaggagc gcatggccga ggccggcgca   1140

aaggccacgc gggaatggct ggcgctgtac ttcgacgacg ccggaataga ggtcgaattt   1200

tctgatccga acgaattgcg cggccagttg tccgacgccg cattcgcaga cctcgaggat   1260

tcgtttcgag ccttgatcgc ggcctag                                       1287


<210> SEQ ID NO 44
<211> LENGTH: 428
<212> TYPE: PRT
<213> ORGANISM: Unknown
<220> FEATURE:
<223> OTHER INFORMATION: Obtained from an environmental sample.

<400> SEQUENCE: 44

Met Ser Ile Thr Val Tyr Arg Lys Pro Ser Gly Gly Phe Gly Ala Ile
 1               5                  10                  15

Val Pro Gln Ala Lys Ile Glu Asn Leu Val Phe Glu Gly Gly Gly Pro
            20                  25                  30

Lys Gly Leu Val Tyr Val Gly Ala Val Glu Val Leu Gly Glu Arg Gly
        35                  40                  45

Leu Leu Glu Gly Ile Ala Asn Val Gly Gly Ala Ser Ala Gly Ala Met
    50                  55                  60

Thr Ala Leu Ala Val Gly Leu Gly Leu Ser Pro Arg Glu Ile Arg Ala
65                  70                  75                  80

Val Val Phe Asn Gln Asn Ile Ala Asp Leu Thr Asp Ile Glu Lys Thr
                85                  90                  95

Val Glu Pro Ser Ser Gly Ile Thr Gly Met Phe Lys Ser Val Phe Lys
            100                 105                 110

Lys Gly Trp Gln Ala Val Arg Asn Val Thr Gly Thr Ser Asp Glu Arg
        115                 120                 125

Gly Arg Gly Leu Tyr Arg Gly Glu Lys Leu Arg Ala Trp Ile Arg Asp
    130                 135                 140

Leu Ile Ala Gln Arg Val Glu Ala Gly Arg Ser Glu Val Leu Ser Arg
145                 150                 155                 160

Ala Asp Ala Asp Gly Arg Asn Phe Tyr Glu Lys Ala Ala Ala Lys Lys
                165                 170                 175

Gly Ala Leu Thr Phe Ala Glu Leu Asp Arg Val Ala Gln Met Ala Pro
            180                 185                 190

Gly Leu Arg Leu Arg Arg Leu Ala Phe Thr Gly Thr Asn Phe Thr Ser
        195                 200                 205

Lys Lys Leu Glu Val Phe Ser Leu His Glu Thr Pro Asp Met Pro Ile
    210                 215                 220

Asp Val Ala Val Arg Ile Ser Ala Ser Leu Pro Trp Phe Phe Lys Ser
225                 230                 235                 240

Val Lys Trp Asn Gly Ser Glu Tyr Ile Asp Gly Gly Cys Leu Ser Asn
                245                 250                 255

Phe Pro Met Pro Ile Phe Asp Val Asp Pro Tyr Arg Gly Asp Ala Ser
            260                 265                 270

Ser Lys Ile Arg Leu Gly Ile Phe Gly Gln Asn Leu Ala Thr Leu Gly
        275                 280                 285

Phe Lys Val Asp Ser Glu Glu Glu Ile Arg Asp Ile Leu Trp Arg Ser
    290                 295                 300

Pro Glu Ser Thr Ser Asp Gly Phe Phe Gln Gly Ile Leu Ser Ser Val
305                 310                 315                 320
```

```
Lys Ala Ser Ala Glu His Trp Val Val Gly Ile Asp Val Glu Gly Ala
                325                 330                 335

Thr Arg Ala Ser Asn Val Ala Val His Gly Lys Tyr Ala Gln Arg Thr
            340                 345                 350

Ile Gln Ile Pro Asp Leu Gly Tyr Ser Thr Phe Lys Phe Asp Leu Ser
        355                 360                 365

Asp Ala Asp Lys Glu Arg Met Ala Glu Ala Gly Ala Lys Ala Thr Arg
    370                 375                 380

Glu Trp Leu Ala Leu Tyr Phe Asp Asp Ala Gly Ile Glu Val Glu Phe
385                 390                 395                 400

Ser Asp Pro Asn Glu Leu Arg Gly Gln Leu Ser Asp Ala Ala Phe Ala
                405                 410                 415

Asp Leu Glu Asp Ser Phe Arg Ala Leu Ile Ala Ala
            420                 425


<210> SEQ ID NO 45
<211> LENGTH: 1038
<212> TYPE: DNA
<213> ORGANISM: Unknown
<220> FEATURE:
<223> OTHER INFORMATION: Obtained from an environmental sample.

<400> SEQUENCE: 45

atgacaaccc aatttagaaa cttgatattt gaaggcggcg gtgtaaaagg tgttgcttac      60

attggcgcca tgcagattct cgaaaatcgt ggcgtgttgc aagatattca ccgagtcgga     120

gggtgcagtg cgggtgcgat taatgcgctg atttttgcgc tgggttacac ggttcgtgag     180

caaaaagaga tcttacaagc caccgatttt aaccagttta tggataactc ttggggtgtt     240

attcgtgata ttcgcaggct tgctcgagac tttggctgga ataagggtga tttctttagt     300

agctggatag gtgatttgat tcatcgtcgt ttggggaatc gccgagcgac gttcaaagat     360

ctgcaaaatg ccaagcttcc tgatctttat gtcatcggta ctaatctgtc tacagggttt     420

gcagaggttt tttctgccga aagacacccc gatatggagc tggcgacagc ggtgcgtatc     480

tccatgtcga taccgctgtt ctttgcagcc gtgcgtcacg gtgatcgaca agatgtgtat     540

gtcgatgggg gtgttcaact taactatccg attaaactgt ttgatcggga gcgttacatt     600

gatctggcca aagatcccgg tgctgttcgg cgaacgggtt attacaacaa agaaaacgct     660

cgctttcagc ttgagcggcc cggtcatagc cctatgttt  acaatcgcca gaccttgggt     720

ttgcgtcttg atagtcgcga gcagataggg ctctttcgtt atgacgaacc cctcaagggc     780

aaacccatta agtccttcac tgactacgct cgacaacttt tcggtgcgtt gatgaatgca     840

caggaaaaga ttcatctaca tggcgatgat tggcaacgca cggtctatat cgatacattg     900

gatgtgggta cgacggactt caatctttct gatgcaacta agcaagcact gattgagcaa     960

ggaattaacg gcaccgaaaa ttatttcgag tggtttgata atccgttaga gaagcccgtg    1020

aatagagtgg agtcatag                                                  1038


<210> SEQ ID NO 46
<211> LENGTH: 345
<212> TYPE: PRT
<213> ORGANISM: Unknown
<220> FEATURE:
<223> OTHER INFORMATION: Obtained from an environmental sample.

<400> SEQUENCE: 46

Met Thr Thr Gln Phe Arg Asn Leu Ile Phe Glu Gly Gly Gly Val Lys
 1               5                  10                  15
```

```
Gly Val Ala Tyr Ile Gly Ala Met Gln Ile Leu Glu Asn Arg Gly Val
            20                  25                  30

Leu Gln Asp Ile His Arg Val Gly Gly Cys Ser Ala Gly Ala Ile Asn
        35                  40                  45

Ala Leu Ile Phe Ala Leu Gly Tyr Thr Val Arg Glu Gln Lys Glu Ile
    50                  55                  60

Leu Gln Ala Thr Asp Phe Asn Gln Phe Met Asp Asn Ser Trp Gly Val
65                  70                  75                  80

Ile Arg Asp Ile Arg Arg Leu Ala Arg Asp Phe Gly Trp Asn Lys Gly
                85                  90                  95

Asp Phe Phe Ser Ser Trp Ile Gly Asp Leu Ile His Arg Arg Leu Gly
            100                 105                 110

Asn Arg Arg Ala Thr Phe Lys Asp Leu Gln Asn Ala Lys Leu Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Ala Lys Asp Pro Gly Ala
        195                 200                 205

Val Arg Arg Thr Gly Tyr Tyr Asn Lys Glu Asn Ala Arg Phe Gln Leu
    210                 215                 220

Glu Arg Pro Gly His Ser Pro Tyr Val Tyr Asn Arg Gln Thr Leu Gly
225                 230                 235                 240

Leu Arg Leu Asp Ser Arg Glu Gln Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Lys Ile His Leu His Gly
        275                 280                 285

Asp Asp Trp Gln Arg Thr Val Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Glu Trp Phe Asp Asn Pro Leu
                325                 330                 335

Glu Lys Pro Val Asn Arg Val Glu Ser
            340                 345
```

<210> SEQ ID NO 47
<211> LENGTH: 1476
<212> TYPE: DNA
<213> ORGANISM: Unknown
<220> FEATURE:
<223> OTHER INFORMATION: Obtained from an environmental sample.

<400> SEQUENCE: 47

```
atgtcaacaa aagtagtatt tgtacatgga tggagcgtta ccaacctaaa tacatatggc      60

gaacttccgt tgagattaaa ggccgaagca ataagcagga acctgaacat cgaagtaaat     120

gaaattttcc tgggccgtta tatcagcttt aatgataaca ttacattaga tgacgtttcg     180
```

```
cgggctttta atacggccat tagcgaacag ttagacaata cagacaggtt tatatgtatt    240

acacattcta ccggagggcc ggttattcgc gaatggttaa ataaatacta ttataatgaa    300

cgtccaccac taagtcattt aataatgctt gcaccggcca attttggttc ggcattggct    360

cgtttaggga aaagtaaatt aagccgtatt aaaagttggt ttgaaggtgt agaaccaggg    420

cagaaaattt tagactggct ggagtgtgga agcaaccaat cgtggttact aaataaagac    480

tggatcgaca atggcaattt tcagattggc gctgataagt atttcccgtt tgttatcatt    540

ggccagtcga ttgatcgtaa actttacgat catcttaact catataccgg cgagcttggg    600

tccgatggtg tagttcgcac ctcaggagct aatcttaatt cgcggtatat taagcttgtt    660

caggacagaa atacaatagc taatggaaat atttccagta cattacgaat tgccgaatat    720

agagaagctt gtgcaacgcc catacgggta gttagaggta aatcgcattc gggcgatgaa    780

atgggtatca tgaaaagtgt taaaaaagaa attactgatg ccggaagcaa ggaaacaata    840

aatgccatat tcgagtgtat tgaagttaca aacaacgaac aatatcaatc cttaattact    900

aaatttgata acgaaacagc acaggtacaa aaggatgagc tgattgaaac ggaaacagaa    960

ttatttttaa tgcaccgtca tttcattcac gaccgctttt cgcaattcat ttttaaagta   1020

actgactcag aagggcaacc tgttacagat tatgatttaa tttttacagc cgggccacaa   1080

aacgatgcga accacttacc ggaaggattt gccattgaca ggcaacaaaa ttcaaataat   1140

aacgaaacca ttacgtatta ttttaattac gatgtattga aaggggctcc cgcaaatgtt   1200

taccgggacg cattaccagg tatttctatg ctggggctaa ccataaaccc aaggccggac   1260

gaaggttttg taagatatat cccatgcagc attaaagcca attccgagtt gatggaaaaa   1320

gcctttaaac caaattctac taccttggtc gatattgtta ttcaacgtgt agttagcaaa   1380

gaagttttc ggttggaaaa gttaactggt agctcaatgc caacagacaa agatgggaat    1440

tttaaaaata ctgaacctgg taacgaaata atatga                             1476
```

<210> SEQ ID NO 48
<211> LENGTH: 491
<212> TYPE: PRT
<213> ORGANISM: Unknown
<220> FEATURE:
<223> OTHER INFORMATION: Obtained from an environmental sample.

<400> SEQUENCE: 48

```
Met Ser Thr Lys Val Val Phe Val His Gly Trp Ser Val Thr Asn Leu
 1               5                  10                  15

Asn Thr Tyr Gly Glu Leu Pro Leu Arg Leu Lys Ala Glu Ala Ile Ser
            20                  25                  30

Arg Asn Leu Asn Ile Glu Val Asn Glu Ile Phe Leu Gly Arg Tyr Ile
        35                  40                  45

Ser Phe Asn Asp Asn Ile Thr Leu Asp Asp Val Ser Arg Ala Phe Asn
    50                  55                  60

Thr Ala Ile Ser Glu Gln Leu Asp Asn Thr Asp Arg Phe Ile Cys Ile
65                  70                  75                  80

Thr His Ser Thr Gly Gly Pro Val Ile Arg Glu Trp Leu Asn Lys Tyr
                85                  90                  95

Tyr Tyr Asn Glu Arg Pro Pro Leu Ser His Leu Ile Met Leu Ala Pro
            100                 105                 110

Ala Asn Phe Gly Ser Ala Leu Ala Arg Leu Gly Lys Ser Lys Leu Ser
        115                 120                 125

Arg Ile Lys Ser Trp Phe Glu Gly Val Glu Pro Gly Gln Lys Ile Leu
    130                 135                 140
```

Asp Trp Leu Glu Cys Gly Ser Asn Gln Ser Trp Leu Leu Asn Lys Asp
145 150 155 160

Trp Ile Asp Asn Gly Asn Phe Gln Ile Gly Ala Asp Lys Tyr Phe Pro
165 170 175

Phe Val Ile Ile Gly Gln Ser Ile Asp Arg Lys Leu Tyr Asp His Leu
180 185 190

Asn Ser Tyr Thr Gly Glu Leu Gly Ser Asp Gly Val Val Arg Thr Ser
195 200 205

Gly Ala Asn Leu Asn Ser Arg Tyr Ile Lys Leu Val Gln Asp Arg Asn
210 215 220

Thr Ile Ala Asn Gly Asn Ile Ser Ser Thr Leu Arg Ile Ala Glu Tyr
225 230 235 240

Arg Glu Ala Cys Ala Thr Pro Ile Arg Val Val Arg Gly Lys Ser His
245 250 255

Ser Gly Asp Glu Met Gly Ile Met Lys Ser Val Lys Lys Glu Ile Thr
260 265 270

Asp Ala Gly Ser Lys Glu Thr Ile Asn Ala Ile Phe Glu Cys Ile Glu
275 280 285

Val Thr Asn Asn Glu Gln Tyr Gln Ser Leu Ile Thr Lys Phe Asp Asn
290 295 300

Glu Thr Ala Gln Val Gln Lys Asp Glu Leu Ile Glu Thr Glu Thr Glu
305 310 315 320

Leu Phe Leu Met His Arg His Phe Ile His Asp Arg Phe Ser Gln Phe
325 330 335

Ile Phe Lys Val Thr Asp Ser Glu Gly Gln Pro Val Thr Asp Tyr Asp
340 345 350

Leu Ile Phe Thr Ala Gly Pro Gln Asn Asp Ala Asn His Leu Pro Glu
355 360 365

Gly Phe Ala Ile Asp Arg Gln Gln Asn Ser Asn Asn Asn Glu Thr Ile
370 375 380

Thr Tyr Tyr Phe Asn Tyr Asp Val Leu Lys Gly Ala Pro Ala Asn Val
385 390 395 400

Tyr Arg Asp Ala Leu Pro Gly Ile Ser Met Leu Gly Leu Thr Ile Asn
405 410 415

Pro Arg Pro Asp Glu Gly Phe Val Arg Tyr Ile Pro Cys Ser Ile Lys
420 425 430

Ala Asn Ser Glu Leu Met Glu Lys Ala Phe Lys Pro Asn Ser Thr Thr
435 440 445

Leu Val Asp Ile Val Ile Gln Arg Val Val Ser Lys Glu Val Phe Arg
450 455 460

Leu Glu Lys Leu Thr Gly Ser Ser Met Pro Thr Asp Lys Asp Gly Asn
465 470 475 480

Phe Lys Asn Thr Glu Pro Gly Asn Glu Ile Ile
485 490

<210> SEQ ID NO 49
<211> LENGTH: 1257
<212> TYPE: DNA
<213> ORGANISM: Unknown
<220> FEATURE:
<223> OTHER INFORMATION: Obtained from an environmental sample.

<400> SEQUENCE: 49
atgaattttt ggtcctttct tcttagtata accttaccta tgggggtagg cgttgctcat 60
gcacagcccg atacggattt tcaatcggct gagccttatg tctcttctgc gccaatgggg 120

```
cgacaaactt atacttacgt gcgttgttgg tatcgcacca gccacagtac ggatgatcca    180

gcgacagatt ggcagtgggc gagaaactcc gatggtagct attttacttt gcaaggatac    240

tggtggagct cggtaagact aaaaaatatg ttttacactc aaacctcgca aaatgttatt    300

cgtcagcgct gcgaacacac tttaagcatt aatcatgata atgcggatat tactttttat    360

gcggcggata atcgtttctc attaaaccat acgatttggt cgaatgatcc tgtcatgcag    420

gctaatcaaa tcaacaagat tgtcgcgttt ggtgacagct tgtccgatac cggtaatatt    480

tttaatgccg cgcagtggcg ttttcctaat cccaatagtt ggtttttggg gcattttttct    540

aacggtttgg tatggactga gtacttagct aaacagaaaa acttaccgat atataactgg    600

gcggttggtg gcgctgctgg ggcgaatcaa tatgtggcgt taaccggtgt tacaggccaa    660

gtgaactctt atttacagta catgggtaaa gcgcaaaact atcgtccaca gaataccttg    720

tacactttgg tcttcggttt gaatgatttt atgaattata accgtgaggt tgctgaggtg    780

gcggctgatt ttgaaacggc attacagcgt ttaacgcaag ctggcgcgca aaatatttta    840

atgatgacgc taccggatgt gactaaagca ccacagttta cctactcaac tcaagcggaa    900

atcgacttga ttcaaggtaa aatcaatgcg ttgaacatca agttaaaaca gttgactgcg    960

caatatattt tacaaggcta tgccattcat ctatttgata cttatgagtt atttgattca   1020

atggtcgctg aaccggaaaa gcatggcttt gctaatgcca gtgaaccttg tttgaatctc   1080

acccgttctt cagcggcgga ttatttgtac cgtcatccca ttaccaatac ttgtgctcgt   1140

tatggtgcag acaaatttgt attttgggat gtcacccatc caaccacggc aactcatcgc   1200

tatatttcac aaacgctgtt agcgccgggt aatggattac aatattttaa tttttaa      1257
```

<210> SEQ ID NO 50
<211> LENGTH: 418
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample.

<400> SEQUENCE: 50

```
Met Asn Phe Trp Ser Phe Leu Leu Ser Ile Thr Leu Pro Met Gly Val
 1               5                  10                  15

Gly Val Ala His Ala Gln Pro Asp Thr Asp Phe Gln Ser Ala Glu Pro
            20                  25                  30

Tyr Val Ser Ser Ala Pro Met Gly Arg Gln Thr Tyr Thr Tyr Val Arg
        35                  40                  45

Cys Trp Tyr Arg Thr Ser His Ser Thr Asp Asp Pro Ala Thr Asp Trp
    50                  55                  60

Gln Trp Ala Arg Asn Ser Asp Gly Ser Tyr Phe Thr Leu Gln Gly Tyr
65                  70                  75                  80

Trp Trp Ser Ser Val Arg Leu Lys Asn Met Phe Tyr Thr Gln Thr Ser
                85                  90                  95

Gln Asn Val Ile Arg Gln Arg Cys Glu His Thr Leu Ser Ile Asn His
            100                 105                 110

Asp Asn Ala Asp Ile Thr Phe Tyr Ala Ala Asp Asn Arg Phe Ser Leu
        115                 120                 125

Asn His Thr Ile Trp Ser Asn Asp Pro Val Met Gln Ala Asn Gln Ile
    130                 135                 140

Asn Lys Ile Val Ala Phe Gly Asp Ser Leu Ser Asp Thr Gly Asn Ile
145                 150                 155                 160
```

```
Phe Asn Ala Ala Gln Trp Arg Phe Pro Asn Pro Asn Ser Trp Phe Leu
                165                 170                 175

Gly His Phe Ser Asn Gly Leu Val Trp Thr Glu Tyr Leu Ala Lys Gln
            180                 185                 190

Lys Asn Leu Pro Ile Tyr Asn Trp Ala Val Gly Gly Ala Ala Gly Ala
        195                 200                 205

Asn Gln Tyr Val Ala Leu Thr Gly Val Thr Gly Gln Val Asn Ser Tyr
    210                 215                 220

Leu Gln Tyr Met Gly Lys Ala Gln Asn Tyr Arg Pro Gln Asn Thr Leu
225                 230                 235                 240

Tyr Thr Leu Val Phe Gly Leu Asn Asp Phe Met Asn Tyr Asn Arg Glu
                245                 250                 255

Val Ala Glu Val Ala Ala Asp Phe Glu Thr Ala Leu Gln Arg Leu Thr
            260                 265                 270

Gln Ala Gly Ala Gln Asn Ile Leu Met Met Thr Leu Pro Asp Val Thr
        275                 280                 285

Lys Ala Pro Gln Phe Thr Tyr Ser Thr Gln Ala Glu Ile Asp Leu Ile
    290                 295                 300

Gln Gly Lys Ile Asn Ala Leu Asn Ile Lys Leu Lys Gln Leu Thr Ala
305                 310                 315                 320

Gln Tyr Ile Leu Gln Gly Tyr Ala Ile His Leu Phe Asp Thr Tyr Glu
                325                 330                 335

Leu Phe Asp Ser Met Val Ala Glu Pro Glu Lys His Gly Phe Ala Asn
            340                 345                 350

Ala Ser Glu Pro Cys Leu Asn Leu Thr Arg Ser Ser Ala Ala Asp Tyr
        355                 360                 365

Leu Tyr Arg His Pro Ile Thr Asn Thr Cys Ala Arg Tyr Gly Ala Asp
    370                 375                 380

Lys Phe Val Phe Trp Asp Val Thr His Pro Thr Thr Ala Thr His Arg
385                 390                 395                 400

Tyr Ile Ser Gln Thr Leu Leu Ala Pro Gly Asn Gly Leu Gln Tyr Phe
                405                 410                 415

Asn Phe
```

<210> SEQ ID NO 51
<211> LENGTH: 1482
<212> TYPE: DNA
<213> ORGANISM: Unknown
<220> FEATURE:
<223> OTHER INFORMATION: Obtained from an environmental sample.

<400> SEQUENCE: 51

```
atgacaatcc gctcaacgga ctatgcgctg ctcgcgcagg agagctacca cgacagccag      60

gtcgatgccg acgtcaaact cgatggcatc gcctacaagg tcttcgccac caccgatgac     120

ccgctcacgg ggttccaggc caccgcgtac cagcgccagg acaccggcga agtcgtcatc     180

gcctatcgtg gtacggaatt cgaccgcgag cccgttcgcg acggcggcgt cgatgccggc     240

atggtgctgc tgggggtgaa tgcccagtcg cctgcctccg agctatttac ccgcgaagtg     300

atcgagaagg cgacgcacga agccgaactc aatgaccgcg agccccggat caccgtgact     360

ggccactccc tcggcggcac cctcgccgaa atcaacgcgg ccaagtacgg cctgcacggc     420

gaaaccttca acgcatacgg tgcggccagc ctcaagggca tcccggaagg cggcaatacc     480

gtgatcgacc acgtgcgcgc tggcgacctc gtcagcgccg ccagcccgca ttacgggcag     540

gtgcgcgtct acgcggccca gcaggatatc gacaccttgc agcatgccgg ctaccgcgac     600
```

gacagcggca tccttagcct gcgcaacccg atcaaggcca cggatttcga cgcgcacgcc 660
atcgacaact tcgtgccgaa cagcaaactg cttggccagt cgatcatcgc gccggaaaac 720
gaagcccgtt acgaagccca caagggcatg gtcgaccgct accgcgatga cgtggctgac 780
atccgcatgc tcgtctccgc tcccctgaac atcccgcgca ccatcggcga tatcaaggat 840
gccgtggaac gcgaggcatt tgagctggct ggcaagggca tcctcgccgt tgaacacggc 900
atcgaagagg tcgtgcacga ggcaaaggaa ggcttcgagc acctcaagga aggctttgag 960
cacctgaagg aagaagtcag cgagggcttc catgccttcg aggaaaaggc ctccagcgcg 1020
tggcatacgc tgacccatcc caaggaatgg ttcgagcacg acaagccgca ggtcgccctg 1080
aaccacccac agcacccgga caacgaactg ttcaagaagg tgctcgaagg cgtgcaccag 1140
gttgatgcga agcagggtcg ttcacccgac cagctcagtg agaacctggc cgcatcgctt 1200
accgttgccg cacgcaagga aggcctggac aaggtcaacc acgtgctgct cgacgacccc 1260
ggcattcgca cctacgccgt gcagggtgag ctcaactcgc cgttgaagca ggtctccagt 1320
gtcgataacg cccaggcggt cgccacaccg gtggcccaga gcagcgcgca atggcagcag 1380
gctgccgagg cgcggcaggc acagcacaat gaggcgcttg cgcagcagca ggcgcaacag 1440
cagcagaaca accggcccaa ccatggggtt gccggcccgt ga 1482

<210> SEQ ID NO 52
<211> LENGTH: 493
<212> TYPE: PRT
<213> ORGANISM: Unknown
<220> FEATURE:
<223> OTHER INFORMATION: Obtained from an environmental sample.

<400> SEQUENCE: 52

Met Thr Ile Arg Ser Thr Asp Tyr Ala Leu Leu Ala Gln Glu Ser Tyr
1 5 10 15

His Asp Ser Gln Val Asp Ala Asp Val Lys Leu Asp Gly Ile Ala Tyr
20 25 30

Lys Val Phe Ala Thr Thr Asp Asp Pro Leu Thr Gly Phe Gln Ala Thr
35 40 45

Ala Tyr Gln Arg Gln Asp Thr Gly Glu Val Val Ile Ala Tyr Arg Gly
50 55 60

Thr Glu Phe Asp Arg Glu Pro Val Arg Asp Gly Gly Val Asp Ala Gly
65 70 75 80

Met Val Leu Leu Gly Val Asn Ala Gln Ser Pro Ala Ser Glu Leu Phe
85 90 95

Thr Arg Glu Val Ile Glu Lys Ala Thr His Glu Ala Glu Leu Asn Asp
100 105 110

Arg Glu Pro Arg Ile Thr Val Thr Gly His Ser Leu Gly Gly Thr Leu
115 120 125

Ala Glu Ile Asn Ala Ala Lys Tyr Gly Leu His Gly Glu Thr Phe Asn
130 135 140

Ala Tyr Gly Ala Ala Ser Leu Lys Gly Ile Pro Glu Gly Gly Asn Thr
145 150 155 160

Val Ile Asp His Val Arg Ala Gly Asp Leu Val Ser Ala Ala Ser Pro
165 170 175

His Tyr Gly Gln Val Arg Val Tyr Ala Ala Gln Gln Asp Ile Asp Thr
180 185 190

Leu Gln His Ala Gly Tyr Arg Asp Asp Ser Gly Ile Leu Ser Leu Arg
195 200 205

```
Asn Pro Ile Lys Ala Thr Asp Phe Asp Ala His Ala Ile Asp Asn Phe
    210                 215                 220

Val Pro Asn Ser Lys Leu Leu Gly Gln Ser Ile Ile Ala Pro Glu Asn
225                 230                 235                 240

Glu Ala Arg Tyr Glu Ala His Lys Gly Met Val Asp Arg Tyr Arg Asp
                245                 250                 255

Asp Val Ala Asp Ile Arg Met Leu Val Ser Ala Pro Leu Asn Ile Pro
            260                 265                 270

Arg Thr Ile Gly Asp Ile Lys Asp Ala Val Glu Arg Glu Ala Phe Glu
        275                 280                 285

Leu Ala Gly Lys Gly Ile Leu Ala Val Glu His Gly Ile Glu Glu Val
    290                 295                 300

Val His Glu Ala Lys Glu Gly Phe Glu His Leu Lys Glu Gly Phe Glu
305                 310                 315                 320

His Leu Lys Glu Glu Val Ser Glu Gly Phe His Ala Phe Glu Glu Lys
                325                 330                 335

Ala Ser Ser Ala Trp His Thr Leu Thr His Pro Lys Glu Trp Phe Glu
            340                 345                 350

His Asp Lys Pro Gln Val Ala Leu Asn His Pro Gln His Pro Asp Asn
        355                 360                 365

Glu Leu Phe Lys Lys Val Leu Glu Gly Val His Gln Val Asp Ala Lys
    370                 375                 380

Gln Gly Arg Ser Pro Asp Gln Leu Ser Glu Asn Leu Ala Ala Ser Leu
385                 390                 395                 400

Thr Val Ala Ala Arg Lys Glu Gly Leu Asp Lys Val Asn His Val Leu
                405                 410                 415

Leu Asp Asp Pro Gly Ile Arg Thr Tyr Ala Val Gln Gly Glu Leu Asn
            420                 425                 430

Ser Pro Leu Lys Gln Val Ser Ser Val Asp Asn Ala Gln Ala Val Ala
        435                 440                 445

Thr Pro Val Ala Gln Ser Ser Ala Gln Trp Gln Gln Ala Ala Glu Ala
    450                 455                 460

Arg Gln Ala Gln His Asn Glu Ala Leu Ala Gln Gln Gln Ala Gln Gln
465                 470                 475                 480

Gln Gln Asn Asn Arg Pro Asn His Gly Val Ala Gly Pro
                485                 490
```

<210> SEQ ID NO 53
<211> LENGTH: 1491
<212> TYPE: DNA
<213> ORGANISM: Unknown
<220> FEATURE:
<223> OTHER INFORMATION: Obtained from an environmental sample.

<400> SEQUENCE: 53

```
atgcgtcagg ttacattagt atttgttcat ggctacagcg ttacaaacat cgacacttat      60

ggtgaaatgc cactcaggct ccgcaacgaa ggagccacac gtgatataga aataaaaatt     120

gagaacattt tcctggggcg ctacatcagc tttaatgatg atgtgagatt aaatgatgtt     180

tccagagcat tggaaacagc cgtacaacaa cagattgcac cgggaaataa aaacaattcc     240

cgttacgtat tcatcaccca ctctaccggc ggaccggtag tgagaaactg gtgggatctg     300

tactataaaa acagcacgaa acaatgccct atgagccacc tcattatgct ggctcctgcc     360

aattttggct cggcactggc acaactggga aaaagcaaac taagccgcat taaatcctgg     420

ttcgatggtg tggaacccgg acagaatgta ttgaattggc tggaactggg aagcgcggaa     480
```

```
gcatggaagc taaacaccga ctggattaag agtgatggaa gtcagatctc ggcacagggt    540

atttttcctt ttgtgatcat aggtcaggac attgaccgca aattatacga tcatttaaac    600

tcctacaccg gtgagctggg ttccgacggc gtggtgcgtt cggccgcagc caatttaaat    660

gctacttatg taaaactcac acaacctaaa cccaccttgg taaatggaaa actggtaaca    720

ggtaatctgg aaataggaga agtaaaacaa gcgccttata cacccatgcg catcgtctca    780

aaaaaatcgc attccaacaa ggatatggga attatgagaa gtgtactgaa atcaacaaat    840

gatgccaaca gcgccgaaac ggtaaacgcc atttttgact gcattaatgt gaaaacctta    900

accgattacc agagcattgc cacacagttt gattcgcaaa caaaagacgt gcaggaaaat    960

tcaattattg aaagggaaaa aacgcccttt ggaactaaaa actatattca cgaccgtttc   1020

tcccaggtca ttttcagagt aacagacagt gaaggttacc cggttaccag ttttgatctg   1080

atcctcaccg gcggcgaaaa aaatgatccc aacgccttgc ctcagggctt ttttgtggac   1140

agacaatgca acagtgtcaa taaatcgacc attacttatt ttttaaatta cgatattatg   1200

aacggcacac cagctatagc aggtataaga ccggcatcca aaggcatgga aaaactgggt   1260

ctgatcatta acccaaggcc tgaagaaggc tttgtgcgtt acattccctg caaaataaac   1320

acatcgcccg atttgtttga cgccgctctg aaacccaacg ccacaacgct tattgatatt   1380

gtattgcaac gcgtggtaag taccgaagta ttccgctttg aaggaacaga cggggtaacg   1440

ccgcctaaaa aagatttctc gaaagtgaaa cccggaacgg atattatttg a            1491
```

<210> SEQ ID NO 54
<211> LENGTH: 496
<212> TYPE: PRT
<213> ORGANISM: Unknown
<220> FEATURE:
<223> OTHER INFORMATION: Obtained from an environmental sample.

<400> SEQUENCE: 54

```
Met Arg Gln Val Thr Leu Val Phe Val His Gly Tyr Ser Val Thr Asn
1               5                   10                  15

Ile Asp Thr Tyr Gly Glu Met Pro Leu Arg Leu Arg Asn Glu Gly Ala
            20                  25                  30

Thr Arg Asp Ile Glu Ile Lys Ile Glu Asn Ile Phe Leu Gly Arg Tyr
        35                  40                  45

Ile Ser Phe Asn Asp Asp Val Arg Leu Asn Asp Val Ser Arg Ala Leu
    50                  55                  60

Glu Thr Ala Val Gln Gln Gln Ile Ala Pro Gly Asn Lys Asn Asn Ser
65                  70                  75                  80

Arg Tyr Val Phe Ile Thr His Ser Thr Gly Gly Pro Val Val Arg Asn
                85                  90                  95

Trp Trp Asp Leu Tyr Tyr Lys Asn Ser Thr Lys Gln Cys Pro Met Ser
            100                 105                 110

His Leu Ile Met Leu Ala Pro Ala Asn Phe Gly Ser Ala Leu Ala Gln
        115                 120                 125

Leu Gly Lys Ser Lys Leu Ser Arg Ile Lys Ser Trp Phe Asp Gly Val
    130                 135                 140

Glu Pro Gly Gln Asn Val Leu Asn Trp Leu Glu Leu Gly Ser Ala Glu
145                 150                 155                 160

Ala Trp Lys Leu Asn Thr Asp Trp Ile Lys Ser Asp Gly Ser Gln Ile
                165                 170                 175

Ser Ala Gln Gly Ile Phe Pro Phe Val Ile Ile Gly Gln Asp Ile Asp
            180                 185                 190
```

```
Arg Lys Leu Tyr Asp His Leu Asn Ser Tyr Thr Gly Glu Leu Gly Ser
        195                 200                 205

Asp Gly Val Val Arg Ser Ala Ala Ala Asn Leu Asn Ala Thr Tyr Val
    210                 215                 220

Lys Leu Thr Gln Pro Lys Pro Thr Leu Val Asn Gly Lys Leu Val Thr
225                 230                 235                 240

Gly Asn Leu Glu Ile Gly Glu Val Lys Gln Ala Pro Tyr Thr Pro Met
                245                 250                 255

Arg Ile Val Ser Lys Lys Ser His Ser Asn Lys Asp Met Gly Ile Met
            260                 265                 270

Arg Ser Val Leu Lys Ser Thr Asn Asp Ala Asn Ser Ala Glu Thr Val
        275                 280                 285

Asn Ala Ile Phe Asp Cys Ile Asn Val Lys Thr Leu Thr Asp Tyr Gln
    290                 295                 300

Ser Ile Ala Thr Gln Phe Asp Ser Gln Thr Lys Asp Val Gln Glu Asn
305                 310                 315                 320

Ser Ile Ile Glu Arg Glu Lys Thr Pro Phe Gly Thr Lys Asn Tyr Ile
                325                 330                 335

His Asp Arg Phe Ser Gln Val Ile Phe Arg Val Thr Asp Ser Glu Gly
            340                 345                 350

Tyr Pro Val Thr Ser Phe Asp Leu Ile Leu Thr Gly Gly Glu Lys Asn
        355                 360                 365

Asp Pro Asn Ala Leu Pro Gln Gly Phe Phe Val Asp Arg Gln Cys Asn
    370                 375                 380

Ser Val Asn Lys Ser Thr Ile Thr Tyr Phe Leu Asn Tyr Asp Ile Met
385                 390                 395                 400

Asn Gly Thr Pro Ala Ile Ala Gly Ile Arg Pro Ala Ser Lys Gly Met
                405                 410                 415

Glu Lys Leu Gly Leu Ile Ile Asn Pro Arg Pro Glu Glu Gly Phe Val
            420                 425                 430

Arg Tyr Ile Pro Cys Lys Ile Asn Thr Ser Pro Asp Leu Phe Asp Ala
        435                 440                 445

Ala Leu Lys Pro Asn Ala Thr Thr Leu Ile Asp Ile Val Leu Gln Arg
    450                 455                 460

Val Val Ser Thr Glu Val Phe Arg Phe Glu Gly Thr Asp Gly Val Thr
465                 470                 475                 480

Pro Pro Lys Lys Asp Phe Ser Lys Val Lys Pro Gly Thr Asp Ile Ile
                485                 490                 495
```

<210> SEQ ID NO 55
<211> LENGTH: 1041
<212> TYPE: DNA
<213> ORGANISM: Unknown
<220> FEATURE:
<223> OTHER INFORMATION: Obtained from an environmental sample.

<400> SEQUENCE: 55

```
atggcttcac aattcagaaa tctggttttt gaaggaggcg gtgtgaaggg catcgcctat      60

atcggcgcca tgcaggtgct ggagcagcgg ggactgctca aggatattgt ccgggtggga     120

ggtaccagtg caggcgccat caacgcgctg atcttttcgc tgggctttac catcaaagag     180

cagcaggata ttctcaactc caccaacttc agggagttta tggacagctc gttcgggttc     240

atccgaaact tccggaggtt atggagcgaa ttcggttgga accgcggcga tgtattttcg     300

gactgggccg gggagctggt gaaagagaag ctcggcaaaa agaacgccac gttcggcgat     360

ctgaaaaagg cgaaacgtcc cgatctgtac gtgatcggca ccaatctctc tacggggttt     420
```

```
tccgagacct tttcgcacga acgccacgcc gacatgcctc tggtagatgc ggtgcggata    480

agcatgtcga tcccgctctt ttttgctgca cggaggctgg gaaaacgtaa ggatgtgtat    540

gtggatggcg gggtgatgct caactatccc gtgaagctgt tcgacaggga gaagtatatc    600

gatttggaga aagagaatga ggcggcccgc tatgtggagt actacaatca agagaatgcc    660

cggtttctgc tcgagcggcc cggccgaagc ccttatgtgt ataaccggca gactctcggt    720

ctgcggctcg acacgcagga agagatcggc ctgttccgtt acgatgagcc gctgaagggc    780

aagcagatca accgtttccc cgaatacgcc agagccctga tcggctcgct gatgcaggta    840

caggagaaca tccacctgaa aagtgacgac tggcagcgaa cgctctacat caacacgctg    900

gatgtgggca ccaccgattt cgacattacc gacgagaaga aaaaagtgct ggtgaatgag    960

gggatcaagg gagcggagac ctatttccgc tggtttgagg atcccgaaga aaaaccggtg   1020

aataaggtga atcttgtctg a                                             1041
```

<210> SEQ ID NO 56
<211> LENGTH: 346
<212> TYPE: PRT
<213> ORGANISM: Unknown
<220> FEATURE:
<223> OTHER INFORMATION: Obtained from an environmental sample.

<400> SEQUENCE: 56

```
Met Ala Ser Gln Phe Arg Asn Leu Val Phe Glu Gly Gly Gly Val Lys
1               5                   10                  15

Gly Ile Ala Tyr Ile Gly Ala Met Gln Val Leu Glu Gln Arg Gly Leu
            20                  25                  30

Leu Lys Asp Ile Val Arg Val Gly Gly Thr Ser Ala Gly Ala Ile Asn
        35                  40                  45

Ala Leu Ile Phe Ser Leu Gly Phe Thr Ile Lys Glu Gln Gln Asp Ile
    50                  55                  60

Leu Asn Ser Thr Asn Phe Arg Glu Phe Met Asp Ser Ser Phe Gly Phe
65                  70                  75                  80

Ile Arg Asn Phe Arg Arg Leu Trp Ser Glu Phe Gly Trp Asn Arg Gly
                85                  90                  95

Asp Val Phe Ser Asp Trp Ala Gly Glu Leu Val Lys Glu Lys Leu Gly
            100                 105                 110

Lys Lys Asn Ala Thr Phe Gly Asp Leu Lys Lys Ala Lys Arg Pro Asp
        115                 120                 125

Leu Tyr Val Ile Gly Thr Asn Leu Ser Thr Gly Phe Ser Glu Thr Phe
    130                 135                 140

Ser His Glu Arg His Ala Asp Met Pro Leu Val Asp Ala Val Arg Ile
145                 150                 155                 160

Ser Met Ser Ile Pro Leu Phe Phe Ala Ala Arg Arg Leu Gly Lys Arg
                165                 170                 175

Lys Asp Val Tyr Val Asp Gly Gly Val Met Leu Asn Tyr Pro Val Lys
            180                 185                 190

Leu Phe Asp Arg Glu Lys Tyr Ile Asp Leu Glu Lys Glu Asn Glu Ala
        195                 200                 205

Ala Arg Tyr Val Glu Tyr Tyr Asn Gln Glu Asn Ala Arg Phe Leu Leu
    210                 215                 220

Glu Arg Pro Gly Arg Ser Pro Tyr Val Tyr Asn Arg Gln Thr Leu Gly
225                 230                 235                 240

Leu Arg Leu Asp Thr Gln Glu Glu Ile Gly Leu Phe Arg Tyr Asp Glu
                245                 250                 255
```

```
Pro Leu Lys Gly Lys Gln Ile Asn Arg Phe Pro Glu Tyr Ala Arg Ala
            260                 265                 270

Leu Ile Gly Ser Leu Met Gln Val Gln Glu Asn Ile His Leu Lys Ser
        275                 280                 285

Asp Asp Trp Gln Arg Thr Leu Tyr Ile Asn Thr Leu Asp Val Gly Thr
    290                 295                 300

Thr Asp Phe Asp Ile Thr Asp Glu Lys Lys Lys Val Leu Val Asn Glu
305                 310                 315                 320

Gly Ile Lys Gly Ala Glu Thr Tyr Phe Arg Trp Phe Glu Asp Pro Glu
                325                 330                 335

Glu Lys Pro Val Asn Lys Val Asn Leu Val
            340                 345


<210> SEQ ID NO 57
<211> LENGTH: 1413
<212> TYPE: DNA
<213> ORGANISM: Unknown
<220> FEATURE:
<223> OTHER INFORMATION: Obtained from an environmental sample.

<400> SEQUENCE: 57

atgcaattag tgttcgtaca cgggtggagt gttacccata ccaataccta tggtgaatta      60

cccgaaagtt tggcggcagg cgccgcgaca cacggcctgc agatcgatat caggcacgtt     120

tttctcggca agtacatcag ctttcacgat gaggtgactc tggatgatat agcacgtgcc     180

ttcgacaagg cgctgagaga catgtcgggt gatggtgaca cggtctcgcc tttctcctgt     240

atcacgcatt cgaccggcgg ccctgtcgtt cggcactgga ttaacaaatt ctacggcgcg     300

cgagggctat cgaaactgcc gctggagcat ttggttatgc tggcgcctgc caaccacggc     360

tccagcctgg cggtactcgg caagcaacgt cttggtcgca tcaagtcctg gttcgatggc     420

gtggagcccg gacaaaaagt gctcgactgg ctatcgctgg gcagcaatgg gcaatgggcg     480

ctcaacaggg atttttgag ctaccgcccg gccaaacatg gcttcttccc ttttgttctg     540

acgggccagg gtatagacac aaaattctac gatttttga acagctacct tgtggagccc     600

ggcagtgacg gtgtggttcg cgtggcgggt gccaatatgc attttcgcta cctctccctg     660

gtacaatctg agaccgtatt acacaccccg ggcaaggtgc tacagctgga atataacgag     720

cggcgccccg tgaagtcccc acaagcggta ccgatgggcg tcttctccca atttagccac     780

tctggcgaca agatggggat tatggcagtc aagcgcaaga aagacgcgca tcaaatgatc     840

gtaacggaag tgctgaagtg tctctgcgta tcggacagcg atgaatatca gcaaagaggc     900

cttgaacttg cagaactgac cgccagcgaa cagcgcaagc ccatcgaaga ccaggacaag     960

attatcagcc gctatagcat gctggtattt agagtgcgcg accaggcggg caatacgatc    1020

ggagtgcacg atttcgatat cctcttactg gccggagata cctatagccc cgacaaactg    1080

ccagaggggt tcttcatgga taaacaggcc aatagagatg ccggctcact gatctactat    1140

gtggatgccg acaaaatgtc cgagatgaaa gatggctgct acggactgcg ggtggtcgtg    1200

cggccggaga aagggttttc ctattacaca acaggtgagt tcaggtcaga gggtatcccc    1260

gtggaccgtg tatttgcagc aaacgaaacc acctatattg atatcaccat gaaccgaagt    1320

gtcgatcaaa atgtattccg gttttcgcct gcaacagagc cacctgaaag cttcaaaaga    1380

accacgccct caggtaccga tatcccttca tag                                 1413


<210> SEQ ID NO 58
<211> LENGTH: 470
```

<212> TYPE: PRT
<213> ORGANISM: Unknown
<220> FEATURE:
<223> OTHER INFORMATION: Obtained from an environmental sample.

<400> SEQUENCE: 58

```
Met Gln Leu Val Phe Val His Gly Trp Ser Val Thr His Thr Asn Thr
 1               5                  10                  15

Tyr Gly Glu Leu Pro Glu Ser Leu Ala Ala Gly Ala Ala Thr His Gly
            20                  25                  30

Leu Gln Ile Asp Ile Arg His Val Phe Leu Gly Lys Tyr Ile Ser Phe
        35                  40                  45

His Asp Glu Val Thr Leu Asp Asp Ile Ala Arg Ala Phe Asp Lys Ala
    50                  55                  60

Leu Arg Asp Met Ser Gly Asp Gly Asp Thr Val Ser Pro Phe Ser Cys
65                  70                  75                  80

Ile Thr His Ser Thr Gly Gly Pro Val Val Arg His Trp Ile Asn Lys
                85                  90                  95

Phe Tyr Gly Ala Arg Gly Leu Ser Lys Leu Pro Leu Glu His Leu Val
            100                 105                 110

Met Leu Ala Pro Ala Asn His Gly Ser Ser Leu Ala Val Leu Gly Lys
        115                 120                 125

Gln Arg Leu Gly Arg Ile Lys Ser Trp Phe Asp Gly Val Glu Pro Gly
    130                 135                 140

Gln Lys Val Leu Asp Trp Leu Ser Leu Gly Ser Asn Gly Gln Trp Ala
145                 150                 155                 160

Leu Asn Arg Asp Phe Leu Ser Tyr Arg Pro Ala Lys His Gly Phe Phe
                165                 170                 175

Pro Phe Val Leu Thr Gly Gln Gly Ile Asp Thr Lys Phe Tyr Asp Phe
            180                 185                 190

Leu Asn Ser Tyr Leu Val Glu Pro Gly Ser Asp Gly Val Val Arg Val
        195                 200                 205

Ala Gly Ala Asn Met His Phe Arg Tyr Leu Ser Leu Val Gln Ser Glu
    210                 215                 220

Thr Val Leu His Thr Pro Gly Lys Val Leu Gln Leu Glu Tyr Asn Glu
225                 230                 235                 240

Arg Arg Pro Val Lys Ser Pro Gln Ala Val Pro Met Gly Val Phe Ser
                245                 250                 255

Gln Phe Ser His Ser Gly Asp Lys Met Gly Ile Met Ala Val Lys Arg
            260                 265                 270

Lys Lys Asp Ala His Gln Met Ile Val Thr Glu Val Leu Lys Cys Leu
        275                 280                 285

Cys Val Ser Asp Ser Asp Glu Tyr Gln Gln Arg Gly Leu Glu Leu Ala
    290                 295                 300

Glu Leu Thr Ala Ser Glu Gln Arg Lys Pro Ile Glu Asp Gln Asp Lys
305                 310                 315                 320

Ile Ile Ser Arg Tyr Ser Met Leu Val Phe Arg Val Arg Asp Gln Ala
                325                 330                 335

Gly Asn Thr Ile Gly Val His Asp Phe Asp Ile Leu Leu Leu Ala Gly
            340                 345                 350

Asp Thr Tyr Ser Pro Asp Lys Leu Pro Glu Gly Phe Phe Met Asp Lys
        355                 360                 365

Gln Ala Asn Arg Asp Ala Gly Ser Leu Ile Tyr Tyr Val Asp Ala Asp
    370                 375                 380

Lys Met Ser Glu Met Lys Asp Gly Cys Tyr Gly Leu Arg Val Val Val
```

```
385                 390                 395                 400

Arg Pro Glu Lys Gly Phe Ser Tyr Tyr Thr Thr Gly Glu Phe Arg Ser
                405                 410                 415

Glu Gly Ile Pro Val Asp Arg Val Phe Ala Ala Asn Glu Thr Thr Tyr
            420                 425                 430

Ile Asp Ile Thr Met Asn Arg Ser Val Asp Gln Asn Val Phe Arg Phe
        435                 440                 445

Ser Pro Ala Thr Glu Pro Pro Glu Ser Phe Lys Arg Thr Thr Pro Ser
    450                 455                 460

Gly Thr Asp Ile Pro Ser
465                 470


<210> SEQ ID NO 59
<211> LENGTH: 1038
<212> TYPE: DNA
<213> ORGANISM: Unknown
<220> FEATURE:
<223> OTHER INFORMATION: Obtained from an environmental sample.

<400> SEQUENCE: 59

atgacaacac aatttagaaa cttgatcttt gaaggcggcg gtgtaaaagg cgttgcttac      60

attggcgcca tgcagattct tgaaaatcgt ggcgtgttgc aagatattcg ccgagtcgga     120

gggtgcagtg cgggtgcgat taacgcgctg atttttgcgc tgggttacac ggtccgtgag     180

caaaaagaga tcttacaagc caccgatttt aaccagttta tggataactc ttggggggtt     240

attcgtgata ttcgcaggct tgctcgagac tttggctgga ataagggtga tttctttagt     300

agctggatag gtgatttgat tcatcgtcgt ttggggaatc gccgagcgac gttcaaagat     360

ctgcaaaagg ccaagcttcc tgatctttat gtcatcggta ctaatctgtc tacagggttt     420

gcagaggtgt tttctgccga aagacacccc gatatggagc tggcgacagc ggtgcgtatc     480

tccatgtcga taccgctgtt ctttgcggca gtgcgtcatg gtgatcgaca agatgtgtat     540

gtcgatgggg gtgttcaact taactatccg attaaactgt ttgatcggga gcgttatatt     600

gatctggcca aagatcccgg tgccgttcgg cgaacgggtt attacaacaa agaaaacgct     660

cgctttcagc ttgatcggcc gggccatagc ccctatgttt acaatcgcca gaccttgggt     720

ttgcgactgg atagtcgcga ggagataggg ctctttcgtt atgacgaacc cctcaagggc     780

aaacccatta agtccttcac tgactacgct cgacaacttt tcggtgcgct gatgaatgca     840

caggaaaaga ttcatctaca tggcgatgat tggcaacgca cggtctatat cgatacactc     900

gatgtgggta cgacggactt caatctttct gatgcaacca agcaagcact gattgagcaa     960

ggaattaacg gcaccgaaaa ttatttcgac tggtttgata atccgttaga gaagcctgtg    1020

aatagagtgg agtcatag                                                  1038


<210> SEQ ID NO 60
<211> LENGTH: 345
<212> TYPE: PRT
<213> ORGANISM: Unknown
<220> FEATURE:
<223> OTHER INFORMATION: Obtained from an environmental sample.

<400> SEQUENCE: 60

Met Thr Thr Gln Phe Arg Asn Leu Ile Phe Glu Gly Gly Gly Val Lys
 1               5                  10                  15

Gly Val Ala Tyr Ile Gly Ala Met Gln Ile Leu Glu Asn Arg Gly Val
            20                  25                  30

Leu Gln Asp Ile Arg Arg Val Gly Gly Cys Ser Ala Gly Ala Ile Asn
```

```
        35                  40                  45

Ala Leu Ile Phe Ala Leu Gly Tyr Thr Val Arg Glu Gln Lys Glu Ile
    50                  55                  60

Leu Gln Ala Thr Asp Phe Asn Gln Phe Met Asp Asn Ser Trp Gly Val
65                  70                  75                  80

Ile Arg Asp Ile Arg Arg Leu Ala Arg Asp Phe Gly Trp Asn Lys Gly
                85                  90                  95

Asp Phe Phe Ser Ser Trp Ile Gly Asp Leu Ile His Arg Arg Leu Gly
            100                 105                 110

Asn Arg Arg Ala Thr Phe Lys Asp Leu Gln Lys Ala Lys Leu Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Ala Lys Asp Pro Gly Ala
        195                 200                 205

Val Arg Arg Thr Gly Tyr Tyr Asn Lys Glu Asn Ala Arg Phe Gln Leu
    210                 215                 220

Asp Arg Pro Gly His Ser Pro Tyr Val Tyr Asn Arg Gln Thr Leu Gly
225                 230                 235                 240

Leu Arg Leu Asp Ser Arg Glu Glu Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Lys Ile His Leu His Gly
        275                 280                 285

Asp Asp Trp Gln Arg Thr Val Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Asp Trp Phe Asp Asn Pro Leu
                325                 330                 335

Glu Lys Pro Val Asn Arg Val Glu Ser
            340                 345
```

```
<210> SEQ ID NO 61
<211> LENGTH: 1257
<212> TYPE: DNA
<213> ORGANISM: Unknown
<220> FEATURE:
<223> OTHER INFORMATION: Obtained from an environmental sample.

<400> SEQUENCE: 61

atgacattaa aactctccct gctgatcgcg agcctgagcg ccgtgtctcc agcagtcttg      60

gcaaacgacg tcaatccagc gccactcatg gcgccgtccg aagcggattc cgcgcagacg     120

ctgggcagtc tgacgtacac ctatgttcgc tgctggtatc gtccggctgc gacgcataat     180

gatccttaca ccacctggga gtgggcgaag aacgcggacg gcagtgattt caccattgat     240

ggctattggt ggtcatcggt gagttacaaa aacatgttct ataccgatac tcagcccgat     300

accatcatgc agcgctgtgc agagacgttg ggttaaccc acgataccgc tgacatcacc      360
```

```
tatgccgcgg ccgatacccg tttctcctac aaccacacca tctggagcaa cgatgtcgcc    420

aacgcgccga gcaaaatcaa taaggtgatc gcctttggtg acagcctgtc agacacgggc    480

aacattttta acgcctcgca atggcgcttc ccgaacccga actcctggtt tgtcggccac    540

ttctcaaacg ggtttgtctg gaccgagtat ctggcgcaag gtttggggct gcccctctac    600

aactgggccg tgggcggcgc ggcggggcgc aatcaatact gggcgctgac tggcgtgaat    660

gaacaggtca gttcgtacct gacctacatg gagatggcgc cgaattaccg tgcggagaac    720

acgctgttta cactcgaatt cggtctgaat gattttatga actacgaccg ttcactggca    780

gacgtcaaag cagattacag ctcggcgctg attcgtctgg tggaagccgg agcgaaaaat    840

atggtgctgt tgaccctacc ggatgccacg cgcgcgccgc agttccaata ttcaacgcaa    900

gaacacatcg acgaggtgcg cgccaaagtg attggcatga acgcgttcat tcgtgagcag    960

gcacgctact tccagatgca gggcatcaac atttcgctgt ttgacgccta cacgctgttt   1020

gatcagatga tcgccgaccc agccgcgcac ggctttgata atgccagcgc gccatgtctt   1080

gatattcagc gcagctctgc ggcggactat ctctacacgc atgctctggc agccgagtgt   1140

gcctcatccg gttcagaccg ctttgtgttc tgggatgtga ctcacccaac cacggcaacg   1200

catcgctaca tcgccgacca cattctggct accggtgttg cgcagttccc gcgttaa      1257
```

```
<210> SEQ ID NO 62
<211> LENGTH: 418
<212> TYPE: PRT
<213> ORGANISM: Unknown
<220> FEATURE:
<221> NAME/KEY: SIGNAL
<222> LOCATION: (1)...(21)
<223> OTHER INFORMATION: Obtained from an environmental sample.

<400> SEQUENCE: 62

Met Thr Leu Lys Leu Ser Leu Leu Ile Ala Ser Leu Ser Ala Val Ser
 1               5                  10                  15

Pro Ala Val Leu Ala Asn Asp Val Asn Pro Ala Pro Leu Met Ala Pro
            20                  25                  30

Ser Glu Ala Asp Ser Ala Gln Thr Leu Gly Ser Leu Thr Tyr Thr Tyr
        35                  40                  45

Val Arg Cys Trp Tyr Arg Pro Ala Ala Thr His Asn Asp Pro Tyr Thr
    50                  55                  60

Thr Trp Glu Trp Ala Lys Asn Ala Asp Gly Ser Asp Phe Thr Ile Asp
65                  70                  75                  80

Gly Tyr Trp Trp Ser Ser Val Ser Tyr Lys Asn Met Phe Tyr Thr Asp
                85                  90                  95

Thr Gln Pro Asp Thr Ile Met Gln Arg Cys Ala Glu Thr Leu Gly Leu
            100                 105                 110

Thr His Asp Thr Ala Asp Ile Thr Tyr Ala Ala Ala Asp Thr Arg Phe
        115                 120                 125

Ser Tyr Asn His Thr Ile Trp Ser Asn Asp Val Ala Asn Ala Pro Ser
    130                 135                 140

Lys Ile Asn Lys Val Ile Ala Phe Gly Asp Ser Leu Ser Asp Thr Gly
145                 150                 155                 160

Asn Ile Phe Asn Ala Ser Gln Trp Arg Phe Pro Asn Pro Asn Ser Trp
                165                 170                 175

Phe Val Gly His Phe Ser Asn Gly Phe Val Trp Thr Glu Tyr Leu Ala
            180                 185                 190

Gln Gly Leu Gly Leu Pro Leu Tyr Asn Trp Ala Val Gly Gly Ala Ala
```

```
        195                 200                 205

Gly Arg Asn Gln Tyr Trp Ala Leu Thr Gly Val Asn Glu Gln Val Ser
    210                 215                 220

Ser Tyr Leu Thr Tyr Met Glu Met Ala Pro Asn Tyr Arg Ala Glu Asn
225                 230                 235                 240

Thr Leu Phe Thr Leu Glu Phe Gly Leu Asn Asp Phe Met Asn Tyr Asp
                245                 250                 255

Arg Ser Leu Ala Asp Val Lys Ala Asp Tyr Ser Ser Ala Leu Ile Arg
            260                 265                 270

Leu Val Glu Ala Gly Ala Lys Asn Met Val Leu Leu Thr Leu Pro Asp
        275                 280                 285

Ala Thr Arg Ala Pro Gln Phe Gln Tyr Ser Thr Gln Glu His Ile Asp
    290                 295                 300

Glu Val Arg Ala Lys Val Ile Gly Met Asn Ala Phe Ile Arg Glu Gln
305                 310                 315                 320

Ala Arg Tyr Phe Gln Met Gln Gly Ile Asn Ile Ser Leu Phe Asp Ala
                325                 330                 335

Tyr Thr Leu Phe Asp Gln Met Ile Ala Asp Pro Ala Ala His Gly Phe
            340                 345                 350

Asp Asn Ala Ser Ala Pro Cys Leu Asp Ile Gln Arg Ser Ser Ala Ala
        355                 360                 365

Asp Tyr Leu Tyr Thr His Ala Leu Ala Ala Glu Cys Ala Ser Ser Gly
    370                 375                 380

Ser Asp Arg Phe Val Phe Trp Asp Val Thr His Pro Thr Thr Ala Thr
385                 390                 395                 400

His Arg Tyr Ile Ala Asp His Ile Leu Ala Thr Gly Val Ala Gln Phe
                405                 410                 415

Pro Arg


<210> SEQ ID NO 63
<211> LENGTH: 1242
<212> TYPE: DNA
<213> ORGANISM: Unknown
<220> FEATURE:
<223> OTHER INFORMATION: Obtained from an environmental sample.

<400> SEQUENCE: 63

atgaaaaata cgttaatttt ggctggctgt atattggcag ctccagccgt cgcagatgac      60

ctaacaatca cccctgaaac tataagtgtg cgctacgcgt ctgaggtgca gaacaaacaa     120

acatacactt atgttcgctg ctggtatcgt ccagcgcaga accatgacga cccttccact     180

gagtgggaat gggctcgtga cgacaatggc gattacttca ctatcgatgg gtactggtgg     240

tcgtctgtct ccttcaaaaa catgttctat accaataccc cgcaaacaga aattgaaaac     300

cgctgtaaag aaacactagg ggttaatcat gatagtgccg atcttcttta ctatgcatca     360

gacaatcgtt tctcctacaa ccatagtatt tggacaaacg acaacgcagt aaacaacaaa     420

atcaatcgta ttgtcgcatt cggtgatagc ctgtctgaca ccggtaatct gtacaatgga     480

tcccaatggg tattccccaa ccgtaattct tggtttctcg gtcacttttc aaacggtttg     540

gtgtggactg aatacttagc gcaaaacaaa aacgtaccac tgtacaactg ggcggtcggt     600

ggcgccgccg gcaccaacca atacgtcgca ttgacaggca tttatgacca agtgacgtct     660

tatcttacgt acatgaagat ggcaaagaac tacaacccaa acaacagttt gatgacgctg     720

gaatttggcc taaatgattt catgaattac ggccgagaag tggcggacgt gaaagctgac     780

ttaagtagcg cattgattcg cttgaccgaa tcaggcgcaa gcaacattct actcttcacg     840
```

ttaccggacg caacaaaggc accgcagttt aaatattcga ctcaggagga aattgagacc 900
gttcgagcta agattcttga gttcaacact tttattgaag aacaagcgtt actctatcaa 960
gctaaaggac tgaatgtggc cctctacgat gctcatagca tctttgatca gctgacatcc 1020
aatcctaaac aacacggttt tgagaactca acagatgcct gtctgaacat caaccgcagt 1080
tcctctgtcg actaccttta cagtcatgag ctaactaacg attgtgcgta tcatagctct 1140
gataaatatg tgttctgggg agtcactcac ccaaccacag caacacataa atacattgcc 1200
gaccaaatca ttcagaccaa gctagaccag ttcaatttct aa 1242

<210> SEQ ID NO 64
<211> LENGTH: 413
<212> TYPE: PRT
<213> ORGANISM: Unknown
<220> FEATURE:
<221> NAME/KEY: SIGNAL
<222> LOCATION: (1)...(18)
<223> OTHER INFORMATION: Obtained from an environmental sample.

<400> SEQUENCE: 64

Met Lys Asn Thr Leu Ile Leu Ala Gly Cys Ile Leu Ala Ala Pro Ala
1 5 10 15

Val Ala Asp Asp Leu Thr Ile Thr Pro Glu Thr Ile Ser Val Arg Tyr
20 25 30

Ala Ser Glu Val Gln Asn Lys Gln Thr Tyr Thr Tyr Val Arg Cys Trp
35 40 45

Tyr Arg Pro Ala Gln Asn His Asp Asp Pro Ser Thr Glu Trp Glu Trp
50 55 60

Ala Arg Asp Asp Asn Gly Asp Tyr Phe Thr Ile Asp Gly Tyr Trp Trp
65 70 75 80

Ser Ser Val Ser Phe Lys Asn Met Phe Tyr Thr Asn Thr Pro Gln Thr
85 90 95

Glu Ile Glu Asn Arg Cys Lys Glu Thr Leu Gly Val Asn His Asp Ser
100 105 110

Ala Asp Leu Leu Tyr Tyr Ala Ser Asp Asn Arg Phe Ser Tyr Asn His
115 120 125

Ser Ile Trp Thr Asn Asp Asn Ala Val Asn Asn Lys Ile Asn Arg Ile
130 135 140

Val Ala Phe Gly Asp Ser Leu Ser Asp Thr Gly Asn Leu Tyr Asn Gly
145 150 155 160

Ser Gln Trp Val Phe Pro Asn Arg Asn Ser Trp Phe Leu Gly His Phe
165 170 175

Ser Asn Gly Leu Val Trp Thr Glu Tyr Leu Ala Gln Asn Lys Asn Val
180 185 190

Pro Leu Tyr Asn Trp Ala Val Gly Gly Ala Ala Gly Thr Asn Gln Tyr
195 200 205

Val Ala Leu Thr Gly Ile Tyr Asp Gln Val Thr Ser Tyr Leu Thr Tyr
210 215 220

Met Lys Met Ala Lys Asn Tyr Asn Pro Asn Asn Ser Leu Met Thr Leu
225 230 235 240

Glu Phe Gly Leu Asn Asp Phe Met Asn Tyr Gly Arg Glu Val Ala Asp
245 250 255

Val Lys Ala Asp Leu Ser Ser Ala Leu Ile Arg Leu Thr Glu Ser Gly
260 265 270

Ala Ser Asn Ile Leu Leu Phe Thr Leu Pro Asp Ala Thr Lys Ala Pro
275 280 285

```
Gln Phe Lys Tyr Ser Thr Gln Glu Glu Ile Glu Thr Val Arg Ala Lys
    290                 295                 300

Ile Leu Glu Phe Asn Thr Phe Ile Glu Glu Gln Ala Leu Leu Tyr Gln
305                 310                 315                 320

Ala Lys Gly Leu Asn Val Ala Leu Tyr Asp Ala His Ser Ile Phe Asp
                325                 330                 335

Gln Leu Thr Ser Asn Pro Lys Gln His Gly Phe Glu Asn Ser Thr Asp
            340                 345                 350

Ala Cys Leu Asn Ile Asn Arg Ser Ser Ser Val Asp Tyr Leu Tyr Ser
        355                 360                 365

His Glu Leu Thr Asn Asp Cys Ala Tyr His Ser Ser Asp Lys Tyr Val
    370                 375                 380

Phe Trp Gly Val Thr His Pro Thr Thr Ala Thr His Lys Tyr Ile Ala
385                 390                 395                 400

Asp Gln Ile Ile Gln Thr Lys Leu Asp Gln Phe Asn Phe
                405                 410
```

<210> SEQ ID NO 65
<211> LENGTH: 1164
<212> TYPE: DNA
<213> ORGANISM: Unknown
<220> FEATURE:
<223> OTHER INFORMATION: Obtained from an environmental sample.

<400> SEQUENCE: 65

```
atgaaccctt ttcttgaaga taaaattaaa tcctccggtc ccaagaaaat cctcgcctgc     60

gatggcggag gtattttggg tttgatgagc gttgaaatcc tagcaaaaat tgaagcggat    120

ttacgcacta agttaggtaa agaccagaac ttcgtgctcg cggattattt cgattttgtc    180

tgcggcacca gcaccggcgc gattatcgct gcctgtattt ctagtggcat gtcgatggct    240

aaaatacgcc aattctatct cgacagtggg aagcaaatgt tcgataaggc ctccttgctt    300

aagcgcttgc aatacagtta tgacgatgag ccattggcga ggcagttgcg tgcagccttt    360

gatgagcaac tgaaggaaac cgatgccaag ctgggtagtg cgcacctaaa aacgctgttg    420

atgatggtga tgcgtaacca cagcaccgac tcaccttggc cggtttccaa taacccttac    480

gcaaaataca ataatatcgc ccgaaaggat tgcaacctca acctgccttt atggcaattg    540

gtccgtgcca gcaccgccgc tccgacgtat ttcccaccgg aagtcatcac tttcgcagat    600

ggcacacccg aagaatacaa cttcatcttc gtcgacggtg gcgtgaccac ctacaacaac    660

ccagcatatc ttgctttcct aatggccact gccaagcctt atgccctcaa ctggccgaca    720

ggcagcaacc agttattgat cgtttccgta ggcaccggaa gtgccgccaa tgtccgacct    780

aatctggacg tggatgatat gaacctgatc cattttgcca aaaacatccc ttcagccctg    840

atgaatgccg catctgccgg ttgggatatg acctgccggg tattgggtga atgccgccat    900

ggtggcatgt tagatcggga gtttggtgac atggtgatgc ccgcgtcaag agatcttaat    960

tttaccggcc ctaagctttt tacttatatg cgttatgatc ccgatgtttc ctttgagggc   1020

ttgaagacta tcggtatatc agatatcgat ccagccaaaa tgcagcaaat ggattccgtc   1080

aataatattc cagatataca acgggtaggt atcgaatatg ccaaacgcca tgttgataca   1140

gctcattttg aggggtttaa ataa                                          1164
```

<210> SEQ ID NO 66
<211> LENGTH: 387
<212> TYPE: PRT
<213> ORGANISM: Unknown

<220> FEATURE:
<223> OTHER INFORMATION: Obtained from an environmental sample.

<400> SEQUENCE: 66

```
Met Asn Pro Phe Leu Glu Asp Lys Ile Lys Ser Ser Gly Pro Lys Lys
 1               5                  10                  15

Ile Leu Ala Cys Asp Gly Gly Gly Ile Leu Gly Leu Met Ser Val Glu
            20                  25                  30

Ile Leu Ala Lys Ile Glu Ala Asp Leu Arg Thr Lys Leu Gly Lys Asp
        35                  40                  45

Gln Asn Phe Val Leu Ala Asp Tyr Phe Asp Phe Val Cys Gly Thr Ser
    50                  55                  60

Thr Gly Ala Ile Ile Ala Ala Cys Ile Ser Ser Gly Met Ser Met Ala
65                  70                  75                  80

Lys Ile Arg Gln Phe Tyr Leu Asp Ser Gly Lys Gln Met Phe Asp Lys
                85                  90                  95

Ala Ser Leu Leu Lys Arg Leu Gln Tyr Ser Tyr Asp Asp Glu Pro Leu
            100                 105                 110

Ala Arg Gln Leu Arg Ala Ala Phe Asp Glu Gln Leu Lys Glu Thr Asp
        115                 120                 125

Ala Lys Leu Gly Ser Ala His Leu Lys Thr Leu Leu Met Met Val Met
    130                 135                 140

Arg Asn His Ser Thr Asp Ser Pro Trp Pro Val Ser Asn Asn Pro Tyr
145                 150                 155                 160

Ala Lys Tyr Asn Asn Ile Ala Arg Lys Asp Cys Asn Leu Asn Leu Pro
                165                 170                 175

Leu Trp Gln Leu Val Arg Ala Ser Thr Ala Ala Pro Thr Tyr Phe Pro
            180                 185                 190

Pro Glu Val Ile Thr Phe Ala Asp Gly Thr Pro Glu Glu Tyr Asn Phe
        195                 200                 205

Ile Phe Val Asp Gly Gly Val Thr Thr Tyr Asn Asn Pro Ala Tyr Leu
    210                 215                 220

Ala Phe Leu Met Ala Thr Ala Lys Pro Tyr Ala Leu Asn Trp Pro Thr
225                 230                 235                 240

Gly Ser Asn Gln Leu Leu Ile Val Ser Val Gly Thr Gly Ser Ala Ala
                245                 250                 255

Asn Val Arg Pro Asn Leu Asp Val Asp Asp Met Asn Leu Ile His Phe
            260                 265                 270

Ala Lys Asn Ile Pro Ser Ala Leu Met Asn Ala Ala Ser Ala Gly Trp
        275                 280                 285

Asp Met Thr Cys Arg Val Leu Gly Glu Cys Arg His Gly Gly Met Leu
    290                 295                 300

Asp Arg Glu Phe Gly Asp Met Val Met Pro Ala Ser Arg Asp Leu Asn
305                 310                 315                 320

Phe Thr Gly Pro Lys Leu Phe Thr Tyr Met Arg Tyr Asp Pro Asp Val
                325                 330                 335

Ser Phe Glu Gly Leu Lys Thr Ile Gly Ile Ser Asp Ile Asp Pro Ala
            340                 345                 350

Lys Met Gln Gln Met Asp Ser Val Asn Asn Ile Pro Asp Ile Gln Arg
        355                 360                 365

Val Gly Ile Glu Tyr Ala Lys Arg His Val Asp Thr Ala His Phe Glu
    370                 375                 380

Gly Phe Lys
385
```

<210> SEQ ID NO 67
<211> LENGTH: 1419
<212> TYPE: DNA
<213> ORGANISM: Unknown
<220> FEATURE:
<223> OTHER INFORMATION: Obtained from an environmental sample.

<400> SEQUENCE: 67

```
atggtcattg tcttcgtcca cggatggagc gtgcgcaaca ccaacacgta cgggcagctg     60

cccttgcgtc tcaagaagag cttcaaagcc gccgggaaac agattcaggt cgagaacatc    120

tacctgggcg agtacgtgag ctttgacgac caggtaacag tcgacgacat cgcccgcgca    180

ttcgattgcg cactgcggga aaaactatac gatccggcga cgaagcagtg gacgaagttc    240

gcctgcatca ctcattccac cggcggcccg gtcgcgcgct tgtggatgga tctctactac    300

ggcgccgcca gactggccga gtgcccgatg tcccacctcg tgatgctcgc cccggccaat    360

catggctcgg cccttgccca gctcggcaag agccgcctca gccgcatcaa gagcttcttc    420

gagggtgtcg aaccgggcca gcgcgtcctc gactggctcg aactcggcag tgagctgagt    480

tgggccctca acacgagatg gctcgactac gactgccgcg ccgccgcctg ctgggtcttc    540

accctcaccg gccagcgcat cgaccggagt ttgtacgacc atctcaacag ctataccggt    600

gagcagggat cggatggcgt cgtgcgcgtc gccgcggcca acatgaacac caagctgctg    660

acctttgaac agaaggggcg caagctcgtg ttcacaggcc agaagaagac cgccgacacc    720

ggccttggcg tcgtgccggg ccggtcgcac tccggccgcg acatgggcat catcgccagc    780

gtgcgcggca ccggcgacca tcccaccctg gaatgggtga ctcgttgcct ggccgtcacc    840

gacgtcaaca cgtacgatgc cgtctgtaag gatctggacg ctctcaccgc ccagacccag    900

aaggatgaaa aggtggaaga ggtcaaaggc ctgctgcgga cggtcagata ccagacggac    960

cgctacgtca tgctcgtctt ccgcctgaag aacgaccgcg gcgactacct ctccgattac   1020

gatctcctgc tcaccgccgg acccaactac tcgcccgacg acctgcccga aggcttcttc   1080

gtcgaccgcc aacggaacca gcggaacccg ggcaagctca cttactacct gaactacgac   1140

gccatggcca aattgaaagg taagaccgcc gagggccgtc tgggcttcaa gatcctggcg   1200

cgcccggtga aaggcggcct cgtctactat gaggttgcgg agttccagtc cgacgtgggc   1260

ggcgtcagca gcatgctgca gcccaacgca acagtgatga tcgacatcac cctcaatcgc   1320

aacgtcgacg cgcgcgtctt ccggttcacc gagaatctgc ccacgggtga ccagggcgag   1380

gaaatcagcg gcgtcccgct ggggcagaac gtcccgtag                          1419
```

<210> SEQ ID NO 68
<211> LENGTH: 472
<212> TYPE: PRT
<213> ORGANISM: Unknown
<220> FEATURE:
<223> OTHER INFORMATION: Obtained from an environmental sample.

<400> SEQUENCE: 68

```
Met Val Ile Val Phe Val His Gly Trp Ser Val Arg Asn Thr Asn Thr
1               5                   10                  15

Tyr Gly Gln Leu Pro Leu Arg Leu Lys Lys Ser Phe Lys Ala Ala Gly
            20                  25                  30

Lys Gln Ile Gln Val Glu Asn Ile Tyr Leu Gly Glu Tyr Val Ser Phe
        35                  40                  45

Asp Asp Gln Val Thr Val Asp Asp Ile Ala Arg Ala Phe Asp Cys Ala
    50                  55                  60
```

-continued

```
Leu Arg Glu Lys Leu Tyr Asp Pro Ala Thr Lys Gln Trp Thr Lys Phe
65                  70                  75                  80

Ala Cys Ile Thr His Ser Thr Gly Gly Pro Val Ala Arg Leu Trp Met
                85                  90                  95

Asp Leu Tyr Tyr Gly Ala Ala Arg Leu Ala Glu Cys Pro Met Ser His
            100                 105                 110

Leu Val Met Leu Ala Pro Ala Asn His Gly Ser Ala Leu Ala Gln Leu
        115                 120                 125

Gly Lys Ser Arg Leu Ser Arg Ile Lys Ser Phe Phe Glu Gly Val Glu
    130                 135                 140

Pro Gly Gln Arg Val Leu Asp Trp Leu Glu Leu Gly Ser Glu Leu Ser
145                 150                 155                 160

Trp Ala Leu Asn Thr Arg Trp Leu Asp Tyr Asp Cys Arg Ala Ala Ala
                165                 170                 175

Cys Trp Val Phe Thr Leu Thr Gly Gln Arg Ile Asp Arg Ser Leu Tyr
            180                 185                 190

Asp His Leu Asn Ser Tyr Thr Gly Glu Gln Gly Ser Asp Gly Val Val
        195                 200                 205

Arg Val Ala Ala Ala Asn Met Asn Thr Lys Leu Leu Thr Phe Glu Gln
    210                 215                 220

Lys Gly Arg Lys Leu Val Phe Thr Gly Gln Lys Lys Thr Ala Asp Thr
225                 230                 235                 240

Gly Leu Gly Val Val Pro Gly Arg Ser His Ser Gly Arg Asp Met Gly
                245                 250                 255

Ile Ile Ala Ser Val Arg Gly Thr Gly Asp His Pro Thr Leu Glu Trp
            260                 265                 270

Val Thr Arg Cys Leu Ala Val Thr Asp Val Asn Thr Tyr Asp Ala Val
        275                 280                 285

Cys Lys Asp Leu Asp Ala Leu Thr Ala Gln Thr Gln Lys Asp Glu Lys
    290                 295                 300

Val Glu Glu Val Lys Gly Leu Leu Arg Thr Val Arg Tyr Gln Thr Asp
305                 310                 315                 320

Arg Tyr Val Met Leu Val Phe Arg Leu Lys Asn Asp Arg Gly Asp Tyr
                325                 330                 335

Leu Ser Asp Tyr Asp Leu Leu Leu Thr Ala Gly Pro Asn Tyr Ser Pro
            340                 345                 350

Asp Asp Leu Pro Glu Gly Phe Phe Val Asp Arg Gln Arg Asn Gln Arg
        355                 360                 365

Asn Pro Gly Lys Leu Thr Tyr Tyr Leu Asn Tyr Asp Ala Met Ala Lys
    370                 375                 380

Leu Lys Gly Lys Thr Ala Glu Gly Arg Leu Gly Phe Lys Ile Leu Ala
385                 390                 395                 400

Arg Pro Val Lys Gly Gly Leu Val Tyr Tyr Glu Val Ala Glu Phe Gln
                405                 410                 415

Ser Asp Val Gly Gly Val Ser Ser Met Leu Gln Pro Asn Ala Thr Val
            420                 425                 430

Met Ile Asp Ile Thr Leu Asn Arg Asn Val Asp Ala Arg Val Phe Arg
        435                 440                 445

Phe Thr Glu Asn Leu Pro Thr Gly Asp Gln Gly Glu Glu Ile Ser Gly
    450                 455                 460

Val Pro Leu Gly Gln Asn Val Pro
465                 470
```

<210> SEQ ID NO 69

<211> LENGTH: 1038
<212> TYPE: DNA
<213> ORGANISM: Unknown
<220> FEATURE:
<223> OTHER INFORMATION: Obtained from an environmental sample.

<400> SEQUENCE: 69
atgacaacac aatttagaaa cttgatattt gaaggcggcg gtgtaaaagg tgttgcttac 60
attggcgcca tgcagattct cgaaaatcgt ggcgtgttgc aagatattcg ccgagtcgga 120
gggtgcagtg cgggtgcgat caacgcgctg atttttgcgc tgggttacac tgtccgtgag 180
caaaaagaga tcttacaagc cacggatttt aaccagttta tggataactc ttggggtgtt 240
attcgtgata ttcgcaggct tgctcgagac tttggctggc acaagggtga cttctttaat 300
agctggatag gtgatttgat tcatcgtcgt ttggggaatc gccgagcgac gttcaaagat 360
ctgcaaaagg ccaagcttcc tgatctttat gtcatcggta ctaatctgtc tacggggtat 420
gcagaggttt tttcagccga aagacacccc gatatggagc tagcgacagc ggtgcgtatc 480
tccatgtcga taccgctgtt ctttgcggcc gtgcgccacg gtgaccgaca agatgtgtat 540
gtcgatgggg gtgttcaact taactatccg attaaacttt ttgatcggga gcgttacatt 600
gatctggcca aagatcccgg tgccgttcgg cgaacgggct attacaacaa agaaaacgct 660
cgctttcagc ttgagcggcc gggctatagc ccctatgttt acaatcgcca gaccttgggt 720
ttgcgactag atagtcgaga ggagataggg ctctttcgtt atgacgaacc cctcaagggc 780
aaacccatta agtccttcac tgactacgct cgacaacttt tcggtgcgtt gatgaatgca 840
caggaaaaga ttcatctaca tggcgatgat tggcagcgca cggtctatat cgatacattg 900
gatgtgggta cgacggactt caatctttct gatgcaacta agcaagcact gattgaacag 960
ggaattaacg gcaccgaaaa ttatttcgag tggtttgata atccgttgga gaagcctgtt 1020
aatagagtgg agtcatag 1038

<210> SEQ ID NO 70
<211> LENGTH: 345
<212> TYPE: PRT
<213> ORGANISM: Unknown
<220> FEATURE:
<223> OTHER INFORMATION: Obtained from an environmental sample.

<400> SEQUENCE: 70

Met Thr Thr Gln Phe Arg Asn Leu Ile Phe Glu Gly Gly Gly Val Lys
1 5 10 15

Gly Val Ala Tyr Ile Gly Ala Met Gln Ile Leu Glu Asn Arg Gly Val
20 25 30

Leu Gln Asp Ile Arg Arg Val Gly Gly Cys Ser Ala Gly Ala Ile Asn
35 40 45

Ala Leu Ile Phe Ala Leu Gly Tyr Thr Val Arg Glu Gln Lys Glu Ile
50 55 60

Leu Gln Ala Thr Asp Phe Asn Gln Phe Met Asp Asn Ser Trp Gly Val
65 70 75 80

Ile Arg Asp Ile Arg Arg Leu Ala Arg Asp Phe Gly Trp His Lys Gly
85 90 95

Asp Phe Phe Asn Ser Trp Ile Gly Asp Leu Ile His Arg Arg Leu Gly
100 105 110

Asn Arg Arg Ala Thr Phe Lys Asp Leu Gln Lys Ala Lys Leu Pro Asp
115 120 125

Leu Tyr Val Ile Gly Thr Asn Leu Ser Thr Gly Tyr Ala Glu Val Phe
130 135 140

```
Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Ala Lys Asp Pro Gly Ala
        195                 200                 205

Val Arg Arg Thr Gly Tyr Tyr Asn Lys Glu Asn Ala Arg Phe Gln Leu
    210                 215                 220

Glu Arg Pro Gly Tyr Ser Pro Tyr Val Tyr Asn Arg Gln Thr Leu Gly
225                 230                 235                 240

Leu Arg Leu Asp Ser Arg Glu Glu Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Lys Ile His Leu His Gly
        275                 280                 285

Asp Asp Trp Gln Arg Thr Val Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Glu Trp Phe Asp Asn Pro Leu
                325                 330                 335

Glu Lys Pro Val Asn Arg Val Glu Ser
            340                 345
```

<210> SEQ ID NO 71
<211> LENGTH: 3264
<212> TYPE: DNA
<213> ORGANISM: Unknown
<220> FEATURE:
<223> OTHER INFORMATION: Obtained from an environmental sample.

<400> SEQUENCE: 71

```
atgtcgctat catcaccgcc cgaaaccccc gaaccccccg aaccccggtc acccggcgcg     60

cgatcgctcc ggggaggatg gagccgccgg gtggccggcc tgctggccct ggtgctgctc    120

accgggctcc tccagatcgt cgtgccgctc gcacggcccg ccgcggcggc cgtacagcag    180

cccgcgatga cgtggaacct gcatggggcc aagaagaccg cggaactggt tcccgatctg    240

atgcgtaacc ataacgtcac cgtcgcggcc ctccaggaag tggccaacgg caacttcctg    300

ggcctcactc ccacagagca cgacgtgccc tacctcaagc cggacggcac gacctcgact    360

ccgccggatc cgcagaaatg gcgggtcgag aagtacaacc tcgccaagga cgatgcaacc    420

gctttcgtga tccggaccgg ctccaacaac cgcgggctcg cgatcgtcac cacccaggac    480

gtcggcgatg tctcgcagaa tgtacacgtc gtcaatgtga ccgaggattg ggaaggcaag    540

atgttccccg ccctgggggt gaagatcgac ggcgcctggt actactccat ccacgcctcc    600

accacgccga agcgcgcgaa caacaacgcc ggcactctgg tcgaggacct ctccaagctg    660

cacgagacgg ccgctttcga aggcgactgg gccgcgatgg gcgactggaa ccggtacccc    720

tccgaggact cgaacgccta cgagaaccaa cggaagcatc tcaaaggcgc catgcggaca    780

aactttccgg ataatcaggc ggcgttgcgc gaagtcctgg agttcgagtc cgacgaacgc    840

gtcatctggc agggtgcgag gacccacgac cacggcgccg agctcgacta catggtggcc    900
```

-continued

```
aagggagccg gtaacgacta caaggccagc cgatcgacgt cgaagcacgg ctccgatcac    960
tacccggtgt tcttcggtat tggggacgat tcggacacct gcatgggcgg cacggcgccg   1020
gtggcggcga acgcgccgcg tgcggccgcc accgagtcct gtcccctgga cgacgatctg   1080
ccggccgtca tcgtctcgat gggggacagc tatatctccg gcgagggagg gcgctggcag   1140
ggcaacgcca acacctcctc cgggggcgac tcctggggca ccgaccgggc cgccgacggc   1200
acggaggtct acgagaagaa ctccgaaggc agcgatgcct gtcaccgctc cgacgtcgcg   1260
gagatcaagc gcgccgacat cgccgacatc ccggcggaac gcaggatcaa catcgcctgc   1320
tcgggcgccg agaccaagca cctgctcacc gagaccttca agggtgaaaa gccccagatc   1380
gagcagctcg ccgacgtcgc cgaaacccac cgggtggaca cgatcgtggt ctccatcggc   1440
ggcaacgacc tcgagttcgc cgacatcgtg agccagtgcg ccacggcctt catgctcggg   1500
gaaggcgcgt gtcacacgga cgtcgacgat acccttgata gccggttggg cgatgtgagc   1560
agatccgtct ccgaggttct ggccgccatc cgcgacacca tgatcgaggc cgggcaggac   1620
gataccagct acaagctcgt tctccagtcc taccctgccc cgttgcccgc gtcggatgag   1680
atgcggtaca cgggcgatca ctacgaccgg tacaccgagg gcggctgccc cttctatgac   1740
gtcgacctgg actggacgcg cgacgtcctc atcaaaaaga tcgaagccac gctgcgcggg   1800
gtggccaaga gtgcggatgc ggccttcctc aacctgacgg acacgttcac ggggcacgag   1860
ctgtgctcga agcacacccg acaggcggag tccggcgaat cgctggcgaa tccaatactg   1920
gaacacgagg ccgagtgggt gcgcttcgta ccaggtctca ccacgccggg tgacacggcc   1980
gaagccatcc atccgaatgc gttcggccag cacgccctca gtagctgcct cagccaggcc   2040
gtccggacga tggacgattc ggaccagagg tacttcgagt gcgacgggcg ggacaccgga   2100
aatccccgcc tcgtgtggcc acgcagttcg cccatcgacg ccgtcgtgga gaccgcggac   2160
ggttggcagg gcgacgactt ccggctcgcc gaccactaca tgttccagcg cggcgtctac   2220
gcccgcttca acccggacgc ggaccggagc ggcgcgatcg atccgggccg aatcaccttc   2280
ggccaaaccg acggatggct cggtgaggtg aaggacactt cgaactggcc gagcctgagt   2340
ggaaccgact tcgtcgacgg catcgacgcc gccgccgagg cacgcaccag caccggtcac   2400
cagctgctgc tgttccacag cggcgttgag gacaaccagt acgtgcgggt cgagatggcg   2460
ccgggcacca ctgacgacca gctcgtcagg ggccccgtgc ccatcacgag gtactggccc   2520
ctcttccagg acaccccttt cgaatggggc gtggatgccg ccgcggggga ccagctgaac   2580
cgggcgatgg tcttcaggca cggctatgtg gggctggtgc aggtctccct cgacgctctc   2640
agcgacgaat ggctcgtgga accgacgttg atcggctcgg cgattccggc gctggagggc   2700
accccgttcg agacaggggt ggacgcggcg atcgtgcggc accagcaacc gacggccatg   2760
tgggtcgacc tgatcagcgg tacgcaggtg gtgacgctgc tggtggactt ggacgatctg   2820
tcgaagagca cgtacatgac gagcatcgtg gagatcacga cgatgtggcc gagcctgcgc   2880
ggcagcatct tcgactggac cggcggagag gcgtggaagc cggagaagat gcagatcaag   2940
accggcgcgg gcgatcccta cgacatggac gccgacgacc ggcaggccaa gcctgcggtg   3000
tcgggctcgc acgagcagtg ccgtccggag ggactagcgc agacccccgg cgtgaacacg   3060
ccgtactgcg aggtgtacga caccgacggc cgcgaatggc tgggcgggaa cgggcacgac   3120
aggcgggtca tcggctactt caccggctgg cgcaccggtg agaacgacca gccgcgctac   3180
ctggtgccga acatcccgtg gtcgaaggtg acccacatca actacgcgtt cgcgaaagtc   3240
gacgacgaca acaagatcca aaga                                          3264
```

<210> SEQ ID NO 72
<211> LENGTH: 1088
<212> TYPE: PRT
<213> ORGANISM: Unknown
<220> FEATURE:
<223> OTHER INFORMATION: Obtained from an environmental sample.

<400> SEQUENCE: 72

Met Ser Leu Ser Ser Pro Pro Glu Thr Pro Glu Pro Pro Glu Pro Pro
1 5 10 15

Ser Pro Gly Ala Arg Ser Leu Arg Gly Gly Trp Ser Arg Arg Val Ala
20 25 30

Gly Leu Leu Ala Leu Val Leu Leu Thr Gly Leu Leu Gln Ile Val Val
35 40 45

Pro Leu Ala Arg Pro Ala Ala Ala Ala Val Gln Gln Pro Ala Met Thr
50 55 60

Trp Asn Leu His Gly Ala Lys Lys Thr Ala Glu Leu Val Pro Asp Leu
65 70 75 80

Met Arg Asn His Asn Val Thr Val Ala Ala Leu Gln Glu Val Ala Asn
85 90 95

Gly Asn Phe Leu Gly Leu Thr Pro Thr Glu His Asp Val Pro Tyr Leu
100 105 110

Lys Pro Asp Gly Thr Thr Ser Thr Pro Pro Asp Pro Gln Lys Trp Arg
115 120 125

Val Glu Lys Tyr Asn Leu Ala Lys Asp Asp Ala Thr Ala Phe Val Ile
130 135 140

Arg Thr Gly Ser Asn Asn Arg Gly Leu Ala Ile Val Thr Thr Gln Asp
145 150 155 160

Val Gly Asp Val Ser Gln Asn Val His Val Val Asn Val Thr Glu Asp
165 170 175

Trp Glu Gly Lys Met Phe Pro Ala Leu Gly Val Lys Ile Asp Gly Ala
180 185 190

Trp Tyr Tyr Ser Ile His Ala Ser Thr Thr Pro Lys Arg Ala Asn Asn
195 200 205

Asn Ala Gly Thr Leu Val Glu Asp Leu Ser Lys Leu His Glu Thr Ala
210 215 220

Ala Phe Glu Gly Asp Trp Ala Ala Met Gly Asp Trp Asn Arg Tyr Pro
225 230 235 240

Ser Glu Asp Ser Asn Ala Tyr Glu Asn Gln Arg Lys His Leu Lys Gly
245 250 255

Ala Met Arg Thr Asn Phe Pro Asp Asn Gln Ala Ala Leu Arg Glu Val
260 265 270

Leu Glu Phe Glu Ser Asp Glu Arg Val Ile Trp Gln Gly Ala Arg Thr
275 280 285

His Asp His Gly Ala Glu Leu Asp Tyr Met Val Ala Lys Gly Ala Gly
290 295 300

Asn Asp Tyr Lys Ala Ser Arg Ser Thr Ser Lys His Gly Ser Asp His
305 310 315 320

Tyr Pro Val Phe Phe Gly Ile Gly Asp Asp Ser Asp Thr Cys Met Gly
325 330 335

Gly Thr Ala Pro Val Ala Ala Asn Ala Pro Arg Ala Ala Ala Thr Glu
340 345 350

Ser Cys Pro Leu Asp Asp Asp Leu Pro Ala Val Ile Val Ser Met Gly
355 360 365

Asp Ser Tyr Ile Ser Gly Glu Gly Gly Arg Trp Gln Gly Asn Ala Asn

```
    370                 375                 380

Thr Ser Ser Gly Gly Asp Ser Trp Gly Thr Asp Arg Ala Ala Asp Gly
385                 390                 395                 400

Thr Glu Val Tyr Glu Lys Asn Ser Glu Gly Ser Asp Ala Cys His Arg
                405                 410                 415

Ser Asp Val Ala Glu Ile Lys Arg Ala Asp Ile Ala Asp Ile Pro Ala
            420                 425                 430

Glu Arg Arg Ile Asn Ile Ala Cys Ser Gly Ala Glu Thr Lys His Leu
        435                 440                 445

Leu Thr Glu Thr Phe Lys Gly Glu Lys Pro Gln Ile Glu Gln Leu Ala
    450                 455                 460

Asp Val Ala Glu Thr His Arg Val Asp Thr Ile Val Val Ser Ile Gly
465                 470                 475                 480

Gly Asn Asp Leu Glu Phe Ala Asp Ile Val Ser Gln Cys Ala Thr Ala
                485                 490                 495

Phe Met Leu Gly Glu Gly Ala Cys His Thr Asp Val Asp Asp Thr Leu
            500                 505                 510

Asp Ser Arg Leu Gly Asp Val Ser Arg Ser Val Ser Glu Val Leu Ala
        515                 520                 525

Ala Ile Arg Asp Thr Met Ile Glu Ala Gly Gln Asp Asp Thr Ser Tyr
    530                 535                 540

Lys Leu Val Leu Gln Ser Tyr Pro Ala Pro Leu Pro Ala Ser Asp Glu
545                 550                 555                 560

Met Arg Tyr Thr Gly Asp His Tyr Asp Arg Tyr Thr Glu Gly Gly Cys
                565                 570                 575

Pro Phe Tyr Asp Val Asp Leu Asp Trp Thr Arg Asp Val Leu Ile Lys
            580                 585                 590

Lys Ile Glu Ala Thr Leu Arg Gly Val Ala Lys Ser Ala Asp Ala Ala
        595                 600                 605

Phe Leu Asn Leu Thr Asp Thr Phe Thr Gly His Glu Leu Cys Ser Lys
    610                 615                 620

His Thr Arg Gln Ala Glu Ser Gly Glu Ser Leu Ala Asn Pro Ile Leu
625                 630                 635                 640

Glu His Glu Ala Glu Trp Val Arg Phe Val Pro Gly Leu Thr Thr Pro
                645                 650                 655

Gly Asp Thr Ala Glu Ala Ile His Pro Asn Ala Phe Gly Gln His Ala
            660                 665                 670

Leu Ser Ser Cys Leu Ser Gln Ala Val Arg Thr Met Asp Asp Ser Asp
        675                 680                 685

Gln Arg Tyr Phe Glu Cys Asp Gly Arg Asp Thr Gly Asn Pro Arg Leu
    690                 695                 700

Val Trp Pro Arg Ser Ser Pro Ile Asp Ala Val Val Glu Thr Ala Asp
705                 710                 715                 720

Gly Trp Gln Gly Asp Asp Phe Arg Leu Ala Asp His Tyr Met Phe Gln
                725                 730                 735

Arg Gly Val Tyr Ala Arg Phe Asn Pro Asp Ala Asp Arg Ser Gly Ala
            740                 745                 750

Ile Asp Pro Gly Arg Ile Thr Phe Gly Gln Thr Asp Gly Trp Leu Gly
        755                 760                 765

Glu Val Lys Asp Thr Ser Asn Trp Pro Ser Leu Ser Gly Thr Asp Phe
    770                 775                 780

Val Asp Gly Ile Asp Ala Ala Ala Glu Ala Arg Thr Ser Thr Gly His
785                 790                 795                 800
```

```
Gln Leu Leu Leu Phe His Ser Gly Val Glu Asp Asn Gln Tyr Val Arg
                805                 810                 815

Val Glu Met Ala Pro Gly Thr Thr Asp Asp Gln Leu Val Arg Gly Pro
            820                 825                 830

Val Pro Ile Thr Arg Tyr Trp Pro Leu Phe Gln Asp Thr Pro Phe Glu
        835                 840                 845

Trp Gly Val Asp Ala Ala Ala Gly Asp Gln Leu Asn Arg Ala Met Val
    850                 855                 860

Phe Arg His Gly Tyr Val Gly Leu Val Gln Val Ser Leu Asp Ala Leu
865                 870                 875                 880

Ser Asp Glu Trp Leu Val Glu Pro Thr Leu Ile Gly Ser Ala Ile Pro
                885                 890                 895

Ala Leu Glu Gly Thr Pro Phe Glu Thr Gly Val Asp Ala Ala Ile Val
            900                 905                 910

Arg His Gln Gln Pro Thr Ala Met Trp Val Asp Leu Ile Ser Gly Thr
        915                 920                 925

Gln Val Val Thr Leu Leu Val Asp Leu Asp Asp Leu Ser Lys Ser Thr
    930                 935                 940

Tyr Met Thr Ser Ile Val Glu Ile Thr Thr Met Trp Pro Ser Leu Arg
945                 950                 955                 960

Gly Ser Ile Phe Asp Trp Thr Gly Gly Glu Ala Trp Lys Pro Glu Lys
                965                 970                 975

Met Gln Ile Lys Thr Gly Ala Gly Asp Pro Tyr Asp Met Asp Ala Asp
            980                 985                 990

Asp Arg Gln Ala Lys Pro Ala Val Ser Gly Ser His Glu Gln Cys Arg
        995                 1000                1005

Pro Glu Gly Leu Ala Gln Thr Pro Gly Val Asn Thr Pro Tyr Cys Glu
    1010                1015                1020

Val Tyr Asp Thr Asp Gly Arg Glu Trp Leu Gly Gly Asn Gly His Asp
1025                1030                1035                1040

Arg Arg Val Ile Gly Tyr Phe Thr Gly Trp Arg Thr Gly Glu Asn Asp
                1045                1050                1055

Gln Pro Arg Tyr Leu Val Pro Asn Ile Pro Trp Ser Lys Val Thr His
            1060                1065                1070

Ile Asn Tyr Ala Phe Ala Lys Val Asp Asp Asp Asn Lys Ile Gln Arg
        1075                1080                1085
```

<210> SEQ ID NO 73
<211> LENGTH: 753
<212> TYPE: DNA
<213> ORGANISM: Unknown
<220> FEATURE:
<223> OTHER INFORMATION: Obtained from an environmental sample.

<400> SEQUENCE: 73

```
atgggaaacg gtgcagcagt tggttccaat gataatggta gagaagaaag tgtttacgta      60

ctttctgtga tcgcctgtaa tgtttattat ttacagaagt gtgaaggtgg ggcatcgcgt     120

gatagcgtga ttagagaaat taatagccaa actcaacctt taggatatga gattgtagca     180

gattctattc gtgatggtca tattggttct tttgcctgta agatggcagt ctttagaaat     240

aatggtaatg gcaattgtgt tttagcgatc aaagggacag atatgaataa tatcaatgac     300

ttggtgaatg atctaaccat gatattagga ggcattggtt ctgttgctgc aatccaacca     360

acgattaaca tggcacaaga actcatcgac caatatggag tgaatttgat tactggtcac     420

tcccttggag gctacatgac tgaaatcatc gctaccaatc gtggactacc aggtattgca     480
```

ttttgcgcac caggttcaaa tggtccaatt gtaaaattag gtggacaaga gacacctggc 540
tttcacaatg ttaactttga acatgatcca gcaggtaacg ttatgactgg ggtttatact 600
catgtccaat ggagtattta tgtaggatgt gatggtatga ctcatggtat tgaaaatatg 660
gtgaattatt ttaaagataa aagagattta accaatcgca atattcaagg aagaagtgaa 720
agtcataata cgggttatta ttacccaaaa taa 753

<210> SEQ ID NO 74
<211> LENGTH: 250
<212> TYPE: PRT
<213> ORGANISM: Unknown
<220> FEATURE:
<223> OTHER INFORMATION: Obtained from an environmental sample.

<400> SEQUENCE: 74

Met Gly Asn Gly Ala Ala Val Gly Ser Asn Asp Asn Gly Arg Glu Glu
1 5 10 15

Ser Val Tyr Val Leu Ser Val Ile Ala Cys Asn Val Tyr Tyr Leu Gln
20 25 30

Lys Cys Glu Gly Gly Ala Ser Arg Asp Ser Val Ile Arg Glu Ile Asn
35 40 45

Ser Gln Thr Gln Pro Leu Gly Tyr Glu Ile Val Ala Asp Ser Ile Arg
50 55 60

Asp Gly His Ile Gly Ser Phe Ala Cys Lys Met Ala Val Phe Arg Asn
65 70 75 80

Asn Gly Asn Gly Asn Cys Val Leu Ala Ile Lys Gly Thr Asp Met Asn
85 90 95

Asn Ile Asn Asp Leu Val Asn Asp Leu Thr Met Ile Leu Gly Gly Ile
100 105 110

Gly Ser Val Ala Ala Ile Gln Pro Thr Ile Asn Met Ala Gln Glu Leu
115 120 125

Ile Asp Gln Tyr Gly Val Asn Leu Ile Thr Gly His Ser Leu Gly Gly
130 135 140

Tyr Met Thr Glu Ile Ile Ala Thr Asn Arg Gly Leu Pro Gly Ile Ala
145 150 155 160

Phe Cys Ala Pro Gly Ser Asn Gly Pro Ile Val Lys Leu Gly Gly Gln
165 170 175

Glu Thr Pro Gly Phe His Asn Val Asn Phe Glu His Asp Pro Ala Gly
180 185 190

Asn Val Met Thr Gly Val Tyr Thr His Val Gln Trp Ser Ile Tyr Val
195 200 205

Gly Cys Asp Gly Met Thr His Gly Ile Glu Asn Met Val Asn Tyr Phe
210 215 220

Lys Asp Lys Arg Asp Leu Thr Asn Arg Asn Ile Gln Gly Arg Ser Glu
225 230 235 240

Ser His Asn Thr Gly Tyr Tyr Tyr Pro Lys
245 250

<210> SEQ ID NO 75
<211> LENGTH: 1335
<212> TYPE: DNA
<213> ORGANISM: Unknown
<220> FEATURE:
<223> OTHER INFORMATION: Obtained from an environmental sample.

<400> SEQUENCE: 75
atgactacta aaatcttttt aattcacgga tggtctgtca agacaacaca aacatatcag 60

-continued

```
gcgctgcacc ttaagttggc agagcaggga tatcagctgg aagatattta cctcgggcgg    120

tatctgtccc ttgaaaatca tatcgaaata cgggatattg caaaagcaat gcaccgtgca    180

ttgctggaga ggattaccga ctggagtcag cctttccatt ttattactca cagtacggga    240

ggtatggtcg ccaaatattg gatattgaat cattataaag gaagtattgc aaaacaaaaa    300

ccactcaaaa atgtagtgtt tctggctgca cctaattttg gttcaaggct ggcacaccat    360

ggacgtacca tgctgggaga aataatggaa ctgggagaaa cagggaagaa gattcttgaa    420

tctctggagt taggaagtgc tttttcgtgg gatgtgaatg agcagttttt taatgcgtcc    480

aattggaaag ataaagaaat aaagttctat aacctgatag gagacagggt caaaacggat    540

ttttttaaat ccaaaatttt tccagctgcg tttgaaagcg ggtcagatat ggtgattcgg    600

gttgcggcag gaaatcagaa ctttgtccgg tacaggtacg atagtcagaa agatagcttt    660

actgttgtca atgagttgaa aggaattgct tttggtgctc tctaccaata tacacattcc    720

aatgatgatt atggaatcct gaacagcatc aaaaaaagtt caacccttga aaaccatcag    780

gcactcagac taattgtaga atgtctgaag gtttcgggag ataaagaata tgaaaatgtt    840

gttgcacagt tggctgcagc gacaaaagaa accagagaaa aacgccaggg atatgcacag    900

ctggatttcc gttttcggga tgatgaaggc tttccaatag atgattatgt tgtagagctg    960

ggagtaatgg taaatggaaa acctaaacca tctaaaacag tagatgacgt gcataagaat   1020

aaaattacac caaaccatct tactgtattc attaacctga aagaactgga acctaatctg   1080

aagtacttta tcaatattaa atcgatatcg gaatcctcca tgtatagtta cgatcctgct   1140

gtcaggacta tagagcttgc ttctaacgag attacaaaaa ttatccgtga ggaccataca   1200

acacagattg atgtgatact ttcccggact cctgctaaaa acctttttcat gtttcatcgc   1260

ggagatgatg aagacctaca tgtgacatgg tcgcggtacg gagaaacaaa aagtacaaag   1320

cagggaataa aataa                                                    1335
```

<210> SEQ ID NO 76
<211> LENGTH: 444
<212> TYPE: PRT
<213> ORGANISM: Unknown
<220> FEATURE:
<223> OTHER INFORMATION: Obtained from an environmental sample.

<400> SEQUENCE: 76

```
Met Thr Thr Lys Ile Phe Leu Ile His Gly Trp Ser Val Lys Thr Thr
 1               5                  10                  15

Gln Thr Tyr Gln Ala Leu His Leu Lys Leu Ala Glu Gln Gly Tyr Gln
            20                  25                  30

Leu Glu Asp Ile Tyr Leu Gly Arg Tyr Leu Ser Leu Glu Asn His Ile
        35                  40                  45

Glu Ile Arg Asp Ile Ala Lys Ala Met His Arg Ala Leu Leu Glu Arg
    50                  55                  60

Ile Thr Asp Trp Ser Gln Pro Phe His Phe Ile Thr His Ser Thr Gly
65                  70                  75                  80

Gly Met Val Ala Lys Tyr Trp Ile Leu Asn His Tyr Lys Gly Ser Ile
                85                  90                  95

Ala Lys Gln Lys Pro Leu Lys Asn Val Val Phe Leu Ala Ala Pro Asn
            100                 105                 110

Phe Gly Ser Arg Leu Ala His His Gly Arg Thr Met Leu Gly Glu Ile
        115                 120                 125

Met Glu Leu Gly Glu Thr Gly Lys Lys Ile Leu Glu Ser Leu Glu Leu
    130                 135                 140
```

```
Gly Ser Ala Phe Ser Trp Asp Val Asn Glu Gln Phe Phe Asn Ala Ser
145                 150                 155                 160

Asn Trp Lys Asp Lys Glu Ile Lys Phe Tyr Asn Leu Ile Gly Asp Arg
                165                 170                 175

Val Lys Thr Asp Phe Phe Lys Ser Lys Ile Phe Pro Ala Ala Phe Glu
            180                 185                 190

Ser Gly Ser Asp Met Val Ile Arg Val Ala Ala Gly Asn Gln Asn Phe
        195                 200                 205

Val Arg Tyr Arg Tyr Asp Ser Gln Lys Asp Ser Phe Thr Val Val Asn
    210                 215                 220

Glu Leu Lys Gly Ile Ala Phe Gly Ala Leu Tyr Gln Tyr Thr His Ser
225                 230                 235                 240

Asn Asp Asp Tyr Gly Ile Leu Asn Ser Ile Lys Lys Ser Ser Thr Leu
                245                 250                 255

Glu Asn His Gln Ala Leu Arg Leu Ile Val Glu Cys Leu Lys Val Ser
            260                 265                 270

Gly Asp Lys Glu Tyr Glu Asn Val Val Ala Gln Leu Ala Ala Ala Thr
        275                 280                 285

Lys Glu Thr Arg Glu Lys Arg Gln Gly Tyr Ala Gln Leu Asp Phe Arg
    290                 295                 300

Phe Arg Asp Asp Glu Gly Phe Pro Ile Asp Asp Tyr Val Val Glu Leu
305                 310                 315                 320

Gly Val Met Val Asn Gly Lys Pro Lys Pro Ser Lys Thr Val Asp Asp
                325                 330                 335

Val His Lys Asn Lys Ile Thr Pro Asn His Leu Thr Val Phe Ile Asn
            340                 345                 350

Leu Lys Glu Leu Glu Pro Asn Leu Lys Tyr Phe Ile Asn Ile Lys Ser
        355                 360                 365

Ile Ser Glu Ser Ser Met Tyr Ser Tyr Asp Pro Ala Val Arg Thr Ile
    370                 375                 380

Glu Leu Ala Ser Asn Glu Ile Thr Lys Ile Ile Arg Glu Asp His Thr
385                 390                 395                 400

Thr Gln Ile Asp Val Ile Leu Ser Arg Thr Pro Ala Lys Asn Leu Phe
                405                 410                 415

Met Phe His Arg Gly Asp Asp Glu Asp Leu His Val Thr Trp Ser Arg
            420                 425                 430

Tyr Gly Glu Thr Lys Ser Thr Lys Gln Gly Ile Lys
        435                 440
```

<210> SEQ ID NO 77
<211> LENGTH: 1026
<212> TYPE: DNA
<213> ORGANISM: Unknown
<220> FEATURE:
<223> OTHER INFORMATION: Obtained from an environmental sample.

<400> SEQUENCE: 77

```
atggcttatc actttaaaaa cttggtcttc gaaggcggtg gcgtgaaagg catcgcctac      60

gtgggtgctc ttgaagtact tgagagagaa ggcattctga aagacatcaa acgcgtggct     120

ggtacttcgg ctggagcgct ggttgccgtc ttaatcagtt tgggctatac cgcccaagaa     180

ttgaaggaca tcctatggaa aatcaatttc caaaactttt tggacagctc gtggggcttg     240

gtgcgcaaca cggcacgttt cattgaggat tacggttggt acaaaggtga gtttttccgc     300

gaattggttg ccggctacat caaggaaaaa acgggcaata gtgaaagcac tttcaaggat     360
```

```
ctggccaaat caaaagattt ccgtggcctc agccttattg gtagcgatct gtccacagga    420

tactcaaagg tgttcagcaa cgaattcacc ccaaacgtca aagtagctga tgcagcccgc    480

atctccatgt cgatacccct gtttttcaaa gccgttcgcg gtgtaaacgg tgatggacac    540

atttacgtcg atggtggact gttagacaac tatgccatca aggtgttcga ccgcgtcaat    600

tacgtaaaga ataagaacaa cgtacggtac accgagtatt atgaaaagac caacaagtcg    660

ctgaaaagca aaaacaagct gaccaacgaa tacgtctaca ataaagaaac tttgggcttc    720

cgattggatg ccaaagaaca gattgagatg tttctcgacc atagtataga accaaaggca    780

aaggacattg actcactatt ctcttacacg aaggctttgg tcaccaccct catcgacttt    840

caaaacaatg tacatttgca tagtgacgac tggcaacgca cagtctatat cgactcttta    900

ggtatcagtt ccactgactt cggcatctct gactctaaaa aacagaaact cgtcgattca    960

ggcattttgc atacgcaaaa atacctggat tggtataaca acgacgaaga gaaagccaac   1020

aaatag                                                               1026
```

```
<210> SEQ ID NO 78
<211> LENGTH: 341
<212> TYPE: PRT
<213> ORGANISM: Unknown
<220> FEATURE:
<223> OTHER INFORMATION: Obtained from an environmental sample.

<400> SEQUENCE: 78

Met Ala Tyr His Phe Lys Asn Leu Val Phe Glu Gly Gly Gly Val Lys
 1               5                  10                  15

Gly Ile Ala Tyr Val Gly Ala Leu Glu Val Leu Glu Arg Glu Gly Ile
            20                  25                  30

Leu Lys Asp Ile Lys Arg Val Ala Gly Thr Ser Ala Gly Ala Leu Val
        35                  40                  45

Ala Val Leu Ile Ser Leu Gly Tyr Thr Ala Gln Glu Leu Lys Asp Ile
    50                  55                  60

Leu Trp Lys Ile Asn Phe Gln Asn Phe Leu Asp Ser Ser Trp Gly Leu
65                  70                  75                  80

Val Arg Asn Thr Ala Arg Phe Ile Glu Asp Tyr Gly Trp Tyr Lys Gly
                85                  90                  95

Glu Phe Phe Arg Glu Leu Val Ala Gly Tyr Ile Lys Glu Lys Thr Gly
            100                 105                 110

Asn Ser Glu Ser Thr Phe Lys Asp Leu Ala Lys Ser Lys Asp Phe Arg
        115                 120                 125

Gly Leu Ser Leu Ile Gly Ser Asp Leu Ser Thr Gly Tyr Ser Lys Val
    130                 135                 140

Phe Ser Asn Glu Phe Thr Pro Asn Val Lys Val Ala Asp Ala Ala Arg
145                 150                 155                 160

Ile Ser Met Ser Ile Pro Leu Phe Phe Lys Ala Val Arg Gly Val Asn
                165                 170                 175

Gly Asp Gly His Ile Tyr Val Asp Gly Gly Leu Leu Asp Asn Tyr Ala
            180                 185                 190

Ile Lys Val Phe Asp Arg Val Asn Tyr Val Lys Asn Lys Asn Asn Val
        195                 200                 205

Arg Tyr Thr Glu Tyr Tyr Glu Lys Thr Asn Lys Ser Leu Lys Ser Lys
    210                 215                 220

Asn Lys Leu Thr Asn Glu Tyr Val Tyr Asn Lys Glu Thr Leu Gly Phe
225                 230                 235                 240

Arg Leu Asp Ala Lys Glu Gln Ile Glu Met Phe Leu Asp His Ser Ile
```

```
                245                 250                 255

Glu Pro Lys Ala Lys Asp Ile Asp Ser Leu Phe Ser Tyr Thr Lys Ala
            260                 265                 270

Leu Val Thr Thr Leu Ile Asp Phe Gln Asn Asn Val His Leu His Ser
        275                 280                 285

Asp Asp Trp Gln Arg Thr Val Tyr Ile Asp Ser Leu Gly Ile Ser Ser
    290                 295                 300

Thr Asp Phe Gly Ile Ser Asp Ser Lys Lys Gln Lys Leu Val Asp Ser
305                 310                 315                 320

Gly Ile Leu His Thr Gln Lys Tyr Leu Asp Trp Tyr Asn Asn Asp Glu
                325                 330                 335

Glu Lys Ala Asn Lys
            340


<210> SEQ ID NO 79
<211> LENGTH: 1701
<212> TYPE: DNA
<213> ORGANISM: Unknown
<220> FEATURE:
<223> OTHER INFORMATION: Obtained from an environmental sample.

<400> SEQUENCE: 79

atgagaaatt tcagcaaggg attgaccagt attttgctta gcatagcgac atccaccagt      60

gcgatggcct ttacccagat cggggccggc ggagcgattc cgatgggcca tgagtggcta     120

acccgccgct cggcgctgga actgctgaat gccgacaatc tggtcggcaa tgacccggcc     180

gacccacgct tgggctggag cgaaggtctc gccaacaatc tcgatctctc gaatgcccag     240

aacgaagtgc agcgcatcaa gagcattacc aagagccacg ccctgtatga gccgcgttac     300

gatgacgttt tcgccgccat cgtcggcgag cgctgggttg ataccgccgg tttcaacgtg     360

gccaaggcca ccgtcggcaa gatcgattgc ttcagcgccg tcgcgcaaga gcccgccgat     420

gtgcaacaag accatttcat gcgccgttat gacgacgtgg gtggacaagg gggcgtgaac     480

gctgcccgcc gcgcgcagca gcgctttatc aatcacttcg tcaacgcagc catggccgaa     540

gagaagagca tcaaggcatg ggatggcggc ggttattctt cgctggaaaa agtcagccac     600

aactacttct tgtttggccg cgccgttcat ttgttccagg attctttcag ccccgaacac     660

accgtgcgcc tgcctgaaga caattacgtc aaagtccgtc aggtcaaggc gtatctctgc     720

tctgaaggtg ccgaacagca tacgcacaac acgcaagatg ccatcaactt caccagcggc     780

gatgtcatct ggaaacagaa cacccgtctg gatgcaggct ggagcaccta caaggccagc     840

aacatgaagc cggtggcatt ggttgccctc gaagccagca aagatttgtg ggccgccttt     900

attcgcacca tggccgtttc ccgcgaggag cgtcgcgccg tcgccgaaca ggaagcgcag     960

gctctcgtca atcactggtt gtcgttcgac gaacaggaaa tgctgaactg gtacgaagaa    1020

gaagagcacc gcgatcatac gtacgtcaag gaacccggcc agagcggccc aggttcgtcg    1080

ttattcgatt gcatggttgg tctgggtgtg gcctcgggca gtcaggcgca acgggtggcg    1140

gaactcgatc agcaacgccg ccaatgtttg ttcaacgtca aggccgctac tggctatggc    1200

gatctgaatg atccacacat ggatattccg tacaactggc aatgggtgtc gtcgacgcaa    1260

tggaaaatcc ctgcggccga ctggaaaatc ccgcagctgc ccgccgattc agggaaatca    1320

gtcgtcatca agaattcgat caatggcgat ccgctggtgg cacctgccgg gctcaagcac    1380

aacaccgatg tttacggtgc accgggtgag gcgattgaat tcattttcgt cggtgatttc    1440

aaccatgagg cgtatttccg caccaaggac aacgcggatc tgttcctgag ttacagcgcg    1500
```

gtatcgggca agggcttgct gtacaacacg cccaaccagg ccggttatcg tgttcagcct 1560
tatggtgtgc tgtggacgat tgagaatacc tactggaatg atttcctctg gtacaacagc 1620
tcgaacgacc gcatctatgt cagcggcacc ggcgctgcca acaagtcaca ctcccagtgg 1680
attattgacg gcttgcagtg a 1701

<210> SEQ ID NO 80
<211> LENGTH: 566
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample.

<400> SEQUENCE: 80

Met Arg Asn Phe Ser Lys Gly Leu Thr Ser Ile Leu Leu Ser Ile Ala
1 5 10 15

Thr Ser Thr Ser Ala Met Ala Phe Thr Gln Ile Gly Ala Gly Gly Ala
20 25 30

Ile Pro Met Gly His Glu Trp Leu Thr Arg Arg Ser Ala Leu Glu Leu
35 40 45

Leu Asn Ala Asp Asn Leu Val Gly Asn Asp Pro Ala Asp Pro Arg Leu
50 55 60

Gly Trp Ser Glu Gly Leu Ala Asn Asn Leu Asp Leu Ser Asn Ala Gln
65 70 75 80

Asn Glu Val Gln Arg Ile Lys Ser Ile Thr Lys Ser His Ala Leu Tyr
85 90 95

Glu Pro Arg Tyr Asp Asp Val Phe Ala Ala Ile Val Gly Glu Arg Trp
100 105 110

Val Asp Thr Ala Gly Phe Asn Val Ala Lys Ala Thr Val Gly Lys Ile
115 120 125

Asp Cys Phe Ser Ala Val Ala Gln Glu Pro Ala Asp Val Gln Gln Asp
130 135 140

His Phe Met Arg Arg Tyr Asp Asp Val Gly Gly Gln Gly Gly Val Asn
145 150 155 160

Ala Ala Arg Arg Ala Gln Gln Arg Phe Ile Asn His Phe Val Asn Ala
165 170 175

Ala Met Ala Glu Glu Lys Ser Ile Lys Ala Trp Asp Gly Gly Gly Tyr
180 185 190

Ser Ser Leu Glu Lys Val Ser His Asn Tyr Phe Leu Phe Gly Arg Ala
195 200 205

Val His Leu Phe Gln Asp Ser Phe Ser Pro Glu His Thr Val Arg Leu
210 215 220

Pro Glu Asp Asn Tyr Val Lys Val Arg Gln Val Lys Ala Tyr Leu Cys
225 230 235 240

Ser Glu Gly Ala Glu Gln His Thr His Asn Thr Gln Asp Ala Ile Asn
245 250 255

Phe Thr Ser Gly Asp Val Ile Trp Lys Gln Asn Thr Arg Leu Asp Ala
260 265 270

Gly Trp Ser Thr Tyr Lys Ala Ser Asn Met Lys Pro Val Ala Leu Val
275 280 285

Ala Leu Glu Ala Ser Lys Asp Leu Trp Ala Ala Phe Ile Arg Thr Met
290 295 300

Ala Val Ser Arg Glu Glu Arg Arg Ala Val Ala Glu Gln Glu Ala Gln
305 310 315 320

-continued

```
Ala Leu Val Asn His Trp Leu Ser Phe Asp Glu Gln Glu Met Leu Asn
                325                 330                 335

Trp Tyr Glu Glu Glu Glu His Arg Asp His Thr Tyr Val Lys Glu Pro
            340                 345                 350

Gly Gln Ser Gly Pro Gly Ser Ser Leu Phe Asp Cys Met Val Gly Leu
        355                 360                 365

Gly Val Ala Ser Gly Ser Gln Ala Gln Arg Val Ala Glu Leu Asp Gln
    370                 375                 380

Gln Arg Arg Gln Cys Leu Phe Asn Val Lys Ala Ala Thr Gly Tyr Gly
385                 390                 395                 400

Asp Leu Asn Asp Pro His Met Asp Ile Pro Tyr Asn Trp Gln Trp Val
                405                 410                 415

Ser Ser Thr Gln Trp Lys Ile Pro Ala Ala Asp Trp Lys Ile Pro Gln
            420                 425                 430

Leu Pro Ala Asp Ser Gly Lys Ser Val Val Ile Lys Asn Ser Ile Asn
        435                 440                 445

Gly Asp Pro Leu Val Ala Pro Ala Gly Leu Lys His Asn Thr Asp Val
    450                 455                 460

Tyr Gly Ala Pro Gly Glu Ala Ile Glu Phe Ile Phe Val Gly Asp Phe
465                 470                 475                 480

Asn His Glu Ala Tyr Phe Arg Thr Lys Asp Asn Ala Asp Leu Phe Leu
                485                 490                 495

Ser Tyr Ser Ala Val Ser Gly Lys Gly Leu Leu Tyr Asn Thr Pro Asn
            500                 505                 510

Gln Ala Gly Tyr Arg Val Gln Pro Tyr Gly Val Leu Trp Thr Ile Glu
        515                 520                 525

Asn Thr Tyr Trp Asn Asp Phe Leu Trp Tyr Asn Ser Ser Asn Asp Arg
    530                 535                 540

Ile Tyr Val Ser Gly Thr Gly Ala Ala Asn Lys Ser His Ser Gln Trp
545                 550                 555                 560

Ile Ile Asp Gly Leu Gln
                565


<210> SEQ ID NO 81
<211> LENGTH: 1422
<212> TYPE: DNA
<213> ORGANISM: Unknown
<220> FEATURE:
<223> OTHER INFORMATION: Obtained from an environmental sample.

<400> SEQUENCE: 81

atgaaaaaga aattatgtac aatggctctt gtaacagcaa tatcttctgg tgttgttacg      60

attccaacag aagcacaagc ttgtggaata ggcgaagtaa tgaaacagga gaaccaagag     120

cacaaacgtg tgaaaagatg gtctgcggag catccgcatc attcaaatga aagtacacat     180

ttatggattg cacgaaatgc gattcaaatt atgagtcgta atcaagataa gacggttcaa     240

gaaaatgaat tacaattttt aaatactcct gaatataagg agttatttga aagaggtctt     300

tatgatgctg attaccttga tgaatttaac gatggaggta caggtacaat cggcattgat     360

gggctaatta gaggagggtg gaaatctcat ttttacgatc ccgatacaag aaagaactat     420

aaaggggaag aagaaccaac agctctttca caaggagata aatattttaa attagcaggt     480

gaatacttta agaagggcga ccaaaaacaa gctttttatt atttaggtgt tgcaacgcat     540

tactttacag atgctactca accaatgcat gctgctaatt ttacagccgt cgacacgagt     600

gctttaaagt ttcatagcgc ttttgaaaat tatgtgacga caattcagac acagtatgaa     660
```

```
gtatctgatg gtgagggcgt atataattta gtgaattcta atgatccaaa acagtggatc    720

catgaaacag cgagactcgc aaaagtggaa atcgggaaca ttaccaatga cgagattaaa    780

tctcactata ataaaggaaa caatgctctt tggcaacaag aagttatgcc agctgtccag    840

aggagtttag agaacgcaca aagaaacacg gcgggattta ttcatttatg gtttaaaaca    900

tttgttggca atactgccgc tgaagaaatt gaaaatactg tagtgaaaga ttctaaagga    960

gaagcaatac aagataataa aaaatacttc gtagtgccaa gtgagtttct aaatagaggt   1020

ttgacctttg aagtatatgc aaggaatgac tatgcactat tatctaatta cgtagatgat   1080

agtaaagttc atggtacgcc agttcagttt gtatttgata aagataataa cggtatcctt   1140

catcgaggag aaagtgtact gctgaaaatg acgcaatcta actatgataa ttacgtattt   1200

ctaaactact ctaacttgac aaactgggta catcttgcgc aacaaaaaac aaatactgca   1260

cagtttaaag tgtatccaaa tccgaataac ccatctgaat attacctata tacagatgga   1320

tacccagtaa attatcaaga aaatggtaac ggaaagagct ggattgtgtt aggaaagaaa   1380

acagatacac caaaagcttg gaaatttata caggctgaat ag                      1422
```

```
<210> SEQ ID NO 82
<211> LENGTH: 473
<212> TYPE: PRT
<213> ORGANISM: Unknown
<220> FEATURE:
<221> NAME/KEY: SIGNAL
<222> LOCATION: (1)...(25)
<223> OTHER INFORMATION: Obtained from an environmental sample.

<400> SEQUENCE: 82

Met Lys Lys Lys Leu Cys Thr Met Ala Leu Val Thr Ala Ile Ser Ser
 1               5                  10                  15

Gly Val Val Thr Ile Pro Thr Glu Ala Gln Ala Cys Gly Ile Gly Glu
            20                  25                  30

Val Met Lys Gln Glu Asn Gln Glu His Lys Arg Val Lys Arg Trp Ser
        35                  40                  45

Ala Glu His Pro His His Ser Asn Glu Ser Thr His Leu Trp Ile Ala
    50                  55                  60

Arg Asn Ala Ile Gln Ile Met Ser Arg Asn Gln Asp Lys Thr Val Gln
65                  70                  75                  80

Glu Asn Glu Leu Gln Phe Leu Asn Thr Pro Glu Tyr Lys Glu Leu Phe
                85                  90                  95

Glu Arg Gly Leu Tyr Asp Ala Asp Tyr Leu Asp Glu Phe Asn Asp Gly
            100                 105                 110

Gly Thr Gly Thr Ile Gly Ile Asp Gly Leu Ile Arg Gly Gly Trp Lys
        115                 120                 125

Ser His Phe Tyr Asp Pro Asp Thr Arg Lys Asn Tyr Lys Gly Glu Glu
    130                 135                 140

Glu Pro Thr Ala Leu Ser Gln Gly Asp Lys Tyr Phe Lys Leu Ala Gly
145                 150                 155                 160

Glu Tyr Phe Lys Lys Gly Asp Gln Lys Gln Ala Phe Tyr Tyr Leu Gly
                165                 170                 175

Val Ala Thr His Tyr Phe Thr Asp Ala Thr Gln Pro Met His Ala Ala
            180                 185                 190

Asn Phe Thr Ala Val Asp Thr Ser Ala Leu Lys Phe His Ser Ala Phe
        195                 200                 205

Glu Asn Tyr Val Thr Thr Ile Gln Thr Gln Tyr Glu Val Ser Asp Gly
    210                 215                 220
```

```
Glu Gly Val Tyr Asn Leu Val Asn Ser Asn Asp Pro Lys Gln Trp Ile
225                 230                 235                 240

His Glu Thr Ala Arg Leu Ala Lys Val Glu Ile Gly Asn Ile Thr Asn
                245                 250                 255

Asp Glu Ile Lys Ser His Tyr Asn Lys Gly Asn Asn Ala Leu Trp Gln
            260                 265                 270

Gln Glu Val Met Pro Ala Val Gln Arg Ser Leu Glu Asn Ala Gln Arg
        275                 280                 285

Asn Thr Ala Gly Phe Ile His Leu Trp Phe Lys Thr Phe Val Gly Asn
    290                 295                 300

Thr Ala Ala Glu Glu Ile Glu Asn Thr Val Val Lys Asp Ser Lys Gly
305                 310                 315                 320

Glu Ala Ile Gln Asp Asn Lys Lys Tyr Phe Val Val Pro Ser Glu Phe
                325                 330                 335

Leu Asn Arg Gly Leu Thr Phe Glu Val Tyr Ala Arg Asn Asp Tyr Ala
            340                 345                 350

Leu Leu Ser Asn Tyr Val Asp Asp Ser Lys Val His Gly Thr Pro Val
        355                 360                 365

Gln Phe Val Phe Asp Lys Asp Asn Asn Gly Ile Leu His Arg Gly Glu
    370                 375                 380

Ser Val Leu Leu Lys Met Thr Gln Ser Asn Tyr Asp Asn Tyr Val Phe
385                 390                 395                 400

Leu Asn Tyr Ser Asn Leu Thr Asn Trp Val His Leu Ala Gln Gln Lys
                405                 410                 415

Thr Asn Thr Ala Gln Phe Lys Val Tyr Pro Asn Pro Asn Asn Pro Ser
            420                 425                 430

Glu Tyr Tyr Leu Tyr Thr Asp Gly Tyr Pro Val Asn Tyr Gln Glu Asn
        435                 440                 445

Gly Asn Gly Lys Ser Trp Ile Val Leu Gly Lys Lys Thr Asp Thr Pro
    450                 455                 460

Lys Ala Trp Lys Phe Ile Gln Ala Glu
465                 470
```

<210> SEQ ID NO 83
<211> LENGTH: 1290
<212> TYPE: DNA
<213> ORGANISM: Unknown
<220> FEATURE:
<223> OTHER INFORMATION: Obtained from an environmental sample.

<400> SEQUENCE: 83

```
atgaaaaaga tagtgattta ttcatttgta gcaggggtta tgacatcagg cggcgtattt      60

gccgccagtg acaatattgt ggagacgtcg accccaccac agcatcaggc cccaagcaga     120

caggacaggg cattattcgc gggtgataca acaacctata taaaatgtgt ctacaaagtg     180

gatggccagg atgacagcaa tccatcctca tcttggttat gggcgaaagt gggtagcaac     240

tatgcgaagc tgaaggggta ttggtataat tcaatgccgc tggcaaacat gttttacact     300

gaagtaccct atgcagaggt gatggacttg tgtaatagca ccctgaaggc ggtaggtgcc     360

aactccactc ttgttattcc atatgcatcg gattacaccc tgtcctatta ctatgtgatt     420

tggaatcaag gggctaacca gccggttatc aacgttggcg gcagagagct tgaccgtatg     480

gtggtctttg gtgacagctt gagcgatacc gtcaatgtct ataacggctc gtacggtacc     540

gtgccgaata gtacctcctg gttattgggc catttctcta acggaaagct ttggcatgaa     600

tacctttcca cggtattgaa tctgcctagc tatgtgtggg cgactggcaa tgcggagagt     660
```

```
ggagagaaac ccttctttaa cggattcagt aagcaggtgg attctttcag ggattatcac    720

gctcgcacta aaggctacga tattagcaag acgttgttta ccgttctgtt tggtggaaat    780

gattttataa cggggggaaa aagcgccgat gaggtcattg agcaatatac ggtgtcattg    840

aactacttgg ctcaactagg ggcgaagcag gttgcaattt tccgcttgcc agatttttca    900

gtgataccca gcgtttcaac gtggacagag gctgataagg acaaactgag agagaatagt    960

gttcagttta atgaccaagc cgagaagctg atcgctaaac taaacgcggc acatccccaa   1020

acgacgtttt atacgctgag gttggatgac gcttttaagc aggtgttgga aaacagcgac   1080

caatacggct ttgttaataa gactgatacc tgcctggata tttcccaagg cggatacaac   1140

tatgccattg gggcccgcgc gaaaacggca tgtaagagca gcaatgcggc gtttgtattc   1200

tgggacaata tgcatccgac caccaaaaca cacggattgt tggccgatct tttaaaagat   1260

gatgtggtac gcggcctcgc tgcgccatga                                    1290


<210> SEQ ID NO 84
<211> LENGTH: 429
<212> TYPE: PRT
<213> ORGANISM: Unknown
<220> FEATURE:
<221> NAME/KEY: SIGNAL
<222> LOCATION: (1)...(22)
<223> OTHER INFORMATION: Obtained from an environmental sample.

<400> SEQUENCE: 84

Met Lys Lys Ile Val Ile Tyr Ser Phe Val Ala Gly Val Met Thr Ser
 1               5                  10                  15

Gly Gly Val Phe Ala Ala Ser Asp Asn Ile Val Glu Thr Ser Thr Pro
            20                  25                  30

Pro Gln His Gln Ala Pro Ser Arg Gln Asp Arg Ala Leu Phe Ala Gly
        35                  40                  45

Asp Thr Thr Thr Tyr Ile Lys Cys Val Tyr Lys Val Asp Gly Gln Asp
    50                  55                  60

Asp Ser Asn Pro Ser Ser Ser Trp Leu Trp Ala Lys Val Gly Ser Asn
65                  70                  75                  80

Tyr Ala Lys Leu Lys Gly Tyr Trp Tyr Asn Ser Met Pro Leu Ala Asn
                85                  90                  95

Met Phe Tyr Thr Glu Val Pro Tyr Ala Glu Val Met Asp Leu Cys Asn
            100                 105                 110

Ser Thr Leu Lys Ala Val Gly Ala Asn Ser Thr Leu Val Ile Pro Tyr
        115                 120                 125

Ala Ser Asp Tyr Thr Leu Ser Tyr Tyr Tyr Val Ile Trp Asn Gln Gly
    130                 135                 140

Ala Asn Gln Pro Val Ile Asn Val Gly Gly Arg Glu Leu Asp Arg Met
145                 150                 155                 160

Val Val Phe Gly Asp Ser Leu Ser Asp Thr Val Asn Val Tyr Asn Gly
                165                 170                 175

Ser Tyr Gly Thr Val Pro Asn Ser Thr Ser Trp Leu Leu Gly His Phe
            180                 185                 190

Ser Asn Gly Lys Leu Trp His Glu Tyr Leu Ser Thr Val Leu Asn Leu
        195                 200                 205

Pro Ser Tyr Val Trp Ala Thr Gly Asn Ala Glu Ser Gly Glu Lys Pro
    210                 215                 220

Phe Phe Asn Gly Phe Ser Lys Gln Val Asp Ser Phe Arg Asp Tyr His
225                 230                 235                 240

Ala Arg Thr Lys Gly Tyr Asp Ile Ser Lys Thr Leu Phe Thr Val Leu
```

```
                245                 250                 255

Phe Gly Gly Asn Asp Phe Ile Thr Gly Gly Lys Ser Ala Asp Glu Val
            260                 265                 270

Ile Glu Gln Tyr Thr Val Ser Leu Asn Tyr Leu Ala Gln Leu Gly Ala
        275                 280                 285

Lys Gln Val Ala Ile Phe Arg Leu Pro Asp Phe Ser Val Ile Pro Ser
    290                 295                 300

Val Ser Thr Trp Thr Glu Ala Asp Lys Asp Lys Leu Arg Glu Asn Ser
305                 310                 315                 320

Val Gln Phe Asn Asp Gln Ala Glu Lys Leu Ile Ala Lys Leu Asn Ala
                325                 330                 335

Ala His Pro Gln Thr Thr Phe Tyr Thr Leu Arg Leu Asp Asp Ala Phe
            340                 345                 350

Lys Gln Val Leu Glu Asn Ser Asp Gln Tyr Gly Phe Val Asn Lys Thr
        355                 360                 365

Asp Thr Cys Leu Asp Ile Ser Gln Gly Gly Tyr Asn Tyr Ala Ile Gly
    370                 375                 380

Ala Arg Ala Lys Thr Ala Cys Lys Ser Ser Asn Ala Ala Phe Val Phe
385                 390                 395                 400

Trp Asp Asn Met His Pro Thr Thr Lys Thr His Gly Leu Leu Ala Asp
                405                 410                 415

Leu Leu Lys Asp Asp Val Val Arg Gly Leu Ala Ala Pro
            420                 425
```

<210> SEQ ID NO 85
<211> LENGTH: 1038
<212> TYPE: DNA
<213> ORGANISM: Unknown
<220> FEATURE:
<223> OTHER INFORMATION: Obtained from an environmental sample.

<400> SEQUENCE: 85

```
atgacaacac aatttagaaa cttgatattt gaaggcggcg gtgtaaaagg tgttgcttac     60

attggcgcca tgcagattct tgaaaatcgt ggcgtgttgc aagatattcg ccgagtcgga    120

gggtgcagtg cgggtgcgat taacgcgctg atttttgcgc taggttacac ggtccgtgaa    180

caaaaagaga tcttacaagc caccgatttt aaccagttta tggataactc ttggggggtt    240

attcgtgata ttcgcaggct tgctcgagac tttggctgga ataagggtga tttctttagt    300

agctggatag gtgatttgat tcatcgtcgt ttggggaatc gccgagcgac gttcaaagat    360

ctgcaaaagg ccaagcttcc tgatctttat gtcatcggta ctaatctgtc tacagggttt    420

gcagaggtgt tttctgccga aagacacccc gatatggagc tggcgacagc ggtgcgtatc    480

tccatgtcga taccgctgtt ctttgcggcc gtgcgtcacg gtgatcgaca agatgtgtat    540

gtcgatgggg gtgttcaact taactatccg attaaactgt ttgatcggga gcgttacatt    600

gatttggcca aagatcccgg tgccgttcgg cgaacgggtt attacaacaa agaaaacgct    660

cgctttcagc ttgatcggcc gggccatagc ccctatgttt acaatcgcca gaccttgggt    720

ttgcgactgg atagtcgcga ggagataggg ctctttcgtt atgacgaacc cctcaagggc    780

aaacccatta agtccttcac tgactacgct cgacaacttt tcggtgcgtt gatgaatgca    840

caggaaaaga ttcatctaca tggcgatgat tggcaacgca cgatctatat cgatacattg    900

gatgtgggta cgacggactt caatctttct gatgcaacta agcaagcact gattgagcaa    960

ggaattaacg gcaccgaaaa ttatttcgag tggtttgata atccgttaga gaagcctgtg   1020

aatagagtgg agtcatag                                                 1038
```

<210> SEQ ID NO 86
<211> LENGTH: 345
<212> TYPE: PRT
<213> ORGANISM: Unknown
<220> FEATURE:
<223> OTHER INFORMATION: Obtained from an environmental sample.

<400> SEQUENCE: 86

```
Met Thr Thr Gln Phe Arg Asn Leu Ile Phe Glu Gly Gly Gly Val Lys
 1               5                  10                  15

Gly Val Ala Tyr Ile Gly Ala Met Gln Ile Leu Glu Asn Arg Gly Val
            20                  25                  30

Leu Gln Asp Ile Arg Arg Val Gly Gly Cys Ser Ala Gly Ala Ile Asn
        35                  40                  45

Ala Leu Ile Phe Ala Leu Gly Tyr Thr Val Arg Glu Gln Lys Glu Ile
    50                  55                  60

Leu Gln Ala Thr Asp Phe Asn Gln Phe Met Asp Asn Ser Trp Gly Val
65                  70                  75                  80

Ile Arg Asp Ile Arg Arg Leu Ala Arg Asp Phe Gly Trp Asn Lys Gly
                85                  90                  95

Asp Phe Phe Ser Ser Trp Ile Gly Asp Leu Ile His Arg Arg Leu Gly
            100                 105                 110

Asn Arg Arg Ala Thr Phe Lys Asp Leu Gln Lys Ala Lys Leu Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Ala Lys Asp Pro Gly Ala
        195                 200                 205

Val Arg Arg Thr Gly Tyr Tyr Asn Lys Glu Asn Ala Arg Phe Gln Leu
    210                 215                 220

Asp Arg Pro Gly His Ser Pro Tyr Val Tyr Asn Arg Gln Thr Leu Gly
225                 230                 235                 240

Leu Arg Leu Asp Ser Arg Glu Glu Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Lys Ile His Leu His Gly
        275                 280                 285

Asp Asp Trp Gln Arg Thr Ile Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Glu Trp Phe Asp Asn Pro Leu
                325                 330                 335

Glu Lys Pro Val Asn Arg Val Glu Ser
            340                 345
```

<210> SEQ ID NO 87
<211> LENGTH: 870

<212> TYPE: DNA
<213> ORGANISM: Unknown
<220> FEATURE:
<223> OTHER INFORMATION: Obtained from an environmental sample.

<400> SEQUENCE: 87

```
atgtcaaaga aactcgtaat atcggtagcg ggcggcggag cactcggaat cggaccactc      60
gcattcctgt gcaagattga acagatgctg ggaaagaaga taccccaggt tgcgcaggca     120
tacgccggca cttcaaccgg agcaataatt gcggcaggac tggccgaagg ctactccgcg     180
catgaactgt tcgacctata caaatcaaat ctcagcaaga tattcaccaa atacagctgg     240
tacaaacgcc tgcagccaac gtgtcctaca tatgacaaca gtaacctaaa gaaattactg     300
aaggacaaat tcaagggcaa ggtcggcgac tggaaaactc ccgtatacat cccggcaaca     360
cacatgaacg gccaatccgt agaaaaggtg tgggacttgg gtgacaagaa tgttgacaag     420
tggtttgcca ttctgacaag taccgcggca ccaacctatt tcgactgcat atacgacgac     480
gagaagaact gctacatcga tggtggcatg tggtgcaacg caccaatcga tgtgcttaat     540
gcaggcctga tcaagtccgg ctggtccaac tacaaggtcc tggacctgga gaccggcatg     600
gacacaccga atacggaaag cggaaacaag acacttctcg gatgggggga atacatcata     660
agcaactggg tagcccgttc cagcaagtcc ggcgaatacg aggtaaaggc cataatcggg     720
gaagacaatg tatgtgttgc ccgtccatac gtaagcaaga aaccgaagat ggatgacgtg     780
gacagcaaga cgctggatga agtcgtggat atctgggaaa actacttcta cgccaagcag     840
aaagacatcg catcgtggct gaaaatctag                                      870
```

<210> SEQ ID NO 88
<211> LENGTH: 289
<212> TYPE: PRT
<213> ORGANISM: Unknown
<220> FEATURE:
<223> OTHER INFORMATION: Obtained from an environmental sample.

<400> SEQUENCE: 88

```
Met Ser Lys Lys Leu Val Ile Ser Val Ala Gly Gly Gly Ala Leu Gly
 1               5                  10                  15

Ile Gly Pro Leu Ala Phe Leu Cys Lys Ile Glu Gln Met Leu Gly Lys
            20                  25                  30

Lys Ile Pro Gln Val Ala Gln Ala Tyr Ala Gly Thr Ser Thr Gly Ala
        35                  40                  45

Ile Ile Ala Ala Gly Leu Ala Glu Gly Tyr Ser Ala His Glu Leu Phe
    50                  55                  60

Asp Leu Tyr Lys Ser Asn Leu Ser Lys Ile Phe Thr Lys Tyr Ser Trp
65                  70                  75                  80

Tyr Lys Arg Leu Gln Pro Thr Cys Pro Thr Tyr Asp Asn Ser Asn Leu
                85                  90                  95

Lys Lys Leu Leu Lys Asp Lys Phe Lys Gly Lys Val Gly Asp Trp Lys
            100                 105                 110

Thr Pro Val Tyr Ile Pro Ala Thr His Met Asn Gly Gln Ser Val Glu
        115                 120                 125

Lys Val Trp Asp Leu Gly Asp Lys Asn Val Asp Lys Trp Phe Ala Ile
    130                 135                 140

Leu Thr Ser Thr Ala Ala Pro Thr Tyr Phe Asp Cys Ile Tyr Asp Asp
145                 150                 155                 160

Glu Lys Asn Cys Tyr Ile Asp Gly Gly Met Trp Cys Asn Ala Pro Ile
                165                 170                 175
```

```
Asp Val Leu Asn Ala Gly Leu Ile Lys Ser Gly Trp Ser Asn Tyr Lys
            180                 185                 190

Val Leu Asp Leu Glu Thr Gly Met Asp Thr Pro Asn Thr Glu Ser Gly
        195                 200                 205

Asn Lys Thr Leu Leu Gly Trp Gly Glu Tyr Ile Ile Ser Asn Trp Val
    210                 215                 220

Ala Arg Ser Ser Lys Ser Gly Glu Tyr Glu Val Lys Ala Ile Ile Gly
225                 230                 235                 240

Glu Asp Asn Val Cys Val Ala Arg Pro Tyr Val Ser Lys Lys Pro Lys
                245                 250                 255

Met Asp Asp Val Asp Ser Lys Thr Leu Asp Glu Val Val Asp Ile Trp
            260                 265                 270

Glu Asn Tyr Phe Tyr Ala Lys Gln Lys Asp Ile Ala Ser Trp Leu Lys
        275                 280                 285

Ile
```

<210> SEQ ID NO 89
<211> LENGTH: 1422
<212> TYPE: DNA
<213> ORGANISM: Unknown
<220> FEATURE:
<223> OTHER INFORMATION: Obtained from an environmental sample.

<400> SEQUENCE: 89

```
atgaaaaaga aattatgtac actggctttt gtaacagcaa tatcttctat cgctatcaca      60
attccaacag aagcacaagc ttgtggaata ggcgaagtaa tgaaacagga gaaccaagag     120
cacaaacgtg tgaagagatg gtctgcggaa catccacatc atcctaatga aagtacgcac     180
ttatggattg cgcgaaatgc aattcaaata atggcccgta atcaagataa gacggttcaa     240
gaaaatgaat tacaattttt aaatactcct gaatataagg agttatttga aagaggtctt     300
tatgatgctg attaccttga tgaatttaac gatggaggta caggtacaat cggcattgat     360
gggctaatta aaggagggtg gaaatctcat ttttacgatc ccgatacgag aaagaactat     420
aaaggggaag aagaaccaac agctctctct caaggagata aatattttaa attagcaggc     480
gattacttta agaaagagga ttggaaacaa gctttctatt atttaggtgt tgcgacgcac     540
tacttcacag atgctactca gccaatgcat gctgctaatt ttacagccgt cgacacgagt     600
gctttaaagt ttcatagcgc ttttgaaaat tatgtgacga caattcagac acagtatgaa     660
gtatctgatg gtgagggcgt atataattta gtgaattcta atgatccaaa acagtggatc     720
catgaaacag cgagactcgc aaaagtggaa atcgggaaca ttaccaatga cgagattaaa     780
tctcactata ataaaggaaa caatgctctt tggcaacaag aagttatgcc agctgtccag     840
aggagtttag agaacgcaca aagaaacacg gcgggattta ttcatttatg gtttaaaaca     900
tttgttggca atactgccgc tgaagaaatt gaaaatactg tagtgaaaga ttctaaagga     960
gaagcaatac aagataataa aaaatacttc gtagtgccaa gtgagtttct aaatagaggt    1020
ttgacctttg aagtatatgc aaggaatgac tatgcactat tatctaatta cgtagatgat    1080
agtaaagttc atggtacgcc agttcagttt gtatttgata aagataataa cggtatcctt    1140
catcgaggag aaagtatact gctgaaaatg acgcaatcta actatgataa ttacgtattt    1200
ctaaactact ctaacttgac aaactgggta catcttgcgc aacaaaaaac aaatactgca    1260
cagtttaaag tgtatccaaa tccgaataac ccatctgaat attacctata tacagatgga    1320
tacccagtaa attatcaaga aaatggtaac ggaaagagct ggattgtgtt aggaaagaaa    1380
acagatacac caaaagcttg gaaatttata caggctgaat ag                       1422
```

<210> SEQ ID NO 90
<211> LENGTH: 473
<212> TYPE: PRT
<213> ORGANISM: Unknown
<220> FEATURE:
<221> NAME/KEY: SIGNAL
<222> LOCATION: (1)...(25)
<223> OTHER INFORMATION: Obtained from an environmental sample.

<400> SEQUENCE: 90

```
Met Lys Lys Lys Leu Cys Thr Leu Ala Phe Val Thr Ala Ile Ser Ser
 1               5                  10                  15

Ile Ala Ile Thr Ile Pro Thr Glu Ala Gln Ala Cys Gly Ile Gly Glu
            20                  25                  30

Val Met Lys Gln Glu Asn Gln Glu His Lys Arg Val Lys Arg Trp Ser
        35                  40                  45

Ala Glu His Pro His His Pro Asn Glu Ser Thr His Leu Trp Ile Ala
    50                  55                  60

Arg Asn Ala Ile Gln Ile Met Ala Arg Asn Gln Asp Lys Thr Val Gln
65                  70                  75                  80

Glu Asn Glu Leu Gln Phe Leu Asn Thr Pro Glu Tyr Lys Glu Leu Phe
                85                  90                  95

Glu Arg Gly Leu Tyr Asp Ala Asp Tyr Leu Asp Glu Phe Asn Asp Gly
            100                 105                 110

Gly Thr Gly Thr Ile Gly Ile Asp Gly Leu Ile Lys Gly Gly Trp Lys
        115                 120                 125

Ser His Phe Tyr Asp Pro Asp Thr Arg Lys Asn Tyr Lys Gly Glu Glu
    130                 135                 140

Glu Pro Thr Ala Leu Ser Gln Gly Asp Lys Tyr Phe Lys Leu Ala Gly
145                 150                 155                 160

Asp Tyr Phe Lys Lys Glu Asp Trp Lys Gln Ala Phe Tyr Tyr Leu Gly
                165                 170                 175

Val Ala Thr His Tyr Phe Thr Asp Ala Thr Gln Pro Met His Ala Ala
            180                 185                 190

Asn Phe Thr Ala Val Asp Thr Ser Ala Leu Lys Phe His Ser Ala Phe
        195                 200                 205

Glu Asn Tyr Val Thr Thr Ile Gln Thr Gln Tyr Glu Val Ser Asp Gly
    210                 215                 220

Glu Gly Val Tyr Asn Leu Val Asn Ser Asn Asp Pro Lys Gln Trp Ile
225                 230                 235                 240

His Glu Thr Ala Arg Leu Ala Lys Val Glu Ile Gly Asn Ile Thr Asn
                245                 250                 255

Asp Glu Ile Lys Ser His Tyr Asn Lys Gly Asn Asn Ala Leu Trp Gln
            260                 265                 270

Gln Glu Val Met Pro Ala Val Gln Arg Ser Leu Glu Asn Ala Gln Arg
        275                 280                 285

Asn Thr Ala Gly Phe Ile His Leu Trp Phe Lys Thr Phe Val Gly Asn
    290                 295                 300

Thr Ala Ala Glu Glu Ile Glu Asn Thr Val Val Lys Asp Ser Lys Gly
305                 310                 315                 320

Glu Ala Ile Gln Asp Asn Lys Lys Tyr Phe Val Val Pro Ser Glu Phe
                325                 330                 335

Leu Asn Arg Gly Leu Thr Phe Glu Val Tyr Ala Arg Asn Asp Tyr Ala
            340                 345                 350

Leu Leu Ser Asn Tyr Val Asp Asp Ser Lys Val His Gly Thr Pro Val
```

```
        355                 360                 365

Gln Phe Val Phe Asp Lys Asp Asn Asn Gly Ile Leu His Arg Gly Glu
    370                 375                 380

Ser Ile Leu Leu Lys Met Thr Gln Ser Asn Tyr Asp Asn Tyr Val Phe
385                 390                 395                 400

Leu Asn Tyr Ser Asn Leu Thr Asn Trp Val His Leu Ala Gln Gln Lys
                405                 410                 415

Thr Asn Thr Ala Gln Phe Lys Val Tyr Pro Asn Pro Asn Asn Pro Ser
            420                 425                 430

Glu Tyr Tyr Leu Tyr Thr Asp Gly Tyr Pro Val Asn Tyr Gln Glu Asn
        435                 440                 445

Gly Asn Gly Lys Ser Trp Ile Val Leu Gly Lys Lys Thr Asp Thr Pro
    450                 455                 460

Lys Ala Trp Lys Phe Ile Gln Ala Glu
465                 470
```

<210> SEQ ID NO 91
<211> LENGTH: 1035
<212> TYPE: DNA
<213> ORGANISM: Unknown
<220> FEATURE:
<223> OTHER INFORMATION: Obtained from an environmental sample.

<400> SEQUENCE: 91

```
atgacaaccc aatttagaaa cctgatcttt gagggcggcg gtgtaaaggg cattgcttac      60

gtcggagcaa tgcagattct tgaaaatcgt ggtgtattac aagatattca ccgagtcgga     120

ggttgtagtg cgggtgcgat taacgcgctg atttttgcgc tgggttacac agtccgtgag     180

caaaaagaga tcttacaaat taccgatttt aaccagttta tggataactc gtggggtgtt     240

attcgggata ttcgcaggct tgcgagagaa tttggctgga ataagggtaa cttctttaat     300

acctggatag gtgatttgat tcatcgtcgt ttgggtaatc gccgagccac gttcaaagat     360

ctgcaaaagg caaagcttcc tgatctttat gtcatcggta ctaatctgtc tacagggttt     420

gcagaggttt tttctgccga aagacacccc gatatggagc tggcgacagc ggtgcgtatc     480

tccatgtcga taccgctgtt ctttgcggcc gtgcgtcacg gtgatcgaca agatgtgtat     540

gtcgatgggg gtgtgcagct taactacccg atcaagctgt ttgatcgaac tcgttatatt     600

gacctcgcca aagatccggg tgctgctcgc cacacgggtt attacaataa agagaatgct     660

cgttttcagc ttgagcgacc gggccacagt ccttatgtgt acaatcgcca aacattaggc     720

ttgcgtcttg acagtcgtga agagatagcg ctgtttcgtt acgacgaacc tcttcagggt     780

aaacccatta agtccttcac tgactacgct cgacaacttt ttggtgcgct gaagaatgca     840

caggaaaaca ttcacctaca tggcgatgat tggcagcgca cggtctatat cgatacattg     900

gatgtgggta cgacggattt caatctttct gatgcaacca agcaagcact gattgaacag     960

ggaattaacg gcaccgaaaa ttatttcgag tggtttgata atccgtttga gaagcctgtg    1020

aatagagtgg agtaa                                                     1035
```

<210> SEQ ID NO 92
<211> LENGTH: 344
<212> TYPE: PRT
<213> ORGANISM: Unknown
<220> FEATURE:
<223> OTHER INFORMATION: Obtained from an environmental sample.

<400> SEQUENCE: 92

```
Met Thr Thr Gln Phe Arg Asn Leu Ile Phe Glu Gly Gly Gly Val Lys
```

-continued

```
1               5                   10                  15

Gly Ile Ala Tyr Val Gly Ala Met Gln Ile Leu Glu Asn Arg Gly Val
            20                  25                  30

Leu Gln Asp Ile His Arg Val Gly Gly Cys Ser Ala Gly Ala Ile Asn
        35                  40                  45

Ala Leu Ile Phe Ala Leu Gly Tyr Thr Val Arg Glu Gln Lys Glu Ile
    50                  55                  60

Leu Gln Ile Thr Asp Phe Asn Gln Phe Met Asp Asn Ser Trp Gly Val
65                  70                  75                  80

Ile Arg Asp Ile Arg Arg Leu Ala Arg Glu Phe Gly Trp Asn Lys Gly
                85                  90                  95

Asn Phe Phe Asn Thr Trp Ile Gly Asp Leu Ile His Arg Arg Leu Gly
            100                 105                 110

Asn Arg Arg Ala Thr Phe Lys Asp Leu Gln Lys Ala Lys Leu Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Thr Arg Tyr Ile Asp Leu Ala Lys Asp Pro Gly Ala
        195                 200                 205

Ala Arg His Thr Gly Tyr Tyr Asn Lys Glu Asn Ala Arg Phe Gln Leu
    210                 215                 220

Glu Arg Pro Gly His Ser Pro Tyr Val Tyr Asn Arg Gln Thr Leu Gly
225                 230                 235                 240

Leu Arg Leu Asp Ser Arg Glu Glu Ile Ala Leu Phe Arg Tyr Asp Glu
                245                 250                 255

Pro Leu Gln Gly Lys Pro Ile Lys Ser Phe Thr Asp Tyr Ala Arg Gln
            260                 265                 270

Leu Phe Gly Ala Leu Lys Asn Ala Gln Glu Asn Ile His Leu His Gly
        275                 280                 285

Asp Asp Trp Gln Arg Thr Val Tyr Ile Asp Thr Leu Asp Val Gly Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Glu Trp Phe Asp Asn Pro Phe
                325                 330                 335

Glu Lys Pro Val Asn Arg Val Glu
            340
```

<210> SEQ ID NO 93
<211> LENGTH: 963
<212> TYPE: DNA
<213> ORGANISM: Unknown
<220> FEATURE:
<223> OTHER INFORMATION: Obtained from an environmental sample.

<400> SEQUENCE: 93

```
gtgattactt tgataaaaaa atgtttatta gtattgacga tgactctatt atcaggggtt     60

ttcgtaccgc tgcagccatc atatgctact gaaaattatc caaatgattt taaactgttg    120

caacataatg tatttttatt gcctgaatca gtttcttatt ggggtcagga cgaacgtgca    180
```

```
gattatatga gtaatgcaga ttactttaag ggacatgatg ctctgctctt aaatgagctt    240

tttgacaatg gaaattcgaa cgtgctgcta atgaacttat ccaaggaata tacatatcaa    300

acgccagtgc ttggccgttc gatgagtgga tgggatgaaa ctagaggaag ctattctaat    360

tttgtacccg aagatggtgg tgtagcaatt atcagtaaat ggccaatcgt ggagaaaata    420

cagcatgttt acgcgaatgg ttgcggtgca gactattatg caaataaagg atttgtttat    480

gcaaaagtac aaaaagggga taaattctat catcttatca gcactcatgc tcaagccgaa    540

gataccgggt gtgatcaggg tgaaggagca gaaattcgtc attcacagtt tcaagaaatc    600

aacgacttta ttaaaaataa aaacattccg aaagatgaag tggtatttat tggtggtgac    660

tttaatgtga tgaagagtga cacaacagag tacaatagca tgttatcaac attaaatgtc    720

aatgcgccta ccgaatattt agggcataac tctacttggg acccagaaac gaacagcatt    780

acaggttaca attaccctga ttatgcgcca cagcatttag attatatttt tgtggaaaaa    840

gatcataaac aaccaagttc atgggtaaat gaaacgatta ctccgaagtc tccaacttgg    900

aaggcaatct atgagtataa tgattattcc gatcactatc ctgttaaagc atacgtaaaa    960

taa                                                                  963
```

```
<210> SEQ ID NO 94
<211> LENGTH: 320
<212> TYPE: PRT
<213> ORGANISM: Unknown
<220> FEATURE:
<221> NAME/KEY: SIGNAL
<222> LOCATION: (1)...(29)
<223> OTHER INFORMATION: Obtained from an environmental sample.

<400> SEQUENCE: 94

Met Ile Thr Leu Ile Lys Lys Cys Leu Leu Val Leu Thr Met Thr Leu
 1               5                  10                  15

Leu Ser Gly Val Phe Val Pro Leu Gln Pro Ser Tyr Ala Thr Glu Asn
            20                  25                  30

Tyr Pro Asn Asp Phe Lys Leu Leu Gln His Asn Val Phe Leu Leu Pro
        35                  40                  45

Glu Ser Val Ser Tyr Trp Gly Gln Asp Glu Arg Ala Asp Tyr Met Ser
    50                  55                  60

Asn Ala Asp Tyr Phe Lys Gly His Asp Ala Leu Leu Leu Asn Glu Leu
65                  70                  75                  80

Phe Asp Asn Gly Asn Ser Asn Val Leu Leu Met Asn Leu Ser Lys Glu
                85                  90                  95

Tyr Thr Tyr Gln Thr Pro Val Leu Gly Arg Ser Met Ser Gly Trp Asp
            100                 105                 110

Glu Thr Arg Gly Ser Tyr Ser Asn Phe Val Pro Glu Asp Gly Gly Val
        115                 120                 125

Ala Ile Ile Ser Lys Trp Pro Ile Val Glu Lys Ile Gln His Val Tyr
    130                 135                 140

Ala Asn Gly Cys Gly Ala Asp Tyr Tyr Ala Asn Lys Gly Phe Val Tyr
145                 150                 155                 160

Ala Lys Val Gln Lys Gly Asp Lys Phe Tyr His Leu Ile Ser Thr His
                165                 170                 175

Ala Gln Ala Glu Asp Thr Gly Cys Asp Gln Gly Glu Gly Ala Glu Ile
            180                 185                 190

Arg His Ser Gln Phe Gln Glu Ile Asn Asp Phe Ile Lys Asn Lys Asn
        195                 200                 205
```

-continued

```
Ile Pro Lys Asp Glu Val Val Phe Ile Gly Gly Asp Phe Asn Val Met
    210                 215                 220

Lys Ser Asp Thr Thr Glu Tyr Asn Ser Met Leu Ser Thr Leu Asn Val
225                 230                 235                 240

Asn Ala Pro Thr Glu Tyr Leu Gly His Asn Ser Thr Trp Asp Pro Glu
                245                 250                 255

Thr Asn Ser Ile Thr Gly Tyr Asn Tyr Pro Asp Tyr Ala Pro Gln His
            260                 265                 270

Leu Asp Tyr Ile Phe Val Glu Lys Asp His Lys Gln Pro Ser Ser Trp
        275                 280                 285

Val Asn Glu Thr Ile Thr Pro Lys Ser Pro Thr Trp Lys Ala Ile Tyr
    290                 295                 300

Glu Tyr Asn Asp Tyr Ser Asp His Tyr Pro Val Lys Ala Tyr Val Lys
305                 310                 315                 320
```

<210> SEQ ID NO 95
<211> LENGTH: 1038
<212> TYPE: DNA
<213> ORGANISM: Unknown
<220> FEATURE:
<223> OTHER INFORMATION: Obtained from an environmental sample.

<400> SEQUENCE: 95

```
atggcttcac aattcaggaa tctggtattt gaaggaggtg gtgtaaaagg gattgcgtac      60

ataggtgcga tgcaggtgct ggatcagcgc ggttatttgg gtgataacat caaacgcgtt     120

ggtggaacca gtgcaggtgc cataaatgcg ctgatttatt cgttaggata tgacatccac     180

gaacaacaag agatactgaa ctctacagat tttaaaaagt ttatggataa ctcttttgga     240

tttgtgaggg atttcagaag gctatggaat gaatttggat ggaatagagg agactttttt     300

cttaaatggt caggtgagct gatcaaaaat aaattgggca cctcaaaagc cacctttcag     360

gatttgaagg atgccggtca gccagatttg tatgtaattg gaacaaattt atcgacgggg     420

ttttccgaga ctttttcata tgaacgtcac cccgatatga ctcttgcaga agccgtaaga     480

atcagtatgt cgcttccgct gtttttcagg gctgtgcggt tgggcgacag gaatgatgta     540

tatgtggatg gtggggttca gctcaattac ccggtaaaac tatttgatcg tgaaaaaatat     600

attgatatgg ataatgaggc ggctgcagca cgatttactg attattacaa caaagaaaat     660

gccagatttt cgctccagcg gcctggacga agcccctatg tatataatcg tcaaaccctt     720

ggtttgagac tggatacagc cgaagaaatt gcgcttttca ggtacgatga acccattcag     780

gggaaagaga tcaaacggtt tccggaatat gcaaaggctc tgatcggcgc actaatgcag     840

gtgcaggaaa acatacatct ccacagtgac gactggcagc gtacgctgta tatcaatacc     900

ctggatgtaa aaaccacaga ttttgaatta accgatgaga aaaaaaagga actggtagaa     960

cagggaatcc ttggcgcgga aacctatttc aaatggtttg aagacaggga tgaagtagtt    1020

gtaaaccgcc ttgcttag                                                  1038
```

<210> SEQ ID NO 96
<211> LENGTH: 345
<212> TYPE: PRT
<213> ORGANISM: Unknown
<220> FEATURE:
<223> OTHER INFORMATION: Obtained from an environmental sample.

<400> SEQUENCE: 96

```
Met Ala Ser Gln Phe Arg Asn Leu Val Phe Glu Gly Gly Gly Val Lys
 1               5                  10                  15
```

```
Gly Ile Ala Tyr Ile Gly Ala Met Gln Val Leu Asp Gln Arg Gly Tyr
            20                  25                  30

Leu Gly Asp Asn Ile Lys Arg Val Gly Gly Thr Ser Ala Gly Ala Ile
        35                  40                  45

Asn Ala Leu Ile Tyr Ser Leu Gly Tyr Asp Ile His Glu Gln Gln Glu
    50                  55                  60

Ile Leu Asn Ser Thr Asp Phe Lys Lys Phe Met Asp Asn Ser Phe Gly
65                  70                  75                  80

Phe Val Arg Asp Phe Arg Arg Leu Trp Asn Glu Phe Gly Trp Asn Arg
                85                  90                  95

Gly Asp Phe Phe Leu Lys Trp Ser Gly Glu Leu Ile Lys Asn Lys Leu
            100                 105                 110

Gly Thr Ser Lys Ala Thr Phe Gln Asp Leu Lys Asp Ala Gly Gln Pro
        115                 120                 125

Asp Leu Tyr Val Ile Gly Thr Asn Leu Ser Thr Gly Phe Ser Glu Thr
    130                 135                 140

Phe Ser Tyr Glu Arg His Pro Asp Met Thr Leu Ala Glu Ala Val Arg
145                 150                 155                 160

Ile Ser Met Ser Leu Pro Leu Phe Phe Arg Ala Val Arg Leu Gly Asp
                165                 170                 175

Arg Asn Asp Val Tyr Val Asp Gly Gly Val Gln Leu Asn Tyr Pro Val
            180                 185                 190

Lys Leu Phe Asp Arg Glu Lys Tyr Ile Asp Met Asp Asn Glu Ala Ala
        195                 200                 205

Ala Ala Arg Phe Thr Asp Tyr Tyr Asn Lys Glu Asn Ala Arg Phe Ser
    210                 215                 220

Leu Gln Arg Pro Gly Arg Ser Pro Tyr Val Tyr Asn Arg Gln Thr Leu
225                 230                 235                 240

Gly Leu Arg Leu Asp Thr Ala Glu Glu Ile Ala Leu Phe Arg Tyr Asp
                245                 250                 255

Glu Pro Ile Gln Gly Lys Glu Ile Lys Arg Phe Pro Glu Tyr Ala Lys
            260                 265                 270

Ala Leu Ile Gly Ala Leu Met Gln Val Gln Glu Asn Ile His Leu His
        275                 280                 285

Ser Asp Asp Trp Gln Arg Thr Leu Tyr Ile Asn Thr Leu Asp Val Lys
    290                 295                 300

Thr Thr Asp Phe Glu Leu Thr Asp Glu Lys Lys Lys Glu Leu Val Glu
305                 310                 315                 320

Gln Gly Ile Leu Gly Ala Glu Thr Tyr Phe Lys Trp Phe Glu Asp Arg
                325                 330                 335

Asp Glu Val Val Val Asn Arg Leu Ala
            340                 345
```

<210> SEQ ID NO 97
<211> LENGTH: 1422
<212> TYPE: DNA
<213> ORGANISM: Unknown
<220> FEATURE:
<223> OTHER INFORMATION: Obtained from an environmental sample.

<400> SEQUENCE: 97

```
atgaaaagga aactatgtac atgggctctc gtaacagcaa tagcttctag tactgcggta      60

attccaacag cagcagaagc ttgtggatta ggagaagtaa tcaaacaaga gaatcaagag     120

cacaaacgtg tgaaaagatg gtctgcggag catccgcatc attcacatga aagtacccat     180

ttatggattg cacaaaatgc gattcaaatt atgagccgta atcaagataa gacggttcaa     240
```

```
gaaaatgaat tacaattttt aaataccccct gaatataagg agttatttga aagaggtctt    300

tatgatgctg attaccttga tgaatttaac gatggaggta caggtataat cggcattgat    360

gggctaattc gaggagggtg gaaatctcat ttctacgatc ccgatacaag aaagaactat    420

aaaggggagg aagaaccaac agctctttct caaggagata aatattttaa attagcaggt    480

gaatacttta agaagaatga ttggaaacag gctttctatt atttaggtgt tgcgacgcac    540

tactttacag atgctactca gccaatgcat gctgctaatt ttacagctgt cgacaggagt    600

gctataaagt ttcatagtgc ttttgaagat tatgtgacga caattcagga acagtttaaa    660

gtatcagatg gagagggaaa atataattta gtaaattcta atgatccgaa acagtggatc    720

catgaaacag cgagactcgc aaaagtggaa atcgggaaca ttaccaatga tgtgattaaa    780

tctcactata ataaaggaaa caatgctctt tggcagcaag aagttatgcc agctgttcag    840

agaagtttag aacaagccca aagaaatacg gcgggattta ttcatttatg gtttaaaaca    900

tatgttggaa aaacagctgc tgaagatatt gaaaatacta tagtgaaaga ttctagggga    960

gaagcaatac aagagaataa aaaatacttt gtagtaccaa gtgagttttt aaatagaggc   1020

ttaacatttg aagtgtatgc tgcttatgac tatgcgttat tatctaacca tgtggatgat   1080

aataatattc atggtacacc ggttcaaatt gtatttgata aagaaaataa tgggatcctt   1140

catcaaggag aaagtgcatt gttaaagatg acacaatcca actacgataa ttatgtattt   1200

ctaaattatt ctatcataac aaattgggta catcttgcaa aaagagaaaa caatactgca   1260

cagtttaaag tgtatccaaa tccaaataat ccaactgaat atttcatata tacagatggc   1320

tatccagtta attatcaaga aaaaggtaaa gagaaaagct ggattgtttt aggaaagaaa   1380

acggataaac caaaagcatg gaaatttata caggcggaat aa                      1422
```

<210> SEQ ID NO 98
<211> LENGTH: 473
<212> TYPE: PRT
<213> ORGANISM: Unknown
<220> FEATURE:
<221> NAME/KEY: SIGNAL
<222> LOCATION: (1)...(25)
<223> OTHER INFORMATION: Obtained from an environmental sample.

<400> SEQUENCE: 98

```
Met Lys Arg Lys Leu Cys Thr Trp Ala Leu Val Thr Ala Ile Ala Ser
 1               5                  10                  15

Ser Thr Ala Val Ile Pro Thr Ala Ala Glu Ala Cys Gly Leu Gly Glu
            20                  25                  30

Val Ile Lys Gln Glu Asn Gln Glu His Lys Arg Val Lys Arg Trp Ser
        35                  40                  45

Ala Glu His Pro His His Ser His Glu Ser Thr His Leu Trp Ile Ala
    50                  55                  60

Gln Asn Ala Ile Gln Ile Met Ser Arg Asn Gln Asp Lys Thr Val Gln
65                  70                  75                  80

Glu Asn Glu Leu Gln Phe Leu Asn Thr Pro Glu Tyr Lys Glu Leu Phe
                85                  90                  95

Glu Arg Gly Leu Tyr Asp Ala Asp Tyr Leu Asp Glu Phe Asn Asp Gly
            100                 105                 110

Gly Thr Gly Ile Ile Gly Ile Asp Gly Leu Ile Arg Gly Gly Trp Lys
        115                 120                 125

Ser His Phe Tyr Asp Pro Asp Thr Arg Lys Asn Tyr Lys Gly Glu Glu
    130                 135                 140
```

-continued

Glu Pro Thr Ala Leu Ser Gln Gly Asp Lys Tyr Phe Lys Leu Ala Gly
145 150 155 160

Glu Tyr Phe Lys Lys Asn Asp Trp Lys Gln Ala Phe Tyr Tyr Leu Gly
165 170 175

Val Ala Thr His Tyr Phe Thr Asp Ala Thr Gln Pro Met His Ala Ala
180 185 190

Asn Phe Thr Ala Val Asp Arg Ser Ala Ile Lys Phe His Ser Ala Phe
195 200 205

Glu Asp Tyr Val Thr Thr Ile Gln Glu Gln Phe Lys Val Ser Asp Gly
210 215 220

Glu Gly Lys Tyr Asn Leu Val Asn Ser Asn Asp Pro Lys Gln Trp Ile
225 230 235 240

His Glu Thr Ala Arg Leu Ala Lys Val Glu Ile Gly Asn Ile Thr Asn
245 250 255

Asp Val Ile Lys Ser His Tyr Asn Lys Gly Asn Asn Ala Leu Trp Gln
260 265 270

Gln Glu Val Met Pro Ala Val Gln Arg Ser Leu Glu Gln Ala Gln Arg
275 280 285

Asn Thr Ala Gly Phe Ile His Leu Trp Phe Lys Thr Tyr Val Gly Lys
290 295 300

Thr Ala Ala Glu Asp Ile Glu Asn Thr Ile Val Lys Asp Ser Arg Gly
305 310 315 320

Glu Ala Ile Gln Glu Asn Lys Lys Tyr Phe Val Val Pro Ser Glu Phe
325 330 335

Leu Asn Arg Gly Leu Thr Phe Glu Val Tyr Ala Ala Tyr Asp Tyr Ala
340 345 350

Leu Leu Ser Asn His Val Asp Asp Asn Asn Ile His Gly Thr Pro Val
355 360 365

Gln Ile Val Phe Asp Lys Glu Asn Asn Gly Ile Leu His Gln Gly Glu
370 375 380

Ser Ala Leu Leu Lys Met Thr Gln Ser Asn Tyr Asp Asn Tyr Val Phe
385 390 395 400

Leu Asn Tyr Ser Ile Ile Thr Asn Trp Val His Leu Ala Lys Arg Glu
405 410 415

Asn Asn Thr Ala Gln Phe Lys Val Tyr Pro Asn Pro Asn Asn Pro Thr
420 425 430

Glu Tyr Phe Ile Tyr Thr Asp Gly Tyr Pro Val Asn Tyr Gln Glu Lys
435 440 445

Gly Lys Glu Lys Ser Trp Ile Val Leu Gly Lys Lys Thr Asp Lys Pro
450 455 460

Lys Ala Trp Lys Phe Ile Gln Ala Glu
465 470

<210> SEQ ID NO 99
<211> LENGTH: 1053
<212> TYPE: DNA
<213> ORGANISM: Unknown
<220> FEATURE:
<223> OTHER INFORMATION: Obtained from an environmental sample.

<400> SEQUENCE: 99
atggcaaagc gttttattct ttcgatcgat ggtggtggca ttcgcgggat catcccggcg 60
gccatcctgg tggagctggc caagcggttg gaggggctgc cgcttcacaa ggcattcgac 120
atgatcgccg ggacatccac cggcggcatc attgcggcgg ggctgacatg cccgcatcct 180
gacgatgagg agacggcggc gtgcacgccg accgatcttc tcaagcttta tgtcgatcac 240

```
ggcggcaaga tcttcgagaa aaacccgatc ctcggcctca tcaacccatt cggcctcaac    300

gatccgcgct accagccaga tgagctggaa aacaggctga aggcgcagct cggcttgacg    360

gcgacgctcg ataaagggct caccaaggtg ctgatcacgg cctatgatat ccagcagcgg    420

caggcgctgt tcatggcaaa caccgacaac gagaacagca atttccgcta ctgggaggca    480

gcgcgggcga catcggccgc acccacctat tttccgccgg cgctgatcga aagggttggc    540

gagaagaaca aggacaagcg cttcgtgcca ttgatcgacg gcggcgtctt cgccaacgat    600

cctatccttg ccgcctatgt ggaggcgcga aagcagaaat ggggcaatga cgagctcgtt    660

ttcctgtcgc ttggtaccgg ccagcaaaac cgcccgatcg cctatcagga ggccaagggc    720

tggggcattt taggctggat gcagccgtct catgacacgc cgctgatctc gatcctgatg    780

cagggacagg cgagcaccgc ctcctatcag gccaatgcgc tgctcaatcc gcccggcacc    840

aagatcgact attcgaccgt ggtgacgaag gacaacgcgg cttcgctcag ctatttccgt    900

ctcgaccggc agctgagctc gaaggagaac gacgcgctgg acgacgcatc gcccgaaaac    960

atcagggcgc tgaaggcaat cgccgcgcaa atcatcaagg ataacgcgcc ggcgctcgac   1020

gaaatcgcca aacgcatcct ggccaaccaa taa                               1053
```

<210> SEQ ID NO 100
<211> LENGTH: 350
<212> TYPE: PRT
<213> ORGANISM: Unknown
<220> FEATURE:
<223> OTHER INFORMATION: Obtained from an environmental sample.

<400> SEQUENCE: 100

```
Met Ala Lys Arg Phe Ile Leu Ser Ile Asp Gly Gly Gly Ile Arg Gly
1               5                   10                  15

Ile Ile Pro Ala Ala Ile Leu Val Glu Leu Ala Lys Arg Leu Glu Gly
            20                  25                  30

Leu Pro Leu His Lys Ala Phe Asp Met Ile Ala Gly Thr Ser Thr Gly
        35                  40                  45

Gly Ile Ile Ala Ala Gly Leu Thr Cys Pro His Pro Asp Asp Glu Glu
    50                  55                  60

Thr Ala Ala Cys Thr Pro Thr Asp Leu Leu Lys Leu Tyr Val Asp His
65                  70                  75                  80

Gly Gly Lys Ile Phe Glu Lys Asn Pro Ile Leu Gly Leu Ile Asn Pro
                85                  90                  95

Phe Gly Leu Asn Asp Pro Arg Tyr Gln Pro Asp Glu Leu Glu Asn Arg
            100                 105                 110

Leu Lys Ala Gln Leu Gly Leu Thr Ala Thr Leu Asp Lys Gly Leu Thr
        115                 120                 125

Lys Val Leu Ile Thr Ala Tyr Asp Ile Gln Gln Arg Gln Ala Leu Phe
    130                 135                 140

Met Ala Asn Thr Asp Asn Glu Asn Ser Asn Phe Arg Tyr Trp Glu Ala
145                 150                 155                 160

Ala Arg Ala Thr Ser Ala Ala Pro Thr Tyr Phe Pro Pro Ala Leu Ile
                165                 170                 175

Glu Arg Val Gly Glu Lys Asn Lys Asp Lys Arg Phe Val Pro Leu Ile
            180                 185                 190

Asp Gly Gly Val Phe Ala Asn Asp Pro Ile Leu Ala Ala Tyr Val Glu
        195                 200                 205

Ala Arg Lys Gln Lys Trp Gly Asn Asp Glu Leu Val Phe Leu Ser Leu
    210                 215                 220
```

```
Gly Thr Gly Gln Gln Asn Arg Pro Ile Ala Tyr Gln Glu Ala Lys Gly
225                 230                 235                 240

Trp Gly Ile Leu Gly Trp Met Gln Pro Ser His Asp Thr Pro Leu Ile
                245                 250                 255

Ser Ile Leu Met Gln Gly Gln Ala Ser Thr Ala Ser Tyr Gln Ala Asn
            260                 265                 270

Ala Leu Leu Asn Pro Pro Gly Thr Lys Ile Asp Tyr Ser Thr Val Val
        275                 280                 285

Thr Lys Asp Asn Ala Ala Ser Leu Ser Tyr Phe Arg Leu Asp Arg Gln
    290                 295                 300

Leu Ser Ser Lys Glu Asn Asp Ala Leu Asp Asp Ala Ser Pro Glu Asn
305                 310                 315                 320

Ile Arg Ala Leu Lys Ala Ile Ala Ala Gln Ile Ile Lys Asp Asn Ala
                325                 330                 335

Pro Ala Leu Asp Glu Ile Ala Lys Arg Ile Leu Ala Asn Gln
            340                 345                 350
```

<210> SEQ ID NO 101
<211> LENGTH: 996
<212> TYPE: DNA
<213> ORGANISM: Bacteria

<400> SEQUENCE: 101

```
ttgtcgctcg tcgcgtcgct ccgccgcgcc cccggcgccg ccctggccct cgcgcttgcc     60

gccgccaccc tggccgtgac cgcgcagggc gcgaccgccg cccccgccgc ggccgccgcc    120

gaggccccgc ggctcaaggt gctcacgtac aacacgttcc tgttctcgaa gacgctctac    180

ccgaactggg gccaggacca ccgggccaag gcgatcccca ccgccccctt ctaccagggc    240

caggacgtcg tggtcctcca ggaggccttc gacaactccg cgtcggacgc cctcaaggcg    300

aactccgccg gccagtaccc ctaccagacc cccgtcgtgg gccgcggcac cggcggctgg    360

gacgccaccg gcgggtccta ctcctcgacc acccccgagg acggcggcgt gacgatcctc    420

agcaagtggc cgatcgtccg caaggagcag tacgtctaca aggacgcgtg cggcgccgac    480

tggtggtcca acaagggctt cgcctacgtc gtgctcaacg tgaacggcag caaggtgcac    540

gtcctcggca cccacgccca gtccaccgac ccgggctgct cggcgggcga ggcggtgcag    600

atgcggagcc gccagttcaa ggcgatcgac gccttcctcg acgccaagaa catcccggcg    660

ggcgagcagg tgatcgtcgc cggcgacatg aacgtcgact cgcgcacgcc cgagtacggc    720

accatgctcg ccgacgccgg tctggcggcg gccgacgcgc gcaccggcca cccgtactcc    780

ttcgacaccg agctgaactc gatcgcctcc gagcgctacc cggacgaccc gcgcgaggac    840

ctcgattacg tcctctaccg cgccgggaac gcccgccccg ccaactggac caacaacgtg    900

gtcctggaga agagcgcccc gtggaccgtc tccagctggg gcaagagcta cacctacacc    960

aacctctccg accactaccc ggtcaccggc ttctga                              996
```

<210> SEQ ID NO 102
<211> LENGTH: 331
<212> TYPE: PRT
<213> ORGANISM: Bacteria
<220> FEATURE:
<221> NAME/KEY: SIGNAL
<222> LOCATION: (1)...(39)

<400> SEQUENCE: 102

```
Leu Ser Leu Val Ala Ser Leu Arg Arg Ala Pro Gly Ala Ala Leu Ala
 1               5                  10                  15
```

```
Leu Ala Leu Ala Ala Ala Thr Leu Ala Val Thr Ala Gln Gly Ala Thr
            20                  25                  30

Ala Ala Pro Ala Ala Ala Ala Ala Glu Ala Pro Arg Leu Lys Val Leu
        35                  40                  45

Thr Tyr Asn Thr Phe Leu Phe Ser Lys Thr Leu Tyr Pro Asn Trp Gly
    50                  55                  60

Gln Asp His Arg Ala Lys Ala Ile Pro Thr Ala Pro Phe Tyr Gln Gly
65                  70                  75                  80

Gln Asp Val Val Val Leu Gln Glu Ala Phe Asp Asn Ser Ala Ser Asp
                85                  90                  95

Ala Leu Lys Ala Asn Ser Ala Gly Gln Tyr Pro Tyr Gln Thr Pro Val
            100                 105                 110

Val Gly Arg Gly Thr Gly Gly Trp Asp Ala Thr Gly Gly Ser Tyr Ser
        115                 120                 125

Ser Thr Thr Pro Glu Asp Gly Gly Val Thr Ile Leu Ser Lys Trp Pro
    130                 135                 140

Ile Val Arg Lys Glu Gln Tyr Val Tyr Lys Asp Ala Cys Gly Ala Asp
145                 150                 155                 160

Trp Trp Ser Asn Lys Gly Phe Ala Tyr Val Val Leu Asn Val Asn Gly
                165                 170                 175

Ser Lys Val His Val Leu Gly Thr His Ala Gln Ser Thr Asp Pro Gly
            180                 185                 190

Cys Ser Ala Gly Glu Ala Val Gln Met Arg Ser Arg Gln Phe Lys Ala
        195                 200                 205

Ile Asp Ala Phe Leu Asp Ala Lys Asn Ile Pro Ala Gly Glu Gln Val
    210                 215                 220

Ile Val Ala Gly Asp Met Asn Val Asp Ser Arg Thr Pro Glu Tyr Gly
225                 230                 235                 240

Thr Met Leu Ala Asp Ala Gly Leu Ala Ala Asp Ala Arg Thr Gly
                245                 250                 255

His Pro Tyr Ser Phe Asp Thr Glu Leu Asn Ser Ile Ala Ser Glu Arg
            260                 265                 270

Tyr Pro Asp Asp Pro Arg Glu Asp Leu Asp Tyr Val Leu Tyr Arg Ala
        275                 280                 285

Gly Asn Ala Arg Pro Ala Asn Trp Thr Asn Asn Val Val Leu Glu Lys
    290                 295                 300

Ser Ala Pro Trp Thr Val Ser Ser Trp Gly Lys Ser Tyr Thr Tyr Thr
305                 310                 315                 320

Asn Leu Ser Asp His Tyr Pro Val Thr Gly Phe
                325                 330
```

<210> SEQ ID NO 103
<211> LENGTH: 2205
<212> TYPE: DNA
<213> ORGANISM: Unknown
<220> FEATURE:
<223> OTHER INFORMATION: Obtained from an environmental sample.

<400> SEQUENCE: 103

```
atgagcgaga agaaggagat tcgcgttgcg ttgatcatgg ggggtggcgt cagcctcggc      60

agtttttcgg gtggtgcgct tctcaagacc atcgagctgc tgcagcacac tgcccgcggt     120

ccggcgaaga tcgatgtcgt gaccggtgcc tcggcgggaa gcatgacgct gggcgtagtc     180

atctaccacc tcatgcgggg atcgtcgacc gatgagattc tccgcgatct gaggcggtcg     240

tgggtggaaa tgatctcgtt cgacggcctc tgtccgccga acctgtcccg tcacgacaag     300
```

```
ccgagcctgt tttccgatga gatcgtccgg aagatcgcgg ccaccgtcat cgatatgggg    360
cgcaagctcg aggcggctcc tcatccgctt ttcgccgacg aactcgtagc ctcgttcgca    420
ctgacgaacc tgaacggcat ccccgcccgt acggagggcc agctcatccg gcaggcaaag    480
ggaggcggag ggtccgagaa gggctcgaaa tccgttttcg ccgacgccgt gcagactacc    540
tttcaccacg acgtgatgcg attcgtggtg cggcgcgatc acaacgggca aggcagcctg    600
ttcgacagcc gttaccgggc acgcatactc cctccatgga atgttgggaa gggcggcgat    660
gcatgggaag cctttcgcac ggcggctgtt gcctcggggg cgtttccggc cgcatttcct    720
cccgtcgaga tcagccgcaa ccgcgacgaa ttcaacatct ggcccgatcg catcgaggac    780
cagaaggcat ttacgttcga ttacgtggac ggcggggtac ttcgcaacga acccctccgg    840
gaggcgattc acctggccgc gctgcgcgat gagggagcga cggacatcga gcgtgtgttc    900
atcctcatcg acccgaacat cagcggcacc ggcgaggtct tcccgctctc ctataaccag    960
cagatgcgga tcaagccgaa ctacgattcc aacggcgacg tccgacagta cgatctcgat   1020
gtgccggact acaccggcaa tctgatcggg gcgatcggtc ggctgggttc ggtgatcgtc   1080
gggcaggcga cgttccgcga ctggctcaag gctgccaaag tgaacagcca gatcgagtgg   1140
cgacgggaat tgctgcccat tctccgcgac ctgaacccga accccgggga ggaggcgcgc   1200
aggggcgtga acgggatgat cgacaagatc taccggcaaa agtatcagcg cgccctcgag   1260
tcaaagagcg ttccggtcga ggaggtggaa cggcgcgttg ccgaagacat cgaacgggac   1320
ctggcgcggc gccgttcgga ggccggcgac aacgacttca ttgcccggct cctcctgctc   1380
gtcgacctga tcggcaacct gcgtgagaag cagaagctga acatggtggc gatcaccccc   1440
gcttccgcgc cgcacaacga cgggcgcccc ttgccgctgg ccggcaattt tatgttcagc   1500
ttcggggggt tcttcaggga ggagtacagg caatacgact tctcggtcgg cgaattcgca   1560
gcatggaacg tcctgagcac gccggcctcc gagacgccct ttcttgccga gaccgccccg   1620
aaaccgcccg cccgacctcc ccagccgccg gcaatcaatc ctacctaccg ctcactcggc   1680
ccgcccatcc agcagcggtt cgaggagttc gttcgtgggc acgttcgcgc ctttatcgct   1740
tcggtcgctc cgctgggaac gagagggatc gtcacgggca agattggcgg aaagcttcga   1800
acgatgctga tggcctcgcg caacgggaaa tcagagtact tccggcttcg cctctccggc   1860
gttgacgggc tctacctccg aggctccaag ggccgcaacc tgagggcggt taacggatcg   1920
atcgacacgg tcgtcggcgt ctatatcgac gaggaagatc agcaccgcga tgagtttttc   1980
ggtccccatg tcttcggcgc gaacggctca ggctttacga tggaactatg ggagtcccgc   2040
ggtttttttcg ggcgtgatcg tcgcgtcgct gtgatcgagt tggagaacaa ccccggcggg   2100
ttcgcaatcg ccgccggatg caggcggcgg cccggcgtgg tgctggatat ggccaggcgt   2160
aacgggcagc cactgcggac ggtggatgtg atggaatttg cgtga                   2205
```

<210> SEQ ID NO 104
<211> LENGTH: 734
<212> TYPE: PRT
<213> ORGANISM: Unknown
<220> FEATURE:
<223> OTHER INFORMATION: Obtained from an environmental sample.

<400> SEQUENCE: 104

```
Met Ser Glu Lys Lys Glu Ile Arg Val Ala Leu Ile Met Gly Gly Gly
 1               5                  10                  15

Val Ser Leu Gly Ser Phe Ser Gly Gly Ala Leu Leu Lys Thr Ile Glu
            20                  25                  30
```

Leu Leu Gln His Thr Ala Arg Gly Pro Ala Lys Ile Asp Val Val Thr
35 40 45

Gly Ala Ser Ala Gly Ser Met Thr Leu Gly Val Val Ile Tyr His Leu
50 55 60

Met Arg Gly Ser Ser Thr Asp Glu Ile Leu Arg Asp Leu Arg Arg Ser
65 70 75 80

Trp Val Glu Met Ile Ser Phe Asp Gly Leu Cys Pro Pro Asn Leu Ser
85 90 95

Arg His Asp Lys Pro Ser Leu Phe Ser Asp Glu Ile Val Arg Lys Ile
100 105 110

Ala Ala Thr Val Ile Asp Met Gly Arg Lys Leu Glu Ala Ala Pro His
115 120 125

Pro Leu Phe Ala Asp Glu Leu Val Ala Ser Phe Ala Leu Thr Asn Leu
130 135 140

Asn Gly Ile Pro Ala Arg Thr Glu Gly Gln Leu Ile Arg Gln Ala Lys
145 150 155 160

Gly Gly Gly Gly Ser Glu Lys Gly Ser Lys Ser Val Phe Ala Asp Ala
165 170 175

Val Gln Thr Thr Phe His His Asp Val Met Arg Phe Val Val Arg Arg
180 185 190

Asp His Asn Gly Gln Gly Ser Leu Phe Asp Ser Arg Tyr Arg Ala Arg
195 200 205

Ile Leu Pro Pro Trp Asn Val Gly Lys Gly Gly Asp Ala Trp Glu Ala
210 215 220

Phe Arg Thr Ala Ala Val Ala Ser Gly Ala Phe Pro Ala Ala Phe Pro
225 230 235 240

Pro Val Glu Ile Ser Arg Asn Arg Asp Glu Phe Asn Ile Trp Pro Asp
245 250 255

Arg Ile Glu Asp Gln Lys Ala Phe Thr Phe Asp Tyr Val Asp Gly Gly
260 265 270

Val Leu Arg Asn Glu Pro Leu Arg Glu Ala Ile His Leu Ala Ala Leu
275 280 285

Arg Asp Glu Gly Ala Thr Asp Ile Glu Arg Val Phe Ile Leu Ile Asp
290 295 300

Pro Asn Ile Ser Gly Thr Gly Glu Val Phe Pro Leu Ser Tyr Asn Gln
305 310 315 320

Gln Met Arg Ile Lys Pro Asn Tyr Asp Ser Asn Gly Asp Val Arg Gln
325 330 335

Tyr Asp Leu Asp Val Pro Asp Tyr Thr Gly Asn Leu Ile Gly Ala Ile
340 345 350

Gly Arg Leu Gly Ser Val Ile Val Gly Gln Ala Thr Phe Arg Asp Trp
355 360 365

Leu Lys Ala Ala Lys Val Asn Ser Gln Ile Glu Trp Arg Arg Glu Leu
370 375 380

Leu Pro Ile Leu Arg Asp Leu Asn Pro Asn Pro Gly Glu Glu Ala Arg
385 390 395 400

Arg Gly Val Asn Gly Met Ile Asp Lys Ile Tyr Arg Gln Lys Tyr Gln
405 410 415

Arg Ala Leu Glu Ser Lys Ser Val Pro Val Glu Glu Val Glu Arg Arg
420 425 430

Val Ala Glu Asp Ile Glu Arg Asp Leu Ala Arg Arg Arg Ser Glu Ala
435 440 445

Gly Asp Asn Asp Phe Ile Ala Arg Leu Leu Leu Leu Val Asp Leu Ile

```
    450                 455                 460

Gly Asn Leu Arg Glu Lys Gln Lys Leu Asn Met Val Ala Ile Thr Pro
465                 470                 475                 480

Ala Ser Ala Pro His Asn Asp Gly Arg Pro Leu Pro Leu Ala Gly Asn
                485                 490                 495

Phe Met Phe Ser Phe Gly Gly Phe Phe Arg Glu Glu Tyr Arg Gln Tyr
            500                 505                 510

Asp Phe Ser Val Gly Glu Phe Ala Ala Trp Asn Val Leu Ser Thr Pro
        515                 520                 525

Ala Ser Glu Thr Pro Phe Leu Ala Glu Thr Ala Pro Lys Pro Pro Ala
    530                 535                 540

Arg Pro Pro Gln Pro Pro Ala Ile Asn Pro Thr Tyr Arg Ser Leu Gly
545                 550                 555                 560

Pro Pro Ile Gln Gln Arg Phe Glu Glu Phe Val Arg Gly His Val Arg
                565                 570                 575

Ala Phe Ile Ala Ser Val Ala Pro Leu Gly Thr Arg Gly Ile Val Thr
            580                 585                 590

Gly Lys Ile Gly Gly Lys Leu Arg Thr Met Leu Met Ala Ser Arg Asn
        595                 600                 605

Gly Lys Ser Glu Tyr Phe Arg Leu Arg Leu Ser Gly Val Asp Gly Leu
    610                 615                 620

Tyr Leu Arg Gly Ser Lys Gly Arg Asn Leu Arg Ala Val Asn Gly Ser
625                 630                 635                 640

Ile Asp Thr Val Val Gly Val Tyr Ile Asp Glu Glu Asp Gln His Arg
                645                 650                 655

Asp Glu Phe Phe Gly Pro His Val Phe Gly Ala Asn Gly Ser Gly Phe
            660                 665                 670

Thr Met Glu Leu Trp Glu Ser Arg Gly Phe Phe Gly Arg Asp Arg Arg
        675                 680                 685

Val Ala Val Ile Glu Leu Glu Asn Asn Pro Gly Gly Phe Ala Ile Ala
    690                 695                 700

Ala Gly Cys Arg Arg Arg Pro Gly Val Val Leu Asp Met Ala Arg Arg
705                 710                 715                 720

Asn Gly Gln Pro Leu Arg Thr Val Asp Val Met Glu Phe Ala
                725                 730
```

<210> SEQ ID NO 105
<211> LENGTH: 756
<212> TYPE: DNA
<213> ORGANISM: Unknown
<220> FEATURE:
<223> OTHER INFORMATION: Obtained from an environmental sample.

<400> SEQUENCE: 105

```
atgaaccgtt gtcggaactc actcaacctc caacttcgcg cggtgaccgt ggcggcgttg     60

gtagtcgtcg catcctcggc cgcgctggcg tgggacagcg cctcgcgcaa tccgacccat    120

cccacccaca gctacctcac cgaatacgcc atcgatcagc ttggggtggc gcggccggag    180

ctccggcaat accgcaagca gatcatcgag ggcgccaaca ccgagctgca cgaactgcca    240

gtcaagggga cggcctatgg cctcgacctc gacgccaagc ggcgggaaca ccgcggcacc    300

aatgccggga cagacgacat cgccggctgg tgggcggaaa gcctccaagc ctatcgcgcc    360

ggtgccaagg aacgcgccta cttcgtgctg ggggtggtgc tgcacatggt cgaggacatg    420

ggcgtgccgg cgcacgcgaa cggcgtctac caccagggca acctgactga attcgacaat    480

ttcgagttca tgggactgtc gaactggaag ccctctttcg ccgacatcaa ccggaccgat    540
```

```
ccgggctacg ccgacccgtc gcgctactac gagttcagcc gagattggac ggcggcagac    600

gcacccggct atcgcgaccg cgacagcttc tcgaagacct gggttctcgc cagcccggcc    660

gaacgtcagc tgcttcagaa ccgccagggc cggaccgcca cggtcgccat gtgggcgtta    720

cggagcgcga cgaaggcgtt cgccgggaaa ccctag                              756


<210> SEQ ID NO 106
<211> LENGTH: 251
<212> TYPE: PRT
<213> ORGANISM: Unknown
<220> FEATURE:
<221> NAME/KEY: SIGNAL
<222> LOCATION: (1)...(30)
<223> OTHER INFORMATION: Obtained from an environmental sample.

<400> SEQUENCE: 106

Met Asn Arg Cys Arg Asn Ser Leu Asn Leu Gln Leu Arg Ala Val Thr
 1               5                  10                  15

Val Ala Ala Leu Val Val Val Ala Ser Ser Ala Ala Leu Ala Trp Asp
            20                  25                  30

Ser Ala Ser Arg Asn Pro Thr His Pro Thr His Ser Tyr Leu Thr Glu
        35                  40                  45

Tyr Ala Ile Asp Gln Leu Gly Val Ala Arg Pro Glu Leu Arg Gln Tyr
    50                  55                  60

Arg Lys Gln Ile Ile Glu Gly Ala Asn Thr Glu Leu His Glu Leu Pro
65                  70                  75                  80

Val Lys Gly Thr Ala Tyr Gly Leu Asp Leu Asp Ala Lys Arg Arg Glu
                85                  90                  95

His Arg Gly Thr Asn Ala Gly Thr Asp Asp Ile Ala Gly Trp Trp Ala
            100                 105                 110

Glu Ser Leu Gln Ala Tyr Arg Ala Gly Ala Lys Glu Arg Ala Tyr Phe
        115                 120                 125

Val Leu Gly Val Val Leu His Met Val Glu Asp Met Gly Val Pro Ala
    130                 135                 140

His Ala Asn Gly Val Tyr His Gln Gly Asn Leu Thr Glu Phe Asp Asn
145                 150                 155                 160

Phe Glu Phe Met Gly Leu Ser Asn Trp Lys Pro Ser Phe Ala Asp Ile
                165                 170                 175

Asn Arg Thr Asp Pro Gly Tyr Ala Asp Pro Ser Arg Tyr Tyr Glu Phe
            180                 185                 190

Ser Arg Asp Trp Thr Ala Ala Asp Ala Pro Gly Tyr Arg Asp Arg Asp
        195                 200                 205

Ser Phe Ser Lys Thr Trp Val Leu Ala Ser Pro Ala Glu Arg Gln Leu
    210                 215                 220

Leu Gln Asn Arg Gln Gly Arg Thr Ala Thr Val Ala Met Trp Ala Leu
225                 230                 235                 240

Arg Ser Ala Thr Lys Ala Phe Ala Gly Lys Pro
                245                 250


<210> SEQ ID NO 107
<211> LENGTH: 990
<212> TYPE: DNA
<213> ORGANISM: Unknown
<220> FEATURE:
<223> OTHER INFORMATION: Obtained from an environmental sample

<400> SEQUENCE: 107

atgagcaata agaagtttat tttgaaatta ttcatatgta gtactatact tagcacattt     60
```

gtatttgctt tcaatgataa gcaagcagtt gctgctagcg ctggtaatgg gcttgaaaac 120
tggtcaaaat ggatgcaacc tatacccgat aacgtaccgt tagcacgaat ttcaattcca 180
ggaacacatg atagtggaac gttcaagttg caaaatccga taaagcaagt atggggaatg 240
acgcaagaat ataattttcg ttaccaaatg gatcacggag ctagaatttt tgatattaga 300
gggcgtttaa cagatgataa tacgatagtt cttcatcatg gaccattata tctttatgta 360
acattgcatg aatttataaa tgaagcgaaa caatttttaa aagataatcc aagtgaaacg 420
attattatgt ctttaaaaaa agagtatgag gatatgaaag gggcagaaga ttcatttagt 480
agtacgtttg aaaaaaaata ttttcctgat cctatctttt taaaaacaga agggaatata 540
agacttggag atgctcgagg aaaaattgtg ctactaaaaa gatacagtgg tagtaatgaa 600
tctggaggat ataataattt ttattggcca gataatgaca cgtttacgac aactgtaaat 660
caaaatgtaa atgtaacagt acaagataaa tataaggtga gttatgatga gaaagtaaca 720
tctattaaag atacgataaa tgaaacgatt aacaacagtg aagattgtaa tcatctatat 780
attaatttta caagcttgtc ttctggtggt acagcatgga atagtccata ttattacgcg 840
tcctacataa atcctgaaat tgcaaactat atgaagcaaa agaatcctac gagagtgggc 900
tgggtaattc aagattatat aaatgaaaaa tggtccccaa tactttatga agaagttata 960
agagcgaata agtcacttgt aaaagagtaa 990

<210> SEQ ID NO 108
<211> LENGTH: 329
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
C, X domain

<400> SEQUENCE: 108

Met Ser Asn Lys Lys Phe Ile Leu Lys Leu Phe Ile Cys Ser Thr Ile
1 5 10 15

Leu Ser Thr Phe Val Phe Ala Phe Asn Asp Lys Gln Ala Val Ala Ala
20 25 30

Ser Ala Gly Asn Gly Leu Glu Asn Trp Ser Lys Trp Met Gln Pro Ile
35 40 45

Pro Asp Asn Val Pro Leu Ala Arg Ile Ser Ile Pro Gly Thr His Asp
50 55 60

Ser Gly Thr Phe Lys Leu Gln Asn Pro Ile Lys Gln Val Trp Gly Met
65 70 75 80

Thr Gln Glu Tyr Asn Phe Arg Tyr Gln Met Asp His Gly Ala Arg Ile
85 90 95

Phe Asp Ile Arg Gly Arg Leu Thr Asp Asp Asn Thr Ile Val Leu His
100 105 110

His Gly Pro Leu Tyr Leu Tyr Val Thr Leu His Glu Phe Ile Asn Glu
115 120 125

Ala Lys Gln Phe Leu Lys Asp Asn Pro Ser Glu Thr Ile Ile Met Ser
130 135 140

Leu Lys Lys Glu Tyr Glu Asp Met Lys Gly Ala Glu Asp Ser Phe Ser
145 150 155 160

-continued

```
Ser Thr Phe Glu Lys Lys Tyr Phe Pro Asp Pro Ile Phe Leu Lys Thr
                165                 170                 175

Glu Gly Asn Ile Arg Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Asp Thr Phe Thr Thr Thr Val Asn Gln Asn Val Asn
    210                 215                 220

Val Thr Val Gln Asp Lys Tyr Lys Val Ser Tyr Asp Glu Lys Val Thr
225                 230                 235                 240

Ser Ile Lys Asp Thr Ile Asn Glu Thr Ile Asn Asn Ser Glu Asp Cys
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Thr Arg Val Gly Trp Val Ile Gln
    290                 295                 300

Asp Tyr Ile Asn Glu Lys Trp Ser Pro Ile Leu Tyr Glu Glu Val Ile
305                 310                 315                 320

Arg Ala Asn Lys Ser Leu Val Lys Glu
                325
```

<210> SEQ ID NO 109
<211> LENGTH: 990
<212> TYPE: DNA
<213> ORGANISM: Unknown
<220> FEATURE:
<223> OTHER INFORMATION: Obtained from an environmental sample

<400> SEQUENCE: 109

```
atgagcaata agaagtttat tttgaaatta ttcatatgta gtactatact tagcacattt      60

gtatttgctt tcaatgataa gcaagcagtt gctgctagcg ctggtaatgg gcttgaaaac     120

tggtcaaaat ggatgcaacc tatacccgat aacgtaccgt tagcacgaat ttcaattcca     180

ggaacacatg atagtggaac gttcaagttg caaaatccga taaagcaagt atggggaatg     240

acgcaagaat ataattttcg ttaccaaatg gatcacggag ctagaatttt tgatattaga     300

gggcgtttaa cagatgataa tacgatagtt cttcatcatg ggccattata tctttatgta     360

acattgcatg aatttataaa tgaagcgaaa caatttttaa aagataatcc aagtgaaacg     420

attattatgt ctttaaaaaa agagtatgag gatatgaaag gggcagaaga ttcatttagt     480

agtacgtttg aaaaaaaata ttttcctgat cctatctttt taaaaacaga agggaatata     540

agacttggag atgctcgagg aaaaattgtg ctactaaaaa gatacagtgg tagtaatgaa     600

tctggaggat ataataattt ttattggcca gataatgaga cgtttacgac aactgtaaat     660

caaaatgtaa atgtaacagt acaagataaa tataaagtga gttatgatga gaaagtaaaa     720

tctattaaag atacgataaa tgaaacgatt aacaacagtg aagattgtaa tcatctatat     780

attaatttta caagcttgtc ttctggtggt acagcatgga atagtccata ttattatgcg     840

tcctacataa atcctgaaat tgcaaactat atgaagcaaa agaatcctat gagagtgggc     900

tgggtaattc aagattatat aaatgaaaaa tggtccccaa tactttatga agaagttata     960

agagcgaata agtcacttgt aaaagagtaa                                      990
```

<210> SEQ ID NO 110
<211> LENGTH: 329

<212> TYPE: PRT
<213> ORGANISM: Unknown
<220> FEATURE:
<221> NAME/KEY: SIGNAL
<222> LOCATION: (1)...(23)
<220> FEATURE:
<221> NAME/KEY: DOMAIN
<222> LOCATION: (56)...(195)
<223> OTHER INFORMATION: Obtained from an environmental sample

<400> SEQUENCE: 110

```
Met Ser Asn Lys Lys Phe Ile Leu Lys Leu Phe Ile Cys Ser Thr Ile
 1               5                  10                  15

Leu Ser Thr Phe Val Phe Ala Phe Asn Asp Lys Gln Ala Val Ala Ala
            20                  25                  30

Ser Ala Gly Asn Gly Leu Glu Asn Trp Ser Lys Trp Met Gln Pro Ile
        35                  40                  45

Pro Asp Asn Val Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asn Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Asp Ser Phe Ser
145                 150                 155                 160

Ser Thr Phe Glu Lys Lys Tyr Phe Pro Asp Pro Ile Phe Leu Lys Thr
                165                 170                 175

Glu Gly Asn Ile Arg Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Thr Thr Val Asn Gln Asn Val Asn
    210                 215                 220

Val Thr Val Gln Asp Lys Tyr Lys Val Ser Tyr Asp Glu Lys Val Lys
225                 230                 235                 240

Ser Ile Lys Asp Thr Ile Asn Glu Thr Ile Asn Asn Ser Glu Asp Cys
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Met Arg Val Gly Trp Val Ile Gln
    290                 295                 300

Asp Tyr Ile Asn Glu Lys Trp Ser Pro Ile Leu Tyr Glu Glu Val Ile
305                 310                 315                 320

Arg Ala Asn Lys Ser Leu Val Lys Glu
                325
```

<210> SEQ ID NO 111
<211> LENGTH: 828
<212> TYPE: DNA
<213> ORGANISM: Bacteria

<400> SEQUENCE: 111

```
gtgggtgccg gggcgatcct tctcaccggg gcccccaccg cctcggccgt ggacacgcgc      60
gcgtggatgg ggggacacgg ggacggcacg ccgctccagc ggctcaccat ccccggcacc     120
cacgactccg gcgcccggtt cggcgggccc tggtcggagt gccagaacac caccatcgcc     180
cagcagctgg acagcgggat ccggttcctg gacgtccggt gccgggtcac cggcgggtcc     240
ttcgccatcc accacggggc ctcctaccag aacatgatgt tcggcgacgt cctcgtcgcc     300
tgccgcgact tcctcgccgc gcacccctcc gagaccgtcc tcatgcgggt caagcaggag     360
tactcgaccg actccgacgc caccttccgg gccgtcttcg acgactacct cgacgcgcgc     420
ggctggcgct ccctgttccg catcggcgac ggggtcccgc tgctcggcga ggcccgcggc     480
cgggtcgtgc tcatcgccga caacggcgga ctgccgggcg gtctgcgctg gggcgacggc     540
tcggccctcg ccatccagga cgactggaac gcgctgcccg accccaagta cgccaagatc     600
gaggcgcact tccgtaccgc cgtcgcccag ccgggccggc tgtacgtgaa cttcgtcagc     660
acctccgcct acctgccgcc ccgctggaac tccgacaacc tcaacccgcg cgtgcaccgc     720
tacctcgaca gcgcggccgc cgcgggcgcg aagggcctcg ggatcgtccc catggacttc     780
cccaacaccc gctcgggtct ggtcgaggcg ctgctccggc acaactga                  828
```

<210> SEQ ID NO 112
<211> LENGTH: 275
<212> TYPE: PRT
<213> ORGANISM: Bacteria
<220> FEATURE:
<221> NAME/KEY: SIGNAL
<222> LOCATION: (1)...(16)
<220> FEATURE:
<221> NAME/KEY: DOMAIN
<222> LOCATION: (34)...(168)
<223> OTHER INFORMATION: Phosphatidylinositol-specific phospholipase
      C, X domain

<400> SEQUENCE: 112

```
Met Gly Ala Gly Ala Ile Leu Leu Thr Gly Ala Pro Thr Ala Ser Ala
 1               5                  10                  15

Val Asp Thr Arg Ala Trp Met Gly Gly His Gly Asp Gly Thr Pro Leu
            20                  25                  30

Gln Arg Leu Thr Ile Pro Gly Thr His Asp Ser Gly Ala Arg Phe Gly
        35                  40                  45

Gly Pro Trp Ser Glu Cys Gln Asn Thr Thr Ile Ala Gln Gln Leu Asp
    50                  55                  60

Ser Gly Ile Arg Phe Leu Asp Val Arg Cys Arg Val Thr Gly Gly Ser
65                  70                  75                  80

Phe Ala Ile His His Gly Ala Ser Tyr Gln Asn Met Met Phe Gly Asp
                85                  90                  95

Val Leu Val Ala Cys Arg Asp Phe Leu Ala Ala His Pro Ser Glu Thr
            100                 105                 110

Val Leu Met Arg Val Lys Gln Glu Tyr Ser Thr Asp Ser Asp Ala Thr
        115                 120                 125

Phe Arg Ala Val Phe Asp Asp Tyr Leu Asp Ala Arg Gly Trp Arg Ser
    130                 135                 140

Leu Phe Arg Ile Gly Asp Gly Val Pro Leu Leu Gly Glu Ala Arg Gly
145                 150                 155                 160

Arg Val Val Leu Ile Ala Asp Asn Gly Gly Leu Pro Gly Gly Leu Arg
                165                 170                 175
```

```
Trp Gly Asp Gly Ser Ala Leu Ala Ile Gln Asp Asp Trp Asn Ala Leu
            180                 185                 190

Pro Asp Pro Lys Tyr Ala Lys Ile Glu Ala His Phe Arg Thr Ala Val
        195                 200                 205

Ala Gln Pro Gly Arg Leu Tyr Val Asn Phe Val Ser Thr Ser Ala Tyr
    210                 215                 220

Leu Pro Pro Arg Trp Asn Ser Asp Asn Leu Asn Pro Arg Val His Arg
225                 230                 235                 240

Tyr Leu Asp Ser Ala Ala Ala Ala Gly Ala Lys Gly Leu Gly Ile Val
                245                 250                 255

Pro Met Asp Phe Pro Asn Thr Arg Ser Gly Leu Val Glu Ala Leu Leu
            260                 265                 270

Arg His Asn
        275


<210> SEQ ID NO 113
<211> LENGTH: 981
<212> TYPE: DNA
<213> ORGANISM: Unknown
<220> FEATURE:
<223> OTHER INFORMATION: Obtained from an environmental sample

<400> SEQUENCE: 113

atgagcaata agaagtttat tttgaaatta ttcatatgta gtactatact tagcacattt      60

gtatttgctt tcaatgataa gcaagcagtt gctgctagcg ctggtaatgg gcttgaaaac     120

tggtcaaaat ggatgcaacc tatacccgat aacgtaccgt tagcacgaat ttcaattcca     180

ggaacacatg atagtggaac gttcaagttg caaaatccga taaagcaagt atggggaatg     240

acgcaagaat ataattttcg ttaccaaatg gatcacggag ctagaatttt tgatattaga     300

gggcgtttaa cagatgataa tacgatagtt cttcatcatg ggccattata tctttatgta     360

acattgcatg aatttataaa tgaagcgaaa caatttttaa aagataatcc aagtgaaacg     420

attattatgt ctttaaaaaa agagtatgag gatatgaaag gggcagaaga ttcatttagt     480

agtacgtttg aaaaaaaata ttttcctgat cctatctttt taaaaacaga agggaatata     540

agacttggag atgctcgagg aaaaattgtg ctactaaaaa gatacagtgg tagtaatgaa     600

tctggaggat ataataattt ttattggcca gataatgaga cgtttacgac aactgtaaat     660

caaaatgtaa atgtaacagt acaagataaa tataaagtga gttatgatga gaaagtaaaa     720

tctattaaag atacgataaa tgaaacgatt aacaacagtg aagattgtaa tcatctatat     780

attaatttta caagcttgtc ttctggtggt acagcatgga atagtccata ttattatgcg     840

tcctacataa atcctgaaat tgcaaactat atgaagcaaa agaatcctat gagagtgggc     900

tgggtaattc aagattatat aaatgaaaaa tggtccccaa tactttatga agaagttata     960

agagcgaata agtcactgta a                                               981


<210> SEQ ID NO 114
<211> LENGTH: 326
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
      C, X domain
```

<400> SEQUENCE: 114

```
Met Ser Asn Lys Lys Phe Ile Leu Lys Leu Phe Ile Cys Ser Thr Ile
 1               5                  10                  15

Leu Ser Thr Phe Val Phe Ala Phe Asn Asp Lys Gln Ala Val Ala Ala
            20                  25                  30

Ser Ala Gly Asn Gly Leu Glu Asn Trp Ser Lys Trp Met Gln Pro Ile
        35                  40                  45

Pro Asp Asn Val Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asn Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Asp Ser Phe Ser
145                 150                 155                 160

Ser Thr Phe Glu Lys Lys Tyr Phe Pro Asp Pro Ile Phe Leu Lys Thr
                165                 170                 175

Glu Gly Asn Ile Arg Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Thr Thr Val Asn Gln Asn Val Asn
    210                 215                 220

Val Thr Val Gln Asp Lys Tyr Lys Val Ser Tyr Asp Glu Lys Val Lys
225                 230                 235                 240

Ser Ile Lys Asp Thr Ile Asn Glu Thr Ile Asn Asn Ser Glu Asp Cys
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Met Arg Val Gly Trp Val Ile Gln
    290                 295                 300

Asp Tyr Ile Asn Glu Lys Trp Ser Pro Ile Leu Tyr Glu Glu Val Ile
305                 310                 315                 320

Arg Ala Asn Lys Ser Leu
                325
```

<210> SEQ ID NO 115
<211> LENGTH: 987
<212> TYPE: DNA
<213> ORGANISM: Unknown
<220> FEATURE:
<223> OTHER INFORMATION: Obtained from an environmental sample

<400> SEQUENCE: 115

```
atgaacaata agaagtttat tttgaagtta ttcatatgta gtatggtact tagcgccttt      60

gtatttgctt tcaatgataa gaaaaccgtt gcagctagct ctattaatga gcttgaaaat     120

tggtctagat ggatgaaacc tataaatgat gacataccgt tagcacgaat ttcaattcca     180
```

```
ggaacacatg atagtggaac gttcaagttg caaaatccga taaagcaagt gtggggaatg    240

acgcaagaat atgattttcg ttatcaaatg gatcatggag ctagaatttt tgatataaga    300

gggcgtttaa cagatgataa tacgatagtt cttcatcatg ggccattata tctttatgta    360

acactgcacg aatttataaa cgaagcgaaa caatttttaa aagataatcc aagtgaaacg    420

attattatgt ctttaaaaaa agagtatgag gatatgaaag gggcggaaag ctcatttagt    480

agtacgtttg agaaaaatta ttttcgtgat ccaatctttt taaaaacaga agggaatata    540

aagcttggag atgctcgtgg gaaaattata ttactaaaac gatatagtgg tagtaatgaa    600

tctgggggat ataataattt ctattggcca gacaatgaga cgtttacctc aactataaat    660

caaaatgtaa atgtcacagt acaagataaa tataaagtga gttatgatga gaaagtaaac    720

gctattaaag atacattaaa tgaaacgatt aacaatagtg aagatgttaa tcatctatat    780

attaatttta taagcttgtc ttctggtggt acagcatgga atagtccata ttattatgcg    840

tcctacataa atcctgaaat tgcaaattat atgaagcaaa agaatcctac gagagtgggc    900

tggataatac aagattatat aaatgaaaaa tggtcaccat tactttatca agaagttata    960

agagcgaata agtcacttgt aaaatag                                        987


<210> SEQ ID NO 116
<211> LENGTH: 328
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
      C, X domain

<400> SEQUENCE: 116

Met Asn Asn Lys Lys Phe Ile Leu Lys Leu Phe Ile Cys Ser Met Val
 1               5                  10                  15

Leu Ser Ala Phe Val Phe Ala Phe Asn Asp Lys Lys Thr Val Ala Ala
            20                  25                  30

Ser Ser Ile Asn Glu Leu Glu Asn Trp Ser Arg Trp Met Lys Pro Ile
        35                  40                  45

Asn Asp Asp Ile Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asp Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Ser Ser Phe Ser
145                 150                 155                 160

Ser Thr Phe Glu Lys Asn Tyr Phe Arg Asp Pro Ile Phe Leu Lys Thr
                165                 170                 175

Glu Gly Asn Ile Lys Leu Gly Asp Ala Arg Gly Lys Ile Ile Leu Leu
```

-continued

```
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Ser Thr Ile Asn Gln Asn Val Asn
    210                 215                 220

Val Thr Val Gln Asp Lys Tyr Lys Val Ser Tyr Asp Glu Lys Val Asn
225                 230                 235                 240

Ala Ile Lys Asp Thr Leu Asn Glu Thr Ile Asn Asn Ser Glu Asp Val
                245                 250                 255

Asn His Leu Tyr Ile Asn Phe Ile Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Thr Arg Val Gly Trp Ile Ile Gln
    290                 295                 300

Asp Tyr Ile Asn Glu Lys Trp Ser Pro Leu Leu Tyr Gln Glu Val Ile
305                 310                 315                 320

Arg Ala Asn Lys Ser Leu Val Lys
                325
```

<210> SEQ ID NO 117
<211> LENGTH: 987
<212> TYPE: DNA
<213> ORGANISM: Unknown
<220> FEATURE:
<223> OTHER INFORMATION: Obtained from an environmental sample

<400> SEQUENCE: 117

```
atgaacaata agaagtttat tttgaagtta ttcatatgta gtatggtact tagcgccttt      60

gtatttgctt tcaatgataa gaaaaccgtt gcagctagct ctattaatga gcttgaaaat     120

tggtctagat ggatgaaacc tataaatgat gacataccgt tagcacgaat ttcaattcca     180

ggaacacatg atagtggaac gttcaagttg caaaatccga taaagcaagt gtggggaatg     240

acgcaagaat atgattttcg ttatcaaatg gatcatggag ctagaatttt tgatataaga     300

gggcgtttaa cagatgataa tacgatagtt cttcatcatg ggccattata tctttatgta     360

acactgcacg aatttataaa cgaagcgaaa caatttttaa aagataatcc aagtgaaacg     420

attattatgt ctttaaaaaa agagtatgag gatatgaaag gggcggaaag ctcatttagt     480

agtacgtttg agaaaaatta ttttcgtgat ccaatctttt taaaaacaga aggaaatata     540

aagcttggag atgctcgtgg gaaaattgta ttactaaaaa gatatagtgg tagtaatgaa     600

tctgggggat ataataattt ctattggcca gacaatgaga cgtttacctc aactataaat     660

caaaatgtaa atgtaacagt acaagataaa tataaagtga gttatgatga gaaaataaac     720

gctattaaag atacattaaa tgaaacgatt aacaatagtg aagatgttaa tcatctatat     780

attaatttta caagcttgtc ttctggtggt acagcatgga atagtccata ttattatgcg     840

tcctacataa atcctgaaat tgcaaattat atgaagcaaa agaatcctac gagagtgggc     900

tggataatac aagattatat aaatgaaaaa tggtcaccat tactttatca agaagttata     960

agagcgaata agtcacttgt aaaatag                                         987
```

<210> SEQ ID NO 118
<211> LENGTH: 328
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
C, X domain

<400> SEQUENCE: 118

```
Met Asn Asn Lys Lys Phe Ile Leu Lys Leu Phe Ile Cys Ser Met Val
 1               5                  10                  15

Leu Ser Ala Phe Val Phe Ala Phe Asn Asp Lys Lys Thr Val Ala Ala
            20                  25                  30

Ser Ser Ile Asn Glu Leu Glu Asn Trp Ser Arg Trp Met Lys Pro Ile
        35                  40                  45

Asn Asp Asp Ile Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asp Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Ser Ser Phe Ser
145                 150                 155                 160

Ser Thr Phe Glu Lys Asn Tyr Phe Arg Asp Pro Ile Phe Leu Lys Thr
                165                 170                 175

Glu Gly Asn Ile Lys Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Ser Thr Ile Asn Gln Asn Val Asn
    210                 215                 220

Val Thr Val Gln Asp Lys Tyr Lys Val Ser Tyr Asp Glu Lys Ile Asn
225                 230                 235                 240

Ala Ile Lys Asp Thr Leu Asn Glu Thr Ile Asn Asn Ser Glu Asp Val
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Thr Arg Val Gly Trp Ile Ile Gln
    290                 295                 300

Asp Tyr Ile Asn Glu Lys Trp Ser Pro Leu Leu Tyr Gln Glu Val Ile
305                 310                 315                 320

Arg Ala Asn Lys Ser Leu Val Lys
                325
```

<210> SEQ ID NO 119
<211> LENGTH: 987
<212> TYPE: DNA
<213> ORGANISM: Unknown
<220> FEATURE:
<223> OTHER INFORMATION: Obtained from an environmental sample

<400> SEQUENCE: 119
atgaacaata agaagtttat tttgaagtta ttcatatgta gtatggtact tagcgccttt 60
gtatttgctt tcaatgataa gaaaaccgtt gcagctagct ctattaatgt gcttgaaaat 120
tggtctagat ggatgaaacc tataaatgat gacataccgt tagcacgaat ttcaattcca 180
ggaacacatg atagtggaac gttcaagttg caaaatccga taaagcaagt gtggggaatg 240
acgcaagaat atgattttcg ttatcaaatg gatcatggag ctagaatttt tgatataaga 300
gggcgtttaa cagatgataa tacgatagtt cttcatcatg ggccattata tctttatgta 360
acactgcacg aatttataaa cgaagcgaaa caatttttaa aagataatcc aagtgaaacg 420
attattatgt ctttaaaaaa agagtatgag gatatgaaag gggcggaaag ctcatttagt 480
agtacgtttg agaaaaatta ttttcgtgat ccaatctttt taaaaacaga agggaatata 540
aagcttggag atgctcgtgg gaaaattgta ttactaaaaa gatatagtgg tagtaatgaa 600
tctgggggat ataataattt ctattggcca gacaatgaga cgtttacctc aactataaat 660
caaaatgtaa atgtaacagt acaagataaa tataaagtga gttatgatga gaaaataaac 720
gctattaaag atacattaaa tgaaacgatt aacaatagtg aagatgttaa tcatctatat 780
attaatttta caagcttgtc ttctggtggt acagcatgga atagtccata ttattatgcg 840
tcctacataa atcctgaaat tgcaaattat atgaagcaaa agaatcctac gagagtgggc 900
tggataatac aagattatat aaatgaaaaa tggtcaccat tactttatca agaagttata 960
agagcgaata agtcacttgt aaaatag 987

<210> SEQ ID NO 120
<211> LENGTH: 328
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
C, X domain

<400> SEQUENCE: 120

Met Asn Asn Lys Lys Phe Ile Leu Lys Leu Phe Ile Cys Ser Met Val
1 5 10 15

Leu Ser Ala Phe Val Phe Ala Phe Asn Asp Lys Lys Thr Val Ala Ala
20 25 30

Ser Ser Ile Asn Val Leu Glu Asn Trp Ser Arg Trp Met Lys Pro Ile
35 40 45

Asn Asp Asp Ile Pro Leu Ala Arg Ile Ser Ile Pro Gly Thr His Asp
50 55 60

Ser Gly Thr Phe Lys Leu Gln Asn Pro Ile Lys Gln Val Trp Gly Met
65 70 75 80

Thr Gln Glu Tyr Asp Phe Arg Tyr Gln Met Asp His Gly Ala Arg Ile
85 90 95

Phe Asp Ile Arg Gly Arg Leu Thr Asp Asp Asn Thr Ile Val Leu His
100 105 110

His Gly Pro Leu Tyr Leu Tyr Val Thr Leu His Glu Phe Ile Asn Glu
115 120 125

Ala Lys Gln Phe Leu Lys Asp Asn Pro Ser Glu Thr Ile Ile Met Ser
130 135 140

```
Leu Lys Lys Glu Tyr Glu Asp Met Lys Gly Ala Glu Ser Ser Phe Ser
145                 150                 155                 160

Ser Thr Phe Glu Lys Asn Tyr Phe Arg Asp Pro Ile Phe Leu Lys Thr
                165                 170                 175

Glu Gly Asn Ile Lys Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Ser Thr Ile Asn Gln Asn Val Asn
    210                 215                 220

Val Thr Val Gln Asp Lys Tyr Lys Val Ser Tyr Asp Glu Lys Ile Asn
225                 230                 235                 240

Ala Ile Lys Asp Thr Leu Asn Glu Thr Ile Asn Asn Ser Glu Asp Val
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Thr Arg Val Gly Trp Ile Ile Gln
    290                 295                 300

Asp Tyr Ile Asn Glu Lys Trp Ser Pro Leu Leu Tyr Gln Glu Val Ile
305                 310                 315                 320

Arg Ala Asn Lys Ser Leu Val Lys
                325
```

<210> SEQ ID NO 121
<211> LENGTH: 990
<212> TYPE: DNA
<213> ORGANISM: Unknown
<220> FEATURE:
<223> OTHER INFORMATION: Obtained from an environmental sample

<400> SEQUENCE: 121

```
atgcgtaata agaagtttat tttgaaatta ttaatatgta gtacggtact tagcaccttt     60

gtatttgctt tcaatgataa gcaaactgtt gcagctagct ctattaatga actcgaaaat    120

tggtctagat ggatgcagcc tatacctgat gacatgccgt tagcaagaat ttcaattcca    180

ggaacacatg atagtggaac gttcaaactg caaaatccga taaagcaagt atggggaatg    240

acgcaagaat atgattttcg ttaccaaatg gatcatgggg ctagaatttt tgatataaga    300

gggcgtttaa cagatgataa tacgatagtc cttcatcatg ggccattata tctttatgta    360

acactgaacg aatttataaa tgaagcgaaa caatttttaa aagataaccc aagtgaaacg    420

attattatgt ctttaaagaa agagtatgag gatatgaaag gggcagaaaa ttcatttagt    480

agtacgtttg aaaaaaaata ttttcttgat cctatctttt taaaaacaga agggaatata    540

aaacttggag atgctcgtgg gaaaattgta ctactaaaaa gatatagtgg tagtaatgaa    600

tctggaggat ataataattt ttattggcca gataacgaga cgtttacgac aactgtaaat    660

caaaatgtaa atgtaacagt acaagataaa tataaagtga gttatgatga gaaagtaaaa    720

tctattaaag atacgataaa tgaaacgatt aacaatagtg aagattttaa tcatctatat    780

attaatttta caagcttgtc ttctggtggt acagcatgga atagtccata ttattatgca    840

tcctacataa atcctgaaat tgcaaaccat atgaagcaaa agaatcctac gagagtgggc    900

tgggtaattc aagattatat aaatgaaaaa tggtcaccaa tactttatca agaagttata    960

agagcgaata agtcacttat aaaagagtag                                     990
```

<210> SEQ ID NO 122
<211> LENGTH: 329
<212> TYPE: PRT
<213> ORGANISM: Unknown
<220> FEATURE:
<221> NAME/KEY: SIGNAL
<222> LOCATION: (1)...(23)
<223> OTHER INFORMATION: Obtained from an environmental sample
<220> FEATURE:
<221> NAME/KEY: DOMAIN
<222> LOCATION: (56)...(195)
<223> OTHER INFORMATION: Phosphatidylinositol-specific phospholipase
C, X domain

<400> SEQUENCE: 122

```
Met Arg Asn Lys Lys Phe Ile Leu Lys Leu Leu Ile Cys Ser Thr Val
 1               5                  10                  15

Leu Ser Thr Phe Val Phe Ala Phe Asn Asp Lys Gln Thr Val Ala Ala
            20                  25                  30

Ser Ser Ile Asn Glu Leu Glu Asn Trp Ser Arg Trp Met Gln Pro Ile
        35                  40                  45

Pro Asp Asp Met Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asp Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu Asn Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Asn Ser Phe Ser
145                 150                 155                 160

Ser Thr Phe Glu Lys Lys Tyr Phe Leu Asp Pro Ile Phe Leu Lys Thr
                165                 170                 175

Glu Gly Asn Ile Lys Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Thr Thr Val Asn Gln Asn Val Asn
    210                 215                 220

Val Thr Val Gln Asp Lys Tyr Lys Val Ser Tyr Asp Glu Lys Val Lys
225                 230                 235                 240

Ser Ile Lys Asp Thr Ile Asn Glu Thr Ile Asn Asn Ser Glu Asp Phe
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn His Met Lys Gln Lys Asn Pro Thr Arg Val Gly Trp Val Ile Gln
    290                 295                 300

Asp Tyr Ile Asn Glu Lys Trp Ser Pro Ile Leu Tyr Gln Glu Val Ile
305                 310                 315                 320

Arg Ala Asn Lys Ser Leu Ile Lys Glu
                325
```

<210> SEQ ID NO 123
<211> LENGTH: 849
<212> TYPE: DNA
<213> ORGANISM: Unknown
<220> FEATURE:
<223> OTHER INFORMATION: Obtained from an environmental sample

<400> SEQUENCE: 123
atgaaaaaga aagtattagc actagcagct atggttgctt tagctgcacc agttcaaagt 60
gtagtgtttg cgcaaacaaa taatagtgaa agtcctgcac cgatcttaag atggtcagct 120
gaggacaagc ataatgaggg agttagtact catttgtgga ttgtaaatcg tgcaattgac 180
atcatgtctc gtaatacagc gattgtgaag ccaaatgaaa ctgctttatt aaatgagtgg 240
cgtactgatt tagaaaatgg tatttattct gctgattacg agaatcctta ttatgataat 300
agtacatatg cttctcattt ttacgatccg gatactggaa aaacatatat tccttttgcg 360
aaacaggcaa aagaaacagg tacaaaatat tttaaacttg ctggtgaagc atacaaaaat 420
caagatatga aacaggcatt cttctattta ggattatcac ttcattattt aggagatgta 480
aatcagccaa tgcatgcagc aaactttacg aatctttctt atccaatggg tttccattct 540
aaatatgaaa attttgttga tacaataaaa aataactata tagtttcaga tagtagtgga 600
tattggaatt ggaaaggggc aaacccagaa gattggattc aaggagcagc agtagcggct 660
aaacaagatt atcctggtat tgtgaacgat acgacaaaag attggtttgt aaaagcagct 720
gtatctcaag catatgcaga taaatggcgt gcagaagtaa caccggtgac aggaaaacgc 780
ttaatggagg cacagcgcgt tacagctggt tatattcatt tatggtttga tacgtatgta 840
aatcactaa 849

<210> SEQ ID NO 124
<211> LENGTH: 282
<212> TYPE: PRT
<213> ORGANISM: Unknown
<220> FEATURE:
<221> NAME/KEY: SIGNAL
<222> LOCATION: (1)...(24)
<223> OTHER INFORMATION: Obtained from an environmental sample
<220> FEATURE:
<221> NAME/KEY: DOMAIN
<222> LOCATION: (1)...(281)
<223> OTHER INFORMATION: Zinc dependent phospholipase C

<400> SEQUENCE: 124

Met Lys Lys Lys Val Leu Ala Leu Ala Ala Met Val Ala Leu Ala Ala
1 5 10 15

Pro Val Gln Ser Val Val Phe Ala Gln Thr Asn Asn Ser Glu Ser Pro
20 25 30

Ala Pro Ile Leu Arg Trp Ser Ala Glu Asp Lys His Asn Glu Gly Val
35 40 45

Ser Thr His Leu Trp Ile Val Asn Arg Ala Ile Asp Ile Met Ser Arg
50 55 60

Asn Thr Ala Ile Val Lys Pro Asn Glu Thr Ala Leu Leu Asn Glu Trp
65 70 75 80

Arg Thr Asp Leu Glu Asn Gly Ile Tyr Ser Ala Asp Tyr Glu Asn Pro
85 90 95

Tyr Tyr Asp Asn Ser Thr Tyr Ala Ser His Phe Tyr Asp Pro Asp Thr
100 105 110

Gly Lys Thr Tyr Ile Pro Phe Ala Lys Gln Ala Lys Glu Thr Gly Thr
115 120 125

Lys Tyr Phe Lys Leu Ala Gly Glu Ala Tyr Lys Asn Gln Asp Met Lys
    130                 135                 140

Gln Ala Phe Phe Tyr Leu Gly Leu Ser Leu His Tyr Leu Gly Asp Val
145                 150                 155                 160

Asn Gln Pro Met His Ala Ala Asn Phe Thr Asn Leu Ser Tyr Pro Met
                165                 170                 175

Gly Phe His Ser Lys Tyr Glu Asn Phe Val Asp Thr Ile Lys Asn Asn
            180                 185                 190

Tyr Ile Val Ser Asp Ser Ser Gly Tyr Trp Asn Trp Lys Gly Ala Asn
        195                 200                 205

Pro Glu Asp Trp Ile Gln Gly Ala Ala Val Ala Ala Lys Gln Asp Tyr
    210                 215                 220

Pro Gly Ile Val Asn Asp Thr Thr Lys Asp Trp Phe Val Lys Ala Ala
225                 230                 235                 240

Val Ser Gln Ala Tyr Ala Asp Lys Trp Arg Ala Glu Val Thr Pro Val
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn His
        275                 280

<210> SEQ ID NO 125
<211> LENGTH: 1710
<212> TYPE: DNA
<213> ORGANISM: Unknown
<220> FEATURE:
<223> OTHER INFORMATION: Obtained from an environmental sample

<400> SEQUENCE: 125
atggctgaca acgagttgcc cctggcgcgg cccagggaga cgccgccgtg ccgcccccggc 60 acgttcgagc ttgggctcgc cctggctggc gcggtctctg gcggcgccta cgccgcggga 120
gtcctggatt tcttctacga agccctcgag cattggtacg aggccaggga ggcgggagcg 180
ccggtgccca accacgacgt gctcctccgg atcatctcgg gtgcgtcggc gggcagtatc 240
aatggcgtgc tttcgggcat cgcgctgccg taccgttttc cccacgtgca cagcgggccc 300
gcgcccgagg gtgccacggg caaccccttc tacgacgcct gggtgaagcg catcgacgtg 360
cgcgaactgt tgggcaacga agacctggcc gatcccacgc agccggtggc atccctgctc 420
gacgccacct gcctggatac gatcgcgaag gacatgctcg gcttctcggc ggcgccggcc 480
acccggccgt acgtcgctaa tccgctgaaa tgcgtgttca cggtgaccaa cctgcgtggc 540
gttccttacg tcgtgcagtt caagggaaac ccggagatcc ccggccacgg catgatggcc 600
cacgccgact ggctgcgctt cgccgtcgac accgggcagg gcgaccggga tggggaatgg 660
atgttccccg atgaacggct cgtcagcggg ccgagccatg cgcggactcc ggcctggcaa 720
ggtttcatgg aggcggcgct cgcttcgtcg gcgttcccgg ccggcttgcg tttccgcgaa 780
gtcgcccggc cctggagcga ttacgaccag cgcgtcgtgg tggtgcccaa ccaggcgggg 840
gccgcggtcc cggtcccgct cccgccggcc tgggcggagg gcgagggcag cgatggggac 900
taccggttcg tcgcggtgga tggtggcgcg atggacaacg agccgttcga acttgcccgt 960
accgagctgg cgggcacgct cggccgcaat ccacgcgaag ggaaccgggt caaccgcatc 1020
gtgatcatgc tcgatccgtt tcccgaggcc gaggcgccgg gacccgcgga agccgcgagc 1080
acgaatctcg tcgaggcgat ggcctcgctg tttggtgcgt ggaaacagca ggcacggttc 1140
aagccggagg aagtggcgct cgccctggat tcgaccgtgt acagccgctt catgatcgcg 1200

```
cccagccggc cgtgcatgga gggcgggcca cggtggatcg gtgggcgagc gctcgccgcg   1260

ggtgcgctgg gtggcttctc ggggttcctg gcggaggcat acaggcacca cgatttcctc   1320

ctgggacgcc gcaactgcca acgcttcctc gccgagcgcc tgttgatccc cgcggacaat   1380

ccgatcttcg ccggctggat cgacgatccc tccctgcagg gctacatccg cgagatcgat   1440

ggcgtgcgtt acgccccggt catcccgctg gtgggcggct gccagggctt gcgcgagccg   1500

ttgcccacgt ggccgcgtgg tgcattcgac ctggactcgc tcatgccgct ggtcgagcgc   1560

cgcatgcagc gcctgtattc ggcggctacc gcgacgctcg gtggccgctt cgccacctgg   1620

ctggcgtggc gcttctacct gcgccgcaag ctcctcgacc tggtctcaag ccgtatccgt   1680

agcgcattga gggacttcgg cctttggtga                                    1710
```

<210> SEQ ID NO 126
<211> LENGTH: 569
<212> TYPE: PRT
<213> ORGANISM: Unknown
<220> FEATURE:
<223> OTHER INFORMATION: Obtained from an environmental sample

<400> SEQUENCE: 126

```
Met Ala Asp Asn Glu Leu Pro Leu Ala Arg Pro Arg Glu Thr Pro Pro
 1               5                  10                  15

Cys Arg Pro Gly Thr Phe Glu Leu Gly Leu Ala Leu Ala Gly Ala Val
            20                  25                  30

Ser Gly Gly Ala Tyr Ala Ala Gly Val Leu Asp Phe Phe Tyr Glu Ala
        35                  40                  45

Leu Glu His Trp Tyr Glu Ala Arg Glu Ala Gly Ala Pro Val Pro Asn
    50                  55                  60

His Asp Val Leu Leu Arg Ile Ile Ser Gly Ala Ser Ala Gly Ser Ile
65                  70                  75                  80

Asn Gly Val Leu Ser Gly Ile Ala Leu Pro Tyr Arg Phe Pro His Val
                85                  90                  95

His Ser Gly Pro Ala Pro Glu Gly Ala Thr Gly Asn Pro Phe Tyr Asp
            100                 105                 110

Ala Trp Val Lys Arg Ile Asp Val Arg Glu Leu Leu Gly Asn Glu Asp
        115                 120                 125

Leu Ala Asp Pro Thr Gln Pro Val Ala Ser Leu Leu Asp Ala Thr Cys
    130                 135                 140

Leu Asp Thr Ile Ala Lys Asp Met Leu Gly Phe Ser Ala Ala Pro Ala
145                 150                 155                 160

Thr Arg Pro Tyr Val Ala Asn Pro Leu Lys Cys Val Phe Thr Val Thr
                165                 170                 175

Asn Leu Arg Gly Val Pro Tyr Val Val Gln Phe Lys Gly Asn Pro Glu
            180                 185                 190

Ile Pro Gly His Gly Met Met Ala His Ala Asp Trp Leu Arg Phe Ala
        195                 200                 205

Val Asp Thr Gly Gln Gly Asp Arg Asp Gly Glu Trp Met Phe Pro Asp
    210                 215                 220

Glu Arg Leu Val Ser Gly Pro Ser His Ala Arg Thr Pro Ala Trp Gln
225                 230                 235                 240

Gly Phe Met Glu Ala Ala Leu Ala Ser Ser Ala Phe Pro Ala Gly Leu
                245                 250                 255

Arg Phe Arg Glu Val Ala Arg Pro Trp Ser Asp Tyr Asp Gln Arg Val
            260                 265                 270
```

```
Val Val Val Pro Asn Gln Ala Gly Ala Ala Val Pro Val Pro Leu Pro
        275                 280                 285

Pro Ala Trp Ala Glu Gly Glu Gly Ser Asp Gly Asp Tyr Arg Phe Val
    290                 295                 300

Ala Val Asp Gly Gly Ala Met Asp Asn Glu Pro Phe Glu Leu Ala Arg
305                 310                 315                 320

Thr Glu Leu Ala Gly Thr Leu Gly Arg Asn Pro Arg Glu Gly Asn Arg
                325                 330                 335

Val Asn Arg Ile Val Ile Met Leu Asp Pro Phe Pro Glu Ala Glu Ala
            340                 345                 350

Pro Gly Pro Ala Glu Ala Ala Ser Thr Asn Leu Val Glu Ala Met Ala
        355                 360                 365

Ser Leu Phe Gly Ala Trp Lys Gln Gln Ala Arg Phe Lys Pro Glu Glu
    370                 375                 380

Val Ala Leu Ala Leu Asp Ser Thr Val Tyr Ser Arg Phe Met Ile Ala
385                 390                 395                 400

Pro Ser Arg Pro Cys Met Glu Gly Gly Pro Arg Trp Ile Gly Gly Arg
                405                 410                 415

Ala Leu Ala Ala Gly Ala Leu Gly Gly Phe Ser Gly Phe Leu Ala Glu
            420                 425                 430

Ala Tyr Arg His His Asp Phe Leu Leu Gly Arg Arg Asn Cys Gln Arg
        435                 440                 445

Phe Leu Ala Glu Arg Leu Leu Ile Pro Ala Asp Asn Pro Ile Phe Ala
    450                 455                 460

Gly Trp Ile Asp Asp Pro Ser Leu Gln Gly Tyr Ile Arg Glu Ile Asp
465                 470                 475                 480

Gly Val Arg Tyr Ala Pro Val Ile Pro Leu Val Gly Gly Cys Gln Gly
                485                 490                 495

Leu Arg Glu Pro Leu Pro Thr Trp Pro Arg Gly Ala Phe Asp Leu Asp
            500                 505                 510

Ser Leu Met Pro Leu Val Glu Arg Arg Met Gln Arg Leu Tyr Ser Ala
        515                 520                 525

Ala Thr Ala Thr Leu Gly Gly Arg Phe Ala Thr Trp Leu Ala Trp Arg
    530                 535                 540

Phe Tyr Leu Arg Arg Lys Leu Leu Asp Leu Val Ser Ser Arg Ile Arg
545                 550                 555                 560

Ser Ala Leu Arg Asp Phe Gly Leu Trp
                565
```

<210> SEQ ID NO 127
<211> LENGTH: 1038
<212> TYPE: DNA
<213> ORGANISM: Unknown
<220> FEATURE:
<223> OTHER INFORMATION: Obtained from an environmental sample

<400> SEQUENCE: 127

```
atgacaaccc aatttagaaa cttgatcttt gaaggtggtg gtgtaaaagg agttgcttac      60

attggcgcca tgcagattct tgaaaatcgt ggcgtgttgc aagatattca ccgagtcgga     120

ggttgcagtg ccggtgcgat taacgcgctg atttttgcgc tgggttacac ggttcgtgag     180

caaaaagaga tcttacaagc caccgatttt aaccagttta tggataactc ttgggggggtt     240

attcgtgata ttcgcaggct tgctcgagac tttggctgga ataagggtgg cttctttaat     300

agctggatag gtgatttgat tcatcgtcgt ttggggaatc gccgagcgac gttcaaggat     360

ctgcaaaagg ccaagcttcc tgatctttat gtcatcggta ctaatctgtc tacagggttt     420
```

gcagaggttt tttctgccga aagacacccc gatatggagc tagcgacagc ggtgcgcatc 480
tccatgtcga taccgctgtt ctttgcggcc gtgcgccacg gtgatcgaca agatgtgtat 540
gtcgatggag gtgttcaact taactatccg attaaactgt ttgatcggga gcgttatatt 600
gatctggcca aagatcccgg tgccgttcgg cgaacgggtt attacaataa agaaaacgct 660
cgctttcagc ttgaacggcc gggccatagc ccctatgttt acaatcgcca gaccttgggt 720
ttgcgactgg atagtcgaga ggagataggg ctttttcgtt atgacgaacc cctcaagggc 780
aaaccgatta agtccttcac tgactacgct cgacaacttt tcggtgcgtt gatgaatgcg 840
caggaaaaca ttcatctaca tggcgatgat tggcagcgca cggtctatat cgacacactg 900
gatgtgagta cgacggactt caatctttct gatgcaacca agcaagcact gattgagcaa 960
ggaattaacg gcaccgaaaa ttatttcgag tggtttgata atccgttaga gaagcctgtg 1020
aatagagtgg agtcatag 1038

<210> SEQ ID NO 128
<211> LENGTH: 345
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (8)...(195)
<223> OTHER INFORMATION: Patatin-like phospholipase

<400> SEQUENCE: 128

Met Thr Thr Gln Phe Arg Asn Leu Ile Phe Glu Gly Gly Gly Val Lys
1 5 10 15

Gly Val Ala Tyr Ile Gly Ala Met Gln Ile Leu Glu Asn Arg Gly Val
20 25 30

Leu Gln Asp Ile His Arg Val Gly Gly Cys Ser Ala Gly Ala Ile Asn
35 40 45

Ala Leu Ile Phe Ala Leu Gly Tyr Thr Val Arg Glu Gln Lys Glu Ile
50 55 60

Leu Gln Ala Thr Asp Phe Asn Gln Phe Met Asp Asn Ser Trp Gly Val
65 70 75 80

Ile Arg Asp Ile Arg Arg Leu Ala Arg Asp Phe Gly Trp Asn Lys Gly
85 90 95

Gly Phe Phe Asn Ser Trp Ile Gly Asp Leu Ile His Arg Arg Leu Gly
100 105 110

Asn Arg Arg Ala Thr Phe Lys Asp Leu Gln Lys Ala Lys Leu Pro Asp
115 120 125

Leu Tyr Val Ile Gly Thr Asn Leu Ser Thr Gly Phe Ala Glu Val Phe
130 135 140

Ser Ala Glu Arg His Pro Asp Met Glu Leu Ala Thr Ala Val Arg Ile
145 150 155 160

Ser Met Ser Ile Pro Leu Phe Phe Ala Ala Val Arg His Gly Asp Arg
165 170 175

Gln Asp Val Tyr Val Asp Gly Gly Val Gln Leu Asn Tyr Pro Ile Lys
180 185 190

Leu Phe Asp Arg Glu Arg Tyr Ile Asp Leu Ala Lys Asp Pro Gly Ala
195 200 205

Val Arg Arg Thr Gly Tyr Tyr Asn Lys Glu Asn Ala Arg Phe Gln Leu
210 215 220

Glu Arg Pro Gly His Ser Pro Tyr Val Tyr Asn Arg Gln Thr Leu Gly

```
225                 230                 235                 240

Leu Arg Leu Asp Ser Arg Glu Glu Ile Gly Leu Phe Arg Tyr Asp Glu
                245                 250                 255

Pro Leu Lys Gly Lys Pro Ile Lys Ser Phe Thr Asp Tyr Ala Arg Gln
            260                 265                 270

Leu Phe Gly Ala Leu Met Asn Ala Gln Glu Asn Ile His Leu His Gly
        275                 280                 285

Asp Asp Trp Gln Arg Thr Val Tyr Ile Asp Thr Leu Asp Val Ser Thr
    290                 295                 300

Thr Asp Phe Asn Leu Ser Asp Ala Thr Lys Gln Ala Leu Ile Glu Gln
305                 310                 315                 320

Gly Ile Asn Gly Thr Glu Asn Tyr Phe Glu Trp Phe Asp Asn Pro Leu
                325                 330                 335

Glu Lys Pro Val Asn Arg Val Glu Ser
            340                 345


<210> SEQ ID NO 129
<211> LENGTH: 1434
<212> TYPE: DNA
<213> ORGANISM: Unknown
<220> FEATURE:
<223> OTHER INFORMATION: Obtained from an environmental sample

<400> SEQUENCE: 129

atgaaaaaga aaatatgtac attggctctt gtatcagcaa taacttctgg agttgtgacg      60

attccaacgg tagcatctgc ttgcagaata ggcgaagaag taatgaaaca ggagaaacag     120

gataatcaag agcacaaacg tgtgaaaaga tggtctgcgg agcatccgca tcattctaat     180

gaaagcacgc acttatggat tgctcgaaat gcgattcaaa ttatgagtcg taatcaagat     240

aacacggtcc aaaacaatga attacagttc ttaaatattc ctgaatataa ggagttattt     300

gaaagaggac tttatgatgc tgattacctt gatgaattta acgatggcgg tacaggtaca     360

atcggcattg atgggctaat taaaggaggg tggaaatctc atttttatga tccagatacg     420

aaaaagaatt ataaaggaga agaagctcca acagccctta cgcaaggaga taaatatttt     480

aaattagcag gagactattt taagaaagag gatttgaaac aagctttcta ctatttaggt     540

gttgcgactc actatttcac agatgctact cagccaatgc atgctgctaa ttttacagct     600

gtcgacatga gtgcgataaa gtttcatagc gcttttgaaa attatgtaac gacaattcag     660

acgccatttg aagtgaagga tgataaagga acctataatt tggttgattc taatgatccg     720

aagcagtgga tacatgaaac agcgaaactc gcaaaagcgg aaattatgaa tattactaat     780

gatactatta aatctcaata taataaaggg aacaatgatc tttggcaaca aggagttatg     840

ccagctgttc agagaagtct ggaaacagca caaaggaaca cggcaggatt tattcattta     900

tggtttaaaa catatgttgg caaaactgct gctgaagata ttgaaaatac acaagtaaaa     960

gattctaacg gagaagcaat acaagaaaat aaaaaatact acgttgtacc gagtgagttt    1020

ttaaatagag gtttgacctt tgaggtatat gctgcaaatg actacgcact attagctaat    1080

cacgtagatg ataataaagt tcatggtaca cctgttcagt ttgtttttga taaagacaat    1140

aacggaattc ttcatcgggg agaaagtgca ctgatgaaaa tgacgcaatc taactatgct    1200

gattatgtat ttctcaatta ctctaatatg acaaattggg tacatcttgc gaaacgaaaa    1260

acaaatactt cacagtttaa agtgtatcca aatccggata actcatctga atatttctta    1320

tatacagatg gatacccggt aaattatcaa gaaaatggta acggaaagag ctggattgtg    1380

ttaggaaaga aaacggataa accaaaagcg tggaaattta tacaggcgga ataa          1434
```

<210> SEQ ID NO 130
<211> LENGTH: 477
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(27)
<220> FEATURE:
<221> NAME/KEY: DOMAIN
<222> LOCATION: (1)...(307)
<223> OTHER INFORMATION: Zinc dependent phospholipase C

<400> SEQUENCE: 130

```
Met Lys Lys Lys Ile Cys Thr Leu Ala Leu Val Ser Ala Ile Thr Ser
 1               5                  10                  15

Gly Val Val Thr Ile Pro Thr Val Ala Ser Ala Cys Arg Ile Gly Glu
            20                  25                  30

Glu Val Met Lys Gln Glu Lys Gln Asp Asn Gln Glu His Lys Arg Val
        35                  40                  45

Lys Arg Trp Ser Ala Glu His Pro His His Ser Asn Glu Ser Thr His
    50                  55                  60

Leu Trp Ile Ala Arg Asn Ala Ile Gln Ile Met Ser Arg Asn Gln Asp
65                  70                  75                  80

Asn Thr Val Gln Asn Asn Glu Leu Gln Phe Leu Asn Ile Pro Glu Tyr
                85                  90                  95

Lys Glu Leu Phe Glu Arg Gly Leu Tyr Asp Ala Asp Tyr Leu Asp Glu
            100                 105                 110

Phe Asn Asp Gly Gly Thr Gly Thr Ile Gly Ile Asp Gly Leu Ile Lys
        115                 120                 125

Gly Gly Trp Lys Ser His Phe Tyr Asp Pro Asp Thr Lys Lys Asn Tyr
    130                 135                 140

Lys Gly Glu Glu Ala Pro Thr Ala Leu Thr Gln Gly Asp Lys Tyr Phe
145                 150                 155                 160

Lys Leu Ala Gly Asp Tyr Phe Lys Lys Glu Asp Leu Lys Gln Ala Phe
                165                 170                 175

Tyr Tyr Leu Gly Val Ala Thr His Tyr Phe Thr Asp Ala Thr Gln Pro
            180                 185                 190

Met His Ala Ala Asn Phe Thr Ala Val Asp Met Ser Ala Ile Lys Phe
        195                 200                 205

His Ser Ala Phe Glu Asn Tyr Val Thr Thr Ile Gln Thr Pro Phe Glu
    210                 215                 220

Val Lys Asp Asp Lys Gly Thr Tyr Asn Leu Val Asp Ser Asn Asp Pro
225                 230                 235                 240

Lys Gln Trp Ile His Glu Thr Ala Lys Leu Ala Lys Ala Glu Ile Met
                245                 250                 255

Asn Ile Thr Asn Asp Thr Ile Lys Ser Gln Tyr Asn Lys Gly Asn Asn
            260                 265                 270

Asp Leu Trp Gln Gln Gly Val Met Pro Ala Val Gln Arg Ser Leu Glu
        275                 280                 285

Thr Ala Gln Arg Asn Thr Ala Gly Phe Ile His Leu Trp Phe Lys Thr
    290                 295                 300

Tyr Val Gly Lys Thr Ala Ala Glu Asp Ile Glu Asn Thr Gln Val Lys
305                 310                 315                 320

Asp Ser Asn Gly Glu Ala Ile Gln Glu Asn Lys Lys Tyr Tyr Val Val
                325                 330                 335
```

Pro Ser Glu Phe Leu Asn Arg Gly Leu Thr Phe Glu Val Tyr Ala Ala
340 345 350

Asn Asp Tyr Ala Leu Leu Ala Asn His Val Asp Asp Asn Lys Val His
355 360 365

Gly Thr Pro Val Gln Phe Val Phe Asp Lys Asp Asn Asn Gly Ile Leu
370 375 380

His Arg Gly Glu Ser Ala Leu Met Lys Met Thr Gln Ser Asn Tyr Ala
385 390 395 400

Asp Tyr Val Phe Leu Asn Tyr Ser Asn Met Thr Asn Trp Val His Leu
405 410 415

Ala Lys Arg Lys Thr Asn Thr Ser Gln Phe Lys Val Tyr Pro Asn Pro
420 425 430

Asp Asn Ser Ser Glu Tyr Phe Leu Tyr Thr Asp Gly Tyr Pro Val Asn
435 440 445

Tyr Gln Glu Asn Gly Asn Gly Lys Ser Trp Ile Val Leu Gly Lys Lys
450 455 460

Thr Asp Lys Pro Lys Ala Trp Lys Phe Ile Gln Ala Glu
465 470 475

<210> SEQ ID NO 131
<211> LENGTH: 927
<212> TYPE: DNA
<213> ORGANISM: Unknown
<220> FEATURE:
<223> OTHER INFORMATION: Obtained from an environmental sample

<400> SEQUENCE: 131
atgccgagcc caaaaagtaa tattgatgtt atcagcatcg atggtggtgg aatacgtgga 60
gtattctccg ttacattatt ggatagatta tgtaagacct atcccaatct tcttaagaaa 120
acatatctgt ttgctggaac atctacaggt gggatcattg ccttaggatt agcaaacaac 180
atgacacctc ttgagataag agccttgtac gagaagaacg gttcaaagat atttcataaa 240
tctgtgtggg aaggcgttaa agatttaggt ggaaccatag gtgcaaagta tagtaacaag 300
aatcttaaat ccgttttgaa aaaatacttt ggttcattga agttaaaaga tttatctaaa 360
aaagtactaa tacctacttt tgatttacac tcagacaaag aagaaggcta tccaatgtgg 420
aagcctaagt tctatcacaa ctttgatgga gaaacggaag atatagaaaa gctcgttctt 480
gatgtagcta tgatgacatc agcagcgccc actttcttcc ctacatacaa cgggcatatt 540
gatggcggtg ttgtagccaa caatccatcg atggccgcat tagcccagat tatggatgaa 600
agatatggca tcaatgcctc tgaagttcat attcttaata taggaacagg ttttaaccct 660
gcttatgtta agatgaatcc aggggaagag aaagactggg gtgaacttca gtggataaaa 720
cctttaatca atcttctagt cgatggctct atggatgttt ctacttatta ttgtaagcaa 780
gtcttacgtg ataattttta tagggttaac atgaaattac ctaagaacgt agaaatggat 840
gatcctaatt ctattcctta tttaattgaa cttgcaaact cagttgatct aactgaatgt 900
atcaactggc ttaattcgag gtggtaa 927

<210> SEQ ID NO 132
<211> LENGTH: 308
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (11)...(194)

<223> OTHER INFORMATION: Patatin-like phospholipase

<400> SEQUENCE: 132

```
Met Pro Ser Pro Lys Ser Asn Ile Asp Val Ile Ser Ile Asp Gly Gly
 1               5                  10                  15

Gly Ile Arg Gly Val Phe Ser Val Thr Leu Leu Asp Arg Leu Cys Lys
            20                  25                  30

Thr Tyr Pro Asn Leu Leu Lys Lys Thr Tyr Leu Phe Ala Gly Thr Ser
        35                  40                  45

Thr Gly Gly Ile Ile Ala Leu Gly Leu Ala Asn Asn Met Thr Pro Leu
    50                  55                  60

Glu Ile Arg Ala Leu Tyr Glu Lys Asn Gly Ser Lys Ile Phe His Lys
65                  70                  75                  80

Ser Val Trp Glu Gly Val Lys Asp Leu Gly Gly Thr Ile Gly Ala Lys
                85                  90                  95

Tyr Ser Asn Lys Asn Leu Lys Ser Val Leu Lys Lys Tyr Phe Gly Ser
            100                 105                 110

Leu Lys Leu Lys Asp Leu Ser Lys Lys Val Leu Ile Pro Thr Phe Asp
        115                 120                 125

Leu His Ser Asp Lys Glu Glu Gly Tyr Pro Met Trp Lys Pro Lys Phe
    130                 135                 140

Tyr His Asn Phe Asp Gly Glu Thr Glu Asp Ile Glu Lys Leu Val Leu
145                 150                 155                 160

Asp Val Ala Met Met Thr Ser Ala Ala Pro Thr Phe Phe Pro Thr Tyr
                165                 170                 175

Asn Gly His Ile Asp Gly Gly Val Val Ala Asn Asn Pro Ser Met Ala
            180                 185                 190

Ala Leu Ala Gln Ile Met Asp Glu Arg Tyr Gly Ile Asn Ala Ser Glu
        195                 200                 205

Val His Ile Leu Asn Ile Gly Thr Gly Phe Asn Pro Ala Tyr Val Lys
    210                 215                 220

Met Asn Pro Gly Glu Glu Lys Asp Trp Gly Glu Leu Gln Trp Ile Lys
225                 230                 235                 240

Pro Leu Ile Asn Leu Leu Val Asp Gly Ser Met Asp Val Ser Thr Tyr
                245                 250                 255

Tyr Cys Lys Gln Val Leu Arg Asp Asn Phe Tyr Arg Val Asn Met Lys
            260                 265                 270

Leu Pro Lys Asn Val Glu Met Asp Asp Pro Asn Ser Ile Pro Tyr Leu
        275                 280                 285

Ile Glu Leu Ala Asn Ser Val Asp Leu Thr Glu Cys Ile Asn Trp Leu
    290                 295                 300

Asn Ser Arg Trp
305
```

<210> SEQ ID NO 133
<211> LENGTH: 1053
<212> TYPE: DNA
<213> ORGANISM: Unknown
<220> FEATURE:
<223> OTHER INFORMATION: Obtained from an environmental sample

<400> SEQUENCE: 133

```
atgactacac agtttcgcaa tctcgttttc gaaggaggcg gcgtcagggg tatagcctat      60

gtgggggcaa tgcaggttct tgagcaacgg ggaatgctca ggaacataga ccgtgcaggc     120

ggcacgagcg ccggtgcgat taacgcactc atcttttcac tcggctatga cataaggtct     180
```

-continued

```
cagctcgaaa tactccattc taccgacttt agaaatttta tggatagttc cttcgggata    240

atcagggata tccgccgtct tgcacgggat ttcggatggt acaagggtga tttcttcaca    300

ggctggattg gcaagcttat aaaagacagg ctcggtagcg agaaagcaac tttccgtgac    360

cttgcagaat cagattgtcc cgatctgtat gtgatcggca ccaacctctc aaccggcttc    420

gccgaggtat tctcagccga gagacatccc gatatgcctc ttgcaacggc tgtccgtatc    480

agcatgtcga tccctctatt ttttgctgca atgcgttatg gtccgaggga agacgtattt    540

gtagacggtg ggtagtact caactatcct gtaaagctgt ttgacaggtt gaaatacatt    600

gaaagcgggg agacggagga agccgcacgc tataccgaat attataacag ggagaacgca    660

cggttccttc tcaaaagtcc cgaccgcagt ccctatgttt ataaccgtca gacactgggt    720

ttgcgtctcg atacgcgtga ggagattgca catttccgtt atgacgagcc cctggagggt    780

aaaaaaatca tacgctttac ggattatgca cgggcactcg tttcaacctt gcttcaggtt    840

caggaaaacc agcatctgca cagtgacgac tggcagcgta cagtttacat tgacacactg    900

gatgtgaaga cgactgattt tgatatcacg gataagcaga aggacatcct gataaagcag    960

ggaattaacg gagcggagaa ctatttgggt tggtttgaag acccgtatga aaaacccgcc   1020

aaccgcctgc ccggtggcag caagtctgac tga                                1053
```

<210> SEQ ID NO 134
<211> LENGTH: 350
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (8)...(195)
<223> OTHER INFORMATION: Patatin-like phospholipase

<400> SEQUENCE: 134

```
Met Thr Thr Gln Phe Arg Asn Leu Val Phe Glu Gly Gly Gly Val Arg
 1               5                  10                  15

Gly Ile Ala Tyr Val Gly Ala Met Gln Val Leu Glu Gln Arg Gly Met
            20                  25                  30

Leu Arg Asn Ile Asp Arg Ala Gly Gly Thr Ser Ala Gly Ala Ile Asn
        35                  40                  45

Ala Leu Ile Phe Ser Leu Gly Tyr Asp Ile Arg Ser Gln Leu Glu Ile
    50                  55                  60

Leu His Ser Thr Asp Phe Arg Asn Phe Met Asp Ser Ser Phe Gly Ile
65                  70                  75                  80

Ile Arg Asp Ile Arg Arg Leu Ala Arg Asp Phe Gly Trp Tyr Lys Gly
                85                  90                  95

Asp Phe Phe Thr Gly Trp Ile Gly Lys Leu Ile Lys Asp Arg Leu Gly
            100                 105                 110

Ser Glu Lys Ala Thr Phe Arg Asp Leu Ala Glu Ser Asp Cys Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Pro Leu Ala Thr Ala Val Arg Ile
145                 150                 155                 160

Ser Met Ser Ile Pro Leu Phe Phe Ala Ala Met Arg Tyr Gly Pro Arg
                165                 170                 175

Glu Asp Val Phe Val Asp Gly Gly Val Val Leu Asn Tyr Pro Val Lys
            180                 185                 190
```

Leu Phe Asp Arg Leu Lys Tyr Ile Glu Ser Gly Glu Thr Glu Glu Ala
195 200 205

Ala Arg Tyr Thr Glu Tyr Tyr Asn Arg Glu Asn Ala Arg Phe Leu Leu
210 215 220

Lys Ser Pro Asp Arg Ser Pro Tyr Val Tyr Asn Arg Gln Thr Leu Gly
225 230 235 240

Leu Arg Leu Asp Thr Arg Glu Glu Ile Ala His Phe Arg Tyr Asp Glu
245 250 255

Pro Leu Glu Gly Lys Lys Ile Ile Arg Phe Thr Asp Tyr Ala Arg Ala
260 265 270

Leu Val Ser Thr Leu Leu Gln Val Gln Glu Asn Gln His Leu His Ser
275 280 285

Asp Asp Trp Gln Arg Thr Val Tyr Ile Asp Thr Leu Asp Val Lys Thr
290 295 300

Thr Asp Phe Asp Ile Thr Asp Lys Gln Lys Asp Ile Leu Ile Lys Gln
305 310 315 320

Gly Ile Asn Gly Ala Glu Asn Tyr Leu Gly Trp Phe Glu Asp Pro Tyr
325 330 335

Glu Lys Pro Ala Asn Arg Leu Pro Gly Gly Ser Lys Ser Asp
340 345 350

<210> SEQ ID NO 135
<211> LENGTH: 1710
<212> TYPE: DNA
<213> ORGANISM: Unknown
<220> FEATURE:
<223> OTHER INFORMATION: Obtained from an environmental sample

<400> SEQUENCE: 135
atggctgaca acgagttacc cctggcccgc cccagggaaa cccctccgtg ccgtcccggc 60
acgttcgagc tggggctggc gctcgccggc gcggtatcgg gcggcgccta cgccgcgggc 120
gtgctggatt tcttctacga ggcgctggag cactggtacg acgcgaaggc gaacggtgcg 180
cccgtgccga gccacgacgt gctgctacgg atcatttcag gcgcctccgc gggcagcatc 240
aacggcgtgc tttccggcat cgcgttgccg taccgcttcc cgcacgtgca cagcggaccc 300
gcgccccggc aggcgacggg aaaccccttc tacgacgcgt gggtgaggcg catcgatgta 360
cgcgagctgc tgggcgaggc cgacctggct aacccggcgc ggccgatcac ctcgctgctt 420
gattccagca gcctggatac gatcgcgaag gacatgctcg gctacgccgg cgtgccggcc 480
gcgcgccctt acatcgcgaa cccgctgaaa tgcgtgttca ccgtgacgaa tcttcgcggc 540
gtgccctacg tggtgcagtt caagggcaac cccgagattc ccggccacgg catgatggcg 600
cacgccgatt ggctgcgctt cgccatcgac tcggggcagg gcgaacgcga tggcgcatgg 660
atgttccccg acgagcgcat cgtcagcggc ccgagccatg cgcgcagccc ggcctggcat 720
gcgctcatgg aggcggccct ggcgtcgtcc gcgttcccgg ccggcctgcg cttccgcgag 780
gtggcccggc cgtggagcga ttacgaccag cgcgtggttg tcgtgcccgg tcaggatggc 840
atggcggtgc cggtaccgct gccaccagcg tggggcgaag gggagggtgg gaagggcgac 900
taccgctttg tcgccgtgga tggtggcgcc atggataacg aaccgttcga gctggcccgc 960
acggagcttg cgggcacgat gggccgcaac ccgcgtgaag gtacccgggt gaatcgtatc 1020
gtgattatgc tcgatccgtt tccggaggcc gaggcgcccg gcccctcgga ggcggcgtcg 1080
acgaacctgg tggaagcgat ggcgtcgctg ttcggtgcat ggaagcagca ggcgcggttc 1140
aagcccgagg aagtggcgct ggccctcgat agcacggtgt acagccgctt catgatcgcg 1200

```
cctagccgcc cctgcacgga tggcggcccg cggtggatcg gcggccgcgc gctcaccgcg   1260

ggcgcactgg gtggcttctc ggggttcctg gccgaggatt accgccacca cgatttcctc   1320

ctgggccggc gtaactgcca gcggtttctc gccgagcggc tgctcgttcc cgcaacgaac   1380

ccgatcttcg ctggatggat cgacgatccc gcactgcagg gctacgtgcg tgagatcgat   1440

ggtgagcgct ttgcccccgt gattccccta gtgggcggct gccaggccct gcaagagccc   1500

ttgccggcgt ggccgcgtgg ggcgttcgac atggatgcgc tcatgcccct ggtcgagaag   1560

cgcatgcagg ccctgtacac ggcggccacc acgaagctgg gtggccgctt cgccatgtgg   1620

ctcgcgtggc gcttcttcat ccgccgcaaa ctcctcgaca tcgtctcaag ccgtatccgc   1680

aatgcgctga aagacttcgg cctttggtga                                    1710
```

<210> SEQ ID NO 136
<211> LENGTH: 569
<212> TYPE: PRT
<213> ORGANISM: Unknown
<220> FEATURE:
<223> OTHER INFORMATION: Obtained from an environmental sample

<400> SEQUENCE: 136

```
Met Ala Asp Asn Glu Leu Pro Leu Ala Arg Pro Arg Glu Thr Pro Pro
 1               5                  10                  15

Cys Arg Pro Gly Thr Phe Glu Leu Gly Leu Ala Leu Ala Gly Ala Val
            20                  25                  30

Ser Gly Gly Ala Tyr Ala Ala Gly Val Leu Asp Phe Phe Tyr Glu Ala
        35                  40                  45

Leu Glu His Trp Tyr Asp Ala Lys Ala Asn Gly Ala Pro Val Pro Ser
    50                  55                  60

His Asp Val Leu Leu Arg Ile Ile Ser Gly Ala Ser Ala Gly Ser Ile
65                  70                  75                  80

Asn Gly Val Leu Ser Gly Ile Ala Leu Pro Tyr Arg Phe Pro His Val
                85                  90                  95

His Ser Gly Pro Ala Pro Arg Gln Ala Thr Gly Asn Pro Phe Tyr Asp
            100                 105                 110

Ala Trp Val Arg Arg Ile Asp Val Arg Glu Leu Leu Gly Glu Ala Asp
        115                 120                 125

Leu Ala Asn Pro Ala Arg Pro Ile Thr Ser Leu Leu Asp Ser Ser Ser
    130                 135                 140

Leu Asp Thr Ile Ala Lys Asp Met Leu Gly Tyr Ala Gly Val Pro Ala
145                 150                 155                 160

Ala Arg Pro Tyr Ile Ala Asn Pro Leu Lys Cys Val Phe Thr Val Thr
                165                 170                 175

Asn Leu Arg Gly Val Pro Tyr Val Val Gln Phe Lys Gly Asn Pro Glu
            180                 185                 190

Ile Pro Gly His Gly Met Met Ala His Ala Asp Trp Leu Arg Phe Ala
        195                 200                 205

Ile Asp Ser Gly Gln Gly Glu Arg Asp Gly Ala Trp Met Phe Pro Asp
    210                 215                 220

Glu Arg Ile Val Ser Gly Pro Ser His Ala Arg Ser Pro Ala Trp His
225                 230                 235                 240

Ala Leu Met Glu Ala Ala Leu Ala Ser Ser Ala Phe Pro Ala Gly Leu
                245                 250                 255

Arg Phe Arg Glu Val Ala Arg Pro Trp Ser Asp Tyr Asp Gln Arg Val
            260                 265                 270

Val Val Val Pro Gly Gln Asp Gly Met Ala Val Pro Val Pro Leu Pro
```

```
        275                 280                 285

Pro Ala Trp Gly Glu Gly Glu Gly Gly Lys Gly Asp Tyr Arg Phe Val
    290                 295                 300

Ala Val Asp Gly Gly Ala Met Asp Asn Glu Pro Phe Glu Leu Ala Arg
305                 310                 315                 320

Thr Glu Leu Ala Gly Thr Met Gly Arg Asn Pro Arg Glu Gly Thr Arg
                325                 330                 335

Val Asn Arg Ile Val Ile Met Leu Asp Pro Phe Pro Glu Ala Glu Ala
            340                 345                 350

Pro Gly Pro Ser Glu Ala Ala Ser Thr Asn Leu Val Glu Ala Met Ala
        355                 360                 365

Ser Leu Phe Gly Ala Trp Lys Gln Gln Ala Arg Phe Lys Pro Glu Glu
    370                 375                 380

Val Ala Leu Ala Leu Asp Ser Thr Val Tyr Ser Arg Phe Met Ile Ala
385                 390                 395                 400

Pro Ser Arg Pro Cys Thr Asp Gly Gly Pro Arg Trp Ile Gly Gly Arg
                405                 410                 415

Ala Leu Thr Ala Gly Ala Leu Gly Gly Phe Ser Gly Phe Leu Ala Glu
            420                 425                 430

Asp Tyr Arg His His Asp Phe Leu Leu Gly Arg Arg Asn Cys Gln Arg
        435                 440                 445

Phe Leu Ala Glu Arg Leu Leu Val Pro Ala Thr Asn Pro Ile Phe Ala
    450                 455                 460

Gly Trp Ile Asp Asp Pro Ala Leu Gln Gly Tyr Val Arg Glu Ile Asp
465                 470                 475                 480

Gly Glu Arg Phe Ala Pro Val Ile Pro Leu Val Gly Gly Cys Gln Ala
                485                 490                 495

Leu Gln Glu Pro Leu Pro Ala Trp Pro Arg Gly Ala Phe Asp Met Asp
            500                 505                 510

Ala Leu Met Pro Leu Val Glu Lys Arg Met Gln Ala Leu Tyr Thr Ala
        515                 520                 525

Ala Thr Thr Lys Leu Gly Gly Arg Phe Ala Met Trp Leu Ala Trp Arg
    530                 535                 540

Phe Phe Ile Arg Arg Lys Leu Leu Asp Ile Val Ser Ser Arg Ile Arg
545                 550                 555                 560

Asn Ala Leu Lys Asp Phe Gly Leu Trp
                565
```

<210> SEQ ID NO 137
<211> LENGTH: 1038
<212> TYPE: DNA
<213> ORGANISM: Unknown
<220> FEATURE:
<223> OTHER INFORMATION: Obtained from an environmental sample

<400> SEQUENCE: 137

```
atgacaacac aatttagaaa cttgatattt gaaggcggcg gtgtaaaagg tgttgcttac      60

attggcgcca tgcagattct tgaaaatcgt ggcgtgttgc aagatattcg ccgagtcgga     120

gggtgcagtg cgggtgcgat taacgcgctg atttttgcgc taggttacac ggtccgtgaa     180

caaaaagaga tcttacaagc caccgatttt aaccagttta tggataactc ttggggggtt     240

attcgtgata ttcgcaggct tgctcgagac tttggctgga ataagggtga tttctttagt     300

agctggatag gtgatttgat tcatcgtcgt ttggggaatc gccgagcgac gttcaaagat     360

ctgcaaaagg ccaagcttcc tgatctttat gtcatcggta ctaatctgtc tacagggttt     420
```

```
gcagaggtgt tttctgccga aagacacccc gatatggagc tggcgacagc ggtgcgtatc    480

tccatgtcga taccgctgtt ctttgcggcc gtgcgtcacg gtgatcgaca agatgtgtat    540

gtcgatgggg gtgttcaact taactatccg attaaactgt ttgatcggga gcgttacatt    600

gatttggcca aagatcccgg tgccgttcgg cgaacgggtt attacaacaa agaaaacgct    660

cgctttcagc ttgatcggcc gggccatagc ccctatgttt acaatcgcca gaccttgggt    720

ttgcgactgg atagtcgcga ggagataggg ctctttcgtt atgacgaacc cctcaagggc    780

aaacccatta agtccttcac tgactacgct cgacaacttt tcggtgcgtt gatgaatgca    840

caggaaaaga ttcatctaca tggcgatgat tggcaacgca cgatctatat cgatacattg    900

gatgtgggta cgacggactt caatctttct gatgcaacta agcaagcact gattgagcaa    960

ggaattaacg gcaccgaaaa ttatttcgag tggtttgata atccgttaga gaagcctgtg   1020

aatagagtgg agtcatag                                                 1038
```

```
<210> SEQ ID NO 138
<211> LENGTH: 345
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (8)...(195)
<223> OTHER INFORMATION: Patatin-like phospholipase

<400> SEQUENCE: 138

Met Thr Thr Gln Phe Arg Asn Leu Ile Phe Glu Gly Gly Gly Val Lys
 1               5                  10                  15

Gly Val Ala Tyr Ile Gly Ala Met Gln Ile Leu Glu Asn Arg Gly Val
            20                  25                  30

Leu Gln Asp Ile Arg Arg Val Gly Gly Cys Ser Ala Gly Ala Ile Asn
        35                  40                  45

Ala Leu Ile Phe Ala Leu Gly Tyr Thr Val Arg Glu Gln Lys Glu Ile
    50                  55                  60

Leu Gln Ala Thr Asp Phe Asn Gln Phe Met Asp Asn Ser Trp Gly Val
65                  70                  75                  80

Ile Arg Asp Ile Arg Arg Leu Ala Arg Asp Phe Gly Trp Asn Lys Gly
                85                  90                  95

Asp Phe Phe Ser Ser Trp Ile Gly Asp Leu Ile His Arg Arg Leu Gly
            100                 105                 110

Asn Arg Arg Ala Thr Phe Lys Asp Leu Gln Lys Ala Lys Leu Pro Asp
        115                 120                 125

Leu Tyr Val Ile Gly Thr Asn Leu Ser Thr Gly Phe Ala Glu Val Phe
    130                 135                 140

Ser Ala Glu Arg His Pro Asp Met Glu Leu Ala Thr Ala Val Arg Ile
145                 150                 155                 160

Ser Met Ser Ile Pro Leu Phe Phe Ala Ala Val Arg His Gly Asp Arg
                165                 170                 175

Gln Asp Val Tyr Val Asp Gly Gly Val Gln Leu Asn Tyr Pro Ile Lys
            180                 185                 190

Leu Phe Asp Arg Glu Arg Tyr Ile Asp Leu Ala Lys Asp Pro Gly Ala
        195                 200                 205

Val Arg Arg Thr Gly Tyr Tyr Asn Lys Glu Asn Ala Arg Phe Gln Leu
    210                 215                 220

Asp Arg Pro Gly His Ser Pro Tyr Val Tyr Asn Arg Gln Thr Leu Gly
225                 230                 235                 240
```

Leu Arg Leu Asp Ser Arg Glu Glu Ile Gly Leu Phe Arg Tyr Asp Glu
245 250 255

Pro Leu Lys Gly Lys Pro Ile Lys Ser Phe Thr Asp Tyr Ala Arg Gln
260 265 270

Leu Phe Gly Ala Leu Met Asn Ala Gln Glu Lys Ile His Leu His Gly
275 280 285

Asp Asp Trp Gln Arg Thr Ile Tyr Ile Asp Thr Leu Asp Val Gly Thr
290 295 300

Thr Asp Phe Asn Leu Ser Asp Ala Thr Lys Gln Ala Leu Ile Glu Gln
305 310 315 320

Gly Ile Asn Gly Thr Glu Asn Tyr Phe Glu Trp Phe Asp Asn Pro Leu
325 330 335

Glu Lys Pro Val Asn Arg Val Glu Ser
340 345

<210> SEQ ID NO 139
<211> LENGTH: 1692
<212> TYPE: DNA
<213> ORGANISM: Unknown
<220> FEATURE:
<223> OTHER INFORMATION: Obtained from an environmental sample

<400> SEQUENCE: 139
atgaaaataa agccgctcac gttttctttt ggattagcag tcactagctc ggtgcaagcc 60
ttcactcaat ttggcggaca aggcgttatg ccgatgggtc acgaatggtt aacgcgcacc 120
gctgctctcg aggtacttaa tgcagagcat atcatcgaag cggatccgaa tgacccaaga 180
tatacttggc aggacggact tgctaaaaac cttgaactta ataccgccca atctgaaatc 240
acgcgcttac aatctcattt aaataataac ccgctctatg agccgagata cgacggtata 300
aactcagcca tcgttggtga acgctgggtc gatattgcag ggtttaacgt cacaacagcc 360
agcgcagacc cgactggccc taattgcttt agcgcagttt cacaagagcc cgcagatatt 420
cagcaagacc actttatgcg ccgctatgat gatattggag gtcaaggtgg agttgatgct 480
gcttatcgcg cacagcaacg atttgtgcaa cactttgtgg atgcggccat ggccgaaaaa 540
aaacgactaa aagtatggga cggtggtggc cattctgcgt tagcagaggt agatcataat 600
tactttttat ttggtcgtgc ggttcaccta tttcaagact catttagtcc agaacacacg 660
gtacggctcc ctcaagataa ctacgaaaaa gtttggcagg ttaaggcata tctttgctca 720
gagggggctg agcaacattc acacgatacc aaagacgtgc tcaactttgc cagtggcgat 780
gttatttggc aacctcaaac ccgactagaa gcaggctggc aatcttacca gatcagcagt 840
atgaagcccg ttgctattgt ggcccttgaa gccagtaaag atctttgggc tgcgtttatt 900
cgcaccatgg cgaccccaaa agcacagaga cgtaacgtgg caacgcaaga agcccaacaa 960
cttgtacaaa actggttgtc ttttgatgag gcccagatgc tgacttggta tcaagatgag 1020
aataagcgtg accatactta tgtgcttgcc cccaatgaaa cgggaaaagg aaaatctctg 1080
gaagcctgta tgacagagct aaaggtaggc actagcagtc aagcagaacg ggttgcgcaa 1140
ctggaagccg agcgtaatca atgcctatac aacattgagg cggaacctgg ctttgcagac 1200
ttaaacgatc cacacctcga tattccatat aactggcgct ggaagtctct gacttggcaa 1260
acgcctccta gtggctggac atacccacaa ctaaatgcag ataccggcga gcaagtcgcc 1320
attaaatcgc cgataaataa tcagtattta tctgcacaaa ctctaagtaa cgacaccccg 1380
atcactctga gtcaagcaca tccaatttcc ttgatccaag tgacgaatgc acagggccag 1440

```
cactatttta ggagcgctca agccccttca ctatttctgg gttatagcaa caaaattgca   1500

ggctacctca agcttgtaga ttcacccaag caagccctat atacgttgat ttatcaaggt   1560

ggtctttgga atatccaaaa tgaattttgg caacagtata tctggttaaa tcaagacaaa   1620

gagcggccgg aattaaatcg ccatggtgag cctagccaat taaacgctca gtggatggtc   1680

gaacacttat aa                                                       1692
```

<210> SEQ ID NO 140
<211> LENGTH: 563
<212> TYPE: PRT
<213> ORGANISM: Unknown
<220> FEATURE:
<221> NAME/KEY: SIGNAL
<222> LOCATION: (1)...(20)
<223> OTHER INFORMATION: Obtained from an environmental sample

<400> SEQUENCE: 140

```
Met Lys Ile Lys Pro Leu Thr Phe Ser Phe Gly Leu Ala Val Thr Ser
 1               5                  10                  15

Ser Val Gln Ala Phe Thr Gln Phe Gly Gly Gln Gly Val Met Pro Met
            20                  25                  30

Gly His Glu Trp Leu Thr Arg Thr Ala Ala Leu Glu Val Leu Asn Ala
        35                  40                  45

Glu His Ile Ile Glu Ala Asp Pro Asn Asp Pro Arg Tyr Thr Trp Gln
    50                  55                  60

Asp Gly Leu Ala Lys Asn Leu Glu Leu Asn Thr Ala Gln Ser Glu Ile
65                  70                  75                  80

Thr Arg Leu Gln Ser His Leu Asn Asn Asn Pro Leu Tyr Glu Pro Arg
                85                  90                  95

Tyr Asp Gly Ile Asn Ser Ala Ile Val Gly Glu Arg Trp Val Asp Ile
            100                 105                 110

Ala Gly Phe Asn Val Thr Thr Ala Ser Ala Asp Pro Thr Gly Pro Asn
        115                 120                 125

Cys Phe Ser Ala Val Ser Gln Glu Pro Ala Asp Ile Gln Gln Asp His
    130                 135                 140

Phe Met Arg Arg Tyr Asp Asp Ile Gly Gly Gln Gly Gly Val Asp Ala
145                 150                 155                 160

Ala Tyr Arg Ala Gln Gln Arg Phe Val Gln His Phe Val Asp Ala Ala
                165                 170                 175

Met Ala Glu Lys Lys Arg Leu Lys Val Trp Asp Gly Gly Gly His Ser
            180                 185                 190

Ala Leu Ala Glu Val Asp His Asn Tyr Phe Leu Phe Gly Arg Ala Val
        195                 200                 205

His Leu Phe Gln Asp Ser Phe Ser Pro Glu His Thr Val Arg Leu Pro
    210                 215                 220

Gln Asp Asn Tyr Glu Lys Val Trp Gln Val Lys Ala Tyr Leu Cys Ser
225                 230                 235                 240

Glu Gly Ala Glu Gln His Ser His Asp Thr Lys Asp Val Leu Asn Phe
                245                 250                 255

Ala Ser Gly Asp Val Ile Trp Gln Pro Gln Thr Arg Leu Glu Ala Gly
            260                 265                 270

Trp Gln Ser Tyr Gln Ile Ser Ser Met Lys Pro Val Ala Ile Val Ala
        275                 280                 285

Leu Glu Ala Ser Lys Asp Leu Trp Ala Ala Phe Ile Arg Thr Met Ala
    290                 295                 300

Thr Pro Lys Ala Gln Arg Arg Asn Val Ala Thr Gln Glu Ala Gln Gln
```

305 310 315 320

Leu Val Gln Asn Trp Leu Ser Phe Asp Glu Ala Gln Met Leu Thr Trp
325 330 335

Tyr Gln Asp Glu Asn Lys Arg Asp His Thr Tyr Val Leu Ala Pro Asn
340 345 350

Glu Thr Gly Lys Gly Lys Ser Leu Glu Ala Cys Met Thr Glu Leu Lys
355 360 365

Val Gly Thr Ser Ser Gln Ala Glu Arg Val Ala Gln Leu Glu Ala Glu
370 375 380

Arg Asn Gln Cys Leu Tyr Asn Ile Glu Ala Glu Pro Gly Phe Ala Asp
385 390 395 400

Leu Asn Asp Pro His Leu Asp Ile Pro Tyr Asn Trp Arg Trp Lys Ser
405 410 415

Leu Thr Trp Gln Thr Pro Pro Ser Gly Trp Thr Tyr Pro Gln Leu Asn
420 425 430

Ala Asp Thr Gly Glu Gln Val Ala Ile Lys Ser Pro Ile Asn Asn Gln
435 440 445

Tyr Leu Ser Ala Gln Thr Leu Ser Asn Asp Thr Pro Ile Thr Leu Ser
450 455 460

Gln Ala His Pro Ile Ser Leu Ile Gln Val Thr Asn Ala Gln Gly Gln
465 470 475 480

His Tyr Phe Arg Ser Ala Gln Ala Pro Ser Leu Phe Leu Gly Tyr Ser
485 490 495

Asn Lys Ile Ala Gly Tyr Leu Lys Leu Val Asp Ser Pro Lys Gln Ala
500 505 510

Leu Tyr Thr Leu Ile Tyr Gln Gly Gly Leu Trp Asn Ile Gln Asn Glu
515 520 525

Phe Trp Gln Gln Tyr Ile Trp Leu Asn Gln Asp Lys Glu Arg Pro Glu
530 535 540

Leu Asn Arg His Gly Glu Pro Ser Gln Leu Asn Ala Gln Trp Met Val
545 550 555 560

Glu His Leu

<210> SEQ ID NO 141
<211> LENGTH: 471
<212> TYPE: DNA
<213> ORGANISM: Unknown
<220> FEATURE:
<223> OTHER INFORMATION: Obtained from environmental sample

<400> SEQUENCE: 141
atgcaaaaaa aaaccagtac atgtgaagac gagggcccgt accgggcagt cttgtttgat 60
ttggacggca ccctgttgga tacggagcgg attggggcgg cctcctggga ccatgcggga 120
gacgaattgg gtctgcgggt gccggaggcg gtaaagcggc agatggtggg tcggacgctg 180
ccggatattc atgcaattgt acgggaaggc atgccggacg tggacgcgga tcgtctgctg 240
gagcgggcca atcatcatta tcaccgtttg gtgaccgaag tgccaccgcc ggtgaaggcc 300
ggggcgcggg aactgctgga atggctgaag ggtgctgggg tgcccatggc ggtggcgact 360
tccagccgcc gggttcaggc cgaagacaaa ttaagccgta ccggcctgcg gcattttttt 420
gatgtgattg tggccggcga tgaaatcgcg cggggcaagc cggatccaaa g 471

<210> SEQ ID NO 142
<211> LENGTH: 157
<212> TYPE: PRT
<213> ORGANISM: Unknown

<220> FEATURE:
<223> OTHER INFORMATION: Obtained from environmental sample
<220> FEATURE:
<221> NAME/KEY: DOMAIN
<222> LOCATION: (14)...(157)
<223> OTHER INFORMATION: haloacid dehalogenase-like hydrolase

<400> SEQUENCE: 142

```
Met Gln Lys Lys Thr Ser Thr Cys Glu Asp Glu Gly Pro Tyr Arg Ala
 1               5                  10                  15

Val Leu Phe Asp Leu Asp Gly Thr Leu Leu Asp Thr Glu Arg Ile Gly
            20                  25                  30

Ala Ala Ser Trp Asp His Ala Gly Asp Glu Leu Gly Leu Arg Val Pro
        35                  40                  45

Glu Ala Val Lys Arg Gln Met Val Gly Arg Thr Leu Pro Asp Ile His
    50                  55                  60

Ala Ile Val Arg Glu Gly Met Pro Asp Val Asp Ala Asp Arg Leu Leu
65                  70                  75                  80

Glu Arg Ala Asn His His Tyr His Arg Leu Val Thr Glu Val Pro Pro
                85                  90                  95

Pro Val Lys Ala Gly Ala Arg Glu Leu Leu Glu Trp Leu Lys Gly Ala
            100                 105                 110

Gly Val Pro Met Ala Val Ala Thr Ser Ser Arg Arg Val Gln Ala Glu
        115                 120                 125

Asp Lys Leu Ser Arg Thr Gly Leu Arg His Phe Phe Asp Val Ile Val
    130                 135                 140

Ala Gly Asp Glu Ile Ala Arg Gly Lys Pro Asp Pro Lys
145                 150                 155
```

<210> SEQ ID NO 143
<211> LENGTH: 603
<212> TYPE: DNA
<213> ORGANISM: Unknown
<220> FEATURE:
<223> OTHER INFORMATION: Obtained from environmental sample

<400> SEQUENCE: 143

```
atgaataaca agagcttcat cacaatccat ggcattcgta agtttggctc ttctcccact     60

cacatgcgcc ctataaacga atcactcctc tctagtaatc tgaggacaat cccagtcaat    120

tatggctaca ccctgctccc aatcacgaac agaaagagtg tttctagggc aattcctgtg    180

ctagaaaacg agctaaagcg agggagggac atcaccctta tcgggtattc taacggcgct    240

tggacagctc tacagcttgc ggaaatggct tatccaatcc aacgtctagt gctcatctct    300

cctgctcttc actctgctca cgccttccct caaatccctt ctcttgagcg tgtagacgtg    360

ttctattgcc ctacagataa tgttggtgat cttgccaaga cttggagggg agttactaga    420

atcatgcctt ggagatggtt ctctccacac ccttacggaa gaatgatgaa aactggattt    480

attggagagg atgaacgtgt ctttaaccac aggcttggcg atcatgtagg ccatgctttc    540

tacaaccatg ctgatgctgt ttcacacatt atagaggtga ttaaatatga aactccttat    600

tag                                                                  603
```

<210> SEQ ID NO 144
<211> LENGTH: 200
<212> TYPE: PRT
<213> ORGANISM: Unknown
<220> FEATURE:
<223> OTHER INFORMATION: Obtained from environmental sample

<400> SEQUENCE: 144

```
Met Asn Asn Lys Ser Phe Ile Thr Ile His Gly Ile Arg Lys Phe Gly
 1               5                  10                  15

Ser Ser Pro Thr His Met Arg Pro Ile Asn Glu Ser Leu Leu Ser Ser
            20                  25                  30

Asn Leu Arg Thr Ile Pro Val Asn Tyr Gly Tyr Thr Leu Leu Pro Ile
        35                  40                  45

Thr Asn Arg Lys Ser Val Ser Arg Ala Ile Pro Val Leu Glu Asn Glu
    50                  55                  60

Leu Lys Arg Gly Arg Asp Ile Thr Leu Ile Gly Tyr Ser Asn Gly Ala
65                  70                  75                  80

Trp Thr Ala Leu Gln Leu Ala Glu Met Ala Tyr Pro Ile Gln Arg Leu
                85                  90                  95

Val Leu Ile Ser Pro Ala Leu His Ser Ala His Ala Phe Pro Gln Ile
            100                 105                 110

Pro Ser Leu Glu Arg Val Asp Val Phe Tyr Cys Pro Thr Asp Asn Val
        115                 120                 125

Gly Asp Leu Ala Lys Thr Trp Arg Gly Val Thr Arg Ile Met Pro Trp
    130                 135                 140

Arg Trp Phe Ser Pro His Pro Tyr Gly Arg Met Met Lys Thr Gly Phe
145                 150                 155                 160

Ile Gly Glu Asp Glu Arg Val Phe Asn His Arg Leu Gly Asp His Val
                165                 170                 175

Gly His Ala Phe Tyr Asn His Ala Asp Ala Val Ser His Ile Ile Glu
            180                 185                 190

Val Ile Lys Tyr Glu Thr Pro Tyr
        195                 200
```

```
<210> SEQ ID NO 145
<211> LENGTH: 1197
<212> TYPE: DNA
<213> ORGANISM: Unknown
<220> FEATURE:
<223> OTHER INFORMATION: Obtained from environmental sample

<400> SEQUENCE: 145

atgaacgcaa cctccgcaac gatcgccgcc accgacaccc agcagcgcgg tggcttcgcc      60

ggcaccgatc cgcaaccggt cgatcgggtg ctggccgcac tgatccagga caactacgac     120

cgcgtcgacc agcgtcgcgg cgacccgccg atcgaccgcc cgctgccgca gggctgggcg     180

cgcatgggcg acgacgaagt gcgcgccgcg ggcatcgatc ctgcgatgca gcacgatgcc     240

aagagcggct tcgacgcctc gttctaccgc gacgaccagg gccgggtggc cctggtctat     300

gccggcagcg acgagggcca ggactggaag cacaacttcg gccagggcct gggtttccag     360

gacgcgcagt acgaccaggc gatcgcgctg gcgcgcgagg cgaaatcggc cttcggcgac     420

cagctcgtgc tgtcgggcca gtcgctcggc ggcggcctgg ccgcggcagc gtccatggtc     480

aacgaggtgc ccgcggtgac cttcaacgcc gccggcgtgc acgaccacac ggtcgagcgc     540

tacggcctgg acgcggacgc ggtcaagcgc caggcggacc agggcctggt ccggcactac     600

gtggtcgaga acgacatcct gacccacctg caggagaacg cgttcccgct caatgcggcg     660

atgccggatg cgcccggcgc gcgcatcgac ctgcccgatc cggatccgct gaccacgttc     720

gagaagctgc tgccctggaa gacctggccg caccgcgtgc ataaccacta catcgaggcg     780

gtgatcgagt ccatggacaa ggccggctac acgctcgaag gcgcggcggc gacgcgggat     840

gcgtcgcagg acaccgccaa ccggctgctc gacgattcgg tgcgcgggct cgcgccgcag     900
```

```
cgcgaacgcc tcgggctgca ggacgacgac cgcttcttca acgcggccgc cggcatggcc    960

gcctcggccg gacgcgatgg cctgcgcagc atccagcacg tggtcgccac gcccgacggc   1020

cacggcgtgt tcgcggtcga aggcgacctg cgcgacgccg gccaccgccg cagcctggtc   1080

gacgtggaac gcggcgccgc gacgccggtc gaggacagcg tggccagcct gcgcgagcac   1140

gcctcgcgtt ccccggagca ggagccgcag cgggagcgcc acctggcgat ggcctga      1197
```

```
<210> SEQ ID NO 146
<211> LENGTH: 398
<212> TYPE: PRT
<213> ORGANISM: Unknown
<220> FEATURE:
<223> OTHER INFORMATION: Obtained from environmental sample

<400> SEQUENCE: 146

Met Asn Ala Thr Ser Ala Thr Ile Ala Ala Thr Asp Thr Gln Gln Arg
1               5                   10                  15

Gly Gly Phe Ala Gly Thr Asp Pro Gln Pro Val Asp Arg Val Leu Ala
            20                  25                  30

Ala Leu Ile Gln Asp Asn Tyr Asp Arg Val Asp Gln Arg Arg Gly Asp
        35                  40                  45

Pro Pro Ile Asp Arg Pro Leu Pro Gln Gly Trp Ala Arg Met Gly Asp
    50                  55                  60

Asp Glu Val Arg Ala Ala Gly Ile Asp Pro Ala Met Gln His Asp Ala
65                  70                  75                  80

Lys Ser Gly Phe Asp Ala Ser Phe Tyr Arg Asp Asp Gln Gly Arg Val
                85                  90                  95

Ala Leu Val Tyr Ala Gly Ser Asp Glu Gly Gln Asp Trp Lys His Asn
            100                 105                 110

Phe Gly Gln Gly Leu Gly Phe Gln Asp Ala Gln Tyr Asp Gln Ala Ile
        115                 120                 125

Ala Leu Ala Arg Glu Ala Lys Ser Ala Phe Gly Asp Gln Leu Val Leu
    130                 135                 140

Ser Gly Gln Ser Leu Gly Gly Gly Leu Ala Ala Ala Ala Ser Met Val
145                 150                 155                 160

Asn Glu Val Pro Ala Val Thr Phe Asn Ala Ala Gly Val His Asp His
                165                 170                 175

Thr Val Glu Arg Tyr Gly Leu Asp Ala Asp Ala Val Lys Arg Gln Ala
            180                 185                 190

Asp Gln Gly Leu Val Arg His Tyr Val Val Glu Asn Asp Ile Leu Thr
        195                 200                 205

His Leu Gln Glu Asn Ala Phe Pro Leu Asn Ala Ala Met Pro Asp Ala
    210                 215                 220

Pro Gly Ala Arg Ile Asp Leu Pro Asp Pro Asp Pro Leu Thr Thr Phe
225                 230                 235                 240

Glu Lys Leu Leu Pro Trp Lys Thr Trp Pro His Arg Val His Asn His
                245                 250                 255

Tyr Ile Glu Ala Val Ile Glu Ser Met Asp Lys Ala Gly Tyr Thr Leu
            260                 265                 270

Glu Gly Ala Ala Ala Thr Arg Asp Ala Ser Gln Asp Thr Ala Asn Arg
        275                 280                 285

Leu Leu Asp Asp Ser Val Arg Gly Leu Ala Pro Gln Arg Glu Arg Leu
    290                 295                 300

Gly Leu Gln Asp Asp Asp Arg Phe Phe Asn Ala Ala Ala Gly Met Ala
305                 310                 315                 320
```

```
Ala Ser Ala Gly Arg Asp Gly Leu Arg Ser Ile Gln His Val Val Ala
                325                 330                 335

Thr Pro Asp Gly His Gly Val Phe Ala Val Glu Gly Asp Leu Arg Asp
            340                 345                 350

Ala Gly His Arg Arg Ser Leu Val Asp Val Glu Arg Gly Ala Ala Thr
        355                 360                 365

Pro Val Glu Asp Ser Val Ala Ser Leu Arg Glu His Ala Ser Arg Ser
    370                 375                 380

Pro Glu Gln Glu Pro Gln Arg Glu Arg His Leu Ala Met Ala
385                 390                 395


<210> SEQ ID NO 147
<211> LENGTH: 1104
<212> TYPE: DNA
<213> ORGANISM: Unknown
<220> FEATURE:
<223> OTHER INFORMATION: Obtained from environmental sample

<400> SEQUENCE: 147

atgcaagtca gtggtgcaat ggaagcaata aatcctgcgc agatgaatgc agcggaagtc      60

acttcatcgc aggtatctga ccagatcatc ggcggcgtta gccaggtgcc ggaagcaggt     120

ttagctagtg aagtcggagc aatggcgatg gcacctgctg ctgaagatgc ggcccttgcc     180

gccatggttg ccggccctgc caatcaagcc agttacggca atttgcccag tgactggacg     240

gaagccgact ataatcatgc tctcgacatg gccaagctgt cttcccaagc ttatagccgg     300

ttcaacgata tcaccgtcga tcttctgttg gctccatttg gtggtattgg tgacataaaa     360

gcgcaggatt ttaccaccga taactggcgc ctaatggaca ccagtggcaa gagtgacttt     420

ttcttacccg tacagagcgg gctggacttc actgtttttg aggcggtagc cgatgacccg     480

gcagctaatg tgaaggaagg ggatattgtg ctcgcatttc gcggcagtga gcctacctcc     540

gcaccggatt ggatcaataa tgtaaaacag gcggcgggta attcctctca gtatgctcag     600

gcggtagaag tcgcgaagga gctgcaaggg caggtagacc agtacaatgc agacaataac     660

ctgaccggca atgatgccag aagcctccat tttaccggcc atagcctggg cgggggattg     720

gcaacagcgg ccgcgctggc cacaggcagt agcgctaccg ccttcaatgc agcgggcctt     780

ggggattcca ccctaaagaa ccttgggctc aatgaagggc tggcggcagg cttccacaat     840

aacgttacca atattaatgt ggaaggcgat ctgttgagcg atgccaaccg ccaaaaggat     900

gtctatacca cgggttcagg catcctcgat gaaaccaggc agtatgggga acaggtttgg     960

ctgcagggcg tcgatgataa ggccagattg ggcggaccgc ttaatcccct gataccggga    1020

gtggctgatg acctggcaat ccaggcactc aaccatgcct ggcatgtgta tacctaccag    1080

ttggaaaatc gcaacttcgc ctaa                                           1104


<210> SEQ ID NO 148
<211> LENGTH: 367
<212> TYPE: PRT
<213> ORGANISM: Unknown
<220> FEATURE:
<223> OTHER INFORMATION: Obtained from environmental sample

<400> SEQUENCE: 148

Met Gln Val Ser Gly Ala Met Glu Ala Ile Asn Pro Ala Gln Met Asn
1               5                   10                  15

Ala Ala Glu Val Thr Ser Ser Gln Val Ser Asp Gln Ile Ile Gly Gly
            20                  25                  30

Val Ser Gln Val Pro Glu Ala Gly Leu Ala Ser Glu Val Gly Ala Met
```

-continued

```
        35                  40                  45

Ala Met Ala Pro Ala Ala Glu Asp Ala Ala Leu Ala Ala Met Val Ala
    50                  55                  60

Gly Pro Ala Asn Gln Ala Ser Tyr Gly Asn Leu Pro Ser Asp Trp Thr
65                  70                  75                  80

Glu Ala Asp Tyr Asn His Ala Leu Asp Met Ala Lys Leu Ser Ser Gln
                85                  90                  95

Ala Tyr Ser Arg Phe Asn Asp Ile Thr Val Asp Leu Leu Leu Ala Pro
            100                 105                 110

Phe Gly Gly Ile Gly Asp Ile Lys Ala Gln Asp Phe Thr Thr Asp Asn
        115                 120                 125

Trp Arg Leu Met Asp Thr Ser Gly Lys Ser Asp Phe Phe Leu Pro Val
    130                 135                 140

Gln Ser Gly Leu Asp Phe Thr Val Phe Glu Ala Val Ala Asp Asp Pro
145                 150                 155                 160

Ala Ala Asn Val Lys Glu Gly Asp Ile Val Leu Ala Phe Arg Gly Ser
                165                 170                 175

Glu Pro Thr Ser Ala Pro Asp Trp Ile Asn Asn Val Lys Gln Ala Ala
            180                 185                 190

Gly Asn Ser Ser Gln Tyr Ala Gln Ala Val Glu Val Ala Lys Glu Leu
        195                 200                 205

Gln Gly Gln Val Asp Gln Tyr Asn Ala Asp Asn Asn Leu Thr Gly Asn
    210                 215                 220

Asp Ala Arg Ser Leu His Phe Thr Gly His Ser Leu Gly Gly Gly Leu
225                 230                 235                 240

Ala Thr Ala Ala Ala Leu Ala Thr Gly Ser Ser Ala Thr Ala Phe Asn
                245                 250                 255

Ala Ala Gly Leu Gly Asp Ser Thr Leu Lys Asn Leu Gly Leu Asn Glu
            260                 265                 270

Gly Leu Ala Ala Gly Phe His Asn Asn Val Thr Asn Ile Asn Val Glu
        275                 280                 285

Gly Asp Leu Leu Ser Asp Ala Asn Arg Gln Lys Asp Val Tyr Thr Thr
    290                 295                 300

Gly Ser Gly Ile Leu Asp Glu Thr Arg Gln Tyr Gly Glu Gln Val Trp
305                 310                 315                 320

Leu Gln Gly Val Asp Asp Lys Ala Arg Leu Gly Gly Pro Leu Asn Pro
                325                 330                 335

Leu Ile Pro Gly Val Ala Asp Asp Leu Ala Ile Gln Ala Leu Asn His
            340                 345                 350

Ala Trp His Val Tyr Thr Tyr Gln Leu Glu Asn Arg Asn Phe Ala
        355                 360                 365
```

<210> SEQ ID NO 149
<211> LENGTH: 975
<212> TYPE: DNA
<213> ORGANISM: Unknown
<220> FEATURE:
<223> OTHER INFORMATION: Obtained from environmental sample

<400> SEQUENCE: 149

```
atgagcgtcc aactgcaacc gagccagctc cagccgactt ggcagaaacc gctggaaccc      60

ctggccccgc cgatccaggc ggcaccgccg ctgccgcaag gctcgtacgc cctggacccc     120

agctaccacc cgcagctggc cgcggtcacc gcgaagcagg cgccggccgc caacgccgcg     180

ccggacccga cctcgttcga ccagcaactg cgcggcaagg attcgcaggc catcgacctg     240
```

-continued

```
gagatggcgc agctctcgca ggcggtctac aaccccgaca ccaagaccgt cggcaactgg    300

acccgtctcg acgacgccca gctgacccag gccggaatcg atcccaagtc gctggagaac    360

agcgacaccg gcttccgcgc cggcatctac accgacggca acggcaagta cgtggtcgcc    420

tacgccggtt ccaacgacgt gcaggactgg atcaccaacg cgcgccaggg catcggctgg    480

gattccaagc agtacgacca ggccgtgcag ctggcccagg acgcgcagca ggccttcggc    540

gagaacatgg tcatcaccgg ccattcgctc ggcggcggcc tggccgcgac cgcggcgctg    600

gccaccgaca ccgccgcagt gaccttcaac gcctccggcg tgcacgacga caccctgcgc    660

ggactgggcc tggacccggg taccgccaag agcgacgccg ccgacggcca gatccgccgc    720

tacaacatcg gcggcgaaat cctgactgcg gcgcaggaag acgtgccgct gctcaacggc    780

attcccgacg cgcccggcca cgagatcaac ctcaacgacc cggacccgcc gaaggccccg    840

gatttcacct ggaacccgat cgagatggcc aagcgcaccg ccgaatacgt ggccgccaag    900

gcgatccgtc cgggcgagct gcacgccatc ggcccggtga tcgaggcgct gcagcagcag    960

acgccctggc aatga                                                      975
```

```
<210> SEQ ID NO 150
<211> LENGTH: 324
<212> TYPE: PRT
<213> ORGANISM: Unknown
<220> FEATURE:
<223> OTHER INFORMATION: Obtained from environmental sample

<400> SEQUENCE: 150

Met Ser Val Gln Leu Gln Pro Ser Gln Leu Gln Pro Thr Trp Gln Lys
1               5                   10                  15

Pro Leu Glu Pro Leu Ala Pro Pro Ile Gln Ala Ala Pro Pro Leu Pro
            20                  25                  30

Gln Gly Ser Tyr Ala Leu Asp Pro Ser Tyr His Pro Gln Leu Ala Ala
        35                  40                  45

Val Thr Ala Lys Gln Ala Pro Ala Ala Asn Ala Ala Pro Asp Pro Thr
    50                  55                  60

Ser Phe Asp Gln Gln Leu Arg Gly Lys Asp Ser Gln Ala Ile Asp Leu
65                  70                  75                  80

Glu Met Ala Gln Leu Ser Gln Ala Val Tyr Asn Pro Asp Thr Lys Thr
                85                  90                  95

Val Gly Asn Trp Thr Arg Leu Asp Asp Ala Gln Leu Thr Gln Ala Gly
            100                 105                 110

Ile Asp Pro Lys Ser Leu Glu Asn Ser Asp Thr Gly Phe Arg Ala Gly
        115                 120                 125

Ile Tyr Thr Asp Gly Asn Gly Lys Tyr Val Val Ala Tyr Ala Gly Ser
    130                 135                 140

Asn Asp Val Gln Asp Trp Ile Thr Asn Ala Arg Gln Gly Ile Gly Trp
145                 150                 155                 160

Asp Ser Lys Gln Tyr Asp Gln Ala Val Gln Leu Ala Gln Asp Ala Gln
                165                 170                 175

Gln Ala Phe Gly Glu Asn Met Val Ile Thr Gly His Ser Leu Gly Gly
            180                 185                 190

Gly Leu Ala Ala Thr Ala Ala Leu Ala Thr Asp Thr Ala Ala Val Thr
        195                 200                 205

Phe Asn Ala Ser Gly Val His Asp Asp Thr Leu Arg Gly Leu Gly Leu
    210                 215                 220

Asp Pro Gly Thr Ala Lys Ser Asp Ala Ala Asp Gly Gln Ile Arg Arg
225                 230                 235                 240
```

Tyr Asn Ile Gly Gly Glu Ile Leu Thr Ala Ala Gln Glu Asp Val Pro
245 250 255

Leu Leu Asn Gly Ile Pro Asp Ala Pro Gly His Glu Ile Asn Leu Asn
260 265 270

Asp Pro Asp Pro Pro Lys Ala Pro Asp Phe Thr Trp Asn Pro Ile Glu
275 280 285

Met Ala Lys Arg Thr Ala Glu Tyr Val Ala Ala Lys Ala Ile Arg Pro
290 295 300

Gly Glu Leu His Ala Ile Gly Pro Val Ile Glu Ala Leu Gln Gln Gln
305 310 315 320

Thr Pro Trp Gln

<210> SEQ ID NO 151
<211> LENGTH: 1341
<212> TYPE: DNA
<213> ORGANISM: Unknown
<220> FEATURE:
<223> OTHER INFORMATION: Obtained from environmental sample

<400> SEQUENCE: 151
atgggcggag aacggcaccc cgatggcgtg agcacgatac cggcaacggc ctcggacctg 60
gcgagctttg accgcgccag tggacagctg gcgacattcg ccgcgcctgt cctccacgac 120
agtggcaaac cagacgatcg tctgttcgtc gcggcgttcg acggcaccgg caacagcatg 180
gtcaaggacg cgccggagaa tcacacgaac gttgcgcgca tcgccaggca gatcgagtcc 240
ctgggcgatc ccgccatcgc gcaaggctat gtggaaggcc cgggcacgca gggcggaatc 300
ggcggaggca tcgacctcat gacagggcag agctacgaag cccgcatgga ggacatgtac 360
ctgcagttcg tgaagcaatc cgccgcgtgg ttgaaggaga acccggatgc ggacatccgc 420
atcgccgcca tcggattcag tcgtggcgcg gaacaggcgg ccggcttcac ccggatggtc 480
gaagaacgcg gcatccggaa tccggaaggc gcgcaggtca cgcgcgacgg cgatggtcgg 540
gtactgcgtg tcgactacat cggtccaccg ctgcgcgaac ccggcaccgt catccaggcg 600
gttggcctgt tcgaccccgt cggcacgggt gagccgcgcg atcacgaccg ccgtctgcca 660
ccgtcggtgg tgtcgggttt ccagatcacc gccgacgatg agcggcgcaa cctgttccag 720
tccacccgcg tgatggatcc tggcgtgacc gatggcgggc gcttcctcaa cgtcaccgtc 780
gccggtgcgc acagcgacat cggcggtggc tatacgcagg atggcatcgc gatccgcagc 840
ggcaacctga tgatcgacta cctcaacggt ctgagcgacc ggccattcct ggacaagcgt 900
gaagaaccgt tcgatcccgc tcgcaacgtg atccatcgct ccgaggaaca ccggttcttc 960
taccgcacct cgatctacga caaggcggga acgcgcggga tgcaggagga actcgcgccg 1020
tcgcacctgt gcaggatcga ctgcctcgat gcacagcccc gcaatgaaac gctcgcgcgc 1080
gagctggcct ggcgacccgt cgagatcgga ccggtcccgg tcggcgcgga ggtgtcgcgt 1140
tcgggcggca tggtcgagcg tctgttgcag gcggccaaac acggcgacgg tggcgccgtc 1200
gagcgcatct cgcgggagta tctgcacgga gacgccgggc aggcgtggct gcaggcaggc 1260
cagcagcggc tcgacgccgc ctccatcacg caggcaccac cggtggaacg ccagcaggag 1320
ccggccgcgc tcgcgcgctg a 1341

<210> SEQ ID NO 152
<211> LENGTH: 446
<212> TYPE: PRT
<213> ORGANISM: Unknown
<220> FEATURE:

<223> OTHER INFORMATION: Obtained from environmental sample

<400> SEQUENCE: 152

Met Gly Gly Glu Arg His Pro Asp Gly Val Ser Thr Ile Pro Ala Thr
1 5 10 15

Ala Ser Asp Leu Ala Ser Phe Asp Arg Ala Ser Gly Gln Leu Ala Thr
20 25 30

Phe Ala Ala Pro Val Leu His Asp Ser Gly Lys Pro Asp Asp Arg Leu
35 40 45

Phe Val Ala Ala Phe Asp Gly Thr Gly Asn Ser Met Val Lys Asp Ala
50 55 60

Pro Glu Asn His Thr Asn Val Ala Arg Ile Ala Arg Gln Ile Glu Ser
65 70 75 80

Leu Gly Asp Pro Ala Ile Ala Gln Gly Tyr Val Glu Gly Pro Gly Thr
85 90 95

Gln Gly Gly Ile Gly Gly Gly Ile Asp Leu Met Thr Gly Gln Ser Tyr
100 105 110

Glu Ala Arg Met Glu Asp Met Tyr Leu Gln Phe Val Lys Gln Ser Ala
115 120 125

Ala Trp Leu Lys Glu Asn Pro Asp Ala Asp Ile Arg Ile Ala Ala Ile
130 135 140

Gly Phe Ser Arg Gly Ala Glu Gln Ala Ala Gly Phe Thr Arg Met Val
145 150 155 160

Glu Glu Arg Gly Ile Arg Asn Pro Glu Gly Ala Gln Val Thr Arg Asp
165 170 175

Gly Asp Gly Arg Val Leu Arg Val Asp Tyr Ile Gly Pro Pro Leu Arg
180 185 190

Glu Pro Gly Thr Val Ile Gln Ala Val Gly Leu Phe Asp Pro Val Gly
195 200 205

Thr Gly Glu Pro Arg Asp His Asp Arg Arg Leu Pro Pro Ser Val Val
210 215 220

Ser Gly Phe Gln Ile Thr Ala Asp Asp Glu Arg Arg Asn Leu Phe Gln
225 230 235 240

Ser Thr Arg Val Met Asp Pro Gly Val Thr Asp Gly Gly Arg Phe Leu
245 250 255

Asn Val Thr Val Ala Gly Ala His Ser Asp Ile Gly Gly Gly Tyr Thr
260 265 270

Gln Asp Gly Ile Ala Ile Arg Ser Gly Asn Leu Met Ile Asp Tyr Leu
275 280 285

Asn Gly Leu Ser Asp Arg Pro Phe Leu Asp Lys Arg Glu Glu Pro Phe
290 295 300

Asp Pro Ala Arg Asn Val Ile His Arg Ser Glu Glu His Arg Phe Phe
305 310 315 320

Tyr Arg Thr Ser Ile Tyr Asp Lys Ala Gly Thr Arg Gly Met Gln Glu
325 330 335

Glu Leu Ala Pro Ser His Leu Cys Arg Ile Asp Cys Leu Asp Ala Gln
340 345 350

Pro Arg Asn Glu Thr Leu Ala Arg Glu Leu Ala Trp Arg Pro Val Glu
355 360 365

Ile Gly Pro Val Pro Val Gly Ala Glu Val Ser Arg Ser Gly Gly Met
370 375 380

Val Glu Arg Leu Leu Gln Ala Ala Lys His Gly Asp Gly Gly Ala Val
385 390 395 400

Glu Arg Ile Ser Arg Glu Tyr Leu His Gly Asp Ala Gly Gln Ala Trp

-continued 405 410 415

Leu Gln Ala Gly Gln Gln Arg Leu Asp Ala Ala Ser Ile Thr Gln Ala
420 425 430

Pro Pro Val Glu Arg Gln Gln Glu Pro Ala Ala Leu Ala Arg
435 440 445

<210> SEQ ID NO 153
<211> LENGTH: 384
<212> TYPE: DNA
<213> ORGANISM: Unknown
<220> FEATURE:
<223> OTHER INFORMATION: Obtained from environmental sample

<400> SEQUENCE: 153
atgtctttac tttatgcacc agaagagttt tggctagcag atgtagaaac tttagaaagt 60
gtatgtaatg gctgtggtac tgaaggctgg aaaggtaaac taattcctaa cagcatgtat 120
ggtctagata tacgcattgc ttgtgatatc catgactgga tgtatcactt tggtaagtca 180
gaaaaagata aagaaaaagc agataaagct tttttaaata atcttattcg ccttatcaat 240
gatgaaggtg gcttcttagc ttggcctaga cgttataggg ctatgactta ttataacgca 300
gtcaaagatt ttggtgggcc tgcattttgg gcaaataaaa accctaaggg tactatgaaa 360
gaacctaagg gtactcctgc ttaa 384

<210> SEQ ID NO 154
<211> LENGTH: 127
<212> TYPE: PRT
<213> ORGANISM: Unknown
<220> FEATURE:
<223> OTHER INFORMATION: Obtained from environmental sample

<400> SEQUENCE: 154

Met Ser Leu Leu Tyr Ala Pro Glu Glu Phe Trp Leu Ala Asp Val Glu
1 5 10 15

Thr Leu Glu Ser Val Cys Asn Gly Cys Gly Thr Glu Gly Trp Lys Gly
20 25 30

Lys Leu Ile Pro Asn Ser Met Tyr Gly Leu Asp Ile Arg Ile Ala Cys
35 40 45

Asp Ile His Asp Trp Met Tyr His Phe Gly Lys Ser Glu Lys Asp Lys
50 55 60

Glu Lys Ala Asp Lys Ala Phe Leu Asn Asn Leu Ile Arg Leu Ile Asn
65 70 75 80

Asp Glu Gly Gly Phe Leu Ala Trp Pro Arg Arg Tyr Arg Ala Met Thr
85 90 95

Tyr Tyr Asn Ala Val Lys Asp Phe Gly Gly Pro Ala Phe Trp Ala Asn
100 105 110

Lys Asn Pro Lys Gly Thr Met Lys Glu Pro Lys Gly Thr Pro Ala
115 120 125

<210> SEQ ID NO 155
<211> LENGTH: 1263
<212> TYPE: DNA
<213> ORGANISM: Unknown
<220> FEATURE:
<223> OTHER INFORMATION: Obtained from environmental sample

<400> SEQUENCE: 155
atgcggacga caactacaaa ttggagacaa atcgtgaaaa gcctgaagct cttcctgatg 60
ggcctttgcc tgttcatttc cgcttcattc gcatcatctg cctatgcact gggcagttac 120

```
acctacacgt acctgcgctg tttctatcgc gtcgatacat ccccgctgaa gcccaagacc    180

acctacgtct ggggcatcga tccgggcagc ggcggctact accgcatcta tggccgctgg    240

tggaaagacg gcttgctgag ctgggaaaac atgttctaca gcgacgtgtc gcaagatacg    300

ctgaaatcgg tttgccagag cacgctcgcc ggctacggca tcaaccgcag cgtcgcactc    360

tcggcggcgg ccgatacgtc gctctcgctc aattacacgg tgtggaccaa cgacagcgca    420

tcgcagggct cacgcatcaa caaaatcgtc gcattcggcg acagcctgtc ggacaaccag    480

aatctgtaca acgcgaccca atggcaactg ccgaaccgca acagttggtt tctcggccgc    540

ttctcgaatg acaggaactg gatcgaatac ctgtcgagca acgtgaatct gccgatgtac    600

aactgggcag tggcgggcgc ggcggcggat cagtactacg tcatcccggg tgtgtcgcaa    660

caggtcgact cgtggatcac ctacatgcag agcgcgccga attaccaggc cgcgaatacg    720

ctgttcaccg tgcttgtcgg cggcaacgat ctggtgaact acggccggtc tgtcgactcg    780

atcatctccg cggagcagca ggcgctggtg aagatgatca atgccggcgc tcgcaacatc    840

ctgttgctga atctgcccga cgtatcgcgc gcaccggtat tccagtatcg cagcgacgcc    900

gccaccatcg ccgcgcaagt ccgcgacttc aaccagaagc tggcgcaact gcgcgacaat    960

cttcaggcga cgtacggccc gtcgctcgtc attcgcatgt tcgataccta caccttgttc   1020

aacgatctgc tgaacaatcc gaccaactat ggcgtgacga acacctggca gtcctgcctc   1080

gacatcaact cggattccgg gtcgaactat ctttatacct ggccgacgcg cgccgaatgc   1140

accaacgccg acagcttcgt gttctgggac acgctgcacc cgaccacgca tacgcacaag   1200

ctgctgggcg acaatgcggc gaatttcgta cgcgccggtt tccccgcatt gtctgcgcct   1260

tga                                                                 1263
```

<210> SEQ ID NO 156
<211> LENGTH: 420
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(36)
<220> FEATURE:
<221> NAME/KEY: DOMAIN
<222> LOCATION: (149)...(406)
<223> OTHER INFORMATION: GDSL-like Lipase/Acylhydrolase

<400> SEQUENCE: 156

```
Met Arg Thr Thr Thr Thr Asn Trp Arg Gln Ile Val Lys Ser Leu Lys
 1               5                  10                  15

Leu Phe Leu Met Gly Leu Cys Leu Phe Ile Ser Ala Ser Phe Ala Ser
            20                  25                  30

Ser Ala Tyr Ala Leu Gly Ser Tyr Thr Tyr Thr Tyr Leu Arg Cys Phe
        35                  40                  45

Tyr Arg Val Asp Thr Ser Pro Leu Lys Pro Lys Thr Thr Tyr Val Trp
    50                  55                  60

Gly Ile Asp Pro Gly Ser Gly Gly Tyr Tyr Arg Ile Tyr Gly Arg Trp
65                  70                  75                  80

Trp Lys Asp Gly Leu Leu Ser Trp Glu Asn Met Phe Tyr Ser Asp Val
                85                  90                  95

Ser Gln Asp Thr Leu Lys Ser Val Cys Gln Ser Thr Leu Ala Gly Tyr
            100                 105                 110

Gly Ile Asn Arg Ser Val Ala Leu Ser Ala Ala Ala Asp Thr Ser Leu
        115                 120                 125
```

```
Ser Leu Asn Tyr Thr Val Trp Thr Asn Asp Ser Ala Ser Gln Gly Ser
    130                 135                 140

Arg Ile Asn Lys Ile Val Ala Phe Gly Asp Ser Leu Ser Asp Asn Gln
145                 150                 155                 160

Asn Leu Tyr Asn Ala Thr Gln Trp Gln Leu Pro Asn Arg Asn Ser Trp
                165                 170                 175

Phe Leu Gly Arg Phe Ser Asn Asp Arg Asn Trp Ile Glu Tyr Leu Ser
            180                 185                 190

Ser Asn Val Asn Leu Pro Met Tyr Asn Trp Ala Val Ala Gly Ala Ala
        195                 200                 205

Ala Asp Gln Tyr Tyr Val Ile Pro Gly Val Ser Gln Gln Val Asp Ser
    210                 215                 220

Trp Ile Thr Tyr Met Gln Ser Ala Pro Asn Tyr Gln Ala Ala Asn Thr
225                 230                 235                 240

Leu Phe Thr Val Leu Val Gly Gly Asn Asp Leu Val Asn Tyr Gly Arg
                245                 250                 255

Ser Val Asp Ser Ile Ile Ser Ala Glu Gln Gln Ala Leu Val Lys Met
            260                 265                 270

Ile Asn Ala Gly Ala Arg Asn Ile Leu Leu Leu Asn Leu Pro Asp Val
        275                 280                 285

Ser Arg Ala Pro Val Phe Gln Tyr Arg Ser Asp Ala Ala Thr Ile Ala
    290                 295                 300

Ala Gln Val Arg Asp Phe Asn Gln Lys Leu Ala Gln Leu Arg Asp Asn
305                 310                 315                 320

Leu Gln Ala Thr Tyr Gly Pro Ser Leu Val Ile Arg Met Phe Asp Thr
                325                 330                 335

Tyr Thr Leu Phe Asn Asp Leu Leu Asn Asn Pro Thr Asn Tyr Gly Val
            340                 345                 350

Thr Asn Thr Trp Gln Ser Cys Leu Asp Ile Asn Ser Asp Ser Gly Ser
        355                 360                 365

Asn Tyr Leu Tyr Thr Trp Pro Thr Arg Ala Glu Cys Thr Asn Ala Asp
    370                 375                 380

Ser Phe Val Phe Trp Asp Thr Leu His Pro Thr Thr His Thr His Lys
385                 390                 395                 400

Leu Leu Gly Asp Asn Ala Ala Asn Phe Val Arg Ala Gly Phe Pro Ala
                405                 410                 415

Leu Ser Ala Pro
            420
```

<210> SEQ ID NO 157
<211> LENGTH: 1329
<212> TYPE: DNA
<213> ORGANISM: Unknown
<220> FEATURE:
<223> OTHER INFORMATION: Obtained from environmental sample

<400> SEQUENCE: 157

```
atgagcctca acagccaaga ctacgctgcg ctatccgaag atgcatacaa ggattatgcg      60

gtcggtcgtc gagcgcctgg tcaagaagaa atcgttccga tcaacgggca caagtacaag     120

atcctcgagc acgttgacaa tcggctgaac ggttatcagg gaacgatcta ccagcgagtc     180

gacaccaatg aaattgtcgt cgcacatcgc ggaaccgaac aaatcgcacg cgatgcgatt     240

ctgaccgatg gtggcatggt cgttgcccgt accaatgtgc aggcgccaga cgcaatcgcg     300

ctgacccaac gcgccctggc ttacgccaag aaggaggggc aggatctcgg ccaacgtccg     360
```

```
cctgaggtca ccgtcaccgg ccactccctc ggcggcgctc tggcccagat cacctcgcac    420

cacttcaacg tcaagggcga gaccttcaac gcctatggcg cggtcagcct cagctaccgc    480

atcccggaag gtggcaacac catgatcaac catgtcatgg cctccgatcc ggtcagcgcg    540

gcgtcgccac atttcggcca ggtgcggatc tacgccaggc cgaatgaaat cagcacgctc    600

gccgcgaacg gtttcagcaa tcactcgttg cgcgccctta tccccgaccg gccgatcatc    660

gccgcaggca gctcgttcgg cgcgcacaag ctgggcaact tcctcggtga cggctcggtg    720

ctgcagcacc cggaaacgca gaagctggca aaagacaacg ccaggatgat cgaggaatac    780

cgcgacgacg ttgaattact gcgccgtggt gtcacccgcg cggcgcgggg cattccgggc    840

ggcgccgtcg acctgtacga ccacatccgc ggcccgctgc agcccggtga gccggcacgc    900

cgcgaagcgg agaagaacgg ccatcacacc agcatgctgc gaatggacga tgccaaccat    960

gtgggcaacc cactgttcaa cgacgcgatc cgtggcgtgc acgcgcagga tgtccgcgtc   1020

ggccgggtac cagacgtgat gagcacgcaa ctggcaggca gtctggccgc cgaaatgcac   1080

gcagcaggcg gcaagcgcat cgacgaagtg gtcatgaatg ccgatgcctc gcgcagcttc   1140

gccgtgcagg gccagggcgg tgaccccgcc caccttcgtg tgtcggtgga tacggcagtg   1200

gcgatgaaca ccccgctgga acagagcagc cagcgcatcg accagcaggc cgccgaccag   1260

cgcgttgcgc tggagcgcga ccagcagctg gaacagcagc ggaaccagac ccgcagcctg   1320

caggcctga                                                           1329
```

<210> SEQ ID NO 158
<211> LENGTH: 442
<212> TYPE: PRT
<213> ORGANISM: Unknown
<220> FEATURE:
<223> OTHER INFORMATION: Obtained from environmental sample

<400> SEQUENCE: 158

```
Met Ser Leu Asn Ser Gln Asp Tyr Ala Ala Leu Ser Glu Asp Ala Tyr
 1               5                  10                  15

Lys Asp Tyr Ala Val Gly Arg Arg Ala Pro Gly Gln Glu Glu Ile Val
            20                  25                  30

Pro Ile Asn Gly His Lys Tyr Lys Ile Leu Glu His Val Asp Asn Arg
        35                  40                  45

Leu Asn Gly Tyr Gln Gly Thr Ile Tyr Gln Arg Val Asp Thr Asn Glu
    50                  55                  60

Ile Val Val Ala His Arg Gly Thr Glu Gln Ile Ala Arg Asp Ala Ile
65                  70                  75                  80

Leu Thr Asp Gly Gly Met Val Val Ala Arg Thr Asn Val Gln Ala Pro
                85                  90                  95

Asp Ala Ile Ala Leu Thr Gln Arg Ala Leu Ala Tyr Ala Lys Lys Glu
            100                 105                 110

Gly Gln Asp Leu Gly Gln Arg Pro Pro Glu Val Thr Val Thr Gly His
        115                 120                 125

Ser Leu Gly Gly Ala Leu Ala Gln Ile Thr Ser His His Phe Asn Val
    130                 135                 140

Lys Gly Glu Thr Phe Asn Ala Tyr Gly Ala Val Ser Leu Ser Tyr Arg
145                 150                 155                 160

Ile Pro Glu Gly Gly Asn Thr Met Ile Asn His Val Met Ala Ser Asp
                165                 170                 175

Pro Val Ser Ala Ala Ser Pro His Phe Gly Gln Val Arg Ile Tyr Ala
            180                 185                 190
```

```
Arg Pro Asn Glu Ile Ser Thr Leu Ala Ala Asn Gly Phe Ser Asn His
        195                 200                 205

Ser Leu Arg Ala Leu Ile Pro Asp Arg Pro Ile Ile Ala Ala Gly Ser
    210                 215                 220

Ser Phe Gly Ala His Lys Leu Gly Asn Phe Leu Gly Asp Gly Ser Val
225                 230                 235                 240

Leu Gln His Pro Glu Thr Gln Lys Leu Ala Lys Asp Asn Ala Arg Met
                245                 250                 255

Ile Glu Glu Tyr Arg Asp Asp Val Glu Leu Leu Arg Arg Gly Val Thr
            260                 265                 270

Arg Ala Ala Arg Gly Ile Pro Gly Gly Ala Val Asp Leu Tyr Asp His
        275                 280                 285

Ile Arg Gly Pro Leu Gln Pro Gly Glu Pro Ala Arg Arg Glu Ala Glu
    290                 295                 300

Lys Asn Gly His His Thr Ser Met Leu Arg Met Asp Asp Ala Asn His
305                 310                 315                 320

Val Gly Asn Pro Leu Phe Asn Asp Ala Ile Arg Gly Val His Ala Gln
                325                 330                 335

Asp Val Arg Val Gly Arg Val Pro Asp Val Met Ser Thr Gln Leu Ala
            340                 345                 350

Gly Ser Leu Ala Ala Glu Met His Ala Ala Gly Gly Lys Arg Ile Asp
        355                 360                 365

Glu Val Val Met Asn Ala Asp Ala Ser Arg Ser Phe Ala Val Gln Gly
    370                 375                 380

Gln Gly Gly Asp Pro Ala His Leu Arg Val Ser Val Asp Thr Ala Val
385                 390                 395                 400

Ala Met Asn Thr Pro Leu Glu Gln Ser Ser Gln Arg Ile Asp Gln Gln
                405                 410                 415

Ala Ala Asp Gln Arg Val Ala Leu Glu Arg Asp Gln Gln Leu Glu Gln
            420                 425                 430

Gln Arg Asn Gln Thr Arg Ser Leu Gln Ala
        435                 440
```

<210> SEQ ID NO 159
<211> LENGTH: 1428
<212> TYPE: DNA
<213> ORGANISM: Unknown
<220> FEATURE:
<223> OTHER INFORMATION: Obtained from environmental sample

<400> SEQUENCE: 159

```
atgtcgatca cgctggtatt cgtgcacggc tggagtgtca caagcaagga cacctacggg      60

aagcttcccg aggccatctc tcaagccgct gcggccgcgg gcatcgatgt agagctgaag     120

gacatctacc tcggccgcta catcagcttt cacgacgagg ttacggtcga cgacatcgcg     180

accgcgatga atcacgcggt ggcgaacgac ttgaaagggg tgaaggagtt ctcgtgcatc     240

acgcactcca cgggcggccc ggtcgtgcgt cgctgggtag atatgttcta cggcgcgaag     300

gacctcgaca actgtccgct gcgtcatctc atcatgctgg cgcctgcaaa ccatggttcc     360

gcgttggccg tcttggggaa gggccgcgtc ggtcgaatcc aggcgtggtg gggtggggtc     420

gagcccggtc agggcgtgct cgactggctt tgcctcggca gctcggaagc gtgggagctc     480

caggacagct tcacggatta ctcgctggac gacgcgaagt tcttcccgtt cgtgctgagc     540

ggcgagacga ttgataagca cttctacgac ttcctcaaca gctatctgga tgaagtgggc     600

tcggatggcg tggttcgtct ggcgggggcc aatctgaact acacgtttat tcggctcgac     660
```

```
caaactgaaa agcgttacga cgacggcgag gaaacgggct acatactgac tgttcggccg     720

cggacaaagc cgcgcccacc cgtaacggcg ttcggagtca taccgagcgc gagtcactcg     780

ggtaacgaca tcggcatcat gcgcagcgtc acgccggcga actccgattc gaagcctgtc     840

gtggcgcaaa tcgtgaaatg cctcggcgtg gagacacaag cggattacaa agcgcgtgtc     900

accgagctgg ccgcgttcac cgccgaaacg cagaaagcca acgccgtgca gtacggcggc     960

aaagagcgcc atttcgtgat gttcatcttc cgcatccgcg acgacagagg gcgcacgata    1020

agcgactacg acctgttgct gctcggcgac ggtttccacc cggacaagct gcccaaggga    1080

ttcttcgttg accgtcaacg caatcccaag tcccaggcgc tggtctacta cctcgactac    1140

gacgcgctga cggctgacga cgacaccgac ttaggtattc gagtgaacgc gcgaccgctc    1200

tatagcgcgc ccggagcagc agagccagac gcattcgcgg gctatcgagc cgccgagtat    1260

cgattcacgg gcaaagtact gaagcaattc gtgcgcccga acgaaactgt gtacgtcgac    1320

atcgtgctga atcgcatggt ggacgttgaa acgctccggc tggagcctct ggaaggatcg    1380

ccgcgtgggt cgttcaagaa aactctgccc aaagggccgg tgagttag                 1428
```

<210> SEQ ID NO 160
<211> LENGTH: 475
<212> TYPE: PRT
<213> ORGANISM: Unknown
<220> FEATURE:
<223> OTHER INFORMATION: Obtained from environmental sample

<400> SEQUENCE: 160

```
Met Ser Ile Thr Leu Val Phe Val His Gly Trp Ser Val Thr Ser Lys
1               5                   10                  15

Asp Thr Tyr Gly Lys Leu Pro Glu Ala Ile Ser Gln Ala Ala Ala Ala
            20                  25                  30

Ala Gly Ile Asp Val Glu Leu Lys Asp Ile Tyr Leu Gly Arg Tyr Ile
        35                  40                  45

Ser Phe His Asp Glu Val Thr Val Asp Asp Ile Ala Thr Ala Met Asn
    50                  55                  60

His Ala Val Ala Asn Asp Leu Lys Gly Val Lys Glu Phe Ser Cys Ile
65                  70                  75                  80

Thr His Ser Thr Gly Gly Pro Val Val Arg Arg Trp Val Asp Met Phe
                85                  90                  95

Tyr Gly Ala Lys Asp Leu Asp Asn Cys Pro Leu Arg His Leu Ile Met
            100                 105                 110

Leu Ala Pro Ala Asn His Gly Ser Ala Leu Ala Val Leu Gly Lys Gly
        115                 120                 125

Arg Val Gly Arg Ile Gln Ala Trp Trp Gly Gly Val Glu Pro Gly Gln
    130                 135                 140

Gly Val Leu Asp Trp Leu Cys Leu Gly Ser Ser Glu Ala Trp Glu Leu
145                 150                 155                 160

Gln Asp Ser Phe Thr Asp Tyr Ser Leu Asp Asp Ala Lys Phe Phe Pro
                165                 170                 175

Phe Val Leu Ser Gly Glu Thr Ile Asp Lys His Phe Tyr Asp Phe Leu
            180                 185                 190

Asn Ser Tyr Leu Asp Glu Val Gly Ser Asp Gly Val Val Arg Leu Ala
        195                 200                 205

Gly Ala Asn Leu Asn Tyr Thr Phe Ile Arg Leu Asp Gln Thr Glu Lys
    210                 215                 220

Arg Tyr Asp Asp Gly Glu Glu Thr Gly Tyr Ile Leu Thr Val Arg Pro
225                 230                 235                 240
```

```
Arg Thr Lys Pro Arg Pro Pro Val Thr Ala Phe Gly Val Ile Pro Ser
                245                 250                 255

Ala Ser His Ser Gly Asn Asp Ile Gly Ile Met Arg Ser Val Thr Pro
            260                 265                 270

Ala Asn Ser Asp Ser Lys Pro Val Val Ala Gln Ile Val Lys Cys Leu
        275                 280                 285

Gly Val Glu Thr Gln Ala Asp Tyr Lys Ala Arg Val Thr Glu Leu Ala
    290                 295                 300

Ala Phe Thr Ala Glu Thr Gln Lys Ala Asn Ala Val Gln Tyr Gly Gly
305                 310                 315                 320

Lys Glu Arg His Phe Val Met Phe Ile Phe Arg Ile Arg Asp Asp Arg
                325                 330                 335

Gly Arg Thr Ile Ser Asp Tyr Asp Leu Leu Leu Leu Gly Asp Gly Phe
            340                 345                 350

His Pro Asp Lys Leu Pro Lys Gly Phe Phe Val Asp Arg Gln Arg Asn
        355                 360                 365

Pro Lys Ser Gln Ala Leu Val Tyr Tyr Leu Asp Tyr Asp Ala Leu Thr
    370                 375                 380

Ala Asp Asp Asp Thr Asp Leu Gly Ile Arg Val Asn Ala Arg Pro Leu
385                 390                 395                 400

Tyr Ser Ala Pro Gly Ala Ala Glu Pro Asp Ala Phe Ala Gly Tyr Arg
                405                 410                 415

Ala Ala Glu Tyr Arg Phe Thr Gly Lys Val Leu Lys Gln Phe Val Arg
            420                 425                 430

Pro Asn Glu Thr Val Tyr Val Asp Ile Val Leu Asn Arg Met Val Asp
        435                 440                 445

Val Glu Thr Leu Arg Leu Glu Pro Leu Glu Gly Ser Pro Arg Gly Ser
    450                 455                 460

Phe Lys Lys Thr Leu Pro Lys Gly Pro Val Ser
465                 470                 475
```

<210> SEQ ID NO 161
<211> LENGTH: 1740
<212> TYPE: DNA
<213> ORGANISM: Unknown
<220> FEATURE:
<223> OTHER INFORMATION: Obtained from environmental sample

<400> SEQUENCE: 161

```
atgaacagaa aattattatc gttatgcttg ggagcaacgt cctgtattgc actatcactt      60

cctgtgcatg catttacgca aaagggtgcg ggtacggaaa tttctaatgg gatacctatg     120

gggcacgaat gggttacgcg tttgtctgca ttggaattgc ttggtggcga tcctattatg     180

ccgccagatc caaatgaccc acgtaaaaac tggactaaag ggaaagccaa aaacctcgat     240

ctttccagcc caggtgcgcg tgcagaagtt gcgcggatta tgagtgttga ttatcacgat     300

aaaatattcc agtcgacgta caaagttgtt ttcgacgcta ttattggcga gcgctgggta     360

gatttggcgg gatataacgt gacgaccagc atgttgggaa aaataaactg ttttgatgct     420

gtagcccaag agccagtaga aatccagtac gatcatttta tgcgtcgtta cgacgagcgc     480

ggtggaaaag gtggagcgac tgctgcgacc aattcacgcg agcgttttgt gcaatatttt     540

gttgcagcgg caatggctcc ccaaacaact atgaaagtat gggatggcgg tgttgttagt     600

gatttggtta ccgtagatag gaattacttt ttatttggca gggctgcgca tttattcgaa     660

gactcattta gttcagaaca tacagtgcgg gtgagtgatg ataattttga actggtgcgc     720
```

```
caagtaaaaa gctacatgtg tgctgcaggt tctgaacagc atacgcattc aaatgaaaaa    780

atatttaatt acaccagtgg cgatgttatt tggaaaccgg gtactggttt ggatccaagt    840

tggtccgcat ataaaccaag caacatgaaa accgtcgcat tggtggcgac cgaagcaact    900

aaagatttat gggcagcgtt tattcgctcc atgggcacgc ctatagcgca gcgtgagcag    960

tgggcgcgta aagaggctaa taaactggcc gataattggt tggcttttga taaatacaaa   1020

ctccccgatt ggtatgacat tgaagctcat cgggatgata cctatgtatt ggctgatggg   1080

cagacaggga aaggccaaac tgttgccgct tgtatgcaaa agttgggggt tgcatcaggc   1140

aagcaggagg ataaggttcg ccaattggaa gcagatcaaa aaacctgttt atacaatgtc   1200

gtggctgaag agggatacgc cgatttattt gatcccgcat ttcacatgcc attcaattgg   1260

cgttggaaaa caggccggtt tggtgattgg ttacaaccac cagcaggatg gaaaattcca   1320

actcgtccag cggatacagg cacacgcgtg aatattctca gtgcgacaaa caatctccct   1380

atggtggcag ctgatggtgt aagccataac cagtgggttt atgttaaagc aggttttcct   1440

gcgctgggtt ttatcaaagt gccggatgaa aataatactg acaaaaagaa tagtattttt   1500

tatcgcgtaa ttaatgatcc cgatttattt ttaagttaca acgccactac tggcgcagta   1560

aaactctggg ccagtccgaa ccaggctaat tatgcaactg aaccaaaatc agggaatatt   1620

gcaatcaaga gtttgtattg ggatcaatat atgtggcttt caaacgaatc cccttatatt   1680

acccgtaccg ggaatcccaa aaatttggat gcccaatgga aagaagtagc cgctaagtaa   1740
```

<210> SEQ ID NO 162
<211> LENGTH: 579
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(24)

<400> SEQUENCE: 162

```
Met Asn Arg Lys Leu Leu Ser Leu Cys Leu Gly Ala Thr Ser Cys Ile
 1               5                  10                  15

Ala Leu Ser Leu Pro Val His Ala Phe Thr Gln Lys Gly Ala Gly Thr
            20                  25                  30

Glu Ile Ser Asn Gly Ile Pro Met Gly His Glu Trp Val Thr Arg Leu
        35                  40                  45

Ser Ala Leu Glu Leu Leu Gly Gly Asp Pro Ile Met Pro Pro Asp Pro
    50                  55                  60

Asn Asp Pro Arg Lys Asn Trp Thr Lys Gly Lys Ala Lys Asn Leu Asp
65                  70                  75                  80

Leu Ser Ser Pro Gly Ala Arg Ala Glu Val Ala Arg Ile Met Ser Val
                85                  90                  95

Asp Tyr His Asp Lys Ile Phe Gln Ser Thr Tyr Lys Val Val Phe Asp
            100                 105                 110

Ala Ile Ile Gly Glu Arg Trp Val Asp Leu Ala Gly Tyr Asn Val Thr
        115                 120                 125

Thr Ser Met Leu Gly Lys Ile Asn Cys Phe Asp Ala Val Ala Gln Glu
    130                 135                 140

Pro Val Glu Ile Gln Tyr Asp His Phe Met Arg Arg Tyr Asp Glu Arg
145                 150                 155                 160

Gly Gly Lys Gly Gly Ala Thr Ala Ala Thr Asn Ser Arg Glu Arg Phe
                165                 170                 175
```

```
Val Gln Tyr Phe Val Ala Ala Ala Met Ala Pro Gln Thr Thr Met Lys
            180                 185                 190

Val Trp Asp Gly Gly Val Val Ser Asp Leu Val Thr Val Asp Arg Asn
        195                 200                 205

Tyr Phe Leu Phe Gly Arg Ala Ala His Leu Phe Glu Asp Ser Phe Ser
    210                 215                 220

Ser Glu His Thr Val Arg Val Ser Asp Asp Asn Phe Glu Leu Val Arg
225                 230                 235                 240

Gln Val Lys Ser Tyr Met Cys Ala Ala Gly Ser Glu Gln His Thr His
                245                 250                 255

Ser Asn Glu Lys Ile Phe Asn Tyr Thr Ser Gly Asp Val Ile Trp Lys
            260                 265                 270

Pro Gly Thr Gly Leu Asp Pro Ser Trp Ser Ala Tyr Lys Pro Ser Asn
        275                 280                 285

Met Lys Thr Val Ala Leu Val Ala Thr Glu Ala Thr Lys Asp Leu Trp
    290                 295                 300

Ala Ala Phe Ile Arg Ser Met Gly Thr Pro Ile Ala Gln Arg Glu Gln
305                 310                 315                 320

Trp Ala Arg Lys Glu Ala Asn Lys Leu Ala Asp Asn Trp Leu Ala Phe
                325                 330                 335

Asp Lys Tyr Lys Leu Pro Asp Trp Tyr Asp Ile Glu Ala His Arg Asp
            340                 345                 350

Asp Thr Tyr Val Leu Ala Asp Gly Gln Thr Gly Lys Gly Gln Thr Val
        355                 360                 365

Ala Ala Cys Met Gln Lys Leu Gly Val Ala Ser Gly Lys Gln Glu Asp
    370                 375                 380

Lys Val Arg Gln Leu Glu Ala Asp Gln Lys Thr Cys Leu Tyr Asn Val
385                 390                 395                 400

Val Ala Glu Glu Gly Tyr Ala Asp Leu Phe Asp Pro Ala Phe His Met
                405                 410                 415

Pro Phe Asn Trp Arg Trp Lys Thr Gly Arg Phe Gly Asp Trp Leu Gln
            420                 425                 430

Pro Pro Ala Gly Trp Lys Ile Pro Thr Arg Pro Ala Asp Thr Gly Thr
        435                 440                 445

Arg Val Asn Ile Leu Ser Ala Thr Asn Asn Leu Pro Met Val Ala Ala
    450                 455                 460

Asp Gly Val Ser His Asn Gln Trp Val Tyr Val Lys Ala Gly Phe Pro
465                 470                 475                 480

Ala Leu Gly Phe Ile Lys Val Pro Asp Glu Asn Asn Thr Asp Lys Lys
                485                 490                 495

Asn Ser Ile Phe Tyr Arg Val Ile Asn Asp Pro Asp Leu Phe Leu Ser
            500                 505                 510

Tyr Asn Ala Thr Thr Gly Ala Val Lys Leu Trp Ala Ser Pro Asn Gln
        515                 520                 525

Ala Asn Tyr Ala Thr Glu Pro Lys Ser Gly Asn Ile Ala Ile Lys Ser
    530                 535                 540

Leu Tyr Trp Asp Gln Tyr Met Trp Leu Ser Asn Glu Ser Pro Tyr Ile
545                 550                 555                 560

Thr Arg Thr Gly Asn Pro Lys Asn Leu Asp Ala Gln Trp Lys Glu Val
                565                 570                 575

Ala Ala Lys
```

<210> SEQ ID NO 163
<211> LENGTH: 1104

<212> TYPE: DNA
<213> ORGANISM: Unknown
<220> FEATURE:
<223> OTHER INFORMATION: Obtained from environmental sample

<400> SEQUENCE: 163

```
atgcaagtca atggtgcaat tgcagttact gatccggcgt tgagcaatgc agtggaagca     60

acctcttacc agacatctga acagattgtg ggtggagtaa gcgaagcggc ggaagcaggg    120

ttggcggcag aagtgggcgc ggcggagacg ttcgctgcag ctgacgatgt tgccctttca    180

tccatggtcg ccggcccggc taatgatgcc tcttacggca acctgcccgc agggtgggat    240

gaggcccggt ttgatcatgc cctggatatg gccaagttgt cctctcaggc ctacagcagt    300

ttcaatgaca gaactgtaga tcttctactg gcgccgttta gcggtatcaa tgacataaaa    360

aatcaagatt tctccaccga taattatctc cctataaatt ccggtggcaa atctgacttc    420

ctgttgcccc tgcagaatgg gctggactat acggtcttcc agcaagtcac cgatcctaat    480

ggtgtcgatc atgccgccaa gactgccggc ggcgatatcg ttctttcctt ccggggcagt    540

gaacccacat ccgccccgga ttgggtgaac aatgtgaagc aggccgctgg ccattctccc    600

caatatgggg ccgcggtaaa tgtggcgagg gatttgcagc agcaagtgga tgcctataat    660

gagaagcatg ggcttgaagg cgacgctgcc atgaagctcc acttcaccgg ccacagcctg    720

ggtggcggat tggccactgc cgctgccctg gctaccggta gcgaagcgac agtctttaat    780

gctgccggtc tctcagacca taccattaac aaccttggcc tggacgcaag ccatgccgac    840

aaggtgacca atattaacgt ggaaggcgat ctgctgagcg atggcaaccg gcagaaggat    900

gctcacacca cgggctctgg tgtctttggc gataccaagc aatatggtga gcaggtctgg    960

ctgcagggtg tagatgaccg cgcaagattt ggcggccctc tcaacttcct ggtgccgggc   1020

tttgtcaacg acctggccat tcaggggctt aatcacgcct ggcatgtgta tacctaccaa   1080

ttggaaaacc gcaactttgc ctga                                          1104
```

<210> SEQ ID NO 164
<211> LENGTH: 367
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (174)...(296)
<223> OTHER INFORMATION: Lipase (class 3)

<400> SEQUENCE: 164

```
Met Gln Val Asn Gly Ala Ile Ala Val Thr Asp Pro Ala Leu Ser Asn
 1               5                  10                  15

Ala Val Glu Ala Thr Ser Tyr Gln Thr Ser Glu Gln Ile Val Gly Gly
            20                  25                  30

Val Ser Glu Ala Ala Glu Ala Gly Leu Ala Ala Glu Val Gly Ala Ala
        35                  40                  45

Glu Thr Phe Ala Ala Ala Asp Asp Val Ala Leu Ser Ser Met Val Ala
    50                  55                  60

Gly Pro Ala Asn Asp Ala Ser Tyr Gly Asn Leu Pro Ala Gly Trp Asp
65                  70                  75                  80

Glu Ala Arg Phe Asp His Ala Leu Asp Met Ala Lys Leu Ser Ser Gln
                85                  90                  95

Ala Tyr Ser Ser Phe Asn Asp Arg Thr Val Asp Leu Leu Leu Ala Pro
            100                 105                 110
```

-continued

```
Phe Ser Gly Ile Asn Asp Ile Lys Asn Gln Asp Phe Ser Thr Asp Asn
        115                 120                 125

Tyr Leu Pro Ile Asn Ser Gly Gly Lys Ser Asp Phe Leu Leu Pro Leu
    130                 135                 140

Gln Asn Gly Leu Asp Tyr Thr Val Phe Gln Gln Val Thr Asp Pro Asn
145                 150                 155                 160

Gly Val Asp His Ala Ala Lys Thr Ala Gly Gly Asp Ile Val Leu Ser
                165                 170                 175

Phe Arg Gly Ser Glu Pro Thr Ser Ala Pro Asp Trp Val Asn Asn Val
            180                 185                 190

Lys Gln Ala Ala Gly His Ser Pro Gln Tyr Gly Ala Ala Val Asn Val
        195                 200                 205

Ala Arg Asp Leu Gln Gln Gln Val Asp Ala Tyr Asn Glu Lys His Gly
    210                 215                 220

Leu Glu Gly Asp Ala Ala Met Lys Leu His Phe Thr Gly His Ser Leu
225                 230                 235                 240

Gly Gly Gly Leu Ala Thr Ala Ala Ala Leu Ala Thr Gly Ser Glu Ala
                245                 250                 255

Thr Val Phe Asn Ala Ala Gly Leu Ser Asp His Thr Ile Asn Asn Leu
            260                 265                 270

Gly Leu Asp Ala Ser His Ala Asp Lys Val Thr Asn Ile Asn Val Glu
        275                 280                 285

Gly Asp Leu Leu Ser Asp Gly Asn Arg Gln Lys Asp Ala His Thr Thr
    290                 295                 300

Gly Ser Gly Val Phe Gly Asp Thr Lys Gln Tyr Gly Glu Gln Val Trp
305                 310                 315                 320

Leu Gln Gly Val Asp Asp Arg Ala Arg Phe Gly Gly Pro Leu Asn Phe
                325                 330                 335

Leu Val Pro Gly Phe Val Asn Asp Leu Ala Ile Gln Gly Leu Asn His
            340                 345                 350

Ala Trp His Val Tyr Thr Tyr Gln Leu Glu Asn Arg Asn Phe Ala
        355                 360                 365
```

<210> SEQ ID NO 165
<211> LENGTH: 927
<212> TYPE: DNA
<213> ORGANISM: Unknown
<220> FEATURE:
<223> OTHER INFORMATION: Obtained from environmental sample

<400> SEQUENCE: 165

```
atgcccaaat acagaattct tagtttggac ggcggcggaa tccgggggct gctcagcgcg      60

attctgctcg agcggttgga agcggaggca cccaattggc tgagccaggt ggacctgatc     120

gccggcacat ccaccggcgg gatcatcgcc ctgggtctcg ccaaaggcct cagcccaacc     180

caactgcgca atctctatca actgcgcggg gcggcgatat tcgatgattc atggtgggac     240

gacgtgctcg atattgggaa gatttcgggc gcggattatg ataacaagca actcaccaaa     300

gagttgaaga cgattctcgg caacacgaaa ctgcgcgagt tgtcgaagcg ggttttgatt     360

tcgagtttcg atctggacag tgaagagcgc gatcccacca aacgaagttg gacgccgaag     420

ttcttccaca acttcccggg catcgacagc gacggcgagc aactggccta caaggtggcg     480

ctgtacacca gtgccgcgcc gacgtatttt ccgaccgtgg acgggtacat cgatggcggt     540

gtggtggcca acaaccccag catggcagcc ctcgcgcaaa cgcaggacac ccgcgcgctg     600

aaaacaccgc cgcgcttctc cgaaatccgg ctgctctcga tcggcacggg caaatccctc     660
```

```
tatcgcatcg aagggcagaa cctggactgg ggctacgccc agtgggccaa gccgctcatc     720

aacatcatga tggacggcgt gatgggtgtg gcagattacc agtgccggca ggtcctggac     780

gacaattatt gccggatttc gcccaccttc ccgcccggcg cggtgtttcc cttggacggt     840

gtcaaacaga ttcccgacct ggtgaccttt gccacttccg tggacctcac gcgcgccgtt     900

cagtggatca agagcaagtg ggcttag                                         927
```

```
<210> SEQ ID NO 166
<211> LENGTH: 308
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (7)...(191)
<223> OTHER INFORMATION: Patatin-like phospholipase

<400> SEQUENCE: 166

Met Pro Lys Tyr Arg Ile Leu Ser Leu Asp Gly Gly Gly Ile Arg Gly
 1               5                  10                  15

Leu Leu Ser Ala Ile Leu Leu Glu Arg Leu Glu Ala Glu Ala Pro Asn
            20                  25                  30

Trp Leu Ser Gln Val Asp Leu Ile Ala Gly Thr Ser Thr Gly Gly Ile
        35                  40                  45

Ile Ala Leu Gly Leu Ala Lys Gly Leu Ser Pro Thr Gln Leu Arg Asn
    50                  55                  60

Leu Tyr Gln Leu Arg Gly Ala Ala Ile Phe Asp Asp Ser Trp Trp Asp
65                  70                  75                  80

Asp Val Leu Asp Ile Gly Lys Ile Ser Gly Ala Asp Tyr Asp Asn Lys
                85                  90                  95

Gln Leu Thr Lys Glu Leu Lys Thr Ile Leu Gly Asn Thr Lys Leu Arg
            100                 105                 110

Glu Leu Ser Lys Arg Val Leu Ile Ser Ser Phe Asp Leu Asp Ser Glu
        115                 120                 125

Glu Arg Asp Pro Thr Lys Arg Ser Trp Thr Pro Lys Phe Phe His Asn
    130                 135                 140

Phe Pro Gly Ile Asp Ser Asp Gly Glu Gln Leu Ala Tyr Lys Val Ala
145                 150                 155                 160

Leu Tyr Thr Ser Ala Ala Pro Thr Tyr Phe Pro Thr Val Asp Gly Tyr
                165                 170                 175

Ile Asp Gly Gly Val Val Ala Asn Asn Pro Ser Met Ala Ala Leu Ala
            180                 185                 190

Gln Thr Gln Asp Thr Arg Ala Leu Lys Thr Pro Pro Arg Phe Ser Glu
        195                 200                 205

Ile Arg Leu Leu Ser Ile Gly Thr Gly Lys Ser Leu Tyr Arg Ile Glu
    210                 215                 220

Gly Gln Asn Leu Asp Trp Gly Tyr Ala Gln Trp Ala Lys Pro Leu Ile
225                 230                 235                 240

Asn Ile Met Met Asp Gly Val Met Gly Val Ala Asp Tyr Gln Cys Arg
                245                 250                 255

Gln Val Leu Asp Asp Asn Tyr Cys Arg Ile Ser Pro Thr Phe Pro Pro
            260                 265                 270

Gly Ala Val Phe Pro Leu Asp Gly Val Lys Gln Ile Pro Asp Leu Val
        275                 280                 285

Thr Phe Ala Thr Ser Val Asp Leu Thr Arg Ala Val Gln Trp Ile Lys
    290                 295                 300
```

Ser Lys Trp Ala
305

<210> SEQ ID NO 167
<211> LENGTH: 522
<212> TYPE: DNA
<213> ORGANISM: Unknown
<220> FEATURE:
<223> OTHER INFORMATION: Obtained from an environmental sample

<400> SEQUENCE: 167
atggcgagga gctggaagtg gaggccgctt cttagctctt tcttattggt atccttggcg 60
cccttctcga cgtccgtgcc ttgcttcaag ctacccggcc ttgagagcgt ggccttctgg 120
ataagcacta ctatgaactt cttcccgttc ctcctctaca cggctatact agcctacgtt 180
aggaaagact acaaaatagt gctagagggg ctcgccctga acgcgttcgt gctcgtcctc 240
aagtactcgt tccacacccc caggccggag ggctctggcc acctaacccc gggctacccc 300
tccggccaca cggcgagggc cttctggctg gcgctcgagc tcgaaggggt ctggaggtac 360
cctatgttaa cctacgcggc tctggtcgcg tggtcgcgcg ttcagctctg cgcgcactac 420
ccgctggacg tagtgggagg agcgttgagc gctttggcct tccgcgactt atgggaggtt 480
ctgctggaga gggtaggagc cttgaggggg cagcgcgctt ag 522

<210> SEQ ID NO 168
<211> LENGTH: 173
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(30)
<220> FEATURE:
<221> NAME/KEY: DOMAIN
<222> LOCATION: (48)...(167)
<223> OTHER INFORMATION: PAP2 superfamily

<400> SEQUENCE: 168

Met Ala Arg Ser Trp Lys Trp Arg Pro Leu Leu Ser Ser Phe Leu Leu
1 5 10 15

Val Ser Leu Ala Pro Phe Ser Thr Ser Val Pro Cys Phe Lys Leu Pro
20 25 30

Gly Leu Glu Ser Val Ala Phe Trp Ile Ser Thr Thr Met Asn Phe Phe
35 40 45

Pro Phe Leu Leu Tyr Thr Ala Ile Leu Ala Tyr Val Arg Lys Asp Tyr
50 55 60

Lys Ile Val Leu Glu Gly Leu Ala Leu Asn Ala Phe Val Leu Val Leu
65 70 75 80

Lys Tyr Ser Phe His Thr Pro Arg Pro Glu Gly Ser Gly His Leu Thr
85 90 95

Pro Gly Tyr Pro Ser Gly His Thr Ala Arg Ala Phe Trp Leu Ala Leu
100 105 110

Glu Leu Glu Gly Val Trp Arg Tyr Pro Met Leu Thr Tyr Ala Ala Leu
115 120 125

Val Ala Trp Ser Arg Val Gln Leu Cys Ala His Tyr Pro Leu Asp Val
130 135 140

Val Gly Gly Ala Leu Ser Ala Leu Ala Phe Arg Asp Leu Trp Glu Val
145 150 155 160

Leu Leu Glu Arg Val Gly Ala Leu Arg Gly Gln Arg Ala 165 170

<210> SEQ ID NO 169
<211> LENGTH: 579
<212> TYPE: DNA
<213> ORGANISM: Unknown
<220> FEATURE:
<223> OTHER INFORMATION: Obtained from environmental sample

<400> SEQUENCE: 169
atgagcattc gcgcagtctt cttcgacctt ggcggagtca tcgtccgcac tgaatatcaa 60
tcaccgcgcc agcagctggc agaccggctt ggcctggact acgatgactt gagcaggatc 120
gtctttgata gcgagacggg catcaaggcg acggttggca cgatcacatc ccagcagcat 180
tgggaagcgg tgatgaaacg cctgaaacgc cctcatgagg aaattaccgc catccgcgat 240
gaattctttg caggcgacat cattgaccgt gagatcatca gtttcctccg ttcactgcgc 300
ggcacctgca aaaccggatt gatctcgaac gcctggagcg acttgcgcga ctttatgaca 360
cgcgaaaaaa taatcgacgc cttcgaccat atcatcatct cgtcggaggt aggtgtggcc 420
aagccggaag cgaagatctt ccagattgcc ctggagcagg ccggggtgag tccgaacgag 480
gcggtgtttg tcgatgattt ttacgtcaat atcgaaggct gtgaaaaagt cggaatgaag 540
ggcattcatt ttaaggaccc cgaatccgct ttggctcaa 579

<210> SEQ ID NO 170
<211> LENGTH: 193
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(187)
<223> OTHER INFORMATION: haloacid dehalogenase-like hydrolase

<400> SEQUENCE: 170

Met Ser Ile Arg Ala Val Phe Phe Asp Leu Gly Gly Val Ile Val Arg
1 5 10 15

Thr Glu Tyr Gln Ser Pro Arg Gln Gln Leu Ala Asp Arg Leu Gly Leu
20 25 30

Asp Tyr Asp Asp Leu Ser Arg Ile Val Phe Asp Ser Glu Thr Gly Ile
35 40 45

Lys Ala Thr Val Gly Thr Ile Thr Ser Gln Gln His Trp Glu Ala Val
50 55 60

Met Lys Arg Leu Lys Arg Pro His Glu Glu Ile Thr Ala Ile Arg Asp
65 70 75 80

Glu Phe Phe Ala Gly Asp Ile Ile Asp Arg Glu Ile Ile Ser Phe Leu
85 90 95

Arg Ser Leu Arg Gly Thr Cys Lys Thr Gly Leu Ile Ser Asn Ala Trp
100 105 110

Ser Asp Leu Arg Asp Phe Met Thr Arg Glu Lys Ile Ile Asp Ala Phe
115 120 125

Asp His Ile Ile Ile Ser Ser Glu Val Gly Val Ala Lys Pro Glu Ala
130 135 140

Lys Ile Phe Gln Ile Ala Leu Glu Gln Ala Gly Val Ser Pro Asn Glu
145 150 155 160

Ala Val Phe Val Asp Asp Phe Tyr Val Asn Ile Glu Gly Cys Glu Lys
165 170 175

Val Gly Met Lys Gly Ile His Phe Lys Asp Pro Glu Ser Ala Leu Ala 180 185 190

Gln

<210> SEQ ID NO 171
<211> LENGTH: 834
<212> TYPE: DNA
<213> ORGANISM: Unknown
<220> FEATURE:
<223> OTHER INFORMATION: Obtained from environmental sample

<400> SEQUENCE: 171
atgggcaaag cgatgttctt cacggcagat gacggggcgc ggctggccta ttctgaccag 60
ggtaaggggc tgccggtcct gtgcctggcc gggctgacgc ggaacatggg cgatttcaat 120
tacgtcgctc cgcatctgtc gggcgtgcgg ctgatccgga tggactatcg cggacgcggg 180
cagtccgacc gcaccggcgc cgccacctat accgtcccgc aggaaggcaa ggatgcgctg 240
gcgctgctgg atcacctggg ggtggacagg gccgcgatcc tgggcacgtc tcgcggcggg 300
ctgatcggga tgctgctggc cgccgtggcg catgaccggc tgctggggct gtgcctgaac 360
gatgtcggcc cggtgatcga gcgcgcgggg ctggagcgga tcttcgacta tgtcgggcgc 420
aacccggcgg cgcggacgca tgaggcgctg gcggaacgac tgcctgcggc catgcccggc 480
ttcacaaatg tccccgatgg ccgttggctg gcggatgcgc agaagcatta cgacgaaacg 540
ccggaggggc tgcggatcaa atatgaccct gccctgcgcg aggcgttcct ggcagccttc 600
gagggcgctg cgccggatct gtggccgctg tgggatgcga ctgcgggact gcccgtcgcg 660
ctgatccggg gggccagttc cgacctgctg tctgctacgg ttgccgccga gatgctgcgc 720
cgccgccccg acacgatctt tgccgaggtt ccgggccgcg cccatgtgcc ttggctggac 780
gagccggaat cgctggatgc gatcaatgcc tggctggatc gctgcgggcg ctag 834

<210> SEQ ID NO 172
<211> LENGTH: 277
<212> TYPE: PRT
<213> ORGANISM: Unknown
<220> FEATURE:
<223> OTHER INFORMATION: Obtained from environmental sample

<400> SEQUENCE: 172

Met Gly Lys Ala Met Phe Phe Thr Ala Asp Asp Gly Ala Arg Leu Ala
1 5 10 15

Tyr Ser Asp Gln Gly Lys Gly Leu Pro Val Leu Cys Leu Ala Gly Leu
20 25 30

Thr Arg Asn Met Gly Asp Phe Asn Tyr Val Ala Pro His Leu Ser Gly
35 40 45

Val Arg Leu Ile Arg Met Asp Tyr Arg Gly Arg Gly Gln Ser Asp Arg
50 55 60

Thr Gly Ala Ala Thr Tyr Thr Val Pro Gln Glu Gly Lys Asp Ala Leu
65 70 75 80

Ala Leu Leu Asp His Leu Gly Val Asp Arg Ala Ala Ile Leu Gly Thr
85 90 95

Ser Arg Gly Gly Leu Ile Gly Met Leu Leu Ala Ala Val Ala His Asp
100 105 110

Arg Leu Leu Gly Leu Cys Leu Asn Asp Val Gly Pro Val Ile Glu Arg
115 120 125

Ala Gly Leu Glu Arg Ile Phe Asp Tyr Val Gly Arg Asn Pro Ala Ala
130 135 140

Arg Thr His Glu Ala Leu Ala Glu Arg Leu Pro Ala Ala Met Pro Gly 145 150 155 160

Phe Thr Asn Val Pro Asp Gly Arg Trp Leu Ala Asp Ala Gln Lys His
165 170 175

Tyr Asp Glu Thr Pro Glu Gly Leu Arg Ile Lys Tyr Asp Pro Ala Leu
180 185 190

Arg Glu Ala Phe Leu Ala Ala Phe Glu Gly Ala Ala Pro Asp Leu Trp
195 200 205

Pro Leu Trp Asp Ala Thr Ala Gly Leu Pro Val Ala Leu Ile Arg Gly
210 215 220

Ala Ser Ser Asp Leu Leu Ser Ala Thr Val Ala Ala Glu Met Leu Arg
225 230 235 240

Arg Arg Pro Asp Thr Ile Phe Ala Glu Val Pro Gly Arg Ala His Val
245 250 255

Pro Trp Leu Asp Glu Pro Glu Ser Leu Asp Ala Ile Asn Ala Trp Leu
260 265 270

Asp Arg Cys Gly Arg
275

<210> SEQ ID NO 173
<211> LENGTH: 642
<212> TYPE: DNA
<213> ORGANISM: Unknown
<220> FEATURE:
<223> OTHER INFORMATION: Obtained from environmental sample

<400> SEQUENCE: 173
gtgagcgggc tggccggggt gctcttcgac atgggtggcg tggtcatgga ctcgccgctg 60
cacgccatcg cgcggtacga gcgggagcgc gggctgccgc cgcactcgat caaccgcgcg 120
atcgcgaccg ccggcgagac gggggcgtgg gcccgactcg agcgcggcga gctgaccgtg 180
gcgacgttct gcgcaccgtt cgaagcggac tgtcgcgccc gcggcgtcga ggtggatggg 240
gcggcggtca tggccgcgat cgccgcggcc ggcgtggcgc gccccgccat gctggaggcg 300
attcgcagac tccgcgcgca cgggctccgc gtcggcgcgc tcaccaacaa ctggcggcga 360
gaaggacccg acgacgacgt gatcccgcac cgtctgcgct cccacttcga cgccttcgtg 420
gaatcacgcg cggtcggcct gcgcaagccc gacccgcgaa tctacgtgct ggcctgccac 480
gagctgggcg tggagccgtc gcggacggcg ttcctcgacg acatcggcgg caacctcaag 540
ccggcgcgcg cgctcgggat ggcgacgatc aaggtggacg acccggagcg ggcgctggtg 600
gagctcggtg tgctcgtgga gatggacctg ctcggcccgt ga 642

<210> SEQ ID NO 174
<211> LENGTH: 213
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (4)...(195)
<223> OTHER INFORMATION: haloacid dehalogenase-like hydrolase

<400> SEQUENCE: 174

Met Ser Gly Leu Ala Gly Val Leu Phe Asp Met Gly Gly Val Val Met
1 5 10 15

Asp Ser Pro Leu His Ala Ile Ala Arg Tyr Glu Arg Glu Arg Gly Leu
20 25 30

Pro Pro His Ser Ile Asn Arg Ala Ile Ala Thr Ala Gly Glu Thr Gly
35 40 45

```
Ala Trp Ala Arg Leu Glu Arg Gly Glu Leu Thr Val Ala Thr Phe Cys
    50                  55                  60

Ala Pro Phe Glu Ala Asp Cys Arg Ala Arg Gly Val Glu Val Asp Gly
65                  70                  75                  80

Ala Ala Val Met Ala Ala Ile Ala Ala Ala Gly Val Ala Arg Pro Ala
                85                  90                  95

Met Leu Glu Ala Ile Arg Arg Leu Arg Ala His Gly Leu Arg Val Gly
            100                 105                 110

Ala Leu Thr Asn Asn Trp Arg Arg Glu Gly Pro Asp Asp Asp Val Ile
        115                 120                 125

Pro His Arg Leu Arg Ser His Phe Asp Ala Phe Val Glu Ser Arg Ala
    130                 135                 140

Val Gly Leu Arg Lys Pro Asp Pro Arg Ile Tyr Val Leu Ala Cys His
145                 150                 155                 160

Glu Leu Gly Val Glu Pro Ser Arg Thr Ala Phe Leu Asp Asp Ile Gly
                165                 170                 175

Gly Asn Leu Lys Pro Ala Arg Ala Leu Gly Met Ala Thr Ile Lys Val
            180                 185                 190

Asp Asp Pro Glu Arg Ala Leu Val Glu Leu Gly Val Leu Val Glu Met
        195                 200                 205

Asp Leu Leu Gly Pro
    210


<210> SEQ ID NO 175
<211> LENGTH: 245
<212> TYPE: PRT
<213> ORGANISM: Unknown
<220> FEATURE:
<223> OTHER INFORMATION: synthetic

<400> SEQUENCE: 175

Trp Ser Ala Glu Asp Lys His Asn Glu Gly Ile Asn Ser His Leu Trp
 1               5                  10                  15

Ile Val Asn Arg Ala Ile Asp Ile Met Ser Arg Asn Thr Thr Ile Val
            20                  25                  30

Asn Pro Asn Glu Thr Ala Leu Leu Asn Glu Trp Arg Ala Asp Leu Glu
        35                  40                  45

Asn Gly Ile Tyr Ser Ala Asp Tyr Glu Asn Pro Tyr Tyr Asp Asp Ser
    50                  55                  60

Thr Tyr Ala Ser His Phe Tyr Asp Pro Asp Thr Gly Thr Thr Tyr Ile
65                  70                  75                  80

Pro Phe Ala Lys His Ala Lys Glu Thr Gly Ala Lys Tyr Phe Asn Leu
                85                  90                  95

Ala Gly Gln Ala Tyr Gln Asn Gln Asp Met Gln Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Met Gly Phe His Ser Lys
    130                 135                 140

Tyr Glu Asn Phe Val Asp Thr Ile Lys Asn Asn Tyr Ile Val Ser Asp
145                 150                 155                 160

Ser Asn Gly Tyr Trp Asn Trp Lys Gly Ala Asn Pro Glu Asp Trp Ile
                165                 170                 175

Glu Gly Ala Ala Val Ala Ala Lys Gln Asp Tyr Pro Gly Val Val Asn
            180                 185                 190
```

```
Asp Thr Thr Lys Asp Trp Phe Val Lys Ala Ala Val Ser Gln Glu Tyr
        195                 200                 205

Ala Asp Lys Trp Arg Ala Glu Val Thr Pro Val Thr Gly Lys Arg Leu
    210                 215                 220

Met Glu Ala Gln Arg Val Thr Ala Gly Tyr Ile His Leu Trp Phe Asp
225                 230                 235                 240

Thr Tyr Val Asn Arg
                245


<210> SEQ ID NO 176
<211> LENGTH: 282
<212> TYPE: PRT
<213> ORGANISM: Unknown
<220> FEATURE:
<221> NAME/KEY: SIGNAL
<222> LOCATION: (1)...(24)
<223> OTHER INFORMATION: synthetic

<400> SEQUENCE: 176

Met Lys Lys Lys Val Leu Ala Leu Ala Ala Met Val Ala Leu Ala Ala
 1               5                  10                  15

Pro Val Gln Ser Val Val Phe Ala Gln Thr Asn Asn Ser Glu Ser Pro
            20                  25                  30

Ala Pro Ile Leu Arg Trp Ser Ala Glu Asp Lys His Asn Glu Gly Ile
        35                  40                  45

Asn Ser His Leu Trp Ile Val Asn Arg Ala Ile Asp Ile Met Ser Arg
    50                  55                  60

Asn Thr Thr Ile Val Asn Pro Asn Glu Thr Ala Leu Leu Asn Glu Trp
65                  70                  75                  80

Arg Ala Asp Leu Glu Asn Gly Ile Tyr Ser Ala Asp Tyr Glu Asn Pro
                85                  90                  95

Tyr Tyr Asp Asp Ser Thr Tyr Ala Ser His Phe Tyr Asp Pro Asp Thr
            100                 105                 110

Gly Thr Thr Tyr Ile Pro Phe Ala Lys His Ala Lys Glu Thr Gly Ala
        115                 120                 125

Lys Tyr Phe Asn Leu Ala Gly Gln Ala Tyr Gln Asn Gln Asp Met Gln
    130                 135                 140

Gln Ala Phe Phe Tyr Leu Gly Leu Ser Leu His Tyr Leu Gly Asp Val
145                 150                 155                 160

Asn Gln Pro Met His Ala Ala Ser Phe Thr Asp Leu Ser Tyr Pro Met
                165                 170                 175

Gly Phe His Ser Lys Tyr Glu Asn Phe Val Asp Thr Ile Lys Asn Asn
            180                 185                 190

Tyr Ile Val Ser Asp Ser Asn Gly Tyr Trp Asn Trp Lys Gly Ala Asn
        195                 200                 205

Pro Glu Asp Trp Ile Glu Gly Ala Ala Val Ala Ala Lys Gln Asp Tyr
    210                 215                 220

Pro Gly Val Val Asn Asp Thr Thr Lys Asp Trp Phe Val Lys Ala Ala
225                 230                 235                 240

Val Ser Gln Glu Tyr Ala Asp Lys Trp Arg Ala Glu Val Thr Pro Val
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn Arg
        275                 280
```